US012674172B2

(12) United States Patent
Farina et al.

(10) Patent No.: US 12,674,172 B2
(45) Date of Patent: Jul. 7, 2026

(54) BACTERIAL HOSTS FOR RECOMBINANT PROTEIN EXPRESSION

(71) Applicant: PELICAN TECHNOLOGY HOLDINGS, INC., San Diego, CA (US)

(72) Inventors: Anthony Farina, Carlsbad, CA (US); Cory M. Schwartz, San Diego, CA (US); Torben Bruck, Lakeside, CA (US); Russell Coleman, San Diego, CA (US); Diane M. Retallack, Poway, CA (US)

(73) Assignee: PELICAN TECHNOLOGY HOLDINGS, INC., San Diego, CA (US)

( * ) Notice: Subject to any disclaimer, the term of this patent is extended or adjusted under 35 U.S.C. 154(b) by 958 days.

(21) Appl. No.: 17/836,919

(22) Filed: Jun. 9, 2022

(65) Prior Publication Data

US 2023/0100757 A1 Mar. 30, 2023

Related U.S. Application Data

(60) Provisional application No. 63/209,239, filed on Jun. 10, 2021.

(51) Int. Cl.

| | |
|---|---|
| *C12N 1/20* | (2026.01) |
| *C07K 16/24* | (2006.01) |
| *C12N 9/90* | (2006.01) |
| *C12N 15/78* | (2006.01) |

(52) U.S. Cl.
CPC ............ *C12N 15/78* (2013.01); *C07K 16/241* (2013.01); *C12N 9/90* (2013.01); *C07K 2317/55* (2013.01)

(58) Field of Classification Search
CPC combination set(s) only.
See application file for complete search history.

(56) References Cited

U.S. PATENT DOCUMENTS

| | | | |
|---|---|---|---|
| 4,551,433 | A | 11/1985 | Deboer |
| 4,695,455 | A | 9/1987 | Barnes et al. |
| 4,755,465 | A | 7/1988 | Gray et al. |
| 4,861,595 | A | 8/1989 | Barnes et al. |
| 5,055,294 | A | 10/1991 | Gilroy |
| 5,128,130 | A | 7/1992 | Gilroy et al. |
| 5,169,760 | A | 12/1992 | Wilcox |
| 5,281,532 | A | 1/1994 | Rammler et al. |
| 5,648,237 | A | 7/1997 | Carter |
| 5,888,808 | A | 3/1999 | Kleid |
| 6,551,795 | B1 | 4/2003 | Rubenfield et al. |
| 7,476,532 | B2 | 1/2009 | Schneider |
| 7,618,799 | B2 | 11/2009 | Coleman et al. |
| 7,794,972 | B2 | 9/2010 | Retallack et al. |
| 7,985,564 | B2 | 7/2011 | Retallack et al. |
| 8,017,355 | B2 | 9/2011 | Schneider et al. |
| 8,288,127 | B2 | 10/2012 | Schneider et al. |
| 8,530,171 | B2 | 9/2013 | Retallack et al. |
| 8,569,015 | B2 | 10/2013 | Rasochova et al. |
| 8,603,824 | B2 | 12/2013 | Ramseier et al. |
| 9,394,571 | B2 | 7/2016 | Ramseier et al. |
| 9,453,251 | B2 | 9/2016 | Retallack et al. |
| 9,458,487 | B2 | 10/2016 | Retallack et al. |
| 9,493,559 | B2 | 11/2016 | Ellis et al. |
| 9,534,217 | B2 | 1/2017 | Soucaille et al. |
| 9,580,719 | B2 | 2/2017 | Retallack et al. |
| 10,118,956 | B2 | 11/2018 | Retallack et al. |
| 2007/0292918 | A1 | 12/2007 | Stelman et al. |
| 2012/0295309 | A1 | 11/2012 | Ellis et al. |
| 2014/0162279 | A1 | 6/2014 | Ramseier et al. |
| 2016/0159877 | A1 | 6/2016 | Retallack et al. |
| 2017/0183646 | A1 | 6/2017 | Retallack et al. |
| 2019/0127744 | A1 | 5/2019 | Coleman |
| 2019/0177734 | A1 | 6/2019 | Emmins et al. |
| 2020/0239896 | A1 | 7/2020 | Daniell |

FOREIGN PATENT DOCUMENTS

| | | |
|---|---|---|
| EP | 0207459 | 3/1991 |
| EP | 1341899 | 9/2003 |
| WO | WO-2005089093 A2 | 9/2005 |
| WO | WO-2008094986 A2 | 8/2008 |
| WO | WO 2011086139 A1 | 7/2011 |

OTHER PUBLICATIONS

Mikayama et al. (Nov. 1993. Proc. Natl.Acad.Sci. USA, vol. 90 : 10056-10060).*
Rudinger et al. (Jun. 1976. Peptide Hormones. Biol. Council. pp. 5-7).*
Bardwell, et al., "Pathways of Disulfide Bond Formation in Proteins in Vivo," 1994, Phosphate Microorg. Chapter 45, pp. 270-275.
Chen, Hongyun et al. "Determination of the optimal aligned spacing between the shine—Dalgarno sequence and the translation initiation codon of *Escherichia coli* mRNAs" Nucleic Acids Research, vol. 22, No. 23, 4953-4957, 1994.
Cimzia Label—Highlights of prescribing information, Sep. 2019.
Da Silva, Nancy Anderson et al. "Communications to the editor theoretical growth yield estimates for recombinant cells", Biotechnology and Bioengineering, vol. XXVIII, pp. 741-746, 1986.
Davis, Bernard D., et al., Mutants of *Escherichia coli* Requiring Methionine or Vitamin B(12), J. Bact., pp. 17-28, vol. 60, 1950.

(Continued)

*Primary Examiner* — Jennifer E Graser

(74) *Attorney, Agent, or Firm* — JONES DAY

(57) ABSTRACT

The present invention provides recombinant gram-negative host cells that do not degrade protease-sensitive recombinant proteins yet grow to high cell density, methods for the use of these host cells to produce high-quality recombinant proteins, including antibodies and antibody fragments, at high yield, as well as compositions and methods relating to periplasmic expression of recombinant proteins or polypeptides of interest in host cells.

44 Claims, 11 Drawing Sheets

Specification includes a Sequence Listing.

(56)                    References Cited

OTHER PUBLICATIONS

Dobin, Alexander, et al. "Star: Ultrafast Universal Rna-Seq Aligner." Bioinformatics 29.1 (2013): 15-21.

Dolinski, et al., "Peptidyl-prolyl isomerases—an overview of the cyclophilin, FKBP and parvulin families in Guidebook to Molecular Chaperones and Protein-Folding Catalysts." (1997) Gething M-J Ed. Oxford University Press Inc. New York. pp. 359-369.

Doudoroff, M., et al., Gram-Negative Aerobic Rods and Cocci, Bergey's Manual of Determinative Bacteriology, 1974, pp. 217-289, edited by Buchanan and Gibbons.

Edwards, Victor H. et al. "Continuous culture of pseudomonas fluorescens with sodium maleate as a carbon source," Biotechnology and Bioengineering, vol. XIV, pp. 123-147, 1972.

Frishman, Dmitrij, et al., Starts of bacterial genes: estimating the reliability of computer predictions, Gene, 1999, vol. 234, Elsevier Science B.V., pp. 257-265.

Hara, H., et al. "Cloning, mapping, and characterization of the *Escherichia coli* prc gene, which is involved in C-terminal processing of penicillin-binding protein 3." Journal of bacteriology 173.15 (1991): 4799-4813.

Higgins, Desmond G. et al. "Clustal: a package for performing multiple sequence alignment on a microcomputer" Gene 73, 237-244, 1988.

Higgins, Desmond G. et al. "Fast and sensitive multiple sequence alignments on a microcomputer", Cabios Communications, vol. 5, No. 2, pp. 151-153, 1989.

Ikehata, O., et al., Primary structure of nitrile hydratase deduced from the nucleotide sequence of a *Rhodococcus* species and its expression in *Escherichia coli*, 1989, Eur. J. Biochem, pp. 563-570, vol. 181.

International Search Report and Written Opinion for International Application No. PCT/US2022/032911, mailed Oct. 4, 2022, (10 Pages).

Kerr, Craig H., et al. "Cross-Feeding of *Escichericia coli* Mutants Defective in the Biosynthesis of Nicotinamide Adenide Dinucleotide", J. Bacteriology, vol. 115, No. 3, p. 982, 1973.

Lawrence, Amba et al. "Characterization of the tail-specific protease (Tsp) from Legionella," J. Gen. Appl. Microbiol. 60, 95-100, 2014.

Liao, Yang, Gordon K. Smyth, and Wei Shi. "Feature Counts: an efficient general purpose program for assigning sequence reads to genomic features." Bioinformatics 30.7 (2014): 923-930.

Lin, Norm S. et al. "Production of heterologous proteins from recombinant DNA *Escherichia coli* in bench fermenters", Methods: a Companion to Methods in Enzymology 4, 159-168, 1992.

Ma, Jiong et al. "Correlations between shine-dalgarno sequences and gene features such as predicted expression levels and operon structures", Journal of Bacteriology, vol. 184, No. 20, 5733-5745, Oct. 2002.

Maier, Christopher et al. "Genetic organization of the aprX-lipA2 operon affects the proteolytic potential of *Pseudomonas* species in milk," Frontiers in Microbiology, Jun. 10, 2020, vol. 11. Art. 1190, pp. 1-13.

Manoil, Colin, "Tagging Exported Proteins Using *Escherichia coli* Alkaline Phosphatase Gene Fusions," 2000, Methods in Enzymol, 326: 35-47.

Needleman, Saul B., et al., "A General Method Applicable to the Search for Similarities in the Amino Acid Sequence of Two Proteins," J. Mol. Biol., 1970, vol. 48, pp. 443-453.

Neidhardt, Frederick C. *Escheerichia coli* and *Salmonella typhimurium* cellular and molecular biology, 1987.

Pallen, Mark J., and Brendan W. Wren. "The HtrA family of serine proteases." *Molecular microbiology* 26.2 (1997): 209-221.

Pearson, William R., et al., "Improved Tools for Biological Sequence Comparison," Proc. Natl. Acad. Sci., Apr. 1988, vol. 85, pp. 2444-2448.

Pearson, William R., "An Introduction to Sequence Similarity ("Homology") Searching", NIH Public Access Curr Protoc BioInformatics, Jun. 2013, 9 pages.

Pearson, William R. "Using the FASTA program to search protein and DNA sequence databases", Methods Molec. Biol. 24:307-31, 1994.

Pearson, William R. "Using the FASTA program to search protein and DNA sequence databases", Methods Molec. Biol. 25:365-89, 1994.

Pearson, William R. "Searching protein sequence libraries: comparison of the sensitivity and selectivity of the Smith-Waterman and FASTA algorithms", Genomics 11, 635-650, 1991.

Riesenberg, D., et al., "High Cell Density Cultivation of *Escherichia coli* at Controlled Specific Growth Rate," Journal of Biotechnology, 1991, vol. 20, Elsevier Science Publishers, B.V, pp. 17-28.

Sambrook, J. et al. Molecular cloning: a laboratory manual second edition, Cold Spring Harbor Laboratory Press, 5 pages, 1989.

Sanchez-Romero, Genetic Engineering of Nonpathogenic Pseudomonas strains as Biocatalysts for Industrial and Environmental Processes, Manual of Industrial Microbiology and Biotechnology, Demain and Davies, eds., pp. 460-474 (ASM Press, Washington DC) 1999.

Schneider et al., (2005) "Auxotrophic markers pyrF and proC can replace antibiotic markers on protein production plasmids in high-cell-density Pseudomonas fluorescens fermentation," 2005a, Biotechnology Progress 21(2): 343-348.

Schweizer, Herbert P., Vectors to Express Foreign Genes and Techniques to Monitor Gene Expression in Pseudomonads, Current Opinion in Biotechnology, 2001, vol. 12, Elsevier Science Ltd., pp. 439-445.

Seemann, Torsten. "Prokka: rapid prokaryotic genome annotation." Bioinformatics 30.14 (2014): 2068-2069.

Shin, Jung-Ho, et al. "Structural basis of peptidoglycan endopeptidase regulation." Proceedings of the National Academy of Sciences 117.21 (2020): 11692-11702.

Singh, Santosh Kumar, et al. "Three redundant murein endopeptidases catalyse an essential cleavage step in peptidoglycan synthesis of *E scherichia coli* K 12." *Molecular microbiology* 86.5 (2012): 1036-1051.

Skórko-Glonek, Joanna, et al. "Site-directed mutagenesis of the HtrA (DegP) serine protease, whose proteolytic activity is indispensable for *Escherichia coli* survival at elevated temperatures." *Gene* 163.1 (1995): 47-52.

Slater, Robert J., and Williams, Ross, "The Expression of Foreign DNA in Bacteria," 2000, Molecular Biology and Biotechnology, Fourth Edition, Chapter 4, The Royal Society of Chemistry, Cambridge, UK, pp. 125-154.

Smith, Temple F. et al. "Comparison of Biosequences" Advances in Applied Mathematics 2, 482-489, 1981.

Smith, Temple F. et al. "Identification of common molecular sequences" J. Mol. Biol. 147, 195-197. 1981.

Suzek, Baris E., et al., "A Probabilistic Method for Identifying Start Codons in Bacterial Genomes." Bioinformatics, 2001, pp. 1123-1130, vol. 17, No. 12, Oxford University Press.

Tong, Huichun et al. "Prokaryotic Aquaporins," Cells, 8:1316. 18 pages, 2019.

Truong, Thao T., Andrea Vettiger, and Thomas G. Bernhardt. "Cell division is antagonized by the activity of peptidoglycan endopeptidases that promote cell elongation." *Molecular microbiology* 114.6 (2020): 966-978.

Vollmer, Waldemar, Didier Blanot, and Miguel A. De Pedro. "Peptidoglycan structure and architecture." *FEMS microbiology reviews* 32.2 (2008): 149-167.

Vollmer, Waldemar, et al. "Bacterial peptidoglycan (murein) hydrolases." *FEMS microbiology reviews* 32.2 (2008): 259-286.

Welch, Mark et al. "Design parameters to control synthetic gene expression in *Escherichia coli*" PLos One, vol. 4:9, Sep. 2009.

Yarwood, et al. "Noninvasive quantitative measurement of bacterial growth in porous media under unsaturated-flow conditions" Applied and Environmental Microbiology vol. 68:7, pp. 3597-3605, Jul. 2002.

* cited by examiner

DC954 (Δprc1prc2)

LB Soy – NaCl + uracil
36°C

DC454                 DC954

1/2X LB Soy – NaCl + uracil
36°C

Adapted cells

Anti-TNFα activity

Growth Curve (OD) Through 124

SEQUENCE LISTING

<160> NUMBER OF SEQ ID NOS: 98

<210> SEQ ID NO 1
<211> LENGTH: 468
<212> TYPE: PRT
<213> ORGANISM: Pseudomonas fluorescens

<400> SEQUENCE: 1

```
Met Thr Thr Glu Pro Ser Lys Ala Pro Pro Leu Tyr Pro Lys Thr His
1               5                   10                  15

Leu Leu Ala Ala Ser Gly Ile Ala Ala Leu Leu Ser Leu Ala Leu Leu
            20                  25                  30

Val Phe Pro Ser Ser Asp Val Glu Ala Lys Arg Thr Ser Leu Ser Leu
        35                  40                  45

Asp Leu Glu Ser Pro Val Glu Gln Leu Thr Gln Asp Gln Asp Ala Ser
    50                  55                  60

Asp Ala Gln Gln Ala Thr Asn Thr Ala Thr Glu Ser Pro Phe Ala Gln
65                  70                  75                  80

Ile Glu Ser Thr Pro Glu Asp Thr Gln Gln Ala Ala Gln Glu Ala Pro
                85                  90                  95

Ala Ala Ala Lys Ser Pro Gln His Arg Glu Val Ile Val Gly Lys Gly
            100                 105                 110
```

-continued

```
Asp Thr Leu Ser Thr Leu Phe Glu Lys Val Gly Leu Pro Ala Ala Ala
        115                 120                 125

Val Asn Asp Val Leu Ala Ser Asp Lys Gln Ala Lys Gln Phe Thr Gln
    130                 135                 140

Leu Lys Arg Gly Gln Lys Leu Glu Phe Glu Leu Thr Pro Asp Gly Gln
145                 150                 155                 160

Leu Asn Asn Leu Tyr Thr Ser Ile Ser Asp Leu Glu Ser Ile Ser Leu
                165                 170                 175

Ser Lys Gly Ala Lys Gly Phe Ala Phe Asn Arg Ile Thr Thr Lys Pro
                180                 185                 190

Val Met Arg Ser Ala Tyr Val His Gly Val Ile Asn Ser Ser Leu Ser
                195                 200                 205

Gln Ser Ala Ala Arg Ala Gly Leu Ser His Ser Met Thr Met Asp Met
        210                 215                 220

Ala Ser Val Phe Gly Tyr Asp Ile Asp Phe Ala Gln Asp Ile Arg Gln
225                 230                 235                 240

Gly Asp Glu Phe Asp Val Ile Tyr Glu Gln Lys Val Ala Asn Gly Lys
                245                 250                 255

Val Val Gly Thr Gly Asn Ile Leu Ser Ala Arg Phe Thr Asn Arg Gly
                260                 265                 270

Lys Thr Tyr Thr Ala Val Arg Tyr Thr Asn Lys Gln Gly Asn Ser Ser
        275                 280                 285

Tyr Tyr Thr Ala Asp Gly Asn Ser Met Arg Lys Ala Phe Ile Arg Thr
        290                 295                 300

Pro Val Asp Phe Ala Arg Ile Ser Ser Arg Phe Ser Met Gly Arg Lys
305                 310                 315                 320

His Pro Ile Leu Asn Lys Ile Arg Ala His Lys Gly Val Asp Tyr Ala
                325                 330                 335

Ala Pro Arg Gly Thr Pro Ile Lys Ala Ala Gly Asp Gly Lys Val Leu
                340                 345                 350

Leu Ala Gly Arg Arg Gly Gly Tyr Gly Asn Thr Val Ile Ile Gln His
        355                 360                 365

Gly Asn Thr Tyr Arg Thr Leu Tyr Gly His Met Gln Gly Phe Ala Lys
        370                 375                 380

Gly Val Lys Thr Gly Gly Asn Val Lys Gln Gly Gln Val Ile Gly Tyr
385                 390                 395                 400

Ile Gly Thr Thr Gly Leu Ser Thr Gly Pro His Leu His Tyr Glu Phe
                405                 410                 415

Gln Val Asn Gly Val His Val Asp Pro Leu Gly Gln Lys Leu Pro Met
                420                 425                 430

Ala Asp Pro Ile Ala Lys Ala Glu Arg Ala Arg Phe Met Gln Gln Ser
        435                 440                 445

Gln Pro Leu Met Ala Arg Met Asp Gln Glu Arg Ser Thr Leu Leu Ala
        450                 455                 460

Ser Ala Lys Arg
465
```

```
<210> SEQ ID NO 2
<211> LENGTH: 1407
<212> TYPE: DNA
<213> ORGANISM: Pseudomonas fluorescens

<400> SEQUENCE: 2
atgaccactg aaccgtctaa agcgccgccg ctttacccga agacccacct gctcgccgca      60
```

-continued

```
agtggtatcg ccgcccttct cagcctggca ctgctggtat tcccttccag tgacgttgaa      120
gccaaacgaa catccctgag ccttgatctg gaaagcccag ttgaacaact gacacaagat      180
caagacgctt ccgacgctca acaagccaca aacactgcaa ctgaatcacc tttcgcccag      240
atcgaaagca cacccgaaga cacccagcaa gccgcccagg aagcacctgc agcagccaag      300
agtccccagc atcgcgaagt catcgtgggc aaaggcgaca cactctcgac cctgttcgaa      360
aaagttgggt tgcctgccgc cgctgtaaat gacgtgctcg ccagcgataa gcaagccaag      420
caattcactc agctcaaacg tggtcaaaag cttgaatttg agctgacgcc agacggccag      480
ttgaacaacc tgtacaccag catcagtgac ttggaaagca tcagcctgag caaaggcgcc      540
aaaggcttcg cattcaacag aatcaccacc aaacccgtca tgcgttccgc ctacgtacat      600
ggcgtgatca acagctccct gtcgcagtcg gccgcgcgtg cgggcctgtc gcatagcatg      660
accatggaca tggccagcgt atttggctac gacatcgact tcgcccagga catccgtcaa      720
ggcgacgaat tcgacgtgat ctacgaacag aaagtagcca acggaaaagt ggtcggcact      780
ggcaacattc tttctgcacg cttcacaaac cgtggcaaaa cctacaccgc cgtgcgctac      840
accaacaaac aaggcaacag cagctactac acggctgatg gcaacagcat gcgtaaggcc      900
ttcatccgta cacccgttga ctttgcccgt attagctcgc gtttctccat gggccgcaag      960
catccaattc tgaacaaaat tcgcgcacac aagggcgtcg actatgccgc gccgcgtggc     1020
acgccaatca aagcagcggg cgacggcaag gtcttgttgg cggggcgccg tggtggttac     1080
ggcaatacgg tgatcatcca gcacggcaac acttaccgca cgctgtacgg ccacatgcaa     1140
gggttcgcca agggcgtcaa gacaggcggc aacgtgaaac agggccaagt gatcggctac     1200
atcggtacca ccggcctctc caccggcccg cacttgcact acgagttcca ggtcaacggc     1260
gtacacgtcg acccattggg ccagaagctg ccgatggccg acccgattgc caaggccgaa     1320
cgcgcgcgct tcatgcaaca gagccagccg ctgatggcac ggatggatca agagcgctcc     1380
accttgctgg cttcggcgaa gcgttaa                                         1407
```

<210> SEQ ID NO 3
<211> LENGTH: 273
<212> TYPE: PRT
<213> ORGANISM: Pseudomonas fluorescens

<400> SEQUENCE: 3

```
Met Pro Arg Leu Leu Ser Leu Leu Met Leu Leu Cys Leu Thr Phe Asn
1               5                   10                  15

Ala His Ala Asp Ser Tyr Ile Thr Arg Thr Leu Asn Lys Pro Val Pro
                20                  25                  30

Gly Gly Val Ala Val Val Glu Leu Gly Pro Ser Ala Thr Ala Pro Lys
            35                  40                  45

Ala Thr Tyr Gln Gly Lys Pro Val Leu Val Val Lys Glu Gln Asp Asn
        50                  55                  60

Trp Leu Ala Ile Val Gly Ile Pro Leu Thr Val Lys Pro Gly Asn Glu
65                  70                  75                  80

Arg Ile Ser Ser Gly Gly Arg Asn Leu Pro Phe Ile Val Gly Tyr Lys
                85                  90                  95

Lys Tyr Pro Glu Gln Arg Ile Thr Leu Lys Asn Lys Ser Gln Val Asn
            100                 105                 110

Pro Asp Pro Ala Gln Leu Lys Arg Ile Glu Gly Glu Leu Ala Val Gln
        115                 120                 125

Leu Lys Ala Tyr Arg Ser Phe Ser Pro Asn Leu Pro Ser Asn Leu Val
```

```
        130                135                140
Leu Asp Lys Pro Val Asn Gly Pro Leu Ser Ser Lys Phe Gly Val Arg
145                150                155                160

Arg Phe Phe Asn Gly Glu Glu Arg Asn Pro His Ser Gly Leu Asp Phe
                165                170                175

Ala Val Pro Ala Gly Thr Pro Ile Lys Thr Pro Ala Asn Gly Lys Val
                180                185                190

Ile Leu Val Gly Asn Tyr Phe Phe Asn Gly Asn Thr Val Phe Val Asp
                195                200                205

His Gly Gln Gly Phe Ile Ser Met Phe Cys His Met Ser Lys Ile Asp
                210                215                220

Val Arg Val Gly Gln Gln Leu Val Arg Gly Ala Val Val Gly Lys Val
225                230                235                240

Gly Ser Thr Gly Arg Ala Thr Gly Pro His Met His Trp Asn Val Ser
                245                250                255

Leu Asn Asp Ala Arg Val Asp Pro Ala Ile Phe Ile Gly Ala Phe Gln
                260                265                270

Pro
```

```
<210> SEQ ID NO 4
<211> LENGTH: 822
<212> TYPE: DNA
<213> ORGANISM: Pseudomonas fluorescens

<400> SEQUENCE: 4
atgccacgcc tactgagcct gttgatgctg ttgtgcctca cgtttaacgc ccacgccgac      60
agctacatca cgcgaaccct gaacaaaccc gtgcctggcg gcgtggccgt cgtcgaacta     120
ggcccttcgg ccacagcgcc gaaagccacc taccagggca agccggtgct ggtggtcaag     180
gagcaggaca actggctggc gattgtcggc atcccgttga cggtcaagcc tggcaacgag     240
cgcatcagca gcggggggcg caacctgccg tttatcgtcg ctacaagaa gtatccggaa     300 caacgcatca ccttgaagaa caaaagccag gtcaaccccg accggcccca gctcaagcgc     360
atcgaaggcg aattggcagt gcagctcaag gcttaccgca gcttcagccc gaatttgccg     420
agcaatctgg tgctggataa accggtgaac gggccgctgt cgagcaagtt cggggtgcga     480
cgcttcttca acggcgaaga gcgcaacccg cactcgggcc tggacttcgc cgtaccggcc     540
ggcacaccga tcaagacacc cgccaatggc aaggtgattc tggtcggcaa ttacttcttc     600
aacggcaata ccgtgtttgt cgaccatggc caggggttta tcagcatgtt ctgccatatg     660
tcgaagatcg atgtgagggt gggtcagcaa ctggtgcgcg gtgcggtagt cggcaaagta     720
ggctcgacag gccgggccac tgggccgcat atgcactgga acgtcagcct gaacgatgca     780
cgggtagatc cggcgattt tatcggcgcg tttcaaccct ga                        822
```

```
<210> SEQ ID NO 5
<211> LENGTH: 209
<212> TYPE: PRT
<213> ORGANISM: Pseudomonas fluorescens

<400> SEQUENCE: 5

Met Leu Asn Arg Phe Ala Pro Leu Val Pro Leu Ala Leu Val Thr Leu
1                5                10                15

Leu Phe Gly Cys Ala Ser His Pro Gln Gln Val Ala Glu Gln Gln Lys
                20                25                30

Pro Gln Val Gln Asn Gln Ala Lys Phe Val Ala Ala Gln Ser Ala Ser
```

```
              35                    40                    45
Val Tyr Glu Glu Glu Val Ala Thr Gly Lys Glu Leu Ala Glu Phe Ser
      50                    55                    60

Asp Ser Lys Pro Tyr Gln Leu Pro Leu Leu Ala Asp Ser Ile Leu Glu
65                    70                    75                    80

Arg Gly Met Ser Leu Ile Gly Thr Arg Tyr Arg Phe Gly Gly Thr Ser
                  85                    90                    95

Glu Ala Gly Phe Asp Cys Ser Gly Phe Ile Gly Tyr Leu Phe Arg Glu
                  100                   105                   110

Glu Ala Gly Met Asn Leu Pro Arg Ser Thr Arg Glu Met Ile Asn Val
                  115                   120                   125

Asn Ala Pro Leu Val Ala Arg Asn Asn Leu Lys Pro Gly Asp Leu Leu
      130                   135                   140

Phe Phe Ser Thr Ser Gly Arg Gly Arg Val Ser His Ala Gly Ile Tyr
145                   150                   155                   160

Leu Gly Asp Asn Gln Phe Ile His Ser Ser Ser Arg Arg Ser Gly Gly
                  165                   170                   175

Val Arg Val Asp Asn Leu Gly Asp Ser Tyr Trp Ser Lys Thr Phe Ile
                  180                   185                   190

Glu Ala Lys Arg Ala Leu Ala Met Ala Pro Thr Thr Val Thr Ala Ser
      195                   200                   205

Lys
```

<210> SEQ ID NO 6
<211> LENGTH: 630
<212> TYPE: DNA
<213> ORGANISM: Pseudomonas fluorescens

<400> SEQUENCE: 6

```
atgctaaatc gcttcgcacc cctcgtgcct ctcgcactcg ttaccctgtt gtttggttgc      60
gcctcccacc ctcagcaggt ggcagaacag caaaaaccac aggttcaaaa tcaggcaaag     120
ttcgttgctg cacagtctgc ttctgtttat gaagaagagg tggcaaccga aaaagaactc     180
gccgagttct ccgacagcaa gccttaccag ctgccacttc tggccgacag catccttgag     240
cgcggcatgt ccttgatcgg tacccgttac cgtttcggcg gcacctcgga agccggtttt     300
gattgcagcg gtttcattgg ctacctgttt cgtgaagaag ccggtatgaa cctgccgcgc     360
tccacgcgcg agatgatcaa cgtgaatgca ccgttggtcg cacgaaacaa cctcaagccc     420
ggtgatctgc ttttctttag taccagtggc cgcggtcgtg tcagccacgc cggtatctac     480
ctgggcgata accagtttat tcattccagc agccgccgca gtggtggtgt tcgggtcgat     540
aacctcggtg acagctactg gagcaaaacc ttcatcgaag ccaagcgcgc actcgccatg     600
gccccgacga cggttaccgc tagtaagtaa                                       630
```

<210> SEQ ID NO 7
<211> LENGTH: 179
<212> TYPE: PRT
<213> ORGANISM: Pseudomonas fluorescens

<400> SEQUENCE: 7

```
Met Ser Thr Ser Ala Arg Leu Met Leu Ile Val Cys Ala Ala Leu Leu
1                 5                   10                    15

Ser Ala Cys Ala Ser Arg Thr Pro Pro Ala Pro Val Ala Val Lys
                  20                  25                    30

Pro Lys Pro Val Phe Asn Tyr Ala Thr Gln Asn Phe Ser Pro Ala Ala
```

-continued 35                         40                          45

Glu Asp Val Leu Phe Arg Ala Leu Gly Leu Val Gly Thr Pro Tyr Arg
    50                          55                          60

Trp Gly Gly Asn Thr Pro Asp Ser Gly Phe Asp Cys Ser Gly Leu Ile
65                          70                          75                          80

Gly Phe Val Phe Arg Asp Ala Ala Gly Ile Ser Leu Pro Arg Thr Thr
                    85                          90                          95

Arg Glu Leu Ile Val Met Arg Ala Gln Asp Val Ser Glu Gln Asn Leu
                    100                         105                         110

Gln Thr Gly Asp Leu Leu Phe Phe Ala Thr Gly Gly Gly Ser Arg Val
                    115                         120                         125

Ser His Ala Gly Ile Tyr Val Gly Glu Gly Arg Phe Val His Ala Pro
    130                         135                         140

Gln Thr Gly Gly Thr Val Lys Leu Asp Thr Leu Ser Lys Ala Tyr Trp
145                         150                         155                         160

Gln Asn Ala Tyr Leu Ser Ala Lys Arg Val Leu Pro Gly Asn Leu Ala
                    165                         170                         175

Arg Asn Pro

<210> SEQ ID NO 8
<211> LENGTH: 540
<212> TYPE: DNA
<213> ORGANISM: Pseudomonas fluorescens

<400> SEQUENCE: 8
atgtcgacct cggcccgcct gatgcttatt gtttgcgccg cgctgctcag cgcctgcgcc      60
agtcgcacac cgccgcccgc gcccgtcgcg gtcaagccta agccggtgtt caactatgcc     120
acccagaatt tctcgccagc tgccgaagac gtgctctttc gtgcgctggg cctggtcggc     180
acgccttatc gctggggcgg caacacaccg gactcgggtt ttgattgcag cggcctgatc     240
ggctttgtat ccgcgacgc tgctggcatc tcattgccgc gcaccacccg tgaactgatc     300
gtgatgcgtg cccaggacgt cagcgaacaa aacctgcaga ccggcgacct gctgttcttc     360
gccaccggtg gtggttcgcg ggtcagccat gcgggtattt atgtggggga ggggcgcttc     420
gtacacgcgc cgcaaaccgg cggtacggtg aagctggata cgctatccaa agcgtattgg     480
cagaatgcct acctgagtgc caaacgcgtg ttgccaggga atctggcgcg taacccctga     540

<210> SEQ ID NO 9
<211> LENGTH: 509
<212> TYPE: PRT
<213> ORGANISM: Pseudomonas fluorescens

<400> SEQUENCE: 9

Met His Ile Pro Val Arg Gln Ser Ser Tyr Ser Arg Pro Ser Asp Lys
1                           5                           10                          15

Leu Gln Pro Asp Leu Ser Pro Asp Glu His Gln Val Val Leu Trp Ala
                    20                          25                          30

Asn Asn Lys Lys Ser Phe Thr Thr Asp Gln Ala Ala Lys His Ile Thr
                    35                          40                          45

Arg Gly Gly Phe Lys Phe His Asp Arg Asn Asn Asp Gly Lys Ile Val
    50                          55                          60

Val Gly Tyr Asn Phe Ala Gly Gly Phe Asn Ala Ala Gln Lys Glu Arg
65                          70                          75                          80

Ala Arg Gln Ala Leu Gln Tyr Trp Ala Asp Val Ala Asn Ile Glu Phe
                    85                          90                          95

-continued

```
Val Glu Asn Gly Pro Asn Thr Asp Gly Thr Ile Ser Ile Lys Gly Val
            100                 105                 110

Pro Gly Ser Ala Gly Val Ala Gly Leu Pro Asn Lys Tyr Asn Ser Asn
            115                 120                 125

Val Gln Ala Asn Ile Gly Thr Gln Gly Gly Gln Asn Pro Ala Met Gly
            130                 135                 140

Ser His Phe Leu Gly Leu Leu Ile His Glu Leu Gly His Thr Leu Gly
145                 150                 155                 160

Leu Ser His Pro Gly Lys Tyr Asp Gly Gln Gly Phe Asn Tyr Asp Arg
                165                 170                 175

Ala Ala Glu Tyr Ala Gln Asp Thr Lys Ala Arg Ser Val Met Ser Tyr
                180                 185                 190

Trp Thr Glu Thr His Gln Pro Gly His Asn Phe Ala Gly Arg Ser Pro
            195                 200                 205

Gly Ala Pro Met Met Asp Asp Ile Ala Ala Ala Gln Arg Leu Tyr Gly
            210                 215                 220

Ala Asn Thr Lys Thr Arg Asn Thr Asp Thr Thr Tyr Gly Phe Asn Ser
225                 230                 235                 240

Asn Ser Gly Arg Glu Ala Tyr Ser Leu Lys Gln Gly Ser Asp Lys Pro
                245                 250                 255

Ile Phe Thr Val Trp Asp Gly Gly Asn Asp Thr Leu Asp Phe Ser
                260                 265                 270

Gly Phe Thr Gln Asn Gln Thr Ile Asn Leu Lys Ala Glu Ser Phe Ser
            275                 280                 285

Asp Val Gly Gly Leu Arg Gly Asn Val Ser Ile Ala Lys Gly Val Ser
            290                 295                 300

Val Glu Asn Ala Ile Gly Gly Thr Gly Asn Asp Thr Leu Thr Gly Asn
305                 310                 315                 320

Glu Gly Asn Asn Arg Leu Thr Gly Gly Lys Gly Ala Asp Lys Leu His
                325                 330                 335

Gly Gly Ala Gly Ala Asp Thr Phe Val Tyr Arg Arg Ala Ser Asp Ser
            340                 345                 350

Thr Pro Gln Ala Pro Asp Ile Ile Gln Asp Phe Gln Ser Gly Ser Asp
            355                 360                 365

Lys Ile Asp Leu Thr Gly Val Val Gln Glu Ala Gly Leu Lys Ser Leu
    370                 375                 380

Ser Phe Val Glu Lys Phe Ser Gly Lys Ala Gly Glu Ala Val Leu Gly
385                 390                 395                 400

Gln Asp Ala Lys Thr Gly Arg Phe Thr Leu Ala Val Asp Thr Thr Gly
                405                 410                 415

Asn Gly Thr Ala Asp Leu Leu Val Ala Ser Gln Ser Gln Ile Lys Gln
                420                 425                 430

Ala Asp Val Ile Trp Asn Gly Gln Ala Pro Thr Val Thr Pro Thr Pro
            435                 440                 445

Glu Pro Thr Val Val Pro Val Ser Asp Pro Val Pro Thr Pro Thr Ser
    450                 455                 460

Glu Pro Thr Glu Pro Glu Pro Thr Pro Glu Pro Ala Pro Leu Pro Val
465                 470                 475                 480

Pro Thr Pro Arg Pro Gly Gly Gly Phe Ile Gly Lys Ile Phe Ser Ser
                485                 490                 495

Phe Lys Gly Phe Ile Lys Lys Val Trp Ser Ile Phe Arg
                500                 505
```

```
<210> SEQ ID NO 10
<211> LENGTH: 1530
<212> TYPE: DNA
<213> ORGANISM: Pseudomonas fluorescens

<400> SEQUENCE: 10
atgcatatcc ctgttaggca gtcttcttac tcgcgtcctt cagataagtt acagcccgat      60
ctttcacccg atgaacacca agttgttctc tgggccaaca ataaaaaatc tttcaccacg     120
gatcaggccg cgaaacacat cacccgcggt ggcttcaagt ttcatgatcg caacaatgat     180
ggaaaaatcg tcgtgggtta taactttgcg ggcggcttca atgcggctca gaaagaacgg     240
gccaggcaag cccttcagta ctgggcggat gttgctaata tcgaatttgt tgaaaatggc     300
ccgaacacgg atggcacaat aagcatcaag ggtgttccgg ttcggcagg cgtcgcgggg      360 ttgcccaaca aatataattc gaacgtccag gccaatatag caccagggg tgggcaaaac      420 ccggcgatgg gcagtcactt cctgggctta ttgatccatg aactgggca taccctgggg      480 ctgagtcatc caggtaaata cgacggccag ggtttcaatt acgatcgggc tgccgaatat     540
gcccaggaca ccaaggctcg cagtgtcatg agctattgga cggagactca tcagccgggg     600
cacaattttg ccgggcgcag cccgggtgcc cgatgatgg acgatatcgc cgccgcccag      660
cggctctacg cgccaacac caaaacccgg aataccgaca ccacctacgg cttcaattcc      720
aattcaggcc gggaggctta tagcctcaag caggggagcg acaagccgat cttcaccgtc     780
tgggacggtg gaggtaatga cacgctcgac ttctccgggt tcacccagaa ccaaaccatc     840
aacctcaagg ctgagtcatt ctcggacgtg gggggcttgc gaggaaatgt gtcgattgcc     900
aagggtgtga gtgtggaaaa cgccattggc ggtacaggca acgatacctt gacggggaac     960
gagggcaaca atcggctcac gggcggcaag ggggccgata agctgcacgg cggagctgga    1020
gcagacacgt ttgtttaccg ccgcgccagc gattcaacgc cgcaggcacc ggacatcatc    1080
caggacttcc agagcgggag cgacaagatc gacctgaccg tgttgttca ggaggcgggg     1140 ctcaagtcgc tgagcttcgt cgagaaattc agcggcaagg cgggcgaggc cgtgctcggc    1200
caagacgcga aaaccggccg tttcacgttg gcggtggaca caacgggaaa tggtacggcg    1260
gatctactgg ttgccagcca aagccagatc aaacaggcgg atgtgatctg gaacggtcag    1320
gcgccgacag tgacgccaac gcctgaaccc actgtggtgc ctgtgtcaga tcccgtgccg    1380
acccctactt cagagccgac tgaacctgaa cccacgcctg agcccgcccc tttgcccgtc    1440
ccgactccac ggcctggagg agggtttatc gggaaaattt tttcatcatt caaggggttc    1500
ataaaaaaag tgtggtcgat attcaggtga                                     1530

<210> SEQ ID NO 11
<211> LENGTH: 24
<212> TYPE: PRT
<213> ORGANISM: Pseudomonas fluorescens

<400> SEQUENCE: 11

Met Arg Ser Arg Leu Phe Asn Phe Leu Ser Cys Leu Leu Leu Ser Ala
1               5                   10                  15

Thr Ala Val Gln Ser Ala Gln Ala
            20

<210> SEQ ID NO 12
<211> LENGTH: 69
<212> TYPE: DNA
<213> ORGANISM: Pseudomonas fluorescens
```

<400> SEQUENCE: 12
atgcgcagtc gccttttcaa cttttttatct tgtctgcttc tttccgccac tgccgttcaa    60
tccgcccag    69

<210> SEQ ID NO 13
<211> LENGTH: 20
<212> TYPE: PRT
<213> ORGANISM: Pseudomonas fluorescens

<400> SEQUENCE: 13

Met Phe Ala Lys Leu Val Ala Val Ser Leu Leu Thr Leu Ala Ser Gly
1               5                   10                  15

Gln Leu Leu Ala
            20

<210> SEQ ID NO 14
<211> LENGTH: 57
<212> TYPE: DNA
<213> ORGANISM: Pseudomonas fluorescens

<400> SEQUENCE: 14
atgtttgcca aactcgttgc tgtttccctg ctgactctgg cgagcggcca gttgctt    57

<210> SEQ ID NO 15
<211> LENGTH: 22
<212> TYPE: PRT
<213> ORGANISM: Pseudomonas fluorescens

<400> SEQUENCE: 15

Met Arg Asn Leu Ile Leu Ser Ala Ala Leu Val Thr Ala Ser Leu Phe
1               5                   10                  15

Gly Met Thr Ala Gln Ala
            20

<210> SEQ ID NO 16
<211> LENGTH: 63
<212> TYPE: DNA
<213> ORGANISM: Pseudomonas fluorescens

<400> SEQUENCE: 16
atgcgtaatc tgatcctcag cgccgctctc gtcactgcca gcctcttcgg catgaccgca    60
caa    63

<210> SEQ ID NO 17
<211> LENGTH: 25
<212> TYPE: PRT
<213> ORGANISM: Pseudomonas fluorescens

<400> SEQUENCE: 17

Met Lys Ser Ala Leu Lys Asn Val Ile Pro Gly Ala Leu Ala Leu Leu
1               5                   10                  15

Leu Leu Phe Pro Val Ala Ala Gln Ala
            20                  25

<210> SEQ ID NO 18
<211> LENGTH: 75
<212> TYPE: DNA
<213> ORGANISM: Pseudomonas fluorescens

<400> SEQUENCE: 18

-continued

```
atgaaatctg cattgaagaa cgttattccg ggcgccctgg cccttctgct gctattcccc          60
gtcgccgccc aggcc                                                          75
```

<210> SEQ ID NO 19
<211> LENGTH: 21
<212> TYPE: PRT
<213> ORGANISM: Pseudomonas fluorescens

<400> SEQUENCE: 19

```
Met Lys Lys Ser Thr Leu Ala Val Ala Val Thr Leu Gly Ala Ile Ala
1               5                   10                  15

Gln Gln Ala Gly Ala
            20
```

<210> SEQ ID NO 20
<211> LENGTH: 63
<212> TYPE: DNA
<213> ORGANISM: Pseudomonas fluorescens

<400> SEQUENCE: 20

```
atgaagaagt ccaccttggc tgtggctgta acgttgggcg caatcgccca gcaagcaggc          60
gcc                                                                       63
```

<210> SEQ ID NO 21
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

-continued

```
Asn Thr Lys Val Asp Lys Lys Val Glu Pro Lys Ser Cys Asp Lys Thr
    210                 215                 220

His Thr Cys Ala Ala
225

<210> SEQ ID NO 22
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gaagtgcaac tggtggagag cggcggtggc ttggttcagc cgggtggctc cctgcgtctg      60
tcgtgtgcgg cctccgggta cgtgttcacc gactacggca tgaactgggt ccgccaggcc     120
ccagggaagg gtctggaatg gatgggctgg atcaacacgt atatcggcga accgatttat     180
gcggacagcg taaaagggcg cttcaccttt agcttggata cctccaaaag tacggcctac     240
ctgcagatga attccctgcg ggcagaggat accgcggtgt attactgcgc tcgcggctac     300
cgcagctacg cgatggacta ctggggccaa ggcaccctgg tgacggtgag ttcggccagc     360
accaagggcc ctagcgtgtt cccactcgcc cccagcagca atcgacctc gggcggtacg      420 gccgcactcg gctgcctggt gaaggactat ttcccggagc cggtgaccgt cagttggaac     480
agtggtgccc tgactagcgg cgtgcacacc tttcccgccg ttctgcagag ctcgggcttg     540
tactccttgt cgtccgtcgt aactgtgccc agcagctcgc tcggcaccca gacctacatc     600
tgcaatgtca accacaagcc gagcaacacc aaagtggata gaaggtcga accgaagtcc      660 tgcgacaaga cccatacctg tgcggcc                                          687

<210> SEQ ID NO 23
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 24
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gacattcaga tgacccagag ccccagcagc ctgagcgcca gcgtagggga ccgcgtgacc      60
atcacctgta aagccagtca aaacgtcggt accaacgtgg catggtatca acaaaaaccg     120
ggtaaagccc ccaaagcgtt gatctactcc gccagtttcc tgtatagcgg cgtgccgtac     180
cgcttcagcg gctccggcag cggtaccgac tttaccctga ccatttcctc gctgcaaccc     240
gaggactttg cgacctacta ttgccagcag tataacatct acccgctgac gttcgggcag     300
ggcacgaagg tcgaaatcaa acggaccgta gcggcaccga gtgtgttcat cttccctccg     360
agcgacgaac agttgaagtc cggcaccgcc tcggtcgtgt gcctgctcaa taacttctac     420
ccacgcgagg ctaaggtgca atggaaggtg gacaacgccc tgcagtcggg caatagtcag     480
gaatcggtga ctgaacagga ttccaaggat agcacctact cgctcagcag cacgctgacc     540
ttgtcgaagg ccgattacga gaagcataag gtctacgcgt gcgaagtgac gcaccagggc     600
ctgtcctcgc cggttactaa gagctttaac cgtggcgagt gc                        642
```

<210> SEQ ID NO 25
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Met Arg Ser Arg Leu Phe Asn Phe Leu Ser Cys Leu Leu Leu Ser Ala
1               5                   10                  15

Thr Ala Val Gln Ser Ala Gln Ala Glu Val Gln Leu Val Glu Ser Gly
                20                  25                  30

Gly Gly Leu Val Gln Pro Gly Gly Ser Leu Arg Leu Ser Cys Ala Ala
            35                  40                  45

Ser Gly Tyr Val Phe Thr Asp Tyr Gly Met Asn Trp Val Arg Gln Ala
        50                  55                  60

Pro Gly Lys Gly Leu Glu Trp Met Gly Trp Ile Asn Thr Tyr Ile Gly
65                  70                  75                  80

Glu Pro Ile Tyr Ala Asp Ser Val Lys Gly Arg Phe Thr Phe Ser Leu
                85                  90                  95

Asp Thr Ser Lys Ser Thr Ala Tyr Leu Gln Met Asn Ser Leu Arg Ala
```

-continued

```
              100                 105                 110
Glu Asp Thr Ala Val Tyr Tyr Cys Ala Arg Gly Tyr Arg Ser Tyr Ala
          115                 120                 125
Met Asp Tyr Trp Gly Gln Gly Thr Leu Val Thr Val Ser Ser Ala Ser
      130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                  165                 170                 175
Glu Pro Val Thr Val Ser Trp Asn Ser Gly Ala Leu Thr Ser Gly Val
              180                 185                 190
His Thr Phe Pro Ala Val Leu Gln Ser Ser Gly Leu Tyr Ser Leu Ser
          195                 200                 205
Ser Val Val Thr Val Pro Ser Ser Ser Leu Gly Thr Gln Thr Tyr Ile
      210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Ala Ala
              245                 250
```

<210> SEQ ID NO 26
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Phe Ala Lys Leu Val Ala Val Ser Leu Leu Thr Leu Ala Ser Gly
1               5                   10                  15
Gln Leu Leu Ala Asp Ile Gln Met Thr Gln Ser Pro Ser Ser Leu Ser
              20                  25                  30
Ala Ser Val Gly Asp Arg Val Thr Ile Thr Cys Lys Ala Ser Gln Asn
          35                  40                  45
Val Gly Thr Asn Val Ala Trp Tyr Gln Gln Lys Pro Gly Lys Ala Pro
      50                  55                  60
Lys Ala Leu Ile Tyr Ser Ala Ser Phe Leu Tyr Ser Gly Val Pro Tyr
65                  70                  75                  80
Arg Phe Ser Gly Ser Gly Ser Gly Thr Asp Phe Thr Leu Thr Ile Ser
                  85                  90                  95
Ser Leu Gln Pro Glu Asp Phe Ala Thr Tyr Tyr Cys Gln Gln Tyr Asn
              100                 105                 110
Ile Tyr Pro Leu Thr Phe Gly Gln Gly Thr Lys Val Glu Ile Lys Arg
          115                 120                 125
Thr Val Ala Ala Pro Ser Val Phe Ile Phe Pro Pro Ser Asp Glu Gln
      130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                  165                 170                 175
Gly Asn Ser Gln Glu Ser Val Thr Glu Gln Asp Ser Lys Asp Ser Thr
              180                 185                 190
Tyr Ser Leu Ser Ser Thr Leu Thr Leu Ser Lys Ala Asp Tyr Glu Lys
          195                 200                 205
```

```
His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 27
<211> LENGTH: 421
<212> TYPE: PRT
<213> ORGANISM: Homo sapiens

<400> SEQUENCE: 27

Leu Tyr Ser Ser Ser Asp Asp Val Ile Glu Leu Thr Pro Ser Asn Phe
1               5                   10                  15

Asn Arg Glu Val Ile Gln Ser Asp Ser Leu Trp Leu Val Glu Phe Tyr
                20                  25                  30

Ala Pro Trp Cys Gly His Cys Gln Arg Leu Thr Pro Glu Trp Lys Lys
            35                  40                  45

Ala Ala Thr Ala Leu Lys Asp Val Val Lys Val Gly Ala Val Asp Ala
        50                  55                  60

Asp Lys His His Ser Leu Gly Gly Gln Tyr Gly Val Gln Gly Phe Pro
65                  70                  75                  80

Thr Ile Lys Ile Phe Gly Ser Asn Lys Asn Arg Pro Glu Asp Tyr Gln
                85                  90                  95

Gly Gly Arg Thr Gly Glu Ala Ile Val Asp Ala Ala Leu Ser Ala Leu
            100                 105                 110

Arg Gln Leu Val Lys Asp Arg Leu Gly Gly Arg Ser Gly Gly Tyr Ser
        115                 120                 125

Ser Gly Lys Gln Gly Arg Ser Asp Ser Ser Ser Lys Lys Asp Val Ile
    130                 135                 140

Glu Leu Thr Asp Asp Ser Phe Asp Lys Asn Val Leu Asp Ser Glu Asp
145                 150                 155                 160

Val Trp Met Val Glu Phe Tyr Ala Pro Trp Cys Gly His Cys Lys Asn
                165                 170                 175

Leu Glu Pro Glu Trp Ala Ala Ala Ala Ser Glu Val Lys Glu Gln Thr
            180                 185                 190

Lys Gly Lys Val Lys Leu Ala Ala Val Asp Ala Thr Val Asn Gln Val
        195                 200                 205

Leu Ala Ser Arg Tyr Gly Ile Arg Gly Phe Pro Thr Ile Lys Ile Phe
    210                 215                 220

Gln Lys Gly Glu Ser Pro Val Asp Tyr Asp Gly Gly Arg Thr Arg Ser
225                 230                 235                 240

Asp Ile Val Ser Arg Ala Leu Asp Leu Phe Ser Asp Asn Ala Pro Pro
                245                 250                 255

Pro Glu Leu Leu Glu Ile Ile Asn Glu Asp Ile Ala Lys Arg Thr Cys
            260                 265                 270

Glu Glu His Gln Leu Cys Val Val Ala Val Leu Pro His Ile Leu Asp
            275                 280                 285

Thr Gly Ala Ala Gly Arg Asn Ser Tyr Leu Glu Val Leu Leu Lys Leu
        290                 295                 300

Ala Asp Lys Tyr Lys Lys Lys Met Trp Gly Trp Leu Trp Thr Glu Ala
305                 310                 315                 320

Gly Ala Gln Ser Glu Leu Glu Thr Ala Leu Gly Ile Gly Gly Phe Gly
                325                 330                 335

Tyr Pro Ala Met Ala Ala Ile Asn Ala Arg Lys Met Lys Phe Ala Leu
            340                 345                 350
```

-continued

```
Leu Lys Gly Ser Phe Ser Glu Gln Gly Ile Asn Glu Phe Leu Arg Glu
        355                 360                 365

Leu Ser Phe Gly Arg Gly Ser Thr Ala Pro Val Gly Gly Gly Ala Phe
    370                 375                 380

Pro Thr Ile Val Glu Arg Glu Pro Trp Asp Gly Arg Asp Gly Glu Leu
385                 390                 395                 400

Pro Val Glu Asp Asp Ile Asp Leu Ser Asp Val Glu Leu Asp Asp Leu
                405                 410                 415

Gly Lys Asp Glu Leu
            420

<210> SEQ ID NO 28
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Lys Lys Ser Thr Leu Ala Val Ala Val Thr Leu Gly Ala Ile Ala
1               5                   10                  15

Gln Gln Ala Gly Ala Leu Tyr Ser Ser Ser Asp Asp Val Ile Glu Leu
            20                  25                  30

Thr Pro Ser Asn Phe Asn Arg Glu Val Ile Gln Ser Asp Ser Leu Trp
        35                  40                  45

Leu Val Glu Phe Tyr Ala Pro Trp Cys Gly His Cys Gln Arg Leu Thr
    50                  55                  60

Pro Glu Trp Lys Lys Ala Ala Thr Ala Leu Lys Asp Val Val Lys Val
65                  70                  75                  80

Gly Ala Val Asp Ala Asp Lys His His Ser Leu Gly Gly Gln Tyr Gly
                85                  90                  95

Val Gln Gly Phe Pro Thr Ile Lys Ile Phe Gly Ser Asn Lys Asn Arg
            100                 105                 110

Pro Glu Asp Tyr Gln Gly Gly Arg Thr Gly Glu Ala Ile Val Asp Ala
            115                 120                 125

Ala Leu Ser Ala Leu Arg Gln Leu Val Lys Asp Arg Leu Gly Gly Arg
    130                 135                 140

Ser Gly Gly Tyr Ser Ser Gly Lys Gln Gly Arg Ser Asp Ser Ser Ser
145                 150                 155                 160

Lys Lys Asp Val Ile Glu Leu Thr Asp Asp Ser Phe Asp Lys Asn Val
            165                 170                 175

Leu Asp Ser Glu Asp Val Trp Met Val Glu Phe Tyr Ala Pro Trp Cys
            180                 185                 190

Gly His Cys Lys Asn Leu Glu Pro Glu Trp Ala Ala Ala Ala Ser Glu
            195                 200                 205

Val Lys Glu Gln Thr Lys Gly Lys Val Lys Leu Ala Ala Val Asp Ala
    210                 215                 220

Thr Val Asn Gln Val Leu Ala Ser Arg Tyr Gly Ile Arg Gly Phe Pro
225                 230                 235                 240

Thr Ile Lys Ile Phe Gln Lys Gly Glu Ser Pro Val Asp Tyr Asp Gly
                245                 250                 255

Gly Arg Thr Arg Ser Asp Ile Val Ser Arg Ala Leu Asp Leu Phe Ser
            260                 265                 270

Asp Asn Ala Pro Pro Glu Leu Leu Glu Ile Ile Asn Glu Asp Ile
```

-continued

```
                275                 280                 285

Ala Lys Arg Thr Cys Glu Glu His Gln Leu Cys Val Val Ala Val Leu
    290                 295                 300

Pro His Ile Leu Asp Thr Gly Ala Ala Gly Arg Asn Ser Tyr Leu Glu
305                 310                 315                 320

Val Leu Leu Lys Leu Ala Asp Lys Tyr Lys Lys Met Trp Gly Trp
                325                 330                 335

Leu Trp Thr Glu Ala Gly Ala Gln Ser Glu Leu Glu Thr Ala Leu Gly
                340                 345                 350

Ile Gly Gly Phe Gly Tyr Pro Ala Met Ala Ala Ile Asn Ala Arg Lys
                355                 360                 365

Met Lys Phe Ala Leu Leu Lys Gly Ser Phe Ser Glu Gln Gly Ile Asn
    370                 375                 380

Glu Phe Leu Arg Glu Leu Ser Phe Gly Arg Gly Ser Thr Ala Pro Val
385                 390                 395                 400

Gly Gly Gly Ala Phe Pro Thr Ile Val Glu Arg Glu Pro Trp Asp Gly
                405                 410                 415

Arg Asp Gly Glu Leu Pro Val Glu Asp Asp Ile Asp Leu Ser Asp Val
                420                 425                 430

Glu Leu Asp Asp Leu Gly Lys Asp Glu Leu
                435                 440

<210> SEQ ID NO 29
<211> LENGTH: 478
<212> TYPE: PRT
<213> ORGANISM: Pseudomonas fluorescens

<400> SEQUENCE: 29

Met Ser Ile Pro Arg Leu Lys Ser Tyr Leu Ser Ile Val Ala Thr Val
1               5                   10                  15

Leu Val Leu Gly Gln Ala Leu Pro Ala Gln Ala Val Glu Leu Pro Asp
                20                  25                  30

Phe Thr Gln Leu Val Glu Gln Ala Ser Pro Ala Val Val Asn Ile Ser
            35                  40                  45

Thr Thr Gln Lys Leu Pro Asp Arg Lys Val Ser Asn Gln Gln Met Pro
    50                  55                  60

Asp Leu Glu Gly Leu Pro Pro Met Leu Arg Glu Phe Phe Glu Arg Gly
65                  70                  75                  80

Met Pro Gln Pro Arg Ser Pro Arg Gly Gly Gly Gln Arg Glu Ala
                85                  90                  95

Gln Ser Leu Gly Ser Gly Phe Ile Ile Ser Pro Asp Gly Tyr Ile Leu
                100                 105                 110

Thr Asn Asn His Val Ile Ala Asp Ala Asp Glu Ile Leu Val Arg Leu
                115                 120                 125

Ala Asp Arg Ser Glu Leu Lys Ala Lys Leu Ile Gly Thr Asp Pro Arg
    130                 135                 140

Ser Asp Val Ala Leu Leu Lys Ile Glu Gly Lys Asp Leu Pro Val Leu
145                 150                 155                 160

Lys Leu Gly Lys Ser Gln Asp Leu Lys Ala Gly Gln Trp Val Val Ala
                165                 170                 175

Ile Gly Ser Pro Phe Gly Phe Asp His Thr Val Thr Gln Gly Ile Val
                180                 185                 190

Ser Ala Ile Gly Arg Ser Leu Pro Asn Glu Asn Tyr Val Pro Phe Ile
                195                 200                 205
```

-continued

```
Gln Thr Asp Val Pro Ile Asn Pro Gly Asn Ala Gly Gly Pro Leu Phe
    210             215             220

Asn Leu Ala Gly Glu Val Val Gly Ile Asn Ser Gln Ile Tyr Thr Arg
225             230             235             240

Ser Gly Gly Phe Met Gly Val Ser Phe Ala Ile Pro Ile Asp Val Ala
            245             250             255

Met Asp Val Ser Asn Gln Leu Lys Ser Gly Gly Lys Val Ser Arg Gly
            260             265             270

Trp Leu Gly Val Val Ile Gln Glu Val Asn Lys Asp Leu Ala Glu Ser
            275             280             285

Phe Gly Leu Asp Lys Pro Ala Gly Ala Leu Val Ala Gln Ile Gln Asp
    290             295             300

Asn Gly Pro Ala Ala Lys Gly Gly Leu Lys Val Gly Asp Val Ile Leu
305             310             315             320

Ser Met Asn Gly Gln Pro Ile Ile Met Ser Ala Asp Leu Pro His Leu
            325             330             335

Val Gly Ala Leu Lys Ala Gly Gly Lys Ala Lys Leu Glu Val Ile Arg
            340             345             350

Asp Gly Lys Arg Gln Asn Val Glu Leu Thr Val Gly Ala Ile Pro Glu
    355             360             365

Glu Gly Ala Thr Leu Asp Ala Leu Gly Asn Ala Lys Pro Gly Ala Glu
    370             375             380

Arg Ser Ser Asn Arg Leu Gly Ile Ala Val Val Glu Leu Thr Ala Glu
385             390             395             400

Gln Lys Lys Thr Phe Asp Leu Gln Ser Gly Val Val Ile Lys Glu Val
            405             410             415

Gln Asp Gly Pro Ala Ala Leu Ile Gly Leu Gln Pro Gly Asp Val Ile
            420             425             430

Thr His Leu Asn Asn Gln Ala Ile Asp Thr Thr Lys Glu Phe Ala Asp
    435             440             445

Ile Ala Lys Ala Leu Pro Lys Asn Arg Ser Val Ser Met Arg Val Leu
    450             455             460

Arg Gln Gly Arg Ala Ser Phe Ile Thr Phe Lys Leu Ala Glu
465             470             475
```

```
<210> SEQ ID NO 30
<211> LENGTH: 1434
<212> TYPE: DNA
<213> ORGANISM: Pseudomonas fluorescens

<400> SEQUENCE: 30
atgtcgatac cacgtttgaa gtcttactta tccatagtcg ccacagtgct ggtgctgggt        60
caggccttac ctgcgcaagc ggtcgagttg cctgacttca cccaactggt ggagcaggcc       120
tcgcctgccg tggtgaacat cagtaccacg cagaagctgc cggatcgcaa agtctcgaac       180
cagcagatgc ccgacctgga aggcttgccg cccatgctgc gcgagttctt cgaacgaggg       240
atgccgcaac cacgctcccc ccgtggcggc ggtggccagc gcgaagccca tccctgggc        300 tccggcttca tcatttcgcc tgacggctat atcctcacca acaaccacgt gattgccgat       360
gccgacgaga ttctcgtgcg cctggccgac cgcagtgaac tcaaggccaa gctgattggc       420
accgatccac gttccgacgt ggccttgctt aaaatcgagg gcaaggactt gccggtgctt       480
aagctgggca gtcccagga cctgaaggcc ggtcagtggg tggtcgcgat cggttcgccg       540
ttcggctttg accacaccgt tacccaaggc atcgtcagcg ccatcggtcg cagcctgccg       600
```

-continued

```
aacgaaaact acgtaccgtt catccagacc gacgtgccga tcaacccggg taacgccggt      660
ggcccgctgt tcaacctggc cggcgaagtg gtggggatca actcgcagat ctacacccgc      720
tccggcggct tcatgggcgt gtctttcgcg atcccaatcg atgtggccat ggacgtctcc      780
aatcagctca aaagcggcgg caaggtcagc cgcggctggt tgggcgtggt aatccaggaa      840
gtgaacaagg acctggctga gtccttcggt ctcgacaagc cggccggtgc cctggttgcg      900
cagattcagg acaatggccc tgcggccaaa ggcggcctga aagtcggtga cgtcatcctg      960
agcatgaacg gccagccgat catcatgtcg gcagacttgc ctcatttggt cggcgcgctc     1020
aaggccggcg gcaaagccaa gctggaagtg attcgtgatg gcaagcgcca gaacgtcgaa     1080
ctgaccgtag gtgccatccc ggaagaaggc gcgaccctgg atgccctggg caacgccaag     1140
cccggtgccg agcgcagcag taaccgcctg ggtatcgccg tggttgaact gaccgccgag     1200
cagaagaaaa ccttcgacct gcaaagcggt gtggtgatca aggaagttca ggacggccca     1260
gccgccttga tcggcctgca accgggtgac gtgatcactc acttgaacaa ccaggcaatc     1320
gataccacca aggaattcgc cgacatcgcc aaggcgttgc cgaagaatcg ctcggtgtcg     1380
atgcgcgtcc tgcgtcaagg ccgtgccagc ttcattacct tcaagctggc tgag           1434
```

```
<210> SEQ ID NO 31
<211> LENGTH: 478
<212> TYPE: PRT
<213> ORGANISM: Pseudomonas fluorescens

<400> SEQUENCE: 31

Met Ser Ile Pro Arg Leu Lys Ser Tyr Leu Ser Ile Val Ala Thr Val
1               5                   10                  15

Leu Val Leu Gly Gln Ala Leu Pro Ala Gln Ala Val Glu Leu Pro Asp
            20                  25                  30

Phe Thr Gln Leu Val Glu Gln Ala Ser Pro Ala Val Val Asn Ile Ser
        35                  40                  45

Thr Thr Gln Lys Leu Pro Asp Arg Lys Val Ser Asn Gln Gln Met Pro
    50                  55                  60

Asp Leu Glu Gly Leu Pro Pro Met Leu Arg Glu Phe Phe Glu Arg Gly
65                  70                  75                  80

Met Pro Gln Pro Arg Ser Pro Arg Gly Gly Gly Gln Arg Glu Ala
                85                  90                  95

Gln Ser Leu Gly Ser Gly Phe Ile Ile Ser Pro Asp Gly Tyr Ile Leu
            100                 105                 110

Thr Asn Asn His Val Ile Ala Asp Ala Asp Glu Ile Leu Val Arg Leu
        115                 120                 125

Ala Asp Arg Ser Glu Leu Lys Ala Lys Leu Ile Gly Thr Asp Pro Arg
    130                 135                 140

Ser Asp Val Ala Leu Leu Lys Ile Glu Gly Lys Asp Leu Pro Val Leu
145                 150                 155                 160

Lys Leu Gly Lys Ser Gln Asp Leu Lys Ala Gly Gln Trp Val Val Ala
                165                 170                 175

Ile Gly Ser Pro Phe Gly Phe Asp His Thr Val Thr Gln Gly Ile Val
            180                 185                 190

Ser Ala Ile Gly Arg Ser Leu Pro Asn Glu Asn Tyr Val Pro Phe Ile
            195                 200                 205

Gln Thr Asp Val Pro Ile Asn Pro Gly Asn Ser Gly Gly Pro Leu Phe
    210                 215                 220

Asn Leu Ala Gly Glu Val Val Gly Ile Asn Ser Gln Ile Tyr Thr Arg
```

-continued

```
225                 230                 235                 240

Ser Gly Gly Phe Met Gly Val Ser Phe Ala Ile Pro Ile Asp Val Ala
                245                 250                 255

Met Asp Val Ser Asn Gln Leu Lys Ser Gly Gly Lys Val Ser Arg Gly
                260                 265                 270

Trp Leu Gly Val Val Ile Gln Glu Val Asn Lys Asp Leu Ala Glu Ser
                275                 280                 285

Phe Gly Leu Asp Lys Pro Ala Gly Ala Leu Val Ala Gln Ile Gln Asp
                290                 295                 300

Asn Gly Pro Ala Ala Lys Gly Gly Leu Lys Val Gly Asp Val Ile Leu
305                 310                 315                 320

Ser Met Asn Gly Gln Pro Ile Ile Met Ser Ala Asp Leu Pro His Leu
                325                 330                 335

Val Gly Ala Leu Lys Ala Gly Gly Lys Ala Lys Leu Glu Val Ile Arg
                340                 345                 350

Asp Gly Lys Arg Gln Asn Val Glu Leu Thr Val Gly Ala Ile Pro Glu
                355                 360                 365

Glu Gly Ala Thr Leu Asp Ala Leu Gly Asn Ala Lys Pro Gly Ala Glu
                370                 375                 380

Arg Ser Ser Asn Arg Leu Gly Ile Ala Val Val Glu Leu Thr Ala Glu
385                 390                 395                 400

Gln Lys Lys Thr Phe Asp Leu Gln Ser Gly Val Val Ile Lys Glu Val
                405                 410                 415

Gln Asp Gly Pro Ala Ala Leu Ile Gly Leu Gln Pro Gly Asp Val Ile
                420                 425                 430

Thr His Leu Asn Asn Gln Ala Ile Asp Thr Thr Lys Glu Phe Ala Asp
                435                 440                 445

Ile Ala Lys Ala Leu Pro Lys Asn Arg Ser Val Ser Met Arg Val Leu
                450                 455                 460

Arg Gln Gly Arg Ala Ser Phe Ile Thr Phe Lys Leu Ala Glu
465                 470                 475

<210> SEQ ID NO 32
<211> LENGTH: 188
<212> TYPE: PRT
<213> ORGANISM: Escherichia coli

<400> SEQUENCE: 32

Met Val Lys Ser Gln Pro Ile Leu Arg Tyr Ile Leu Arg Gly Ile Pro
1                 5                 10                 15

Ala Ile Ala Val Ala Val Leu Leu Ser Ala Cys Ser Ala Asn Asn Thr
                20                 25                 30

Ala Lys Asn Met His Pro Glu Thr Arg Ala Val Gly Ser Glu Thr Ser
                35                 40                 45

Ser Leu Gln Ala Ser Gln Asp Glu Phe Glu Asn Leu Val Arg Asn Val
                50                 55                 60

Asp Val Lys Ser Arg Ile Met Asp Gln Tyr Ala Asp Trp Lys Gly Val
65                 70                 75                 80

Arg Tyr Arg Leu Gly Gly Ser Thr Lys Lys Gly Ile Asp Cys Ser Gly
                85                 90                 95

Phe Val Gln Arg Thr Phe Arg Glu Gln Phe Gly Leu Glu Leu Pro Arg
                100                 105                 110

Ser Thr Tyr Glu Gln Gln Glu Met Gly Lys Ser Val Ser Arg Ser Asn
                115                 120                 125
```

```
Leu Arg Thr Gly Asp Leu Val Leu Phe Arg Ala Gly Ser Thr Gly Arg
    130                 135                 140

His Val Gly Ile Tyr Ile Gly Asn Asn Gln Phe Val His Ala Ser Thr
145                 150                 155                 160

Ser Ser Gly Val Ile Ile Ser Ser Met Asn Glu Pro Tyr Trp Lys Lys
                165                 170                 175

Arg Tyr Asn Glu Ala Arg Arg Val Leu Ser Arg Ser
            180                 185

<210> SEQ ID NO 33
<211> LENGTH: 693
<212> TYPE: PRT
<213> ORGANISM: Pseudomonas fluorescens

<400> SEQUENCE: 33

Met Lys His Leu Phe Pro Ser Thr Ala Leu Ala Phe Phe Ile Gly Leu
1               5                   10                  15

Gly Phe Ala Ser Met Ser Thr Asn Thr Phe Ala Ala Asn Ser Trp Asp
                20                  25                  30

Asn Leu Gln Pro Asp Arg Asp Glu Val Ile Ala Ser Leu Asn Val Val
            35                  40                  45

Glu Leu Leu Lys Arg His His Tyr Ser Lys Pro Pro Leu Asp Asp Ala
        50                  55                  60

Arg Ser Val Ile Ile Tyr Asp Ser Tyr Leu Lys Leu Leu Asp Pro Ser
65                  70                  75                  80

Arg Ser Tyr Phe Leu Ala Ser Asp Ile Ala Glu Phe Asp Lys Trp Lys
                85                  90                  95

Thr Gln Phe Asp Asp Phe Leu Lys Ser Gly Asp Leu Gln Pro Gly Phe
                100                 105                 110

Thr Ile Tyr Lys Arg Tyr Leu Asp Arg Val Lys Ala Arg Leu Asp Phe
            115                 120                 125

Ala Leu Gly Glu Leu Asn Lys Gly Val Asp Lys Leu Asp Phe Thr Gln
    130                 135                 140

Lys Glu Thr Leu Leu Val Asp Arg Lys Asp Ala Pro Trp Leu Thr Ser
145                 150                 155                 160

Thr Ala Ala Leu Asp Asp Leu Trp Arg Lys Arg Val Lys Asp Glu Val
                165                 170                 175

Leu Arg Leu Lys Ile Ala Gly Lys Glu Pro Lys Ala Ile Gln Glu Leu
            180                 185                 190

Leu Thr Lys Arg Tyr Lys Asn Gln Leu Ala Arg Leu Asp Gln Thr Arg
            195                 200                 205

Ala Glu Asp Ile Phe Gln Ala Tyr Ile Asn Thr Phe Ala Met Ser Tyr
    210                 215                 220

Asp Pro His Thr Asn Tyr Leu Ser Pro Asp Asn Ala Glu Asn Phe Asp
225                 230                 235                 240

Ile Asn Met Ser Leu Ser Leu Glu Gly Ile Gly Ala Val Leu Gln Ser
                245                 250                 255

Asp Asn Asp Gln Val Lys Ile Val Arg Leu Val Pro Ala Gly Pro Ala
            260                 265                 270

Asp Lys Thr Lys Gln Val Ala Pro Ala Asp Lys Ile Ile Gly Val Ala
            275                 280                 285

Gln Ala Asp Lys Glu Met Val Asp Val Val Gly Trp Arg Leu Asp Glu
    290                 295                 300

Val Val Lys Leu Ile Arg Gly Pro Lys Gly Ser Val Val Arg Leu Glu
305                 310                 315                 320
```

-continued

```
Val Ile Pro His Thr Asn Ala Pro Asn Asp Gln Thr Ser Lys Ile Val
         325             330             335

Ser Ile Thr Arg Glu Ala Val Lys Leu Glu Asp Gln Ala Val Gln Lys
         340             345             350

Lys Val Leu Asn Leu Lys Gln Asp Gly Lys Asp Tyr Lys Leu Gly Val
         355             360             365

Ile Glu Ile Pro Ala Phe Tyr Leu Asp Phe Lys Ala Phe Arg Ala Gly
     370             375             380

Asp Pro Asp Tyr Lys Ser Thr Thr Arg Asp Val Lys Lys Ile Leu Thr
 385             390             395             400

Glu Leu Gln Lys Glu Lys Val Asp Gly Val Val Ile Asp Leu Arg Asn
             405             410             415

Asn Gly Gly Gly Ser Leu Gln Glu Ala Thr Glu Leu Thr Ser Leu Phe
             420             425             430

Ile Asp Lys Gly Pro Thr Val Leu Val Arg Asn Ala Asp Gly Arg Val
             435             440             445

Asp Val Leu Glu Asp Glu Asn Pro Gly Ala Phe Tyr Lys Gly Pro Met
     450             455             460

Ala Leu Leu Val Asn Arg Leu Ser Ala Ser Ala Ser Glu Ile Phe Ala
 465             470             475             480

Gly Ala Met Gln Asp Tyr His Arg Ala Leu Ile Ile Gly Gly Gln Thr
             485             490             495

Phe Gly Lys Gly Thr Val Gln Thr Ile Gln Pro Leu Asn His Gly Glu
             500             505             510

Leu Lys Leu Thr Leu Ala Lys Phe Tyr Arg Val Ser Gly Gln Ser Thr
             515             520             525

Gln His Gln Gly Val Leu Pro Asp Ile Asp Phe Pro Ser Ile Ile Asp
     530             535             540

Thr Lys Glu Ile Gly Glu Ser Ala Leu Pro Glu Ala Met Pro Trp Asp
 545             550             555             560

Thr Ile Arg Pro Ala Ile Lys Pro Ala Ser Asp Pro Phe Lys Pro Phe
             565             570             575

Leu Ala Gln Leu Lys Ala Asp His Asp Thr Arg Ser Ala Lys Asp Ala
             580             585             590

Glu Phe Val Phe Ile Arg Asp Lys Leu Ala Leu Ala Lys Lys Leu Met
             595             600             605

Glu Glu Lys Thr Val Ser Leu Asn Glu Ala Asp Arg Arg Ala Gln His
             610             615             620

Ser Ser Ile Glu Asn Gln Gln Leu Val Leu Glu Asn Thr Arg Arg Lys
 625             630             635             640

Ala Lys Gly Glu Asp Pro Leu Lys Glu Leu Lys Lys Glu Asp Glu Asp
             645             650             655

Ala Leu Pro Thr Glu Ala Asp Lys Thr Lys Pro Glu Asp Asp Ala Tyr
             660             665             670

Leu Ala Glu Thr Gly Arg Ile Leu Leu Asp Tyr Leu Lys Ile Thr Lys
             675             680             685

Gln Val Ala Lys Gln
     690
```

<210> SEQ ID NO 34
<211> LENGTH: 2082
<212> TYPE: DNA
<213> ORGANISM: Pseudomonas fluorescens -continued

```
<400> SEQUENCE: 34
atgaagcatc tgttccccag caccgccctc gcttttttca ttggtctcgg cttcgcgtcg      60
atgtcgacca atacgttcgc agccaatagc tgggacaacc ttcagcctga tcgcgatgag     120
gtgattgcca gccttaacgt cgtcgagttg cttaagcgcc atcactacag caagccgccg     180
ctggacgacg ctcgctcagt gatcatctac gacagctacc tcaagctgct ggacccgtcg     240
cgcagctact tcctggccag cgatatcgct gagttcgaca agtggaagac gcaattcgac     300
gacttcctca agagcggcga cctgcagcct ggcttcacca tctacaagcg ctacctagac     360
cgcgtcaaag cgcgtctgga cttcgccctg ggtgagctga acaaaggcgt cgacaagctc     420 gatttcacc  agaaagaaac ccttctggtg gaccgcaagg acgccccttg gctgaccagc     480
accgcagccc tagacgacct gtggcgcaaa cgcgtcaagg acgaagtgct gcgcttgaag     540
atcgccggca aagagcccaa ggccattcaa gagctgttga ccaagcgcta caaaaaccag     600
ctggcgcgcc tggaccagac ccgtgccgag gatatcttcc aggcctacat caacaccttt     660
gcgatgtcct acgacccgca caccaattat ctgtcgccag ataacgcgga aaatttcgat     720
atcaatatga gtctgtccct ggaaggcatc ggtgccgtcc tgcaaagcga caatgaccag     780
gtgaagattg tacgtctggt gccggcaggc ccggctgaca aaaccaagca agtggcaccg     840
gccgacaaga tcatcggcgt ggcccaggcc gacaaagaga tggtcgatgt ggtcggctgg     900
cgcctggacg aagtggtcaa gctgatccgt gggcctaaag cagcgtggt  gcgcctggaa     960 gtgattccgc acaccaatgc accgaacgac cagaccagca agatcgtgtc catcacccgt    1020
gaagcggtga agctcgaaga ccaggccgtg cagaagaaag tcctcaacct caagcaggat    1080
ggcaaggact acaagctggg ggtgattgaa atcccggcct tctacctgga cttcaaggcg    1140
ttccgtgccg gtgatccgga ctacaagtcc accacccgcg acgtgaagaa aatcctcaca    1200
gaactgcaga aagagaaagt cgacggcgtg gtcatcgacc tgcgcaacaa cggcggcggc    1260
tccctgcagg aagccaccga gctgaccagc ctgtttatcg acaagggccc gaccgtgttg    1320
gtacgcaacg ctgacggccg tgtcgacgtg ctcgaagacg agaacccggg ggccttctac    1380
aaagggccga tggcgctgct ggtcaaccgc ctctcggcct cggcctcgga gattttcgcc    1440
ggtgccatgc aggactacca ccgtgcactg atcatcggcg gccagacctt cggcaaaggc    1500
accgtgcaga ccatccagcc gctgaaccat ggcgagctta agctgacact ggccaagttc    1560
taccgggtct ccgggcagag cacccagcat cagggcgtac tgccggatat cgatttcccg    1620
tcgatcatcg acaccaagga aattggcgaa agcgccctgc ctgaagccat gccgtgggac    1680
accatccgcc ctgcgatcaa gccggcgtcg gatccgttca agccgttcct ggcacagctg    1740
aaggctgacc acgacacccg ctctgccaag gatgccgagt cgtgtttat  ccgcgacaag    1800 ctggccctgg ccaagaagct gatggaagag aagaccgtca gcctcaacga agcggatcgc    1860
cgtgcacagc actccagcat cgagaatcag caactggtgc tggaaaacac ccgccgcaag    1920
gccaaaggtg aagacccgct caaagagctg aagaaagaag atgaagacgc gctgccgacc    1980
gaggcggata aaaccaagcc ggaagacgac gcctacttgg ccgagactgg ccggatcctg    2040
ctggattacc tgaagatcac caagcaggtg gccaagcagt aa                       2082
```

```
<210> SEQ ID NO 35
<211> LENGTH: 437
<212> TYPE: PRT
<213> ORGANISM: Pseudomonas fluorescens

<400> SEQUENCE: 35
```

-continued

```
Met Leu His Leu Ser Arg Leu Thr Ser Leu Ala Leu Thr Ile Ala Leu
1               5                   10                  15

Val Ile Gly Ala Pro Leu Ala Phe Ala Asp Gln Ala Ala Pro Ala Ala
            20                  25                  30

Pro Ala Thr Ala Ala Thr Thr Lys Ala Pro Leu Pro Leu Asp Glu Leu
        35                  40                  45

Arg Thr Phe Ala Glu Val Met Asp Arg Ile Lys Ala Ala Tyr Val Glu
    50                  55                  60

Pro Val Asp Asp Lys Ala Leu Leu Glu Asn Ala Ile Lys Gly Met Leu
65                  70                  75                  80

Ser Asn Leu Asp Pro His Ser Ala Tyr Leu Gly Pro Glu Asp Phe Ala
                85                  90                  95

Glu Leu Gln Glu Ser Thr Ser Gly Glu Phe Gly Gly Leu Gly Ile Glu
            100                 105                 110

Val Gly Ser Glu Asp Gly Gln Ile Lys Val Val Ser Pro Ile Asp Asp
        115                 120                 125

Thr Pro Ala Ser Lys Ala Gly Ile Gln Ala Gly Asp Leu Ile Val Lys
    130                 135                 140

Ile Asn Gly Gln Pro Thr Arg Gly Gln Thr Met Thr Glu Ala Val Asp
145                 150                 155                 160

Lys Met Arg Gly Lys Leu Gly Gln Lys Ile Thr Leu Thr Leu Val Arg
                165                 170                 175

Asp Gly Gly Asn Pro Phe Asp Val Thr Leu Ala Arg Ala Thr Ile Thr
            180                 185                 190

Val Lys Ser Val Lys Ser Gln Leu Leu Glu Ser Gly Tyr Gly Tyr Ile
            195                 200                 205

Arg Ile Thr Gln Phe Gln Val Lys Thr Gly Asp Glu Val Ala Lys Ala
    210                 215                 220

Leu Ala Lys Leu Arg Lys Asp Asn Gly Lys Lys Leu Asn Gly Ile Val
225                 230                 235                 240

Leu Asp Leu Arg Asn Asn Pro Gly Gly Val Leu Gln Ser Ala Val Glu
                245                 250                 255

Val Val Asp His Phe Val Thr Lys Gly Leu Ile Val Tyr Thr Lys Gly
            260                 265                 270

Arg Ile Ala Asn Ser Glu Leu Arg Phe Ser Ala Thr Gly Asn Asp Leu
            275                 280                 285

Ser Glu Asn Val Pro Leu Ala Val Leu Ile Asn Gly Gly Ser Ala Ser
    290                 295                 300

Ala Ser Glu Ile Val Ala Gly Ala Leu Gln Asp Leu Lys Arg Gly Val
305                 310                 315                 320

Leu Met Gly Thr Thr Ser Phe Gly Lys Gly Ser Val Gln Thr Val Leu
                325                 330                 335

Pro Leu Asn Asn Glu Arg Ala Leu Lys Ile Thr Thr Ala Leu Tyr Tyr
            340                 345                 350

Thr Pro Asn Gly Arg Ser Ile Gln Ala Gln Gly Ile Val Pro Asp Ile
            355                 360                 365

Glu Val Arg Arg Ala Lys Ile Thr Asn Glu Ile Asp Gly Glu Tyr Tyr
    370                 375                 380

Lys Glu Ala Asp Leu Gln Gly His Leu Gly Asn Gly Asn Gly Gly Ala
385                 390                 395                 400

Asp Gln Pro Thr Gly Ser Arg Ala Lys Ala Lys Pro Met Pro Gln Asp
                405                 410                 415
```

```
Asp Asp Tyr Gln Leu Ala Gln Ala Leu Ser Leu Leu Lys Gly Leu Ser
            420                 425                 430

Ile Thr Arg Ser Arg
        435
```

<210> SEQ ID NO 36
<211> LENGTH: 1314
<212> TYPE: DNA
<213> ORGANISM: Pseudomonas fluorescens

<400> SEQUENCE: 36

```
atgctgcatt tgtcccgcct cacttcgctg gccctgacga tcgccctggt gatcggcgcg      60
cctctggctt ttgccgacca ggccgcaccg gctgcacccg ccacggctgc gacgaccaag     120
gcgccattgc cgctggacga gctgcgtacc tttgccgagg tcatggaccg gatcaaggca     180
gcgtatgtcg aacccgtaga cgacaaggcc ctgctggaaa atgccatcaa gggcatgctc     240
agcaacctcg acccgcactc cgcctacctg ggcccggaag atttcgccga gctgcaggaa     300
agcaccagcg gtgagttcgg cggcctgggc atcgaagtgg ctccgaaga cggccagatc      360 aaagtggtct cgcctatcga cgacaccccg gcgtccaagg ccggtatcca ggccggcgac     420
ctgatcgtga agatcaacgg ccagccaacc cgcggccaga ccatgaccga gccgtcgac      480 aagatgcgcg gcaagctcgg ccagaagatc accctgaccc tggtacgcga cggcggcaac     540
ccgtttgacg tgaccctggc ccgcgcgacc atcacggtca agagcgtgaa aagccagctg     600
ctggagtcgg gctacggtta tatccgtatc acccagttcc aggtcaagac cggcgacgaa     660
gtggccaagg ccctggccaa gctgcgcaaa gacaacggca agaagctcaa cggcatcgtg     720
cttgacctgc gcaacaaccc aggcggcgtg ttgcagtcgg cggtcgaggt ggtcgaccac     780
ttcgtcacca agggcctgat cgtctacacc aagggccgta tcgccaactc agagttgcgc     840
ttctcggcca ccggcaacga cctcagcgag aacgtgccac tggcggtatt gatcaacggt     900
ggcagcgcct cggcttcgga aatcgtcgcc ggtgccctgc aagacctcaa gcgcggcgtg     960
ctgatgggca ccaccagctt cggcaaaggc tcggtgcaga ccgtattgcc gctgaacaac    1020
gagcgtgcgc tgaagatcac cacggcgctg tactacacgc ccaacggccg ctcgatccag    1080
gcccagggca tcgtgccgga catcgaagta cgccgcgcca agatcaccaa cgagatcgac    1140
ggcgaatact acaaagaggc cgacctgcaa ggtcacctgg caatggcaa cggcggtgcc     1200 gaccagccaa ccggcagccg cgccaaggcc aagccgatgc cgcaggacga tgactaccaa    1260
ctggcccagg cactcagcct gctcaagggc ttgagcatca cccgcagccg ttga          1314
```

<210> SEQ ID NO 37
<211> LENGTH: 445
<212> TYPE: PRT
<213> ORGANISM: Pseudomonas fluorescens

<400> SEQUENCE: 37

```
Met Ser Met Thr Pro Arg Glu Ile Val His Glu Leu Asn Arg His Ile
1               5                  10                  15

Ile Gly Gln Asp Asp Ala Lys Arg Ala Val Ala Ile Ala Leu Arg Asn
            20                  25                  30

Arg Trp Arg Arg Met Gln Leu Pro Glu Glu Leu Arg Val Glu Val Thr
        35                  40                  45

Pro Lys Asn Ile Leu Met Ile Gly Pro Thr Gly Val Gly Lys Thr Glu
    50                  55                  60

Ile Ala Arg Arg Leu Ala Lys Leu Ala Asn Ala Pro Phe Ile Lys Val
```

```
65               70                75                80
Glu Ala Thr Lys Phe Thr Glu Val Gly Tyr Val Gly Arg Asp Val Glu
            85                90                95
Ser Ile Ile Arg Asp Leu Ala Asp Ala Ala Leu Lys Met Leu Arg Glu
            100               105               110
Gln Glu Val Thr Lys Val Ser His Arg Ala Glu Asp Ala Ala Glu Glu
            115               120               125
Arg Ile Leu Asp Ala Leu Leu Pro Pro Ala Arg Met Gly Phe Asn Glu
        130               135               140
Asp Ala Ala Pro Ala Thr Asp Ser Asn Thr Arg Gln Leu Phe Arg Lys
    145               150               155               160
Arg Leu Arg Glu Gly Gln Leu Asp Asp Lys Glu Ile Glu Ile Glu Val
                165               170               175
Ala Glu Val Ser Gly Val Asp Ile Ser Ala Pro Pro Gly Met Glu Glu
                180               185               190
Met Thr Ser Gln Leu Gln Asn Leu Phe Ala Asn Met Gly Lys Gly Lys
                195               200               205
Lys Lys Ser Arg Lys Leu Lys Val Lys Glu Ala Leu Lys Leu Val Arg
    210               215               220
Asp Glu Glu Ala Gly Arg Leu Val Asn Glu Glu Glu Leu Lys Ala Lys
225               230               235               240
Ala Leu Glu Ala Val Glu Gln His Gly Ile Val Phe Ile Asp Glu Ile
                245               250               255
Asp Lys Val Ala Lys Arg Gly Asn Ser Gly Gly Val Asp Val Ser Arg
                260               265               270
Glu Gly Val Gln Arg Asp Leu Leu Pro Leu Ile Glu Gly Cys Thr Val
            275               280               285
Asn Thr Lys Leu Gly Met Val Lys Thr Asp His Ile Leu Phe Ile Ala
    290               295               300
Ser Gly Ala Phe His Leu Ser Lys Pro Ser Asp Leu Val Pro Glu Leu
305               310               315               320
Gln Gly Arg Leu Pro Ile Arg Val Glu Leu Lys Ala Leu Thr Pro Gly
                325               330               335
Asp Phe Glu Arg Ile Leu Ser Glu Pro His Ala Ser Leu Thr Glu Gln
                340               345               350
Tyr Arg Glu Leu Leu Lys Thr Glu Gly Leu Gly Ile Glu Phe Gln Ala
            355               360               365
Asp Gly Ile Lys Arg Leu Ala Glu Ile Ala Trp Gln Val Asn Glu Lys
    370               375               380
Thr Glu Asn Ile Gly Ala Arg Arg Leu His Thr Leu Leu Glu Arg Leu
385               390               395               400
Leu Glu Glu Val Ser Phe Ser Ala Gly Asp Met Ala Gly Ala Gln Asn
                405               410               415
Gly Glu Ala Ile Lys Ile Asp Ala Asp Tyr Val Asn Ser His Leu Gly
            420               425               430
Glu Leu Ala Gln Asn Glu Asp Leu Ser Arg Tyr Ile Leu
        435               440               445
```

<210> SEQ ID NO 38
<211> LENGTH: 176
<212> TYPE: PRT
<213> ORGANISM: Pseudomonas fluorescens

<400> SEQUENCE: 38

```
Met Thr Thr Ile Val Ser Val Arg Arg His Gly Lys Val Val Met Gly
1               5                   10                  15

Gly Asp Gly Gln Val Ser Leu Gly Asn Thr Val Met Lys Gly Asn Ala
            20                  25                  30

Lys Lys Val Arg Arg Leu Tyr His Gly Gln Val Leu Ala Gly Phe Ala
            35                  40                  45

Gly Ala Thr Ala Asp Ala Phe Thr Leu Phe Glu Arg Phe Glu Gly Gln
    50                  55                  60

Leu Glu Lys His Gln Gly His Leu Val Arg Ala Ala Val Glu Leu Ala
65                  70                  75                  80

Lys Glu Trp Arg Thr Asp Arg Ser Leu Ser Arg Leu Glu Ala Met Leu
                85                  90                  95

Ala Val Ala Asn Lys Asp Ala Ser Leu Ile Ile Thr Gly Asn Gly Asp
            100                 105                 110

Val Val Glu Pro Glu His Gly Leu Ile Ala Met Gly Ser Gly Gly Gly
            115                 120                 125

Tyr Ala Gln Ala Ala Ala Ser Ala Leu Leu Lys Lys Thr Asp Leu Ser
    130                 135                 140

Ala Arg Glu Ile Val Glu Thr Ala Leu Gly Ile Ala Gly Asp Ile Cys
145                 150                 155                 160

Val Phe Thr Asn His Asn Gln Thr Ile Glu Glu Gln Asp Leu Ala Glu
                165                 170                 175
```

<210> SEQ ID NO 39
<211> LENGTH: 295
<212> TYPE: PRT
<213> ORGANISM: Pseudomonas fluorescens

<400> SEQUENCE: 39

```
Met Met Arg Ile Leu Leu Phe Leu Ala Thr Asn Leu Ala Val Val Leu
1               5                   10                  15

Ile Ala Ser Val Thr Leu Ser Leu Phe Gly Phe Asn Gly Phe Met Ala
            20                  25                  30

Ala Asn Gly Val Asp Leu Asn Leu Asn Gln Leu Leu Ile Phe Cys Ala
            35                  40                  45

Val Phe Gly Phe Ala Gly Ser Leu Phe Ser Leu Phe Ile Ser Lys Trp
    50                  55                  60

Met Ala Lys Met Ser Thr Ser Thr Gln Ile Ile Thr Gln Pro Arg Thr
65                  70                  75                  80

Arg His Glu Gln Trp Leu Met Gln Thr Val Glu Gln Leu Ser Gln Glu
                85                  90                  95

Ala Gly Ile Lys Met Pro Glu Val Gly Ile Phe Pro Ala Tyr Glu Ala
            100                 105                 110

Asn Ala Phe Ala Thr Gly Trp Asn Lys Asn Asp Ala Leu Val Ala Val
            115                 120                 125

Ser Gln Gly Leu Leu Glu Arg Phe Ser Pro Asp Glu Val Lys Ala Val
    130                 135                 140

Leu Ala His Glu Ile Gly His Val Ala Asn Gly Asp Met Val Thr Leu
145                 150                 155                 160

Ala Leu Val Gln Gly Val Val Asn Thr Phe Val Met Phe Phe Ala Arg
                165                 170                 175

Ile Ile Gly Asn Phe Val Asp Lys Val Ile Phe Lys Asn Glu Glu Gly
            180                 185                 190

Arg Gly Ile Ala Tyr Phe Val Ala Thr Ile Phe Ala Glu Leu Val Leu
    195                 200                 205
```

```
Gly Phe Leu Ala Ser Ala Ile Val Met Trp Phe Ser Arg Lys Arg Glu
    210                 215                 220

Phe Arg Ala Asp Glu Ala Gly Ala Arg Leu Ala Gly Thr Ser Ala Met
225                 230                 235                 240

Ile Gly Ala Leu Gln Arg Leu Arg Ser Glu Gln Gly Leu Pro Val His
                245                 250                 255

Met Pro Asp Ser Leu Thr Ala Phe Gly Ile Asn Gly Gly Ile Lys Gln
            260                 265                 270

Gly Leu Ala Arg Leu Phe Met Ser His Pro Pro Leu Glu Glu Arg Ile
        275                 280                 285

Asp Ala Leu Arg Arg Arg Gly
    290                 295
```

<210> SEQ ID NO 40
<211> LENGTH: 888
<212> TYPE: DNA
<213> ORGANISM: Pseudomonas fluorescens

<400> SEQUENCE: 40

```
atgatgcgca tcctgctgtt cttggccact aacctggcgg tcgtactgat tgccagcgtc      60
accctgagcc tttttggctt caacgggttc atggcggcca atggggttga tctgaacctc     120
aatcagctgc tgattttctg tgcggtcttt ggttttgccg gctcgctgtt ctcgctgttc     180
atctccaagt ggatggcgaa gatgagcacc agcacccaga tcatcactca accccgcact     240
cgccatgaac aatggctgat gcaaaccgtg gagcagttgt ctcaagaagc aggcatcaaa     300
atgcccgaag tggggatttt tcctgcttat gaggccaacg cctttgccac cggctggaac     360
aagaacgacg cactggtggc tgtgagccag ggcctgctgg agcggttttc gcccgatgaa     420
gtcaaggcgg tgctggccca cgagatcggc cacgtagcca acgcgacat ggtcaccctg      480 gcactggtac agggcgtggt gaacaccttc gtgatgttct ttgcgcggat catcggcaac     540
tttgtcgaca aggtcatctt caagaacgaa gaaggccgtg gcattgccta cttcgtggcg     600
accattttcg ccgagttggt cctgggcttc ctggccagcg ccatcgtgat gtggttctcg     660
cgcaaacgcg agttccgcgc agatgaagcc ggcgcacgcc tggcgggcac cagcgcaatg     720
atcggcgcgc tgcaacgcct cgctccgaa caggcctgc cggtgcatat gccggacagc      780
ctgaccgcct tcggcatcaa cggcggcatc aagcagggcc tggctcgctt gttcatgagc     840
cacccgccgc tggaagagcg gattgacgca ctgcgtcgcc ggggctga                  888
```

<210> SEQ ID NO 41
<211> LENGTH: 533
<212> TYPE: PRT
<213> ORGANISM: Pseudomonas fluorescens

<400> SEQUENCE: 41

```
Met Phe Lys Lys His Ala Cys Tyr Leu Ser Ile Cys Leu Leu Val Ala
1               5                  10                  15

Pro Leu Val Ala Thr Ala Glu Thr Leu Pro Leu Glu Pro Leu Pro Val
                20                  25                  30

Thr Thr Pro Ala Pro Val Ala Leu Ala Pro Leu Gln Gln Ala Leu Ala
            35                  40                  45

Gln Leu Thr Ser Val Cys Pro His Leu Ala Pro Arg Ile Asp Ala Ala
        50                  55                  60

Ala Leu Ala Arg Leu Gln Thr Phe Tyr Gln Gln Gly Asp Ala Pro
65                  70                  75                  80
```

-continued

Leu Trp Ala Ala Asp Glu Arg Arg Gln Ala Leu His Ala Gln Leu Leu
                85                  90                  95

Met Leu Ala Asp Asp Gly Leu Asp Pro Thr His Tyr Ser Leu Pro Ala
               100                 105                 110

Val Asp Ala Thr Ala Asn Val Leu Cys Ser Asp Ile Ala Asn Ser Gln
               115                 120                 125

Gln Tyr Leu Gln Ala Leu Gln Asp Leu His Tyr Gly Arg Leu Gln Gln
          130                 135                 140

Ser Arg Phe Glu Pro Leu Trp His Ser Gln Pro Pro Ser Gly Asp Pro
145                 150                 155                 160

Asn Thr Glu Val Leu Ala Phe Ala Ala Thr Gly Leu His Asp Met Ala
               165                 170                 175

Gln Ala Phe Asp Gln Ala Arg Pro Ser Ala Asp Leu Tyr Arg Ser Leu
               180                 185                 190

Arg Asn Ala Tyr Ala Gly Val Arg Gln Gln Pro Leu Pro His Trp Asp
          195                 200                 205

Pro Val Ala Glu Gly Thr Leu Leu Arg Pro Gly Met Asn Asp Pro Arg
          210                 215                 220

Val Pro Glu Leu Ala Arg Arg Leu His Ser Gly Gly Tyr Leu Ala Gln
225                 230                 235                 240

Leu Pro Ser Gly Asn Gly Lys Gln Tyr Gln Gly Glu Leu Val Lys Ala
               245                 250                 255

Val Lys Ala Phe Gln Leu Ser His Ser Leu Gln Ala Asp Gly Val Ile
               260                 265                 270

Gly Ala Gly Thr Val Ala Glu Leu Asn Ile Ser Pro Ala Met Arg Arg
               275                 280                 285

Glu Gln Leu Arg Ile Asn Leu Glu Arg Phe Arg Trp Leu Ala Gln Asp
          290                 295                 300

Leu Glu Pro Glu Gly Val Val Val Asn Val Ala Ala Ala Gln Leu Ser
305                 310                 315                 320

Val Tyr Gln Ser Gly Ile Pro Val Trp Gln Thr Arg Leu Gln Val Gly
               325                 330                 335

Arg Ala Glu Arg Gln Thr Pro Leu Leu Lys Ser Arg Ile Thr Arg Leu
          340                 345                 350

Thr Leu Asn Pro Thr Trp Thr Ile Pro Pro Thr Ile Met Arg Glu Asp
          355                 360                 365

Lys Leu Pro Ala Ile Arg Leu Asn Pro Glu Tyr Leu Arg Gln Gln Asn
     370                 375                 380

Leu Gln Val Leu Asp Ala Glu Gly His Pro Leu Thr Pro Asp Gln Val
385                 390                 395                 400

Asp Trp Ala Arg Pro Gly Asn Ile Leu Leu Arg Gln Gln Ala Gly Pro
               405                 410                 415

Arg Asn Pro Leu Gly Lys Ile Val Met Arg Phe Pro Asn Pro Tyr Ser
          420                 425                 430

Val Tyr Leu His Asp Thr Pro Ser Gln Pro Leu Phe Thr Lys Gly Pro
          435                 440                 445

Arg Ala Phe Ser Ser Gly Cys Val Arg Val Glu Gln Pro Leu Leu Leu
     450                 455                 460

Arg Asp Leu Leu Val Thr Pro Ala Glu Arg Thr Arg Thr Asp Glu Leu
465                 470                 475                 480

Leu Ala Thr Gly Glu Thr His Glu Phe Arg Leu Ala Thr Pro Val Pro
               485                 490                 495

-continued

```
Val Leu Leu Gly Tyr Trp Thr Val Glu Val Asp Arg Gln Gly Glu Leu
        500                 505                 510

Val Tyr Ala Pro Asp Ile Tyr Ala Arg Asp Pro Ala Leu Ile Lys Ala
        515                 520                 525

Met Gly Ser Val Leu
    530

<210> SEQ ID NO 42
<211> LENGTH: 1602
<212> TYPE: DNA
<213> ORGANISM: Pseudomonas fluorescens

<400> SEQUENCE: 42
atgttcaaaa aacacgcatg ttacttgagc atttgcctgc tcgttgcacc attggtcgct        60
acagccgaaa cgctgccgtt agaaccactg cccgtcacca cccctgcacc ggtcgcgctc       120
gcgccgctgc aacaggcctt ggcgcagttg accagtgtct gcccgcacct tgcgccgcgt       180
atcgatgccg ccgcgttggc gcgcctgcaa accttttacc agcagcaggg cgatgccccg       240
ctatgggcgg ctgacgaacg ccggcaagcc ttgcatgccc agttgctgat gcttgccgac       300
gatggcctgg accccaccca ctatagcttg cctgcggtgg atgccacggc caacgtgctg       360
tgcagcgata tcgccaacag ccagcagtac ctgcaagctc tgcaggattt gcactacggg       420
cgcctgcagc aatcgcgctt tgagcccctc tggcattccc agccacccag tggcgatccg       480
aataccgagg tgctggcgtt cgccgccacc ggcctgcacg acatggccca agccttcgat       540
caggcccggc ccagcgccga tttgtaccgc agcctgcgca atgcctatgc cggcgtgcgc       600
cagcaaccgc tgccccattg ggacccggtc gccgagggca cgttgttgcg tcctgggatg       660
aatgaccctc gcgtgccgga actggcgcgg cgcctgcaca gcggcggcta cctggcccag       720
ttacccagcg gcaacggcaa gcagtaccag ggcgaactgg tcaaggcggt gaaagccttc       780
cagctcagcc actcgttgca ggccgacggc gtgatcggcg ccggcaccgt ggccgaactc       840
aatatcagcc cggcgatgcg tcgtgaacaa ctgcgcatca acctcgagcg tttccgctgg       900
ctggcccagg acctggagcc tgaaggcgtc gtggtcaatg tggccgccgc gcaactgagc       960
gtgtaccaga gcggcatccc agtgtggcaa acccgcctgc aagtgggccg ggccgaacgc      1020
cagacgccgt tgctcaagtc gcgcatcacc cggctgaccc tcaaccccac ctggaccatc      1080
ccgccgacca tcatgcgcga ggacaaactg ccggccatcc gcctcaaccc tgaatacctg      1140
cgccagcaaa acctgcaagt gctcgacgcc gaaggtcacc cgttgacccc cgaccaggtc      1200
gactgggcgc gccccggcaa tatcctgctg cgccagcagg ccggcccgcg taacccgctg      1260
ggcaagattg tgatgcgttt ccccaatccg tattccgtat atctgcacga cacccccagc      1320
caacccttgt tcaccaaggg gccgcgggcg ttcagttcgg gatgcgtgcg ggtcgagcaa      1380
ccgttgttat tgcgcgacct gctggtaacg ccggccgaac gcactcgcac cgatgagctg      1440
ctggcgaccg gcgaaaccca tgaattcagg ttggccacgc cggtaccggt gctgttgggg      1500
tattggaccg tggaagtgga tcgccagggc gagctggtgt acgcgccgga tatttatgcg      1560
cgtgacccgg cgttgatcaa ggccatgggt agcgtgttat ag                        1602

<210> SEQ ID NO 43
<211> LENGTH: 2665
<212> TYPE: PRT
<213> ORGANISM: Pseudomonas fluorescens

<400> SEQUENCE: 43
```

-continued

```
Met Asp Val Arg Gln Phe Ala Phe Leu Ala Arg Gln Pro Ser Ala Ala
1               5                   10                  15

Leu Lys Arg Arg Asp Ala Phe Phe Gly Leu Pro Lys Arg Gly Leu Ala
            20                  25                  30

Leu Ile Leu Ala Asn Ala Leu Phe Trp Gln Pro Leu Leu Ala Gln Ala
            35                  40                  45

Glu Gly Ile Val Val Ser Ala Pro Gly Thr Thr Val Gly Ala Ala Gly
    50                  55                  60

Asn Gly Val Pro Val Val Asn Ile Ala Thr Pro Asn Gly Ala Gly Leu
65                  70                  75                  80

Ser His Asn Gln Phe Lys Asp Tyr Asn Val Gly Pro Asn Gly Val Ile
                85                  90                  95

Leu Asn Asn Gly Asn Gly Ala Met Val Asn Thr Gln Leu Gly Gly Ile
            100                 105                 110

Ile Val Gly Asn Pro Asn Leu Lys Gly Gly Ala Ala Asn Val Ile Leu
            115                 120                 125

Asn Glu Val Asn Gly Gly Ser Pro Ser Gln Leu Arg Gly Tyr Thr Glu
    130                 135                 140

Val Ala Gly Gln Ser Ala Lys Val Ile Val Ala Asn Pro Tyr Gly Val
145                 150                 155                 160

Thr Cys Ser Gly Cys Gly Phe Ile Asn Thr Pro Asn Val Thr Leu Thr
            165                 170                 175

Thr Gly Lys Pro Val Leu Asp Ala Ser Gly Gln Leu Gln Arg Tyr Glu
            180                 185                 190

Val Asp Gly Gly Ala Val Thr Ile Asp Gly Gln Gly Leu Asn Ala Ser
            195                 200                 205

Asn Val Glu Arg Phe Asp Ile Ile Thr Arg Ser Ala Lys Ile Asn Ala
    210                 215                 220

Gln Ile Asn Ala Arg Glu Leu Asn Val Ile Ala Gly Arg Asn Asp Val
225                 230                 235                 240

Asp Ala Gln Ser Leu Lys Thr Thr Ala Arg Ala Asp Asp Gly Ser Ala
            245                 250                 255

Lys Pro Glu Leu Ala Ile Asp Ser Ser Ala Leu Gly Gly Met Tyr Ala
            260                 265                 270

Gly Ala Ile Lys Leu Val Gly Thr Glu Ala Gly Val Gly Val Lys Leu
            275                 280                 285

Asp Gly Thr Leu Ala Ala Ser Gly Gly Asp Ile Gln Leu Asp Ala Asn
    290                 295                 300

Gly Arg Leu Ser Met Ala Gln Ala Ala Thr Gly Asn Val Lys Val
305                 310                 315                 320

Thr Ala Gln Asn Val Asp Leu Thr Asp Lys Val Tyr Ala Asn Gly Asn
            325                 330                 335

Val Gln Val Thr Ser Ala Gln Ala Leu Val Asn Arg Lys Ser Ile Ala
            340                 345                 350

Ala Gly Gln Arg Ile Glu Ile Asn Ala Ala Ser Val Asn Asn Pro Gly
            355                 360                 365

Ile Ile Glu Ala Gly Val Ala Ala Asp Asn Ser Arg Asn Thr Thr Gly
    370                 375                 380

Asp Leu Val Val Asn Ala Gln Thr Val Thr Thr Ser Gly Asn Leu Leu
385                 390                 395                 400

Ala Ser Arg Ala Leu Ala Ile Thr Ala Ala Gln Ala Leu Thr Asn Gln
            405                 410                 415

Gly Ala Ile Ile Gln Ala Lys Thr Val Glu Val Ser Ser Ala Lys Leu
```

-continued

```
                420               425               430
Thr Asn Gln Gly Ala Ser Ala Arg Leu Phe Gly Glu Gln Ser Leu Ala
        435               440               445

Ile Asn Ser Pro Ala Ile Val Asn Leu Gly Gly Leu Ile Arg Phe Gly
        450               455               460

Glu Gly Gln Ala Ala Thr Leu Asn Ser Ala Ser Leu Asp Asn Arg Gln
465               470               475               480

Gly Arg Ile Glu Met Ala Gly Gly Ser Leu Val Leu Thr Ser Ala Asp
                485               490               495

Leu Asn Asn Ser Gly Gly Gln Val Ile Ala Asn Asp Leu Thr Val Asn
                500               505               510

Ala Gly Asn Leu Asn Asn Gln Asn Gly Val Leu Val Ala Lys Thr Ala
        515               520               525

Thr Val Thr Ala Ser Asn Leu Asp Asn Ser Leu Lys Gly Leu Ile Gln
        530               535               540

Ala Asp Gly Gly Ala Leu Asn Leu Ala Val Ser Asn Thr Phe Asn Asn
545               550               555               560

Asn Gln Gly Phe Ala Gln Ala Ser Thr Asp Leu Asn Val Thr Ala Gly
                565               570               575

Thr Leu Ser Ser Asn Ala Gly Gly Val Leu Ser Ala Asp Thr Gly Lys
                580               585               590

Leu Thr Leu Thr Ala Ala Gln Gln Leu Asn Asn Ala Gln Gly Arg Leu
        595               600               605

Gln Ala Gly Gln Gly Asp Ile Glu Leu His Ala Ala Asn Leu Asp Asn
        610               615               620

Gln Ser Gly Thr Ile Val Gly Lys Gln Leu Leu Leu Asp Val Ala Gly
625               630               635               640

Gly Asp Ile Asp Asn Arg Ala Gly Arg Val Leu Gly Asp His Leu Asp
                645               650               655

Val Arg Ala Ser Gly Leu Asp Asn Arg Asn Ala Gly Leu Leu Ala Gly
                660               665               670

Gly Ala Gln Gly Val Ser Leu Leu Leu Lys Gly Pro Gly Gln Leu Leu
        675               680               685

Asn Ala Gln Gly Arg Ile Gln Ser Glu Gly Leu Leu Gln Leu Gln Gly
        690               695               700

Glu Arg Phe Asp Asn Ser Ala Gly Ile Leu Leu Gly Gln Thr Val Asp
705               710               715               720

Val Thr Ala Gln Thr Phe Asn Asn Ser Asn Lys Gly Ala Leu Val Ser
                725               730               735

Asp Gly Gly Asp Val Val Phe Lys Val Ser Asp Leu Leu Thr Asn Val
                740               745               750

Gly Gly Gln Ile Asp Ala Gly Glu Arg Ser Val Leu Val Lys Gln Leu
        755               760               765

Thr Thr Leu Asn Asn Asp Gly Gly Thr Leu Arg Gly Lys Arg Leu Asp
        770               775               780

Ile Ala Ala Gln His Leu Asn Asn Asp Asn Gly Gln Leu Leu Ala Gly
785               790               795               800

Ala Glu Gly Leu Ser Tyr Ser Gly Gln Asp Val Ser Asn Arg Lys Gly
                805               810               815

Leu Ile Leu Ser Gly Gly Ala Leu Thr Glu Leu Asn Thr Thr Arg Leu
                820               825               830

Asp Asn Gln Gly Gly Thr Val Gln Gly Asp Ser Leu Thr Val Thr Ala
        835               840               845
```

```
Asn Asn Val Asp Asn Gly Ser Gly Gly Leu Met Ala Ser Leu Val Gly
    850                 855                 860

Asn Leu Gln Leu Thr Val Glu Ala Leu Ala Asn Arg Gly Gly Lys Leu
865                 870                 875                 880

Phe Gly Lys Glu Gln Val Thr Val Ser Gly Ala Ser Leu Asp Asn Ser
                885                 890                 895

Ala Gly Gln Ile Ser Gly Asn Gln Ile Asn Leu Thr Ser Arg Asp Thr
            900                 905                 910

Leu Thr Asn Gln Gly Gly Leu Val Glu Ala Asn Gln Gly Leu Thr Leu
        915                 920                 925

Thr Gly Gly Asn Leu Asp Asn Ser Ala Asn Gly Gln Leu Arg Ala Leu
    930                 935                 940

Gly Gly Ala Ser Ser Arg Val Asn Leu Ser Gly Ala Leu Asn Asn Gln
945                 950                 955                 960

Asn Gly Thr Leu Glu Phe Gly Ser Gln Ala Phe Ser Leu Asp Ala Ala
                965                 970                 975

Ser Leu Asn Asn Gln Asn Gly Met Leu Gln His Ala Gly Thr Gly Leu
            980                 985                 990

Phe His Leu Asn Ile Ala Ser Leu  Glu Gly Ser Gln Gly  Asn Ile Gln
        995                 1000                 1005

Gly Met  Gly Ser Ala Asp Trp  Ala Phe Gly Lys Val  Asp Gly Leu
    1010                 1015                 1020

Gly Arg  Val Gln Leu Asn Asp  Val Leu Thr Tyr Lys  Ser Asp Gln
    1025                 1030                 1035

Gly Leu  Ala Leu Gln Ala Gly  Asp Arg Met Ala Ser  Ala Lys Gly
    1040                 1045                 1050

Leu Ile  Leu Asn Val Ala Ser  Leu Asp Asn Gly Gly  Glu Leu Leu
    1055                 1060                 1065

Ser Asp  Gly Asp Ile Ser Ile  Thr Thr Gly Asp Ile  Thr Asn Ser
    1070                 1075                 1080

Gly Arg  Val Ser Ala Leu Gln  Thr Leu Thr Val Ala  Ala Asn Asn
    1085                 1090                 1095

Leu Ser  Gln Asn Gly Gly Arg  Leu Ala Ala Thr Asn  Ala Arg Leu
    1100                 1105                 1110

Thr Leu  Gly Gly Thr Leu Asp  Asn Leu Gly Phe Leu  Thr Ala Arg
    1115                 1120                 1125

Gln Gln  Leu Asp Ile Ala Ala  Ala Gln Ile Asn Asn  Arg Gly Thr
    1130                 1135                 1140

Leu Gly  Ala Gln Gly Ala Val  Asn Leu Thr Ala Val  Asn Gly Ile
    1145                 1150                 1155

Thr Asn  Ala Ala Asp Thr Leu  Leu Phe Ser Gly Gly  Asp Met Thr
    1160                 1165                 1170

Leu Arg  Ser Asn Gly Phe Ser  Asn Ser Tyr Gly Asp  Val Tyr Ser
    1175                 1180                 1185

Lys Gly  Asn Leu Ser Phe Ala  Ala Arg Asp Gly Gly  Arg Ala Val
    1190                 1195                 1200

Leu Phe  Ser Asn Arg Ser Gly  Thr Val Glu Ser Glu  Gly Ser Ile
    1205                 1210                 1215

Gly Ile  Asn Ala Gly Phe Ile  Glu Asn Ala Lys Asp  Glu Phe Glu
    1220                 1225                 1230

Leu Gly  Gln Thr Leu Thr Thr  Gly Ser Leu Ser Trp  Ile Cys Gly
    1235                 1240                 1245
```

-continued

```
Gln His Cys Gly Glu Ser Asp Asn Trp Glu Arg Gly Glu Ile Thr
    1250                1255                1260

Ile Tyr Glu Thr Tyr Leu Glu Ala Ala Thr Lys Asp Ser Val Ala
    1265                1270                1275

Ala Arg Leu Val Ala Gly Lys Asn Met Leu Leu Gln Gly Asp Thr
    1280                1285                1290

Val Gln Asn Arg Tyr Ser Leu Met Ala Ala Asn Gly Asp Leu Ser
    1295                1300                1305

Ile Thr Ala Gly Asp Leu Leu Asn Gln Gly Ala Ala Thr Arg Thr
    1310                1315                1320

Gly Gln Arg Lys Leu Val Ile Gly Thr Pro Gly His Val Ser Asp
    1325                1330                1335

Asp Leu Phe Glu Arg Met Gln Tyr Val Asp Val Pro Ala Phe Asn
    1340                1345                1350

Ala Ala Thr Ala Ala Gly Asn Phe Asp Lys Ala Arg Phe Glu Glu
    1355                1360                1365

Leu Lys Ser Arg Ser Pro Asn Ser Leu Pro Phe Ala Tyr Ala Ser
    1370                1375                1380

Asp Val Thr Thr Trp Thr Asn Asn Ser Gly Pro Gly Tyr Asp Ala
    1385                1390                1395

Thr Leu Gln Ala Gly Gly Thr Val Asn Leu Asn Val Ala Arg Thr
    1400                1405                1410

Leu Gln Asn Gly Thr Leu His Asn Asn Thr Leu Ala Gln Leu Thr
    1415                1420                1425

Gly Thr Leu Gly Asp Asp Gln Thr Gly Ile Pro Val Gly Gly Ile
    1430                1435                1440

Asn Ile Asn Leu Ser Lys His Ala Asn Asp Pro Ser Ala Gln Ala
    1445                1450                1455

Pro Gly Ser Val Leu Pro Val Val Gly Val Ala Pro Gly Gly Gly
    1460                1465                1470

Phe Val Pro Val Asp Tyr Thr Gly Thr Ala Phe Ala Pro Val Asp
    1475                1480                1485

Pro Thr Thr Ser Pro Thr Phe Gln Leu Pro Lys Gly Glu Tyr Gly
    1490                1495                1500

Leu Phe Val Lys Asn Ala Asp Pro Thr Ser His Tyr Leu Ile Glu
    1505                1510                1515

Thr Asn Pro Glu Phe Thr Ser Val Ser Gly Phe Phe Ser Ser Asp
    1520                1525                1530

Tyr Met Leu Gly Lys Leu Gly Phe Thr Ala Asp Asn Ala Trp Arg
    1535                1540                1545

Arg Leu Gly Asp Gly Gln Tyr Glu Thr Arg Leu Ile Arg Asp Ala
    1550                1555                1560

Val Leu Ala Gln Thr Gly Gln Arg Phe Leu Ala Gly Gly Leu Tyr
    1565                1570                1575

Ser Asp Ala Asp Gln Phe Arg Tyr Leu Met Asp Asn Gly Leu Ala
    1580                1585                1590

Ser Lys Asp Ala Leu Arg Leu Ser Leu Gly Val Ala Leu Thr Asp
    1595                1600                1605

Gln Gln Val Gly Ala Leu Thr His Asp Ile Val Trp Met Glu Asn
    1610                1615                1620

Arg Val Ile Glu Gly Gln Thr Val Leu Val Pro Val Leu Tyr Leu
    1625                1630                1635

Ala Gln Ala Asp Ser Arg Asn Val Arg Gly Asn Ser Leu Ile Gln
```

-continued

```
        1640                1645                1650

Gly Arg  Asp Leu Asn Leu Val  Thr Gly Gly Asp Leu  Ile Asn Val
    1655                1660                1665

Gly Thr  Leu Arg Ala Ser Asn  Asn Leu Ser Ala Ile  Ser Ser Gly
    1670                1675                1680

Ser Ile  Tyr Thr Gly Gly Leu  Val Glu Ala Gly Asn  Asn Leu Ser
    1685                1690                1695

Leu Leu  Ala Gln Asp Ser Ile  Arg Asn Ala Met Ala  Gly Glu Ile
    1700                1705                1710

Arg Gly  Lys Gln Val Ser Leu  Thr Ala Leu Lys Gly  Asp Ile Thr
    1715                1720                1725

Asn Glu  Thr Thr Ala Ile Gln  Val Arg Asp Gly Ala  Gly Met Arg
    1730                1735                1740

Thr Leu  Thr Asp Thr Ser Ala  Gly Thr Ile Val Ala  Arg Glu Asn
    1745                1750                1755

Leu Ala  Ile Asp Ala Gly Arg  Asp Leu Thr Asn Arg  Gly Ala Leu
    1760                1765                1770

Val Ala  Gly Asn Asp Ala Asn  Leu Thr Ala Gly Arg  Asp Leu Asn
    1775                1780                1785

Leu Ile  Ala Ala Ser Asp Thr  Arg Val Lys His Glu  Thr Arg Asp
    1790                1795                1800

Gly Gly  Glu Lys Ser Ser Ile  Thr Thr Asp Val Lys  Asn Leu Ala
    1805                1810                1815

Ala Ser  Val Thr Ala Gly Gly  Asn Leu Asn Met Gln  Ala Gly Gln
    1820                1825                1830

Asp Val  Asn Ile Ile Gly Ser  Asn Ala Thr Ala Gly  Lys Asp Leu
    1835                1840                1845

Asn Ile  Ala Ala Gly Arg Asp  Leu Asn Val Ala Ser  Val Ser Asp
    1850                1855                1860

Met His  Asn Val Glu Gly Lys  Glu Lys Asp Gly Lys  Lys Arg Ile
    1865                1870                1875

Arg Thr  Ser Asp Asp Gln Thr  Thr Gln Val Ala Ser  Val Leu Thr
    1880                1885                1890

Ala Gly  Gly Asp Phe Val Ser  Gln Ala Gly Arg Asp  Thr Thr Ile
    1895                1900                1905

Val Ala  Ser Met Ile Ser Ala  Gly Asn Glu Ala Tyr  Leu Tyr Ser
    1910                1915                1920

Gly Asp  Lys Leu Ser Leu Leu  Ala Ala Glu Asn Ser  Thr His Thr
    1925                1930                1935

Leu Tyr  Asp Met Lys Glu Lys  Gly Ser Trp Gly Ala  Lys Lys Ala
    1940                1945                1950

Gln Met  Asp Glu Val Thr Arg  Thr Thr Gln Val Gly  Thr Glu Ile
    1955                1960                1965

Lys Thr  Gly Gly Asn Leu Val  Leu Lys Ser Asp Gly  Asp Gln Leu
    1970                1975                1980

Tyr Gln  Val Ala Lys Leu Asn  Ser Gly Lys Asp Ile  Ile Leu Asp
    1985                1990                1995

Ser Gly  Gly Ala Ile Val Phe  Glu Gly Val Lys Asp  Leu His Asp
    2000                2005                2010

Glu Ser  His Thr Lys Ser Lys  Ser Asp Leu Ser Trp  Phe Ser Ala
    2015                2020                2025

Lys Gly  Lys Gly Asn Thr Asp  Glu Thr Leu Arg Gln  Ser Glu Leu
    2030                2035                2040
```

-continued

```
Val Ala  Gln Gly Gln Leu Val  Ile Lys Ala Ala Glu  Gly Ile Arg
    2045             2050             2055

Ile Asp  Val Lys Gln Val Asp  Gln Gln Thr Val Ser  Gln Thr Val
    2060             2065             2070

Asp Ala  Met Val Lys Ala Asp  Pro Asn Leu Ala Trp  Leu Lys Gln
    2075             2080             2085

Ala Glu  Ala Arg Gly Asp Ile  Asp Trp Arg Gln Val  Lys Glu Ile
    2090             2095             2100

His Glu  Ser Phe Lys Tyr Asp  Asn Ser Gly Leu Gly  Ala Gly Ala
    2105             2110             2115

Lys Ile  Ala Ile Ala Ile Met  Met Ala Ala Ile Met  Gly Pro Val
    2120             2125             2130

Gly Phe  Gly Leu Gln Gly Ala  Thr Leu Ala Val Ser  Thr Ser Leu
    2135             2140             2145

Ser Thr  Thr Ala Val Thr Ser  Thr Ile Asn Asn Lys  Gly Asn Leu
    2150             2155             2160

Gly Ala  Ala Leu Lys Glu Thr  Val Ser Ala Asn Ser  Leu Lys Ser
    2165             2170             2175

Ala Ala  Val Ala Gly Phe Thr  Ala Gly Ala Leu Glu  Tyr Ala Asp
    2180             2185             2190

Thr Asn  Trp Phe Ala Gly Ala  Asp Gly Ala Gly Ala  Gly Ala Gly
    2195             2200             2205

Thr Ser  Thr Ser Thr Val Gln  Gly Val Thr Pro Ser  Thr Gly Ser
    2210             2215             2220

Thr Leu  Ala Val Thr Asn Ser  Ser Lys Asp Ile Phe  Thr Trp Thr
    2225             2230             2235

Ser Ala  Gly Asp Ile Ala Leu  Arg Thr Gly Gly Arg  Ala Val Ile
    2240             2245             2250

Ser Ser  Gly Ile Ser Thr Ala  Ile Gln Gly Gly Ser  Phe Gly Asp
    2255             2260             2265

Asn Phe  Asn Ala Ala Leu Leu  Gly Glu Ala Gly Asn  Val Ala Met
    2270             2275             2280

Ala Thr  Gly Phe Asn Trp Val  Gly Asp Tyr Val Thr  Phe Pro Asn
    2285             2290             2295

Gly Ser  Pro Gln Lys Ile Ile  Ala His Ala Leu Met  Gly Gly Leu
    2300             2305             2310

Leu Ala  Glu Ala Thr Gly Ser  Asp Phe Lys Thr Gly  Ala Ala Ala
    2315             2320             2325

Ala Gly  Leu Asn Glu Ala Leu  Ile Asn Gln Leu Val  Trp Ala Ala
    2330             2335             2340

Gln Gly  Asn Asp Asp Ile Thr  Leu Met Leu Ser Gln  Leu Thr Gly
    2345             2350             2355

Leu Leu  Ala Ala Ala Ala Val  Asp Gly Asp Leu Glu  Lys Gly Ser
    2360             2365             2370

Gln Ile  Ala Gln Lys Ala Thr  Thr Phe Asn Tyr Leu  Tyr His Glu
    2375             2380             2385

Glu Val  Glu Glu Met Leu Arg  Glu Val Asp Ser Lys  Thr Thr Glu
    2390             2395             2400

Gln Glu  Lys Arg Glu Val Arg  Gln Arg Tyr Ala Glu  Leu Asp Gln
    2405             2410             2415

Gln Arg  Asn Asp Glu Leu Asp  Ala Leu Cys Ala Arg  Asp Pro Gln
    2420             2425             2430
```

```
Arg Cys Arg Gly Ile Ala Thr Ser Leu Ala Asn Asp Asp Gln Lys
    2435                2440                2445

Leu Val Asp Leu Val Gly Arg Leu Arg Ser Gln Gly Gln Gly Gly
    2450                2455                2460

Ala Ala Ser Ala Val Gly Phe Val Ile Gly Asn Asn Leu Asp Ala
    2465                2470                2475

Ser Ser Gln Ile Ala Ala Asp Ile Ser Ser Ala Gly Gly Gly Pro
    2480                2485                2490

Leu Val Lys Leu Gly Ala Glu Ala Ile Lys Ala Gly Val Gly Ile
    2495                2500                2505

Thr Leu Pro Ser Arg Ser Ser Ser Gly Lys Gly Lys Gly Ser Gln
    2510                2515                2520

Val Gly Ala Gly Ser Leu Glu Glu Ala Ala Gly Pro Lys Ala Thr
    2525                2530                2535

Gly Glu Val Val Pro Pro Ala Pro Ile Val Thr Ser Gly Ala Thr
    2540                2545                2550

Arg Thr Gly Val Val Arg Thr Asn Ala Ala Asp Trp Arg Ala Leu
    2555                2560                2565

Arg Asn Asn Trp Asp Asp Leu Gly Tyr Gly Gln Ile Leu Ser Thr
    2570                2575                2580

Glu Asn Arg Ala Ala Ile Ala Lys Gly Arg Thr Pro Lys Val Asp
    2585                2590                2595

Asp Ala Trp Val Lys Val Phe Pro Glu Asp Ala Gly Leu Lys Gly
    2600                2605                2610

Glu Arg Ile Pro Met His His Val Gln Gly Ser Pro Leu Thr Val
    2615                2620                2625

Pro Leu Pro Asp Thr Arg His Leu Asp Ala His Met Pro Gly Gly
    2630                2635                2640

Phe Arg Tyr Asn Pro Gly Gly Pro Gly Ser Ala Leu Pro Ala Tyr
    2645                2650                2655

Pro Pro Lys Lys Gly Ala Glu
    2660                2665
```

<210> SEQ ID NO 44
<211> LENGTH: 7998
<212> TYPE: DNA
<213> ORGANISM: Pseudomonas fluorescens

<400> SEQUENCE: 44

```
atggatgttc gccaattcgc cttcctggcc cgccaacctt ctgccgccct gaagcgccgg      60
gacgcgttct tcggcctgcc caagcgcggg ctggccttga tccttgccaa cgcactgttc     120
tggcagccgc tgctggccca ggccgagggc attgtggtca gtcgccgggg caccaccgtg     180
ggcgcggcag gcaatggcgt gccggtggta aacattgcca cccccaatgg cgcgggcttg     240
tcccataacc agttcaagga ctacaacgtc ggccccaacg gcgtgattct caacaatggc     300
aacggcgcca tggtcaacac ccagctgggc gggatcatcg tcggcaaccc caacctcaag     360
ggcggcgcgg cgaacgtcat cctcaacgaa gtcaacggcg gcagccccag ccagttgcgc     420
ggctataccg aagtggcggg gcagtcggcc aaggtcatcg tggccaaccc gtacggcgtg     480
acgtgcagcg gttgcggctt tatcaacacc cccaacgtca ccctcaccac cggcaaaccg     540
gtgctcgacg ccagcggtca attgcagcgc tatgaagtgg atggcggcgc ggtgaccatc     600 gacgccaag gcttgaacgc cagcaacgtc gaacgcttcg acatcatcac ccgctcggcc     660
aagatcaacg cacaaatcaa cgcccgcgaa ctcaacgtga tcgccgggcg caacgacgtc     720
```

-continued

```
gatgcgcaaa gcctgaaaac caccgcccgc gccgatgacg gcagcgccaa gcccgagctg      780
gcgatcgact cgtcggccct gggcggcatg tatgccggcg cgatcaaact ggtgggcacc      840
gaggccggtg tgggcgtgaa gctcgacggc accctggccg ccagtggcgg cgatattcag      900
ctcgacgcca acgggcgcct gagcatggcg caggcggcgg ccaccggtaa cgtcaaggtc      960
accgcgcaaa acgtcgacct caccgacaag gtctacgcca acggcaacgt gcaggtcacc     1020
agcgcccagg ctttggtcaa ccgcaagagc atcgccgccg gccagcgcat cgagatcaac     1080
gcggccagcg tgaacaaccc cggcatcatc gaagccggcg tcgccgccga taacagccgc     1140
aacaccacgg gcgacctggt ggtgaacgcg caaaccgtca ccaccagcgg caacctgttg     1200
gccagccgcg ccctggcgat cactgccgcg caagcgctga ccaaccaggg cgcgatcatc     1260
caggccaaga ccgtcgaggt cagcagcgcc aaactcacca accagggcgc cagcgctcgc     1320
ctgtttggcg agcagagcct ggcgatcaac tcgccggcca tcgtcaacct cggcggcttg     1380
atccgcttcg gcgaaggcca ggccgccacg ctcaacagcg cctccctgga caaccgccaa     1440
ggccgtatcg aaatggccgg tggcagcctg gtgctcacca gtgccgacct gaacaacagc     1500
ggcgggcaag tcatcgccaa cgacctgacc gtcaacgccg gcaacctgaa caaccagaac     1560
ggcgtgctgg tggccaagac cgcgaccgtc actgccagca accttgacaa cagcctcaag     1620
ggtttgatcc aggctgacgg tggcgcgctc aacctcgccg tttccaacac cttcaacaac     1680
aaccagggtt tcgcccaggc cagcaccgat ctgaacgtta cggccggcac cctcagcagc     1740
aacgcaggcg gcgtactgag cgccgacacc ggcaagctca ccctcaccgc cgcacaacaa     1800
ctcaacaacg cccagggccg cttgcaggcc gggcagggcg atatcgaact gcacgccgcg     1860
aacctggata accagagcgg cacgatcgtc ggcaagcaac tgctgctcga cgtggccggc     1920
ggcgacatcg acaaccgtgc cgggcgcgtg ttgggtgacc acctcgacgt gcgcgcctcg     1980
ggcctggaca accgcaacgc cggcctgctg gccggtggtg cccagggcgt aagcctgctg     2040
ctcaaaggcc cgggccagtt gctcaacgcc cagggccgca tccagagcga gggcctgctg     2100
caactgcaag gcgagcgctt cgacaacagc gccggcatcc tgctgggcca gaccgtcgac     2160
gtgaccgcgc agaccttcaa caacagcaac aaaggcgcgc tggtcagcga tggcggtgat     2220
gtggtgttca aggtcagcga cctgctcacc aacgtcggtg gccagatcga cgcgggcgaa     2280
cgcagcgtgt tggtcaagca gctcaccacc ctcaacaacg acggcggcac cctgcgcggc     2340
aagcgcctgg acatcgccgc ccagcacctg aacaacgaca acggccaact gctggccggc     2400
gccgaaggcc tgagctacag cggccaggat gtgagcaacc gcaagggcct gatcctcagc     2460
ggcggcgccc tcaccgaact gaacaccacc cgcctggata tcagggcgg cactgtgcag     2520 ggcgacagcc tgaccgtcac cgccaacaac gtcgacaacg gcagcggcgg cctgatggca     2580
agcctggtcg gcaacctgca gctcactgtc gaagccctgg ccaaccgtgg cggcaagctg     2640
ttcggcaaag aacaagtgac cgtcagcggc gccagcctcg acaacagcgc gggccagatc     2700
agcggcaatc agatcaacct gacctcacgc gacacgctca ccaaccaggg cggtttggtt     2760
gaagccaacc agggcctgac cctcactggt ggcaacctcg ataacagcgc caacggccaa     2820
ctgcgtgccc tgggcggcgc cagcagccgc gtcaacctca gcggtgcgtt gaacaaccag     2880
aacggcaccc tcgaattcgg tagccaggcc ttcagccttg acgcggccag cctcaacaac     2940
cagaacggga tgctgcaaca cgccggcacc ggcctgttcc acctcaacat cgccagcctc     3000
gaaggcagcc agggcaatat ccagggcatg ggcagcgccg actgggcatt cggcaaggtc     3060
```

-continued

```
gacggcctgg gccgcgtgca actcaacgat gtgctcacct acaagagcga ccaagggctg    3120
gccctccagg ccggcgaccg catggccagc gccaagggct tgatcctcaa cgtggccagc    3180
ctggacaacg gcggcgaact gctcagcgac ggtgacatca gcatcaccac cggcgatatc    3240
accaacagcg gccgcgtctc ggccctgcaa acactcaccg tcgccgccaa caacctcagc    3300
cagaacggcg gccgcctggc cgcaaccaat gcccgcctga ccctgggcgg caccctggac    3360
aacctcggtt tcctcaccgc ccgccagcaa ctggacatcg ccgccgcgca aatcaacaac    3420
cgtggcaccc tcggtgccca gggcgcagtg aacctcacgg cggtcaacgg catcaccaac    3480
gccgccgaca cgctgctgtt cagcggcggc gacatgaccc tgcgcagcaa tggcttcagc    3540
aacagctatg gcgatgtcta cagcaaaggc aacctgagtt tcgccgcccg cgatggcgga    3600
cgtgccgtgc tgttcagcaa ccgctccggc accgtggaaa gcgaaggctc aattggcatc    3660
aatgcaggct ttatcgaaaa cgccaaagac gaattcgaac tcgggcagac actgaccacc    3720
ggtagcttga gctggatctg tggccagcac tgcggcgaga gcgacaactg ggaacgtggc    3780
gagatcacca tctacgaaac gtacctcgag gcggcgacca aggactcggt agcggcgcgc    3840
ctggtggcgg gcaaaaacat gctgctgcaa ggcgacacgg tgcagaaccg ctacagcctg    3900
atggccgcca atggcgacct gagcatcact gccggagacc tgctcaacca gggcgccgcc    3960
acgcgcacgg gccagcgcaa gcttgtcatc ggcacgccag gtcacgtctc cgacgatttg    4020
tttgaacgca tgcaatatgt tgatgtgccc gcgttcaatg cggccacggc ggctgggaat    4080
ttcgacaagg cgcgcttcga agaactcaaa agccgctcac ccaatagcct gccgttcgcc    4140
tacgccagtg acgtcaccac ctggaccaac aacagcggcc ccggctacga cgccaccctg    4200
caagcgggcg gcacggtcaa cctcaacgtc gcccgcaccc tgcaaaacgg cacgctgcac    4260
aacaacaccc tggcccagtt gaccggcacc ctcggcgacg accagaccgg catccccgtc    4320
ggcggcatca acatcaacct gagcaaacac gccaacgacc cgagcgccca ggcgcccggc    4380
agtgtcttgc ccgtcgtggg cgtggcccct ggtggcggct tcgtgcccgt ggattacacc    4440
ggcaccgcgt ttgccccggt cgaccccacc acctcgccca ccttccaact gcccaagggc    4500
gaatacggcc tgttcgtcaa aaacgccgac cccaccagcc actacctgat cgagaccaac    4560
cccgagttca cctcggtgtc gggcttcttc agctccgact acatgctcgg caaactcggt    4620
ttcaccgccg acaacgcctg cgccgcgcctc ggtgacggcc agtacgaaac ccgcctgatc    4680
cgcgacgccg tcctcgcgca aaccggccag cgcttcctcg ccggcggcct gtacagcgac    4740
gccgaccagt tccgctacct gatggacaac ggcctcgcca gcaaagacgc cctgcgcctg    4800
agcctgggcg tggccctcac cgaccagcaa gtcggcgccc tgacccacga catcgtgtgg    4860
atggaaaacc gcgtcatcga aggccagacc gtgctcgtgc cggtgctgta cctggcccag    4920
gccgactcgc gcaacgtgcg cggcaacagc ctcatccagg gccgcgacct caacctggtc    4980
accggcggcg acctgatcaa cgtcggcacc ctgcgcgcca gcaacaacct ctccgccatc    5040
agtagcggca gcatttatac cggcggcctg gtcgaagccg gcaacaatct cagcctgctg    5100
gcccaggaca gcatccgcaa cgccatggcc ggcgaaatcc gcggcaagca agtcagcctc    5160
acggcgctca aaggcgatat caccaacgaa accaccgcca tccaggtgcg tgacggcgcc    5220
ggtatgcgca ccctcaccga caccagcgcc ggcaccatcg tcgcccgcga aaacctcgcc    5280
atcgacgctg gccgcgacct caccaaccga ggcgcgctgg tagcgggcaa cgacgccaac    5340
ctcaccgccg gccgcgacct caacctcatc gccgccagcg acacccgcgt caaacacgag    5400
acccgcgacg gcggcgagaa atccagcatc accaccgacg tcaaaaacct cgccgccagc    5460
```

-continued

```
gtcacggcgg gcggcaacct caacatgcag gccgggcaag acgtcaacat catcggcagc    5520
aatgccacgg ccggcaaaga cctcaacatc gccgccggcc gcgacctcaa cgtcgcctcg    5580
gtcagcgaca tgcacaacgt cgagggcaag gaaaaggacg gcaaaaaacg catcaggacc    5640
tcggacgacc agaccactca agtggcaagc gtgctgacgg cgggtgggga ttttgtcagc    5700
caggcggggc gtgataccac gattgtggcg agcatgatca gtgcggggaa tgaggcttat    5760
ctgtatagcg gggataagtt gagtttgttg gcggctgaga acagtacgca tacgttgtat    5820
gacatgaagg agaagggaag ctggggcgct aaaaaggcgc agatggatga agtgacccgc    5880
accacccagg tagggaccga gatcaagaca ggtggcaacc tagtccttaa aagcgacggc    5940
gaccagctgt atcaagttgc gaagcttaat agcggcaagg acatcatcct tgatagcggt    6000
ggtgcaattg tctttgaagg cgtcaaggac ctgcacgatg agagccacac taagagcaaa    6060
agcgacctct cgtggttcag cgctaagggc aaaggtaata cagacgaaac cttgcgtcag    6120
agcgagttgg ttgcccaagg acagcttgtc atcaaggccg ccgaaggcat tcgtatcgac    6180
gtcaaacagg tcgatcagca gactgtaagc cagaccgttg atgcgatggt caaggctgat    6240
cctaatttgg cctggctcaa gcaagctgag gcacgtggcg acattgattg cgccaggta    6300 aaggagattc acgagagctt caagtacgac aactcagggt tgggcgccgg tgccaagatt    6360
gcgattgcga tcatgatggc ggcgatcatg gggccggtag gattcgggtt gcagggagcc    6420
acccttgcgg tgagcaccag cctgagtacg acggcagtca ctagcaccat caacaacaaa    6480
ggcaatttgg gtgcagcgct taaggaaacg gtcagcgcca atagcctgaa aagcgcagca    6540
gtcgccgggt tcacggcggg ggctcttgag tatgccgaca ccaattggtt cgctggtgct    6600
gacggtgcag gtgcaggtgc aggcacaagt acaagcacag tccaaggtgt tacccccgagt    6660 acgggttcaa ccttggcggt tacgaactcc tccaaagata ttttcacctg gacgtcagca    6720
ggcgatatcg cgctgcgtac cggtggccgg gcggtaatct ctagcggaat atcgacggcc    6780
attcaagggg gaagcttcgg cgacaacttc aatgcggccc tgttgggaga ggctggcaac    6840
gttgcaatgg ctaccggttt taattgggtg ggtgactacg tcacgttccc caatggcagc    6900
cctcaaaaga ttattgcgca cgctttgatg gggggattgc tggctgaagc cacaggtagc    6960
gatttcaaaa ccggggctgc cgctgccggg ctgaatgagg cactcatcaa tcagttggtg    7020
tgggctgctc aaggcaatga cgacatcacg ctgatgcttt cacagctgac aggcttgtta    7080
gcagctgcgg cggtcgatgg agatttggaa aaaggctctc agattgctca gaaggcgacg    7140
acgttcaact atctttacca cgaagaagtc gaggaaatgc ttcgggaggt agatagcaag    7200
actacggagc aagagaagcg tgaggtcagg cagcgctatg cggaacttga tcagcagaga    7260
aatgacgagt tggatgcgct ttgcgcacgc gatccgcaac gctgccgagg tattgccact    7320
tccttggcga acgatgatca gaaactcgtt gatctggtag gtaggttgag atcccaaggg    7380
cagggcggtc tgcttctgc ggttggtttt gtgataggga acaacctaga cgcgtccagc    7440
caaattgcag cagatatcag ctctgcgggc ggtgggccat tagttaagct cggtgcggag    7500
gcaattaagg ccggagttgg gatcacactg ccttcacgtt caagctctgg taaggggaaa    7560
ggaagccaag tcgcgcgggg ttcccttgaa gaggcggcgg gtccaaaggc gacaggcgaa    7620
gtagtgcctc ccgcgcctat tgtgacttct ggtgcgacta ggacaggtgt tgttcgtaca    7680
aatgccgcag attggagagc actgcgtaat aattgggatg accttgggta tggtcaaatc    7740
ttaagtactg aaaatcgggc cgcgattgct aaaggacgga ctccaaaagt cgacgatgca    7800
```

-continued

```
tgggttaagg tttttcctga agatgcaggg ctaaagggcg agagaattcc tatgcaccat      7860
gttcagggtt cgccacttac tgtgccactg cctgatacac ggcatttgga tgcgcatatg      7920
ccaggagggt ttagatataa tccaggcggt ccagggtcgg ctctcccggc ataccctcca      7980
aaaaaaggag ctgaataa                                                    7998
```

<210> SEQ ID NO 45
<211> LENGTH: 607
<212> TYPE: PRT
<213> ORGANISM: Pseudomonas fluorescens

<400> SEQUENCE: 45

```
Met Phe Arg Arg Leu Arg Gly Ile Pro Leu Leu Gly Cys Leu Met Gly
1               5                   10                  15

Ser Ile Gly Cys His Ser Gln Pro Pro Ala Pro Pro Ile Gln Lys
            20                  25                  30

Gly Asp Tyr Gly Ala Ile Ile Arg Tyr Leu Gln Thr Arg Ile Pro Arg
        35                  40                  45

Glu Met Ala Arg Asp Asn Val Ala Gly Leu Ser Ile Ala Leu Val Asn
    50                  55                  60

Gly Gln Glu Leu Ile Trp Ala Arg Gly Phe Gly Leu Ala Asp Lys Asp
65                  70                  75                  80

Gln Gly Val Pro Val Thr Pro Asn Thr Ala Phe Arg Ala Gly Gly Ile
                85                  90                  95

Ser Lys Leu Leu Ser Ala Thr Ala Ala Leu Gln Leu Val Glu Gln His
            100                 105                 110

His Leu Ala Leu Asp Ala Pro Ile Gln Gln Thr Leu Arg Glu Phe Tyr
            115                 120                 125

Val Arg Ser Arg Phe His Ser Asp Gln Ala Glu Ala Asp Arg Ala Ile
    130                 135                 140

Thr Leu Arg Arg Leu Leu Ser His Gln Ser Gly Leu Pro Ser Glu His
145                 150                 155                 160

Leu Arg Asp Leu Arg Ser Thr Tyr Ala Met Gly Gln Met Pro Met Arg
                165                 170                 175

Val Ser Gly Val Trp Leu Ser Ser Leu Pro Gly Ser Gln Val Ala Tyr
            180                 185                 190

Ser Asn Leu Gly Tyr Ser Leu Val Gly Ala Ala Ile Glu Arg Ser Ser
            195                 200                 205

Gly Lys Ser Phe Glu Ala Gln Leu Gln Ser Ser Leu Leu Thr Pro Leu
    210                 215                 220

Arg Met Asn Gln Ser Ser Phe Val Gly Thr Gly Ala Gln Met Gly Phe
225                 230                 235                 240

Arg Ala His Gly Tyr Glu Asp Gly Lys Ala Ser Thr Asp Ala Gln Val
                245                 250                 255

Arg Asp Leu Ala Ala Gly Gly Leu Trp Thr Ser Pro Lys Asp Leu Ser
            260                 265                 270

Arg Tyr Val Arg Met Leu Phe Ala Asn Gly Thr Tyr Lys Gly Ser Gln
            275                 280                 285

Ile Leu Gly Ser Ala Ser Ile Asp Ala Met Phe Thr Gln Gln Asn Thr
    290                 295                 300

Gly Asn Ala Leu Asp Phe Asp Cys Gln Ile Gly Leu Gly Trp Phe Leu
305                 310                 315                 320

Ala Pro Cys Gly Asp Glu Pro Ile Gly Pro Gly Val Arg Thr Tyr Gln
                325                 330                 335
```

```
His Ser Gly Gly Gly Asp Asp Phe Val Ala Gln Leu Thr Leu Leu Pro
            340                 345                 350

Asp Gln Gln Leu Ala Val Ile Ile Met Ala Asn Asp Ser Asn Ala Glu
            355                 360                 365

Asp Met Val Val Ser Leu Thr Thr Asp Ser Leu Arg Leu Met Leu Gln
    370                 375                 380

Ala Gln Thr Gly Gln Pro Val Cys Ala Asp Asp Cys Gln Ala Pro Ser
385                 390                 395                 400

His Gly Leu Lys Leu Arg His Val Pro Ala Ala Val Asp Arg Lys Arg
                405                 410                 415

Leu Ala Gly Phe Tyr Ala Thr Ala Trp Gly Val Phe Arg Ile Arg Asp
            420                 425                 430

Tyr His Ala Arg Leu Thr Gly Glu Leu Ala Gly Tyr Asp Phe Glu Leu
            435                 440                 445

Leu Arg Asp Glu Gln Gly Trp Leu Arg Ala Gln Lys Lys Ile Leu Gly
    450                 455                 460

Phe Trp Arg Lys Asp Leu Gly Glu Leu Gly Arg Val Gln Leu Asp Val
465                 470                 475                 480

Ile Gln Val Gln Gly Arg Gln Met Leu Thr Ala Arg Ser His Gly Gln
                485                 490                 495

Arg Ile Ala Ile Gly Glu Arg Ile Glu Pro Pro Leu Pro Ala Ala
            500                 505                 510

Trp Ala Asn Thr Val Gly Thr Tyr Gln Val Leu Ser Ser His Glu Pro
            515                 520                 525

Asp Ala Pro Leu Ser Gly Ile Ser Val Arg Gln Glu Asp Gly Phe Leu
    530                 535                 540

Val Ile Arg Gly Gln Leu His Gly Glu Pro Leu Thr Asp Tyr Ile Leu
545                 550                 555                 560

Leu Pro Ile Asp Asn Ala His Ala Val Leu Ala Gly Asn Gly Tyr Gly
                565                 570                 575

Leu Gly Asp Thr Val Ser Arg Gln Val Asn Gly Leu Ser Ala Ser Gly
            580                 585                 590

Tyr Ser Phe Lys Arg Thr Gln Ser Pro His Ile Pro Ser Asn Phe
            595                 600                 605
```

```
<210> SEQ ID NO 46
<211> LENGTH: 1824
<212> TYPE: DNA
<213> ORGANISM: Pseudomonas fluorescens

<400> SEQUENCE: 46
atgtttcgca ggttgcgcgg tattccgctc ttgggttgcc tgatgggcag tatcggttgc      60
cactcgcaac cgcctgcccc gccgccgatt caaaaaggcg attacggcgc aatcatccgc     120
tacttgcaaa cccgcattcc ccgggagatg gctcgggaca atgtggcagg tttgtcgatt     180
gcgctggtca atggccagga gctgatctgg gctcgtggct ttggcctggc tgacaaagac     240
cagggggtgc cggtcacgcc caataccgcg tttcgcgccg gtggcatttc caaactgctg     300
agcgccacgg cggcgctgca gctggtggag cagcaccacc tggcgctgga tgcaccgatc     360
cagcagaccc tgcgtgagtt ctacgtacgt tcacgctttc acagcgacca ggccgaggcg     420
gatcgagcga tcactttgcg gcgcttgctc agccatcaat ccggcttgcc cagcgagcac     480
ctgcgcgacc tgcgcagcac ctacgccatg gggcaaatgc caatgcgcgt gtcgggtgtg     540
tggctgagca gcctgccggg gtcccaggtg gcgtactcca accttggtta ttcactggtg     600
```

```
ggcgcggcca tcgagcgcag cagcggtaaa agctttgaag cccagttgca aagcagcctg     660
ctcacgcccc tgcgaatgaa ccagtccagc ttcgtaggca ccggtgcaca aatgggcttt     720
cgcgcccatg gttacgagga cggcaaggcc agcaccgacg cccaagtgcg tgacctcgcc     780
gccggtggcc tgtggaccag ccccaaagac ctcagccgct acgtacgcat gctgtttgcc     840
aacggcacct acaagggcag ccagatcctc ggcagcgctt ctatcgacgc catgtttacc     900
cagcaaaaca ccggcaacgc cctggatttc gactgccaga tcggcctggg ctggtttctg     960
gcgccctgcg gtgacgagcc catcggcccc ggtgtgcgca cctaccagca cagcggtggc    1020
ggcgatgact cgtcgcccca attgaccctg ctaccggatc agcagctggc ggtgatcatc    1080
atggccaacg acagcaacgc cgaagacatg gtggtgtcac tgaccaccga cagcctgcgc    1140
ctgatgctcc aggcacagac tggccagccc gtgtgcgccg atgactgcca ggcgccgagc    1200
cacggcctca agctgcgcca tgtgccggcg gcggtggatc gcaagcgcct ggctggtttc    1260
tatgcgaccg cctggggcgt gttccgcatc agggattacc atgcacgctt gaccggcgaa    1320
ctggccggct acgatttcga gctgttacgt gatgaacaag gctggctgcg cgcgcagaaa    1380
aagatcctcg gcttctggcg caaggacctg ggcgagttgg gccgcgtgca gttggatgta    1440
atccaggtac aaggccgcca aatgctcacc gcgcgcagcc acggccaacg cattgccatc    1500
ggtgaacgca tcgagccacc gcccttgcct gccgcctggg ccaacacggt cggcacctat    1560
caggtgctca gcagccatga acccgacgcg ccattgagtg gcatcagcgt gcgtcaggag    1620
gacggctttc tggtgattcg tggccaattg cacggcgagc cgctgaccga ctacatcctg    1680
ctacccatcg acaacgccca tgcggtactg gccggcaacg gttacggctt gggcgatacc    1740
gtcagccgcc aggtcaacgg gctgagcgct tcgggttatt ccttcaaacg tacccaatca    1800
ccccacatac cctcgaattt ctaa                                          1824
```

```
<210> SEQ ID NO 47
<211> LENGTH: 814
<212> TYPE: PRT
<213> ORGANISM: Pseudomonas fluorescens

<400> SEQUENCE: 47

Met Arg Val Pro Gly Pro Thr Ala Thr Asn Ser Asn Ala Gly Gln Val
1               5                   10                  15

Pro Asp Pro Arg Ser Gly Ile Ser Pro Glu Gly Pro Thr Gln Val Tyr
            20                  25                  30

Thr Leu Asn Ser Lys Lys Thr Val Phe Thr Thr Glu Gln Ala Gly Lys
        35                  40                  45

His Ile Thr Arg Ser Gly Phe Lys Phe His Asp Ser Asn Gly Asp Gly
    50                  55                  60

Lys Thr Thr Leu Ser Tyr Arg Val Ser Lys Gly Phe Thr Pro Gln Gln
65                  70                  75                  80

Ala Asp Gln Ala Arg Gln Ala Leu Gln Ser Trp Gln Asp Val Ala Asn
                85                  90                  95

Val Thr Phe Thr Glu Lys Arg Gln Gly Ala Asp Gly His Ile Asp Ile
            100                 105                 110

Asn Glu Met His Gly Thr Ser Gly Gly Met Ala Ser Leu Pro Asn Arg
        115                 120                 125

Tyr Met Ser Gln Thr Phe Ala Asn Val Gly Thr Ala Asn Ala Gly Ala
    130                 135                 140

Asn Pro Pro Arg Gly His Tyr Phe Arg Glu Val Leu Val His Glu Ile
145                 150                 155                 160
```

-continued

```
Gly His Thr Ile Gly Leu Glu His Pro Gly Asp Tyr Asp Gly Ser Gly
                165                 170                 175

Asn Tyr Gly Arg Asp Ala Ala Tyr Ala Gly Asp Thr Arg Ala Arg Ser
                180                 185                 190

Val Met Ser Tyr Tyr Ser Glu Lys Asn Gln Pro Gly His Asp Phe Lys
                195                 200                 205

Ser Leu Asn Pro Ser Ala Pro Met Met Asp Asp Ile Ser Ala Val Gln
                210                 215                 220

Lys Leu Tyr Gly Ala Asn Thr Lys Thr Arg Asn Thr Asp Thr Thr Tyr
225                 230                 235                 240

Gly Phe Asn Ser Asn Thr Asn Arg Glu Ala Tyr Ser Leu Lys Ser Ala
                245                 250                 255

Asn Asp Thr Pro Ile Phe Cys Val Trp Asp Gly Gly Gly Asn Asp Thr
                260                 265                 270

Leu Asp Phe Ser Gly Tyr Ser His His Gln Lys Ile Asn Leu Asn Ala
                275                 280                 285

Glu Ser Phe Ser Asp Val Gly Ala Leu Lys Gly Asn Val Ser Val Ala
                290                 295                 300

Lys Gly Val Thr Leu Glu Asn Ala Val Gly Gly Lys Gly Asp Asp Thr
305                 310                 315                 320

Leu Ile Gly Asn His Val Ala Asn Arg Leu Lys Gly Gly Ala Gly Ala
                325                 330                 335

Asp Arg Leu Ser Gly Gly Gly Ala Asp Thr Phe Val Tyr Asp His
                340                 345                 350

Ala Ser Asp Ser Thr Pro Asp Asn Pro Asp Val Ile Leu Asp Phe Ala
                355                 360                 365

Ser Gly Ala Asp Lys Ile Asp Val Ser Ala Val Leu Lys Arg Ala Asn
                370                 375                 380

Val Ser Ala Leu Lys Phe Val Asp Arg Leu Thr Gly Gln Pro Gly Gln
385                 390                 395                 400

Ala Val Met Ser Tyr Asp Glu Gly Arg Asn Glu Gly Gly Leu Ala Leu
                405                 410                 415

Asp Leu Thr Gly Asn Gly Lys Ala Asp Leu Leu Ile Lys Ser Ile Gly
                420                 425                 430

Gln Ile Lys Ala Ala Asp Ile Leu Ala His Gly Asp Thr Thr Ala Pro
                435                 440                 445

Asn Pro Glu Pro Lys Asp Pro Lys Pro Gln Pro Arg Pro Gln Pro Glu
                450                 455                 460

Glu Pro Lys Pro Lys Pro Glu Ser Lys Pro Lys Glu Pro Lys Pro Glu
465                 470                 475                 480

Glu Pro Lys Pro Arg Pro Asp Ser Cys Glu Pro Lys Pro Arg Pro Asp
                485                 490                 495

Pro Cys Glu Pro Lys Pro Arg Pro Asp Pro Cys Glu Pro Lys Pro Arg
                500                 505                 510

Pro Asp Ser Cys Glu Pro Lys Pro Arg Pro Asp Pro Cys Glu Pro Lys
                515                 520                 525

Pro Arg Pro Asp Pro Arg Glu Pro Gln Pro Arg Pro Asp Pro Arg Glu
                530                 535                 540

Pro Gln Pro Arg Pro Asp Pro Arg Glu Pro Gln Pro Arg Pro Asp Pro
545                 550                 555                 560

Arg Glu Pro Gln Pro Cys Pro Asp Pro Arg Glu Pro Gln Pro Arg Pro
                565                 570                 575
```

```
Asp Pro Cys Glu Pro Gln Pro Arg Pro Asp Pro Cys Glu Pro Gln Pro
             580                 585                 590

Arg Pro Asp Pro Arg Glu Pro Arg Pro Arg Pro Asn Pro Arg Glu Pro
             595                 600                 605

Gln Pro Arg Pro Asp Pro Arg Glu Pro Gln Pro Gln Pro Arg Pro Asp
             610                 615                 620

Pro Arg Glu Pro Tyr Pro Arg Pro Asp Pro Arg Glu Pro Arg Pro Arg
625                 630                 635                 640

Pro Asn Pro Arg Glu Pro Arg Pro Arg Pro Asn Pro Arg Glu Pro Gln
             645                 650                 655

Pro Arg Pro Asp Pro Arg Glu Pro Arg Pro Arg Pro Asp Pro Cys Glu
             660                 665                 670

Pro Gln Pro Arg Pro Asp Pro Arg Glu Pro Arg Pro Arg Pro Asn Pro
             675                 680                 685

Arg Glu Pro Gln Pro Arg Pro Asp Pro Arg Glu Pro Gln Pro Arg Pro
             690                 695                 700

Asp Pro Arg Glu Pro Arg Pro Arg Pro Asp Pro Arg Glu Pro Gln Pro
705                 710                 715                 720

Arg Pro Asp Pro Cys Glu Pro Gln Pro Arg Pro Glu Pro Cys Glu Pro
             725                 730                 735

Arg Pro Arg Pro Asn Pro Arg Glu Pro Gln Pro Arg Pro Asp Pro Cys
             740                 745                 750

Glu Pro Lys Pro Thr Pro Arg Thr Asp Pro Cys Glu Pro Lys Ala Val
             755                 760                 765

Thr Arg Asn Val Arg Pro Ala Tyr Gly Leu Ser Ala His Ser Gly Glu
             770                 775                 780

Tyr Arg Ala Met Gln Ala Pro Ala Phe Asp Ser Arg His Phe Gln Gly
785                 790                 795                 800

Gly Leu Ala Gly Glu Phe Ile Arg Arg Gln Lys Arg Ala Glu
             805                 810
```

<210> SEQ ID NO 48
<211> LENGTH: 2445
<212> TYPE: DNA
<213> ORGANISM: Pseudomonas fluorescens

<400> SEQUENCE: 48

```
atgagagtgc caggaccaac cgcaacgaat tctaatgcag ggcaggtgcc agatccgagg      60
agtggcatca gcccggaggg ccctacgcag gtatatacac taaacagcaa aaaaaccgtc     120
ttcactacgg aacaggccgg gaaacatatc acccgcagcg gtttcaagtt tcatgacagt     180
aacggtgatg gcaaaaccac gttgtcctat cgtgtttcca agggctttac cccacagcag     240
gcagatcaag ccaggcaggc actgcaatcc tggcaggatg tcgctaacgt cacattcact     300
gaaaaaaggc aggggggctga cggccatata gatatcaatg agatgcacgg aacctctggg     360
ggtatggcct cactccccaa ccgctatatg agtcaaactt tcgcaaatgt cggaacagcg     420
aatgcaggtg caaaccctcc acggggtcat tattttcgcg aagttctagt tcacgaaata     480
ggccacacca ttgggctgga cacccggggg gactatgatg gctctggtaa ctatggacgg     540
gacgcagcgt atgccgggga tactcgagcg cgttctgtga tgagttacta ttcggaaaaa     600
aaccagccgg gacatgattt caaatcattg aaccccctctg cgccgatgat ggatgatata     660
tcggccgttc agaaactcta tggggcgaat actaaaacgc gtaataccga tacgacgtat     720
ggatttaatt ccaatacaaa ccgtgaagcc tatagtttga agtcggctaa cgacacaccc     780
```

-continued

```
attttctgtg tgtgggatgg tggtggtaat gacacattgg atttctctgg gtattcacac      840
catcagaaaa tcaacctcaa tgccgagtcc ttttcggatg tagggggcgtt gaaaggtaac      900 gtttccgttg ccaagggcgt cacgctggaa aatgcagtgg gcggtaaggg cgacgacaca      960
cttatcggta atcatgttgc caatcgcctc aaaggggggg cgggagccga cagactgtct     1020 gggggggggcg gcgcagatac ctttgtttac gaccatgcca gtgattccac cccggataac     1080
cctgatgtca tcctggattt tgcgagtggc gcagataaga ttgatgtatc cgcagtcctt     1140
aaaagagcga atgtcagtgc tctcaagttc gtcgatcgct taactggcca acccggccag     1200
gctgtgatga gttatgacga gggccgcaac gaggggggggc tggccctgga tctgacaggc     1260
aacggcaagg ctgatctatt aataaaaagc attggccaga taaaagctgc tgatatcttg     1320
gcgcacggcg atacaaccgc gccaaaccct gaacccaaag atcccaagcc gcagccgcgt     1380
cctcaacccg aggagcccaa acccaagcct gaatccaaac cgaaggagcc aaaaccggag     1440
gaaccaaaac cgcgtccgga ctcgtgtgaa ccaaagccgc gtccggatcc gtgtgagccg     1500
aagccgcgtc cggatccgtg cgagccgaag ccgcgtccgg attcgtgtga gccaaagccg     1560
cgtccggatc cgtgcgagcc gaagccgcgt ccagatccac gcgaaccgca gccacgtccg     1620
gacccgcgcg agccgcagcc gcgtccagat ccacgcgaac cgcagccacg tccagaccca     1680
cgtgaaccgc agccatgtcc ggatccacgc gaaccgcagc cgcgtccgga cccgtgtgag     1740
ccgcagccgc gtccggaccc gtgtgagcca cagccgcgtc cagacccacg tgaaccgagg     1800
ccgcgtccga acccacgtga accgcagcca cgtccggacc cacgcgagcc gcagccgcag     1860
ccgcgtccgg acccacgtga accgtaccca cgtccagacc cacgtgaacc gaggccgcgc     1920
ccgaacccac gtgagccgag gccgcgtccg aacccacgtg aaccacagcc gcgtccagac     1980
ccacgtgagc cgaggccgcg tccggacccg tgtgagccac agccgcgtcc agacccacgt     2040
gagccgaggc cgcgtccgaa cccacgtgaa ccacagccgc gtccagaccc acgtgaaccg     2100
cagccacgcc cggacccgcg tgagccgagg ccgcgtccgg acccacgtga accgcagcca     2160
cgcccggacc cgtgtgagcc acagccgcgt ccggaaccat gtgagccgag accgcgtccg     2220
aacccacgtg aaccgcaacc acgtccggac ccgtgcgagc ctaaaccaac ccctcgcaca     2280
gatccttgcg agccgaaagc tgtcactcga aacgtaaggc cagcctatgg cttgagtgcc     2340
cattcaggcg agtaccgggc gatgcaggcg ccagcctttg atagtcgtca tttccagggc     2400
gggcttgcag gggaattcat tcgacgtcag aagcgcgctg aatag                     2445
```

<210> SEQ ID NO 49
<211> LENGTH: 262
<212> TYPE: PRT
<213> ORGANISM: Pseudomonas fluorescens

<400> SEQUENCE: 49

```
Met Ala Ser Thr Arg Val Arg Phe Gln Phe Arg Gln Asp Glu Ser Gly
1               5                   10                  15

Glu Leu Arg Val Tyr Gly Leu His Thr Gln Pro Gly Ser Gly Ala Asp
            20                  25                  30

Arg Val Pro Val Ala Gln Ala Arg Trp Asn Val Asp Lys Ser Ala Met
        35                  40                  45

Val Ala Val Leu Asp Gly Ile Ser Ile Thr Trp Thr Pro Asn Leu Gly
    50                  55                  60

Pro Val Val Ser Val Pro Ser Pro Tyr Pro Gly Thr Pro Glu Arg Leu
65                  70                  75                  80
```

-continued

```
Asp Asn Met Phe Val His Pro Ile Ala Val Gly Gln Asp Ser Ala Ile
             85              90              95

Ser His Tyr Pro Gly Arg Asp Ala Glu Asn Ile Thr Trp Gln Asp Thr
             100             105             110

Ile Ile Ser Phe Pro Ala Asp Ser Gly Val Pro Pro Leu Tyr Leu Val
             115             120             125

Phe Ala Lys Pro Ala Val Arg Pro Leu Glu Val Asp Ile Tyr Gly Ala
    130             135             140

Phe Ser Gly Arg Leu Arg Asn Gly Leu His Val Asp His Ile Pro Ser
145             150             155             160

Gln Ala Ala Ile Arg Arg His Leu Glu Arg Tyr Ala Ile Ser Phe Thr
             165             170             175

Glu Lys Gln Leu Lys Glu Ala Leu Asn Asn Ala Ala Ser Ile Ala Ile
             180             185             190

Pro Ser Tyr Ile His Gln Lys Phe Ser Glu Thr Tyr Gly Trp Arg Asn
             195             200             205

Thr Glu Lys Lys Gln Thr Leu Asp Ala Asp Asp Leu Arg Gln Ala Ala
             210             215             220

Asp Asn Asn Phe Asp Ala Ile Lys Pro Tyr Leu Leu Asp His Gly Phe
225             230             235             240

Ala Glu Thr Asp Leu Glu Met Ala Arg Thr Arg Met His Lys Val Asn
             245             250             255

Glu Asn Gln Gly Trp Tyr
             260
```

```
<210> SEQ ID NO 50
<211> LENGTH: 789
<212> TYPE: DNA
<213> ORGANISM: Pseudomonas fluorescens

<400> SEQUENCE: 50
atggccagca cgcgagtgcg tttccagttt cgccaggatg agtccggtga actgcgtgtt        60
tacggcctac ataccaacc tggcagtggc gccgaccgtg tgccggttgc acaagcccgg       120
tggaatgtgg acaaaagcgc gatggtcgcg gtgctggatg gcatcagcat cacatggacg       180
ccgaacctcg gcccggttgt cagcgtgccg agcccgtatc ccggaacacc ggaacgcttg       240
gataacatgt ttgttcatcc gattgcggtg gggcaagatt cggcgatcag tcactatcca       300
gggcgggatg cagaaaacat cacctggcag gatacgatca tttcgtttcc ggctgattcg       360
ggtgtgccgc cgttgtattt ggtgtttgcc aagccggcgg tcaggccgtt ggaagttgat       420
atttacggtg cgttcagtgg acgactgcgc aacgggttgc acgtggatca cataccctcg       480
caggcagcga taagacgtca tctcgaacgc tatgcaataa gctttacaga gaagcagctc       540
aaggaagcgt taataatgc tgcgagcatt gctattccgt cttacatcca tcaaaagttt       600
agtgagactt acggttggcg aaacacggag aaaaagcaga cgttagatgc cgacgatctt       660
cgtcaggcgg cagacaacaa ttttgatgct atcaagccat acctcctgga tcacggcttc       720
gctgagactg atctcgagat ggcacgcacc cgaatgcata aggtcaacga aaaccagggg       780
tggtactag                                                              789
```

```
<210> SEQ ID NO 51
<211> LENGTH: 4677
<212> TYPE: PRT
<213> ORGANISM: Pseudomonas fluorescens

<400> SEQUENCE: 51
```

```
Met Asn Ala Glu Asp Ser Leu Lys Leu Ala Arg Arg Phe Ile Gly Leu
1               5                   10                  15

Pro Leu Glu Lys Arg Gln Leu Phe Leu Gln Ala Leu Gln Lys Glu Gly
                20                  25                  30

Val Asp Phe Ser Arg Phe Pro Ile Pro Ala Gly Val Glu Val Glu Asp
            35                  40                  45

Arg Gln Ala Leu Ser Tyr Ala Gln Gln Arg Met Trp Phe Leu Trp Gln
    50                  55                  60

Leu Asp Pro Ala Ser Gly Ala Tyr Asn Leu Pro Gly Ala Val Arg Leu
65                  70                  75                  80

Ser Gly Val Leu Ser Leu Pro Ala Leu Glu Gln Ala Phe Ala Ser Leu
                85                  90                  95

Val Ala Arg His Glu Thr Leu Arg Thr Val Phe Gln Arg Gln Ala Asp
            100                 105                 110

Glu Arg Leu Ala Gln Val Ala Val Glu Pro Ser Val Ala Val Glu His
    115                 120                 125

Leu Asp Phe Thr Ala Leu Ala Phe Asp Ala Arg Glu Gln Ala Val Asn
    130                 135                 140

Ala Ala Ala Thr Arg Gln Ser Leu Leu Pro Phe Asp Leu Glu His Gly
145                 150                 155                 160

Pro Leu Leu Arg Val Gln Leu Leu Lys Leu Ala Glu Gln Glu His Val
                165                 170                 175

Leu Leu Leu Thr Leu His His Ile Val Ser Asp Gly Trp Ser Met Asn
            180                 185                 190

Val Leu Ile Asp Glu Phe Ile Arg Cys Tyr Asp Ala His Glu Arg Asp
            195                 200                 205

Glu Ala Pro Gln Leu Pro Ala Leu Pro Ile Gln Tyr Ser Asp Tyr Ala
    210                 215                 220

Leu Trp Gln Arg Arg Trp Leu Glu Ala Gly Glu Gln Ala Arg Gln Leu
225                 230                 235                 240

Glu Tyr Trp Gln Ala Arg Leu Gly Asp Glu His Pro Val Leu Glu Leu
                245                 250                 255

Pro Thr Asp His Pro Arg Pro Ala Met Pro Ser Tyr Gln Gly Thr Arg
                260                 265                 270

His Asn Phe Ala Ile Glu Pro Ala Leu Ala Ala Gln Leu Arg Ser Cys
        275                 280                 285

Ala Gln Lys His Asn Val Thr Leu Phe Met Leu Leu Leu Gly Ala Phe
    290                 295                 300

Asn Val Leu Leu His Arg Tyr Thr Gly Gln Gly Asp Ile Arg Val Gly
305                 310                 315                 320

Val Pro Ile Ala Asn Arg Asn Arg Thr Glu Val Glu Gly Leu Ile Gly
                325                 330                 335

Phe Phe Val Asn Thr Gln Val Leu Arg Thr Glu Leu Ser Gly Gln Thr
            340                 345                 350

Arg Val Ala Glu Leu Leu Gln Gly Ile Lys Glu His Ala Leu Gly Ala
    355                 360                 365

Gln Ala His Gln Glu Leu Pro Phe Glu Arg Leu Val Glu Ala Leu Lys
    370                 375                 380

Ile Glu Arg Ser Leu Ser His Thr Pro Leu Phe Gln Val Met Tyr Asn
385                 390                 395                 400

His Gln Pro Val Val Ala Asp Ile Ala Ser Val Ser Thr Ala Ser Gly
                405                 410                 415
```

-continued

```
Leu Glu Leu Ala Leu Val Glu Trp Gln Gly Arg Thr Thr Gln Phe Asp
            420             425             430

Leu Thr Leu Asp Thr Tyr Glu Lys Ser Gly Thr Leu His Ala Ala Leu
            435             440             445

Thr Tyr Ala Asn Asp Leu Phe Asp Thr Pro Thr Ile Glu Arg Met Ala
    450             455             460

Arg His Trp Thr Arg Leu Leu Gln Ala Met Val Leu Asp Gly Glu Gln
465             470             475             480

Arg Ile Gly Glu Leu Pro Met Leu Asp Ala Ala Glu Gln Gln Arg Leu
            485             490             495

Leu His Thr Trp Asn His Thr Ala Glu Ala Tyr Pro Thr Glu Arg Gly
            500             505             510

Ile His His Leu Ile Glu Asp Gln Ala Arg Arg Ser Pro Asp Ala Pro
            515             520             525

Ala Leu Val Phe Gly Thr Thr Thr Leu Thr Tyr Ala Gln Leu Asp Ala
    530             535             540

Arg Ala Asn Gln Leu Ala His Ala Leu Gly Glu Gln Gly Val Gly Pro
545             550             555             560

Asp Val Leu Val Gly Ile Cys Ile Glu Arg Ser Ile Glu Met Val Val
            565             570             575

Gly Leu Leu Ala Ile Leu Lys Ala Gly Gly Ala Tyr Val Pro Leu Asp
            580             585             590

Pro Glu Tyr Pro Gln Glu Arg Leu Ala Tyr Met Ile Glu Asp Ser Gly
            595             600             605

Ile Gln Leu Leu Leu Ser Gln Gln Ser Leu Leu Ala Ser Leu Pro Val
    610             615             620

Ala Gly Ile Gln Val Ile Ala Leu Asp Gln Pro Ala Leu Trp Leu Asp
625             630             635             640

Gly Tyr Ser Ser Glu Ser Pro Asn Val Ala Leu His Ala Leu Asn Leu
            645             650             655

Ala Tyr Val Ile Tyr Thr Ser Gly Ser Thr Gly Lys Pro Lys Gly Ala
            660             665             670

Gly Asn Ser His Arg Ala Leu Val Asn Arg Leu Ser Trp Met Gln Gln
            675             680             685

Ala Tyr Gly Leu Gly Ala Asn Asp Ala Val Leu Gln Lys Thr Pro Phe
    690             695             700

Ser Phe Asp Val Ser Val Trp Glu Phe Phe Trp Pro Leu Met Ser Gly
705             710             715             720

Ala Arg Leu Val Val Ala Ala Pro Gly Glu His Arg Glu Pro Ala Arg
            725             730             735

Leu Ile Asp Thr Ile Gly Arg His Ala Ile Thr Thr Leu His Phe Val
            740             745             750

Pro Ser Met Leu Gln Ala Phe Ile His Glu Pro Gly Val Gln Ala Cys
            755             760             765

Ala Ser Leu Thr Arg Ile Val Cys Ser Gly Glu Ala Leu Pro Leu Asp
    770             775             780

Ala Gln Gln Gln Val Phe Ala Lys Leu Pro Ala Ala Ala Leu Tyr Asn
785             790             795             800

Leu Tyr Gly Pro Thr Glu Ala Ala Ile Asp Val Thr His Trp Thr Cys
            805             810             815

Ile Asp Glu Gly Val Asp Ser Val Pro Ile Gly Arg Pro Ile Ala Asn
            820             825             830

Leu Gly Thr Tyr Val Leu Asp Ala Gln Leu Asn Pro Val Pro Ala Gly
```

```
              835                    840                    845

Val Ser Gly Glu Leu Tyr Leu Gly Gly Val Gly Leu Ala Arg Ser Tyr
    850                    855                    860

His Arg Arg Pro Ala Leu Thr Ala Glu Arg Phe Val Pro Ser Pro Phe
865                    870                    875                    880

Val Thr Gly Glu Arg Leu Tyr Arg Thr Gly Asp Arg Val Arg Gln Arg
                    885                    890                    895

Ala Asp Gly Val Ile Glu Tyr Leu Gly Arg Leu Asp His Gln Val Lys
                900                    905                    910

Leu Arg Gly Leu Arg Ile Glu Leu Gly Glu Ile Glu Ala Arg Leu Met
                915                    920                    925

Gln His Pro His Val Arg Glu Ala Val Val Leu Val His Gly Gly Lys
    930                    935                    940

Gln Leu Val Ala Tyr Leu Val His Pro Gly Glu Ala Pro Thr Asp Leu
945                    950                    955                    960

Lys Ala Trp Leu Leu Ser Ser Leu Pro Glu Tyr Met Val Pro Thr His
                965                    970                    975

Phe Ile Ala Leu Pro Lys Leu Pro Val Thr Ala Asn Gly Lys Leu Asp
                980                    985                    990

Arg Lys Ala Leu Pro Val Pro Asp  Ala Ala Leu Gln Gln  Ala Phe Val
                995                    1000                    1005

Ala Pro  Gln Gly Asp Leu Gln  Thr Ala Leu Ala Ala  Ile Trp Ser
    1010                    1015                    1020

Asp Val  Leu Gly Val Glu Glu  Val Gly Gln Asp Asp  Asn Phe Phe
    1025                    1030                    1035

Glu Leu  Gly Gly Asp Ser Ile  Ile Ser Ile Gln Val  Val Ser Arg
    1040                    1045                    1050

Ala Arg  Gln Ala Gly Ile Arg  Leu Ser Pro Arg Asp  Leu Phe Gln
    1055                    1060                    1065

Tyr Gln  Ser Ile Arg Ser Leu  Ala Leu Val Ala Arg  Phe Glu Gln
    1070                    1075                    1080

Val Ser  Leu Ile Asp Gln Gly  Pro Val Ser Gly Glu  Val Met Leu
    1085                    1090                    1095

Thr Pro  Val Gln His Ser Phe  Phe Asp Gln Pro Ile  Pro Ala Arg
    1100                    1105                    1110

His His  Trp Asn Gln Ser Leu  Leu Leu Val Pro Gly  Glu Val Leu
    1115                    1120                    1125

Glu Pro  Ala Arg Leu Glu Ala  Thr Leu Ala Arg Leu  Ile Glu His
    1130                    1135                    1140

His Asp  Ala Leu Arg Leu Arg  Phe Val Gln Gln Ala  Asp Gly Trp
    1145                    1150                    1155

Gln Gln  Ser His Ala Ala Tyr  Val Ser Glu Pro Leu  Leu Trp Gln
    1160                    1165                    1170

Cys Gln  Ala Ser Thr Asp Ala  Glu Leu Ala Ala Leu  Cys Asp Glu
    1175                    1180                    1185

Ala Gln  Arg Ser Leu Asp Leu  Ala Gln Gly Pro Leu  Leu Arg Ala
    1190                    1195                    1200

Ala Leu  Val Asn Leu Ala Asp  Gly Ser Gln Arg Val  Leu Leu Val
    1205                    1210                    1215

Ile His  His Leu Val Val Asp  Gly Val Ser Trp Arg  Ile Leu Leu
    1220                    1225                    1230

Glu Asp  Leu Gln Gln Ala Tyr  Arg Asp Gln Ala Leu  Pro Ala Lys
    1235                    1240                    1245
```

-continued

```
Thr Ser  Ala Tyr Gln Arg Trp  Ala Gln Gln Leu His  Arg His Ala
    1250             1255              1260

Gln Ser  Leu Asp Gln Gln Leu  Pro Tyr Trp Gln Ala  Gln Ser Ile
    1265             1270              1275

Asp Ala  Glu Leu Pro Cys Asp  His Pro Glu Gly Gly  Leu Gln Asn
    1280             1285              1290

Arg Leu  Gly Ala Lys Leu Glu  Thr Arg Leu Asp Val  Glu His Thr
    1295             1300              1305

Arg Arg  Leu Leu Gln Asp Ala  Pro Ala Ala Tyr Arg  Thr Gln Val
    1310             1315              1320

Asn Asp  Leu Leu Leu Thr Ala  Leu Ala Arg Val Ile  Ser Arg Trp
    1325             1330              1335

Ser Glu  Gln Pro Ala Ala Leu  Ile Gln Leu Glu Gly  His Gly Arg
    1340             1345              1350

Glu Asp  Leu Phe Asp Asp Ile  Asp Leu Ser Arg Thr  Val Gly Trp
    1355             1360              1365

Phe Thr  Ser Leu Tyr Pro Val  Arg Leu His Ala Glu  Gly Glu Leu
    1370             1375              1380

Ser Ala  Ala Ile Lys Ser Val  Lys Glu Gln Leu Arg  Ala Val Pro
    1385             1390              1395

Asn Lys  Gly Ile Gly Tyr Gly  Leu Leu Arg Tyr Leu  Gly Thr Pro
    1400             1405              1410

Asp Thr  Arg Glu Ala Leu Ser  Thr Leu Ala Ala Pro  Arg Ile Thr
    1415             1420              1425

Phe Asn  Tyr Leu Gly Gln Phe  Asp Arg Gln Phe Asn  Asp Ser Ala
    1430             1435              1440

Leu Phe  Val Pro Ala Arg Gln  Gly Ser Gly Gln Ala  Gln Asp Ala
    1445             1450              1455

Glu Ala  Pro Leu Ala Asn Trp  Leu Thr Val Glu Gly  Gln Val Tyr
    1460             1465              1470

Gly Gly  Glu Leu Ser Leu Gln  Trp Gly Phe Ser Arg  Glu Met Phe
    1475             1480              1485

Glu Ala  Ala Thr Val Gln Arg  Leu Ala Asp Glu Tyr  Ala Ala Glu
    1490             1495              1500

Leu Asn  Ala Leu Ile Glu His  Cys Cys Ala Thr Pro  Ala Gly Gln
    1505             1510              1515

Val Ser  Pro Ser Asp Phe Pro  Leu Ala Arg Leu Thr  Gln Gln Gln
    1520             1525              1530

Leu Asp  Ala Leu Pro Val Ala  Gly Pro Ala Ile Ala  Asp Leu Tyr
    1535             1540              1545

Pro Leu  Ser Pro Met Gln Gln  Gly Met Leu Phe His  Thr Leu Leu
    1550             1555              1560

Glu Pro  Glu Ala Gln Ala Tyr  Ile Asn Gln Leu Arg  Leu Asp Ile
    1565             1570              1575

Glu Gly  Leu Asp Val Leu Ala  Phe Gly Arg Ala Trp  Gln Ala Ala
    1580             1585              1590

Leu Asp  Arg His Asp Ile Leu  Arg Ser Ser Phe His  Trp Leu Gly
    1595             1600              1605

Leu Asp  Ser Ala His Gln Leu  Ile Gln Arg Gln Val  Asp Leu Gln
    1610             1615              1620

Leu Gln  Val Ile Glu Asp Pro  Asn Ala Asp Phe Asp  Thr Leu Ala
    1625             1630              1635
```

-continued

```
His Ala Glu Arg Glu Arg Gly Phe Ala Leu Asn Ala Ala Pro Leu
    1640            1645            1650

Phe Arg Leu Thr Leu Val Arg Gly Ala Gly Ala Ala Trp His Phe
    1655            1660            1665

Ile Phe Thr Ser His His Ile Leu Met Asp Gly Trp Ser Asn Ala
    1670            1675            1680

Gln Leu Leu Ala Glu Val Ile Ala His Tyr Ala Gly Gln Ala Val
    1685            1690            1695

Pro Ala Pro Leu Gly Gln Phe Arg Asp Tyr Leu Ala Trp Leu Gln
    1700            1705            1710

Gln Gln Ser Ser Gly Glu Ala Phe Trp Lys Thr Ala Leu Ala Ala
    1715            1720            1725

Leu Pro Ala Pro Thr Leu Leu Ala Gln Ala Leu Arg Thr Pro Val
    1730            1735            1740

Asp Gly Val Gly Met Ala Asp His His Val Ala Leu Glu Ser Asn
    1745            1750            1755

Phe Thr Arg Arg Leu Gly Glu Phe Ala Arg Gln His Lys Val Thr
    1760            1765            1770

Leu Asn Thr Leu Leu Gln Gly Ala Trp Ser Leu Leu Leu Gln Arg
    1775            1780            1785

Tyr Thr Gly Gln Asp Cys Val Ala Phe Gly Ala Thr Val Ala Gly
    1790            1795            1800

Arg Ser Ala Pro Leu Pro Gly Ile Glu Gln Gln Leu Gly Leu Phe
    1805            1810            1815

Ile Asn Thr Leu Pro Ile Ile Ser Ala Ala Ser Pro Ala Gln Ser
    1820            1825            1830

Ala Ala Thr Trp Leu Ser Glu Leu Gln Val Leu Asn Leu Ser Leu
    1835            1840            1845

Arg Asp His Glu His Val Pro Leu Tyr Asp Ile Gln Gly Trp Ala
    1850            1855            1860

Gly Gln Gln Gly Ala Leu Phe Asp Thr Leu Leu Val Phe Glu Asn
    1865            1870            1875

Phe Pro Val Ala Glu Ala Leu Lys Gln Gly Ala Pro Ala Gly Leu
    1880            1885            1890

Thr Phe Gly Arg Leu His Asn His Glu Arg Thr His Tyr Pro Leu
    1895            1900            1905

Thr Leu Gly Ile Glu Leu Gly Ala Ser Leu Arg Leu Glu Phe Ser
    1910            1915            1920

Tyr Asp Arg Ala Gln Phe Ser Glu Ala Gln Val Ala Gln Leu Ser
    1925            1930            1935

Ala Asn Leu Gln His Leu Leu Ala Gln Leu Leu Ala Asp Ala His
    1940            1945            1950

Met Pro Leu Gly Asn Leu Arg Leu Leu Asp Ala Pro Ala Gln Gln
    1955            1960            1965

Gln Met Leu Ala Leu Ser Arg Ser Ala Ala Ala Pro Gln Ala Asn
    1970            1975            1980

Glu Arg Val His Gln Arg Ile Ala Ala Gln Ala Glu Ala Thr Pro
    1985            1990            1995

Asp Ala Leu Ala Val Gln Ala Gly Asp Ala Ser Val Ser Tyr Ala
    2000            2005            2010

Gln Leu Asn Gln Arg Ala Asn Arg Leu Ala His Arg Leu Leu Ala
    2015            2020            2025

Leu Gly Val Gly Pro Gly Gln Arg Val Gly Leu Ala Ser Arg Arg
```

-continued

```
        2030                     2035                     2040

Gly Pro  Gln Leu Ile Val Ser  Leu Leu Ala Val Leu  Lys Ser Gly
    2045                     2050                     2055

Ala Ala  Tyr Val Pro Leu Asp  Pro Glu Tyr Pro Ala  Glu Arg Leu
    2060                     2065                     2070

Ala Tyr  Met Leu Ala Asp Ser  Arg Leu Asp Leu Leu  Leu Ser Glu
    2075                     2080                     2085

Thr Gly  Leu Leu Ala Asp Leu  Pro Leu Pro Arg Gly  Leu Thr Arg
    2090                     2095                     2100

Val Asp  Phe Ser Ala Cys Gly  Glu Glu Leu Thr Gly  Tyr Pro Thr
    2105                     2110                     2115

Thr Asn  Pro Pro Asn His Ala  Ala Ala Ala Asp Leu  Ala Tyr Val
    2120                     2125                     2130

Ile Tyr  Thr Ser Gly Ser Thr  Gly Gln Pro Lys Gly  Val Ala Ile
    2135                     2140                     2145

Asp His  Ala Ala Leu Gly Gln  Phe Cys Asp Ser Ala  Thr Leu Tyr
    2150                     2155                     2160

Ser Arg  Leu Ser Ala Glu Asp  Arg Val Leu Gln Phe  Ala Thr Phe
    2165                     2170                     2175

Ser Phe  Asp Gly Phe Val Glu  Gln Cys Phe Pro Pro  Leu Cys Ala
    2180                     2185                     2190

Gly Ala  Ala Leu Ile Met Arg  Gly Asp Glu Leu Trp  Asp Ala Gly
    2195                     2200                     2205

Gln Leu  Ala Arg Glu Ile Val  Glu Gln Gly Val Thr  Leu Ala Asp
    2210                     2215                     2220

Leu Pro  Ala Ala Tyr Trp Tyr  Leu Leu Ala Gln Glu  Cys Ala Glu
    2225                     2230                     2235

His Arg  Arg Ser Leu Gly Lys  Leu Arg Gln Val His  Val Gly Gly
    2240                     2245                     2250

Glu Ala  Met Ser Val Glu Gly  Val Arg Ala Trp Tyr  Ala Ala Gly
    2255                     2260                     2265

Leu Gly  Asn Val Arg Leu Val  Asn Thr Tyr Gly Pro  Thr Glu Ala
    2270                     2275                     2280

Thr Val  Val Ser Ser Val His  Glu Cys Gln Leu Ala  Asp Ala Asn
    2285                     2290                     2295

Asp Ala  Tyr Gly Val Pro Ile  Gly Gln Ala Ile Ala  Gly Arg Ala
    2300                     2305                     2310

Leu Tyr  Val Leu Asp Asn Gly  Phe Glu Leu Leu Ala  Thr Asp Gly
    2315                     2320                     2325

Val Gly  Glu Leu Cys Ile Gly  Ala Glu Val Gly Leu  Ala Gln Arg
    2330                     2335                     2340

Tyr Phe  Asp Arg Pro Ala Leu  Thr Ala Glu Arg Phe  Leu Pro Asp
    2345                     2350                     2355

Pro Ile  Ser Ala Thr Pro Gly  Ala Arg Leu Tyr Arg  Ser Gly Asp
    2360                     2365                     2370

Leu Ala  Arg Tyr Asn Pro Ala  Gly Ala Leu Glu Tyr  Val Gly Arg
    2375                     2380                     2385

Ile Asp  His Gln Val Lys Ile  Arg Gly Leu Arg Ile  Glu Met Gly
    2390                     2395                     2400

Glu Ile  Glu Ala Ser Leu Gln  Ala Leu Ser Asn Val  Arg Glu Ala
    2405                     2410                     2415

Ala Val  Leu Ala Gln Pro Ser  Ala Thr Gly Val Gln  Leu Val Ala
    2420                     2425                     2430
```

```
Tyr Val Val Pro Ala Glu Gly  Gln Ala Leu Ala Thr  Gln Ala Leu
    2435                2440                2445

Ala Ala Arg Leu Arg Gln Thr  Leu Pro Asp Tyr Met  Val Pro Gly
    2450                2455                2460

His Trp Val Ala Leu Asp Ala  Leu Pro Leu Asn His  Asn Gly Lys
    2465                2470                2475

Leu Asp Arg Arg Ala Leu Pro  Thr Pro Asp Leu Asn  Gln Ala Ser
    2480                2485                2490

Thr Thr Tyr Val Ala Pro Gln  Ser Pro Leu Gln Ile  Gln Leu Ala
    2495                2500                2505

Ala Ile Trp Gln Ala Val Leu  Gln Val Glu Gln Val  Gly Leu Glu
    2510                2515                2520

Asp His Phe Phe Glu Arg Gly  Gly His Ser Leu Leu  Ala Thr Gln
    2525                2530                2535

Val Ile Ser Arg Val Arg His  Asp Leu Lys Leu Glu  Val Pro Leu
    2540                2545                2550

Arg Ala Leu Phe Glu Gln Pro  Thr Leu Ala Ala Phe  Ala Ala Ala
    2555                2560                2565

Cys Ala Gly Val Gln Val Asp  Thr Ala Pro Val Ile  Gln Ala Val
    2570                2575                2580

Gly Arg Asp Gln Pro Leu Ala  Leu Ser Phe Ala Gln  Glu Arg Gln
    2585                2590                2595

Trp Phe Leu Trp Gln Leu Asp  Pro Thr Ser Ala Ala  Tyr His Val
    2600                2605                2610

Pro Thr Ala Leu His Leu Arg  Gly Glu Leu Asp Ile  Ala Ala Leu
    2615                2620                2625

Glu Arg Ala Val Glu Ala Leu  Val Gln Arg His Glu  Pro Leu Arg
    2630                2635                2640

Thr Thr Phe Val Glu Ser Gly  Glu His Thr Val Gln  Val Ile His
    2645                2650                2655

Pro Ser Leu Ala Val Pro Val  Glu Gln Gln Lys Val  Asp Ala Gly
    2660                2665                2670

Thr Ile Glu Gln Ala Val Ile  Glu Glu Ile Gln Arg  Pro Phe Asp
    2675                2680                2685

Leu Arg Asn Gly Pro Leu Met  Arg Val Lys Leu Leu  Ile Val Ala
    2690                2695                2700

Pro Asp His His Val Leu Val  Ile Thr Gln His His  Ile Ile Ser
    2705                2710                2715

Asp Gly Trp Ser Met Gln Val  Met Ile Asp Glu Trp  Val Ala Leu
    2720                2725                2730

Tyr Gln Gly Asp Val Gly Leu  Pro Ala Leu Pro Ile  Gln Tyr Ala
    2735                2740                2745

Asp Tyr Ala Gln Trp Gln Arg  Asp Trp Met Ala Ala  Gly Glu Gln
    2750                2755                2760

Gln Arg Gln Leu Asp Tyr Trp  Cys Ala Arg Leu Gly  His Glu His
    2765                2770                2775

Ser Leu Leu Asp Leu Pro Leu  Asp His Pro Arg Pro  Ala Val Gln
    2780                2785                2790

Ser His Arg Gly Ala Arg Arg  Gln Ile His Leu Glu  Arg Val Leu
    2795                2800                2805

Leu Thr Glu Leu Lys Ala Leu  Ala Gln Arg Gln Asp  Val Thr Leu
    2810                2815                2820
```

```
Phe Met Leu Leu Leu Ala Ser Phe Gln Thr Leu Leu His Arg Tyr
    2825               2830               2835

Ser Gly Gln Ala Gln Val Arg Val Gly Val Pro Val Ala Asn Arg
    2840               2845               2850

Asn Arg Phe Glu Thr Glu Arg Leu Leu Gly Phe Phe Val Asn Thr
    2855               2860               2865

Gln Val Leu Gln Ala Asp Val His Gly Gln Met Pro Phe Asp Gln
    2870               2875               2880

Leu Leu Ala Gln Val Lys Leu Arg Ala Leu Glu Ala Gln Ala His
    2885               2890               2895

Gln Asp Leu Pro Phe Glu Gln Leu Val Gln Val Leu Gln Pro Glu
    2900               2905               2910

Arg Ser Leu Ser His Asn Pro Leu Phe Gln Val Met Phe Asn His
    2915               2920               2925

Gln Asp Ser Leu Arg Ser Ala Pro Val Gln Leu Pro Gly Leu Ala
    2930               2935               2940

Leu Gln Pro Val Asp Trp Ala Gly His Ser Thr Gln Phe Asp Leu
    2945               2950               2955

Asn Leu Glu Thr Glu Glu Ser Val Asp Gly Leu Trp Ala Ser Leu
    2960               2965               2970

Thr Tyr Ala Thr Asp Leu Phe Asp Ala Ala Thr Ala Glu Arg Leu
    2975               2980               2985

Ala Glu His Trp Gln Asn Leu Leu Arg Ala Val Leu Gln Asp Ala
    2990               2995               3000

Ser Val Ala Leu Asp Asp Leu Ala Met Leu Ser Pro Ser Gln Ser
    3005               3010               3015

Gln Gln Met Val His Asp Trp Asn Arg Ser Asp Thr Asp Tyr Pro
    3020               3025               3030

Arg Glu Arg Cys Val His Gln Leu Phe Glu Ala Gln Ala Ala Ala
    3035               3040               3045

Gln Pro Asp Ala Ile Ala Leu His Phe Asn Asp Glu Arg Leu Ser
    3050               3055               3060

Tyr Gly Glu Leu Asn Arg Arg Ala Asn Arg Leu Ala His Arg Leu
    3065               3070               3075

Ile Asp Met Gly Val Gly Pro Asp Val Leu Val Ala Val His Val
    3080               3085               3090

Glu Arg Ser Leu Asp Met Val Val Gly Leu Leu Ala Thr Leu Lys
    3095               3100               3105

Ala Gly Gly Ala Tyr Val Pro Leu Asp Pro Gln Phe Pro Ala Glu
    3110               3115               3120

Arg Leu Ala Tyr Met Leu Glu Asp Ser Arg Ala Arg Val Leu Leu
    3125               3130               3135

Thr Gln Pro His Leu Leu Gly His Leu Ala Gln Pro His Gly Val
    3140               3145               3150

Gln Val Leu Met Val Glu Glu Ala Gly Thr Ala Gln His Asn Pro
    3155               3160               3165

Gln Val Ala Val Thr Pro Glu His Leu Ala Tyr Val Ile Tyr Thr
    3170               3175               3180

Ser Gly Ser Thr Gly Lys Pro Lys Gly Val Met Val Arg His Lys
    3185               3190               3195

Ala Leu Cys Ser Phe Thr Ser Ala Met Ala Gly Thr Leu Ser Ile
    3200               3205               3210

Gly Gln Asp Ala Arg Leu Leu Ser Leu Thr Thr Phe Ser Phe Asp
```

-continued

```
        3215                3220                3225

Ile Phe  Ala Leu Glu Leu Tyr  Val Pro Leu Ser Val  Gly Gly Thr
    3230                3235                3240

Val Leu  Leu Ser Ala Gln Ala  Met Ala Leu Asp Pro  Glu Ala Ile
    3245                3250                3255

Leu Asp  Leu Ala Gln Arg Gln  Ala Ala Asn Val Leu  Gln Ala Thr
    3260                3265                3270

Pro Ser  Thr Trp Arg Met Leu  Leu Asp Ser Pro Arg  Ala His Ala
    3275                3280                3285

Leu Arg  Gly Ile Ala Cys Leu  Cys Gly Gly Glu Ala  Leu Pro Val
    3290                3295                3300

Asp Leu  Ala Gln Arg Met Leu  Asp Leu Gln Gly Pro  Leu Trp Asn
    3305                3310                3315

Leu Tyr  Gly Pro Thr Glu Thr  Thr Ile Trp Ser Ala  Ala His Arg
    3320                3325                3330

Leu His  Gln Ala Leu Pro Phe  Val Gly Arg Pro Ile  Ala Asn Thr
    3335                3340                3345

Arg Leu  Phe Ile Leu Asn Ala  Gly Leu Thr Pro Cys  Pro Gln Gly
    3350                3355                3360

Val Ser  Gly Glu Leu Leu Ile  Gly Gly Val Gly Leu  Ala Arg Gly
    3365                3370                3375

Tyr His  Gly Gln Pro Ala Leu  Thr Ala Glu Arg Phe  Val Pro Asn
    3380                3385                3390

Pro Phe  Gly Ala Ser Gly Glu  Arg Leu Tyr Arg Thr  Gly Asp Leu
    3395                3400                3405

Ala Arg  Tyr Gln Ala Asp Gly  Val Val Glu Tyr Ile  Gly Arg Val
    3410                3415                3420

Asp His  Gln Val Lys Val Arg  Gly Phe Arg Ile Glu  Leu Gly Glu
    3425                3430                3435

Ile Glu  Ala Cys Leu Arg Glu  Phe Asp Gly Val Arg  Glu Ala Val
    3440                3445                3450

Val Leu  Ala Asp Asn Asp Arg  Leu Ile Ala Tyr Leu  Val Ser Thr
    3455                3460                3465

Ala Pro  Gln Ala Pro Gln Val  Tyr Lys Ala Ala Leu  Arg Glu Arg
    3470                3475                3480

Leu Pro  Asp Tyr Met Val Pro  Ala Gln Trp Leu Phe  Leu Asp Ser
    3485                3490                3495

Leu Pro  Leu Thr Pro Asn Gly  Lys Leu Asp Arg Lys  Ala Leu Pro
    3500                3505                3510

Lys Pro  Asp Ala Ser Leu Ser  Leu Lys Gly His Val  Ala Pro Val
    3515                3520                3525

Thr Pro  Arg Glu Gln Gln Val  Ala Ala Ile Trp Ala  Glu Val Leu
    3530                3535                3540

Glu Leu  Pro Arg Val Gly Leu  Asp Asp His Phe Phe  Glu Leu Gly
    3545                3550                3555

Gly His  Ser Leu Leu Ala Thr  Arg Val Val Ser Arg  Val Arg Gln
    3560                3565                3570

Ala Leu  Ala Leu Glu Val Pro  Leu Lys Ala Leu Phe  Glu Gln Pro
    3575                3580                3585

Leu Leu  Gly Asp Phe Val Arg  Ala Leu Gly Glu Glu  Gly Val Thr
    3590                3595                3600

Ala Pro  Ala Leu Ile Lys Ala  Asp Arg Thr Gln Pro  Leu Pro Leu
    3605                3610                3615
```

-continued

```
Ser Tyr  Ala Gln Glu Arg Gln  Trp Phe Leu Trp Gln  Leu Asp Pro
    3620             3625              3630

Ala Gly  Ala Ala Tyr His Ile  Pro Ser Ala Leu Arg  Leu Gln Gly
    3635             3640              3645

Pro Leu  Asp Leu Thr Ala Leu  Gln Glu Ser Phe Asp  Ser Leu Leu
    3650             3655              3660

Ala Arg  His Glu Ser Leu Arg  Thr Tyr Phe Arg Gln  Asp Ala Thr
    3665             3670              3675

Gly Ala  Val Gln Val Ile Asp  Ala Gln Ser Arg Val  Asp Ile Glu
    3680             3685              3690

Gln Val  Asp Ser Asp Tyr Ala  Gly Leu Lys Ala Arg  Val Ala Gln
    3695             3700              3705

Val Val  Ala Gln Pro Phe Asp  Leu Leu Arg Gly Pro  Leu Leu Arg
    3710             3715              3720

Val Thr  Leu Leu Arg Leu Ala  Glu Asp Asp His Val  Leu Val Leu
    3725             3730              3735

Val Gln  His His Ile Val Ser  Asp Gly Trp Ser Met  Gln Leu Met
    3740             3745              3750

Val Glu  Glu Leu Val Gln Ala  Tyr Ala Ala Asn Ser  Gln Gly Gln
    3755             3760              3765

Asp Val  Gln Leu Pro Thr Leu  Pro Ile Gln Tyr Ala  Asp Tyr Ala
    3770             3775              3780

Val Trp  Gln Arg Asp Trp Met  Glu Ala Gly Glu Gln  Ala Arg Gln
    3785             3790              3795

Leu Ala  Tyr Trp Arg Glu Gln  Leu Ser Gly Glu Gln  Pro Val Leu
    3800             3805              3810

Glu Leu  Pro Phe Asp His Pro  Arg Pro Ala Gln Pro  Ser His Arg
    3815             3820              3825

Gly Ala  Arg Leu Gly Ile Glu  Leu His Pro Glu Leu  Leu Gly Ser
    3830             3835              3840

Leu Arg  Ala Leu Ala Gln His  Ala Gly Val Thr Leu  Pro Met Leu
    3845             3850              3855

Leu Leu  Ala Ser Tyr Gln Ala  Leu Leu His Arg Tyr  Ser Gly Gln
    3860             3865              3870

Glu Asp  Val Arg Val Gly Val  Pro Ile Ala Asn Arg  Asn Arg Leu
    3875             3880              3885

Glu Thr  Glu Gly Leu Ile Gly  Phe Phe Val Asn Thr  Gln Val Leu
    3890             3895              3900

Lys Ala  Asp Ile His Gly Gln  Met Ser Thr Glu Gln  Leu Leu His
    3905             3910              3915

Gln Val  Arg Gln Arg Ser Leu  Glu Ala Gln Ala His  Gln Asp Leu
    3920             3925              3930

Pro Phe  Glu Gln Leu Val Gln  Ala Leu Gln Pro Glu  Arg Ser Leu
    3935             3940              3945

Ser Leu  Ser Pro Leu Phe Gln  Val Leu Phe Asn His  Arg Val Ser
    3950             3955              3960

Ala Ala  Asp Ser His Leu His  Arg Leu Ala Asp Leu  His Val Glu
    3965             3970              3975

Val Leu  Asp Leu Asp Glu Gly  Val Ala Gln Phe Asp  Leu Ala Leu
    3980             3985              3990

Asp Val  Glu Glu Ser Pro Thr  Ala Leu Arg Ala Ser  Leu Ser Tyr
    3995             4000              4005
```

-continued

```
Ala Thr  Asp Leu Phe Ala Val  Ala Thr Ile Glu Arg  Met Ala Gly
    4010             4015              4020

His Trp  Gln Asn Leu Leu Arg  Ala Met Val Val Asp  Pro Gln Gln
    4025             4030              4035

Pro Ile  Ser Gln Leu Ser Leu  Leu Gly Glu Asp Glu  Gln Gln Gln
    4040             4045              4050

Ile Leu  Glu Leu Trp Asn Gln  Thr Asp Ala Gly Phe  Ser Ala Glu
    4055             4060              4065

Arg Leu  Val His Glu Leu Val  Gly Asp Arg Ala Arg  Glu Thr Pro
    4070             4075              4080

Asp Ala  Val Ala Val Lys Phe  Asp Ala Gln Thr Leu  Ser Tyr Gly
    4085             4090              4095

Glu Leu  Asp Arg Gln Ala Asn  Arg Leu Ala His Ala  Leu Ile Ala
    4100             4105              4110

Arg Gly  Val Gly Arg Glu Val  Arg Val Ala Ile Ala  Met Pro Arg
    4115             4120              4125

Ser Ala  Glu Ser Met Val Ala  Phe Leu Ala Val Met  Lys Ala Gly
    4130             4135              4140

Gly Val  Tyr Val Pro Leu Asp  Ile Glu Tyr Pro Arg  Asp Arg Leu
    4145             4150              4155

Leu Tyr  Met Met Gln Asp Ser  Arg Ala Gln Leu Leu  Leu Thr His
    4160             4165              4170

Ser Arg  Ala Leu Gln Gln Leu  Pro Val Pro Glu Gly  Leu Glu Thr
    4175             4180              4185

Leu Ala  Ile Asp Arg Thr Glu  Glu Trp Ala Gly Tyr  Ser Asp Thr
    4190             4195              4200

Ala Pro  Asp Val Ala Leu Asp  Gly Asp Asn Leu Ala  Tyr Val Ile
    4205             4210              4215

Tyr Thr  Ser Gly Ser Thr Gly  Leu Pro Lys Gly Val  Ala Val Ser
    4220             4225              4230

His Gly  Pro Leu Val Ala His  Ile Ile Ala Thr Gly  Glu Arg Tyr
    4235             4240              4245

Glu Thr  Ser Pro Ala Asp Cys  Glu Leu His Phe Met  Ser Phe Ala
    4250             4255              4260

Phe Asp  Gly Ser His Glu Gly  Trp Met His Pro Leu  Ile Asn Gly
    4265             4270              4275

Ala Ser  Val Leu Ile Arg Asp  Asp Ser Leu Trp Leu  Pro Glu Tyr
    4280             4285              4290

Thr Tyr  Glu Gln Met His Arg  His Asn Val Thr Met  Ala Val Phe
    4295             4300              4305

Pro Pro  Val Tyr Leu Gln Gln  Leu Ala Glu His Ala  Glu Arg Asp
    4310             4315              4320

Gly Asn  Pro Pro Ala Val Arg  Val Tyr Cys Phe Gly  Gly Asp Ala
    4325             4330              4335

Val Ala  Gln Ala Ser Tyr Asp  Leu Ala Trp Arg Ala  Leu Lys Pro
    4340             4345              4350

Lys Tyr  Leu Phe Asn Gly Tyr  Gly Pro Thr Glu Thr  Val Val Thr
    4355             4360              4365

Pro Leu  Leu Trp Lys Ala Arg  Lys Gly Asp Pro Cys  Gly Ala Val
    4370             4375              4380

Tyr Ala  Pro Ile Gly Thr Leu  Leu Gly Asn Arg Ser  Gly Tyr Val
    4385             4390              4395

Leu Asp  Ala Gln Leu Asn Leu  Gln Pro Ile Gly Val  Ala Gly Glu
```

```
        4400              4405              4410

Leu Tyr  Leu Gly Gly Glu Gly  Val Ala Arg Gly Tyr  Leu Glu Arg
    4415              4420              4425

Pro Ala  Leu Thr Ala Glu Arg  Phe Val Pro Asp Pro  Phe Gly Lys
    4430              4435              4440

Pro Gly  Ser Arg Val Tyr Arg  Ser Gly Asp Leu Thr  Arg Gly Arg
    4445              4450              4455

Pro Asp  Gly Val Val Asp Tyr  Leu Gly Arg Val Asp  His Gln Val
    4460              4465              4470

Lys Ile  Arg Gly Phe Arg Ile  Glu Leu Gly Glu Ile  Glu Ala Arg
    4475              4480              4485

Leu Arg  Glu Gln Ala Ser Val  Gly Glu Thr Val Val  Val Ala Gln
    4490              4495              4500

Glu Gly  Pro Thr Gly Lys Gln  Leu Val Ala Tyr Val  Val Pro Ala
    4505              4510              4515

Asp Ala  Ser Leu Ala Asp Pro  Val Glu Phe Arg Asp  Ala Leu Arg
    4520              4525              4530

Arg Ala  Leu Lys Ala Asp Leu  Pro Asp Tyr Met Val  Pro Ser His
    4535              4540              4545

Phe Val  Phe Leu Ala Gln Met  Pro Leu Thr Pro Asn  Gly Lys Leu
    4550              4555              4560

Asp Arg  Lys Gly Leu Pro Leu  Pro Asp Ala Ser Gln  Met Gln Gln
    4565              4570              4575

Gln Tyr  Leu Ala Pro Gln Thr  Glu Leu Glu Gln Gln  Ile Ala Thr
    4580              4585              4590

Ile Trp  Ala Asp Ile Leu His  Leu Pro Gln Val Gly  Leu Asn Asp
    4595              4600              4605

Asn Phe  Phe Asp Val Gly Gly  His Ser Leu Leu Ala  Ile Gln Ile
    4610              4615              4620

Thr Ser  Arg Val Gln Ala Glu  Leu Gly Leu Asp Val  Pro Leu Met
    4625              4630              4635

Glu Leu  Phe Gln Thr Glu Ser  Leu Arg Ala Tyr Val  Gln Ala Ala
    4640              4645              4650

Ala Thr  Phe Arg Ala Gly Ser  Val Glu Asp Phe Asp  Asp Leu Arg
    4655              4660              4665

Asp Phe  Leu Ser Glu Leu Glu  Ala Ile
    4670              4675

<210> SEQ ID NO 52
<211> LENGTH: 14034
<212> TYPE: DNA
<213> ORGANISM: Pseudomonas fluorescens

<400> SEQUENCE: 52
atgaatgctg aagactcctt gaaacttgct cgccggttta tcgggctgcc cctggaaaaa      60
cgccaattgt tcctgcaagc cttgcagaaa gaaggcgtgg attttccaag gtttccgatt     120
ccggcagggg tggaggtgga ggaccgccag gcgctgtcct acgcacagca gcgcatgtgg     180
tttctatggc agttggaccc ggccagtggc gcctacaatt gcccggcgc ggtgcgttta     240 agtggcgtgt tgagcctgcc agcgctggag caagcgttcg ccagcctggt ggcgcgtcac     300
gaaaccctgc gcacagtgtt ccagcgtcag gccgatgagc ggctggcgca ggtggcggtg     360
gagccgtcgg tggccgtcga gcacctggac ttcaccgcct ggcctttga tgcgcgggag     420 caggccgtca cgccgccgc cacccgtcaa tcgctgttgc cgttcgacct ggaacatggg     480
```

-continued

```
ccactgctgc gcgtgcaact gctcaagctt gccgagcagg aacacgtgct gctgctgacc      540
ctgcaccaca tcgtctccga cggttggtcg atgaatgtgc tgatcgacga attcatccgt      600
tgctatgacg cccacgagcg cgacgaagcg ccccaactgc cggcgctgcc catccaatac      660
agcgactacg ccctgtggca gcgccgctgg ctggaagcgg gcgagcaggc gcgccaattg      720
gaatattggc aggcccgcct gggtgatgag catccggtgc tggaactgcc cactgatcac      780
ccacgccccg cgatgcccag ctaccagggc acacggcata acttcgcgat tgagccggca      840
ctggccgcgc aactgcgcag ttgcgcgcaa aaacacaacg ttaccctgtt catgctgctg      900
ctcggtgcct tcaatgtgct gttgcaccgc tataccggcc agggcgacat tcgcgtcggt      960
gtgccgattg ccaatcgcaa tcgcaccgaa gtcgagggcc tgatcggttt cttcgtcaac     1020
acccaggtgt tgcgcaccga actgagcggg caaacccggg ttgccgagtt gctgcaaggt     1080
atcaaggagc atgccctggg cgcccaggct catcaggaat tgccctttga acgtctggtg     1140
gaagcgctga aaatcgagcg cagcctgagc cacacgccgc tgtttcaggt gatgtataac     1200
catcagccgg tagtcgccga catcgcctcg gtcagtaccg catcgggtct ggaattggcc     1260
ctggtggaat ggcaaggccg taccacccag ttcgacctga ccctggacac ctatgaaaag     1320
tccggcaccc tgcatgccgc gctgacctac gccaatgact tgttcgatac gcccaccatc     1380
gagcgcatgg cccggcactg gacccgcctg ctgcaagcta tggtgctcga tggcgaacag     1440
cgcattggcg aattgcccat gcttgacgcg gctgaacagc aacggttgct ccacacctgg     1500
aaccacaccg ccgaggcgta cccgaccgag cgcggcattc atcacctgat cgaagaccag     1560
gcacggcgca gccccgatgc tccggcactg gtgttcggta ccaccacctt gacctacgcc     1620
caactggatg cgcgcgccaa ccaattggcc catgccctgg gcgagcaggg cgtagggccc     1680
gacgtattgg tgggtatctg catcgagcgc tccatcgaaa tggtggttgg cctgctggcg     1740
attctcaagg ccggtggcgc ctacgtgccc ctcgaccctg agtacccccca ggaacgcctg     1800 gcctacatga tcgaagacag tggcattcag ttgttactca gccagcagag cctgctggcg     1860
tcgctgcccg tcgccggtat ccaggtgatt gccctggacc agccggcgct atggctcgac     1920
ggatacagca gcgaatcgcc gaacgtggcc ctgcatgccc tgaacctggc ctatgtgatc     1980
tacacctcgg gctccaccgg caagcccaaa ggcgctggca acagccatcg cgcgttggtc     2040
aaccgcttga gctggatgca acaggcgtat ggcctgggtg ccaatgacgc ggtcttgcag     2100
aaaaccccat tcagctttga tgtgtcggtg tgggagttct tctggccgct gatgagcggc     2160
gcacgcctgg tggtcgcggc gcctggcgag caccgtgaac cggcgcgcct gattgacacc     2220
attggccggc acgccatcac caccttgcac ttcgtgccgt cgatgttgca ggcgtttatc     2280
catgagccgg gcgtacaggc gtgcgcgagc ctcacgcgta tcgtctgcag cggcgaagcc     2340
ttgcccctgg atgcgcaaca gcaagtgttc gccaagttgc ccgctgcggc gctgtacaac     2400
ctctatggcc cgaccgaggc ggccatcgac gtcacgcact ggacctgcat tgacgaaggc     2460
gtcgacagcg tgcccatcgg ccgcccatc gccaacctcg gcacctacgt gctggacgca     2520
caactcaacc cggtgccggc tggcgtcagc ggcgaactct atctcggcgg cgttggcctg     2580
gcgcgcagtt accaccgacg cccggcgctg accgccgaac gttttgtgcc cagcccgttc     2640
gtgacgggcg agcgcctgta tcgcaccggt gaccgcgtgc gccaacgtgc cgatggggtg     2700
atcgaatacc tcgccgtct cgatcatcag gtcaagttgc gcggcttgcg tatcgagctg     2760
ggcgaaatcg aagcacgcct gatgcagcat ccacacgtgc gcgaagccgt ggtactggta     2820
```

-continued

```
catggcggca agcagttggt cgcctatctg gtgcacccag gcgaggcgcc aacggacctc   2880
aaggcctggt tgctcagcag cttgccggaa tacatggtgc cgacgcattt catcgcgctg   2940
cccaagctgc cggtgaccgc caatggcaag ctcgatcgca aggcgttgcc agtgccagac   3000
gcggcactgc aacaggcgtt tgtcgccccc caaggcgacc tgcaaacagc cctggctgcc   3060
atctggagcg acgtactggg cgttgaggag gtcggccagg acgataactt cttcgagctg   3120
ggcggcgatt cgatcatctc catccaagta gtcagccgcg cccgtcaggc cggcattcgc   3180
ctgagcccgc gtgacctgtt ccagtaccag agcatccgca gcctggccct ggtggcgcgc   3240
tttgagcagg tcagcctgat cgaccagggc ccggtcagcg gcgaggtcat gctgacgccc   3300
gtgcaacaca gctttttcga ccagccgatc ccggcgcggc atcactggaa tcaatccttg   3360
ttgctggtgc ccggcgaggt gcttgagcct gcacggttgg aggcaacgct ggcgcggttg   3420
atcgagcatc acgacgcctt gcgcctgcgt tttgtgcagc aggctgacgg ctggcagcag   3480
agccatgccg cctacgtcag cgaaccgctg ttgtggcaat gccaggccag caccgacgcc   3540
gaactggcgg cgctgtgtga tgaagcccag cgcagccttg accttgccca aggcccgctg   3600
ctgcgcgccg cgttggtgaa tttggccgat ggcagccaac gtgtgctgct ggtgatccac   3660
cacctggtgg tggatggcgt gtcctggcgc atcctgcttg aagacctgca acaggcctac   3720
cgcgaccagg cgctgccggc gaaaaccagt gcctaccagc gctgggcgca acagttgcac   3780
cgccacgcgc agtccctcga ccagcaactg ccgtactggc aagcccaatc catcgacgcc   3840
gagctgccgt gtgatcaccc cgaaggcggc ctgcaaaacc gcctgggtgc caagctggaa   3900
acacgcctcg acgtcgagca cacccgccga ctgctgcaag acgcgccagc ggcctatcgc   3960
acccaggtca acgacctgct gttgaccgcc ctggcgcggg tgatcagccg ttggagcgag   4020
caacctgctg cgctcattca attggaaggt catggtcggg aagacctgtt tgacgacatc   4080
gacctgagcc gcaccgtcgg ctggttcacc agcctgtacc cggtgcgcct gcacgccgaa   4140
ggggaactgt cggcggcgat caagtcggtg aaggagcaac tgcgcgccgt gccgaacaaa   4200
ggcattggct acggcctgtt gcgttacctc ggcacgcctg acacccgcga agcgttgtcg   4260
accctggccg cgccgcgcat cacgttcaac tacctgggcc agttcgaccg ccagttcaat   4320
gactcggcac tgttcgtgcc ggcccgccag ggcagtgggc aggctcagga tgcagaggca   4380
ccgctggcca actggttgac ggtggaaggg caggtgtatg gcggtgagct gtcgcttcaa   4440
tggggcttca gtcgagagat gttcgaggcg gcaactgtgc agcgtctggc ggatgagtac   4500
gcagccgaac tcaatgcgct gatcgagcat tgctgtgcca cgccggcagg ccaggtgagc   4560
ccgtcggatt tcccgctggc acgcctcacc cagcagcaac tggatgcgtt gcccgtggcc   4620
gggcggcgca ttgccgacct ttatccgctg tcgccgatgc agcaaggcat gctgttccac   4680
accctgttgg aacccgaggc ccaggcctac atcaaccagt tgcgcctcga catcgagggc   4740
ctcgatgtgc tcgctttcgg gcgtgcctgg caggctgcac tggatcgtca tgacatcctg   4800
cgcagcagct tccattggct gggcctggac agtgctcatc agctgatcca cgcgccaggtc   4860 gacctgcaac tgcaagtgat cgaagaccca aacgccgact tcgacaccct ggcccacgcc   4920
gaacgcgaac gtggttttgc cctgaatgcc gcgccgctgt ttcgcctgac gctggtgcgt   4980
ggtgccggtg cggcctggca ctttatcttt accagccacc acatcctcat ggacggctgg   5040
agtaacgcgc agttgctcgc cgaggtcatc gcgcattatg cggggcaggc agtaccggcg   5100
ccgctcgggc agtccgccga ttacctcgcc tggctgcaac aacagtcctc gggcgaggcg   5160
ttctggaaaa ccgccctggc ggcattgccg gcgccgactc tgctggcgca agcgctgcgc   5220
```

-continued

```
acgccggtcg acggggtggg catggctgac catcacgtgg cactggagag caactttacc     5280
cgccgcctcg gcgagttcgc acgccagcac aaagtcaccc tcaataccct gttgcaaggg     5340
gcttggagcc tgttgctgca acgctacacc ggccaggact gcgtcgcctt cggtgccacg     5400
gtggccgggc gttccgcgcc gctgccgggg atcgagcagc aactgggcct gttcatcaac     5460
accttgccga tcatcagcgc agcctcgcca gcccagtcgg ctgcgacttg gctcagcgaa     5520
ctgcaagtgc tcaacctcag cctgcgcgac catgaacatg tgccgctcta cgacatccag     5580
ggctgggccg gccagcaagg cgcgctgttc gacaccttgc tggtgttcga gaacttcccg     5640
gtcgccgagg cgctcaagca aggcgcgccg gccggcctga ccttcggtcg cctgcacaac     5700
catgagcgca cgcactatcc attaaccctg ggcatcgaac tgggcgccag cctgcgcctg     5760
gagttcagct atgaccgtgc ccagttcagc gaggcgcaag tggcgcagtt gagcgccaac     5820
ctgcaacacc tgctggcgca attgctcgca gacgctcaca tgccgctggg caacctgcgc     5880
cttctcgacg cccctgcgca acagcagatg ctcgcgctga gccgctcagc cgcagcgcca     5940
caggccaacg agcgcgtgca tcagcgtata gccgcccagg ccgaggcgac gccggacgcc     6000
ctggctgtgc aggccggtga cgccagcgtg agctacgccc agttgaacca gcgcgccaac     6060
cgcctggccc atcgcctgtt ggcgctgggt gtcggccccg gccaacgggt gggcctggct     6120
tcgcggcgtg gcccgcagtt gatcgtcagc ctgctggcag tgctcaaaag cggggcggcc     6180
tacgtaccgc tggaccctga atacccggcg gagcgtttgg cctacatgct cgccgacagc     6240
cgcctggacc tgctgctcag cgaaaccggc ttgctcgccg acttgccttt gccccgcggc     6300
ctgacccgcg tggatttcag cgcctgtggc gaggagctca ccggctaccc gacgaccaat     6360
ccgcctaatc acgcagcggc ggctgacctg gcctacgtga tctacacctc tggctccacc     6420
ggccagccca agggtgtggc catcgaccat gccgccctcg gccagttctg cgacagcgcc     6480
acgctgtaca gccgactgag cgccgaggac gcgcgtgttgc agtttgcgac cttcagtttc     6540
gatggttttg tcgaacagtg cttcccgccc ctgtgtgcgg gtgcggcgtt gatcatgcgt     6600
ggcgatgaac tctgggacgc cgggcaactg gcgcgagaaa tcgttgagca gggcgtgact     6660
ctggccgatt tgcccgccgc ctactggtac ctgttggcgc aggaatgcgc cgagcaccgt     6720
cgctccctgg gcaagctgcg ccaggtgcat gtgggtggtg aagccatgtc agtggaaggc     6780
gtgcgtgcgt ggtacgccgc gggcttgggc aatgtgcgcc tggtcaacac ctacgggccc     6840
accgaagcca cggttgtgtc cagtgtgcat gagtgccaat tggccgatgc caacgacgcc     6900
tacggcgtgc caatcgggca ggcgattgcc gggcgcgcgc tgtatgtact cgacaacggt     6960
ttcgaactgt tggccaccga tggcgtgggc gagctgtgca ttggcgccga ggttggcttg     7020
gcgcaacgct acttcgaccg cccggcgctg accgccgagc gcttcttgcc ggacccgatt     7080
tccgccacgc ccggtgcgcg gctttatcgc agtggcgacc tggcccggta caacccggcg     7140
ggtgcgctga gtacgtcgg gcgtatcgac catcaagtga agattcgtgg cctgcgtatc     7200
gaaatgggcg aaatcgaagc cagcctgcaa gccttgtcca atgtgcgcga agccgccgtg     7260
cttgcgcagc cgagcgcgac cggcgtgcag ttggtggcgt acgtggtgcc agccgaaggc     7320
caagcgctgg cgaccaggc actggcagcg cgcttgcgcc agacattgcc ggactacatg     7380
gtgccgggcc attgggtggc ccttgatgcc ttgccgttga accacaacgg caagctcgac     7440
cgccgtgcac tgcccacacc cgacctgaac caagccagca ccacctacgt ggcgccgcag     7500
agtccattgc aaatccagtt ggcggcgatc tggcaagcag tgttgcaggt cgagcaggtt     7560
```

-continued

```
ggcctggaag atcacttctt cgaacgcggc ggccactctt tgttggctac ccaagtgatc    7620
tcccgggtgc gccacgacct caagctggaa gtgccgttgc gggcgctgtt cgaacagccg    7680
acgctggcag cctttgctgc ggcgtgcgca ggcgtgcagg tcgatacggc gcccgtgatc    7740
caggcagttg gccgtgacca gccactggcg ttgtcatttg ctcaggaacg gcagtggttt    7800
ctctggcaat tggatcccac cagcgcggcc tatcatgtgc ccaccgcttt gcacctgcgc    7860
ggtgaactcg acatcgcggc gctggagcgc gccgtcgagg ccctggtgca gcgccatgaa    7920
ccgctgcgca ccacctttgt ggagtcgggc gagcacactg tgcaagtcat ccacccaagc    7980
ctggcagtgc cggttgagca acaaaaggtc gacgccggca ctatcgagca ggctgtcatc    8040
gaagagatcc agcgcccgtt cgacctgcgc aacggcccgc tgatgcgcgt caagttgctg    8100
atcgtcgcgc ctgatcacca tgtgctggtt atcacccagc accacatcat ctctgacggc    8160
tggtcgatgc aagtgatgat cgacgagtgg gtggcgctgt accaaggcga cgttggcttg    8220
ccggccttgc cgatccagta cgccgactac gcccagtggc agcgcgactg gatggcggct    8280
ggggaacaac aacgccagct cgattactgg tgcgctcgtc tgggtcacga acattcgctg    8340
ctggacctgc ccctcgacca tccgcgcccc gcagtgcaga gccatcgtgg cgcgcgccgc    8400
cagattcatc tggaacgtgt gctgttgact gaactcaagg ccctggccca gcgtcaggac    8460
gtgacgctgt tcatgctgtt gctggcctcg ttccagacct tgctgcaccg ctacagcggc    8520
caggcgcagg tgcgtgtcgg cgtgccggtc gccaaccgta atcgcttcga aaccgaacga    8580
ctgctgggct tttttcgtcaa cacccaggtg ctgcaagctg acgtgcacgg acagatgccg    8640
ttcgaccagt tgctggccca ggtcaagctg cgtgccctgg aggcgcaggc ccatcaggac    8700
ctgccgttcg agcagctcgt gcaagtgttg cagcccgagc gcagcctgag ccataacccg    8760
ctgttccagg tgatgttcaa ccatcaggac agcctgcgtt cagcgccggt gcaattgccc    8820
ggcctggctt tgcagcccgt ggattgggcc ggtcacagca cgcagttcga cctgaacctg    8880
gaaaccgagg aatcggtgga cggtctctgg gcctcgctga cttacgccac ggatctgttt    8940
gacgcggcga ccgcggaacg cctggccgag cattggcaaa acctgctgcg cgcggtcctg    9000
caggatgcct cggtggcctt ggacgacctg gcgatgctca gcccgtcgca atcgcagcaa    9060
atggtgcacg actggaaccg cagcgacact gactacccgc gcgaacgctg cgtacaccag    9120
ttgtttgagg cccaggccgc ggcgcaaccc gacgccattg cgctgcactt caatgacgag    9180
cgcctgagct acggcgaact caaccgccgc gccaatcggc tggcccatcg tctgatcgac    9240
atgggcgtcg gcccggacgt gctggtggcg gtgcacgtgg agcgttccct ggacatggtg    9300
gttggcttgc tcgcgaccct caaggccggt ggcgcctatg tgccgctcga cccacaattc    9360
ccggcagagc gcctggccta catgcttgaa gacagccgcg cccgggtatt gctgacgcaa    9420
ccgcacctgc tggggcacct ggcgcagccg cacggcgtgc aggtgctgat ggtggaggag    9480
gccggcacag cgcagcacaa tccccaggtt gccgtgacac cggagcatct ggcctacgtg    9540
atctacacct ctggctccac tggcaagccc aaaggggtga tggttcgtca caaggcgctg    9600
tgcagcttca ccagcgccat ggccggcacg ttgagtatcg gccaggatgc gcggctgttg    9660
tcgctgacca ccttctcgtt cgacattttc gccctggagc tgtatgtgcc gctgagtgtc    9720
ggcggtaccg tgttgctgag cgcccaggca atggccctcg acccggaggc gatcctcgat    9780
ctggcccagc gccaggcggc gaatgtgctg caagccacgc cctcgacctg gcgcatgttg    9840
ctcgacagcc cacgggctca tgcactgcgt ggcatcgcct gcctctgcgg tggcgaagcg    9900 ctgccccgtcg atttggccca gcgcatgctc gatctgcaag gcccgttgtg gaacctctat    9960
```

-continued

```
ggtccgacgg aaaccaccat ctggtcggcg gctcatcgtt tgcaccaggc attgccgttc   10020
gtggggcggc ccatcgccaa tacccgcttg ttcattctca atgccggtct cacgccatgc   10080
ccccaaggtg tgtccggtga gctgctgatc ggcggtgtcg gcctggcgcg cggttaccac   10140
gggcagccgg cgctgaccgc cgaacgcttc gtgcctaacc cgtttggggc atcgggcgaa   10200
cgcctgtacc gtaccggcga cctggcacgc tatcaggcgg acggcgtggt ggaatacatc   10260
ggccgtgtcg accatcaggt caaggtccgg ggtttccgta tcgagctggg tgaaatcgaa   10320
gcctgcctgc gtgagttcga cggcgtacgt gaagccgtgg tgctggccga taacgaccgg   10380
ctgatcgctt acctggtcag caccgcgccg caggcaccgc aggtgtataa agccgcgctg   10440
cgcgagcgtc tgccggacta catggtgcca gcgcagtggc tgttcctcga cagcctgccg   10500 ctgacccccca acggtaagct cgaccgcaag gcactgccca aaccggatgc cagcctgtcg   10560
ctcaaaggcc atgtagcgcc cgtcaccccg cgcgagcagc aggtggcggc gatctgggcc   10620
gaggtactgg aattgccccg tgtgggcctc gacgatcatt tcttcgagtt gggcgggcat   10680
tcattgctgg ccacgcgggt ggtgtcacgg gtgcgtcagg ccctggcgct ggaggtccca   10740
ctcaaagcct tgttcgaaca gccgctactg ggtgatttcg tgcgggcctt gggcgaggag   10800
ggcgtcaccg cgcctgcgct gatcaaggcc gaccgcacgc aacctctacc gctgtcttat   10860
gcccaggagc gccaatggtt cctttggcaa ctggacccgg ccggcgccgc gtatcacatc   10920
cccagcgcct tgcgtttgca ggggccgttg gacctgaccg cgctgcaaga gagcttcgat   10980
agcttgctgg ctcgccatga aagcctgcgc acgtatttcc gtcaggacgc caccggcgcg   11040
gttcaagtca ttgacgcgca gagccgggtc gatatcgagc aggtcgacag cgactatgcc   11100
ggcctcaagg cgcgggtcgc gcaggtggtc gcccagcctt tcgacctgct gcgtgggccg   11160
ctgctgcggg ttaccttgct gcgcctggcc gaggacgacc atgtgctggt gctggtgcag   11220
catcacatcg tctctgacgg ctggtcgatg cagttgatgg tcgaggaact ggtgcaggcg   11280
tatgccgcta acagccaagg ccaggacgtg caattgccga cgctgccgat ccagtacgcc   11340
gattatgccg tgtggcagcg cgattggatg gaggcgggtg agcaggcgcg tcaattggcc   11400
tactggcgtg agcaattgag cggcgagcaa ccggtgctgg agttgccgtt cgaccacccg   11460
cgcccggcac agccaagcca tcgcggcgca cgcttgggta tcgagttgca tccggagttg   11520
ttgggcagtt tgcgcgcgct ggcgcagcac gctggcgtca cgctgccgat gctgctgctg   11580
gcgtcttacc aggcattgct gcatcgctac agcggccagg aagatgtgcg cgtgggcgtg   11640
ccgattgcca accgtaatcg cctggaaacc gagggggttga tcggcttctt cgtcaacacc   11700
caagtgctca aggccgatat ccacgggcaa atgagcaccg agcaattgct gcaccaggtg   11760
cgtcagcgtt ccctcgaggc ccaggctcac caggacctgc cgttcgaaca gcttgtgcag   11820
gcattgcaac cggagcgcag cctgagcctg agccgttgt tccaagtgtt gttcaaccac   11880
cgtgtgagcg ctgccgacag ccacctgcat cgcctggccg acctgcacgt cgaagtcctg   11940
gatttggacg agggcgtggc ccagttcgac ctggcgctgg atgtggaaga aagcccgacg   12000
gccctgcgtg cctccctgag ttatgccacc gacctgttcg ccgtggcgac catcgagcgc   12060
atggccgggc attggcagaa cctgttgcgg gcaatggtgg tcgacccaca gcagcccatt   12120
agccaattga gcctgctggg cgaggatgag caacagcaga ttcttgaatt gtggaaccag   12180
accgacgccg gtttttcagc cgagcgcctg gtgcacgaat tggtcggtga tcgcgcccgg   12240
gaaacccccg gacgcggtggc ggtgaaattc gatgctcaaa ccctgagtta cggcgagctg   12300
```

-continued

```
gatcgtcagg ccaaccgcct ggcccatgcc ttgatcgccc gtggcgtcgg cagggaagtg    12360
cgggtggcca tcgccatgcc gcgcagtgcc gagagcatgg tggcgttcct ggcggtgatg    12420
aaagccggcg gtgtgtatgt gccgctggat atcgaatacc cacgtgatcg cctgctgtac    12480
atgatgcaag acagccgtgc gcaactgctg ctgactcaca gccgggcgct gcagcaactg    12540
ccagtccccg agggcctgga gaccctggcg attgatcgca ccgaagagtg ggccggttac    12600
agcgatacgg caccggatgt ggcgctggac ggcgacaacc ttgcctacgt gatctatacc    12660
tccggctcca ccgtttgcc caagggcgtg gcggtgtcac acgggccgct ggtggcgcat    12720
atcatcgcta ccggcgagcg ctatgaaacc tcaccggccg attgcgaact gcacttcatg    12780
tccttcgcct tcgacggttc ccacgaaggc tggatgcacc cgctgatcaa cggcgccagc    12840
gtgttgatcc gtgacgacag cctgtggctg ccggaataca cctacgagca gatgcaccgc    12900
cacaacgtga ccatggcggt gttcccaccg gtgtacttgc aacagttggc cgaacatgcc    12960
gagcgcgacg gcaacccgcc ggcggtgcgg gtgtattgct tcggcggtga tgccgttgct    13020
caagccagct atgacctggc ctggcgcgcg ctgaaaccca gtacctgtt caacggctat    13080 ggcccgacgg aaaccgtggt tacaccgttg ttgtggaagg cccgcaaagg cgatccctgc    13140
ggcgctgtct atgcgcccat cggcaccttg ctgggcaacc gcagtggcta cgtgctggat    13200
gcgcaactga atctgcaacc catcggcgtg gccggcgagt tgtacctggg cggcgagggc    13260
gtggcccggg gttacctgga gcgtccggca ctgactgccg agcgtttcgt accgacccg    13320 ttcggcaaac cgggcagccg cgtgtatcgc agcggcgacc tgacccgtgg gcgtccggat    13380
ggcgtggtgg attacctggg gcgtgtggac catcaagtga agatccgcgg ttttcgtatc    13440
gaactggggg aaatcgaagc gcgtctgcgt gagcaagcca gtgtcggtga aaccgtggtg    13500
gtggcccagg aggggccgac cggtaagcaa ctggtggcct atgtggtacc ggccgacgcc    13560
agcctggccg acccggttga gttccgtgac gccctgcgtc gtgccctgaa agccgacctg    13620
ccggactaca tggtgcccag ccacttcgta ttcctggcgc agatgccgct gacccccaac    13680
ggcaagctcg accgcaaggg cctgccgctg ccggatgcga gccagatgca gcagcagtac    13740
ctggctccgc aaaccgagct tgagcagcag atcgccacga tctgggccga catcctgcac    13800
ctgccgcaag tgggcctgaa cgacaacttc tttgacgtcg gtggccactc cttgctggcg    13860
atccagatta cctcgcgggt gcaggccgag ctcggcctgg acgtaccgtt gatggaactg    13920
ttccagaccg aatcgctgcg cgcctacgtg caggccgcag ccactttccg cgccggcagc    13980
gtggaagatt ttgatgacct tcgtgacttt ttgagcgaac tagaggcgat ttga          14034
```

<210> SEQ ID NO 53
<211> LENGTH: 2321
<212> TYPE: PRT
<213> ORGANISM: Pseudomonas fluorescens

<400> SEQUENCE: 53

```
Met Thr Gly Gly Glu His Phe Glu Asn Leu Val Pro Gly Thr Thr Pro
1               5                   10                  15

Val Asn Thr Thr Val Thr Asp Thr Pro Gly Thr Asp Asn Thr Thr Thr
            20                  25                  30

Val Thr Leu Thr Ala Pro Ser Ala Val Asn Glu Gly Gly Gln Ile Thr
        35                  40                  45

Tyr Thr Ala Thr Leu Ser Asn Lys Ala Gly Thr Asp Val Thr Leu Lys
    50                  55                  60

Leu Asp Asn Gly Ser Ser Ile Thr Ile Lys Ala Gly Glu Thr Val Gly
```

```
65                    70                    75                    80

Thr Val Thr Val Pro Ala Pro Thr Asp Asp Val Phe Ile Asp Lys Ser
                85                    90                    95

Thr Gln Thr Val Lys Ile Thr Glu Thr Thr Gly Gly Asn Phe Glu Lys
                100                   105                   110

Leu Glu Val Ala Gly Asn Gly Ala Thr Thr Thr Ile Asn Asp Thr Ile
                115                   120                   125

Asp Lys Val Asp Val Val Leu Thr Ala Thr Thr Thr Val Gly Glu Gly
        130                   135                   140

Gly Asn Ile Val Tyr Thr Ala Ser Leu Val Asp Lys Asn Gly Ala Pro
145                   150                   155                   160

Val Thr Asn Ile Thr Asn Pro Leu Thr Val Thr Leu Asp Asn Gly Gln
                165                   170                   175

Thr Ile Thr Ile Gly Val Asn Gln Ser Ser Gly Ser Ile Thr Thr Ile
                180                   185                   190

Ala Pro Asp Asp Val Tyr Lys Gly Asp Gln Thr Val Thr Thr Ala Ile
                195                   200                   205

Lys Gly Val Thr Gly Gly Glu His Phe Glu Asn Leu Val Pro Gly Thr
        210                   215                   220

Thr Pro Val Asn Thr Thr Val Thr Asp Thr Pro Gly Thr Asp Asn Thr
225                   230                   235                   240

Thr Thr Val Thr Leu Thr Ala Pro Ala Glu Ala Asn Glu Gly Gly Gln
                245                   250                   255

Ile Thr Tyr Thr Ala Thr Leu Ser Asn Lys Ala Gly Thr Asp Val Thr
                260                   265                   270

Leu Lys Leu Asp Asn Gly Ser Ser Ile Thr Ile Lys Ala Gly Asp Thr
        275                   280                   285

Val Gly Thr Val Thr Val Pro Ala Pro Ser Asp Asp Val Phe Ile Asp
        290                   295                   300

Lys Ser Thr Gln Thr Val Lys Ile Thr Asp Ala Ser Gly Gly Asn Phe
305                   310                   315                   320

Glu Lys Leu Glu Val Ala Gly Asn Gly Ala Thr Thr Thr Ile Asn Asp
                325                   330                   335

Thr Ile Asp Lys Val Asp Val Val Leu Thr Ala Thr Thr Thr Val Gly
                340                   345                   350

Glu Gly Gly Asn Ile Val Tyr Thr Ala Ser Leu Val Asp Lys Asn Gly
        355                   360                   365

Ala Pro Val Thr Asn Ile Thr Asn Pro Leu Thr Val Thr Leu Asp Asn
        370                   375                   380

Gly Lys Thr Ile Thr Ile Gly Val Asn Gln Ser Ser Gly Ser Val Ser
385                   390                   395                   400

Val Leu Ala Pro Asp Asp Val Tyr Lys Gly Asp Gln Thr Val Thr Thr
                405                   410                   415

Ala Ile Lys Gly Val Thr Gly Gly Glu His Phe Glu Asn Leu Val Pro
                420                   425                   430

Gly Thr Thr Ala Val Asn Thr Thr Val Thr Asp Thr Pro Gly Thr Asp
        435                   440                   445

Asn Thr Thr Thr Val Thr Leu Thr Ala Pro Ser Ala Val Asn Glu Gly
        450                   455                   460

Gly Gln Ile Thr Tyr Thr Ala Thr Leu Ser Asn Lys Ala Gly Thr Asp
465                   470                   475                   480

Val Thr Leu Lys Leu Asp Asn Gly Ser Ser Ile Thr Ile Lys Ala Gly
                485                   490                   495
```

-continued

```
Glu Thr Val Gly Thr Val Thr Val Pro Ala Pro Thr Asp Asp Val Phe
        500                 505                 510

Ile Asp Lys Ser Thr Gln Thr Val Lys Ile Thr Asp Ala Ser Gly Gly
        515                 520                 525

Asn Phe Glu Lys Leu Glu Val Ala Gly Ser Gly Ala Thr Thr Thr Ile
        530                 535                 540

Asn Asp Thr Ile Asp Lys Val Asp Val Val Leu Thr Ala Thr Thr Thr
545                 550                 555                 560

Val Gly Glu Gly Gly Asn Ile Val Tyr Thr Ala Ser Leu Val Asp Lys
                565                 570                 575

Asn Gly Ala Pro Val Thr Asn Ile Thr Asn Pro Leu Thr Val Thr Leu
                580                 585                 590

Asp Asn Gly Lys Thr Ile Thr Ile Gly Val Asn Gln Ser Ser Gly Ser
                595                 600                 605

Val Ser Val Leu Ala Pro Asp Asp Val Tyr Lys Gly Asp Gln Thr Val
        610                 615                 620

Thr Thr Ala Ile Lys Gly Val Thr Gly Gly Glu His Phe Glu Asn Leu
625                 630                 635                 640

Val Pro Gly Thr Thr Pro Val Asn Thr Thr Val Thr Asp Thr Pro Gly
                645                 650                 655

Thr Asp Asn Thr Thr Thr Val Thr Leu Thr Ala Pro Ser Ala Val Asn
                660                 665                 670

Glu Gly Gly Gln Ile Thr Tyr Thr Ala Thr Leu Ser Asn Lys Ala Gly
        675                 680                 685

Thr Asp Val Thr Leu Lys Leu Asp Asn Gly Ser Ser Ile Thr Ile Lys
        690                 695                 700

Ala Gly Glu Thr Val Gly Thr Val Thr Val Pro Ala Pro Thr Asp Asp
705                 710                 715                 720

Val Phe Ile Asp Lys Ser Thr Gln Thr Val Lys Ile Thr Glu Thr Thr
                725                 730                 735

Gly Gly Asn Phe Glu Lys Leu Glu Val Ala Gly Asn Gly Ala Thr Thr
                740                 745                 750

Thr Ile Asn Asp Thr Ile Asp Lys Val Asp Val Val Leu Thr Ala Thr
        755                 760                 765

Thr Thr Val Gly Glu Gly Gly Asn Ile Val Tyr Thr Ala Ser Leu Val
        770                 775                 780

Asp Lys Asn Gly Ala Pro Val Thr Asn Ile Thr Asn Pro Leu Thr Val
785                 790                 795                 800

Thr Leu Asp Asn Gly Lys Thr Ile Thr Ile Gly Val Asn Gln Ser Ser
                805                 810                 815

Gly Ser Ile Thr Thr Val Ala Pro Asn Asp Val Tyr Lys Gly Asp Gln
                820                 825                 830

Thr Val Thr Thr Ala Ile Lys Gly Val Thr Gly Gly Glu His Phe Glu
        835                 840                 845

Asn Leu Val Pro Gly Thr Thr Ala Val Asn Thr Thr Val Thr Asp Thr
        850                 855                 860

Pro Gly Ser Thr Asp Leu Thr Thr Val Thr Leu Thr Ala Pro Thr Ala
865                 870                 875                 880

Val Asn Glu Gly Gly Gln Ile Thr Tyr Thr Ala Thr Leu Ser Asn Lys
                885                 890                 895

Ala Gly Ser Asp Met Leu Val Gln Leu Asp Asn Gly Ser Ser Ile Thr
                900                 905                 910
```

-continued

```
Ile Lys Gln Gly Glu Thr Val Gly Thr Val Thr Val Pro Ala Pro Thr
        915                 920                 925

Asp Asp Val Phe Ile Asp Lys Ser Thr Gln Thr Val Lys Ile Thr Gly
        930                 935                 940

Thr Thr Gly Gly Asn Phe Glu Gly Val Thr Ile Thr Pro Ala Gly Ala
945                 950                 955                 960

Thr Thr Thr Ile Asn Asp Thr Ile Asp Asp Val Thr Val Val Leu Lys
                965                 970                 975

Ala Thr Gly Ser Val Ser Glu Gly Gly Gln Ile Val Tyr Thr Ala Ser
                980                 985                 990

Leu Val Asp Lys Asn Gly Val Ala  Val Asn Asn Val Gly  Ser Asp Leu
        995                 1000                1005

Val Val  Lys Leu Asp Asn Gly  Ser Thr Ile Thr Ile  Gly Asn Gly
    1010                1015                1020

Lys Ser  Thr Ser Phe Thr Thr  Ala Thr Ala Pro Asn  Asp Ala Tyr
    1025                1030                1035

Val Gly  Ala Asn Asp Val Thr  Thr Lys Ile Thr Gly  Val Val Ser
    1040                1045                1050

Gly Gly  Asp Lys Tyr Glu His  Leu Ile Val Asp Gly  Ser Thr Val
    1055                1060                1065

Val Thr  Lys Val Thr Asp Val  Val Ser Asn Thr Thr  Ile Ser Ile
    1070                1075                1080

Thr Gly  Asp Ala Ser Val Thr  Glu Gly Gly Thr Ala  His Tyr Thr
    1085                1090                1095

Leu Thr  Leu Ser Asn Pro Pro  Gln Thr Asp Val Thr  Val Thr Leu
    1100                1105                1110

Lys Tyr  Ser Gly Thr Ala Thr  Asp Gly Ser Asp Phe  Asn Gly Val
    1115                1120                1125

Tyr Thr  Val Lys Ile Pro Ala  Gly Ser Ser Ser Val  Pro Phe Asp
    1130                1135                1140

Ile Arg  Thr Leu Asp Asp Lys  Ile Thr Glu Pro Thr  Glu Asn Ile
    1145                1150                1155

Val Ile  Thr Ile Asp Lys Thr  Thr Gly Gly Asn Phe  Glu Asn Leu
    1160                1165                1170

Val Val  Gly Asn Gly Ser Val  Thr Thr Asn Ile Ile  Asp Asn Asp
    1175                1180                1185

Ala Pro  Pro Val Ile Asp Leu  Asp Ala Asn Asn Ser  Ser Gly Ala
    1190                1195                1200

Ser Gly  Ala Asp Phe Lys Thr  Thr Phe Thr Glu Gly  Gly Thr Gly
    1205                1210                1215

Val Ser  Ile Ala Asp Thr Asp  Ile Lys Ile Thr Asp  Pro Asp Ser
    1220                1225                1230

Thr Gln  Leu Thr Gly Ala Thr  Val Val Leu Thr Asn  Ser Gln Pro
    1235                1240                1245

Gly Asp  Ser Leu Asn Phe Ser  Gly Val Ser Gly Ile  Thr Val Thr
    1250                1255                1260

Pro Thr  Thr Asp Pro Val Thr  Gly Lys Ile Thr Leu  Thr Leu Thr
    1265                1270                1275

Gly Thr  Ala Ser Leu Ala Asp  Tyr Met Gln Gln Ile  Lys Asn Ile
    1280                1285                1290

Thr Phe  Thr Asn Asn Ser His  Asp Pro Ser Thr Thr  Pro Arg Thr
    1295                1300                1305

Ile Thr  Val Thr Val Thr Asp  Gly Gly Asn Tyr Ser  Asn Val Ala
```

```
            1310                1315                1320

Thr Thr  Thr Val Asn Val Val  Ala Val Asn Asp Ala  Pro Val Ala
    1325                1330                1335

Thr Gly  Gly Ala Val Thr Gly  Thr Glu Asp Thr Ala  Leu Ala Leu
    1340                1345                1350

Thr Trp  Ala Asn Phe Gly Val  Ser Asp Val Asp Ser  Pro Gln Ala
    1355                1360                1365

Ser Leu  Gly Val Lys Ile Thr  Glu Leu Pro Val Ala  Gly Lys Leu
    1370                1375                1380

Gln Tyr  Leu Ala Ala Asp Gly  Ser Thr Trp Thr Asn  Val Thr Ser
    1385                1390                1395

Gly Gln  Thr Phe Thr Lys Ala  Gln Ile Asp Gly Gly  Gln Leu Arg
    1400                1405                1410

Phe Thr  Pro Asn Ala Asn Glu  Ser Gly Ala Asp Gly  Tyr Gly Gly
    1415                1420                1425

Thr Gly  Val Gly Asn Lys Gln  Ala Asp Tyr Ala Gln  Phe Lys Phe
    1430                1435                1440

Gln Pro  Thr Asp Gly Lys Asp  Leu Gly Thr Ser Ala  Thr Val Lys
    1445                1450                1455

Val Asp  Ile Thr Pro Val Ala  Asp Ala Pro Thr Leu  Ser Val Ala
    1460                1465                1470

Asp Asn  Asn Val Ala Ser Thr  Gly Leu Val Lys Gln  Gly Trp Asn
    1475                1480                1485

Ser Ile  Ala Gly Leu Gly Asn  Asn Gly Asn Gly Ala  Ala Pro Asp
    1490                1495                1500

Val Leu  Lys Lys Ala Ile Asp  Asn Ala Gly Thr Pro  Asn Asn Thr
    1505                1510                1515

Ser Val  Val Thr Asn Val Glu  Ser Val Asp Asn Val  Ala Ala Gly
    1520                1525                1530

Ser Gly  Ser Lys Ile Ser Gly  Leu Ile Tyr Met Glu  Ala Gly Lys
    1535                1540                1545

Ser Tyr  Thr Phe Ser Gly Ile  Ala Asp Asp Ser Val  Val Val Asn
    1550                1555                1560

Val Gly  Gly Lys Asp Val Ala  Ser Gly Leu Trp Gly  Thr Asn Ser
    1565                1570                1575

Gly Lys  Phe Ser Gly Ser Phe  Thr Pro Thr Thr Thr  Gly Tyr Tyr
    1580                1585                1590

Ser Leu  Glu Ile Tyr Gln Ala  Asn Gln Ala Gly Pro  Gly Ser Phe
    1595                1600                1605

Asp Val  Asn Leu Ser Ile Asn  Gly Gly Ala Val Gln  Asn Leu Ser
    1610                1615                1620

Thr Ser  Thr Val Pro Leu Tyr  Thr Gly Leu Thr Asp  Leu Thr Asn
    1625                1630                1635

Ala Gly  Val Thr Val Ser Asp  Leu His Gly Ser Asn  Gly Asp Gly
    1640                1645                1650

Tyr Tyr  Val Gly Tyr Lys Leu  Asn Glu Gly Gln Glu  Asn Gly Thr
    1655                1660                1665

Val Lys  Leu Ser Lys Val Thr  Thr Ala Leu Thr Asp  Thr Asp Gly
    1670                1675                1680

Ser Glu  Thr Leu Ser Val Lys  Ile Ser Gly Ile Pro  Ala Gly Ser
    1685                1690                1695

Val Leu  Thr Asp Ala Ser Gly  His Thr Phe Thr Ala  Gly Lys Thr
    1700                1705                1710
```

```
Val Gly Glu Val Asn Val Thr  Gly Trp Asp Leu Asn  Thr Leu Thr
    1715             1720              1725

Ile Lys Pro Pro Thr Tyr Tyr  Ser Gly Gln Phe Asn  Leu Thr Val
    1730             1735              1740

Thr Ser Thr Ser Thr Glu Ser  Ile Gly Gly Ser Ala  Thr Thr Thr
    1745             1750              1755

Ala Gln Leu Pro Val Thr Val  His Pro Ala Thr Tyr  Asn Ser Val
    1760             1765              1770

Thr Gly Thr Ser Gly Ser Asp  Thr Ile Asn Gly Ser  Asp Gly Asn
    1775             1780              1785

Asp Ile Val Val Ala Asp Ile  Ala Gly Leu Asn Val  Val Gln Gly
    1790             1795              1800

Lys Asn Tyr Asn Ile Ala Phe  Met Val Asp Ser Ser  Gly Ser Met
    1805             1810              1815

Ser Val Ala Ser Leu Asp Ala  Ala Lys Ala Ser Leu  Thr Ser Val
    1820             1825              1830

Phe Asn Ser Leu Lys Asp Ser  Leu Gly Ala Asn Thr  Ser Gly Thr
    1835             1840              1845

Val Asn Ile Phe Leu Ala Asp  Phe Asp Ser Gln Val  Lys Lys Ser
    1850             1855              1860

Val Ala Ile Asn Leu Asn Asp  Pro Asn Ala Leu Thr  Gln Leu Lys
    1865             1870              1875

Ala Val Leu Asp Ser Met Ala  Ser Gly Gly Gly Thr  Asn Tyr Glu
    1880             1885              1890

Asp Val Phe Lys Ala Thr Ala  Asn Phe Phe Gln Ser  Asp Leu Ala
    1895             1900              1905

Thr Lys Asn Thr Gly Ala Thr  Asn Leu Thr Tyr Phe  Ile Thr Asp
    1910             1915              1920

Gly Lys Pro Thr Tyr His Gln  Ser Gly Glu Gln Ile  Asn Pro Val
    1925             1930              1935

Val Thr Asp Phe Tyr Asp Phe  Arg Thr Thr Asp Gly  Arg Leu Asp
    1940             1945              1950

Asp Tyr Ile Ser Ala Asn Asn  Tyr Val Leu Gly Asn  Thr Phe Ser
    1955             1960              1965

Ile Asn Val Asn Gly Ala Asn  Leu Gln Leu Ile Asp  Ser Gln Gly
    1970             1975              1980

Gln Leu His Gln Trp Lys Gln  Thr Phe Leu Gly Gly  Trp Tyr Asp
    1985             1990              1995

Asn Gly Val Ile Gly Thr Val  His Ala Gln Gly Asp  Gly Thr Phe
    2000             2005              2010

Glu Val Ser Tyr Leu Asp Gly  Ser Gly Ser Ser Thr  Thr Thr Ala
    2015             2020              2025

Thr Ile Asn Asn Ala Asn Ser  Gly Phe Ala Leu Leu  Lys Gly Leu
    2030             2035              2040

Ser Ala Val Glu Ala Ile Gly  Ile Asn Gly Asp Ile  Ser Leu Asp
    2045             2050              2055

Asp Leu Lys Pro Tyr Asp Thr  Asp Gly Lys Pro Gln  Thr Asn Ile
    2060             2065              2070

Asp Pro Lys Asp Leu Ala Asn  Ala Ile Leu Gly His  Thr Glu Ala
    2075             2080              2085

Thr Leu Pro Gly Ala Asp Thr  Val Ser Gly Gly Asp  Gly Asn Asp
    2090             2095              2100
```

```
Ile Leu  Phe Gly Asp Leu Val  Ser Phe Ser Gly Ile  Asn Gly Glu
    2105              2110              2115

Gly Tyr  Asn Ala Leu Gln Ala  Phe Val Ala Gln Lys  Thr Gly Val
    2120              2125              2130

Ala Val  Ser Ala Val Thr Ala  Ser Asn Val His Gln  Tyr Val Thr
    2135              2140              2145

Glu His  Tyr Val Asp Phe Asp  Val Ser Gly Ala Lys  Asp Ala Gly
    2150              2155              2160

Asp Thr  Leu Leu Gly Gly Ala  Gly Asp Asp Ile Leu  Phe Gly Gln
    2165              2170              2175

Gly Gly  Asn Asp Thr Leu Asp  Gly Gly Lys Gly Asn  Asp Ile Leu
    2180              2185              2190

Leu Gly  Gly Thr Gly Asn Asp  Thr Leu Ile Gly Gly  Gln Gly Asn
    2195              2200              2205

Asp Ile  Leu Ile Gly Gly Ser  Gly Ala Asp Thr Phe  Val Trp Lys
    2210              2215              2220

Ser Gly  Asp Ile Gly Asn Asp  Val Ile Lys Asp Phe  Lys Ala Ser
    2225              2230              2235

Glu Gly  Asp Arg Ile Asp Leu  Arg Asp Leu Leu Lys  Gly Glu Thr
    2240              2245              2250

Asp Ser  Thr Ile Asp Asn Tyr  Leu Lys Ile Thr Thr  Val Asp Gly
    2255              2260              2265

Val Ser  Thr Leu Gln Val Ser  Ser Glu Gly Lys Leu  Asn Ala Ala
    2270              2275              2280

Gly Gly  Leu Ala Asn Ala Asp  Val Thr Ile Lys Leu  Glu Gly Asn
    2285              2290              2295

Asp Trp  Ser His Thr Ser Ile  Asn Ser Leu Ile Ser  Gly Ala Asp
    2300              2305              2310

Pro Thr  Ile Lys Ile Asp His  Thr
    2315              2320
```

<210> SEQ ID NO 54
<211> LENGTH: 6966
<212> TYPE: DNA
<213> ORGANISM: Pseudomonas fluorescens

<400> SEQUENCE: 54

```
atgaccggcg gcgagcactt tgaaaatctg gttccaggta ctaccccggt taacaccacc         60
gttacggaca caccgggtac cgataacacc accaccgtta cgctgacagc gccaagtgcc        120
gttaacgaag gtgggcagat tacgtacacc gcaacgcttt ccaataaagc gggcactgat        180
gtcacgctga agttagataa cggttcgtcg atcaccatca aggccggcga aaccgtcggc        240
accgtgactg tccctgcgcc taccgatgac gtgtttatcg ataagagcac ccagaccgtc        300
aagatcaccg aaaccactgg cggcaacttc gaaaaactcg aagtggcagg aaacggcgca        360
accaccacga tcaacgacac catcgacaaa gtcgatgtgg tcctgaccgc cactaccacc        420
gtcggcgaag gcggcaatat cgtctacacc gccagccttg tggataagaa cggcgcaccg        480
gtgaccaaca tcaccaatcc gctgaccgtg acattggata acggccagac catcactatt        540
ggcgtaaacc agtcgagcgg ttctatcacc accatcgcgc cagacgatgt ctacaaaggc        600
gaccagaccg tcactaccgc catcaaaggc gtgaccggcg gcgagcactt tgaaaatctg        660
gttccaggta ctaccccggt taataccacc gttacggata caccaggcac tgacaacacc        720
actacggtga cgctgaccgc tccggccgag gcaaacgaag gtgggcagat cacgtacacc        780
```

-continued

```
gccacgcttt ccaacaaagc gggcactgac gtaacgctga aactcgacaa cggttcttcg      840
atcaccatca aggctggcga cactgttggc actgtgactg tgcccgctcc aagcgatgac      900
gtgttcatcg ataaaagtac ccagaccgtc aagattactg acgcttccgg cggcaacttc      960
gaaaaactcg aagtcgcagg taacggcgca acgaccacga tcaacgacac catcgacaag     1020
gtggatgtag ttctaactgc taccactacc gtcggcgaag gcggcaacat cgtctacacc     1080
gccagccttg tggataagaa cggcgcgccg gtgaccaaca tcaccaaccc gctgaccgtg     1140
acattggata acggtaaaac catcaccatc ggcgtaaacc aatcgagcgg tagcgtttcg     1200
gttcttgctc ctgatgatgt gtacaagggc gaccaaactg tcaccaccgc tataaagggt     1260
gtgaccggcg gcgagcattt cgagaacctg gtgcctggca ctacggcagt gaacaccact     1320
gtcaccgata cccccggtac cgacaacacc accactgtga cgctgacagc gccaagtgcc     1380
gttaacgaag gtggtcagat cacttacacc gcgaccttga gcaacaaggc cggtactgac     1440
gtcaccttga agctggataa cggctcttcg atcaccatca aagctggcga gaccgtcggt     1500
actgtgaccg tgcctgcgcc taccgatgac gtgttcatcg ataagagcac tcagaccgtc     1560
aagatcaccg acgcttcggg cggtaacttc gaaaaactgg aagttgcagg cagcggcgcg     1620
accactacga tcaacgacac tatcgacaag gtcgatgtgg tcctgaccgc caccaccacc     1680
gtcggcgaag gcggcaacat cgtttacacc gccagcctcg tggataaaaa cggcgcaccg     1740
gtgaccaaca tcaccaatcc gctgaccgtg accctggata acggcaagac catcaccatc     1800
ggcgtaaacc aatcgagcgg tagcgtttcg gttcttgctc cggatgatgt gtacaagggc     1860
gaccaaactg tcaccaccgc tatcaagggt gtgaccggcg gcgagcactt tgaaaatctg     1920
gttccaggta ctaccccggt aacaccacc gttacggaca caccgggtac cgataacacc      1980
accaccgtta cgctgacagc gccaagtgcc gttaacgaag gtgggcagat tacgtacacc     2040
gcaacgcttt ccaataaagc gggcactgat gtcacgctga agttagataa cggttcgtcg     2100
atcaccatca aggccggcga aaccgtcggc accgtgactg tccctgcgcc taccgatgac     2160
gtgtttatcg ataagagcac ccagaccgtc aagatcaccg aaaccactgg cggcaacttc     2220
gaaaaactcg aagtggcagg aaacggcgca accaccacga tcaacgacac catcgacaaa     2280
gtcgatgtgg tcctgaccgc cactaccacc gtcggcgaag gcggcaacat cgtctacacc     2340
gccagccttg tggataagaa cggcgcaccg gtgaccaaca tcaccaatcc gctgaccgtg     2400
accctggata acggcaagac catcaccatc ggtgtgaatc agtcgagcgg ttccatcacc     2460
accgtagcgc caaacgacgt ctacaaaggc gaccaaaccg tcaccaccgc catcaaaggc     2520
gtgaccggcg gcgagcactt cgagaacctg gtgccgggca cgacggcggt gaacaccacc     2580
gtcaccgaca caccaggctc caccgacctg accaccgtta ccctgactgc cccgaccgcg     2640
gtcaacgaag gcggccagat cacctacacc gccaccttga gcaacaaggc cggtagcgac     2700
atgctggtcc agctcgacaa cggttcgagc atcactatca agcaaggtga gaccgtgggc     2760
acggtgaccg tcccggcgcc taccgatgac gtgttcatcg acaagagcac ccagaccgtc     2820
aagatcaccg gcaccaccgg cggcaatttc gagggcgtga ccatcacacc tgcgggcgcc     2880
acgaccacca tcaacgacac catcgatgac gtgaccgtgg tactcaaggc cactggctcg     2940
gtcagcgaag gcgggcagat cgtgtacacc gcgtccctgg tcgacaagaa cggtgtggcg     3000
gtgaacaacg ttggctcaga cctggtcgtc aagctggata acggctcgac cattaccatc     3060
ggcaatggca agtccaccag cttcaccacc gccaccgcac ctaacgatgc gtatgtcggc     3120
gccaatgacg tcaccactaa aatcacgggt gtggtcagcg gtggcgacaa gtacgaacac     3180
```

-continued

```
ttgatcgtcg acggcagcac cgtggttacc aaagtgaccg atgtggtcag caacaccacc     3240
atcagcatta ccggcgatgc gtcggtgact gaaggcggta cggcgcacta cacgctgacc     3300
ctgagcaacc cgccgcaaac cgacgtgacc gtgacgctca agtacagcgg caccgctacc     3360
gacggttcag acttcaatgg cgtgtacacc gtgaagattc cggcaggctc cagcagcgta     3420
ccgtttgata tccgcacgct cgacgacaag atcaccgagc cgacggaaaa tatcgtcatc     3480
accatcgaca agaccactgg cggcaacttc gaaaacctgg tggtcggcaa tggcagtgtt     3540
accaccaaca tcatcgacaa tgatgcgccg ccggtcatcg atctggatgc caacaactcc     3600
agcggcgcca gcggtgcgga cttcaagacc accttcaccg aaggcggcac cggtgtgtca     3660
attgctgaca ctgacattaa gatcaccgac ccggacagca cccaactgac cggcgccacc     3720
gtggtattga ccaacagcca gccaggcgac tcgctgaact tcagcggcgt gagcggcatc     3780
accgtgaccc cgactaccga ccctgtgacc ggtaaaatca ccttgaccct gaccgggacg     3840
gcgtcgctgg ccgactacat gcagcagatc aagaacatca cgttcaccaa caacagccac     3900
gacccgagca ccacgccgcg caccatcacc gtgacggtga ccgatggcgg caactactcc     3960
aacgtggcta ccaccaccgt caacgtggta gcagtcaacg atgcaccagt ggccactggc     4020
ggtgccgtga ccggtacgga agacaccgcg ctggccctga cctgggccaa cttcggcgtg     4080
agcgatgtgg actcgccaca agccagcctc ggggtgaaaa tcaccgagct gccggtagcc     4140
ggcaagctgc aatacctggc ggcggacggc agcacctgga ccaacgtgac cagcggccag     4200
acctttacca aggctcagat cgatggcggc caactgcgct ttacgccgaa cgccaacgag     4260
tccggcgccg acggttatgg cggcactggc gtgggtaaca agcaggcgga ttacgcgcag     4320
ttcaagttcc aaccaaccga tggcaaggac ctgggtacca gcgccaccggt gaaagtcgat     4380 atcacgccgg tagccgacgc gccgaccctg agcgtggcag acaacaacgt tgcctccacc     4440
ggcctggtca aacagggctg gaacagcatt gccggcctcg gcaacaacgg caacggcgct     4500
gcaccggacg tgctgaaaaa agccatcgat aacgcgggca cgccgaacaa cacctcggtg     4560
gtgaccaacg tcgagtctgt cgacaatgtc gccgccggct ctggctcaaa aatctccggc     4620
ctgatctaca tggaagccgg caagagctac accttcagcg gcatcgccga tgacagcgtg     4680
gtggtcaacg ttggcggtaa agatgttgcc agcggtttgt ggggcaccaa cagcggcaag     4740
ttcagcggct cgttcacgcc aacgaccacc ggttactaca gccttgagat ctaccaggcc     4800
aaccaggcgg gcccaggcag cttcgacgtt aacctgtcga tcaacggcgg ggcggtgcag     4860
aacctgagca ccagcaccgt gccgttgtac accggcctta ccgacctgac caacgccggc     4920
gtcaccgtat ccgacctgca tggcagcaac ggtgacggct actacgtggg ctacaagctc     4980
aacgaaggcc aggaaaacgg cacggtcaaa ctgtccaagg tcaccaccgc gctgaccgat     5040
accgacggct ccgaaaccct gagcgtaaag atcagcggca ttccggcagg ctcggtgctt     5100
accgacgcgt cggggcacac ctttactgcg ggtaaaaccg tgggcgaagt gaatgtcacc     5160
ggctgggacc tgaacaccct gaccatcaag ccgccgacct actacagcgg ccagttcaac     5220
ctgacggtca cctcgacttc caccgagagc atcggcggtt cagcgaccac caccgcgcaa     5280
ttgccagtca cggtgcatcc ggcgacctac aattcggtca ccggcacctc gggcagcgac     5340
accatcaatg gcagcgatgg caacgacatc gtcgtggccg acatcgccgg cctgaacgtg     5400
gtgcagggta agaactacaa catcgcgttc atggtggaca gctccggcag tatgagcgtc     5460
gcctcgctcg acgcggcgaa ggcctcgttg acttcggtgt tcaactcgct caaggacagc     5520
```

-continued

```
ctggcgcca acacatcggg gaccgtgaat atcttcctgg cggactttga tagccaagtg     5580
aaaaagtcgg tggctatcaa cctcaacgat cctaatgcat tgactcagct gaaagcggtg     5640
ctggactcga tggcatcggg aggaggtact aactacgaag acgtgttcaa ggccactgcc     5700
aacttcttcc agagcgacct ggcgaccaaa aacaccggtg caaccaactt gacgtacttc     5760
atcaccgacg gcaagccgac ctaccaccag agcggcgagc agatcaaccc ggtagtgact     5820
gacttctacg acttccgcac caccgatggg cgcttggacg actacatcag tgcgaacaac     5880
tatgtgctgg gtaacacgtt cagcatcaac gtcaatggcg ctaacctgca gttgatcgac     5940
agccagggcc aactgcacca atggaagcag acgttcctgg gtggctggta cgacaacggc     6000
gtcataggta ccgtgcacgc ccagggtgac gggacttttg aagtctccta cctcgacggc     6060
tccggtagta gcaccaccac cgcgaccatt aacaacgcca acagcggttt tgcactgctc     6120
aaaggtttgt cggcggtgga agcaatcggc atcaacggcg acatcagtct cgacgatctc     6180
aagccgtacg ataccgatgg caagccgcaa accaacatcg atccgaagga cctggccaac     6240
gctatcctcg gccacaccga ggcgacgttg ccgggcgcgg acaccgtcag cggtggcgac     6300
ggcaacgaca tcctgttcgg cgacctggtg agtttcagcg ggatcaatgg cgagggttac     6360
aacgcactgc aggcctttgt cgcacagaag accggcgtgg ctgtctcggc agtgactgcc     6420
tctaacgttc accagtacgt caccgagcac tatgtggact tcgacgtctc cggcgccaaa     6480
gatgccggcg acacactgtt gggcggcgct ggcgatgaca tcttgttcgg ccaaggcggc     6540
aacgacacgc tcgatggcgg caaaggcaat gacatcctgc tgggtggcac gggtaacgac     6600
acgttgattg gcggccaggg caacgacatc ctgatcggtg gctcgggtgc cgacaccttt     6660
gtgtggaagt ctggcgacat cggcaacgat gtgatcaagg acttcaaggc gtccgaaggc     6720
gaccgcattg acctgcgtga tttgttgaaa ggtgaaaccg cacagcaccat cgacaactac     6780 ctcaagatca ccacggtaga cggcgtgtcg accctgcaag tgagcagtga aggcaagctc     6840
aacgccgccg gtggcttggc caatgccgat gtgacgatca agctggaagg caacgactgg     6900
tcccacacca gcatcaactc gctgatcagt ggtgccgacc cgaccatcaa gatcgaccac     6960
acttaa                                                              6966
```

```
<210> SEQ ID NO 55
<211> LENGTH: 574
<212> TYPE: PRT
<213> ORGANISM: Pseudomonas fluorescens

<400> SEQUENCE: 55

Met Ser Leu Phe Leu Pro Arg Thr Trp Leu Leu Leu Gly Val Cys Leu
1               5                   10                  15

Leu Thr Gly Phe Ala Leu Asn Ser Ala Ser Ala Ala Pro Thr Pro Gly
            20                  25                  30

Asp Gln Asp Leu Ile Arg Asp Arg Gln Asn Arg Leu Leu Glu Glu Gln
        35                  40                  45

Gln Arg Arg Leu Glu Glu Leu Lys Asp Leu Pro Gly Asn Glu Ala Lys
    50                  55                  60

Pro Val Ala Pro Ala Ala Pro Val Asn Thr Arg Cys Phe Pro Ile Lys
65                  70                  75                  80

Asp Ile Glu Leu Lys Gly Ala Asp Ser Leu Pro Ala Ala Asp Arg Glu
                85                  90                  95

Arg Leu Leu Lys Pro Tyr Ile Gly Gln Cys Leu Gly Val Ser Gln Leu
            100                 105                 110
```

-continued

```
Asn Glu Leu Leu Lys Ala Ile Thr Asp Tyr Tyr Ile Asp Lys Gly Leu
        115                 120                 125

Val Thr Ser Arg Ala Tyr Leu Pro Gln Gln Asp Leu Ser Lys Gly His
    130                 135                 140

Leu Gln Val Leu Val Val Glu Gly Lys Leu Glu Gly Leu Lys Gly Ala
145                 150                 155                 160

Asp Asn Ser Lys Leu Ser Asp Arg Glu Leu Ala Met Ala Phe Pro Gly
                165                 170                 175

Lys Asn Gly Asp Leu Leu Asn Leu Arg Glu Ile Glu Gln Ala Ile Asp
                180                 185                 190

Gln Leu Asn Arg Leu Pro Ser Asn Gln Ala Gln Met Glu Leu Thr Pro
                195                 200                 205

Gly Asp Ala Val Gly Gly Ser Ser Val Leu Val Lys Asn Asn Pro Gln
    210                 215                 220

Lys Pro Trp Arg Ala Ser Leu Ser Arg Asn Asn Asp Gly Gln Lys Ser
225                 230                 235                 240

Thr Gly Glu Gln Gln Trp Gly Thr Gly Phe Glu Trp Asp Ser Pro Leu
                245                 250                 255

Gly Leu Ala Asp Gln Leu Ile Leu Arg Gly Gly His Asp Ala Ile Ser
                260                 265                 270

Asp His Gln Lys Thr Ser Lys Asn Val Leu Leu Tyr Tyr Asn Val Pro
        275                 280                 285

Trp Gly Trp Trp Asn Phe Ser Tyr Ser Tyr Asn Gln Ser Asp Tyr Arg
    290                 295                 300

Ser Val Ala Gln Ala Asp Thr Tyr Asn Phe Lys Gln Ser Gly Asp Ser
305                 310                 315                 320

Gln Asn His Gln Leu Arg Ala Glu Arg Val Ile His Arg Asp Ala Val
                325                 330                 335

Ser Lys Thr Ser Val Asn Val Gly Leu Ser His Leu Arg Thr Asn Asn
                340                 345                 350

Tyr Ile Glu Asp Ser Arg Leu Asp Val Ser Ser Asn Arg Leu Ser Glu
        355                 360                 365

Leu Gln Leu Gly Ile Asn His Gly Arg Arg Ile Gly Ser Ala Phe Val
    370                 375                 380

Asn Ile Asp Leu Gly Val Gln Asn Gly Ile Gly Ala Phe Asp Ala Gln
385                 390                 395                 400

Arg Asn Asp Gln Gln Arg Asp Gln Arg Gly Asn Leu Thr Pro Thr Pro
                405                 410                 415

Asp Tyr Arg Lys Tyr Thr Ala Thr Val Ser Tyr Leu Gln Pro Phe Thr
        420                 425                 430

Leu Trp Gly Glu Ser Phe Ser Phe Thr Ser Leu Ala Thr Gly Gln Arg
        435                 440                 445

Ser Glu Asp Val Leu Phe Ser Pro Gln Arg Met Ser Leu Gly Gly Ser
    450                 455                 460

Ser Ser Ile Arg Gly Phe Lys Asp Gln Gln Leu Thr Gly Asp Ser Gly
465                 470                 475                 480

Gly Tyr Trp Arg Asn Asp Leu Arg Trp Ala Arg Pro Val Thr Trp Asp
                485                 490                 495

Trp Met Arg Pro Val Phe Ala Glu Tyr Gly Ala Ser Val Gly Tyr Asp
                500                 505                 510

Gln Gly Val Ile Arg Asn Asp Arg Tyr Asn Gly Glu Val His Gly Arg
        515                 520                 525

Val Ser Ser Asn Ser Leu Glu Leu Phe Ala Arg Gly Lys Tyr Val Ser
```

-continued

```
              530                535                540
Thr Ser Val Thr Phe Ala His Ser Leu Glu Arg Pro Ala Val Leu Thr
545                550                555                560
Glu Arg Glu Ala Pro Ile Tyr Phe Arg Met Gly Phe Phe Leu
                    565                570
```

<210> SEQ ID NO 56
<211> LENGTH: 1725
<212> TYPE: DNA
<213> ORGANISM: Pseudomonas fluorescens

<400> SEQUENCE: 56

```
atgtctttat tcctgccacg gacttggctg ctacttggcg tctgcctgct gactggcttc        60
gcgctgaaca gcgcgtcggc tgcacctacg cccggcgatc aggacttgat ccgcgaccgg       120
caaaatcgcc tgctggaaga acaacagcgg cgtcttgaag agctcaagga tttgcccggc       180
aacgaggcca agcccgtcgc tcccgccgct ccagtgaaca cccgttgctt ccccatcaaa       240
gacatcgagc tcaaaggcgc cgacagcctg cctgccgctg accgcgagcg cttgctcaag       300
ccctatatcg gccagtgcct gggtgtgtcc cagctcaatg aactgctcaa ggccatcacc       360
gattactaca tcgacaaagg cctggtcacc agccgagctt acttgccgca acaggacctg       420
tccaaggggc acctgcaagt gttggtggtg gaaggcaaac tcgaaggttt gaaaggcgcc       480
gacaacagca agctctcgga ccgcgaattg gccatggcct ttcccgggaa aaacggcgac       540
ttgctgaacc tgcgagaaat cgagcaagcc atcgaccaac tcaaccgctt gccatccaac       600
caggcgcaaa tggagctgac gccaggtgat gccgttggcg gcagttcggt gctggtgaaa       660
aacaacccac agaagccttg gcgcgccagc ttgtcgcgca ataacgacgg ccagaaaagc       720
accggcgaac agcaatgggg taccgggttt gaatgggaca gcccattggg cctggccgat       780
caactgattc tgcgcggcgg ccacgacgcc atcagtgacc accagaaaac ctcgaaaaac       840
gtgttgcttt actacaacgt gccctggggc tggtggaact tcagctacag ctacaaccag       900
agcgattacc gctcggttgc tcaggccgac acctacaact tcaagcaaag cggcgacagc       960
cagaaccacc aactgcgcgc cgaacgtgtg atccaccgcg acgctgtaag taagacctcg      1020
gttaacgtcg gcctatccca cctgcgcacc aacaactaca tcgaagacag ccgtctggac      1080
gtcagcagca atcgcttgag cgaactgcaa ctgggcatca accacgggcg acggatcggc      1140
agtgccttcg tcaacatcga cctcggtgtg cagaacggca taggtgcctt cgatgcccag      1200
cgcaacgatc agcagcgcga ccagcgtggc aacctcaccc ccaccccgga ctaccgcaaa      1260
tacaccgcga ccgtcagcta tttgcagccg ttcacgttgt ggggcgagtc cttcagcttt      1320
accagcctgg ccaccgggca gcgcagtgaa gacgtgctgt tcagccctca gcgcatgagc      1380
ctgggtggtt cgtcgtcgat acgcggtttc aaggaccagc aactgaccgg cgacagcggc      1440
ggctactggc gcaacgacct cgcgctgggc gcgcccggtga cctgggattg gatgcgtccg      1500
gtttttgccg aatacggtgc cagtgtcggt tacgaccagg gtgtgattcg caatgaccgc      1560
tacaacgggg aagtgcacgg tcgggtgtcg agcaactcgc tggagctatt tgcccgcggc      1620
aaatacgtca gcaccagcgt gacctttgcc cattccctgg aacgaccggc agtgctgacc      1680
gagcgcgaag cgccgatcta cttccgcatg ggtttcttcc tgtaa                     1725
```

<210> SEQ ID NO 57
<211> LENGTH: 1437
<212> TYPE: DNA
<213> ORGANISM: Pseudomonas fluorescens -continued

<400> SEQUENCE: 57

```
atgtcgatac cacgtttgaa gtcttactta tccatagtcg ccacagtgct ggtgctgggt      60
caggccttac ctgcgcaagc ggtcgagttg cctgacttca cccaactggt ggagcaggcc     120
tcgcctgccg tggtgaacat cagtaccacg cagaagctgc cggatcgcaa agtctcgaac     180
cagcagatgc ccgacctgga aggcttgccg cccatgctgc gcgagttctt cgaacgaggg     240
atgccgcaac cacgctcccc ccgtggcggc ggtggccagc gcgaagccca atccctgggc     300
tccggcttca tcatttcgcc tgacggctat atcctcacca acaaccacgt gattgccgat     360
gccgacgaga ttctcgtgcg cctggccgac cgcagtgaac tcaaggccaa gctgattggc     420
accgatccac gttccgacgt ggccttgctt aaaatcgagg gcaaggactt gccggtgctt     480
aagctgggca gtcccagga cctgaaggcc ggtcagtggg tggtcgcgat cggttcgccg     540
ttcggctttg accacaccgt tacccaaggc atcgtcagcg ccatcggtcg cagcctgccg     600
aacgaaaact acgtaccgtt catccagacc gacgtgccga tcaacccggg taactccggt     660
ggcccgctgt tcaacctggc cggcgaagtg gtggggatca actcgcagat ctacacccgc     720
tccggcggct tcatgggcgt gtctttcgcg atcccaatcg atgtggccat ggacgtctcc     780
aatcagctca aaagcggcgg caaggtcagc cgcggctggt tgggcgtggt aatccaggaa     840
gtgaacaagg acctggctga gtccttcggt ctcgacaagc cggccggtgc cctggttgcg     900
cagattcagg acaatggccc tgcggccaaa ggcggcctga aagtcggtga cgtcatcctg     960
agcatgaacg gccagccgat catcatgtcg gcagacttgc ctcatttggt cggcgcgctc    1020
aaggccggcg gcaaagccaa gctggaagtg attcgtgatg gcaagcgcca gaacgtcgaa    1080
ctgaccgtag gtgccatccc ggaagaaggc gcgaccctgg atgccctggg caacgccaag    1140
cccggtgccg agcgcagcag taaccgcctg ggtatcgccg tggttgaact gaccgccgag    1200
cagaagaaaa ccttcgacct gcaaagcggt gtggtgatca aggaagttca ggacggccca    1260
gccgccttga tcggcctgca accgggtgac gtgatcactc acttgaacaa ccaggcaatc    1320
gataccacca aggaattcgc cgacatcgcc aaggcgttgc cgaagaatcg ctcggtgtcg    1380
atgcgcgtcc tgcgtcaagg ccgtgccagc ttcattacct tcaagctggc tgagtaa      1437
```

<210> SEQ ID NO 58
<211> LENGTH: 430
<212> TYPE: PRT
<213> ORGANISM: Vibrio cholera

<400> SEQUENCE: 58

```
Met Ile Ser Lys Ser Ile Ile Leu Arg Phe Ser Glu Leu Ser Met Arg
1               5                   10                  15

Lys Lys Val Thr Leu Val Gly Leu Pro Leu Leu Ala Val Ala Ala Ile
            20                  25                  30

Ser Ser Ser Leu Asn Ser Pro Thr Arg Gln Gln Arg Ile Glu Leu Ser
        35                  40                  45

Leu Pro Glu Ser Pro Leu Val Gln Phe Ser Ser Ala Glu His Thr Val
    50                  55                  60

Glu Val Val Lys Val Gly His Pro Asp Tyr Glu Tyr Glu Ile Lys Pro
65                  70                  75                  80

Gly Asp Asn Leu Ser Thr Ile Phe Asn Gln Leu Gly Phe Ala Tyr Thr
                85                  90                  95

Glu Leu Met Lys Val Met Glu Thr Asp Leu Asn Tyr Leu Ala Leu Asp
            100                 105                 110
```

-continued

```
Thr Leu Arg Pro Gly Asn Val Leu Arg Phe Trp Lys Gly Ser Asp Asn
        115                 120                 125

Thr Leu Ala Lys Met Glu Leu Glu Phe Ser Leu Val Asp Arg Ala Val
    130                 135                 140

Tyr Thr Arg Leu Asn Asp Gly Ser Tyr Glu Phe Glu Glu Arg Lys Ile
145                 150                 155                 160

Pro Gly Thr Trp Lys Val Glu Pro Leu Ile Gly Glu Val Asp Gly Ser
                165                 170                 175

Phe Ser Leu Ser Ala Asn Arg Ala Gly Leu Gly Ala Ala Asp Val Asp
                180                 185                 190

Gln Ile Val Thr Leu Leu Lys Asp Lys Ile Asn Phe Gly Arg Asp Leu
        195                 200                 205

Arg Arg Gly Asp Arg Phe Glu Val Val Leu Ser Arg Gln Leu Val Gly
    210                 215                 220

Glu Lys Leu Thr Gly Asn Ser Glu Ile Gln Ala Ile Lys Ile Phe Asn
225                 230                 235                 240

Arg Gly Lys Glu Ile Thr Ala Tyr Leu His Gln Asp Gly Gln Tyr Tyr
                245                 250                 255

Asp Lys Asn Gly Asp Ser Leu Gln Arg Ala Phe Gln Arg Tyr Pro Val
                260                 265                 270

Asp Ser Lys Trp Arg Ile Ser Ser Asn Phe Asp Pro Arg Arg Leu His
        275                 280                 285

Pro Val Thr Lys Arg Val Ala Pro His Asn Gly Thr Asp Phe Ala Met
    290                 295                 300

Pro Ile Gly Thr Pro Val Tyr Thr Ser Gly Asp Gly Val Val Val Met
305                 310                 315                 320

Thr Arg Asn His Pro Tyr Ala Gly Asn Tyr Val Val Ile Gln His Gly
                325                 330                 335

Asn Thr Tyr Met Thr Arg Tyr Leu His Leu Ser Lys Ile Leu Val Lys
                340                 345                 350

Lys Gly Gln Lys Val Ser Arg Gly Gln Arg Ile Gly Leu Ser Gly Asn
        355                 360                 365

Thr Gly Arg Val Thr Gly Pro His Leu His Tyr Glu Leu Ile Val Arg
    370                 375                 380

Gly Arg Pro Val Asn Ala Met Lys Ala Asn Ile Pro Met Ala Ser Ser
385                 390                 395                 400

Val Pro Lys Lys Glu Met Ala Gln Phe Ile Ala Lys Arg Lys Glu Leu
                405                 410                 415

Asp Gln Met Leu Ala Arg Gln Glu Ser Met Leu Ala Ala Gln
        420                 425                 430
```

<210> SEQ ID NO 59
<211> LENGTH: 6
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 59 aggagg                                                              6

<210> SEQ ID NO 60
<211> LENGTH: 243
<212> TYPE: PRT
<213> ORGANISM: Pseudomonas fluorescens

<400> SEQUENCE: 60

```
Met Arg Leu Thr Gln Ile Ile Ala Ala Ala Ala Ile Ala Leu Val Ser
1               5                   10                  15

Thr Phe Ala Leu Ala Asp Asp Ala Ala Glu Gln Thr Ile Arg Lys Ser
            20                  25                  30

Leu Ala Asn Leu Ala Leu Asp Thr Pro Ile Glu Ser Ile Ser Ala Ser
            35                  40                  45

Pro Met Ala Gly Leu Tyr Glu Val Lys Leu Lys Gly Ser Arg Val Leu
    50                  55                  60

Tyr Ala Ser Ala Asp Gly Gln Tyr Ile Val Gln Gly Tyr Leu Phe Gln
65                  70                  75                  80

Leu Lys Asp Gly Lys Pro Val Asn Leu Thr Glu Lys Ala Glu Arg Leu
                85                  90                  95

Gly Val Ser Lys Leu Ile Asn Gly Ile Pro Val Ala Glu Thr Val Val
            100                 105                 110

Tyr Pro Ala Ile Gly Glu Thr Lys Thr His Ile Thr Val Phe Thr Asp
            115                 120                 125

Thr Thr Cys Pro Tyr Cys His Lys Leu His Ala Glu Ile Pro Ala Leu
            130                 135                 140

Asn Lys Leu Gly Val Glu Val Arg Tyr Val Ala Phe Pro Arg Gln Gly
145                 150                 155                 160

Leu Gly Ser Pro Gly Asp Glu Gln Leu Gln Ala Val Trp Cys Ser Ala
                165                 170                 175

Asp Lys Lys Ala Ala Met Asp Lys Met Val Asp Gly Lys Glu Ile Lys
            180                 185                 190

Ser Ala Lys Cys Ala Asn Pro Val Ser Lys Gln Phe Ala Leu Gly Gln
            195                 200                 205

Ser Ile Gly Val Asn Gly Thr Pro Ala Ile Val Leu Ala Asp Gly Gln
    210                 215                 220

Val Ile Pro Gly Tyr Gln Pro Ala Pro Gln Val Ala Lys Leu Ala Leu
225                 230                 235                 240

Gly Ala Lys
```

<210> SEQ ID NO 61
<211> LENGTH: 1038
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 61

```
gcttgacgct gctgggcacc ggtgatgcgc ggcaggttcc ggtgcatggc tgcgagtgtg      60
ctgcgtgcgg gttggcgcgc agtgatcaaa gccgccccag ccgcaggtgc cgcgtaatca     120
caatgacctg acgctggcgc tgcagagcat cgaagacacc ggggcgcagt ggggggggggc     180 tgacccatgt ggggcatacg ttggatacgt ggttgctggc gcatcgtcat gagttgccc      240 gacatgtctc ggtaggttgg gacaatcgag tcgtgtaagg cgtggccttg ttagcaatca     300
gacaagaagc ttgatgttca gtttgttttt tccagtgtgt ttgattgttt ttctggatgt     360
ttgaagcgtg tcgcttgatt gagtcaagtt tgttgtttgc actttttttt cttcggtggc     420
atcaaggttt gagagtgctt gggggatgcg agtattccac ctcgaataaa acatgtgtgg     480
ttttattact gccatgttta atggtgggtt gttgaaatga aatgtgagcc cagtcactat     540
```

-continued

```
tcgctaaccc cccccgacaa gcctgcccag gcaggcgtct gtgtgccagg caacgacctc     600
ccgtggggtt ctcagtccag ggaaccccac gattgcacta gaacctttct cttacttctg     660
accgtatacg cgtgcggcgc tgcgtgcctg cttatcaagt gagcatggct actttcaagc     720
cacgttcatg tcgtgttttt ttccaccaaac tatcaggggt tggtgatgcc ttccggtttt     780
ttcagttatt caaaactccc gttgactcac tcactgggtt tattgcctgt gcgttattca     840
tgttcccgtt tcagaggtgt cggactgatc gcctgttgca gtgcattgaa tgactcatgt     900
gcggcagacg gaagtcgctg tatgtggaat gctgatttt tccttcatgt tctattctat     960
tgttcgccat tcaagttggt agtcgcctgg gggacgtgaa aaatatgagg gtggatgcat    1020
attcaattgc gtctcagg                                                  1038
```

```
<210> SEQ ID NO 62
<211> LENGTH: 474
<212> TYPE: PRT
<213> ORGANISM: Escherichia coli

<400> SEQUENCE: 62

Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
                20                  25                  30

Thr Thr Ala Gln Gln Met Pro Ser Leu Ala Pro Met Leu Glu Lys Val
            35                  40                  45

Met Pro Ser Val Val Ser Ile Asn Val Glu Gly Ser Thr Thr Val Asn
        50                  55                  60

Thr Pro Arg Met Pro Arg Asn Phe Gln Gln Phe Phe Gly Asp Asp Ser
65                  70                  75                  80

Pro Phe Cys Gln Glu Gly Ser Pro Phe Gln Ser Ser Pro Phe Cys Gln
                85                  90                  95

Gly Gly Gln Gly Gly Asn Gly Gly Gly Gln Gln Gln Lys Phe Met Ala
            100                 105                 110

Leu Gly Ser Gly Val Ile Ile Asp Ala Asp Lys Gly Tyr Val Val Thr
        115                 120                 125

Asn Asn His Val Val Asp Asn Ala Thr Val Ile Lys Val Gln Leu Ser
    130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175

Lys Met Ala Asp Ser Asp Ala Leu Arg Val Gly Asp Tyr Thr Val Ala
            180                 185                 190

Ile Gly Asn Pro Phe Gly Leu Gly Glu Thr Val Thr Ser Gly Ile Val
        195                 200                 205

Ser Ala Leu Gly Arg Ser Gly Leu Asn Ala Glu Asn Tyr Glu Asn Phe
    210                 215                 220

Ile Gln Thr Asp Ala Ala Ile Asn Arg Gly Asn Ser Gly Gly Ala Leu
225                 230                 235                 240

Val Asn Leu Asn Gly Glu Leu Ile Gly Ile Asn Thr Ala Ile Leu Ala
                245                 250                 255

Pro Asp Gly Gly Asn Ile Gly Ile Gly Phe Ala Ile Pro Ser Asn Met
            260                 265                 270

Val Lys Asn Leu Thr Ser Gln Met Val Glu Tyr Gly Gln Val Lys Arg
        275                 280                 285
```

```
Gly Glu Leu Gly Ile Met Gly Thr Glu Leu Asn Ser Glu Leu Ala Lys
    290             295             300

Ala Met Lys Val Asp Ala Gln Arg Gly Ala Phe Val Ser Gln Val Leu
305             310             315             320

Pro Asn Ser Ser Ala Ala Lys Ala Gly Ile Lys Ala Gly Asp Val Ile
            325             330             335

Thr Ser Leu Asn Gly Lys Pro Ile Ser Ser Phe Ala Ala Leu Arg Ala
            340             345             350

Gln Val Gly Thr Met Pro Val Gly Ser Lys Leu Thr Leu Gly Leu Leu
            355             360             365

Arg Asp Gly Lys Gln Val Asn Val Asn Leu Glu Leu Gln Gln Ser Ser
    370             375             380

Gln Asn Gln Val Asp Ser Ser Ser Ile Phe Asn Gly Ile Glu Gly Ala
385             390             395             400

Glu Met Ser Asn Lys Gly Lys Asp Gln Gly Val Val Val Asn Asn Val
            405             410             415

Lys Thr Gly Thr Pro Ala Ala Gln Ile Gly Leu Lys Lys Gly Asp Val
            420             425             430

Ile Ile Gly Ala Asn Gln Gln Ala Val Lys Asn Ile Ala Glu Leu Arg
            435             440             445

Lys Val Leu Asp Ser Lys Pro Ser Val Leu Ala Leu Asn Ile Gln Arg
    450             455             460

Gly Asp Ser Thr Ile Tyr Leu Leu Met Gln
465             470

<210> SEQ ID NO 63
<211> LENGTH: 440
<212> TYPE: PRT
<213> ORGANISM: Escherichia coli

<400> SEQUENCE: 63

Met Gln Gln Ile Ala Arg Ser Val Ala Leu Ala Phe Asn Asn Leu Pro
1               5               10              15

Arg Pro His Arg Val Met Leu Gly Ser Leu Thr Val Leu Thr Leu Ala
            20              25              30

Val Ala Val Trp Arg Pro Tyr Val Tyr His Arg Asp Ala Thr Pro Ile
            35              40              45

Val Lys Thr Ile Glu Leu Glu Gln Asn Glu Ile Arg Ser Leu Leu Pro
    50              55              60

Glu Ala Ser Glu Pro Ile Asp Gln Ala Ala Gln Glu Asp Glu Ala Ile
65              70              75              80

Pro Gln Asp Glu Leu Asp Asp Lys Ile Ala Gly Glu Ala Gly Val His
            85              90              95

Glu Tyr Val Val Ser Thr Gly Asp Thr Leu Ser Ser Ile Leu Asn Gln
            100             105             110

Tyr Gly Ile Asp Met Gly Asp Ile Thr Gln Leu Ala Ala Ala Asp Lys
            115             120             125

Glu Leu Arg Asn Leu Lys Ile Gly Gln Gln Leu Ser Trp Thr Leu Thr
    130             135             140

Ala Asp Gly Glu Leu Gln Arg Leu Thr Trp Glu Val Ser Arg Arg Glu
145             150             155             160

Thr Arg Thr Tyr Asp Arg Thr Ala Ala Asn Gly Phe Lys Met Thr Ser
            165             170             175

Glu Met Gln Gln Gly Glu Trp Val Asn Asn Leu Leu Lys Gly Thr Val
```

-continued

```
                  180              185                 190
Gly Gly Ser Phe Val Ala Ser Ala Arg Asn Ala Gly Leu Thr Ser Ala
            195                 200                 205
Glu Val Ser Ala Val Ile Lys Ala Met Gln Trp Gln Met Asp Phe Arg
        210                 215                 220
Lys Leu Lys Lys Gly Asp Glu Phe Ala Val Leu Met Ser Arg Glu Met
225                 230                 235                 240
Leu Asp Gly Lys Arg Glu Gln Ser Gln Leu Leu Gly Val Arg Leu Arg
                245                 250                 255
Ser Glu Gly Lys Asp Tyr Tyr Ala Ile Arg Ala Glu Asp Gly Lys Phe
            260                 265                 270
Tyr Asp Arg Asn Gly Thr Gly Leu Ala Lys Gly Phe Leu Arg Phe Pro
        275                 280                 285
Thr Ala Lys Gln Phe Arg Ile Ser Ser Asn Phe Asn Pro Arg Arg Thr
    290                 295                 300
Asn Pro Val Thr Gly Arg Val Ala Pro His Arg Gly Val Asp Phe Ala
305                 310                 315                 320
Met Pro Gln Gly Thr Pro Val Leu Ser Val Gly Asp Gly Glu Val Val
                325                 330                 335
Val Ala Lys Arg Ser Gly Ala Ala Gly Tyr Tyr Val Ala Ile Arg His
                340                 345                 350
Gly Arg Ser Tyr Thr Thr Arg Tyr Met His Leu Arg Lys Ile Leu Val
                355                 360                 365
Lys Pro Gly Gln Lys Val Lys Arg Gly Asp Arg Ile Ala Leu Ser Gly
        370                 375                 380
Asn Thr Gly Arg Ser Thr Gly Pro His Leu His Tyr Glu Val Trp Ile
385                 390                 395                 400
Asn Gln Gln Ala Val Asn Pro Leu Thr Ala Lys Leu Pro Arg Thr Glu
                405                 410                 415
Gly Leu Thr Gly Ser Asp Arg Arg Glu Phe Leu Ala Gln Ala Lys Glu
                420                 425                 430
Ile Val Pro Gln Leu Arg Phe Asp
            435                 440
```

<210> SEQ ID NO 64
<211> LENGTH: 267
<212> TYPE: PRT
<213> ORGANISM: Escherichia coli

<400> SEQUENCE: 64

```
Met Pro Arg Leu Leu Ala Pro Leu Leu Ala Leu Ser Leu Leu Leu Leu
1               5                   10                  15
Ala Gly Gly Ala Gln Ala Ser Tyr Ile Thr Arg Thr Leu Asn Lys Pro
            20                  25                  30
Val Pro Gly Gly Val Ala Val Val Asp Leu Gly Pro Ala Ala Ser Ala
        35                  40                  45
Pro Ser Ala Arg Phe Asp Gly Lys Pro Val Leu Val Lys Glu Gln
    50                  55                  60
Asp Asn Trp Leu Ala Ile Val Gly Ile Pro Leu Thr Gln Lys Pro Gly
65                  70                  75                  80
Thr Ala Val Leu Ser Gln Gly Gly Arg Thr Leu Pro Phe Thr Val Gly
                85                  90                  95
Ser Lys Lys Tyr Pro Glu Gln Arg Ile Thr Leu Lys Asn Thr Arg Gln
            100                 105                 110
```

Val Asn Pro Asn Pro Ala Asp Leu Lys Arg Ile Asp Arg Glu Leu Ala
        115                 120                 125

Glu Gln Ile Lys Ala Tyr Arg Ser Phe Ser Pro Thr Leu Pro Ser Asn
    130                 135                 140

Leu Ile Leu Asp Lys Pro Val Ser Gly Pro Leu Ser Ser Lys Phe Gly
145                 150                 155                 160

Val Arg Arg Phe Phe Asn Gly Glu Glu Arg Asn Pro His Ala Gly Leu
            165                 170                 175

Asp Phe Ala Val Pro Ala Gly Thr Pro Ile Lys Thr Pro Ala Asn Gly
            180                 185                 190

Lys Val Ile Leu Val Gly Asp Tyr Phe Phe Asn Gly Arg Thr Val Phe
        195                 200                 205

Val Asp His Gly Gln Gly Phe Ile Ser Met Phe Cys His Met Ser Lys
    210                 215                 220

Ile Asp Val Gln Val Gly Gln Gln Leu Arg Arg Gly Glu Val Val Gly
225                 230                 235                 240

Arg Val Gly Ser Thr Gly Arg Ala Thr Gly Pro His Met His Trp Asn
            245                 250                 255

Val Ser Leu Asn Asp Ala Arg Val Asp Pro Ala
            260                 265

<210> SEQ ID NO 65
<211> LENGTH: 470
<212> TYPE: PRT
<213> ORGANISM: Pseudomonas putida

<400> SEQUENCE: 65

Met Thr Asn Glu Pro Thr Lys Ala Pro Pro Leu Tyr Pro Lys Ser His
1               5                   10                  15

Leu Leu Ala Ala Ser Gly Ile Ala Ala Leu Leu Ser Leu Ala Leu Leu
            20                  25                  30

Val Phe Pro Ser Ser Glu Val Glu Ala Lys Lys Thr Thr Leu Asn Leu
        35                  40                  45

Glu Leu Glu Ser Pro Ala Glu Gln Leu Lys Gln Gln Glu Thr Thr Gln
    50                  55                  60

Ala Asp Val Arg Glu Glu Thr Thr Ala Ser Pro Phe Ala Gln Ile Asp
65                  70                  75                  80

Thr Ala Pro Ala Pro Thr Glu Glu Thr Ala Lys Thr Glu Pro Thr Pro
            85                  90                  95

Thr Ala Glu Pro Ala Lys Asp Pro Ser His Arg Glu Val Thr Val Ala
            100                 105                 110

Arg Gly Asp Thr Leu Ser Thr Leu Phe Ala Lys Val Gly Leu Pro Ala
        115                 120                 125

Asn Val Val His Glu Val Leu Ala Ser Asn Lys Gln Ala Lys Gln Phe
    130                 135                 140

Ser Gln Leu Lys His Gly Gln Val Leu Glu Ile Glu Leu Asp Lys Asp
145                 150                 155                 160

Gly Gln Leu Ala Ser Leu His Ser Lys Val Ser Asp Leu Glu Thr Ile
            165                 170                 175

Arg Leu Thr Lys Gly Asp Lys Gly Tyr Ala Phe Asn Arg Glu Ile Thr
            180                 185                 190

Lys Pro Val Val Arg Ser Ala Tyr Val His Gly Val Ile Lys Ser Ser
        195                 200                 205

Leu Ser Ala Ser Ala Gln Arg Ala Gly Leu Asn His Ser Leu Thr Met
    210                 215                 220

-continued

```
Asp Met Ala Arg Ile Phe Gly Tyr Asp Ile Asp Phe Ala Gln Asp Ile
225                 230                 235                 240

Arg Gln Gly Asp Glu Phe Asp Val Ile Tyr Glu Gln Lys Val Val Asn
                245                 250                 255

Gly Lys Val Val Gly Asn Gly Asn Ile Leu Ser Ala Arg Phe Thr Asn
                260                 265                 270

Arg Gly Lys Ser Phe Thr Ala Val Arg Tyr Thr Asn Lys Gln Gly Asn
                275                 280                 285

Thr Ser Tyr Tyr Thr Ala Asp Gly Asn Ser Met Arg Lys Ala Phe Ile
    290                 295                 300

Arg Thr Pro Val Asp Phe Ala Arg Ile Ser Ser Arg Phe Ser Ala Gly
305                 310                 315                 320

Arg Lys His Pro Ile Leu Asn Lys Ile Arg Ala His Lys Gly Val Asp
                325                 330                 335

Tyr Ala Ala Pro Arg Gly Thr Pro Ile Lys Ala Ala Gly Asp Gly Lys
                340                 345                 350

Val Leu Leu Ala Gly Arg Arg Gly Gly Tyr Gly Asn Thr Val Ile Ile
                355                 360                 365

Lys His Gly Asn Thr Tyr Gln Thr Leu Tyr Gly His Met Gln Gly Phe
    370                 375                 380

Ala Lys Gly Ile Lys Thr Gly Gly Thr Val Lys Gln Gly Gln Val Ile
385                 390                 395                 400

Gly Tyr Ile Gly Thr Thr Gly Leu Ser Thr Gly Pro His Leu His Tyr
                405                 410                 415

Glu Phe Gln Val Asn Gly Val His Val Asp Pro Leu Gly Gln Lys Leu
                420                 425                 430

Pro Met Ala Asp Pro Ile Ala Lys Ala Glu Arg Gln Arg Phe Leu Gln
                435                 440                 445

Gln Ser Gln Pro Leu Met Ala Arg Met Glu Gln Glu Lys Ala Thr Met
    450                 455                 460

Leu Ala Ser Ala Lys Arg
465                 470

<210> SEQ ID NO 66
<211> LENGTH: 447
<212> TYPE: PRT
<213> ORGANISM: Pseudomonas aeruginosa

<400> SEQUENCE: 66

Met Phe Pro Ser Ser Glu Val Glu Ala Lys Arg Thr Thr Leu Asn Leu
1               5                   10                  15

Glu Leu Glu Ser Asn Thr Asp Arg Leu Leu Gln Glu Lys Asp Asp Leu
                20                  25                  30

Leu Pro Gln Ser Val Thr Asn Ser Ser Asp Glu Gly Thr Pro Phe Ala
        35                  40                  45

Gln Val Glu Gly Ala Ser Asp Asp Asn Thr Ala Glu Gln Asp Ser Asp
    50                  55                  60

Lys Pro Gly Ala Ser Val Ala Asp Ala Asp Thr Lys Pro Val Asp Pro
65                  70                  75                  80

Glu Trp Lys Thr Ile Thr Val Ala Ser Gly Asp Thr Leu Ser Thr Val
                85                  90                  95

Phe Thr Lys Ala Gly Leu Ser Thr Ser Ala Met His Asp Met Leu Thr
                100                 105                 110

Ser Ser Lys Asp Ala Lys Arg Phe Thr His Leu Lys Val Gly Gln Glu
```

-continued

```
          115                 120                 125
Val Lys Leu Lys Leu Asp Pro Lys Gly Glu Leu Gln Ala Leu Arg Val
    130                 135                 140

Lys Gln Ser Glu Leu Glu Thr Ile Gly Leu Asp Lys Thr Asp Lys Gly
145                 150                 155                 160

Tyr Ser Phe Lys Arg Glu Lys Ala Gln Ile Asp Leu His Thr Ala Tyr
                165                 170                 175

Ala His Gly Arg Ile Thr Ser Ser Leu Phe Val Ala Gly Arg Asn Ala
            180                 185                 190

Gly Leu Pro Tyr Asn Leu Val Thr Ser Leu Ser Asn Ile Phe Gly Tyr
            195                 200                 205

Asp Ile Asp Phe Ala Leu Asp Leu Arg Glu Gly Asp Glu Phe Asp Val
    210                 215                 220

Ile Tyr Glu Gln His Lys Val Asn Gly Lys Gln Val Ala Thr Gly Asn
225                 230                 235                 240

Ile Leu Ala Ala Arg Phe Val Asn Arg Gly Lys Thr Tyr Thr Ala Val
            245                 250                 255

Arg Tyr Thr Asn Lys Gln Gly Asn Thr Ser Tyr Tyr Arg Ala Asp Gly
            260                 265                 270

Ser Ser Met Arg Lys Ala Phe Ile Arg Thr Pro Val Asp Phe Ala Arg
            275                 280                 285

Ile Ser Ser Arg Phe Ser Leu Gly Arg Arg His Pro Ile Leu Asn Lys
    290                 295                 300

Ile Arg Ala His Lys Gly Val Asp Tyr Ala Ala Pro Ile Gly Thr Pro
305                 310                 315                 320

Ile Lys Ala Thr Gly Asp Gly Lys Ile Leu Glu Ala Gly Arg Lys Gly
            325                 330                 335

Gly Tyr Gly Asn Ala Val Val Ile Gln His Gly Gln Arg Tyr Arg Thr
            340                 345                 350

Ile Tyr Gly His Met Ser Arg Phe Ala Lys Gly Ile Arg Ala Gly Thr
            355                 360                 365

Ser Val Lys Gln Gly Gln Ile Ile Gly Tyr Val Gly Met Thr Gly Leu
    370                 375                 380

Ala Thr Gly Pro His Leu His Tyr Glu Phe Gln Ile Asn Gly Arg His
385                 390                 395                 400

Val Asp Pro Leu Ser Ala Lys Leu Pro Met Ala Asp Pro Leu Gly Gly
                405                 410                 415

Ala Asp Arg Lys Arg Phe Met Ala Gln Thr Gln Pro Met Ile Ala Arg
            420                 425                 430

Met Asp Gln Glu Lys Lys Thr Leu Leu Ala Leu Asn Lys Gln Arg
            435                 440                 445

<210> SEQ ID NO 67
<211> LENGTH: 274
<212> TYPE: PRT
<213> ORGANISM: Pseudomonas putida

<400> SEQUENCE: 67

Met Pro Arg Phe Phe Ala Pro Leu Leu Leu Leu Cys Leu Thr Ser Phe
1               5                   10                  15

Asn Ala His Ala Asp Ser Tyr Ile Thr Arg Leu Leu Asn Lys Pro Val
                20                  25                  30

Pro Gly Gly Val Ala Val Val Asp Leu Gly Ser Ala Thr Gln Ala Ser
            35                  40                  45
```

-continued

```
Lys Ala Thr Tyr Gln Gly Lys Pro Val Leu Val Val Lys Glu Gln Asn
    50              55                  60

Asn Trp Leu Ala Ile Val Gly Val Pro Leu Thr Val Lys Pro Gly Ser
65              70              75                  80

Gln Gln Ile Ser Ser Gly Gly Arg Asn Leu Pro Phe Thr Val Gly Asn
                85              90              95

Lys Lys Tyr Pro Glu Gln His Ile Thr Leu Lys Asn Thr Gln Gln Val
            100             105             110

Asn Pro Asn Pro Ala Asn Leu Lys Arg Ile Glu Gly Glu Leu Ala Glu
            115             120             125

Gln Ile Lys Ala Tyr Arg Ser Phe Ser Pro Asn Thr Pro Ser Asn Leu
    130             135             140

Leu Leu Asp Lys Pro Val Asn Gly Pro Leu Ser Ser Lys Phe Gly Val
145             150             155             160

Arg Arg Phe Phe Asn Gly Glu Glu Arg Asn Pro His Ala Gly Leu Asp
            165             170             175

Phe Ala Val Pro Ala Gly Thr Pro Ile Lys Thr Pro Ala Ala Gly Lys
            180             185             190

Val Ile Leu Thr Gly Asn Tyr Phe Phe Asn Gly Asn Thr Val Phe Val
            195             200             205

Asp His Gly Gln Gly Phe Ile Ser Met Phe Cys His Met Ser Lys Ile
    210             215             220

Asp Val Lys Val Gly Asp Gln Leu Ala Arg Gly Ala Val Val Gly Lys
225             230             235             240

Val Gly Ser Thr Gly Arg Ala Thr Gly Pro His Met His Trp Asn Ile
            245             250             255

Ser Leu Asn Asp Ala Arg Val Asp Pro Ala Ile Phe Ile Gly Ala Phe
            260             265             270

Gln Pro
```

<210> SEQ ID NO 68
<211> LENGTH: 282
<212> TYPE: PRT
<213> ORGANISM: Pseudomonas aeruginosa

<400> SEQUENCE: 68

```
Met Pro Arg Thr Leu Ala Phe Val Ser Thr Leu Leu Leu Ala Ala Phe
1               5                   10                  15

Cys Ala Leu Pro Thr Gln Ala Asp Ser Phe Ile Met Arg Leu Leu Asn
            20              25              30

Lys Pro Val Pro Gly Gly Val Ala Val Val Asp Leu Gly Glu Glu Gly
            35              40              45

Pro Pro Pro Arg Ala Phe Tyr Gln Gly Lys Pro Val Leu Val Val Arg
    50              55                  60

Glu Glu Gly Arg Arg Trp Ile Ala Val Val Gly Ile Pro Leu Ser Thr
65              70              75                  80

Lys Pro Gly Pro Gln Lys Leu Glu Val Arg Ala Ala Thr Gly Asn His
            85              90              95

Glu Glu Arg Phe Ser Val Gly Ser Lys His Tyr Arg Glu Gln Arg Ile
            100             105             110

Thr Leu Lys Asn Lys Arg Gln Val Asn Pro Leu Pro Glu Asp Leu Lys
            115             120             125

Arg Ile Glu Arg Glu Leu Ala Glu Gln Thr Ala Ala Tyr Arg Arg Phe
    130             135             140
```

-continued

```
Ser Pro Gly Leu Pro Ser Asn Leu Met Leu Asp Lys Pro Val Asp Gly
145                 150                 155                 160

Pro Leu Ser Ser Pro Phe Gly Leu Arg Arg Phe Phe Asn Gly Glu Glu
                165                 170                 175

Arg Asn Pro His Ser Gly Leu Asp Phe Ala Val Pro Ala Gly Thr Pro
            180                 185                 190

Ile Lys Ala Pro Ala Ala Gly Lys Val Ile Leu Ile Gly Asp Tyr Phe
        195                 200                 205

Phe Asn Gly Lys Thr Val Phe Val Asp His Gly Gln Gly Phe Ile Ser
    210                 215                 220

Met Phe Cys His Leu Ser Lys Ile Asp Val Lys Leu Gly Gln Gln Val
225                 230                 235                 240

Pro Arg Gly Gly Val Leu Gly Lys Val Gly Ala Thr Gly Arg Ala Thr
                245                 250                 255

Gly Pro His Met His Trp Asn Val Ser Leu Asn Asp Ala Arg Val Asp
            260                 265                 270

Pro Ala Ile Phe Ile Gly Ala Phe Gln Pro
        275                 280

<210> SEQ ID NO 69
<211> LENGTH: 386
<212> TYPE: PRT
<213> ORGANISM: Pseudomonas fluorescens

<400> SEQUENCE: 69

Met Leu Lys Ala Leu Arg Phe Phe Gly Trp Pro Leu Leu Ala Gly Val
1                   5                   10                  15

Leu Ile Ala Met Leu Ile Ile Gln Arg Tyr Pro Gln Trp Val Gly Leu
                20                  25                  30

Pro Thr Leu Asp Val Asn Leu Gln Gln Ala Pro Gln Thr Asn Thr Val
            35                  40                  45

Val Gln Gly Pro Val Thr Tyr Ala Asp Ala Val Val Ile Ala Ala Pro
        50                  55                  60

Ala Val Val Asn Leu Tyr Thr Thr Lys Val Ile Asn Lys Pro Ala His
65                  70                  75                  80

Pro Leu Phe Glu Asp Pro Gln Phe Arg Arg Tyr Phe Gly Asp Asn Gly
                85                  90                  95

Pro Lys Gln Arg Arg Met Glu Ser Ser Leu Gly Ser Gly Val Ile Met
            100                 105                 110

Ser Pro Glu Gly Tyr Ile Leu Thr Asn Asn His Val Thr Thr Gly Ala
            115                 120                 125

Asp Gln Ile Val Val Ala Leu Arg Asp Gly Arg Glu Thr Leu Ala Arg
        130                 135                 140

Val Val Gly Ser Asp Pro Glu Thr Asp Leu Ala Val Leu Lys Ile Asp
145                 150                 155                 160

Leu Lys Asn Leu Pro Ala Ile Thr Leu Gly Arg Ser Asp Gly Leu Arg
                165                 170                 175

Val Gly Asp Val Ala Leu Ala Ile Gly Asn Pro Phe Gly Val Gly Gln
            180                 185                 190

Thr Val Thr Met Gly Ile Ile Ser Ala Thr Gly Arg Asn Gln Leu Gly
            195                 200                 205

Leu Asn Ser Tyr Glu Asp Phe Ile Gln Thr Asp Ala Ala Ile Asn Pro
    210                 215                 220

Gly Asn Ser Gly Gly Ala Leu Val Asp Ala Asn Gly Asn Leu Thr Gly
225                 230                 235                 240
```

-continued

```
Ile Asn Thr Ala Ile Phe Ser Lys Ser Gly Gly Ser Gln Gly Ile Gly
            245                 250                 255

Phe Ala Ile Pro Val Lys Leu Ala Met Glu Val Met Lys Ser Ile Ile
            260                 265                 270

Glu His Gly Gln Val Ile Arg Gly Trp Leu Gly Ile Glu Val Gln Pro
            275                 280                 285

Leu Thr Lys Glu Leu Ala Glu Ser Phe Gly Leu Thr Gly Arg Pro Gly
            290                 295                 300

Ile Val Val Ala Gly Ile Phe Arg Asp Gly Pro Ala Gln Lys Ala Gly
305                 310                 315                 320

Leu Gln Leu Gly Asp Val Ile Leu Ser Ile Asp Gly Ala Pro Ala Gly
            325                 330                 335

Asp Gly Arg Lys Ser Met Asn Gln Val Ala Arg Ile Lys Pro Thr Asp
            340                 345                 350

Lys Val Ala Ile Leu Val Met Arg Asn Gly Lys Glu Ile Lys Leu Ser
            355                 360                 365

Ala Glu Ile Gly Leu Arg Pro Pro Pro Ala Thr Ala Pro Val Lys Glu
            370                 375                 380

Glu Gln
385

<210> SEQ ID NO 70
<211> LENGTH: 293
<212> TYPE: PRT
<213> ORGANISM: Escherichia coli

<400> SEQUENCE: 70

Met Met Arg Ile Ala Leu Phe Leu Leu Thr Asn Leu Ala Val Met Val
1               5                   10                  15

Val Phe Gly Leu Val Leu Ser Leu Thr Gly Ile Gln Ser Ser Ser Val
            20                  25                  30

Gln Gly Leu Met Ile Met Ala Leu Leu Phe Gly Phe Gly Gly Ser Phe
            35                  40                  45

Val Ser Leu Leu Met Ser Lys Trp Met Ala Leu Arg Ser Val Gly Gly
            50                  55                  60

Glu Val Ile Glu Gln Pro Arg Asn Glu Arg Glu Arg Trp Leu Val Asn
65                  70                  75                  80

Thr Val Ala Thr Gln Ala Arg Gln Ala Gly Ile Ala Met Pro Gln Val
            85                  90                  95

Ala Ile Tyr His Ala Pro Asp Ile Asn Ala Phe Ala Thr Gly Ala Arg
            100                 105                 110

Arg Asp Ala Ser Leu Val Ala Val Ser Thr Gly Leu Leu Gln Asn Met
            115                 120                 125

Ser Pro Asp Glu Ala Glu Ala Val Ile Ala His Glu Ile Ser His Ile
            130                 135                 140

Ala Asn Gly Asp Met Val Thr Met Thr Leu Ile Gln Gly Val Val Asn
145                 150                 155                 160

Thr Phe Val Ile Phe Ile Ser Arg Ile Leu Ala Gln Leu Ala Ala Gly
            165                 170                 175

Phe Met Gly Gly Asn Arg Asp Glu Gly Glu Glu Ser Asn Gly Asn Pro
            180                 185                 190

Leu Ile Tyr Phe Ala Val Ala Thr Val Leu Glu Leu Val Phe Gly Ile
            195                 200                 205

Leu Ala Ser Ile Ile Thr Met Trp Phe Ser Arg His Arg Glu Phe His
```

```
              210              215              220

Ala Asp Ala Gly Ser Ala Lys Leu Val Gly Arg Glu Lys Met Ile Ala
225                 230                 235                 240

Ala Leu Gln Arg Leu Lys Thr Ser Tyr Glu Pro Gln Glu Ala Thr Ser
                245                 250                 255

Met Met Ala Leu Cys Ile Asn Gly Lys Ser Lys Ser Leu Ser Glu Leu
                260                 265                 270

Phe Met Thr His Pro Pro Leu Asp Lys Arg Ile Glu Ala Leu Arg Thr
                275                 280                 285

Gly Glu Tyr Leu Lys
        290

<210> SEQ ID NO 71
<211> LENGTH: 682
<212> TYPE: PRT
<213> ORGANISM: Escherichia coli

<400> SEQUENCE: 71

Met Asn Met Phe Phe Arg Leu Thr Ala Leu Ala Gly Leu Leu Ala Ile
1               5                   10                  15

Ala Gly Gln Thr Phe Ala Val Glu Asp Ile Thr Arg Ala Asp Gln Ile
                20                  25                  30

Pro Val Leu Lys Glu Glu Thr Gln His Ala Thr Val Ser Glu Arg Val
            35                  40                  45

Thr Ser Arg Phe Thr Arg Ser His Tyr Arg Gln Phe Asp Leu Asp Gln
        50                  55                  60

Ala Phe Ser Ala Lys Ile Phe Asp Arg Tyr Leu Asn Leu Leu Asp Tyr
65                  70                  75                  80

Ser His Asn Val Leu Leu Ala Ser Asp Val Glu Gln Phe Ala Lys Lys
                85                  90                  95

Lys Thr Glu Leu Gly Asp Glu Leu Arg Ser Gly Lys Leu Asp Val Phe
                100                 105                 110

Tyr Asp Leu Tyr Asn Leu Ala Gln Lys Arg Arg Phe Glu Arg Tyr Gln
            115                 120                 125

Tyr Ala Leu Ser Val Leu Glu Lys Pro Met Asp Phe Thr Gly Asn Asp
        130                 135                 140

Thr Tyr Asn Leu Asp Arg Ser Lys Ala Pro Trp Pro Lys Asn Glu Ala
145                 150                 155                 160

Glu Leu Asn Ala Leu Trp Asp Ser Lys Val Lys Phe Asp Glu Leu Ser
                165                 170                 175

Leu Lys Leu Thr Gly Lys Thr Asp Lys Glu Ile Arg Glu Thr Leu Thr
                180                 185                 190

Arg Arg Tyr Lys Phe Ala Ile Arg Arg Leu Ala Gln Thr Asn Ser Glu
            195                 200                 205

Asp Val Phe Ser Leu Ala Met Thr Ala Phe Ala Arg Glu Ile Asp Pro
        210                 215                 220

His Thr Asn Tyr Leu Ser Pro Arg Asn Thr Glu Gln Phe Asn Thr Glu
225                 230                 235                 240

Met Ser Leu Ser Leu Glu Gly Ile Gly Ala Val Leu Gln Met Asp Asp
                245                 250                 255

Asp Tyr Thr Val Ile Asn Ser Met Val Ala Gly Gly Pro Ala Ala Lys
            260                 265                 270

Ser Lys Ala Ile Ser Val Gly Asp Lys Ile Val Gly Val Gly Gln Thr
        275                 280                 285
```

```
Gly Lys Pro Met Val Asp Val Ile Gly Trp Arg Leu Asp Asp Val Val
    290             295             300

Ala Leu Ile Lys Gly Pro Lys Gly Ser Lys Val Arg Leu Glu Ile Leu
305             310             315             320

Pro Ala Gly Lys Gly Thr Lys Thr Arg Thr Val Thr Leu Thr Arg Glu
                325             330             335

Arg Ile Arg Leu Glu Asp Arg Ala Val Lys Met Ser Val Lys Thr Val
            340             345             350

Gly Lys Glu Lys Val Gly Val Leu Asp Ile Pro Gly Phe Tyr Val Gly
            355             360             365

Leu Thr Asp Asp Val Lys Val Gln Leu Gln Lys Leu Glu Lys Gln Asn
    370             375             380

Val Ser Ser Val Ile Ile Asp Leu Arg Ser Asn Gly Gly Gly Ala Leu
385             390             395             400

Thr Glu Ala Val Ser Leu Ser Gly Leu Phe Ile Pro Ala Gly Pro Ile
                405             410             415

Val Gln Val Arg Asp Asn Asn Gly Lys Val Arg Glu Asp Ser Asp Thr
            420             425             430

Asp Gly Gln Val Phe Tyr Lys Gly Pro Leu Val Val Leu Val Asp Arg
            435             440             445

Phe Ser Ala Ser Ala Ser Glu Ile Phe Ala Ala Ala Met Gln Asp Tyr
    450             455             460

Gly Arg Ala Leu Val Val Gly Glu Pro Thr Phe Gly Lys Gly Thr Val
465             470             475             480

Gln Gln Tyr Arg Ser Leu Asn Arg Ile Tyr Asp Gln Met Leu Arg Pro
            485             490             495

Glu Trp Pro Ala Leu Gly Ser Val Gln Tyr Thr Ile Gln Lys Phe Tyr
            500             505             510

Arg Val Asn Gly Gly Ser Thr Gln Arg Lys Gly Val Thr Pro Asp Ile
            515             520             525

Ile Met Pro Thr Gly Asn Glu Glu Thr Glu Thr Gly Glu Lys Phe Glu
    530             535             540

Asp Asn Ala Leu Pro Trp Asp Ser Ile Asp Ala Ala Thr Tyr Val Lys
545             550             555             560

Ser Gly Asp Leu Thr Ala Phe Glu Pro Glu Leu Leu Lys Glu His Asn
            565             570             575

Ala Arg Ile Ala Lys Asp Pro Glu Phe Gln Asn Ile Met Lys Asp Ile
            580             585             590

Ala Arg Phe Asn Ala Met Lys Asp Lys Arg Asn Ile Val Ser Leu Asn
            595             600             605

Tyr Ala Val Arg Glu Lys Glu Asn Asn Glu Asp Asp Ala Thr Arg Leu
    610             615             620

Ala Arg Leu Asn Glu Arg Phe Lys Arg Glu Gly Lys Pro Glu Leu Lys
625             630             635             640

Lys Leu Asp Asp Leu Pro Lys Asp Tyr Gln Glu Pro Asp Pro Tyr Leu
            645             650             655

Asp Glu Thr Val Asn Ile Ala Leu Asp Leu Ala Lys Leu Glu Lys Ala
            660             665             670

Arg Pro Ala Glu Gln Pro Ala Pro Val Lys
    675             680
```

<210> SEQ ID NO 72
<211> LENGTH: 214
<212> TYPE: PRT

<213> ORGANISM: Pseudomonas putida

<400> SEQUENCE: 72

Met Pro Met Leu Lys Arg Phe Ala Pro Leu Val Pro Leu Ala Leu Val
1               5                   10                  15

Thr Leu Leu Phe Gly Cys Ala Ala Gln Gly Pro Val Ser Gln Pro Gln
            20                  25                  30

Asp His Thr Pro Ile Thr Ala Gln Ser Ala Ile Asn Ala Lys Ala Ser
        35                  40                  45

Ser Ser Ser Val Phe Gly Glu Pro Glu Glu Leu Ala Thr Glu Asp Asp
    50                  55                  60

Leu Ala Ser Phe Ser Gly Gly Lys Pro Tyr Gln Leu Pro Val Leu Ala
65                  70                  75                  80

Asp Ser Ile Leu Glu Arg Gly Met Ser Leu Ile Gly Thr Arg Tyr Arg
                85                  90                  95

Phe Gly Gly Thr Ser Glu Lys Ser Gly Phe Asp Cys Ser Gly Phe Ile
            100                 105                 110

Gly Tyr Leu Phe Arg Glu Glu Ala Gly Met Thr Leu Pro Arg Ser Thr
        115                 120                 125

Arg Glu Met Ile Asn Val Asp Ala Pro Lys Val Ala Arg Asn Lys Leu
    130                 135                 140

Lys Pro Gly Asp Leu Leu Phe Phe Ser Thr Asn Gly Arg Gly Arg Val
145                 150                 155                 160

Ser His Ala Gly Ile Tyr Leu Gly Asp Asn Gln Phe Ile His Ser Ser
                165                 170                 175

Ser Arg Arg Ser Gly Gly Val Arg Ile Asp Ser Leu Gly Asp Arg Tyr
            180                 185                 190

Trp Ser Lys Thr Phe Ile Glu Ala Lys Arg Ala Leu Ala Met Ala Pro
        195                 200                 205

Thr Asn Ile Ala Arg Asn
    210

<210> SEQ ID NO 73
<211> LENGTH: 189
<212> TYPE: PRT
<213> ORGANISM: Pseudomonas aeruginosa

<400> SEQUENCE: 73

Met Val Lys Ser Gln Pro Ile Leu Arg Tyr Ile Leu Arg Val Ala Pro
1               5                   10                  15

Ala Ile Ala Val Ala Val Leu Leu Ser Ala Cys Ser Ser Thr Ser Thr
            20                  25                  30

Ala Arg Asn Met His Ser Glu Thr His Ala Val Gly Ser Gly Asp Leu
        35                  40                  45

Ser Ser Leu Gln Ala Ser Gln Asp Glu Phe Glu Thr Met Val Arg Asn
    50                  55                  60

Leu Asp Val Lys Ser Arg Leu Met Asp Gln Tyr Ala Ser Trp Lys Gly
65                  70                  75                  80

Val Arg Tyr Arg Leu Gly Gly Ser Thr Arg Lys Gly Ile Asp Cys Ser
                85                  90                  95

Ala Phe Val Gln Arg Thr Phe Arg Glu Gln Phe Gly Leu Glu Leu Pro
            100                 105                 110

Arg Ser Thr Ser Glu Gln Gln Glu Thr Gly Lys Ser Ile Ser Arg Thr
        115                 120                 125

Gln Leu Arg Thr Gly Asp Leu Val Leu Phe Arg Ala Gly Ser Thr Gly

```
        130             135             140

Arg His Val Gly Ile Tyr Leu Gly Asn Asn Gln Phe Val His Ala Ser
145             150             155             160

Thr Ser Ser Gly Val Thr Ile Ser Ser Met Asp Glu Pro Tyr Trp Lys
                165             170             175

Lys Arg Tyr Asn Glu Ala Arg Arg Val Leu Ser Arg Ser
            180             185
```

<210> SEQ ID NO 74
<211> LENGTH: 1338
<212> TYPE: DNA
<213> ORGANISM: Pseudomonas fluorescens

<400> SEQUENCE: 74

```
atgtccatga ctccccgcga aatcgtccat gaactcaatc gccatatcat cggccaggac      60
gatgccaagc gcgccgttgc cattgcgctg cgtaaccgct ggcgccggat gcaactgccg     120
gaagaactgc gcgttgaagt aacgcccaag aacatcctga tgatcggccc caccggcgtg     180
ggtaaaaccg agatcgcccg cgcctggcc aaactggcca atgcaccgtt catcaaggtc      240
gaagcgacca agttcaccga agtcggctat gtgggccgcg atgtcgagtc gatcattcgt     300
gacctggctg acgccgccct gaagatgctg cgcgaacagg aagtaaccaa ggtcagccac     360
cgcgccgaag acgccgctga agagcgcatc ctcgacgccc tgttgccacc ggcacgcatg     420
ggtttcaacg aagacgccgc accggctacc gattccaaca ctcgccagct gttccgcaag     480
cgcctgcgtg aaggccagct ggatgacaag gaaatcgaga tcgaagtggc tgaagtgtcc     540
ggcgtggata tttctgcccc gcctggcatg gaagaaatga ccagccagct gcagaacctg     600
ttcgccaaca tgggcaaggg caagaagaaa agccgcaagc tcaaggtgaa agaggcgctc     660
aagctcgtgc gcgacgaaga agccgggcgc ctggtcaatg aggaagaact caaggccaag     720
gccctggaag cggtcgagca acatggcatc gtgtttatcg acgagatcga caaagtggcc     780
aagcgaggca actcaggcgg cgtggatgtg tcccgcgaag gcgtgcagcg cgatttgctg     840
ccgctgatcg agggctgcac ggtcaacacc aagctgggca tggtcaagac tgaccacatc     900
ctgtttatcg cttccggtgc tttccacctg agcaagccca gcgacctggt gcccgagctg     960
caaggccgct tgccgattcg ggtggagctc aaggcgctga cgccgggcga cttcgagcgc    1020
atcctcagcg agccgcatgc ctcgctcacc gagcagtacc gcgagttgct gaaaaccgaa    1080
gggctgggta tcgaattcca ggcagacggg atcaagcgcc tggcggagat cgcctggcag    1140
gtcaacgaga agaccgagaa catcggtgcc cgtcgcctgc ataccttgct tgagcgcctg    1200
ctggaggaag tgtccttcag tgccggcgac atggccggtg cgcagaatgg cgaagcgatc    1260
aagatcgatg ctgattacgt caacagccac ttgggcgaat ggcgcagaa cgaagatctg     1320 tctcgttata tcctgtaa                                                  1338
```

<210> SEQ ID NO 75
<211> LENGTH: 531
<212> TYPE: DNA
<213> ORGANISM: Pseudomonas fluorescens

<400> SEQUENCE: 75

```
atgaccacca tcgtttcagt acgtcgccac ggcaaagttg tcatgggcgg cgacggccag      60
gtttccctgg caacaccgt gatgaaaggc aacgccaaga aagtcgccg cctgtaccac      120 ggccaggtgc ttgccggctt cgcaggcgca accgccgacg cctttaccct gttcgagcgt     180
```

-continued

```
ttcgaaggcc agcttgagaa acaccagggc cacctggtgc gcgccgctgt ggaactagcc      240
aaagaatggc gcaccgaccg ctccctcagc cgcctggagg ccatgctcgc ggttgcgaac      300
aaagacgctt ccctgatcat cactggcaac ggcgacgtgg ttgaacccga gcatggcctg      360
atcgccatgg gttccggcgg cggctacgcc caggctgcgg ccagcgcgct gttgaagaaa      420
accgacctgt cggcccgtga aatcgtcgag accgccctgg gtatcgctgg cgatatctgc      480
gtgttcacca accacaacca gaccattgag gagcaggacc tcgccgagta a               531
```

<210> SEQ ID NO 76
<211> LENGTH: 196
<212> TYPE: PRT
<213> ORGANISM: Pseudomonas fluorescens

<400> SEQUENCE: 76

```
Met Ser Lys Thr Leu Glu Phe Phe Phe Asp Leu Gly Ser Pro Ala Thr
1               5                   10                  15

Tyr Leu Ala Tyr Thr Arg Leu Pro Ala Leu Cys Ala Glu Thr Gly Ala
                20                  25                  30

Gln Val Val Tyr Gln Pro Met Leu Leu Gly Gly Val Phe Lys Ala Thr
            35                  40                  45

Gly Asn Ala Ser Pro Ile Thr Val Pro Ala Lys Gly Arg Tyr Met Leu
        50                  55                  60

Asp Asp Leu Ala Arg Tyr Ala Lys Arg Tyr Asn Val Pro Leu Arg Phe
65                  70                  75                  80

Asn Pro His Phe Pro Ile Asn Thr Leu Leu Leu Met Arg Ala Val Thr
                85                  90                  95

Gly Ile Gln Ile His Gln Pro Glu Arg Phe Leu Asp Phe Ile Gly Cys
            100                 105                 110

Leu Phe Arg Ala Leu Trp Val Glu Gly Arg His Leu Gly Asp Pro Glu
        115                 120                 125

Val Val Ala Asn Val Leu Thr Glu Gln Gly Phe Asp Pro Glu Gln Val
        130                 135                 140

Leu Ala Leu Ser Asn Asp Ala Ala Val Lys Asp Ala Leu Lys Asp Lys
145                 150                 155                 160

Thr Glu Gln Ala Ile Lys Arg Gly Val Phe Gly Ala Pro Ser Phe Phe
                165                 170                 175

Val Gly Asn Gln Leu Phe Phe Gly Gln Asp Arg Leu Asp Phe Val Arg
            180                 185                 190

Glu Ala Leu Ser
        195
```

<210> SEQ ID NO 77
<211> LENGTH: 211
<212> TYPE: PRT
<213> ORGANISM: Pseudomonas fluorescens

<400> SEQUENCE: 77

```
Met Arg Asn Leu Ile Leu Ser Ala Ala Leu Val Thr Ala Ser Leu Phe
1               5                   10                  15

Gly Met Thr Ala Gln Ala Ala Asp Val Pro Leu Glu Ala Gly Lys Thr
                20                  25                  30

Tyr Val Glu Leu Ala Asn Pro Val Pro Val Ala Val Pro Gly Lys Ile
            35                  40                  45

Glu Val Val Glu Leu Phe Trp Tyr Gly Cys Pro His Cys Tyr Ala Phe
        50                  55                  60
```

-continued

Glu Pro Thr Ile Asn Pro Trp Ala Glu Lys Leu Pro Lys Asp Val Asn
65                  70                  75                  80

Phe Arg Arg Ile Pro Ala Met Phe Gly Gly Pro Trp Asp Ala His Gly
                85                  90                  95

Gln Leu Phe Leu Thr Leu Glu Ala Met Gly Val Glu His Lys Val His
            100                 105                 110

Asn Ala Val Phe Glu Ala Ile Gln Lys Gln Gly Lys Arg Leu Thr Lys
        115                 120                 125

Pro Asp Glu Met Ala Asp Phe Val Ala Thr Gln Gly Val Asp Lys Asp
        130                 135                 140

Lys Phe Leu Ala Thr Phe Asn Ser Phe Ala Ile Gln Gly Gln Ile Lys
145                 150                 155                 160

Gln Ala Lys Glu Leu Ala Gln Lys Tyr Gly Val Gln Gly Val Pro Thr
                165                 170                 175

Leu Ile Val Asn Gly Lys Tyr Arg Phe Asp Leu Gly Ser Thr Gly Gly
            180                 185                 190

Pro Glu Ala Thr Leu Asn Val Ala Asp Gln Leu Ile Ala Lys Glu Arg
            195                 200                 205

Ala Ala Lys
    210

<210> SEQ ID NO 78
<211> LENGTH: 168
<212> TYPE: PRT
<213> ORGANISM: Pseudomonas fluorescens

<400> SEQUENCE: 78

Met Ile Asp Asp Met Arg Leu Gly Arg Glu Arg Arg Phe Leu Val Leu
1                   5                   10                  15

Leu Gly Ile Ile Cys Leu Ala Leu Ile Gly Gly Ala Leu Tyr Met Gln
                20                  25                  30

Val Val Leu Gly Glu Ala Pro Cys Pro Leu Cys Ile Leu Gln Arg Tyr
            35                  40                  45

Ala Leu Leu Leu Ile Ala Leu Phe Ala Phe Ile Gly Ala Ala Met Arg
        50                  55                  60

Thr Lys Gly Ala Leu Thr Phe Phe Glu Gly Leu Val Val Leu Ser Ala
65                  70                  75                  80

Leu Gly Gly Val Ala Ala Ala Gly His His Val Tyr Thr Gln Phe Phe
                85                  90                  95

Pro Gln Val Ser Cys Gly Ile Asp Val Leu Gln Pro Ile Val Asp Asp
            100                 105                 110

Leu Pro Leu Ala Lys Val Phe Pro Leu Gly Phe Gln Val Asp Gly Phe
        115                 120                 125

Cys Ser Thr Pro Tyr Pro Pro Ile Leu Gly Leu Ser Leu Ala Gln Trp
        130                 135                 140

Ala Leu Val Ala Phe Val Leu Thr Ala Ile Leu Val Pro Leu Cys Ile
145                 150                 155                 160

Tyr Arg Asn Arg His Pro Lys Ala
                165

<210> SEQ ID NO 79
<211> LENGTH: 729
<212> TYPE: DNA
<213> ORGANISM: Pseudomonas fluorescens

<400> SEQUENCE: 79

-continued

```
atgcgcttga cccagattat tgccgccgca gccattgcgt tggtttccac ctttgcgctc      60
gccgatgatg cggccgagca gaccatccgc aagagcctgg ccaacctggc gctcgacacg     120
cctatcgaaa gcattagcgc cagccccatg gccggcctgt acgaagtcaa gctcaagggc     180
agccgcgtgc tgtacgccag tgccgatggc cagtacatcg tccagggcta cctgttccag     240
ctcaaggacg gcaagccggt caacctgacc gagaaggccg agcgcctggg cgtgtccaag     300
ctgatcaacg gcatcccggt ggctgaaacc gtggtttacc cggccattgg cgaaaccaag     360
acccacatca ccgtgttcac cgacaccacc tgcccgtact gccacaagct gcacgctgaa     420
atcccggcac tgaacaagct gggcgtggaa gtgcgctacg tcgcgttccc cgcgccagggc    480 ctgggttcgc cgggtgacga gcagttgcaa gccgtatggt gttcggccga caaaaaggcg     540
gccatggaca agatggtcga cggcaaggaa atcaaatcgg ccaaatgcgc caacccggtt     600
tccaagcagt tcgccctggg ccagtccatt ggtgtgaacg gtacaccggc catcgtttttg    660 gccgacggcc aggtgattcc gggctaccag ccggcgccgc aagttgccaa actggcactg     720
ggtgccaag                                                            729
```

```
<210> SEQ ID NO 80
<211> LENGTH: 575
<212> TYPE: PRT
<213> ORGANISM: Pseudomonas fluorescens

<400> SEQUENCE: 80

Met Arg His Leu Phe Thr Phe Leu Leu Val Leu Phe Ala Gly Phe Ala
1               5                   10                  15

Gln Ala Ala Pro Gly Ser Pro Phe Glu Thr Lys Pro Asp Phe Leu Pro
                20                  25                  30

Val Gly Lys Ala Phe Ala Phe Thr Ser Glu Arg Leu Glu Ser Gly Glu
            35                  40                  45

Thr Gln Leu Phe Trp Gln Ile Ala Asp Gly Tyr Tyr Leu Tyr Gln Gln
        50                  55                  60

Arg Met Lys Phe Asp Gly Leu Ala Glu Lys Pro Val Leu Pro Glu Gly
65                  70                  75                  80

Glu Ala His Ser Asp Glu Phe Phe Gly Glu Gln Gln Val Tyr Arg Gln
                85                  90                  95

Gly Leu Glu Val Lys Ile Pro Ala Gly Thr Thr Gly Gln Val Lys Leu
            100                 105                 110

Gly Trp Gln Gly Cys Ala Asp Ala Gly Leu Cys Tyr Pro Pro Gln Ser
            115                 120                 125

Ile Thr Val Asp Leu Gly Gly Asn Pro Ala Val Ala Ala Thr Ala Gln
        130                 135                 140

Ala Gln Asp Gln Ser Leu Ala Ser Gly Leu Gln Gln Arg Ser Leu Gly
145                 150                 155                 160

Trp Ser Leu Leu Val Phe Phe Gly Leu Gly Leu Leu Leu Ala Phe Ala
                165                 170                 175

Pro Cys Ser Leu Pro Met Leu Pro Ile Leu Ala Gly Leu Val Val Gly
            180                 185                 190

Ser Gly Ala Ser Pro Arg Arg Gly Phe Ala Leu Ala Gly Ser Tyr Val
            195                 200                 205

Val Cys Met Ala Leu Val Tyr Ala Ala Leu Gly Val Met Ala Ala Leu
        210                 215                 220

Leu Gly Ala Asn Leu Ala Ala Leu Leu Gln Thr Pro Trp Ile Leu Gly
225                 230                 235                 240
```

-continued

Ser Phe Ala Ala Leu Phe Val Leu Leu Ala Leu Pro Met Phe Gly Phe
                245                 250                 255

Phe Glu Leu Gln Leu Pro Ala Phe Leu Arg Asp Arg Leu Asp Asn Val
                260                 265                 270

Ser Arg Gln Gln Ser Gly Gly Ser Leu Val Gly Ala Gly Val Leu Gly
                275                 280                 285

Ala Leu Ser Gly Leu Leu Val Gly Pro Cys Met Thr Ala Pro Leu Ala
        290                 295                 300

Gly Ala Leu Leu Tyr Ile Ala Gln Ser Gly Asn Ala Leu His Gly Gly
305                 310                 315                 320

Leu Ile Leu Phe Ala Met Gly Ile Gly Ile Gly Ile Pro Leu Leu Leu
                325                 330                 335

Leu Val Thr Val Gly Asn Arg Phe Leu Pro Lys Pro Gly Thr Trp Met
                340                 345                 350

Asn Val Leu Lys Gly Ile Phe Gly Phe Leu Phe Leu Gly Thr Ala Val
                355                 360                 365

Leu Met Ile Arg Pro Val Val Gly Asp Ser Leu Trp Ile Gly Leu Trp
        370                 375                 380

Gly Ala Leu Ala Leu Val Met Ala Tyr Cys Gly Trp Ala Leu Ala Arg
385                 390                 395                 400

Glu Ser Gly Leu Ala Ala Lys Val Phe Gly Ala Gly Ser Leu Val Leu
                405                 410                 415

Gly Leu Trp Gly Ala Val Leu Val Val Gly Ala Ala Gly Gly Ser Asp
                420                 425                 430

Glu Leu Trp Gln Pro Leu Lys Val Tyr Ser Gly Ser Arg Val Ala Asp
                435                 440                 445

Ala Pro Ser Ala His Asp Ala Phe Thr Thr Val Ser Asp Pro Ala Val
        450                 455                 460

Leu Gln Ser Gln Leu Asp Ser Ala Lys Ala Gln Gly Gln Trp Val Leu
465                 470                 475                 480

Leu Asp Tyr Tyr Ala Asp Trp Cys Val Ser Cys Lys Ile Met Glu Lys
                485                 490                 495

Gln Val Phe Gly Lys Pro Glu Val Met Asp Ala Leu Lys Asp Val Arg
                500                 505                 510

Leu Leu Arg Leu Asp Val Thr Ala Asp Asn Ala Ala Ser Arg Glu Leu
                515                 520                 525

Leu Gly Arg Tyr Lys Val Pro Gly Pro Pro Ser Phe Val Trp Ile Gly
        530                 535                 540

Pro Asp Gly Glu Glu Arg Arg Ala Gln Arg Ile Thr Gly Glu Val Asp
545                 550                 555                 560

Ala Ala Ala Phe Leu Gln Arg Trp Thr Gln Thr Arg Asp Ala Arg
                565                 570                 575

<210> SEQ ID NO 81
<211> LENGTH: 253
<212> TYPE: PRT
<213> ORGANISM: Pseudomonas fluorescens

<400> SEQUENCE: 81

Met Pro Arg Leu Arg His Leu Leu Thr Leu Leu Pro Leu Thr Leu Ala
1               5                   10                  15

Ala Ala Leu Ala Gln Ala Glu Asp Leu Pro Ala Pro Ile Lys Gln Ile
                20                  25                  30

Glu Ala Lys Gly Ala Lys Ile Ile Gly Lys Phe Asp Ala Pro Ser Gly
        35                  40                  45

```
Leu Thr Gly Tyr Ala Ala Gln Tyr Gln Asn Arg Gly Met Ala Leu Tyr
    50                  55                  60

Leu Thr Ala Asp Gly Lys Asn Val Ile Ala Gly Asn Leu Tyr Asp Ala
65                  70                  75                  80

Gln Gly Asn Asp Leu Ser Thr Ala Pro Leu Glu Lys Leu Val Tyr Ala
                85                  90                  95

Pro Met Ala Lys Glu Val Trp Ala Lys Met Glu Asn Ser Ser Trp Ile
                100                 105                 110

Gln Asp Gly Asp Lys Asn Ala Pro Arg Thr Ile Tyr Leu Phe Ser Asp
                115                 120                 125

Pro Asn Cys Pro Tyr Cys Asn Met Phe Trp Glu Gln Ala Arg Pro Trp
    130                 135                 140

Val Lys Ala Gly Lys Val Gln Leu Arg His Ile Met Val Gly Ile Ile
145                 150                 155                 160

Arg Glu Asp Ser Pro Gly Lys Ser Ala Ala Leu Leu Ala Ala Lys Asp
                165                 170                 175

Pro Gln Lys Ala Leu Gln Asp His Glu Ala Ala Gly Lys Gly Ser Lys
                180                 185                 190

Leu Lys Ala Leu Glu Lys Ile Pro Ala Glu Val Glu Ala Lys Leu Asp
                195                 200                 205

Ala Asn Met Lys Leu Met Asp Glu Leu Glu Leu Ser Ala Thr Pro Ala
    210                 215                 220

Ile Phe Tyr Leu Asp Asp Lys Gly Gly Leu Gln Gln Gln Gly Ala
225                 230                 235                 240

Pro Ser Pro Asp Lys Leu Val Lys Ile Leu Gly Pro Lys
                245                 250
```

<210> SEQ ID NO 82
<211> LENGTH: 440
<212> TYPE: PRT
<213> ORGANISM: Mus musculus

<400> SEQUENCE: 82

```
Met Ala Arg Leu Val Leu Gly Leu Val Ser Cys Thr Phe Phe Leu Ala
1               5                   10                  15

Val Ser Gly Leu Tyr Ser Ser Ser Asp Asp Val Ile Glu Leu Thr Pro
                20                  25                  30

Ser Asn Phe Asn Arg Glu Val Ile Gln Ser Asp Gly Leu Trp Leu Val
                35                  40                  45

Glu Phe Tyr Ala Pro Trp Cys Gly His Cys Gln Arg Leu Thr Pro Glu
    50                  55                  60

Trp Lys Lys Ala Ala Thr Ala Leu Lys Asp Val Val Lys Val Gly Ala
65                  70                  75                  80

Val Asn Ala Asp Lys His Gln Ser Leu Gly Gly Gln Tyr Gly Val Gln
                85                  90                  95

Gly Phe Pro Thr Ile Lys Ile Phe Gly Ala Asn Lys Asn Lys Pro Glu
                100                 105                 110

Asp Tyr Gln Gly Gly Arg Thr Gly Glu Ala Ile Val Asp Ala Ala Leu
                115                 120                 125

Ser Ala Leu Arg Gln Leu Val Lys Asp Arg Leu Gly Gly Arg Ser Gly
    130                 135                 140

Gly Tyr Ser Ser Gly Lys Gln Gly Arg Gly Asp Ser Ser Ser Lys Lys
145                 150                 155                 160

Asp Val Val Glu Leu Thr Asp Asp Thr Phe Asp Lys Asn Val Leu Asp
```

-continued

```
                165               170               175

Ser Glu Asp Val Trp Met Val Glu Phe Tyr Ala Pro Trp Cys Gly His
            180               185               190

Cys Lys Asn Leu Glu Pro Glu Trp Ala Ala Ala Ala Thr Glu Val Lys
            195               200               205

Glu Gln Thr Lys Gly Lys Val Lys Leu Ala Ala Val Asp Ala Thr Val
            210               215               220

Asn Gln Val Leu Ala Ser Arg Tyr Gly Ile Lys Gly Phe Pro Thr Ile
225               230               235               240

Lys Ile Phe Gln Lys Gly Glu Ser Pro Val Asp Tyr Asp Gly Gly Arg
            245               250               255

Thr Arg Ser Asp Ile Val Ser Arg Ala Leu Asp Leu Phe Ser Asp Asn
            260               265               270

Ala Pro Pro Pro Glu Leu Leu Glu Ile Ile Asn Glu Asp Ile Ala Lys
            275               280               285

Lys Thr Cys Glu Glu His Gln Leu Cys Val Val Ala Val Leu Pro His
            290               295               300

Ile Leu Asp Thr Gly Ala Ala Gly Arg Asn Ser Tyr Leu Glu Val Leu
305               310               315               320

Leu Lys Leu Ala Asp Lys Tyr Lys Lys Lys Met Trp Gly Trp Leu Trp
            325               330               335

Thr Glu Ala Gly Ala Gln Tyr Glu Leu Glu Asn Ala Leu Gly Ile Gly
            340               345               350

Gly Phe Gly Tyr Pro Ala Met Ala Ala Ile Asn Ala Arg Lys Met Lys
            355               360               365

Phe Ala Leu Leu Lys Gly Ser Phe Ser Glu Gln Gly Ile Asn Glu Phe
            370               375               380

Leu Arg Glu Leu Ser Phe Gly Arg Gly Ser Thr Ala Pro Val Gly Gly
385               390               395               400

Gly Ser Phe Pro Thr Ile Thr Pro Arg Glu Pro Trp Asp Gly Lys Asp
            405               410               415

Gly Glu Leu Pro Val Glu Asp Asp Ile Asp Leu Ser Asp Val Glu Leu
            420               425               430

Asp Asp Leu Glu Lys Asp Glu Leu
            435               440
```

```
<210> SEQ ID NO 83
<211> LENGTH: 445
<212> TYPE: PRT
<213> ORGANISM: Mus musculus

<400> SEQUENCE: 83

Met Arg Val Ile Gly Met Ala Arg Leu Val Leu Gly Leu Val Ser Cys
1               5                10               15

Thr Phe Phe Leu Ala Val Ser Gly Leu Tyr Ser Ser Ser Asp Asp Val
            20               25               30

Ile Glu Leu Thr Pro Ser Asn Phe Asn Arg Glu Val Ile Gln Ser Asp
            35               40               45

Gly Leu Trp Leu Val Glu Phe Tyr Ala Pro Trp Cys Gly His Cys Gln
            50               55               60

Arg Leu Thr Pro Glu Trp Lys Lys Ala Ala Thr Ala Leu Lys Asp Val
65               70               75               80

Val Lys Val Gly Ala Val Asn Ala Asp Lys His Gln Ser Leu Gly Gly
            85               90               95
```

-continued

Gln Tyr Gly Val Gln Gly Phe Pro Thr Ile Lys Ile Phe Gly Ala Asn
            100                 105                 110

Lys Asn Lys Pro Glu Asp Tyr Gln Gly Gly Arg Thr Gly Glu Ala Ile
            115                 120                 125

Val Asp Ala Ala Leu Ser Ala Leu Arg Gln Leu Val Lys Asp Arg Leu
            130                 135                 140

Gly Gly Arg Ser Gly Gly Tyr Ser Ser Gly Lys Gln Gly Arg Gly Asp
145                 150                 155                 160

Ser Ser Ser Lys Lys Asp Val Val Glu Leu Thr Asp Asp Thr Phe Asp
                165                 170                 175

Lys Asn Val Leu Asp Ser Glu Asp Val Trp Met Val Glu Phe Tyr Ala
                180                 185                 190

Pro Trp Cys Gly His Cys Lys Asn Leu Glu Pro Glu Trp Ala Ala Ala
            195                 200                 205

Ala Thr Glu Val Lys Glu Gln Thr Lys Gly Lys Val Lys Leu Ala Ala
        210                 215                 220

Val Asp Ala Thr Met Asn Gln Val Leu Ala Ser Arg Tyr Gly Ile Lys
225                 230                 235                 240

Gly Phe Pro Thr Ile Lys Ile Phe Gln Lys Gly Glu Ser Pro Val Asp
                245                 250                 255

Tyr Asp Gly Gly Arg Thr Arg Ser Asp Ile Val Ser Arg Ala Leu Asp
            260                 265                 270

Leu Phe Ser Asp Asn Ala Pro Pro Glu Leu Leu Glu Ile Ile Asn
            275                 280                 285

Glu Asp Ile Ala Lys Lys Thr Cys Glu Glu His Gln Leu Cys Val Val
        290                 295                 300

Ala Val Leu Pro His Ile Leu Asp Thr Gly Ala Ala Gly Arg Asn Ser
305                 310                 315                 320

Tyr Leu Glu Val Leu Leu Lys Leu Ala Asp Lys Tyr Lys Lys Lys Met
                325                 330                 335

Trp Gly Trp Leu Trp Thr Glu Ala Gly Ala Gln Tyr Glu Leu Glu Asn
            340                 345                 350

Ala Leu Gly Ile Gly Gly Phe Gly Tyr Pro Ala Met Ala Ala Ile Asn
            355                 360                 365

Ala Arg Lys Met Lys Phe Ala Leu Leu Lys Gly Ser Phe Ser Glu Gln
        370                 375                 380

Gly Ile Asn Glu Phe Leu Arg Glu Leu Ser Phe Gly Arg Gly Ser Thr
385                 390                 395                 400

Ala Pro Val Gly Gly Gly Ser Phe Pro Thr Ile Thr Pro Arg Glu Pro
            405                 410                 415

Trp Asp Gly Lys Asp Gly Glu Leu Pro Val Glu Asp Asp Ile Asp Leu
            420                 425                 430

Ser Asp Val Glu Leu Asp Asp Leu Glu Lys Asp Glu Leu
            435                 440                 445

<210> SEQ ID NO 84
<211> LENGTH: 440
<212> TYPE: PRT
<213> ORGANISM: Rattus norvegicus

<400> SEQUENCE: 84

Met Ala Arg Leu Val Leu Gly Leu Val Ser Cys Thr Phe Phe Leu Ala
1               5                   10                  15

Val Ser Ala Leu Tyr Ser Ser Ser Asp Asp Val Ile Glu Leu Thr Pro
            20                  25                  30

-continued

```
Ser Asn Phe Asn Arg Glu Val Ile Gln Ser Asp Ser Leu Trp Leu Val
    35                  40                  45

Glu Phe Tyr Ala Pro Trp Cys Gly His Cys Gln Arg Leu Thr Pro Glu
    50                  55                  60

Trp Lys Lys Ala Ala Ser Ala Leu Lys Asp Val Val Lys Val Gly Ala
65                  70                  75                  80

Val Asn Ala Asp Lys His Gln Ser Leu Gly Gly Gln Tyr Gly Val Gln
                85                  90                  95

Gly Phe Pro Thr Ile Lys Ile Phe Gly Ala Asn Lys Asn Lys Pro Glu
                100                 105                 110

Asp Tyr Gln Gly Gly Arg Thr Gly Glu Ala Ile Val Asp Ala Ala Leu
            115                 120                 125

Ser Ala Leu Arg Gln Leu Val Lys Asp Arg Leu Gly Gly Arg Ser Gly
    130                 135                 140

Gly Tyr Ser Ser Gly Lys Gln Gly Arg Gly Asp Ser Ser Ser Lys Lys
145                 150                 155                 160

Asp Val Val Glu Leu Thr Asp Asp Thr Phe Asp Lys Asn Val Leu Asp
                165                 170                 175

Ser Glu Asp Val Trp Met Val Glu Phe Tyr Ala Pro Trp Cys Gly His
            180                 185                 190

Cys Lys Asn Leu Glu Pro Glu Trp Ala Ala Ala Ala Thr Glu Val Lys
            195                 200                 205

Glu Gln Thr Lys Gly Lys Val Lys Leu Ala Ala Val Asp Ala Thr Val
    210                 215                 220

Asn Gln Val Leu Ala Ser Arg Tyr Gly Ile Lys Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270

Ala Pro Pro Pro Glu Leu Leu Glu Ile Ile Asn Glu Asp Ile Ala Lys
            275                 280                 285

Lys Thr Cys Glu Glu His Gln Leu Cys Val Val Ala Val Leu Pro His
    290                 295                 300

Ile Leu Asp Thr Gly Ala Thr Gly Arg Asn Ser Tyr Leu Glu Val Leu
305                 310                 315                 320

Leu Lys Leu Ala Asp Lys Tyr Lys Lys Met Trp Gly Trp Leu Trp
            325                 330                 335

Thr Glu Ala Gly Ala Gln Tyr Glu Leu Glu Asn Ala Leu Gly Ile Gly
            340                 345                 350

Gly Phe Gly Tyr Pro Ala Met Ala Ala Ile Asn Ala Arg Lys Met Lys
            355                 360                 365

Phe Ala Leu Leu Lys Gly Ser Phe Ser Glu Gln Gly Ile Asn Glu Phe
    370                 375                 380

Leu Arg Glu Leu Ser Phe Gly Arg Gly Ser Thr Ala Pro Val Gly Gly
385                 390                 395                 400

Gly Ser Phe Pro Asn Ile Thr Pro Arg Glu Pro Trp Asp Gly Lys Asp
                405                 410                 415

Gly Glu Leu Pro Val Glu Asp Asp Ile Asp Leu Ser Asp Val Glu Leu
            420                 425                 430

Asp Asp Leu Glu Lys Asp Glu Leu
        435                 440
```

-continued

```
<210> SEQ ID NO 85
<211> LENGTH: 448
<212> TYPE: PRT
<213> ORGANISM: Equus caballus

<400> SEQUENCE: 85

Met Lys Pro Ala Ile Asn Gly Val Leu Phe Val Val Ser Pro Gly Leu
1               5                   10                  15

Met Ser Cys Thr Leu Phe Leu Ala Val Asn Gly Leu Tyr Ser Ser Ser
                20                  25                  30

Asp Asp Val Ile Glu Leu Thr Pro Ser Asn Phe Asn Arg Glu Val Ile
            35                  40                  45

Gln Ser Asp Ser Leu Trp Leu Val Glu Phe Tyr Ala Pro Trp Cys Gly
        50                  55                  60

His Cys Gln Arg Leu Thr Pro Glu Trp Lys Lys Val Ala Thr Ala Leu
65                  70                  75                  80

Lys Asp Val Val Lys Val Gly Ala Val Asp Ala Asp Lys His Gln Ser
                85                  90                  95

Leu Gly Gly Gln Tyr Gly Val Gln Gly Phe Pro Thr Ile Lys Ile Phe
            100                 105                 110

Gly Ala Asn Lys Asn Arg Pro Glu Asp Tyr Gln Gly Gly Arg Ser Gly
        115                 120                 125

Glu Ala Ile Val Asp Ala Ala Leu Ser Ala Leu Arg Gln Leu Val Lys
        130                 135                 140

Asp Arg Leu Gly Gly Arg Ser Gly Gly Tyr Ser Ser Gly Lys Gln Gly
145                 150                 155                 160

Arg Ser Glu Ser Ser Ser Lys Lys Asp Val Ile Glu Leu Thr Asp Asp
                165                 170                 175

Ser Phe Asp Lys Asn Val Leu Asp Ser Glu Asp Val Trp Met Val Glu
            180                 185                 190

Phe Tyr Ala Pro Trp Cys Gly His Cys Lys Asn Leu Glu Pro Glu Trp
            195                 200                 205

Ala Ala Ala Ala Thr Glu Val Lys Glu Gln Thr Lys Gly Lys Val Lys
        210                 215                 220

Leu Ala Ala Val Asp Ala Thr Val Asn Gln Val Leu Ala Ser Arg Tyr
225                 230                 235                 240

Gly Ile Arg Gly Phe Pro Thr Ile Lys Ile Phe Gln Lys Gly Glu Ser
                245                 250                 255

Pro Val Asp Tyr Asp Gly Gly Arg Thr Arg Ser Asp Ile Ile Ser Arg
            260                 265                 270

Ala Leu Asp Leu Phe Ser Asp Asn Ala Pro Pro Glu Leu Leu Glu
        275                 280                 285

Ile Ile Asn Glu Asp Ile Ala Lys Lys Thr Cys Glu Glu His Gln Leu
        290                 295                 300

Cys Val Val Ala Val Leu Pro His Ile Leu Asp Thr Gly Ala Ala Gly
305                 310                 315                 320

Arg Asn Ser Tyr Leu Glu Val Leu Leu Lys Leu Ala Asp Lys Tyr Lys
            325                 330                 335

Lys Lys Met Trp Gly Trp Leu Trp Thr Glu Ala Gly Ala Gln Ser Glu
            340                 345                 350

Leu Glu Thr Ala Leu Gly Ile Gly Gly Phe Gly Tyr Pro Ala Met Ala
            355                 360                 365

Ala Ile Asn Ala Arg Lys Met Lys Phe Ala Leu Leu Lys Gly Ser Phe
        370                 375                 380
```

-continued

```
Ser Glu Gln Gly Ile Asn Glu Phe Leu Arg Glu Leu Ser Phe Gly Arg
385                 390                 395                 400

Gly Ser Thr Ala Pro Val Gly Gly Gly Ala Phe Pro Ala Ile Ser Thr
                405                 410                 415

Arg Glu Pro Trp Asp Gly Lys Asp Gly Glu Leu Pro Val Glu Asp Asp
                420                 425                 430

Ile Asp Leu Ser Asp Val Glu Leu Asp Asp Leu Glu Lys Asp Glu Leu
            435                 440                 445

<210> SEQ ID NO 86
<211> LENGTH: 590
<212> TYPE: PRT
<213> ORGANISM: Sus scrofa

<400> SEQUENCE: 86

Met Ala Arg Leu Val Leu Gly Leu Met Ser Cys Thr Leu Phe Val Ala
1               5                   10                  15

Val Asn Gly Leu Tyr Ser Ser Ser Asp Asp Val Ile Glu Leu Thr Pro
            20                  25                  30

Ser Asn Phe Asn Arg Glu Val Ile Gln Ser Asp Ser Leu Trp Leu Val
            35                  40                  45

Glu Phe Tyr Ala Pro Trp Cys Gly His Cys Gln Arg Leu Thr Pro Glu
    50                  55                  60

Trp Lys Lys Val Ala Thr Ala Leu Lys Asp Val Val Lys Val Gly Ala
65                  70                  75                  80

Val Asp Ala Asp Lys His Gln Ser Leu Gly Gly Gln Tyr Gly Val Gln
                85                  90                  95

Gly Phe Pro Thr Ile Lys Ile Phe Gly Ser Asn Lys Asn Arg Pro Glu
            100                 105                 110

Asp Tyr Gln Gly Gly Arg Thr Gly Glu Ala Ile Val Asp Ala Ala Leu
            115                 120                 125

Ser Ala Leu Arg Gln Leu Val Lys Asp Arg Leu Gly Gly Arg Gly Gly
    130                 135                 140

Gly Tyr Ser Ser Gly Lys Gln Gly Arg Ser Glu Gly Ser Gly Lys Lys
145                 150                 155                 160

Asp Val Ile Glu Leu Thr Asp Asp Thr Phe Asp Lys Asn Val Leu Asp
                165                 170                 175

Ser Glu Asp Val Trp Met Val Glu Phe Tyr Ala Pro Trp Cys Gly His
                180                 185                 190

Cys Lys Asn Leu Glu Pro Glu Trp Ala Ala Ala Ala Thr Glu Val Lys
            195                 200                 205

Glu Gln Thr Lys Gly Lys Val Lys Leu Ala Ala Val Asp Ala Thr Val
    210                 215                 220

Asn Gln Val Leu Ala Ser Arg Tyr Gly Ile Arg Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Thr Arg Ala Leu Asp Leu Phe Ser Asp Asn
                260                 265                 270

Ala Pro Pro Pro Glu Leu Leu Glu Ile Ile Ser Glu Asp Val Ala Lys
            275                 280                 285

Lys Ser Cys Glu Glu His Gln Leu Cys Val Val Ala Val Leu Pro His
    290                 295                 300

Ile Leu Asp Thr Gly Ala Ala Gly Arg Asn Ser Tyr Leu Glu Val Leu
```

-continued

```
305              310              315              320

Leu Lys Leu Ala Asp Lys Tyr Lys Lys Lys Met Trp Gly Trp Leu Trp
                 325              330              335

Thr Glu Ala Gly Ala Gln Thr Glu Leu Glu His Ala Leu Gly Ile Gly
                 340              345              350

Gly Phe Gly Tyr Pro Ala Met Ala Ala Ile Asn Ala Arg Lys Met Lys
                 355              360              365

Phe Ala Leu Leu Lys Gly Ser Phe Ser Glu Gln Gly Ile Asn Glu Phe
                 370              375              380

Leu Arg Glu Leu Ser Phe Gly Arg Gly Ser Thr Ala Pro Val Gly Gly
385              390              395              400

Gly Ala Phe Pro Ala Ile Ser Thr Arg Glu Pro Trp Asp Gly Lys Asp
                 405              410              415

Gly Glu Val Ser Pro Ala Thr Arg Glu Pro Gly Asp Gly Lys Asp Gly
                 420              425              430

Gln Ala Ser Pro Ala Thr Arg Glu Pro Trp Asp Gly Lys Asp Gly Gln
                 435              440              445

Ala Ser Pro Ala Thr Arg Glu Pro Gly Asp Gly Lys Asp Gly Glu Ala
     450              455              460

Ser Pro Ala Glu Pro Arg Gly Gln Asp Ala Ser Arg Leu Trp Leu Ser
465              470              475              480

Phe Leu Ala Ser Leu Gly Pro Glu Ala Gly Cys Glu Pro Gly Leu Cys
                 485              490              495

Ile Arg Ala Ala Pro Arg Ala Gly Pro Ala Val Ala Pro Pro Gly Pro
                 500              505              510

Arg Gly Leu Leu Leu Ser Ser Ser Ser Ala Pro Leu Pro Pro Ala Thr
                 515              520              525

Pro Gln Ala Lys Ala Pro Gly Ser Cys Ser Pro Gly His Ser Pro Gln
     530              535              540

Ala Glu Arg Phe Ser Thr Trp Arg Glu Ala Gln Arg Gly His Phe Glu
545              550              555              560

Val Ser Leu Asp Ser Arg Thr Leu Pro Ser Gly Leu Glu Arg Pro Thr
                 565              570              575

Ser Val Ala Pro Gly Val Cys Pro Arg Asp Asp Gly Arg Ser
                 580              585              590
```

```
<210> SEQ ID NO 87
<211> LENGTH: 439
<212> TYPE: PRT
<213> ORGANISM: Mesocricetus auratus

<400> SEQUENCE: 87

Met Ala Arg Leu Gly Phe Gly Leu Val Ser Cys Thr Phe Phe Leu Ala
1                5                10               15

Ala Ser Gly Leu Tyr Ser Ser Ser Asp Asp Val Ile Glu Leu Thr Pro
                 20               25               30

Ser Asn Phe Asn Arg Glu Val Ile Gln Ser Asn Ser Leu Trp Leu Val
                 35               40               45

Glu Phe Tyr Ala Pro Trp Cys Gly His Cys Gln Arg Leu Thr Pro Glu
     50               55               60

Trp Lys Lys Ala Ala Thr Ala Leu Lys Asp Val Val Lys Val Gly Ala
65               70               75               80

Val Asp Ala Asp Lys His Gln Ser Leu Gly Gly Gln Tyr Gly Val Gln
                 85               90               95
```

Gly Phe Pro Thr Ile Lys Ile Phe Gly Ala Asn Lys Asn Lys Pro Glu
            100                 105                 110

Asp Tyr Gln Gly Gly Arg Thr Gly Glu Ala Ile Val Asp Ala Ala Leu
            115                 120                 125

Ser Ala Leu Arg Gln Leu Val Lys Asp Arg Leu Ser Gly Arg Ser Gly
        130                 135                 140

Gly Tyr Ser Ser Gly Lys Gln Gly Arg Gly Asp Ser Ser Ser Lys Lys
145                 150                 155                 160

Asp Val Ile Glu Leu Thr Asp Asp Thr Phe Asp Lys Asn Val Leu Asp
                165                 170                 175

Ser Asp Asp Val Trp Met Val Glu Phe Tyr Ala Pro Trp Cys Gly His
            180                 185                 190

Cys Lys Asn Leu Glu Pro Glu Trp Ala Thr Ala Ala Thr Glu Val Lys
        195                 200                 205

Glu Gln Thr Lys Gly Lys Val Lys Leu Ala Ala Val Asp Ala Thr Val
    210                 215                 220

Asn Gln Val Leu Ala Asn Arg Tyr Gly Ile Arg Gly Phe Pro Thr Ile
225                 230                 235                 240

Lys Ile Phe Gln Lys Gly Glu Ala Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270

Ala Pro Pro Pro Glu Leu Leu Glu Ile Ile Asn Glu Asp Val Ala Lys
            275                 280                 285

Lys Met Cys Glu Glu His Gln Leu Cys Val Val Ala Val Leu Pro His
        290                 295                 300

Ile Leu Asp Thr Gly Ala Ala Arg Asn Ser Tyr Leu Glu Ile Leu Leu
305                 310                 315                 320

Lys Leu Ala Asp Lys Tyr Lys Lys Lys Met Trp Gly Trp Leu Trp Thr
                325                 330                 335

Glu Ala Gly Ala Gln Ser Glu Leu Glu Asn Ala Leu Gly Ile Gly Gly
            340                 345                 350

Phe Gly Tyr Pro Ala Met Ala Arg Ile Asn Ala Arg Lys Met Lys Phe
            355                 360                 365

Ala Leu Leu Lys Gly Ser Phe Ser Glu Gln Gly Ile Asn Glu Phe Leu
        370                 375                 380

Arg Glu Leu Ser Phe Gly Arg Ala Ser Thr Ala Pro Val Gly Gly Gly
385                 390                 395                 400

Ser Phe Pro Ala Ile Thr Ala Arg Glu Pro Trp Asp Gly Arg Asp Gly
                405                 410                 415

Glu Leu Pro Val Glu Asp Asp Ile Asp Leu Ser Asp Val Glu Leu Asp
            420                 425                 430

Asp Leu Glu Lys Asp Glu Leu
        435

<210> SEQ ID NO 88
<211> LENGTH: 440
<212> TYPE: PRT
<213> ORGANISM: Pongo abelii

<400> SEQUENCE: 88

Met Ala Leu Leu Val Leu Gly Leu Val Ser Cys Ala Phe Phe Leu Glu
1               5                   10                  15

Val Asn Gly Leu Tyr Ser Ser Ser Asp Asp Val Ile Glu Leu Thr Pro
            20                  25                  30

-continued

```
Ser Asn Phe Asn Arg Glu Val Ile Gln Ser Asp Ser Leu Trp Leu Val
        35              40              45

Glu Phe Tyr Ala Pro Trp Cys Gly His Cys Gln Arg Leu Thr Pro Glu
    50              55              60

Trp Lys Lys Ala Ala Thr Ala Leu Lys Asp Val Val Lys Val Gly Ala
65              70              75              80

Val Asp Ala Asp Lys His His Ser Leu Gly Gly Gln Tyr Gly Val Gln
            85              90              95

Gly Phe Pro Thr Ile Lys Ile Phe Gly Ser Asn Lys Asn Arg Pro Glu
            100             105             110

Asp Tyr Gln Gly Gly Arg Thr Gly Glu Ala Ile Val Asp Ala Ala Leu
        115             120             125

Ser Ala Leu Arg Gln Leu Val Lys Asp Arg Leu Gly Gly Gln Ser Gly
    130             135             140

Gly Tyr Ser Ser Gly Lys Gln Gly Arg Ser Asp Ser Ser Ser Lys Lys
145             150             155             160

Asp Val Ile Glu Leu Thr Asp Asp Ser Phe Asp Lys Asn Val Leu Asp
            165             170             175

Ser Glu Asp Val Trp Met Val Glu Phe Tyr Ala Pro Trp Cys Gly His
            180             185             190

Cys Lys Asn Leu Glu Pro Glu Trp Ala Ala Ala Ala Ser Glu Val Lys
            195             200             205

Glu Gln Thr Lys Gly Lys Val Lys Leu Ala Ala Val Asp Ala Thr Val
    210             215             220

Asn Gln Val Leu Ala Ser Arg Tyr Gly Ile Arg Gly Phe Pro Thr Ile
225             230             235             240

Lys Ile Phe Gln Lys Gly Glu Ser Pro Val Asp Tyr Asp Gly Gly Arg
            245             250             255

Thr Arg Ser Asp Ile Val Ser Arg Ala Leu Asp Leu Phe Ser Asp Asn
            260             265             270

Ala Pro Pro Pro Glu Leu Leu Glu Ile Ile Ser Glu Asp Ile Ala Lys
            275             280             285

Arg Thr Cys Glu Glu His Gln Leu Cys Val Val Ser Val Leu Pro His
    290             295             300

Ile Leu Asp Thr Gly Ala Ala Gly Arg Asn Ser Tyr Leu Glu Val Leu
305             310             315             320

Leu Lys Leu Ala Asp Lys Tyr Lys Lys Met Trp Gly Trp Leu Trp
            325             330             335

Thr Glu Ala Gly Ala Gln Ser Glu Leu Glu Thr Ala Leu Gly Ile Gly
            340             345             350

Gly Phe Gly Tyr Pro Ala Met Ala Ala Ile Asn Ala Arg Lys Met Lys
        355             360             365

Phe Ala Leu Leu Lys Gly Ser Phe Ser Glu Gln Gly Ile Asn Glu Phe
    370             375             380

Leu Arg Glu Leu Ser Phe Gly Arg Gly Ser Thr Ala Pro Val Gly Gly
385             390             395             400

Gly Ala Phe Pro Thr Ile Val Glu Arg Glu Pro Trp Asp Gly Arg Asp
            405             410             415

Gly Glu Leu Pro Val Glu Asp Asp Ile Asp Leu Ser Asp Val Glu Leu
            420             425             430

Asp Asp Leu Gly Lys Asp Glu Leu
        435             440
```

```
<210> SEQ ID NO 89
<211> LENGTH: 454
<212> TYPE: PRT
<213> ORGANISM: Ficedula albicollis

<400> SEQUENCE: 89

Met Arg Glu Ser His Lys Cys Ser Thr Gly Gln Leu Met Ser Leu Leu
1               5                   10                  15

Phe Leu Val Gly Thr Val Ser Cys Thr Leu Phe Leu Ala Val Asn Gly
                20                  25                  30

Leu Tyr Ser Ala Ser Asp Asp Val Ile Glu Leu Thr Pro Thr Asn Phe
            35                  40                  45

Asn Lys Glu Val Ile Gln Ser Glu Ser Leu Trp Leu Val Glu Phe Tyr
        50                  55                  60

Ala Pro Trp Cys Gly His Cys Gln Arg Leu Thr Pro Glu Trp Lys Lys
65                  70                  75                  80

Ala Ala Thr Ala Leu Lys Gly Val Val Lys Val Gly Ala Val Asp Ala
                85                  90                  95

Asp Lys His Gln Ser Leu Gly Gly Gln Tyr Gly Val Arg Gly Phe Pro
            100                 105                 110

Thr Ile Lys Ile Phe Gly Ala Asn Lys Asn Lys Ala Glu Asp Tyr Gln
        115                 120                 125

Gly Gly Arg Thr Ser Asp Ala Ile Val Asp Ala Ala Leu Ser Ala Leu
    130                 135                 140

Arg Ser Leu Val Lys Glu Arg Leu Ser Gly Arg Ser Gly Gly Tyr Ser
145                 150                 155                 160

Ser Gly Lys Gln Ser Arg Gly Ser Gly Gly Asp Lys Lys Asp Val
                165                 170                 175

Ile Glu Leu Thr Asp Asp Ser Phe Asp Lys Asn Val Ile Asn Ser Asp
            180                 185                 190

Asp Val Trp Met Val Glu Phe Tyr Ala Pro Trp Cys Gly His Cys Lys
            195                 200                 205

Asn Leu Glu Pro Glu Trp Ala Ala Ala Ala Thr Glu Val Lys Glu Gln
        210                 215                 220

Thr Lys Gly Lys Val Lys Leu Ala Ala Val Asp Ala Thr Val Asn Gln
225                 230                 235                 240

Val Leu Ala Ser Arg Tyr Gly Ile Arg Gly Phe Pro Thr Ile Lys Ile
                245                 250                 255

Phe Gln Lys Gly Glu Asp Pro Val Asp Tyr Asp Gly Gly Arg Thr Arg
            260                 265                 270

Ser Asp Ile Val Ser Arg Ala Leu Asp Leu Phe Ser Asp Asn Ala Pro
        275                 280                 285

Pro Pro Glu Leu Leu Glu Ile Ile Ser Glu Asp Val Leu Lys Ser Thr
        290                 295                 300

Cys Asp Ala His Gln Leu Cys Ile Ile Ser Val Leu Pro His Ile Leu
305                 310                 315                 320

Asp Thr Gly Ala Ser Gly Arg Asn Ser Tyr Leu Asp Val Met Leu Lys
                325                 330                 335

Met Ala Glu Lys Tyr Lys Lys Lys Met Trp Gly Trp Leu Trp Thr Glu
            340                 345                 350

Ala Gly Ala Gln Pro Asp Leu Glu Ser Ser Leu Gly Ile Gly Gly Phe
        355                 360                 365

Gly Tyr Pro Ala Met Ala Ala Val Asn Ala Arg Lys Met Lys Phe Ala
    370                 375                 380
```

-continued

```
Leu Leu Lys Gly Ser Phe Ser Glu Gln Gly Ile Asn Glu Phe Leu Arg
385                 390                 395                 400

Glu Leu Ser Val Gly Arg Gly Ser Thr Ala Pro Val Gly Gly Gly Ala
                    405                 410                 415

Phe Pro Lys Ile His Ser Val Glu Pro Trp Asp Gly Lys Asp Gly Glu
                420                 425                 430

Leu Pro Val Glu Asp Asp Ile Asp Leu Ser Asp Val Asp Leu Asp Asp
                435                 440                 445

Phe Gly Lys Asp Glu Leu
        450

<210> SEQ ID NO 90
<211> LENGTH: 505
<212> TYPE: PRT
<213> ORGANISM: Homo sapiens

<400> SEQUENCE: 90

Met His Lys Ala Gln Lys Phe Ala Leu Gly Leu Leu Ala Ala Ala Ala
1               5                   10                  15

Val Ala Thr Ala Ser Asp Val Val Gln Leu Lys Lys Asp Thr Phe Asp
                20                  25                  30

Asp Phe Ile Lys Thr Asn Asp Leu Val Leu Ala Glu Phe Phe Ala Pro
            35                  40                  45

Trp Cys Gly His Cys Lys Ala Leu Ala Pro Glu Tyr Glu Glu Ala Ala
        50                  55                  60

Thr Thr Leu Lys Glu Lys Asn Ile Lys Leu Ala Lys Val Asp Cys Thr
65                  70                  75                  80

Glu Glu Thr Asp Leu Cys Gln Gln His Gly Val Glu Gly Tyr Pro Thr
                85                  90                  95

Leu Lys Val Phe Arg Gly Leu Asp Asn Val Ser Pro Tyr Lys Gly Gln
                100                 105                 110

Arg Lys Ala Ala Ala Ile Thr Ser Tyr Met Ile Lys Gln Ser Leu Pro
                115                 120                 125

Ala Val Ser Glu Val Thr Lys Asp Asn Leu Glu Glu Phe Lys Lys Ala
                130                 135                 140

Asp Lys Ala Val Leu Val Ala Tyr Val Asp Ala Ser Asp Lys Ala Ser
145                 150                 155                 160

Ser Glu Val Phe Thr Gln Val Ala Glu Lys Leu Arg Asp Asn Tyr Pro
                165                 170                 175

Phe Gly Ser Ser Ser Asp Ala Ala Leu Ala Glu Ala Glu Gly Val Lys
                180                 185                 190

Ala Pro Ala Ile Val Leu Tyr Lys Asp Phe Asp Glu Gly Lys Ala Val
                195                 200                 205

Phe Ser Glu Lys Phe Glu Val Glu Ala Ile Glu Lys Phe Ala Lys Thr
        210                 215                 220

Gly Ala Thr Pro Leu Ile Gly Glu Ile Gly Pro Glu Thr Tyr Ser Asp
225                 230                 235                 240

Tyr Met Ser Ala Gly Ile Pro Leu Ala Tyr Ile Phe Ala Glu Thr Ala
                245                 250                 255

Glu Glu Arg Lys Glu Leu Ser Asp Lys Leu Lys Pro Ile Ala Glu Ala
                260                 265                 270

Gln Arg Gly Val Ile Asn Phe Gly Thr Ile Asp Ala Lys Ala Phe Gly
                275                 280                 285

Ala His Ala Gly Asn Leu Asn Leu Lys Thr Asp Lys Phe Pro Ala Phe
```

-continued

```
            290                295                300
Ala Ile Gln Glu Val Ala Lys Asn Gln Lys Phe Pro Phe Asp Gln Glu
305                310                315                320

Lys Glu Ile Thr Phe Glu Ala Ile Lys Ala Phe Val Asp Asp Phe Val
                325                330                335

Ala Gly Lys Ile Glu Pro Ser Ile Lys Ser Glu Pro Ile Pro Glu Lys
                340                345                350

Gln Glu Gly Pro Val Thr Val Val Ala Lys Asn Tyr Asn Glu Ile
            355                360                365

Val Leu Asp Asp Thr Lys Asp Val Leu Ile Glu Phe Tyr Ala Pro Trp
            370                375                380

Cys Gly His Cys Lys Ala Leu Ala Pro Lys Tyr Glu Glu Leu Gly Ala
385                390                395                400

Leu Tyr Ala Lys Ser Glu Phe Lys Asp Arg Val Val Ile Ala Lys Val
                405                410                415

Asp Ala Thr Ala Asn Asp Val Pro Asp Glu Ile Gln Gly Phe Pro Thr
                420                425                430

Ile Lys Leu Tyr Pro Ala Gly Ala Lys Gly Gln Pro Val Thr Tyr Ser
            435                440                445

Gly Ser Arg Thr Val Glu Asp Leu Ile Lys Phe Ile Ala Glu Asn Gly
            450                455                460

Lys Tyr Lys Ala Ala Ile Ser Glu Asp Ala Glu Glu Thr Ser Ser Ala
465                470                475                480

Thr Glu Thr Thr Thr Glu Thr Ala Thr Lys Ser Glu Glu Ala Ala Lys
                485                490                495

Glu Thr Ala Thr Glu His Asp Glu Leu
                500                505
```

<210> SEQ ID NO 91
<211> LENGTH: 359
<212> TYPE: PRT
<213> ORGANISM: Schizosaccharomyces pombe

<400> SEQUENCE: 91

```
Met Arg Leu Pro Leu Leu Ser Phe Val Ile Phe Ala Leu Phe Ala Leu
1                5                10                15

Val Phe Ala Ser Gly Val Val Glu Leu Gln Ser Leu Asn Glu Leu Glu
                20                25                30

Asn Thr Ile Arg Ala Ser Lys Lys Gly Ala Leu Ile Glu Phe Tyr Ala
            35                40                45

Thr Trp Cys Gly His Cys Lys Ser Leu Ala Pro Val Tyr Glu Glu Leu
50                55                60

Gly Ala Leu Phe Glu Asp His Asn Asp Val Leu Ile Gly Lys Ile Asp
65                70                75                80

Ala Asp Thr His Ser Asp Val Ala Asp Lys Tyr His Ile Thr Gly Phe
                85                90                95

Pro Thr Leu Ile Trp Phe Pro Pro Asp Gly Ser Glu Pro Val Gln Tyr
                100                105                110

Ser Asn Ala Arg Asp Val Asp Ser Leu Thr Gln Phe Val Ser Glu Lys
            115                120                125

Thr Gly Ile Lys Lys Arg Lys Ile Val Leu Pro Ser Asn Val Val Glu
            130                135                140

Leu Asp Ser Leu Asn Phe Asp Lys Val Val Met Asp Asp Lys Lys Asp
145                150                155                160
```

-continued

```
Val Leu Val Glu Phe Tyr Ala Asp Trp Cys Gly Tyr Cys Lys Arg Leu
            165                 170                 175

Ala Pro Thr Tyr Glu Thr Leu Gly Lys Val Phe Lys Asn Glu Pro Asn
            180                 185                 190

Val Glu Ile Val Lys Ile Asn Ala Asp Val Phe Ala Asp Ile Gly Arg
            195                 200                 205

Leu His Glu Val Ala Ser Phe Pro Thr Ile Lys Phe Phe Pro Lys Asp
        210                 215                 220

Asp Lys Asp Lys Pro Glu Leu Tyr Glu Gly Asp Arg Ser Leu Glu Ser
225                 230                 235                 240

Leu Ile Glu Tyr Ile Asn Lys Lys Ser Gly Thr Gln Arg Ser Pro Asp
                245                 250                 255

Gly Thr Leu Leu Ser Thr Ala Gly Arg Ile Pro Thr Phe Asp Glu Phe
            260                 265                 270

Ala Ala Glu Phe Leu Asp Met Ser Asn Ala Ala Lys Glu Val Val Leu
            275                 280                 285

Glu Lys Val Lys Gln Leu Ala Leu Glu Asp Ser Ser Arg Trp Thr Lys
        290                 295                 300

Tyr Tyr Lys Lys Val Phe Glu Lys Ile Leu Asn Asp Glu Asn Trp Val
305                 310                 315                 320

His Lys Glu Ala Lys Arg Leu Ser Lys Leu Leu Arg Gln Lys Ser Ile
                325                 330                 335

Ala Leu Ala Ser Ala Asp Asp Phe Lys Thr Arg Leu Asn Ile Leu Asn
            340                 345                 350

Ser Phe Leu Pro Gly Asn His
            355
```

```
<210> SEQ ID NO 92
<211> LENGTH: 435
<212> TYPE: PRT
<213> ORGANISM: Haemaphysalis longicornis
<220> FEATURE:
<221> NAME/KEY: MOD_RES
<222> LOCATION: (241)..(241)
<223> OTHER INFORMATION: Any amino acid
```

```
<400> SEQUENCE: 92

Met Ala Thr Ala Leu Leu Ala Val Leu Ala Ala Leu Ser Pro Met Ala
1               5                   10                  15

Leu Ala Met Tyr Gly Pro His Thr Glu Val Val Asp Leu Ser Pro Ala
            20                  25                  30

Asn Phe Lys Asn Arg Val Val Asp Ser Asp Glu Val Trp Ile Val Glu
            35                  40                  45

Phe Tyr Ala Pro Trp Cys Gly His Cys Gln Ser Phe Ala Pro Glu Tyr
        50                  55                  60

Thr Lys Ala Ala Ala Ala Leu Lys Gly Ile Val Lys Val Gly Ala Val
65                  70                  75                  80

Asp Ala Asp Lys Asp Lys Ser Leu Gly Gly Gln Tyr Gly Val Arg Gly
                85                  90                  95

Phe Pro Thr Val Lys Ile Phe Gly Ala Asn Lys His Asn Pro Thr Asp
            100                 105                 110

Tyr Ser Gly Pro Arg Thr Ala Asp Gly Val Ala Ser Ala Ala Leu Gln
            115                 120                 125

Glu Ala Arg Lys Val Val Asp Gln Arg Leu Gly Arg Lys Thr Ser Gly
        130                 135                 140

Gly Ser Ser Gly Gly Lys Ser Asp Val Val Glu Leu Asp Glu Ser Asn
```

-continued

```
       145                    150                    155                    160

Phe Glu Glu Leu Val Leu Lys Ser Asp Asp Leu Trp Leu Val Glu Phe
                    165                    170                    175

Phe Ala Pro Trp Cys Gly His Cys Lys Asn Leu Ala Pro His Trp Ala
                    180                    185                    190

Lys Ala Ala Thr Glu Leu Lys Gly Lys Val Lys Leu Gly Ala Val Asp
                    195                    200                    205

Ala Thr Val His Gln Gly Leu Ala Ser Gln Phe Asp Val Lys Gly Tyr
                    210                    215                    220

Pro Thr Ile Lys Phe Phe Pro Gly Gly Lys Lys Asp Arg His Ser Ala
225                    230                    235                    240

Xaa Glu Tyr Asn Gly Gly Arg Thr Ala Asp Asp Ile Val Gln Trp Gly
                    245                    250                    255

Leu Asp Lys Ala Ala Glu Ser Ala Pro Ala Pro Glu Leu His Gln Val
                    260                    265                    270

Thr Ser Pro Ser Val Leu Lys Asp Ala Cys Glu Glu Ser Gln Leu Cys
                    275                    280                    285

Val Val Ser Val Leu Pro His Ile Tyr Asp Cys Gln Ser Glu Cys Arg
                    290                    295                    300

Gln Gly Tyr Leu Asp Val Leu Lys Arg Leu Gly Glu Lys Tyr Lys Arg
305                    310                    315                    320

Asn Arg Trp Gly Trp Leu Trp Ser Glu Ala Leu Ala Gln Pro Lys Leu
                    325                    330                    335

Glu Glu Ala Leu Glu Ile Gly Gly Phe Gly Tyr Pro Ala Leu Ala Val
                    340                    345                    350

Leu Asn Ser Arg Lys Met Lys Tyr Ser Leu Leu Arg Gly Ser Phe Ser
                    355                    360                    365

Tyr Asp Gly Ile Asn Glu Phe Leu Arg Glu Leu Ala Val Gly Arg Gly
                    370                    375                    380

Ser Ser Val Pro Val Lys Gly Ala Lys Leu Pro Glu Val Gln Thr Val
385                    390                    395                    400

Glu Pro Trp Asp Gly Lys Asp Ala Lys Leu Glu Glu Pro Glu Asp Ile
                    405                    410                    415

Asp Leu Ser Asp Val Glu Leu Glu Pro Glu Glu Pro Gly Lys Lys His
                    420                    425                    430

Val Glu Leu
       435
```

<210> SEQ ID NO 93
<211> LENGTH: 482
<212> TYPE: PRT
<213> ORGANISM: Plasmodium chabaudi

<400> SEQUENCE: 93

```
Met Asn Ser Lys Tyr Phe Ser Phe Leu Leu Phe Leu Ile Pro Phe Leu
1                    5                     10                    15

Phe Gln Asn Cys Val Arg Ser His Glu Asp Leu Phe Asn Glu His Val
                    20                    25                    30

Thr Ser Ile His Asp Gly Glu Leu Thr Asn Phe Ile Thr Lys Asn Asp
                    35                    40                    45

Ile Val Leu Val Met Phe Tyr Ala Pro Trp Cys Gly His Cys Lys Arg
       50                    55                    60

Leu Ile Pro Glu Tyr Asn Asp Ala Ala Ile Met Leu Ala Glu Lys Lys
65                    70                    75                    80
```

-continued

```
Ser Glu Ile Lys Leu Ala Ser Val Asp Ala Thr Ile Glu Arg Gly Leu
              85                  90                  95

Ser Gln Glu Tyr Gly Ile Thr Gly Tyr Pro Thr Met Ile Leu Phe Asn
             100                 105                 110

Lys Lys Asn Arg Ile Asn Tyr Gly Gly Gly Arg Thr Ala Gln Thr Ile
             115                 120                 125

Val Asp Trp Ile Leu Gln Met Thr Gly Pro Val Ser Thr Glu Ile Thr
130                 135                 140

Gly Asn Ile Glu Asp Val Leu Lys Glu Lys Asn Ile Asn Val Ala Phe
145                 150                 155                 160

Tyr Ile Glu Tyr Thr Ser Glu Asp His Glu Leu Phe Lys Lys Phe Asn
                 165                 170                 175

Glu Val Gly Asp Lys Asn Arg Glu Ile Ala Lys Tyr Phe Met Lys Lys
             180                 185                 190

Asn Asp Lys His Asn Lys Ile Tyr Cys Tyr Arg Lys Asp Glu Lys Thr
             195                 200                 205

Val Glu Tyr Asp Glu Lys Thr Pro Leu Ser Asp Phe Ile Thr Ile Glu
210                 215                 220

Ser Phe Pro Leu Phe Gly Glu Ile Asn Thr Glu Asn Tyr Arg Phe Tyr
225                 230                 235                 240

Ala Glu Ser Pro Lys Glu Leu Val Trp Val Cys Ala Thr Ile Glu Gln
                 245                 250                 255

Tyr Asn Glu Ile Lys Glu Glu Val Arg Leu Ala Ala Ala Glu Leu Arg
             260                 265                 270

Asn Lys Thr His Phe Val Leu Leu Asn Ile Pro Glu Tyr Ala Asp His
             275                 280                 285

Ala Lys Ala Ser Leu Gly Ile Asn Glu Phe Pro Gly Leu Ala Tyr Gln
             290                 295                 300

Ser Ser Glu Gly Arg Tyr Val Leu Thr Asn Pro Lys Gln Ser Leu Lys
305                 310                 315                 320

Asn His Lys Asp Ile Ile Thr Phe Phe Lys Asp Val Glu Ala Gly Lys
                 325                 330                 335

Ile Glu Lys Ser Leu Lys Ser Glu Pro Ile Pro Glu Glu Asp Lys Asp
             340                 345                 350

Ala Pro Val Lys Val Val Val Gly Asn Ser Phe Ile Asp Val Val Leu
             355                 360                 365

Lys Ser Gly Lys Asp Val Leu Ile Glu Ile Tyr Ala Pro Trp Cys Gly
370                 375                 380

His Cys Lys Lys Leu Glu Pro Val Tyr Glu Glu Leu Gly Arg Lys Leu
385                 390                 395                 400

Lys Lys Tyr Asp His Ile Ile Val Ala Lys Met Asp Gly Thr Leu Asn
             405                 410                 415

Glu Thr Ala Leu Lys Glu Phe Glu Trp Ser Gly Phe Pro Thr Ile Phe
             420                 425                 430

Phe Val Lys Ala Gly Ser Lys Ile Pro Leu Pro Tyr Glu Gly Glu Arg
             435                 440                 445

Ser Leu Lys Gly Phe Val Asp Phe Leu Asn Lys His Ser Thr Lys Thr
             450                 455                 460

Pro Ile Thr Ile Asp Gly Val Ser Gln Ser Asp Asp Gly Ala Ser Glu
465                 470                 475                 480

Glu Leu
```

<210> SEQ ID NO 94

```
<211> LENGTH: 514
<212> TYPE: PRT
<213> ORGANISM: Aspergillus steynii

<400> SEQUENCE: 94

Met Arg Ser Phe Thr Pro Trp Val Leu Gly Leu Leu Gly Ala Ser Ala
1               5                   10                  15

Val Val Ser Ala Gly Asp Ala Gln Ala Asp Val Pro Ser Asp Val Lys
            20                  25                  30

Ser Leu Thr Gln Asp Thr Phe Asn Asp Phe Ile Lys Glu His Asp Leu
        35                  40                  45

Val Leu Ala Glu Phe Phe Ala Pro Trp Cys Gly His Cys Lys Ala Leu
    50                  55                  60

Ala Pro Lys Tyr Glu Glu Ala Ala Ser Gln Leu Lys Asp Lys Asn Ile
65                  70                  75                  80

Pro Leu Val Lys Ile Asp Cys Thr Glu Glu Glu Leu Cys Arg Asp
                85                  90                  95

Gln Gly Val Glu Gly Tyr Pro Thr Leu Lys Ile Phe Arg Gly Val Asp
            100                 105                 110

Ser Ser Lys Pro Tyr Gln Gly Ala Arg Gln Thr Glu Ser Leu Val Ser
        115                 120                 125

Tyr Met Ile Lys Gln Ser Leu Pro Ala Val Ser Ser Val Asn Glu Glu
    130                 135                 140

Asn Leu Glu Asp Thr Lys Thr Met Asp Lys Ile Val Val Ile Gly Tyr
145                 150                 155                 160

Phe Ser Ser Asp Asp Gln Ala Ala Asn Asp Ala Phe Asn Ala Leu Ala
            165                 170                 175

Glu Ala Gln Arg Asp Asn Tyr Leu Phe Ala Ala Thr Asp Asp Ala Ala
            180                 185                 190

Ile Ala Lys Ala Glu Gly Val Glu Gln Pro Ser Leu Val Leu Tyr Lys
        195                 200                 205

Asp Phe Asp Glu Lys Lys Ala Ile Tyr Thr Gly Glu Ile Glu Gln Asp
    210                 215                 220

Ala Val Leu Thr Trp Val Lys Thr Ala Ser Thr Pro Leu Val Gly Glu
225                 230                 235                 240

Ile Gly Pro Glu Thr Tyr Ser Ser Tyr Ile Thr Ala Gly Ile Pro Leu
            245                 250                 255

Ala Tyr Ile Phe Ala Glu Thr Ser Glu Glu Arg Glu Lys Phe Thr Glu
            260                 265                 270

Asp Phe Lys Pro Ile Ala Glu Lys His Lys Gly Leu Ile Asn Ile Ala
        275                 280                 285

Thr Ile Asp Ala Lys Met Phe Gly Ala His Ala Gly Asn Leu Asn Leu
    290                 295                 300

Asp Pro Gln Thr Phe Pro Ala Phe Ala Ile Gln Asp Pro Glu Lys Lys
305                 310                 315                 320

Ala Lys Tyr Pro Tyr Asp Gln Ser Lys Glu Ile Thr Ala Lys Asp Val
            325                 330                 335

Gly Lys Phe Ile Gln Asp Val Leu Gly Gly Lys Val Glu Pro Ser Ile
            340                 345                 350

Lys Ser Glu Pro Ile Pro Glu Ser Gln Glu Gly Pro Val Thr Val Val
        355                 360                 365

Val Ala His Ser Tyr Lys Glu Leu Val Val Asp Asn Glu Lys Asp Val
    370                 375                 380

Leu Leu Glu Phe Tyr Ala Pro Trp Cys Gly His Cys Lys Ala Leu Ala
```

-continued

```
385                390                395                400

Pro Lys Tyr Glu Glu Leu Ala Ser Leu Tyr Ala Asp Val Pro Asp Leu
                405                410                415

Ala Ser Lys Val Thr Ile Ala Lys Ile Asp Ala Thr Ala Asn Asp Val
            420                425                430

Pro Asp Ser Ile Thr Gly Phe Pro Thr Ile Lys Leu Tyr Pro Ala Gly
            435                440                445

Gly Lys Asp Ala Pro Val Glu Tyr Ala Gly Ser Arg Thr Val Glu Asp
        450                455                460

Leu Val Asn Phe Val Lys Glu Asn Gly Gln His Lys Val Asp Ala Leu
465                470                475                480

Ala Asn Thr Gln Glu Gly Gly Asp Ala Thr Glu Ser Pro Ser Ala Ser
                485                490                495

Ser Glu Thr Glu Ala Pro Ala Ala Thr Asp Asp Lys Ala Asp His Asp
            500                505                510

Glu Leu
```

```
<210> SEQ ID NO 95
<211> LENGTH: 530
<212> TYPE: PRT
<213> ORGANISM: Emmonsia crescens

<400> SEQUENCE: 95
```

```
Met Arg Gln Phe Arg Asp Phe Ala Phe Gly Leu Ala Ala Leu Gly Leu
1                5                10                15

Thr Ala Leu Ala Ser Ala Thr Glu Ala Glu Ala Glu Ser Asp Val His
            20                25                30

Val Leu Lys Lys Asp Thr Phe Asn Asp Phe Met Asn Ser His Asp Leu
        35                40                45

Val Leu Ala Glu Phe Tyr Ala Pro Trp Cys Gly His Cys Lys Ala Leu
    50                55                60

Ala Pro Glu Tyr Glu Val Ala Ala Thr Glu Leu Lys Glu Lys Asn Ile
65                70                75                80

His Leu Ala Lys Ile Asp Cys Thr Glu Glu Ala Asp Leu Cys Gln Glu
                85                90                95

His Gly Val Glu Gly Tyr Pro Thr Leu Lys Ile Phe Arg Gly Leu Glu
            100                105                110

Asn Val Lys Pro Tyr Thr Gly Pro Arg Lys Ser Gly Pro Ile Ala Ser
        115                120                125

Phe Met Val Lys Gln Ser Leu Pro Pro Val Thr Thr Val Thr Ala Asp
    130                135                140

Asn Ile Glu Asp Val Lys Thr Leu Asp Lys Ile Val Val Ile Gly Tyr
145                150                155                160

Phe Ala Glu Asp Asp Lys Ala Ser Asn Glu Thr Phe Thr Ala Val Ala
                165                170                175

Glu Ala Leu Arg Asp Asp Tyr Leu Phe Ala Gly Thr Asn Asp Ala Lys
            180                185                190

Leu Ala Ala Ala Glu Asp Val Lys Gln Pro Ala Ile Val Leu Tyr Lys
        195                200                205

Glu Phe Asp Glu Arg Lys Ala Val Phe Lys Asn Lys Phe Val Gln Asp
    210                215                220

Asp Ile Ser Lys Phe Val Lys Thr Ala Ser Ile Pro Leu Val Gly Glu
225                230                235                240

Val Gly Pro Asp Thr Tyr Ala Gly Tyr Met Ala Ser Gly Leu Pro Leu
```

```
                    245              250              255

Ala Tyr Val Phe Ala Glu Thr Pro Glu Glu Arg Glu Glu Phe Ala Ala
        260              265              270

Met Leu Lys Pro Ile Ala Gln Lys Gln Lys Gly Ser Ile Asn Ile Ala
        275              280              285

Thr Ile Asp Ala Lys Ala Phe Gly Ala His Ala Gly Asn Leu Asn Leu
    290              295              300

Asp Pro Glu Lys Phe Pro Ala Phe Ala Ile Gln Asp Thr Thr Asn Asn
305              310              315              320

Lys Lys Tyr Pro Phe Asp Gln Thr Lys Lys Ile Thr His Asp Asp Ile
                325              330              335

Ala Lys Phe Val Gln Asp Val Leu Asp Gly Lys Val Glu Pro Ser Ile
                340              345              350

Lys Ser Glu Pro Ile Pro Glu Ser Gln Asp Ala Ala Val Thr Val Val
                355              360              365

Val Ala His Ser Phe Gln Glu Ile Val Ile Asp Asn Asp Lys Asp Val
        370              375              380

Leu Val Glu Tyr Tyr Ala Pro Trp Cys Gly His Cys Lys Ala Leu Ala
385              390              395              400

Pro Lys Tyr Glu Gln Leu Gly Gln Leu Tyr Ala Asp Val Pro Glu Phe
                405              410              415

Ala Ser Lys Val Thr Ile Ala Lys Ile Asp Ala Thr Ala Asn Asp Val
                420              425              430

Pro Glu Asp Ile Gln Gly Phe Pro Thr Ile Lys Leu Tyr Ala Ala Gly
                435              440              445

Ser Lys Gly Ser Pro Val Asp Tyr Asp Gly Ser Arg Thr Ile Glu Asp
        450              455              460

Leu Ala Lys Phe Val Arg Asp Asn Gly Lys His Gly Val Asp Ala Tyr
465              470              475              480

Val Ala Glu Lys Val Val Glu Asp Gly Gly Asp Val Thr Asn Ser Pro
                485              490              495

Ala Ala Ala Ser Pro Ser Ser Thr Ala Ala Asp Lys Glu Ser Glu Thr
                500              505              510

Ser Ser Ser Asp Asp Ala Glu Glu Thr Ala Glu Ala Pro Arg His Glu
        515              520              525

Glu Leu
    530

<210> SEQ ID NO 96

<400> SEQUENCE: 96

000

<210> SEQ ID NO 97
<211> LENGTH: 517
<212> TYPE: PRT
<213> ORGANISM: Aspergillus fumigatus

<400> SEQUENCE: 97

Met Arg Ser Phe Ala Pro Leu Val Leu Ser Leu Leu Gly Ala Ser Ala
1               5               10               15

Val Ala Ser Ala Asp Ala Thr Ala Asp Thr Thr Ser Asp Val Val Ser
                20               25               30

Leu Thr Lys Asp Ser Phe Lys Asp Phe Met Lys Glu His Asp Leu Val
        35               40               45
```

-continued

```
Leu Ala Glu Phe Tyr Ala Pro Trp Cys Gly His Cys Lys Ala Leu Ala
    50                  55                  60

Pro Lys Tyr Glu Glu Ala Ala Thr Glu Leu Lys Gly Lys Asn Ile Pro
65                  70                  75                  80

Leu Val Lys Val Asp Cys Thr Glu Glu Glu Asp Leu Cys Lys Glu Asn
                85                  90                  95

Gly Val Glu Gly Tyr Pro Thr Leu Lys Ile Phe Arg Gly Pro Asp Ser
                100                 105                 110

Ser Lys Pro Tyr Gln Gly Ala Arg Gln Ala Asp Ser Ile Val Ser Tyr
                115                 120                 125

Met Ile Lys Gln Ser Leu Pro Ala Val Ser Ala Val Thr Glu Glu Asn
    130                 135                 140

Leu Glu Glu Ile Lys Thr Met Asp Lys Ile Val Val Ile Gly Tyr Phe
145                 150                 155                 160

Ala Ser Asp Asp Lys Ala Ala Asn Asp Val Phe Thr Ser Phe Ala Glu
                165                 170                 175

Ser Gln Arg Asp Asn Tyr Leu Phe Ala Ala Thr Ser Asp Ser Ala Ile
                180                 185                 190

Ala Lys Ala Glu Gly Val Lys Gln Pro Ser Ile Val Leu Tyr Lys Asp
                195                 200                 205

Phe Asp Glu Lys Lys Ala Val Tyr Asp Gly Ala Ile Glu Gln Glu Ala
    210                 215                 220

Ile Leu Ser Trp Val Lys Thr Ala Ser Thr Pro Leu Val Gly Glu Ile
225                 230                 235                 240

Gly Pro Glu Thr Tyr Ser Ser Tyr Ile Thr Ala Gly Ile Pro Leu Ala
                245                 250                 255

Tyr Ile Phe Ala Glu Thr Lys Glu Glu Arg Asp Gln Tyr Ala Glu Asp
                260                 265                 270

Phe Lys Pro Val Ala Glu Lys His Lys Gly Ala Ile Asn Ile Ala Thr
    275                 280                 285

Ile Asp Ala Lys Met Phe Gly Ala His Ala Gly Asn Leu Asn Leu Asp
    290                 295                 300

Pro Gln Thr Phe Pro Ala Phe Ala Ile Gln Asp Pro Glu Lys Asn Ala
305                 310                 315                 320

Lys Tyr Pro Tyr Asp Gln Ser Arg Glu Phe Asn Ala Lys Glu Ile Gly
                325                 330                 335

Lys Phe Ile Gln Asp Val Leu Asp Gly Lys Val Glu Pro Ser Ile Lys
                340                 345                 350

Ser Glu Pro Ile Pro Glu Thr Gln Glu Gly Pro Val Thr Val Val Val
                355                 360                 365

Ala His Ser Tyr Gln Asp Ile Val Ile Asn Asn Asp Lys Asp Val Leu
    370                 375                 380

Leu Glu Phe Tyr Ala Pro Trp Cys Gly His Cys Lys Ala Leu Ala Pro
385                 390                 395                 400

Lys Tyr Glu Glu Leu Ala Ala Leu Tyr Ala Gly Asp Phe Lys Asp Lys
                405                 410                 415

Val Thr Ile Ala Lys Ile Asp Ala Thr Ala Asn Asp Val Pro Asp Ser
                420                 425                 430

Ile Thr Gly Phe Pro Thr Ile Lys Leu Tyr Pro Ala Gly Ala Lys Asp
                435                 440                 445

Ser Pro Val Glu Tyr Ser Gly Ser Arg Thr Val Glu Asp Leu Ala Asn
    450                 455                 460
```

-continued

```
Phe Ile Lys Glu Asn Gly Lys Tyr Lys Val Asp Ala Leu Val Ala Ala
465                 470                 475                 480

Ser Glu Lys Val Glu Glu Gly Pro Asp Val Thr Ala Ser Pro Ser Ala
                485                 490                 495

Thr Ser Thr Glu Ala Glu Ala Pro Ala Ala Thr Gly Asp Glu Lys Gly
                500                 505                 510

Asp His Asp Glu Leu
        515

<210> SEQ ID NO 98
<211> LENGTH: 217
<212> TYPE: PRT
<213> ORGANISM: Pseudomonas fluorescens

<400> SEQUENCE: 98

Met Ser Thr Pro Leu Lys Ile Asp Phe Val Ser Asp Val Ser Cys Pro
1                 5                   10                  15

Trp Cys Ile Ile Gly Leu Arg Gly Leu Thr Glu Ala Leu Asp Gln Leu
                20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
                100                 105                 110

Gly Leu Glu Gly Leu Gln Tyr Asn Leu Lys Glu Ala Leu Phe Lys Ala
                115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
                180                 185                 190

Tyr Ala Val Ser Gly Gly Gln Pro Ala Glu Ala Phe Val Gly Ala Ile
    195                 200                 205

Arg Gln Ile Ile Asn Glu Ser Lys Ser
    210                 215
```

BACTERIAL HOSTS FOR RECOMBINANT PROTEIN EXPRESSION

CROSS-REFERENCE

This application claims the benefit of U.S. Provisional Application No. 63/209,239 filed Jun. 10, 2021, the contents of which are incorporated herein by reference in their entirety.

BACKGROUND OF THE INVENTION

Microbial host cell expression systems are used for production of recombinant proteins with varying degrees of success. Recombinant protein degradation and low yield remain challenges. Alterations of the host cell genome to optimize the production of high-quality protein often result in frustratingly low host cell growth and production yields. Recombinant host cells that achieve both high quality and high yield of recombinant proteins remain needed.

SEQUENCE LISTING

The instant application contains a Sequence Listing which has been submitted in ASCII format via EFS-Web and is hereby incorporated by reference in its entirety. Said ASCII copy, created on Sep. 19, 2022, is named 94931757201US-SequenceListing.txt and is 364,544 bytes in size.

SUMMARY OF THE INVENTION

The present invention provides recombinant bacterial host cells and methods for their use to produce high quality recombinant proteins at high yield. In particular, the compositions and methods provided by the invention are useful for producing recombinant proteins that are sensitive to proteolysis, including antibodies and antibody fragments. The invention includes recombinant gram-negative bacterial host cells comprising combinations of genetic modifications that result in reduced degradation of a recombinant protein while allowing growth to high cell density. In some embodiments, a recombinant gram-negative bacterial host cell of the present invention is deficient in first protease activity and a second protease activity, wherein the first protease activity is a tail-specific protease activity and the second protease activity is a murein DD-endopeptidase activity. In some embodiments, the invention relates to a recombinant gram-negative bacterial host cell that is deficient in tail-specific protease activity and a murein DD-endopeptidase activity, wherein the host cell produces high quality, undegraded, recombinant protein, and grows to a high cell density. In some embodiments, the murein DD-endopeptidase activity is a MepM activity. In some embodiments, the gram-negative bacterial host cell is not deficient in a MepS activity. In some embodiments, the recombinant gram-negative bacterial host cell deficient in a first protease activity and a second protease activity, wherein the first protease activity is a tail-specific protease activity, and the second protease activity is a MepM murein DD-endopeptidase activity, is further deficient in at least one additional protease activity, at least one autolytic factor activity, or both. In some embodiments, the at least one additional protease activity is a serralysin precursor activity. The deficiency in a protein activity, e.g., the first protease, the second protease, an additional protease, or an autolytic factor, can result from a mutation in one or more gene. The invention further provides methods for producing intact, soluble, and/or active recombinant proteins of interest at high yield using the inventive recombinant gram-negative bacterial host cells. In some embodiments, the recombinant protein of interest is a Fab'. In some embodiments, the Fab' binds to TNF-α.

The present invention includes a recombinant gram-negative bacterial host cell for recombinant protein expression, wherein the host cell is: (a) deficient in a first protease activity, wherein the first protease activity is tail-specific protease activity, wherein the deficient first protease activity results from a mutation in at least one gene encoding a tail-specific protease; (b) deficient in a second protease activity, wherein the second protease activity is murein DD-endopeptidase activity, wherein the deficient second protease activity results from a mutation in at least one gene encoding a murein DD-endopeptidase. In some embodiments, the recombinant gram-negative bacterial host cell further: (c) is deficient in at least one additional protease activity, wherein the deficient additional protease activity results from a mutation in at least one gene encoding an additional protease, wherein the additional protease is different from the proteases of (a) and (b); (d) is deficient in one or more autolytic factor activity, wherein the deficient autolytic factor activity results from a mutation in at least one gene encoding an autolytic factor; (e) overexpresses one or more inactivated protease; (f) overexpresses one or more folding modulator; or (g) any combination of (c), (d), (e) and (f). In some embodiments, the deficient tail-specific protease activity results from a mutation in a gene encoding one or more of: (i) a Prc1 tail-specific protease having the amino acid sequence set forth as SEQ ID NO: 33, a homologue of SEQ ID NO: 33, or a Prc1 tail-specific protease related protein having an amino acid sequence at least 30% similar to SEQ ID NO: 33; (ii) a Prc2 tail-specific protease having the amino acid sequence set forth as SEQ ID NO: 35, a homologue of SEQ ID NO: 35, or a Prc2 tail-specific protease related protein having an amino acid sequence at least 30% similar to SEQ ID NO: 35; or (iii) a Tsp tail-specific protease having the amino acid sequence set forth as SEQ ID NO: 71, a homologue of SEQ ID NO: 71, or an Tsp tail-specific protease related protein having an amino acid sequence at least 30% similar to SEQ ID NO: 71. In some embodiments, the deficient murein DD-endopeptidase activity results from a mutation in a gene encoding one or more of: (i) a MepM1 murein DD-endopeptidase having the amino acid sequence set forth as SEQ ID NO: 1, a homologue of SEQ ID NO: 1, or a murein DD-endopeptidase related protein having an amino acid sequence at least 30% similar to SEQ ID NO: 1; (ii) a MepM murein DD-endopeptidase having the amino acid sequence set forth as SEQ ID NO: 63, a homologue of SEQ ID NO: 63, or a murein DD-endopeptidase related protein having an amino acid sequence at least 30% similar to SEQ ID NO: 63; (iii) a MepM1 murein DD-endopeptidase having the amino acid sequence set forth as SEQ ID NO: 65, a homologue of SEQ ID NO: 65, or a murein DD-endopeptidase related protein having an amino acid sequence at least 30% similar to SEQ ID NO: 65; and (iv) a MepM1 murein DD-endopeptidase having the amino acid sequence set forth as SEQ ID NO: 66, a homologue of SEQ ID NO: 66, or a murein DD-endopeptidase related protein having an amino acid sequence at least 30% similar to SEQ ID NO: 66. In some embodiments, the host cell of (c) is deficient in 1 to 10 different additional protease activities; the host cell of (d) is deficient in 1-5 different autolytic factor activities; the host cell of (e) overexpresses 1 to 10 different inactivated proteases, wherein each inactivated protease is different; the host cell of (f) overexpresses 1-10 different folding modulators, or any combination thereof. In some embodiments, the one or more deficient additional protease activity of (c) results from a mutation of at least one gene encoding an additional protease independently selected from: a serralysin precursor, a membrane-localized protease, a murein L,D transpepti-dase, a hemolysin precursor, a D-alanyl-D-alanine carboxy-peptidase/endopeptidase AmpH precursor, a periplasmic serine endoprotease, an AAA+ family proteolytic machine, and a murein DD-endopeptidase different from that of (a); the one or more deficient autolytic factor activity of (d) results from a mutation of at least one gene encoding an autolytic factor independently selected from: an S-type pyocin, a linear gramicidin synthase subunit D, a hemolysin precursor, a leukotoxin, and a porin; the one or more inactivated protease of (e) is a mutant periplasmic serine endoprotease; and the one or more folding modulator of (f) is a disulfide isomerase. In some embodiments, the serraly-sin precursor is selected from: a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9; a serralysin precursor having the amino acid sequence set forth as SEQ ID NO: 47; a homologue of the serralysin precursor having the amino acid sequence set forth as SEQ ID NO: 47; a serralysin precursor related protein having at least 60% similarity or at least 60% identity to the amino acid sequence set forth as SEQ ID NO: 47; the membrane-localized protease is an HtpX having the amino acid sequence set forth as SEQ ID NO: 39, a homologue of the HtpX having the amino acid sequence set forth as SEQ ID NO: 39, or an HtpX related protein having at least 60% similarity or at least 60% identity to the amino acid sequence set forth as SEQ ID NO: 39; the murein L,D transpeptidase is a murein L,D transpeptidase having the amino acid sequence set forth as SEQ ID NO: 41, a homologue of the murein L,D transpeptidase having the amino acid sequence set forth as SEQ ID NO: 41, or a murein L,D transpeptidase related protein having at least 60% similarity or at least 60% identity to the amino acid sequence set forth as SEQ ID NO: 41; the hemolysin precursor is a hemolysin precursor having the amino acid sequence set forth as SEQ ID NO: 43, a homologue of the hemolysin precursor having the amino acid sequence set forth as SEQ ID NO: 43, or a hemolysin precursor related protein having at least 60% similarity or at least 60% identity to the amino acid sequence set forth as SEQ ID NO: 43; the D-alanyl-D-alanine carboxypeptidase/endopeptidase AmpH precursor is a D-alanyl-D-alanine carboxypeptidase/endopeptidase AmpH precursor having the amino acid sequence set forth as SEQ ID NO: 45, a homologue of the D-alanyl-D-alanine carboxypeptidase/endopeptidase AmpH precursor having the amino acid sequence set forth as SEQ ID NO: 45, or a D-alanyl-D-alanine carboxypeptidase/en-dopeptidase AmpH precursor related protein having at least 60% similarity or at least 60% identity to the amino acid sequence set forth as SEQ ID NO: 45; the periplasmic serine endoprotease is selected from: a DegP2 having the amino acid sequence set forth as SEQ ID NO: 31; a homologue of the DegP2 having the amino acid sequence set forth as SEQ ID NO: 31; a DegP2 related protein having at least 60% similarity or at least 60% identity to the amino acid sequence set forth as SEQ ID NO: 31; a DegP having the amino acid sequence set forth as SEQ ID NO: 69; a homologue of the DegP having the amino acid sequence set forth as SEQ ID NO: 69; a DegP related protein having at least 60% similarity or at least 60% identity to the amino acid sequence set forth as SEQ ID NO: 69; a DegP having the amino acid sequence set forth as SEQ ID NO: 62; a homologue of the DegP having the amino acid sequence set forth as SEQ ID NO: 62; and a DegP related protein having at least 60% similarity or at least 60% identity to the amino acid sequence set forth as SEQ ID NO: 62; the AAA+ family proteolytic machine comprises an HslU protease having the amino acid sequence set forth as SEQ ID NO: 37, a homologue of the HslU protease having the amino acid sequence set forth as SEQ ID NO: 37, or a HslU related protein having at least 60% similarity or at least 60% identity to the amino acid sequence set forth as SEQ ID NO: 37; and an HslV protease having the amino acid sequence set forth as SEQ ID NO: 38, a homologue of the HslV protease having the amino acid sequence set forth as SEQ ID NO: 38, or a HslV related protein having at least 60% similarity or at least 60% identity to the amino acid sequence set forth as SEQ ID NO: 38; the murein DD-endopeptidase is selected from: a MepM2 protease having the amino acid sequence set forth as SEQ ID NO: 3; a homologue of the MepM2 protease having the amino acid sequence set forth as SEQ ID NO: 3; a MepM2-related protein having at least 60% similarity or at least 60% identity to the amino acid sequence set forth as SEQ ID NO: 3; a MepM2 protease having the amino acid sequence set forth as SEQ ID NO: 64; a homologue of the MepM2 protease having the amino acid sequence set forth as SEQ ID NO: 64; or a MepM2-related protein having at least 60% similarity or at least 60% identity to the amino acid sequence set forth as SEQ ID NO: 64; a MepM2 protease having the amino acid sequence set forth as SEQ ID NO: 67; a homologue of the MepM2 protease having the amino acid sequence set forth as SEQ ID NO: 67; a MepM2-related protein having at least 60% similarity or at least 60% identity to the amino acid sequence set forth as SEQ ID NO: 67; a MepM2 protease having the amino acid sequence set forth as SEQ ID NO: 68; a homologue of the MepM2 protease having the amino acid sequence set forth as SEQ ID NO: 68; and a MepM2-related protein having at least 60% similarity or at least 60% identity to the amino acid sequence set forth as SEQ ID NO: 68; the S-type Pyocin is an S-type Pyocin having the amino acid sequence set forth as SEQ ID NO: 49, a homologue of the S-type Pyocin having the amino acid sequence set forth as SEQ ID NO: 49, or an S-type Pyocin related protein having at least 60% similarity or at least 60% identity to the amino acid sequence set forth as SEQ ID NO: 49; the linear gramicidin synthase is a linear gramicidin synthase having the amino acid sequence set forth as SEQ ID NO: 51, a homologue of the linear gramicidin synthase having the amino acid sequence set forth as SEQ ID NO: 51, or a linear gramicidin synthase related protein having at least 60% similarity or at least 60% identity to the amino acid sequence set forth as SEQ ID NO: 51; the leukotoxin is a leukotoxin having the amino acid sequence set forth as SEQ ID NO: 53, a homologue of the leukotoxin having the amino acid sequence set forth as SEQ ID NO: 53, or a leukotoxin related protein having at least 60% similarity or at least 60% identity to the amino acid sequence set forth as SEQ ID NO: 53; the ShlB hemolysin transporter is an ShlB hemolysin transporter having the amino acid sequence set forth as SEQ ID NO: 55, a homologue of the an ShlB hemolysin transporter having the amino acid sequence set forth as SEQ ID NO: 55, or an ShlB hemolysin transporter related protein having at least 60% similarity or at least 60% identity to the amino acid sequence set forth as SEQ ID NO: 55; each of the one or more overexpressed inactivated proteases is independently selected from: *P. fluorescens* DegP2 S219A; an inactivated DegP2 comprising an amino acid substitution or disruption of the amino acid sequence set forth as SEQ ID NO: 31; an inactivated DegP2 comprising an amino acid substitution or disruption of a homologue of the amino acid sequence set forth as SEQ ID NO: 31; an inactivated DegP2-related protein comprising an amino acid substitution or disruption of a DegP2 having at least 60% similarity or at least 35% identity to amino acid sequence set forth as SEQ ID NO: 31; an inactivated DegP comprising an amino acid substitution or disruption of the amino acid sequence set forth as SEQ ID NO: 69; an inactivated DegP comprising an amino acid substitution or disruption of a homologue of the amino acid sequence set forth as SEQ ID NO: 69; an inactivated DegP-related protein comprising an amino acid substitution or disruption of a DegP having at least 60% similarity or at least 35% identity to amino acid sequence set forth as SEQ ID NO: 69; an inactivated DegP/HtrA comprising an amino acid substitution or disruption of the amino acid sequence set forth as SEQ ID NO: 62; an inactivated DegP/HtrA comprising an amino acid substitution or disruption of a homologue of the amino acid sequence set forth as SEQ ID NO: 62; an inactivated DegP/HtrA-related protein comprising an amino acid substitution or disruption of a DegP having at least 60% similarity or at least 35% identity to amino acid sequence set forth as SEQ ID NO: 62; an inactivated DegP, DegP-related protein, or DegP homologue having a substitution or disruption of an amino acid at a position corresponding to any one of 131 (His), 134 (Asp) and 236 (Ser) (SEQ ID NO: 62, referring to numbering including leader sequence 1-26), or respective positions 105, 108, and 210, when excluding the leader sequence; an inactivated DegP, DegP-related protein, or DegP homologue having an amino acid substitution corresponding to *E. coli* Htr S210A; an inactivated DegP, DegP-related protein, or DegP homologue having an amino acid substitution corresponding to *E. coli* Htr H105R; and an inactivated DegP, DegP-related protein, or DegP homologue having a substitution or disruption of any one or more amino acid at a position corresponding to any one of: 108, 109, 110, 111, 112, 113, 114, 115, 116, 117, 118, 146, 147, 148, 149, 150, 151, 152, 217, 218, 219, 220, 221, 222, 223, 224, 225, 226, 227, 228, 229, 230, 231, 232, 233, and 234 of SEQ ID NO: 31; and each of the one or more folding modulators is independently selected from: a disulfide bond isomerase having an amino acid sequence set forth as any one of SEQ ID NOS: 76-81; a homologue of a disulfide bond isomerase having an amino acid sequence set forth as any one of SEQ ID NOS: 76-81; a disulfide bond isomerase-related protein having at least 60% similarity or at least 60% identity to an amino acid sequence set forth as any one of SEQ ID NOS: 76-81; a protein disulfide isomerase having an amino acid sequence set forth as any one of SEQ ID NOS: 27 and 82-98; a homologue of a protein disulfide isomerase having an amino acid sequence set forth as any one of SEQ ID NOS: 27 and 82-98; and a protein disulfide isomerase-related protein having at least 60% similarity or at least 60% identity to an amino acid sequence set forth as SEQ ID NOS: 27 and 82-98.

In some embodiments, the mutation is in a coding sequence or noncoding sequence of the corresponding gene, and the mutation is independently selected from: (i) a complete gene deletion, (ii) a partial gene deletion, (iii) a missense mutation, (iv) a nonsense mutation, (v) a frameshift mutation, (vi) an insertion, and (vii) any combination of (ii), (iii), (iv), (v) and (vi). In some embodiments, the missense mutation of (iii) results in a conservative or non-conservative amino acid substitution. In some embodiments, the noncoding sequence is a regulatory sequence. In some embodiments, the gram-negative bacterial host cell further comprises a functional protease activity, wherein the functional protease activity is the activity of: a MepS1 having the amino acid sequence set forth as SEQ ID NO: 5; a homologue of the MepS1 having the amino acid sequence set forth as SEQ ID NO: 5; or a MepS1 related protein having at least 50% sequence similarity to the *P. fluorescens* MepS1 protease amino acid sequence set forth as SEQ ID NO: 5. In some embodiments, the gram-negative bacterial host cell further comprises a functional protease activity, wherein the functional protease activity is: a MepS2 having the amino acid sequence set forth as SEQ ID NO: 7; a homologue of the MepS2 having the amino acid sequence set forth as SEQ ID NO: 7; or a MepS2 related protein having at least 50% sequence similarity to the *P. fluorescens* MepS2 protease amino acid sequence set forth as SEQ ID NO: 7. In some embodiments, the gram-negative bacterial host cell is a *Pseudomonad*. In some embodiments, the gram-negative bacterial host cell is a *Pseudomonad*, and the deficient first protease activity results from a mutation of a coding sequence and/or noncoding sequence of a gene encoding *P. fluorescens* Prc1 and/or a mutation of a coding sequence and/or noncoding sequence of a gene encoding *P. fluorescens* Prc2. In some embodiments, the second protease activity is deficient due to a mutation that results in a conservative or non-conservative substitution in an active site amino acid or an allosteric site amino acid of a protease having the second protease activity. In some embodiments, the deficient second protease activity results from at least one mutation of the second protease gene, wherein the mutation results in a disruption of the amino acid sequence at a position corresponding to: (i) any one or more of residues 134 to 145 of SEQ ID NO: 1; (ii) any one or more of residues 319 to 411 of SEQ ID NO: 1; (iii) one or more of residues any 361 to 378 of SEQ ID NO: 1; (iv) any one or more residue selected from 248, 319, 330, 332, 334, 337, 378, 410, and 411 of SEQ ID NO: 1; or any combination of (i), (ii), (iii), and (iv). In some embodiments, the bacterial host cell is *Pseudomonas fluorescens*, and the deficient second protease activity results from a gene mutation that results in an amino acid substitution of SEQ ID NO: 1 selected from: Y248stop, G332S, D334N, A337T, H411Y, P410L, and any conservative or non-conservative amino acid substitution of any one of R319, H330, D334, H378, and H411.

In some embodiments, the recombinant gram-negative bacterial host cell is capable of high-density cell growth in culture. In some embodiments, the high-density cell growth in culture comprises growth to OD575 of about 80 to about 300. In some embodiments, the high-density cell growth in culture is increased in comparison to a control cell by about 2-fold to about 15-fold. In some embodiments, the recombinant gram-negative bacterial host cell and the control cell, respectively, are selected from: (i) a recombinant gram-negative bacterial host cell deficient in the first protease activity and the second protease activity, and a corresponding gram-negative bacterial host cell deficient in the first protease activity and wherein the second protease is functional; (ii) a recombinant gram-negative bacterial host cell deficient in the first protease activity, the second protease activity, and an additional protease activity as recited in 2(c) hereinabove, and a corresponding gram-negative bacterial host cell deficient in the first protease activity and the second protease activity, and wherein the additional protease activity of 2(c) that is deficient in the compared recombinant gram-negative bacterial host cell is functional; and (iii) a recombinant gram-negative bacterial host cell deficient in the first protease activity and the second protease activity, and comprising a functional protease that is: a MepS1 having the amino acid sequence set forth as SEQ ID NO: 5; a homologue of the MepS1 having the amino acid sequence set forth as SEQ ID NO: 5; or a MepS1 related protein having at least 50% sequence similarity to the *P. fluorescens* MepS1 amino acid sequence set forth as SEQ ID NO: 5, and a corresponding gram-negative bacterial host cell deficient in the activity of the first protease and the second protease, and deficient in the functional protease of the compared recombinant gram-negative bacterial host cell. In some embodiments, the additional protease activity of 2(c) is an activity of a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9.

In some embodiments, the recombinant gram-negative bacterial host cell further comprises at least one expression construct, each expression construct comprising at least one nucleic acid sequence encoding a recombinant protein of interest. In some embodiments, the recombinant protein of interest is native or heterologous to the recombinant gram-negative bacterial host cell. In some embodiments, the recombinant protein of interest is selected from: an antibody, antibody fragment, or derivative of an antibody or antibody fragment; an antibody-based drug, a non-antibody binding protein (e.g., an antibody mimetic, including, but not limited to, an alphabody, an iBody, an affibody, an affilin, an affitin, or an anticalin), a reagent protein; a vaccine antigen; a therapeutic protein or enzyme; non-natural protein; a pathogen protein or derivative thereof; a microbial toxin, a lipoprotein; an extracellular receptor or ligand; a protease; a kinase; a blood protein; a chemokine; a cytokine; a bone morphogenic protein; an anticoagulant; a blood factor; a bone morphogenetic protein; an engineered protein scaffold; an enzyme, e.g., a biocatalytic enzyme; a growth factor; an interferon; an interleukin; a thrombolytic agent; a hormone; and a TGF-beta family member protein. In some embodiments, the recombinant protein of interest is human, murine, rat, rabbit, guinea pig, camelid, shark, avian, yeast, fungal, gram-negative bacterial, or gram-positive bacterial. In some embodiments, the antibody, antibody fragment, or derivative thereof is selected from: a monoclonal antibody; a complementarity determining region (CDR) fragment; a CDR-grafted antibody; a single-chain antibody; a single chain antibody fragment; modified antibody, a bispecific antibody, a chimeric antibody; a diabody; a triabody; a tetrabody; a minibody; a linear antibody; a chelating recombinant antibody; a bibody; a tribody; an intrabody; a nanobody; a small modular immunopharmaceutical (SMIP); an antigen-binding-domain immunoglobulin fusion protein; a camelid antibody; a shark single domain antibody, an avian antibody (e.g., a chicken antibody), a VHH-containing antibody; a F(ab); a F(ab)'; F(ab)'$_2$; scFv; an Fc fragment generated from the heavy chain constant region of an antibody; a reduced IgG fragment (e.g., generated by reducing the hinge region disulfide bonds of IgG); an Fc fusion protein (e.g., comprising the Fc domain of IgG fused together with a protein or peptide of interest); a domain antibody; a VL; a VNAR; a VH; and a VHH. In some embodiments, the VHH-containing antibody is a VHH concatenated antibody. In some embodiments, the antibody, antibody fragment, or derivative thereof, binds to a target selected from: a cytokine; a chemokine; a drug; a cell-surface protein, e.g., a receptor, cell-surface marker, pathogen surface-protein, etc.; a growth factor; a growth factor receptor; immune checkpoint molecule, and a blood factor. In some embodiments, the antibody, antibody fragment, or derivative thereof is a Fab'. In some embodiments, the Fab' binds to a target selected from: Carcinoembryonic antigen (CEA); CD22; fibrin II, beta chain; TNF-alpha; and NCA-90 (granulocyte antigen). In some embodiments, the at least one expression construct encoding the antibody, antibody fragment, or derivative thereof comprises at least one nucleic acid sequence encoding a heavy chain, at least one nucleic acid sequence encoding a light chain, or both, wherein the heavy chain is full-length or a heavy chain fragment, and the light chain is full-length or a light chain fragment. In some embodiments, the at least one expression construct encoding the antibody, antibody fragment, or derivative thereof comprises at least two nucleic acid sequences, each encoding a heavy chain. In some embodiments, the at least one expression construct encoding the antibody, antibody fragment, or derivative thereof comprises a nucleic acid sequence encoding a heavy chain and a nucleic acid sequence encoding a light chain, wherein the heavy and light chain are expressed from the same mRNA transcript. In some embodiments, the at least one expression construct encoding the antibody, an antibody fragment, or derivative thereof comprises a nucleic acid sequence encoding a heavy chain and a nucleic acid sequence encoding a light chain, wherein the heavy and light chain are expressed from different mRNA transcripts. In some embodiments, each heavy chain-encoding nucleic acid sequence and each light chain-encoding nucleic acid sequence is individually operably linked to an independently selected nucleic acid sequence encoding a periplasmic secretion signal. In some embodiments, the periplasmic secretion signal has the amino acid sequence set forth as SEQ ID NO: 11, 13, 15, or 17. In some embodiments, the expression construct comprises: a nucleic acid sequence encoding an antibody heavy chain, operably linked to a nucleic acid sequence encoding a periplasmic secretion signal, wherein the periplasmic secretion signal has the amino acid sequence set forth as SEQ ID NOS: 11, 13, 15, or 17; a nucleic acid sequence encoding a light chain, operably linked to a nucleic acid sequence encoding a periplasmic secretion signal, wherein the periplasmic secretion signal has the amino acid sequence set forth as SEQ ID NOS: 11, 13, 15, or 17; or both. In some embodiments, the antibody, antibody fragment, or derivative thereof is humanized. In some embodiments, the Fab' is certolizumab. In some embodiments, the Fab' heavy chain has the amino acid sequence set forth as SEQ ID NO: 21, and the Fab' light chain has the amino acid sequence set forth as SEQ ID NO: 23. In some embodiments, the nucleic acid sequence encoding the heavy chain is operably linked to a nucleic acid sequence encoding a secretion leader having the amino acid sequence set forth as SEQ ID NO: 11, and the nucleic acid sequence encoding the light chain is operably linked to a nucleic acid sequence encoding a secretion leader having the amino acid sequence set forth as SEQ ID NO: 13.

In some embodiments, the recombinant gram-negative bacterial host cell is deficient in: (i) the first protease activity; (ii) the second protease activity; (iii) the activity of a serralysin precursor having the amino acid sequence set forth as SEQ ID NO: 9, a homologue of the serralysin precursor having the amino acid sequence set forth as SEQ ID NO: 9, or a serralysin precursor related protein having at least 60% similarity or at least 60% identity to the amino acid sequence set forth as SEQ ID NO: 9; (iv) an HslU protease having the amino acid sequence set forth as SEQ ID NO: 37, a homologue of the HslU protease having the amino acid sequence set forth as SEQ ID NO: 37, or a HslU related protein having at least 60% similarity or at least 60% identity to the amino acid sequence set forth as SEQ ID NO: 37; and (v) an HslV protease having the amino acid sequence set forth as SEQ ID NO: 38, a homologue of the HslV protease having the amino acid sequence set forth as SEQ ID NO: 38, or a HslV related protein having at least 60% similarity or at least 60% identity to the amino acid sequence set forth as SEQ ID NO: 38. In some embodiments, the host cell further overexpresses an exogenous inactivated DegP, wherein the inactivated DegP is selected from: *P. fluorescens* DegP2 S219A; an inactivated DegP2 derived from the amino acid sequence set forth as SEQ ID NO: 31; an inactivated DegP2 derived from the amino acid sequence set forth as SEQ ID NO: 62; an inactivated DegP2 derived from a homologue of the amino acid sequence set forth as SEQ ID NO: 31; an inactivated DegP2 derived from a DegP2 having at least 60% similarity or at least 60% identity to amino acid sequence set forth as SEQ ID NO: 31; an inactivated DegP2 derived from a DegP2 having at least 60% similarity or at least 60% identity to amino acid sequence set forth as SEQ ID NO: 62; and each of the proteases having the amino acid sequence set forth as SEQ ID NO: 31 comprising a conservative or nonconservative amino acid substitution or disruption of any one or more of residues 116, 146, 219, 108, 109, 110, 111, 112, 113, 114, 115, 116, 117, 118, 146, 147, 148, 149, 150, 151, 152, 217, 218, 219, 220, 221, 222, 223, 224, 225, 226, 227, 228, 229, 230, 231, 232, 233, and 234. In some embodiments, the recombinant gram-negative bacterial host cell overexpresses an exogenous disulfide isomerase selected from any one of: a disulfide isomerase having at least 60% similarity or at least 60% identity to an amino acid sequence set forth as SEQ ID NO: 27, 62, 63, 64, 65, 66, 67, 68, 69, 70, 71, 72, or 73, and a homologue of a disulfide isomerase having the amino acid sequence set forth as SEQ ID NO: 27, 62, 63, 64, 65, 66, 67, 68, 69, 70, 71, 72, and 73.

In some embodiments, the recombinant gram-negative bacterial host cell is selected from: a *Pseudomonad* host cell; an *E. coli* host cell; and a *Vibrio* host cell. In some embodiments, the host cell is a gram-positive host cell, e.g., a *Bacillus* host cell. In some embodiments, the *Pseudomonad* host cell is a *Pseudomonas* host cell. In some embodiments, the *Pseudomonas* host cell is *P. fluorescens, P. putida,* or *P. aeruginosa.* In some embodiments, the recombinant gram-negative bacterial host cell is: (i) lsc::lacIQ1; (ii) Prc1–; (ii) Prc2–; (iii) HslU–; (iv) HslV–; (v) MepM1–; (vi) PyrF–; and (vii) deficient in a serralysin precursor that is: a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9; wherein the serralysin precursor deficiency results from a mutation in a gene encoding the serralysin precursor. In some embodiments, the recombinant gram-negative bacterial host cell is *P. fluorescens*, the Prc1 has the amino acid sequence set forth in SEQ ID NO: 33, the Prc2 has the amino acid sequence set forth in (SEQ ID NO: 35), the HslU has the amino acid sequence set forth in (SEQ ID NO: 37), the HslV has the amino acid sequence set forth in (SEQ ID NO: 38), the MepM1 has the amino acid sequence set forth in (SEQ ID NO: 1), and the serralysin precursor has the amino acid sequence set forth as SEQ ID NO: 9. In some embodiments, the host cell further comprises an expression vector comprising a nucleic acid sequence encoding DegP2 S219A (SEQ ID NO: 29). In some embodiments, the recombinant gram-negative bacterial host cell further comprises an expression vector comprising a nucleic acid sequence encoding disulfide isomerase PDIA6 (SEQ ID NO: 27). In some embodiments, the host cell further comprises an expression vector encoding a recombinant protein. In some embodiments, the expression vector encodes a Fab'. In some embodiments, the expression vector comprising the nucleic acid sequence encoding DegP2 S219A or disulfide isomerase PDIA6 further comprises a nucleic acid sequence encoding the Fab'. In some embodiments, the Fab' heavy chain is encoded by SEQ ID NO: 21, and the Fab' light chain is encoded by SEQ ID NO: 23. In some embodiments, the recombinant gram-negative bacterial host cell is a *Pseudomonad* having the genotype of strain STR94975, STR94976, or STR94977. In some embodiments, the recombinant gram-negative bacterial host cell, further comprises the expression construct or constructs comprised by a plasmid of STR94975, STR94976, or STR94977, for use in producing a recombinant anti-TNF-alpha Fab'. In some embodiments, the gram-negative bacterial host cell is not *E. coli*.

The present invention further includes a method for producing a recombinant protein of interest comprising: (a) recovering the recombinant protein of interest from a recombinant gram-negative bacterial host cell of the invention cultured under suitable fermentation conditions, wherein the recombinant gram-negative host cell is transformed with a plasmid comprising a nucleic acid encoding the recombinant protein of interest. In some embodiments, transcription of the nucleic acid sequence encoding the recombinant protein of interest is regulated by an inducible promoter. In some embodiments, the inducible promoter is selected from: a tac promoter, a mannitol promoter, a Pben, a T7 promoter, a lac promoter, a T5 promoter, a xylose promoter, and an arabinose promoter. In some embodiments, the recombinant gram-negative bacterial host cell can grow to high cell density. In some embodiments, the high cell density comprises an OD575 of about 80 to about 300. In some embodiments, the suitable fermentation conditions comprise induction of the inducible promoter at: an OD575 of about 80 to about 160, a culture pH of about 5.8 to about 7.0, a temperature of about 28-33 deg C., fed-batch, and a titer range of about 0.2 to about 5 g/L. In some embodiments, the inducible promoter is induced by IPTG, and wherein the IPTG is added to a final concentration of about 0.08-0.3 mM. In some embodiments, the IPTG is added to a final concentration of about 0.2 mM. In some embodiments, induction is carried out at a culture pH of about 6.0 to about 6.5. In some embodiments, induction is carried out at a temperature of about 28-33 deg C. In some embodiments, induction is carried out at a temperature of about 32 deg C. In some embodiments, the recombinant gram-negative bacterial host cell grows to a cell density that is increased in comparison to a control cell grown under the same fermentation conditions. In some embodiments, the increase in cell density is about 2-fold to about 15-fold. In some embodiments, the method further comprises: (b) measuring the yield of intact, soluble, and/or active, recombinant protein of interest recovered from the recombinant gram-negative bacterial host cell. In some embodiments, the measured yield of intact, soluble, and/or active, recombinant protein is about 0.1 to about 10 g/L. In some embodiments, the method further comprises: (c) measuring the yield of recombinant protein of interest recovered from a control cell that is intact, soluble, active, or a combination thereof. In some embodiments, the method further comprises (d) comparing the yield measured in step (b) to the yield measured in step (c). In some embodiments, the yield measured in step (b) is about 2-fold to about 100-fold higher than that measured in step (c). In some embodiments, the recombinant gram-negative bacterial host cell and the control cell, respectively, are selected from: (i) a recombinant gram-negative bacterial host cell deficient in the first protease activity and the second protease activity, and a corresponding gram-negative bacterial host cell deficient in the first protease activity and wherein the second protease is functional; (ii) a recombinant gram-negative bacterial host cell deficient in the first protease activity, the second protease activity, and an additional protease activity as recited in 2(a), and a corresponding gram-negative bacterial host cell deficient in the first protease activity and the second protease activity, and wherein the additional protease activity of 2(a) that is deficient in the compared recombinant gram-negative bacterial host cell is functional; and (iii) a recombinant gram-negative bacterial host cell deficient in the first protease activity and the second protease activity, and comprising a functional protease that is: a MepS1 having the amino acid sequence set forth as SEQ ID NO: 5; a homologue of the MepS1 having the amino acid sequence set forth as SEQ ID NO: 5; or a MepS1 related protein having at least 50% sequence similarity to the *P. fluorescens* MepS1 amino acid sequence set forth as SEQ ID NO: 5, and a corresponding gram-negative bacterial host cell deficient in the activity of the first protease and the second protease, and deficient in the functional protease of the compared recombinant gram-negative bacterial host cell. In some embodiments, the gram-negative bacterial host cell is not *E. coli*.

The invention also includes a recombinant polypeptide comprising: a secretion signal peptide operably linked to a heterologous protein or polypeptide of interest, wherein the secretion signal peptide has the amino acid sequence set forth in SEQ ID NO: 11. The protein or polypeptide of interest can be: an antibody, antibody fragment, or a derivative of an antibody or an antibody fragment; an enzyme; a cytokine; a chemokine; a growth factor; a fusion protein; and a vaccine antigen. In some embodiments, the antibody, antibody fragment, or a derivative of an antibody or antibody fragment is selected from: a monoclonal antibody; a full chain antibody; a complementarity determining region (CDR) fragment; a CDR-grafted antibody; a single-chain antibody; a single chain antibody fragment; a modified antibody; a variable-region only antibody fragment; a bispecific antibody, a chimeric antibody; a triabody; a tetrabody; a minibody; a linear antibody; a chelating recombinant antibody; a bibody; a diabody; an intrabody; a nanobody; a small modular immunopharmaceutical; an antigen-binding-domain immunoglobulin fusion protein; a camelid antibody; a shark single domain antibody (VNAR); an avian antibody; a VHH; a VHH-containing antibody; a VHH concatemer; a F(ab); a F(ab)'; F(ab)'2; an scFv; an Fc fragment generated from the heavy chain constant region of an antibody; a reduced IgG fragment; an Fc fusion protein; a domain antibody; a VL; and a VH. In some embodiments, the antibody, antibody fragment, or derivative of the antibody or antibody fragment is humanized. In some embodiments, the enzyme is a therapeutic enzyme. In some embodiments, the therapeutic enzyme is selected from: a peptidase; a lactase; an amylase; a PEP; a digestive enzyme; a uricase; a rhodanase; a urokinase; a streptokinase; a staphylokinase; a phenylase; a sacrosidase; a lysozyme; a chitinase; a ribonuclease; a glutaminase; an arginase; a vibrilase; a chondroitinase; a hyaluronidase; a galactosidase; a glucuronidase; a glucocerebrosidase; a thymidine phosphorylase; a carbonic anhydrase; a uricase thiosulfate-cyanide; a sulfurtransferase; a phosphothioesterase; an alcohol oxidase; an alcohol dehydrogenase; an asparaginase; a glutamine synthase; an adenosine deaminase; bovine pegademase; alglucerase; dornase alpha; imiglucerase; sacrosidase; rasburicase; agalsidase beta; and nattokinase. In some embodiments, the fusion protein is selected from: an enzyme fusion protein; a protein A fusion protein; an albumin fusion protein; a thioredoxin fusion protein; a ubiquitin fusion protein; a streptavidin fusion protein; a maltose binding protein fusion protein; a chitin being protein fusion protein; a SUMO fusion protein; and a glutathione-S-transferase fusion protein. In some embodiments, the polypeptide further comprises a linker. In some embodiments, the polypeptide further comprises a cleavage domain. In some embodiments, the secretion signal peptide directs expression of the protein or polypeptide of interest to the periplasm or the extracellular space of a prokaryotic host cell. In some embodiments, the protein or polypeptide of interest is expressed in the periplasm properly cleaved from the secretion signal peptide. In some embodiments, the secretion signal peptide directs expression of the protein or polypeptide of interest to the periplasm or the extracellular space of a prokaryotic host cell in properly cleaved form, soluble form, active form, or any combination thereof. A properly cleaved protein or polypeptide of interest may have an intact or substantially intact N-terminus. In some embodiments, the properly cleaved protein or polypeptide of interest having an intact or substantially intact N-terminus comprises the N-terminal methionine. In some embodiments, the properly cleaved protein or polypeptide of interest having an intact or substantially intact N-terminus does not comprise the N-terminal methionine. In some embodiments, the protein or polypeptide of interest requires a substantially intact N-terminus for substantial activity. In some embodiments, the protein or polypeptide of interest having a substantially intact N-terminus has about 90-100% of its activity when compared to the same protein or polypeptide of interest having an intact N-terminus. The prokaryotic host cell may a gram-negative bacterium. The prokaryotic host cell may be a gram-positive bacterium. The gram-negative bacterium may be a *Pseudomonad, V. natriegens*, or *E. coli*. The gram-positive bacterium may be a *Corynebacterium* or a *Bacillus*. The invention includes an expression vector comprising a nucleic acid sequence encoding the recombinant polypeptide. The invention includes a prokaryotic host cell comprising an expression vector comprising a nucleic acid sequence encoding the recombinant polypeptide. In some embodiments, an expression vector and/or a nucleic acid construct encoding the recombinant polypeptide comprises a nucleic acid sequence that encodes the secretion signal peptide of SEQ ID NO: 11, operably linked to a nucleic acid sequence that encodes the heterologous protein or polypeptide of interest. In some embodiments, the secretion signal peptide amino acid sequence is encoded by a nucleic acid sequence having 85-100% sequence identity to SEQ ID NO: 12. The prokaryotic host cell may be a gram-negative bacterium. The prokaryotic host may be a gram-positive bacterium. The gram-negative bacterium may be a *Pseudomonad, V. natriegens*, or *E. coli*. The gram-positive bacterium may be a *Corynebacterium* or a *Bacillus*. In some embodiments, the nucleic acid sequence encoding the recombinant polypeptide is optimized for expression in the prokaryotic host cell. The invention also includes the use of a recombinant polypeptide, an expression vector, or a prokaryotic host cell, as described herein, for expressing a protein or polypeptide of interest in the periplasm or the extracellular space of a prokaryotic host cell.

The invention further includes a method of producing a protein or polypeptide of interest in a prokaryotic host cell, the method comprising: producing the protein or polypeptide of interest in the periplasm of a prokaryotic host cell cultured in a cell culture growth medium, wherein the prokaryotic host cell comprises an expression construct comprising a nucleic acid encoding a recombinant polypeptide comprising the protein or polypeptide of interest operably linked to a secretion signal peptide that directs expression of the protein or polypeptide of interest to the periplasm of the prokaryotic host cell, wherein the secretion signal peptide comprises the amino acid sequence set forth in SEQ ID NO: 11, and wherein the secretion signal peptide is not native to the protein or polypeptide of interest. The method may further comprise isolating the produced protein or polypeptide of interest. The protein or polypeptide of interest may be selected from: an antibody, antibody fragment, or a derivative of an antibody or an antibody fragment; an enzyme; a cytokine; a chemokine; a growth factor; a fusion protein; and a vaccine antigen. In some embodiments, the antibody, antibody fragment, or a derivative of an antibody or an antibody fragment is selected from: a monoclonal antibody; a full chain antibody; a complementarity determining region (CDR) fragment; a CDR-grafted antibody; a single-chain antibody; a single chain antibody fragment; a modified antibody; a variable-region only antibody fragment; a bispecific antibody, a chimeric antibody; a triabody; a tetrabody; a minibody; a linear antibody; a chelating recombinant antibody; a bibody; a dibody; an intrabody; a nanobody; a small modular immunopharmaceutical; an antigen-binding-domain immunoglobulin fusion protein; a camelid antibody; a shark single domain antibody (VNAR); an avian antibody; a VHH; a VHH-containing antibody; a VHH concatemer; a F(ab); a F(ab)'; F(ab)'2; an scFv; an Fc fragment generated from the heavy chain constant region of an antibody; a reduced IgG fragment; an Fc fusion protein; a domain antibody; a VL; and a VH. In some embodiments, the antibody, antibody fragment, or derivative of the antibody or antibody fragment is humanized. In some embodiments, the enzyme is a therapeutic enzyme. In some embodiments, the therapeutic enzyme is selected from: a peptidase; a lactase; an amylase; a PEP; a digestive enzyme; a uricase; a rhodanase; a urokinase; a streptokinase; a staphylokinase; a phenylase; a sacrosidase; a lysozyme; a chitinase; a ribonuclease; a glutaminase; an arginase; a vibrilase; a chondroitinase; a hyaluronidase; a galactosidase; a glucuronidase; a glucocerebrosidase; a thymidine phosphorylase; a carbonic anhydrase; a uricase thiosulfate-cyanide; a sulfurtransferase; a phosphothioesterase; an alcohol oxidase; an alcohol dehydrogenase; an asparaginase; a glutamine synthase; an adenosine deaminase; bovine pegademase; alglucerase; dornase alpha; imiglucerase; sacrosidase; rasburicase; agalsidase beta; and nattokinase. In some embodiments, the fusion protein is selected from: an enzyme fusion protein; a protein A fusion protein; an albumin fusion protein; a thioredoxin fusion protein; a ubiquitin fusion protein; a streptavidin fusion protein; a maltose binding protein fusion protein; a chitin being protein fusion protein; a SUMO fusion protein; and a glutathione-S-transferase fusion protein. In some embodiments, the nucleic acid encodes a linker. In some embodiments, the linker comprises a cleavage domain. The prokaryotic host cell may be a gram-negative bacterium. The prokaryotic host cell may be a gram-positive bacterium. The gram-negative bacterium may be a *Pseudomonad*, *V. natriegens*, or *E. coli*. The gram-positive bacterium may be a *Corynebacterium* or a *Bacillus*.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Closed circles: STR36306 (Fab' expression plasmid; growth to a max OD575 of about 27)

Diamonds: STR94998 (DC1032+null plasmid; growth to a max OD575 of about 50)

Triangles: STR94994 (DC1032 MepS1 deletion+p688-048; growth to a max OD575 of about 23)

Squares: STR94995 (DC1032 MepS2 deletion+p688-048; growth to a max OD575 of about 33)

Open circles: STR94996 (DC1032 MepS1 deletion and MepS2 deletion+p688-048; growth to a max OD575 of about 22).

Figure 3A:
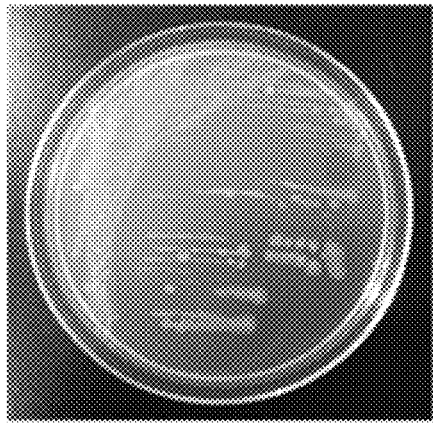
Figure 3B:
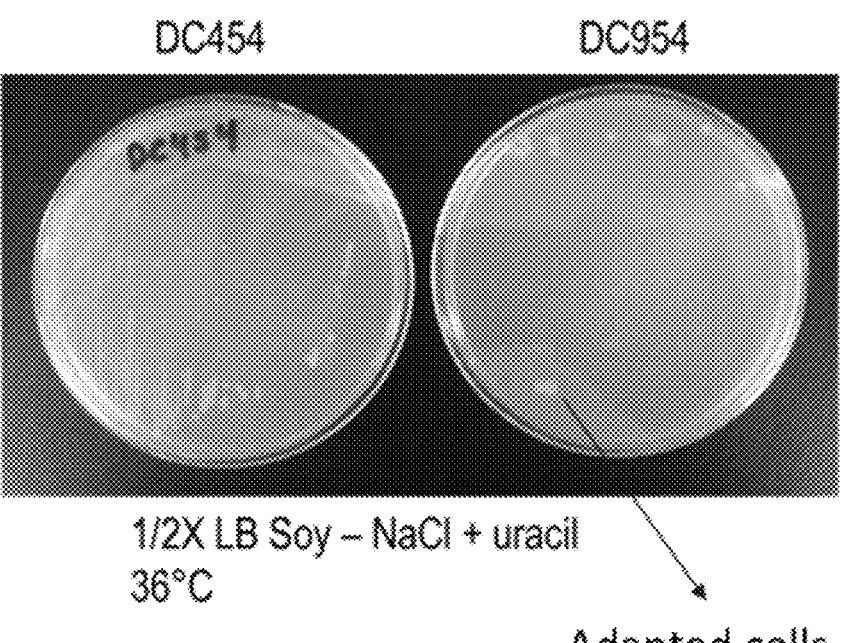

FIGS. 3A and 3B. Prc1- and Prc2-deficient host strain growth at sub-optimal conditions. 3A. Growth of DC954 colonies on 1×LB agar medium in the absence of NaCl and in the presence of uracil (to allow growth given the pyrF deletion) at 36 deg C. Colonies with background growth are visible. 3B. The plate on the left shows growth of DC454 (no protease deletion) on 0.5×LB agar medium in the absence of NaCl, with uracil, at 36 deg C. Growth was slower than on 1×LB, but these growth conditions were not lethal. The plate on the right shows growth of DC954 on 0.5×LB agar medium in the absence of NaCl, with uracil, at 36 deg C. The adapted (evolved) cells are capable of growth.

Figure 4:
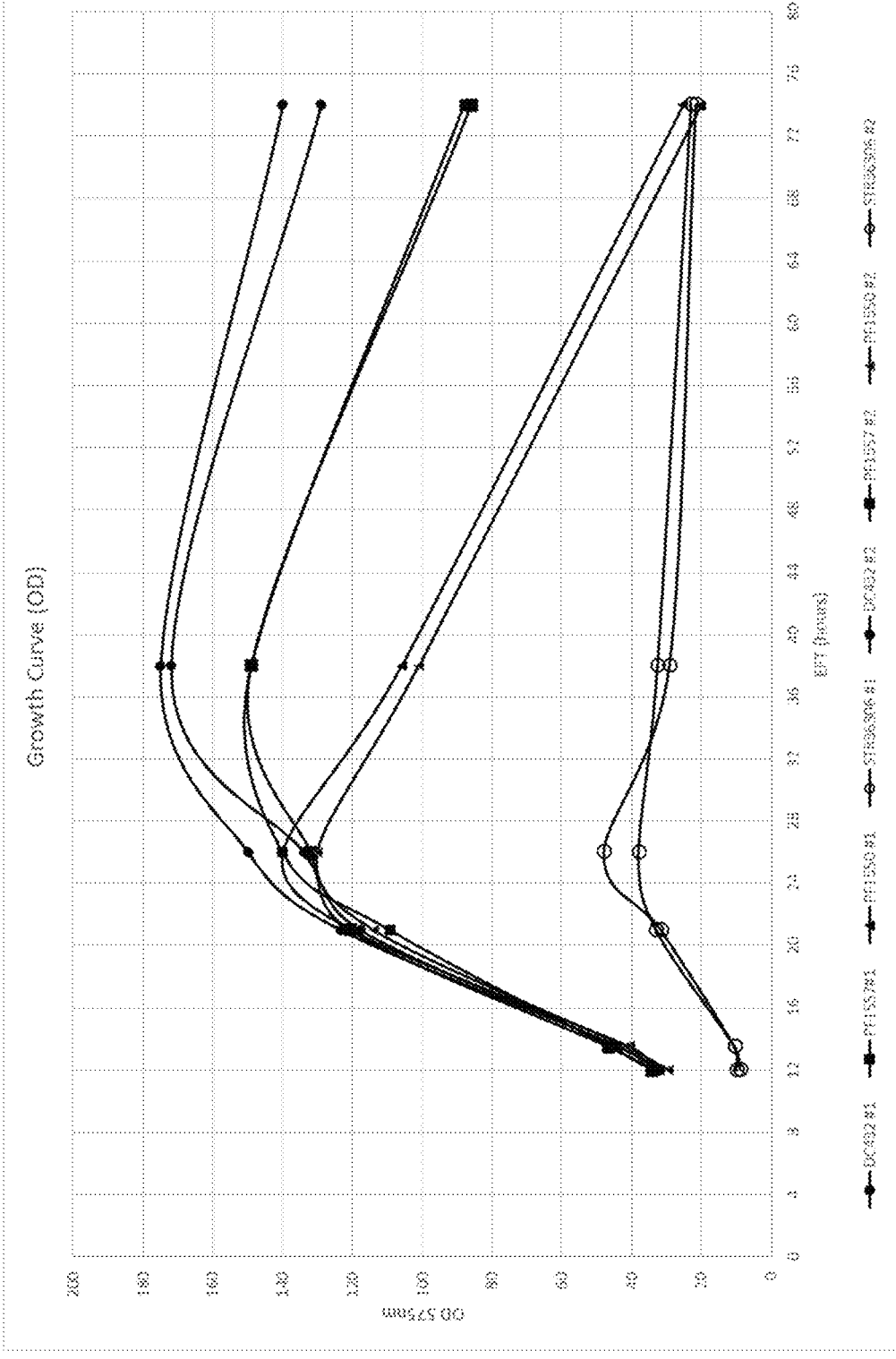

FIG. 4. Growth of evolved host strains at 2 L scale. Y-axis: OD575, X-axis: fermentation time in hours. The gridlines mark 4-hour intervals, with the last timepoint taken at 74 hours (induction at 25.5 hours). Two cultures of each strain were grown, corresponding to the two curves for each strain #.

Triangles: PF1550, evolved from host DC954 to include MepM1 deficiency, resulting genotype Δprc1, Δprc2, MepM1(P410L), ΔpyrF, lsc::lacIQ1+p688-48 (Fab')

Open circles: STR36306, host DC1032 having genotype Δprc1, Δprc2, ΔhslUV, ΔpyrF, lsc::lacIQ1+p688-48 (Fab')

Squares: PF1557 evolved having genotype Δprc1, Δprc2, MepM1(P410L), ΔpyrF, lsc::lacIQ1+pDOW1169 (empty expression vector)

Closed circles: DC432, host DC454 having genotype ΔpyrF+pDOW1169 (empty expression vector).

Figure 5:
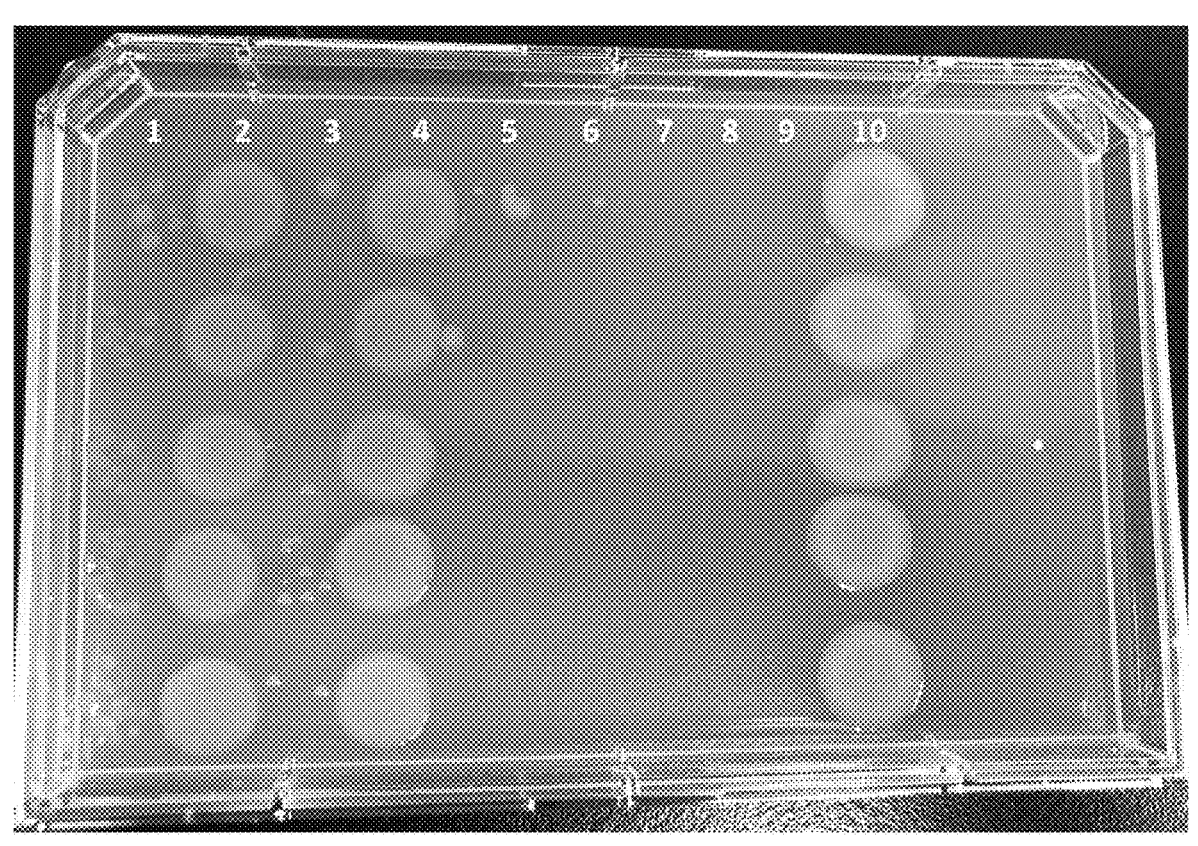

FIG. 5. Growth+ combinatorial MepM and MepS mutants. Examples of growth by selected combinatorial mutants. From left to right, each of the following mutant strains (all Δprc1, Δprc2 except DC454 control; see Table 6 for genotypes) was spotted on 0.5×LB+250 ug/ml uracil agar medium in the absence of NaCl, and incubated for 48 hours at 36 deg C. In each row, five 10-fold serial dilutions were spotted, in descending concentration from the top to the bottom of the plate as oriented in the figure.

Column 1: DC1032 (Prc−)
　　Column 2: PF1559
　　Column 3: PF1588
　　Column 4: PF1560
　　Column 5: PF1590
　　Column 6: PF1572
　　Column 7: PF1577
　　Column 8: PF1573
　　Column 9: PF1575
　　Column 10: DC454 (Prc+)

Figure 6:
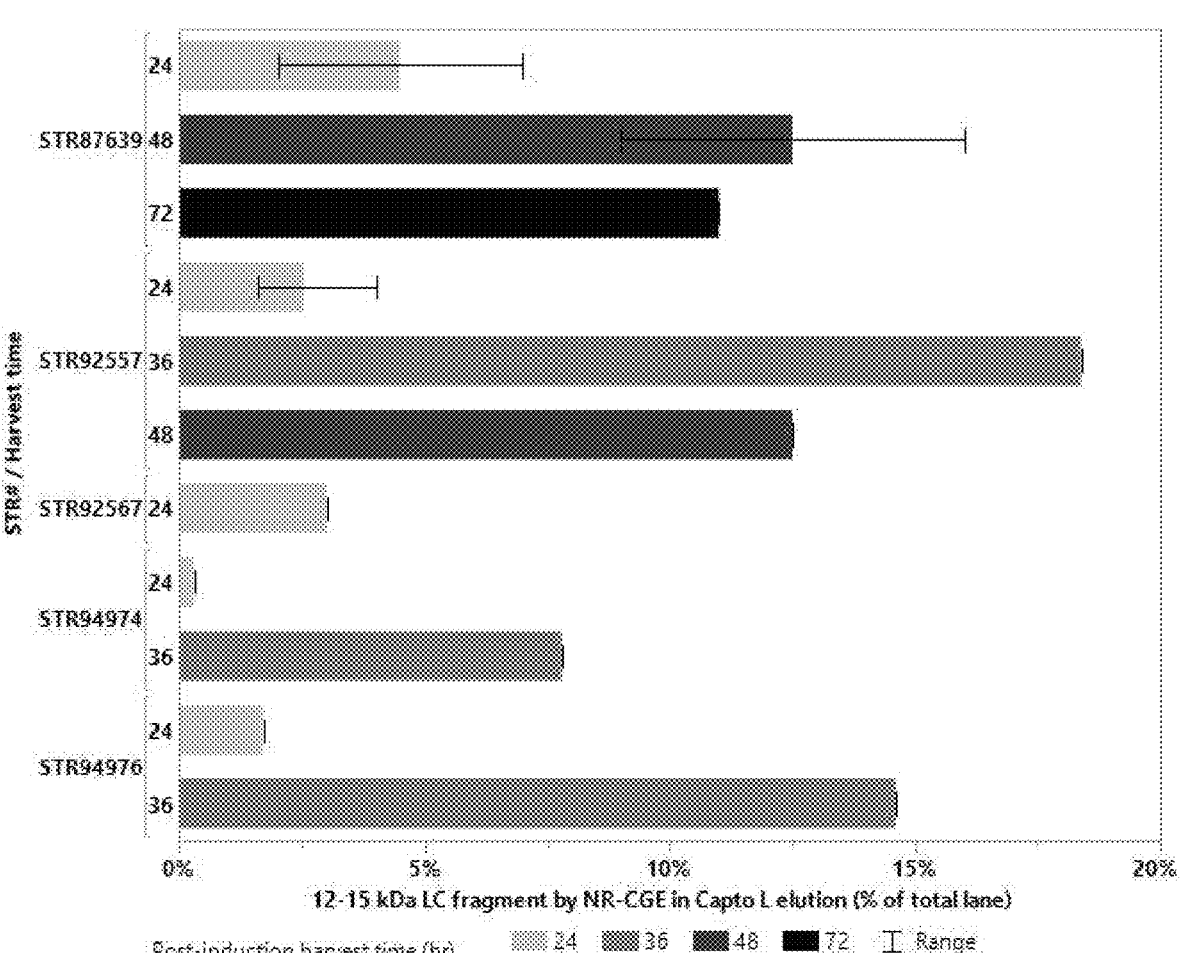

FIG. 6. Light chain proteolysis in protease-deficient host strains. STR87639, STR92557, STR92567, STR94974, and STR94976 were grown and harvested at the post-induction times (in hours) as shown on the y-axis, and the recombinant protein Capto-L enriched and analyzed by NR-SDS-CGE. The x-axis shows the percent of proteolyzed light chain species in each lane.

Figure 7:
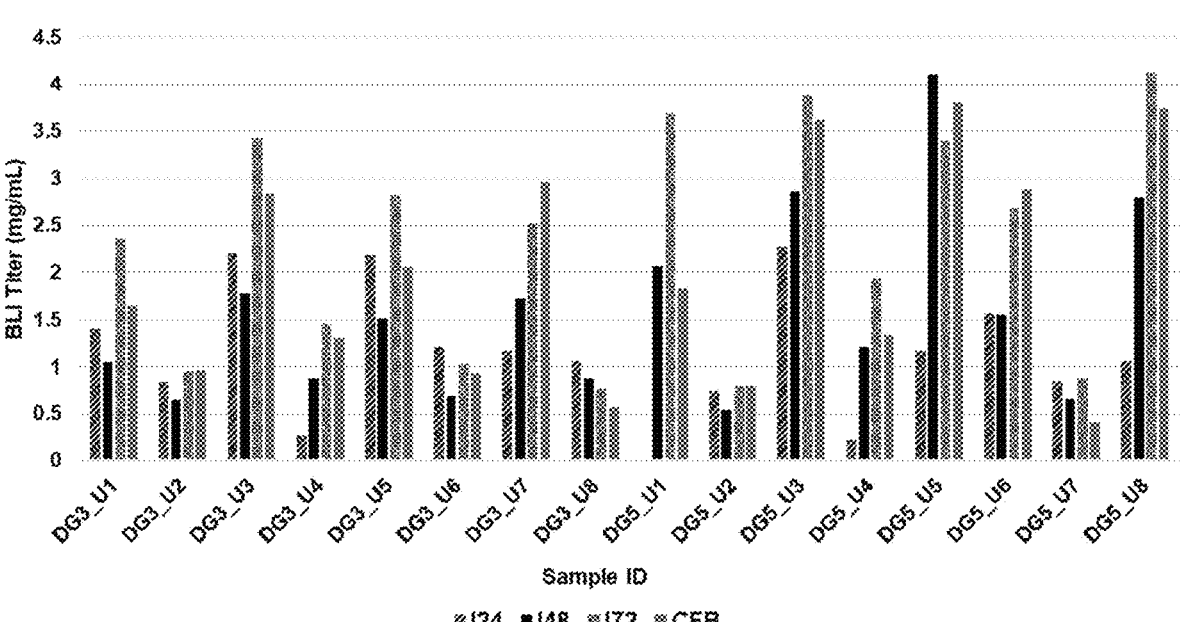

FIG. 7. Titer of recombinant Fab' produced by protease-deficient host strains under various fermentation conditions. Fab' titer (Y-axis) from strains STR94974, STR94975, and STR4977 induced under varying pH and temperature conditions at the 2 L fermenter scale was assessed by BLI measuring Fab' binding to TNF-alpha. Growth was performed at 2 L bioreactor scale at 32 deg C., pH 6.5 and induced with 0.2 mM IPTG+/−5 g/L mannitol at OD575 at various pH and temperature values. The fermentation unit identifiers are shown along the X-axis. DG3_u1 (STR94974, 28 deg C. and induced at pH 6.5), DG3_u2 (STR94974 25 deg C. and pH6), DG3_u3 (STR94974 32 deg C. and pH6), DG3_u4 (STR94974 25 deg C. and pH 7), DG3_u5 (STR94975 28 deg C., pH 6.5, 5 g/L mannitol), DG3_u6 (STR94975 25 deg C., pH 6.0, 5 g/L mannitol), DG3_u7 (STR94975 32 deg C., pH 6.0 and 5 g/L mannitol), DG3_u8 (STR94975 25 deg C., pH 7.0), DG5_u1 (STR94977 28 deg C., pH6.5), DG5_u2 (STR94977 25 deg C., pH 6.0), DG5_u3 (STR94977, 32 deg C. pH 6.0), DG5_u4

(STR94977 25 deg C., pH 7.0), DG5_u5 (STR94974 32 deg C., pH 6.0), DG5_u6 (STR94975 32 deg C., PH 6.0, 5 g/L mannitol), DG5_u7 (STR94975 25 deg C. pH 7, 5 g/L mannitol), DG3_u8 (STR94977 32 deg C., pH 6.0). Samples of whole cell broth at post-induction times 24, 48 and 72 hrs were processed and analyzed. At 72 hrs cells were separated from the media to assess Fab' titer in cell free broth (CFB).

Figure 8A:
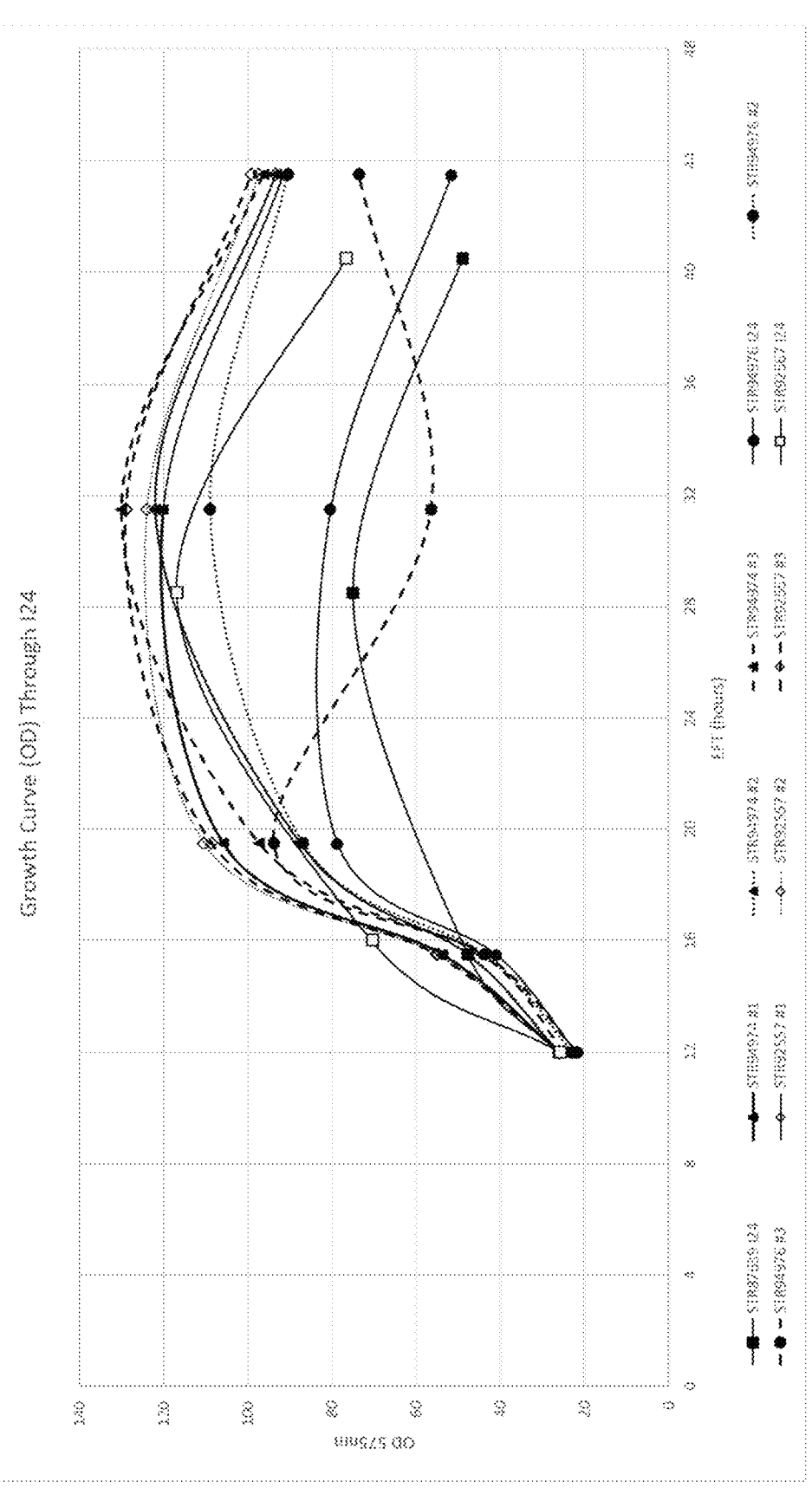
Figure 8B:

FIGS. 8A and 8B. Growth comparisons of strain STR87639 with STR92557, STR92567, STR94974, and STR94976. Graphs comparing the growth of Fab' expression strains grown at 32 deg C. and pH 6.5. Cultures were induced at elapsed fermentation time (EFT) 19.5 hours with 0.2 mM IPTG and at 32 deg C., pH 6.0. OD575 is shown on the Y-axis and EFT on the X-axis. 8A. Representative growth curves of the strains up to 24 hrs post induction. 8B. Growth curves of the strains up to 48 hrs post-induction. In both 8A and 8B:

Closed squares, solid line: STR87639 I24
　　Triangles, solid line: STR94974 #1
　　Triangles, dotted line: STR94974 #2
　　Triangles, dashed line: STR94974 #3
　　Circles, solid line: STR94976 I24
　　Circles, dotted line: STR94976 #2
　　Circles, dashed line: STR94976 #3
　　Open diamonds, solid line: STR92557 #1
　　Open diamonds, dotted line: STR92557 #2
　　Open diamonds, dashed line: STR92557 #3
　　Open squares, solid line: STR92567 I24.

Figure 9:
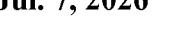

FIG. 9. Growth comparisons of strain STR87639 with STR92473, STR94994, STR94995, STR94996, and STR94998.

Graph compares growth of Prc-deficient Fab' expression strains STR87639, STR92473, STR94994, STR94995, and STR94996, and STR94998. Growth phase was conducted at 32 deg C., pH 6.5.

Closed circles, solid line: STR87639
　　Triangles, solid line: STR92473
　　Diamonds, solid line: STR94995
　　Circles, dashed line: STR94998
　　Open circles, solid line: STR94996
　　Squares, solid line: STR94994

Figure 10:
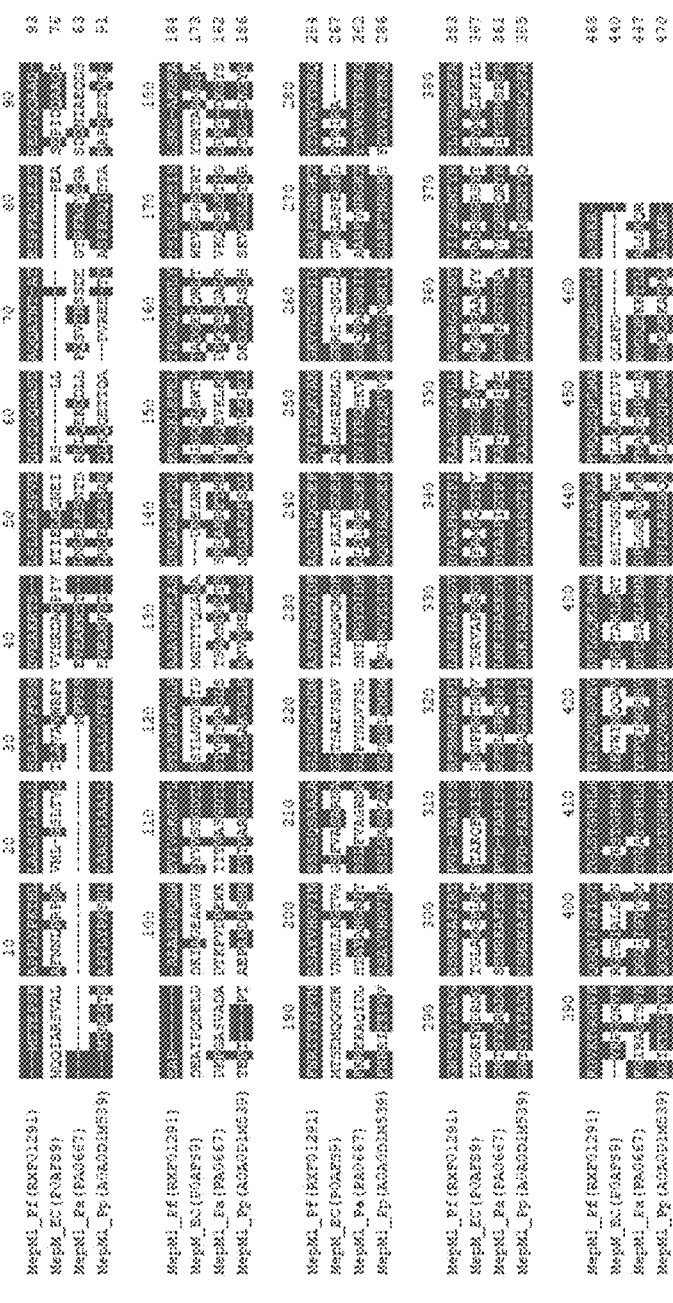

FIG. 10. Alignment showing murein DD-endopeptidase conserved amino acid residues. Conserved residues are in white lettering on dark background. Row 1 (top row)=*P. fluorescens* MepM1 (SEQ ID NO: 1); Row 2 (second from top)=*E. coli* MepM (SEQ ID NO: 63, also known as YebA); Row 3=*P. aeruginosa* MepM1 (SEQ ID NO: 66); Row 4 (bottom row): *P. putida* MepM1 (SEQ ID NO: 65).

DETAILED DESCRIPTION OF THE INVENTION

Provided herein are compositions and methods for producing high quality recombinant proteins at high yield.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In some embodiments of any of the compositions and methods provided herein, "comprising" may be replaced with "consisting essentially of" or "consisting of." The phrase "consisting essentially of" is used herein to require the specified feature(s) as well as those which do not materially affect the character or function of the claimed invention. As used herein, the term "consisting" is used to indicate the presence of the recited feature alone. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "embodiments," "certain embodiments," "preferred embodiments," "specific embodiments," "some embodiments," "an embodiment," "one embodiment" or "other embodiments" mean that a particular feature, structure, or characteristic described in connection with the embodiments is included in at least some embodiments, but not necessarily all embodiments, of the present disclosure.

Recombinant Protein Expression in Bacterial Host Cells

Recombinant proteins expressed in bacterial host cells are subject to degradation by any of several dozen host cell proteases. Degradation lowers protein quality and yield, often making production of useful quantities of proteolytically sensitive proteins impossible. Although the introduction of protease deficiencies in the host cell can reduce recombinant protein degradation, such deficiencies can prevent the host cell from growing to high density. Poor cell growth reduces recombinant protein yield, negating the advantage of the protease gene mutation. For example, as described herein, despite showing reduced degradation of recombinant proteins, bacteria deficient in tail-specific protease activity grow poorly.

The present invention relates to recombinant gram-negative bacterial host cells that are genetically engineered to produce high quality recombinant proteins without compromising cell growth. In some embodiments, the present invention relates to recombinant gram-negative bacterial host cells deficient in tail-specific protease activity, that are further modified to restore growth to high cell density. The growth inhibition resulting from deficient tail-specific protease activity is overcome by the introduction of one or more further genetic modifications resulting in deficiency of protease activity. Often more than one host cell protease activity causes unwanted recombinant protein degradation. To remedy this, the invention also provides host cells having additional protein deficiencies discovered to further enhance recombinant protein quality. Also provided are methods for use of the inventive host cells to produce high quality (e.g., active, soluble, and/or intact) recombinant proteins of interest, at high yield.

Host Cell Protein Deficiencies that Enhance Recombinant Protein Production

The present invention provides recombinant gram-negative bacterial host cells deficient in a first protease activity and a second protease activity. In some embodiments, a recombinant gram-negative bacterial host cell of the invention is: deficient in a first protease activity and a second protease activity, and further (a) is deficient in one or more additional protease activity; (b) is deficient in one or more autolytic factor activity; (c) overexpresses one or more inactivated protease; (d) overexpresses one or more chaperone or folding modulator protein; or (e) any combination of (a), (b), (c) and (d). In some embodiments, an additional protease, an autolytic factor, an inactivated protease, a chaperone or folding modulator, the first protease and the second protease, are each different. In some embodiments, an additional protease, an autolytic factor, an inactivated protease, or a chaperone or folding modulator, are the same as the first protease and/or the second protease. In some embodiments, the protease that is inactivated is the same as an additional protease. It is understood that the overexpressed inactivated protease of (c) and the overexpressed chaperone or folding modulator protein of (d) are different from a recombinant protein of interest to be overexpressed in the host cell. An overexpressed inactivated protease of (c) and/or an overexpressed chaperone or folding modulator protein of (d) can thus be co-overexpressed with a recombinant protein of interest.

In some embodiments, a recombinant gram-negative bacterial host cells is deficient in a first protease activity and a second protease activity, and deficient in one or more additional protease activity. In some embodiments, a recombinant gram-negative bacterial host cells is deficient in a first protease activity and a second protease activity, and deficient in one or more autolytic factor activity. In some embodiments, a recombinant gram-negative bacterial host cell is deficient in a first protease activity and a second protease activity, and overexpresses one or more inactivated proteases. In some embodiments, a recombinant gram-negative bacterial host cell is deficient in a first protease activity and a second protease activity, and overexpresses one or more chaperones.

In some embodiments, a recombinant gram-negative bacterial host cell is deficient in a first protease activity and a second protease activity, is deficient in one or more additional protease activity, and deficient in one or more autolytic factor activity. In some embodiments, a recombinant gram-negative bacterial host cell is deficient in a first protease activity and a second protease activity, is deficient in one or more additional protease activity, and overexpresses one or more inactivated proteases. In some embodiments, a recombinant gram-negative bacterial host cell is deficient in a first protease activity and a second protease activity, is deficient in one or more additional protease activity, and overexpresses one or more chaperones.

In some embodiments, a recombinant gram-negative bacterial host cell is deficient in a first protease activity and a second protease activity, is deficient in one or more autolytic factor activity, and overexpresses one or more chaperones. In some embodiments, a recombinant gram-negative bacterial host cell is deficient in a first protease activity and a second protease activity, overexpress one or more inactivated proteases, and overexpresses one or more chaperones. In some embodiments, a recombinant gram-negative bacterial host cell is deficient in a first protease activity and a second protease activity, is deficient in one or more additional proteases, is deficient in one or more autolytic factor activity, and overexpresses one or more inactivated proteases. In some embodiments, a recombinant gram-negative bacterial host cell is deficient in a first protease activity and a second protease activity, is deficient in one or more additional protease activity, is deficient in one or more autolytic factor activity, and overexpresses one or more chaperones. In some embodiments, a recombinant gram-negative bacterial host cell is deficient in a first protease activity and a second protease activity, is deficient in one or more additional protease activity, is deficient in one or more autolytic factor activity, overexpress one or more inactivated proteases, and overexpresses one or more chaperones.

In some embodiments, an additional protease activity is different from the first protease activity. In some embodiments, an additional protease activity is different from the second protease activity. In some embodiments, an additional deficient protease activity is different from the first protease activity and the second protease activity. In some embodiments, an autolytic factor activity is different from the first protease activity. In some embodiments, an autolytic factor activity is different from the second protease activity. In some embodiments, an autolytic factor activity is different from an additional protease activity. In some embodiments, an autolytic factor activity is different from the normal activity of an overexpressed inactivated protease. In some embodiments, an autolytic factor activity is different from the activity of an overexpressed chaperone. In some embodiments, an autolytic factor activity is different from the first protease activity and the second protease activity. In some embodiments, the normal activity of an overexpressed inactivated protease is different from the first protease activity. In some embodiments, the normal activity of an overexpressed inactivated protease is different from the second protease activity. In some embodiments, the normal activity of an overexpressed inactivated protease is different from the first protease activity and the second protease activity. In some embodiments, the normal activity of an overexpressed inactivated protease is the same as the first protease activity. In some embodiments, the normal activity of an overexpressed inactivated protease is the same as the second protease activity. In some embodiments, the normal activity of an overexpressed inactivated protease is the same as an additional deficient protease activity.

In some embodiments, the activity of an overexpressed chaperone is different from the first protease activity. In some embodiments, the activity of an overexpressed chaperone is different from the second protease activity. In some embodiments, the activity of an overexpressed chaperone is different from the first protease activity and the second protease activity. In some embodiments, the activity of an overexpressed chaperone is different from an additional protease activity. In some embodiments, the activity of an overexpressed chaperone is different from an overexpressed inactivated protease activity.

In some embodiments, a deficiency in a host cell protein activity, e.g., a protease activity or autolytic factor activity, results from a mutation of a gene encoding a protein having the activity. In some embodiments, a deficiency in a protein activity results from the mutation of at least two genes encoding proteins having the activity, wherein each of the at least two genes encodes a related protein as described herein. The related proteins may be homologues, share a minimum sequence similarity or identity, or both. In some embodiments, a deficiency in a protein activity results from mutation of any gene corresponding to any related protein or any protein homologue. In some embodiments, a deficiency in a protease activity results from mutation of a gene corresponding to any related protease and/or protease homologue. In some embodiments, a deficiency in an autolytic factor activity results from mutation of a gene corresponding to any related autolytic factor and/or autolytic factor homologue.

Bacterial Tail-Specific Proteases

The present invention provides recombinant gram-negative bacterial host cells deficient in a first protease activity, wherein the first protease activity is a tail-specific protease activity. Tail-specific proteases (Prc/Tsp) are described in, e.g., Expasy enzyme EC 3.4.21.102, incorporated herein by reference. Prc is an ATP-dependent periplasmic protease designated a tail-specific protease (Tsp) because it cleaves protein C-termini in a sequence-dependent manner as described by, e.g., Kerr, C. H., et al., 2014, "Salinity-Dependent Impacts of ProQ, Prc, and Spr Deficiencies on *Escherichia coli* Cell Structure, J. Bact. 196(6):1286-1296, incorporated by reference herein. Inactivation of the prc gene in *E. coli* confers thermosensitive cell growth under low osmolality (e.g., Hara H., et al., 1991, "Cloning, mapping, and characterization of the *Escherichia coli* prc gene, which is involved in C-terminal processing of penicillin-binding protein 3," J. Bact. 173(15):4799-813, incorporated by reference herein). Some gram-negative bacteria have genes encoding two or more Prc-related proteins or homologues, e.g., *P. fluorescens* Prc1 and Prc2. Tail-specific proteases are found in many gram-negative bacteria, including *Escherichia, Vibrio, Erwinia, Salmonella, Klebsiella, Legionella* and *Pseudomonads*.

The tail-specific protease can degrade a recombinant protein expressed in a bacterial host cell. Thus, a recombinant host cell that is deficient in tail-specific protease activity can produce a higher quality recombinant protein of interest than a corresponding host cell having a functional tail-specific protease. For example, antibody fragments produced in bacteria deficient in tail-specific protease activity are less degraded. (See, e.g., the Examples herein, and U.S. Pat. No. 9,493,559, "Bacterial host strain expressing recombinant DsbC and having reduced Tsp activity," each incorporated herein by reference in its entirety.) However, as also shown, recombinant bacterial host cells that are deficient in tail-specific protease activity fail to grow to high cell density. Poor cell growth in turn leads to reduced yield of recombinant protein. The present invention overcomes this problem by further modifying a recombinant host cell deficient in tail-specific protease activity, to introduce a second protease deficiency, thereby allowing growth to high cell density. Also provided are ways to increase recombinant protein yield by additional strategic modifications.

In some embodiments, the first protease activity is a tail-specific protease activity. A host cell deficient in tail-specific protease activity can be achieved by mutation of a gene encoding a tail-specific protease, tail-specific protease related protein, and/or a tail-specific protease homologue. In some embodiments, tail-specific protease deficiency results from mutation of a gene encoding a *Pseudomonad* Prc. In some embodiments, tail-specific protease deficiency results from mutation of a gene encoding Prc1, a Prc1-related protein, or a Prc1 homologue. In some embodiments, Prc1 has the amino acid sequence of SEQ ID NO: 33. In some embodiments, a Prc1-related protein has at least 60% similarity or at least 60% identity to the amino acid sequence of SEQ ID NO: 33. In some embodiments, tail-specific protease deficiency results from mutation of a gene encoding Prc2, a Prc2-related protein, or a Prc2 homologue. In some embodiments, the Prc2 has the amino acid sequence of SEQ ID NO: 35. In some embodiments, a Prc2-related protein has at least 60% similarity or at least 60% identity to the amino acid sequence of SEQ ID NO: 35. In some embodiments, tail-specific protease deficiency results from mutation of a gene encoding both Prc1, a Prc1-related protein, or a Prc1 homologue, and mutation of a gene encoding Prc2, a Prc2-related protein, or a Prc2 homologue. In some embodiments, tail-specific protease deficiency results from mutation of a gene encoding *E. coli* Prc (Tsp). In some embodiments, tail-specific protease deficiency results from mutation of a gene encoding *E. coli* Tsp, a Tsp-related protein, or a Tsp homologue. In some embodiments, a Tsp has the amino acid sequence of *E. coli* Tsp (SEQ ID NO: 71). In some embodiments, a Tsp-related protein has at least 60% similarity or at least 60% identity to the amino acid sequence of SEQ ID NO: 71. In some embodiments, a Tsp-related protein is a homologue of SEQ ID NO: 71.

In some embodiments, the tail-specific protease deficiency results from mutation of a gene encoding any one or more of: a Prc1 having the amino acid sequence of SEQ ID NO: 33, a Prc1-related protein having at least 60% similarity or at least 60% identity to the amino acid sequence of SEQ ID NO: 33, a homologue of Prc1 having the amino acid sequence of SEQ ID NO: 33, a Prc2 having the amino acid sequence of SEQ ID NO: 35, a Prc1-related protein having at least 60% similarity or at least 60% identity to the amino acid sequence of SEQ ID NO: 35, a homologue of Prc2 having the amino acid sequence of SEQ ID NO: 35, a Tsp having the amino acid sequence of SEQ ID NO: 71, a Tsp-related protein having at least 60% similarity or at least 60% identity to the amino acid sequence of SEQ ID NO: 71, and a homologue of Tsp having the amino acid sequence of SEQ ID NO: 71.

Bacterial Peptidoglycan Hydrolases

Bacterial peptidoglycan hydrolases cleave bonds in the peptidoglycan sacculus and/or its fragments. Peptidoglycan hydrolase activity is important in the regulation of cell wall growth, the turnover of peptidoglycan during growth, and the separation of daughter cells during cell division and autolysis. Peptidoglycan hydrolases also are involved in lysis phenomena occurring in bacterial populations.

The peptidoglycan sacculus is composed of glycan strands cross-linked by short peptides, and forms a closed, bag-shaped structure surrounding the cytoplasmic membrane of most bacteria. The glycan strands of the sacculus are made up of alternating N-acetylglucosamine (GlcNAc) and N-acetylmuramic acid (MurNAc) residues linked by 131-4 bonds. The D-lactoyl group of each MurNAc residue is substituted by a peptide stem typically having composition L-Ala-γ-D-Glu-meso-A2pm (or L-Lys)-D-Ala-D-Ala (A2pm, 2,6-diaminopimelic acid) in nascent peptidoglycan, the last D-Ala residue absent in the mature macromolecule. See, e.g., Vollmer, W. et al., 2008, "Peptidoglycan structure and architecture," FEMS Micro. Rev. 32:149-167, incorporated herein by reference in its entirety.

Murein DD-Endopeptidases

In some embodiments, the recombinant gram-negative bacterial host cell of the present invention is deficient in a first protease activity and a second protease activity, wherein the second protease activity is a murein DD-endopeptidase activity. Murein DD-endopeptidases cleave DD-bonds in the stem peptides of the sacculus glycan strands. See, e.g., Vollmer, W. et al., 2008, "Bacterial peptidoglycan (murein) hydrolases," FEMS Micro. Rev. 32:259-286, incorporated herein by reference in its entirety. Murein DD-endopeptidases from many bacteria, including *Escherichia, Vibrio, Erwinia, Salmonella, Klebsiella, Legionella* and *Pseudomonads*, have been described in the literature.

A host cell deficient in Murein DD-endopeptidase activity can be achieved by mutation of one or more gene encoding a murein DD-endopeptidase, murein DD-endopeptidase related protein, and/or a murein DD-endopeptidase homologue. In some embodiments, the murein DD-endopeptidase gene encodes a protease having the amino acid sequence of any one of *P. fluorescens* MepM1 (SEQ ID NO: 1), *E. coli* MepM (also referred to as YebA) (SEQ ID NO: 63), *P. aeruginosa* MepM1 (SEQ ID NO: 66), and *P. putida* MepM1 (SEQ ID NO: 65). In some embodiments, murein DD-endopeptidase deficiency results from mutation of a gene encoding a protease having the amino acid sequence of *P. fluorescens* MepM1 (SEQ ID NO: 1), a *P. fluorescens* MepM1-related protein, or a *P. fluorescens* MepM1 homologue. In some embodiments, a murein DD-endopeptidase-related protein has at least 60% similarity or at least 60% identity to the amino acid sequence of SEQ ID NO: 1. In some embodiments, murein DD-endopeptidase deficiency results from mutation of a gene encoding a protease having the amino acid sequence of *E. coli* MepM (also referred to as YebA) (SEQ ID NO: 63), an *E. coli* MepM-related protein, or an *E. coli* MepM homologue. In some embodiments, murein DD-endopeptidase has the amino acid sequence of SEQ ID NO: 63. In some embodiments, murein DD-endopeptidase-related protein has at least 60% similarity or at least 60% identity to the amino acid sequence of SEQ ID NO: 63. In some embodiments, murein DD-endopeptidase deficiency results from mutation of a gene encoding a protease having the amino acid sequence of *P. aeruginosa* MepM1 (SEQ ID NO: 66), a *P. aeruginosa* MepM1-related protein, or a *P. aeruginosa* MepM1 homologue. In some embodiments, a murein DD-endopeptidase-related protein has at least 60% similarity or at least 60% identity to the amino acid sequence of SEQ ID NO: 66. In some embodiments, murein DD-endopeptidase deficiency results from mutation of a gene encoding a protease having the amino acid sequence of *P. putida* MepM1 (SEQ ID NO: 65), a *P. putida* MepM1-related protein, or a *P. putida* MepM1 homologue. In some embodiments, a murein DD-endopeptidase-related protein has at least 60% similarity or at least 60% identity to the amino acid sequence of SEQ ID NO: 65.

In some embodiments, murein DD-endopeptidase deficiency results from mutation of a gene encoding any one or more of: a murein DD-endopeptidase having the amino acid sequence of SEQ ID NO: 1, a murein DD-endopeptidase-related protein having at least 60% similarity or at least 60% identity to the amino acid sequence of SEQ ID NO: 1, a homologue of murein DD-endopeptidase having the amino acid sequence of SEQ ID NO: 1, a murein DD-endopeptidase having the amino acid sequence of SEQ ID NO: 63, a murein DD-endopeptidase-related protein having at least 60% similarity or at least 60% identity to the amino acid sequence of SEQ ID NO: 63, a homologue of murein DD-endopeptidase having the amino acid sequence of SEQ ID NO: 63, a murein DD-endopeptidase having the amino acid sequence of SEQ ID NO: 65, a murein DD-endopeptidase-related protein having at least 60% similarity or at least 60% identity to the amino acid sequence of SEQ ID NO: 65, a homologue of murein DD-endopeptidase having the amino acid sequence of SEQ ID NO: 65, a murein DD-endopeptidase having the amino acid sequence of SEQ ID NO: 66, a murein DD-endopeptidase-related protein having at least 60% similarity or at least 60% identity to the amino acid sequence of SEQ ID NO: 66, and a homologue of a murein DD-endopeptidase having the amino acid sequence of SEQ ID NO: 66.

The murein DD-endopeptidase deficiency can result from any one or more mutation in a host cell gene encoding the murein DD-endopeptidase, as described elsewhere herein, e.g, (i) a complete gene deletion, (ii) a partial gene deletion, (iii) a missense mutation, (iv) a nonsense mutation, (v) a frameshift mutation, (vi) an insertion, or (vii) any combination of (ii), (iii), (iv), (v) and (vi). In some embodiments, the protease deficiency results from a mutation that changes an amino acid in a conserved region of the murein DD-endopeptidase having the amino acid sequence set forth as SEQ ID NO: 1 or the analogous conserved region of a murein DD-endopeptidase having at least 60% similarity to the murein DD-endopeptidase amino acid sequence set forth as SEQ ID NO: 1. FIG. 10 shows an exemplary amino acid alignment indicating residues conserved across murein DD-endopeptidases SEQ ID NO: 1 (*P. fluorescens* MepM1), SEQ ID NO: 63 (*E. coli* MepM, also referred to as YebA), SEQ ID NO: 66 (*P. aeruginosa* MepM1), and/or SEQ ID NO: 65 (*P. putida* MepM1). In some embodiments, the deficiency in a murein DD-endopeptidase results from a mutation that changes or otherwise disrupts (e.g., by substitution, deletion, insertion, or truncation) an amino acid at a conserved position. A conserved position can be identified by one of skill in the art by any known method. In some embodiments, a conserved position is identified by comparison of the murein DD-endopeptidase amino acid sequence with any one or more of SEQ ID NOS: 1, 63, 66, and 65. For example, the amino acid sequences may be compared as shown in FIG. 10, by CLUSTAL Omega using Genious Prime Software. FIG. 10 shows the aligned corresponding amino acid positions among the compared murein DD-endopeptidases, including the corresponding conserved amino acid positions as indicated in white lettering with dark shading. In some embodiments, the mutation is a non-conservative amino acid substitution. As described herein, an amino acid substitution can be a conservative or non-conservative substitution. Conservative and non-conservative amino acid substitutions are described in the literature and can readily be identified by methods well-known to those of skill in the art and as described herein (see, e.g., Table 2, listing conservative amino acid substitutions). In some embodiments, a mutation, e.g., a non-conservative amino acid substitution, replaces or otherwise disrupts an amino acid residue in a murein DD-endopeptidase amino acid sequence at a position corresponding to any of the following positions: SEQ ID NO: 1 positions listed in Table 1, column 2; SEQ ID NO: 63 positions listed in Table 1, column 4; SEQ ID NO: 65 positions listed in Table 1, column 8; and SEQ ID NO: 66 positions listed in Table 1, column 6. In some embodiments, a mutation, e.g., a non-conservative amino acid substitution, replaces or otherwise disrupts an amino acid residue in a murein DD-endopeptidase amino acid sequence, wherein the replaced or disrupted amino acid residue is an amino acid residue selected from any of: SEQ ID NO: 1 residues listed in Table 1, column 3; SEQ ID NO: 63 residues listed in Table 1, column 5; SEQ ID NO: 65 residues listed in Table 1, column 9; and SEQ ID NO: 66 residues listed in Table 1, column 7. Bold text indicates active site conserved positions in each of SEQ ID NOS: 1, 63, 66, and 65.

TABLE 1

| | FIG. 10 Corresponding Conserved Amino Acid Positions | | | | | | | |
|---|---|---|---|---|---|---|---|---|
| Row | Position SEQ ID NO: 1 (P. f.) | AA Residue SEQ ID NO: 1 | Position SEQ ID NO: 63 (E. coli) | AA Residue SEQ ID NO: 63 | Position SEQ ID NO: 66 (P. a.) | AA Residue SEQ ID NO: 66 | Position SEQ ID NO: 65 (P. p.) | AA Residue SEQ ID NO: 65 |
| 1 | 44 | T | 46 | T | 12 | T | 44 | T |
| 2 | 50 | L | 54 | L | 18 | L | 50 | L |
| 3 | 51 | E | 55 | E | 19 | E | 51 | E |
| 4 | 109 | V | 100 | V | 87 | V | 111 | V |
| 5 | 112 | G | 103 | G | 90 | G | 114 | G |
| 6 | 113 | D | 104 | D | 91 | D | 115 | D |
| 7 | 114 | T | 105 | T | 92 | T | 116 | T |
| 8 | 115 | L | 106 | L | 93 | L | 117 | L |
| 9 | 116 | S | 107 | S | 94 | S | 118 | S |
| 10 | 123 | G | 114 | G | 101 | G | 125 | G |
| 11 | 140 | K | 128 | K | 118 | K | 142 | K |
| 12 | 145 | L | 133 | L | 123 | L | 147 | L |
| 13 | 146 | K | 134 | K | 124 | K | 148 | K |
| 14 | 148 | G | 136 | G | 126 | G | 150 | G |
| 15 | 149 | Q | 137 | Q | 127 | Q | 151 | Q |
| 16 | 155 | L | 143 | L | 133 | L | 157 | L |
| 17 | 159 | G | 147 | G | 137 | G | 161 | G |
| 18 | 161 | L | 149 | L | 139 | L | 163 | L |
| 19 | 164 | L | 152 | L | 142 | L | 166 | L |
| 20 | 169 | S | 157 | S | 147 | S | 171 | S |
| 21 | 172 | E | 160 | E | 150 | E | 174 | E |
| 22 | 182 | G | 171 | G | 160 | G | 184 | G |
| 23 | 201 | G | 190 | G | 179 | G | 203 | G |
| 24 | 206 | S | 195 | S | 184 | S | 208 | S |
| 25 | 214 | A | 203 | A | 192 | A | 216 | A |
| 26 | 215 | G | 204 | G | 193 | G | 217 | G |
| 27 | 216 | L | 205 | L | 194 | L | 218 | L |
| 28 | 233 | D | 222 | D | 211 | D | 235 | D |
| 29 | 234 | F | 223 | F | 212 | F | 236 | F |
| 30 | 241 | G | 229 | G | 219 | G | 243 | G |
| 31 | 242 | D | 230 | D | 220 | D | 244 | D |
| 32 | 243 | E | 231 | E | 221 | E | 245 | E |
| 33 | 244 | F | 232 | F | 222 | F | 246 | F |
| 34 | 246 | V | 234 | V | 224 | V | 248 | V |
| 35 | 255 | G | 243 | G | 233 | G | 257 | G |
| 36 | 256 | K | 244 | K | 234 | K | 258 | K |
| 37 | 264 | L | 251 | L | 242 | L | 266 | L |
| 38 | 267 | R | 254 | R | 245 | R | 269 | R |
| 39 | 272 | G | 259 | G | 250 | G | 274 | G |
| 40 | 273 | K | 260 | K | 251 | K | 275 | K |
| 41 | 277 | A | 264 | A | 255 | A | 279 | A |
| 42 | 279 | R | 266 | R | 257 | R | 281 | R |
| 43 | 290 | Y | 273 | Y | 268 | Y | 292 | Y |
| 44 | 294 | G | 277 | G | 272 | G | 296 | G |
| 45 | 299 | K | 282 | K | 277 | K | 301 | K |
| 46 | 301 | F | 284 | F | 279 | F | 303 | F |
| 47 | 303 | R | 286 | R | 281 | R | 305 | R |

TABLE 1-continued

| | FIG. 10 Corresponding Conserved Amino Acid Positions | | | | | | | |
|---|---|---|---|---|---|---|---|---|
| Row | Position SEQ ID NO: 1 (P. f.) | AA Residue SEQ ID NO: 1 | Position SEQ ID NO: 63 (E. coli) | AA Residue SEQ ID NO: 63 | Position SEQ ID NO: 66 (P. a.) | AA Residue SEQ ID NO: 66 | Position SEQ ID NO: 65 (P. p.) | AA Residue SEQ ID NO: 65 |
| 48 | 305 | P | 288 | P | 283 | P | 307 | P |
| 49 | 310 | R | 294 | R | 288 | R | 312 | R |
| 50 | 311 | I | 295 | I | 289 | I | 313 | I |
| 51 | 312 | S | 296 | S | 290 | S | 314 | S |
| 52 | 313 | S | 297 | S | 291 | S | 315 | S |
| 53 | 315 | F | 299 | F | 293 | F | 317 | F |
| 54 | 319 | R | 303 | R | 297 | R | 321 | R |
| 55 | 322 | P | 306 | P | 300 | P | 324 | P |
| 56 | 330 | H | 314 | H | 308 | H | 332 | H |
| 57 | 332 | G | 316 | G | 310 | G | 334 | G |
| 58 | 333 | V | 317 | V | 311 | V | 335 | V |
| 59 | 334 | D | 318 | D | 312 | D | 336 | D |
| 60 | 336 | A | 320 | A | 314 | A | 338 | A |
| 61 | 338 | P | 322 | P | 316 | P | 340 | P |
| 62 | 340 | G | 324 | G | 318 | G | 342 | G |
| 63 | 341 | T | 325 | T | 319 | T | 343 | T |
| 64 | 342 | P | 326 | P | 320 | P | 344 | P |
| 65 | 347 | G | 331 | G | 325 | G | 349 | G |
| 66 | 348 | D | 332 | D | 326 | D | 350 | D |
| 67 | 349 | G | 333 | G | 327 | G | 351 | G |
| 68 | 354 | A | 338 | A | 332 | A | 356 | A |
| 69 | 356 | R | 340 | R | 334 | R | 358 | R |
| 70 | 358 | G | 342 | G | 336 | G | 360 | G |
| 71 | 361 | G | 345 | G | 339 | G | 363 | G |
| 72 | 364 | V | 348 | V | 342 | V | 366 | V |
| 73 | 366 | I | 350 | I | 344 | I | 368 | I |
| 74 | 368 | H | 352 | H | 346 | H | 370 | H |
| 75 | 369 | G | 353 | G | 347 | G | 371 | G |
| 76 | 372 | Y | 356 | Y | 350 | Y | 374 | Y |
| 77 | 374 | T | 358 | T | 352 | T | 376 | T |
| 78 | 376 | Y | 360 | Y | 354 | Y | 378 | Y |
| 79 | 378 | H | 362 | H | 356 | H | 380 | H |
| 80 | 389 | G | 371 | G | 367 | G | 391 | G |
| 81 | 392 | V | 374 | V | 370 | V | 394 | V |
| 82 | 393 | K | 375 | K | 371 | K | 395 | K |
| 83 | 395 | G | 377 | G | 373 | G | 397 | G |
| 84 | 398 | I | 380 | I | 376 | I | 400 | I |
| 85 | 402 | G | 384 | G | 380 | G | 404 | G |
| 86 | 404 | T | 386 | T | 382 | T | 406 | T |
| 87 | 405 | G | 387 | G | 383 | G | 407 | G |
| 88 | 408 | T | 390 | T | 386 | T | 410 | T |
| 89 | 409 | G | 391 | G | 387 | G | 411 | G |
| 90 | 410 | P | 392 | P | 388 | P | 412 | P |
| 91 | 411 | H | 393 | H | 389 | H | 413 | H |
| 92 | 412 | L | 394 | L | 390 | L | 414 | L |
| 93 | 413 | H | 395 | H | 391 | H | 415 | H |
| 94 | 414 | Y | 396 | Y | 392 | Y | 416 | Y |
| 95 | 415 | E | 397 | E | 393 | E | 417 | E |
| 96 | 419 | N | 401 | N | 397 | N | 421 | N |
| 97 | 423 | V | 405 | V | 401 | V | 425 | V |
| 98 | 425 | P | 407 | P | 403 | P | 427 | P |
| 99 | 426 | L | 408 | L | 404 | L | 428 | L |
| 100 | 429 | K | 411 | K | 407 | K | 431 | K |
| 101 | 430 | L | 412 | L | 408 | L | 432 | L |
| 102 | 431 | P | 413 | P | 409 | P | 433 | P |
| 103 | 441 | R | 423 | R | 419 | R | 443 | R |
| 104 | 444 | F | 426 | F | 422 | F | 446 | F |
| 105 | 447 | Q | 429 | Q | 425 | Q | 449 | Q |

In *Vibrio cholera*, activity of the major endopeptidase ShyA (homologue of *E. coli* MepM) was reported to be regulated by mutations affecting accessibility of the catalytic site (Shin, J-H et al., "Structural basis of peptidoglycan endopeptidase regulation," PNAS 117(21): 11692-11702, 2020, incorporated herein by reference, esp. with regard to ShyA active site and allosteric site amino acids and positions). Shin, et al. reported that ShyA forms an open conformation potentially allowing exposure of the active site for substrate binding, and a closed conformation. Based on structural predictions, Shin, et al. postulated that hydropho-bic and electrostatic interactions between ShyA binding Domains 1 and 3 (separated by a linker Domain 2) bring them into close proximity to form the closed conformation. They found that allosteric site mutations, including Domain 2 mutations, that stabilized the inactive conformation resulted in lower ShyA activity. *P. fluorescens* MepM1 has 65% similarity to *Vibrio cholera* ShyA (SEQ ID NO: 58).

In some embodiments, the mutation in a gene encoding a murine DD-endopeptidase, homologue thereof, or murein DD-endopeptidase having at least 60% similarity to the murein DD-endopeptidase amino acid sequence set forth as
SEQ ID NO: 1, 63, 66, or 65, changes or otherwise disrupts
an allosteric site amino acid.

In some embodiments, the mutation in a gene encoding a
murein DD-endopeptidase having at least 60% similarity to
the murein DD-endopeptidase amino acid sequence set forth
as SEQ ID NO: 1, 63, 66, or 65 changes or otherwise
disrupts an amino acid at an active site position. In some
embodiments, the active site position corresponds to any
position in the regions 319 to 411 of SEQ ID NO: 1.

In some embodiments, the mutation in a gene encoding a
murein DD-endopeptidase having at least 60% similarity to
the murein DD-endopeptidase amino acid sequence set forth
as SEQ ID NO: 1, 63, 66, or 65 changes or otherwise
disrupts an amino acid at a conserved catalytic (active) site
position. In some embodiments, the disrupted conserved
active site position corresponds to any conserved position in
the region 319 to 411 (listed in Table 1 at rows 54-91). In
some embodiments, the active site amino acid residue cor-
responds to any one of catalytic amino acid residues R319,
H330, D334, H378, and H411, of SEQ ID NO: 1. In some
embodiments, the mutation results in deletion of an amino
acid residue corresponding to catalytic site amino acid
residue R319, H330, D334, H378, and H411, and any
combination thereof, of SEQ ID NO: 1. In some embodi-
ments, the mutation is a nonsense mutation at a position
corresponding to Y248 of SEQ ID NO: 1. In some embodi-
ments, the mutation is a G to S substitution at a position
corresponding to 332 of SEQ ID NO: 1. In some embodi-
ments, the mutation is a D to N substitution at a position
corresponding to 334 of SEQ ID NO: 1. In some embodi-
ments, the mutation is an A to T substitution at a position
corresponding to 337 of SEQ ID NO: 1. In some embodi-
ments, the mutation is an H to Y substitution at a position
corresponding to 411 of SEQ ID NO: 1. In some embodi-
ments, the mutation is a P to L substitution at a position
corresponding to 410 of SEQ ID NO: 1.

In some embodiments, the mutation in a gene encoding a
murein DD-endopeptidase having at least 60% similarity to
the murein DD-endopeptidase amino acid sequence set forth
as SEQ ID NO: 1, 63, 66, 65, and/or 71 changes or otherwise
disrupts an amino acid at an allosteric site position. In some
embodiments, the allosteric site position corresponds to any
position in the regions 134 to 145, and 361 to 378 of SEQ
ID NO: 1.

In some embodiments, the mutation in a gene encoding a
murein DD-endopeptidase having at least 60% similarity to
the murein DD-endopeptidase amino acid sequence set forth
as SEQ ID NO: 1, 63, 66, 65, and/or 71 changes or otherwise
disrupts (e.g., by substitution, deletion, insertion, or trunca-
tion) an amino acid at a conserved allosteric site position. In
some embodiments, the disrupted conserved allosteric site
position corresponds to any conserved position in the
regions 134 to 145 (listed in Table 1 at rows 11 and 12), and
361 to 378 of SEQ ID NO: 1 (listed in Table 1 at rows
71-79).

In some embodiments, the mutation in a gene encoding a
murein DD-endopeptidase having at least 60% similarity to
the murein DD-endopeptidase amino acid sequence set forth
as SEQ ID NO: 1 changes or otherwise disrupts (e.g., by
substitution, deletion, insertion, or truncation) an amino acid
corresponding to any position in the regions 134 to 145, 361
to 378, and 319 to 411 of SEQ ID NO: 1. In some
embodiments, the mutation results in a non-conservative
substitution of an amino acid corresponding to the amino
acid in any position in the regions 134 to 145, 361 to 378,
and 319 to 411 of SEQ ID NO: 1.

28

In some embodiments, the mutation in a gene encoding
murein DD-endopeptidase having at least 60% similarity to
the murein DD-endopeptidase amino acid sequence set forth
as SEQ ID NO: 1 changes or otherwise disrupts (e.g., by
substitution, deletion, insertion, or truncation) an amino acid
corresponding to any one or more of: K140, L145, Y248,
R319, P322, H330, G332, V333, D334, A336, A337, P338,
G340, T341, P342, G347, D348, G349, A354, R356, G358,
G361, V364, I366, H368, G369, Y372, T374, Y376, H378,
G389, V392, K393, G395, I398, G402, T404, G405, T408,
G409, P410, and H411, of SEQ ID NO: 1. In some embodi-
ments, the mutation results in a non-conservative substitu-
tion of an amino acid corresponding to any one or more of:
K140, L145, Y248, R319, P322, H330, G332, V333, D334,
A336, A337, P338, G340, T341, P342, G347, D348, G349,
A354, R356, G358, G361, V364, I366, H368, G369, Y372,
T374, Y376, H378, G389, V392, K393, G395, I398, G402,
T404, G405, T408, G409, P410, and H411, of SEQ ID NO:
1.

MepS/Spr

An important gram-negative bacterial murein DD-endo-
peptidase is MepS, also known as Spr in *E. coli*. (See, e.g.,
Expasy enzyme EC 3.4.17.13, and Singh, S. K. et al., 2012,
"Three redundant murein endopeptidases catalyse an essen-
tial cleavage step in peptidoglycan synthesis of *Escherichia
coli* K12," Mol. Microbiol. 86(5): 1036-1051, both incor-
porated herein by reference.) Truong, T. T. et al., 2020 ("Cell
division is antagonized by the activity of peptidoglycan
endopeptidases that promote cell elongation," Mol. Micro-
biol. 114: 966-978, incorporated herein by reference),
reported that unchecked MepS protein turnover by tail-
specific protease degradation (e.g., in the absence of Prc/
Tsp) results in cell growth inhibition and the occurrence of
morphological defects during cell division.

In the context of *E. coli* it was reported that deletion of prc
inhibits growth at high density fermentation, and that inac-
tivation of MepS by amino acid substitution is required to
restore growth to optical densities (ODs)>=200 at 575 nm
(Hara, H. et al. 1996, U.S. Pat. No. 9,493,559, and
EP1341899B1, each incorporated herein by reference).
Similarly, complete inactivation of both Prc genes in
*Pseudomonads* prevents high cell density growth in biore-
actors and cultures fail to grow past OD575's of 20-50 when
compared to strains that express both Prc genes, which reach
OD575 up to 180 in 2 L bioreactors (see Examples herein).
However, as shown in the Examples, in *P. fluorescens*
complete removal of MepS homologues does not rescue the
growth defect resulting from the deficiency in Prc activity.
Rather, deficiency in MepM1 activity was shown to restore
high density cell growth. Furthermore, in *Pseudomonad* host
cells deficient in Prc and MepM1 activity, a deficiency in
MepS1 had an adverse effect on cell growth, negating the
restoration of growth observed upon introduction of the
deficiency of MepM1 activity.

In some embodiments, the present invention provides a
recombinant gram-negative bacterial host cell that is: defi-
cient in a first protease activity and a second protease
activity, and optionally further (a) is deficient in one or more
additional protease activity; (b) is deficient in one or more
autolytic factor activity; (c) overexpresses one or more
inactivated protease; (d) overexpresses one or more chap-
erone protein; or (e) any combination of (a), (b), (c) and (d);
wherein the host cell produces a functional MepS murein
DD-endopeptidase. In some embodiments, the present
invention provides a recombinant gram-negative bacterial
host cell that is: deficient in a first protease activity and a
second protease activity, and optionally further (a) is deficient in one or more additional protease activity; (b) is deficient in one or more autolytic factor activity; (c) over-expresses one or more inactivated protease; (d) overex-presses one or more chaperone protein; or (e) any combi-nation of (a), (b), (c) and (d); wherein the host cell is not deficient in a MepS murein DD-endopeptidase. In some embodiments, the recombinant host cell deficient in a first protease activity, a second protease activity, and having a functional MepS murein DD-endopeptidase and/or not defi-cient in a MepS murein DD-endopeptidase is a *Pseudomonad*. In some embodiments, the recombinant host cell deficient in a first protease activity, a second protease activity, having a functional MepS murein DD-endopepti-dase and/or not deficient in a MepS murein DD-endopepti-dase is not *E. coli*. In some embodiments, the functional and/or not deficient MepS murein DD-endopeptidase has an amino acid sequence set forth as SEQ ID NO: 5, SEQ ID NO: 7, SEQ ID NO: 72, or SEQ ID NO: 73, an amino acid sequence at least 60% similar or at least 60% identical to SEQ ID NO: 5, SEQ ID NO: 7, SEQ ID NO: 72, or SEQ ID NO: 73, or is a homologue of SEQ ID NO: 5, SEQ ID NO: 7, SEQ ID NO: 72, or SEQ ID NO: 73. In some embodi-ments, the host cell is a *Pseudomonad*, e.g., *P. fluorescens*, and the functional and/or not deficient MepS murein DD-endopeptidase is MepS1 (SEQ ID NO: 5). In some embodi-ments, the host cell is a *Pseudomonad*, e.g., *P. fluorescens*, and the functional and/or not deficient MepS murein DD-endopeptidase is MepS2 (SEQ ID NO: 7). In some embodi-ments, the recombinant host cell is a *Pseudomonad*, e.g., *P. fluorescens*, having a functional and/or not deficient MepS1 (SEQ ID NO: 5) and MepS2 (SEQ ID NO: 7).

Additional Deficient Protein Activities

As set forth herein, a recombinant gram-negative bacterial host cell deficient in a tail-specific protease activity and a murein-DD-endopeptidase activity can be further: deficient in at least one additional protein activity. Deficiencies in one or more additional protein activities were found to provide higher quality and yield of recombinant protein. These additional proteins include additional proteases, and autolytic factors. In some embodiments, the recombinant gram-negative host cell is deficient in one or more additional protein activity. In some embodiments, the additional pro-tein activity is a protease activity or autolytic factor activity.

In some embodiments, the recombinant gram-negative host cell deficient in a tail-specific protease activity and a murein-DD-endopeptidase activity is further deficient in 1 to 10 different additional protease activities. In some embodi-ments, a deficient additional protease activity results from a mutation in at least one gene encoding an additional pro-tease, that has the additional protease activity. In some embodiments, a deficient additional protease activity results from a mutation in at least two genes encoding an additional protease(s) that have the additional protease activity. In some embodiments, the 1-10 different additional protease activities result from mutations in 1 to 30 genes encoding corresponding additional protease(s).

In some embodiments, the additional protease is a ser-ralysin precursor (e.g., an extracellular alkaline metallopro-tease, e.g., RXF04495.2, or an autolytic serralysin precursor, e.g., RXF4500), membrane-localized protease (e.g., HtpX, FtsH, OmpT), murein L,D transpeptidase, hemolysin pre-cursor, D-alanyl-D-alanine carboxypeptidase/endopeptidase AmpH precursor, periplasmic serine endoprotease (e.g., DegP or DegP2), AAA+ family proteolytic machine (e.g., HslU/HslV), or a murein DD-endopeptidase (e.g., a MepM, e.g., a *Pseudomonad* MepM2).

In some embodiments, an additional protease is selected from:

a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9;

a serralysin precursor having the amino acid sequence set forth as SEQ ID NO: 47; a homologue of the serralysin precursor having the amino acid sequence set forth as SEQ ID NO: 47; or a serralysin precursor related protein having at least 60% similarity or at least 60% identity to the amino acid sequence set forth as SEQ ID NO: 47;

a membrane-localized protease that is an HtpX having the amino acid sequence set forth as SEQ ID NO: 39; a homologue of the HtpX having the amino acid sequence set forth as SEQ ID NO: 39; or an HtpX related protein having at least 60% similarity or at least 60% identity to the amino acid sequence set forth as SEQ ID NO: 39;

a murein L,D transpeptidase having the amino acid sequence set forth as SEQ ID NO: 41; a homologue of the murein L,D transpeptidase having the amino acid sequence set forth as SEQ ID NO: 41; or a murein L,D transpeptidase related protein having at least 60% simi-larity or at least 60% identity to the amino acid sequence set forth as SEQ ID NO: 41;

a hemolysin precursor having the amino acid sequence set forth as SEQ ID NO: 43; a homologue of the hemolysin precursor having the amino acid sequence set forth as SEQ ID NO: 43; or a hemolysin precursor related protein having at least 60% similarity or at least 60% identity to the amino acid sequence set forth as SEQ ID NO: 43;

a D-alanyl-D-alanine carboxypeptidase/endopeptidase AmpH precursor having the amino acid sequence set forth as SEQ ID NO: 45; a homologue of the D-alanyl-D-alanine carboxypeptidase/endopeptidase AmpH pre-cursor having the amino acid sequence set forth as SEQ ID NO: 45; or a D-alanyl-D-alanine carboxypeptidase/endopeptidase AmpH precursor related protein having at least 60% similarity or at least 60% identity to the amino acid sequence set forth as SEQ ID NO: 45;

a periplasmic serine endoprotease that is a DegP2 having the amino acid sequence set forth as SEQ ID NO: 31; a homologue of the DegP2 having the amino acid sequence set forth as SEQ ID NO: 31; or a DegP2 related protein having at least 60% similarity or at least 60% identity to the amino acid sequence set forth as SEQ ID NO: 31;

a periplasmic serine endoprotease that is a DegP having the amino acid sequence set forth as SEQ ID NO: 69; a homologue of the DegP2 having the amino acid sequence set forth as SEQ ID NO: 69; or a DegP2 related protein having at least 60% similarity or at least 60% identity to the amino acid sequence set forth as SEQ ID NO: 69;

a periplasmic serine endoprotease that is a DegP having the amino acid sequence set forth as SEQ ID NO: 62; a homologue of the DegP2 having the amino acid sequence set forth as SEQ ID NO: 62; or a DegP2 related protein having at least 60% similarity or at least 60% identity to the amino acid sequence set forth as SEQ ID NO: 62;

an AAA+ family proteolytic machine that comprises: an HslU protease having the amino acid sequence set forth as SEQ ID NO: 37; a homologue of the HslU protease having the amino acid sequence set forth as SEQ ID NO: 37; or a HslU related protein having at least 60% similarity or at least 60% identity to the amino acid sequence set forth as SEQ ID NO: 37, and an HslV protease having the amino acid sequence set forth as SEQ ID NO: 38; a homologue of the HslV protease having the amino acid sequence set forth as SEQ ID NO: 38; or a HslV related protein having at least 60% similarity or at least 60% identity to the amino acid sequence set forth as SEQ ID NO: 38;

a murein DD-endopeptidase that is a protease having the amino acid sequence set forth as SEQ ID NO: 3 (*P. fluorescens* MepM2), a homologue of the MepM2 protease having the amino acid sequence set forth as SEQ ID NO: 3, or a MepM2-related protein having at least 60% similarity or 60% sequence identity to the amino acid sequence set forth as SEQ ID NO: 3;

a murein DD-endopeptidase that is a protease having the amino acid sequence set forth as SEQ ID NO: 64 (*E. coli* MepM2), a homologue of the MepM2 protease having the amino acid sequence set forth as SEQ ID NO: 64, or a MepM2-related protein having at least 60% similarity or 60% sequence identity y to the amino acid sequence set forth as SEQ ID NO: 64;

a murein DD-endopeptidase that is a protease having the amino acid sequence set forth as SEQ ID NO: 67 (*P. putida* MepM2), a homologue of the MepM2 protease having the amino acid sequence set forth as SEQ ID NO: 67, or a MepM2-related protein having at least 60% similarity or 60% sequence identity to the amino acid sequence set forth as SEQ ID NO: 67; and a murein DD-endopeptidase that is a MepM2 protease having the amino acid sequence set forth as SEQ ID NO: 68 (*P. aeruginosa*), a homologue of the MepM2 protease having the amino acid sequence set forth as SEQ ID NO: 68, or a MepM2-related protein having at least 60% similarity or 60% sequence identity to the amino acid sequence set forth as SEQ ID NO: 68.

A deficiency in an additional protease activity may result from a mutation in an aminopeptidase; dipeptidase; dipeptidyl-peptidase; tripeptidyl peptidase; peptidyl-dipeptidase; serine-type carboxypeptidase; metallocarboxypeptidase; cysteine-type carboxypeptidase; omegapeptidase; serine proteinase; cysteine proteinase; aspartic proteinase; metallo proteinase; or a proteinase of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zinc d-ala-d-ala carboxypeptidase, carboxypeptidase A2, membrane pro-x carboxypeptidase, tubulinyl-tyr carboxypeptidase, carboxypeptidase t. Omegapeptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component c1r55, complement component c1s55, classical-complement pathway c3/c5 convertase, complement factor I, complement factor D, alternative-complement pathway c3/c5 convertase, cerevisin, hypodermin C, lysyl endopeptidase, endopeptidase 1a, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, limulus clotting factor c, limulus clotting factor, limulus clotting enzyme, omptin, repressor lexa, bacterial leader peptidase I, togavirin, flavirin. Cysteine proteinases include cathepsin B, papain, ficin, chymopapain, asclepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrierpepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudolysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

Certain proteases have both protease and chaperone-like activity. When these proteases are negatively affecting protein yield and/or quality it is often useful to specifically delete their protease activity, and they are overexpressed when their chaperone activity may positively affect protein yield and/or quality. These proteases include, but are not limited to: Hsp100(Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

These and other proteases and folding modulators are known in the art and described in the literature, e.g., in U.S. Pat. No. 8,603,824, "Process for improved protein expression by strain engineering," incorporated by reference in its entirety. For example, Table D of the '824 patent describes Tig (tig, Trigger factor, FKBP type ppiase (ec 5.2.1.8) RXF04655, UniProtKB—P0A850 (TIG_ECOLI)). U.S. Pat. Nos. 9,394,571 and 9,580,719, both titled "Method for Rapidly Screening Microbial Hosts to Identify Certain Strains with Improved Yield and/or Quality in the Expression of Heterologous Proteins," describe Tig (RXF04655.2, SEQ ID NO: 34 therein), LepB (RXF01181.1, SEQ ID NO: 56 therein), DegP1 (RXF01250, SEQ ID NO: 57 therein), AprA (RXF04304.1, SEQ ID NO: 86 therein), Prc1 (RXF06586.1, SEQ ID NO: 120 therein), DegP2, (RXF07210.1, SEQ ID NO: 124 therein), Lon (RXF04653, SEQ ID NO: 92 therein); DsbA (RXF01002.1, SEQ ID NO: 25 therein), and DsbC (RXF03307.1, SEQ ID NO: 26 therein). These sequences and those for other proteases and folding modulators also are set forth in U.S. Pat. No. 9,580,719 (Table of SEQ ID NOS in columns 93-98 therein), incorporated herein by reference in its entirety. For example, U.S. Pat. No. 9,580,719 provides the sequence encoding HslU (RXF01957.2) and HslV (RXF01961.2) as SEQ ID NOS 18 and 19, respectively.

In some embodiments, the recombinant gram-negative host cell is deficient in 1 additional protease activity to 10 additional protease activities. In some embodiments, the recombinant gram-negative host cell is deficient in 1 additional protease activity to 10 additional protease activities. In some embodiments, the recombinant gram-negative host cell is deficient in 1 additional protease activity to 2 additional protease activities, 1 additional protease activity to 3 additional protease activities, 1 additional protease activity to 4 additional protease activities, 1 additional protease activity to 5 additional protease activities, 1 additional protease activity to 6 additional protease activities, 1 additional protease activity to 7 additional protease activities, 1 additional protease activity to 8 additional protease activities, 1 additional protease activity to 9 additional protease activities, 1 additional protease activity to 10 additional protease activities, 2 additional protease activities to 3 additional protease activities, 2 additional protease activities to 4 additional protease activities, 2 additional protease activities to 5 additional protease activities, 2 additional protease activities to 6 additional protease activities, 2 additional protease activities to 7 additional protease activities, 2 additional protease activities to 8 additional protease activities, 2 additional protease activities to 9 additional protease activities, 2 additional protease activities to 10 additional protease activities, 3 additional protease activities to 4 additional protease activities, 3 additional protease activities to 5 additional protease activities, 3 additional protease activities to 6 additional protease activities, 3 additional protease activities to 7 additional protease activities, 3 additional protease activities to 8 additional protease activities, 3 additional protease activities to 9 additional protease activities, 3 additional protease activities to 10 additional protease activities, 4 additional protease activities to 5 additional protease activities, 4 additional protease activities to 6 additional protease activities, 4 additional protease activities to 7 additional protease activities, 4 additional protease activities to 8 additional protease activities, 4 additional protease activities to 9 additional protease activities, 4 additional protease activities to 10 additional protease activities, 5 additional protease activities to 6 additional protease activities, 5 additional protease activities to 7 additional protease activities, 5 additional protease activities to 8 additional protease activities, 5 additional protease activities to 9 additional protease activities, 5 additional protease activities to 10 additional protease activities, 6 additional protease activities to 7 additional protease activities, 6 additional protease activities to 8 additional protease activities, 6 additional protease activities to 9 additional protease activities, 6 additional protease activities to 10 additional protease activities, 7 additional protease activities to 8 additional protease activities, 7 additional protease activities to 9 additional protease activities, 7 additional protease activities to 10 additional protease activities, 8 additional protease activities to 9 additional protease activities, 8 additional protease activities to 10 additional protease activities, or 9 additional protease activities to 10 additional protease activities. In some embodiments, the recombinant gram-negative host cell is deficient in 1 additional protease activity, 2 additional protease activities, 3 additional protease activities, 4 additional protease activities, 5 additional protease activities, 6 additional protease activities, 7 additional protease activities, 8 additional protease activities, 9 additional protease activities, or 10 additional protease activities. In some embodiments, the recombinant gram-negative host cell is deficient in at least 1 additional protease activity, 2 additional protease activities, 3 additional protease activities, 4 additional protease activities, 5 additional protease activities, 6 additional protease activities, 7 additional protease activities, 8 additional protease activities, or 9 additional protease activities. In some embodiments, the recombinant gram-negative host cell is deficient in at most 2 additional protease activities, 3 additional protease activities, 4 additional protease activities, 5 additional protease activities, 6 additional protease activities, 7 additional protease activities, 8 additional protease activities, 9 additional protease activities, or 10 additional protease activities.

In some embodiments, a deficient additional protease activity results from a mutation in 1 additional protease gene to 30 additional protease genes. In some embodiments, a deficient additional protease activity results from a mutation in 1 additional protease gene to 2 additional protease genes, 1 additional protease gene to 3 additional protease genes, 1 additional protease gene to 4 additional protease genes, 1 additional protease gene to 5 additional protease genes, 1 additional protease gene to 6 additional protease genes, 1 additional protease gene to 8 additional protease genes, 1 additional protease gene to 10 additional protease genes, 1 additional protease gene to 15 additional protease genes, 1 additional protease gene to 20 additional protease genes, 1 additional protease gene to 25 additional protease genes, 1 additional protease gene to 30 additional protease genes, 2 additional protease genes to 3 additional protease genes, 2 additional protease genes to 4 additional protease genes, 2 additional protease genes to 5 additional protease genes, 2 additional protease genes to 6 additional protease genes, 2 additional protease genes to 8 additional protease genes, 2 additional protease genes to 10 additional protease genes, 2 additional protease genes to 15 additional protease genes, 2 additional protease genes to 20 additional protease genes, 2 additional protease genes to 25 additional protease genes, 2 additional protease genes to 30 additional protease genes, 3 additional protease genes to 4 additional protease genes, 3 additional protease genes to 5 additional protease genes, 3 additional protease genes to 6 additional protease genes, 3 additional protease genes to 8 additional protease genes, 3 additional protease genes to 10 additional protease genes, 3 additional protease genes to 15 additional protease genes, 3 additional protease genes to 20 additional protease genes, 3 additional protease genes to 25 additional protease genes, 3 additional protease genes to 30 additional protease genes, 4 additional protease genes to 5 additional protease genes, 4 additional protease genes to 6 additional protease genes, 4 additional protease genes to 8 additional protease genes, 4 additional protease genes to 10 additional protease genes, 4 additional protease genes to 15 additional protease genes, 4 additional protease genes to 20 additional protease genes, 4 additional protease genes to 25 additional protease genes, 4 additional protease genes to 30 additional protease genes, 5 additional protease genes to 6 additional protease genes, 5 additional protease genes to 8 additional protease genes, 5 additional protease genes to 10 additional protease genes, 5 additional protease genes to 15 additional protease genes, 5 additional protease genes to 20 additional protease genes, 5 additional protease genes to 25 additional protease genes, 5 additional protease genes to 30 additional protease genes, 6 additional protease genes to 8 additional protease genes, 6 additional protease genes to 10 additional protease genes, 6 additional protease genes to 15 additional protease genes, 6 additional protease genes to 20 additional protease genes, 6 additional protease genes to 25 additional protease genes, 6 additional protease genes to 30 additional protease genes, 8 additional protease genes to 10 additional protease genes, 8 additional protease genes to 15 additional protease genes, 8 additional protease genes to 20 additional protease genes, 8 additional protease genes to 25 additional protease genes, 8 additional protease genes to 30 additional protease genes, 10 additional protease genes to 15 additional protease genes, 10 additional protease genes to 20 additional protease genes, 10 additional protease genes to 25 additional protease genes, 10 additional protease genes to 30 additional protease genes, 15 additional protease genes to 20 additional protease genes, 15 additional protease genes to 25 additional protease genes, 15 additional protease genes to 30 additional protease genes, 20 additional protease genes to 25 additional protease genes, 20 additional protease genes to 30 additional protease genes, or 25 additional protease genes to 30 additional protease genes. In some embodiments, a deficient additional protease activity results from a mutation in 1 additional protease gene, 2 additional protease genes, 3 additional protease genes, 4 additional protease genes, 5 additional protease genes, 6 additional protease genes, 8 additional protease genes, 10 additional protease genes, 15 additional protease genes, 20 additional protease genes, 25 additional protease genes, or 30 additional protease genes. In some embodiments, a deficient additional protease activity results from a mutation in at least 1 additional protease gene, 2 additional protease genes, 3 additional protease genes, 4 additional protease genes, 5 additional protease genes, 6 additional protease genes, 8 additional protease genes, 10 additional protease genes, 15 additional protease genes, 20 additional protease genes, or 25 additional protease genes. In some embodiments, a deficient additional protease activity results from a mutation in at most 2 additional protease genes, 3 additional protease genes, 4 additional protease genes, 5 additional protease genes, 6 additional protease genes, 8 additional protease genes, 10 additional protease genes, 15 additional protease genes, 20 additional protease genes, 25 additional protease genes, or 30 additional protease genes.

In some embodiments, e.g., in *E. coli*, the additional protease activity results from a mutation is in a murein DD-endopeptidase gene encoding one or more of: a murein DD-endopeptidase having the amino acid sequence of SEQ ID NO: 5 (*Pseudomonad* MepS1), a murein DD-endopeptidase-related protein having at least 60% similarity or at least 60% identity to the amino acid sequence of SEQ ID NO: 5, a homologue of murein DD-endopeptidase having the amino acid sequence of SEQ ID NO: 5, a murein DD-endopeptidase having the amino acid sequence of SEQ ID NO: 7 (*Pseudomonad* MepS2), a murein DD-endopeptidase-related protein having at least 60% similarity or at least 60% identity to the amino acid sequence of SEQ ID NO: 7, a homologue of murein DD-endopeptidase having the amino acid sequence of SEQ ID NO: 7, a murein DD-endopeptidase having the amino acid sequence of SEQ ID NO: 72 (*Pseudomonad* MepS), a murein DD-endopeptidase-related protein having at least 60% similarity or at least 60% identity to the amino acid sequence of SEQ ID NO: 72, a homologue of murein DD-endopeptidase having the amino acid sequence of SEQ ID NO: 72, a murein DD-endopeptidase having the amino acid sequence of SEQ ID NO: 73 (*Pseudomonad* MepS), a murein DD-endopeptidase-related protein having at least 60% similarity or at least 60% identity to the amino acid sequence of SEQ ID NO: 73, a homologue of murein DD-endopeptidase having the amino acid sequence of SEQ ID NO: 73, a murein DD-endopeptidase having the amino acid sequence of SEQ ID NO: 32 (*E. coli* MepS), a murein DD-endopeptidase-related protein having at least 60% similarity or at least 60% identity to the amino acid sequence of SEQ ID NO: 32, or a homologue of murein DD-endopeptidase having the amino acid sequence of SEQ ID NO: 32.

In some embodiments, the recombinant gram-negative host cell deficient in a tail-specific protease activity and a murein-DD-endopeptidase activity is further deficient in 1 to 10 different autolytic factor activities. In some embodiments, a deficient autolytic factor activity results from a mutation in at least one gene encoding an autolytic factor, that has the corresponding autolytic factor activity. In some embodiments, a deficient autolytic factor activity results from a mutation in at least two genes encoding autolytic factor(s) that have the autolytic factor activity. In some embodiments, the 1-10 different autolytic factor activities result from mutations in 1 to 30 genes encoding corresponding autolytic factor(s).

In some embodiments, the autolytic factor is an S-type pyocin, linear gramicidin synthase subunit D, hemolysin precursor, leukotoxin, or porin.

In some embodiments, the autolytic factor is selected from:

an S-type Pyocin having the amino acid sequence set forth as SEQ ID NO: 49; a homologue of the S-type Pyocin having the amino acid sequence set forth as SEQ ID NO: 49; or an S-type Pyocin related protein having at least 60% similarity or at least 60% identity to the amino acid sequence set forth as SEQ ID NO: 49;

a linear gramicidin synthase having the amino acid sequence set forth as SEQ ID NO: 51; a homologue of the linear gramicidin synthase having the amino acid sequence set forth as SEQ ID NO: 51; or a linear gramicidin synthase related protein having at least 60% similarity or at least 60% identity to the amino acid sequence set forth as SEQ ID NO: 51;

a leukotoxin having the amino acid sequence set forth as SEQ ID NO: 53; a homologue of the leukotoxin having the amino acid sequence set forth as SEQ ID NO: 53; or a leukotoxin related protein having at least 60% similarity or at least 60% identity to the amino acid sequence set forth as SEQ ID NO: 53; and an ShlB hemolysin transporter having the amino acid sequence set forth as SEQ ID NO: 55; a homologue of the an ShlB hemolysin transporter having the amino acid sequence set forth as SEQ ID NO: 55; or an ShlB hemolysin transporter related protein having at least 60% similarity or at least 60% identity to the amino acid sequence set forth as SEQ ID NO: 55.

In some embodiments, the recombinant gram-negative host cell is deficient in 1 autolytic factor activity to 10 autolytic factor activities. In some embodiments, the recombinant gram-negative host cell is deficient in 1 autolytic factor activity to 2 autolytic factor activities, 1 autolytic factor activity to 3 autolytic factor activities, 1 autolytic factor activity to 4 autolytic factor activities, 1 autolytic factor activity to 5 autolytic factor activities, 1 autolytic factor activity to 6 autolytic factor activities, 1 autolytic factor activity to 7 autolytic factor activities, 1 autolytic factor activity to 8 autolytic factor activities, 1 autolytic factor activity to 9 autolytic factor activities, 1 autolytic factor activity to 10 autolytic factor activities, 2 autolytic factor activities to 3 autolytic factor activities, 2 autolytic factor activities to 4 autolytic factor activities, 2 autolytic factor activities to 5 autolytic factor activities, 2 autolytic factor activities to 6 autolytic factor activities, 2 autolytic factor activities to 7 autolytic factor activities, 2 autolytic factor activities to 8 autolytic factor activities, 2 autolytic factor activities to 9 autolytic factor activities, 2 autolytic factor activities to 10 autolytic factor activities, 3 autolytic factor activities to 4 autolytic factor activities, 3 autolytic factor activities to 5 autolytic factor activities, 3 autolytic factor activities to 6 autolytic factor activities, 3 autolytic factor activities to 7 autolytic factor activities, 3 autolytic factor activities to 8 autolytic factor activities, 3 autolytic factor activities to 9 autolytic factor activities, 3 autolytic factor activities to 10 autolytic factor activities, 4 autolytic factor activities to 5 autolytic factor activities, 4 autolytic factor activities to 6 autolytic factor activities, 4 autolytic factor activities to 7 autolytic factor activities, 4 autolytic factor activities to 8 autolytic factor activities, 4 autolytic factor activities to 9 autolytic factor activities, 4 autolytic factor activities to 10 autolytic factor activities, 5 autolytic factor activities to 6 autolytic factor activities, 5 autolytic factor activities to 7 autolytic factor activities, 5 autolytic factor activities to 8 autolytic factor activities, 5 autolytic factor activities to 9 autolytic factor activities, 5 autolytic factor activities to 10 autolytic factor activities, 6 autolytic factor activities to 7 autolytic factor activities, 6 autolytic factor activities to 8 autolytic factor activities, 6 autolytic factor activities to 9 autolytic factor activities, 6 autolytic factor activities to 10 autolytic factor activities, 7 autolytic factor activities to 8 autolytic factor activities, 7 autolytic factor activities to 9 autolytic factor activities, 7 autolytic factor activities to 10 autolytic factor activities, 8 autolytic factor activities to 9 autolytic factor activities, 8 autolytic factor activities to 10 autolytic factor activities, or 9 autolytic factor activities to 10 autolytic factor activities. In some embodiments, the recombinant gram-negative host cell is deficient in 1 autolytic factor activity, 2 autolytic factor activities, 3 autolytic factor activities, 4 autolytic factor activities, 5 autolytic factor activities, 6 autolytic factor activities, 7 autolytic factor activities, 8 autolytic factor activities, 9 autolytic factor activities, or 10 autolytic factor activities. In some embodiments, the recombinant gram-negative host cell is deficient in at least 1 autolytic factor activity, 2 autolytic factor activities, 3 autolytic factor activities, 4 autolytic factor activities, 5 autolytic factor activities, 6 autolytic factor activities, 7 autolytic factor activities, 8 autolytic factor activities, or 9 autolytic factor activities. In some embodiments, the recombinant gram-negative host cell is deficient in at most 2 autolytic factor activities, 3 autolytic factor activities, 4 autolytic factor activities, 5 autolytic factor activities, 6 autolytic factor activities, 7 autolytic factor activities, 8 autolytic factor activities, 9 autolytic factor activities, or 10 autolytic factor activities.

In some embodiments, a deficient additional protease activity results from a mutation in 1 autolytic factor gene to 30 autolytic factor genes. In some embodiments, a deficient additional protease activity results from a mutation in 1 autolytic factor gene to 2 autolytic factor genes, 1 autolytic factor gene to 3 autolytic factor genes, 1 autolytic factor gene to 4 autolytic factor genes, 1 autolytic factor gene to 5 autolytic factor genes, 1 autolytic factor gene to 6 autolytic factor genes, 1 autolytic factor gene to 8 autolytic factor genes, 1 autolytic factor gene to 10 autolytic factor genes, 1 autolytic factor gene to 15 autolytic factor genes, 1 autolytic factor gene to 20 autolytic factor genes, 1 autolytic factor gene to 25 autolytic factor genes, 1 autolytic factor gene to 30 autolytic factor genes, 2 autolytic factor genes to 3 autolytic factor genes, 2 autolytic factor genes to 4 autolytic factor genes, 2 autolytic factor genes to 5 autolytic factor genes, 2 autolytic factor genes to 6 autolytic factor genes, 2 autolytic factor genes to 8 autolytic factor genes, 2 autolytic factor genes to 10 autolytic factor genes, 2 autolytic factor genes to 15 autolytic factor genes, 2 autolytic factor genes to 20 autolytic factor genes, 2 autolytic factor genes to 25 autolytic factor genes, 2 autolytic factor genes to 30 autolytic factor genes, 3 autolytic factor genes to 4 autolytic factor genes, 3 autolytic factor genes to 5 autolytic factor genes, 3 autolytic factor genes to 6 autolytic factor genes, 3 autolytic factor genes to 8 autolytic factor genes, 3 autolytic factor genes to 10 autolytic factor genes, 3 autolytic factor genes to 15 autolytic factor genes, 3 autolytic factor genes to 20 autolytic factor genes, 3 autolytic factor genes to 25 autolytic factor genes, 3 autolytic factor genes to 30 autolytic factor genes, 4 autolytic factor genes to 5 autolytic factor genes, 4 autolytic factor genes to 6 autolytic factor genes, 4 autolytic factor genes to 8 autolytic factor genes, 4 autolytic factor genes to 10 autolytic factor genes, 4 autolytic factor genes to 15 autolytic factor genes, 4 autolytic factor genes to 20 autolytic factor genes, 4 autolytic factor genes to 25 autolytic factor genes, 4 autolytic factor genes to 30 autolytic factor genes, 5 autolytic factor genes to 6 autolytic factor genes, 5 autolytic factor genes to 8 autolytic factor genes, 5 autolytic factor genes to 10 autolytic factor genes, 5 autolytic factor genes to 15 autolytic factor genes, 5 autolytic factor genes to 20 autolytic factor genes, 5 autolytic factor genes to 25 autolytic factor genes, 5 autolytic factor genes to 30 autolytic factor genes, 6 autolytic factor genes to 8 autolytic factor genes, 6 autolytic factor genes to 10 autolytic factor genes, 6 autolytic factor genes to 15 autolytic factor genes, 6 autolytic factor genes to 20 autolytic factor genes, 6 autolytic factor genes to 25 autolytic factor genes, 6 autolytic factor genes to 30 autolytic factor genes, 8 autolytic factor genes to 10 autolytic factor genes, 8 autolytic factor genes to 15 autolytic factor genes, 8 autolytic factor genes to 20 autolytic factor genes, 8 autolytic factor genes to 25 autolytic factor genes, 8 autolytic factor genes to 30 autolytic factor genes, 10 autolytic factor genes to 15 autolytic factor genes, 10 autolytic factor genes to 20 autolytic factor genes, 10 autolytic factor genes to 25 autolytic factor genes, 10 autolytic factor genes to 30 autolytic factor genes, 15 autolytic factor genes to 20 autolytic factor genes, 15 autolytic factor genes to 25 autolytic factor genes, 15 autolytic factor genes to 30 autolytic factor genes, 20 autolytic factor genes to 25 autolytic factor genes, 20 autolytic factor genes to 30 autolytic factor genes, or 25 autolytic factor genes to 30 autolytic factor genes. In some embodiments, a deficient additional protease activity results from a mutation in 1 autolytic factor gene, 2 autolytic factor genes, 3 autolytic factor genes, 4 autolytic factor genes, 5 autolytic factor genes, 6 autolytic factor genes, 8 autolytic factor genes, 10 autolytic factor genes, 15 autolytic factor genes, 20 autolytic factor genes, 25 autolytic factor genes, or 30 autolytic factor genes. In some embodiments, a deficient additional protease activity results from a mutation in at least 1 autolytic factor gene, 2 autolytic factor genes, 3 autolytic factor genes, 4 autolytic factor genes, 5 autolytic factor genes, 6 autolytic factor genes, 8 autolytic factor genes, 10 autolytic factor genes, 15 autolytic factor genes, 20 autolytic factor genes, or 25 autolytic factor genes. In some embodiments, a deficient additional protease activity results from a mutation in at most 2 autolytic factor genes, 3 autolytic factor genes, 4 autolytic factor genes, 5 autolytic factor genes, 6 autolytic factor genes, 8 autolytic factor genes, 10 autolytic factor genes, 15 autolytic factor genes, 20 autolytic factor genes, 25 autolytic factor genes, or 30 autolytic factor genes.

In some embodiments, the deficiency in an additional protein activity results from a mutation in a gene encoding an additional protein that is different from the first and/or second protease. In some embodiments, the mutation is not in a gene encoding a tail-specific protease. In some embodiments, the additional protein deficiency does not result from mutation of a gene encoding any one or more of: a Prc1 having the amino acid sequence of SEQ ID NO: 33, a Prc1-related protein having at least 60% similarity or at least 60% identity to the amino acid sequence of SEQ ID NO: 33, a homologue of Prc1 having the amino acid sequence of SEQ ID NO: 33, a Prc2 having the amino acid sequence of SEQ ID NO: 35, a Prc1-related protein having at least 60% similarity or at least 60% identity to the amino acid sequence of SEQ ID NO: 35, a homologue of Prc2 having the amino acid sequence of SEQ ID NO: 35, a Tsp having the amino acid sequence of SEQ ID NO: 71, a Tsp-related protein having at least 60% similarity or at least 60% identity to the amino acid sequence of SEQ ID NO: 71, and a homologue of Tsp having the amino acid sequence of SEQ ID NO: 71.

In some embodiments, the mutation is in a gene encoding a protein having an amino acid sequence that has less than 60% similarity or identity, less than 50% similarity or identity, less than 40% similarity or identity, or less than 30% similarity or identity, to the amino acid sequence of any one of SEQ ID NOS: 33, 35, and 71.

In some embodiments, the deficiency in an additional protein (e.g., protease or autolytic factor) activity results from a mutation in a gene encoding a murein DD-endopeptidase that is different from a gene encoding the first protease and/or the second protease. In some embodiments, the deficiency in an additional protein activity does not result from a mutation in a gene encoding a MepM1 murein DD-endopeptidase. In some embodiments, in any one or more gram-negative bacterial host cell, the mutation is not in a gene encoding any one or more of: a murein DD-endopeptidase having the amino acid sequence of SEQ ID NO: 1 (MepM), a murein DD-endopeptidase-related protein having at least 60% similarity or at least 60% identity to the amino acid sequence of SEQ ID NO: 1, a homologue of murein DD-endopeptidase having the amino acid sequence of SEQ ID NO: 1, a murein DD-endopeptidase having the amino acid sequence of SEQ ID NO: 63 (MepM), a murein DD-endopeptidase-related protein having at least 60% similarity or at least 60% identity to the amino acid sequence of SEQ ID NO: 63, a homologue of murein DD-endopeptidase having the amino acid sequence of SEQ ID NO: 63, a murein DD-endopeptidase having the amino acid sequence of SEQ ID NO: 65 (MepM), a murein DD-endopeptidase-related protein having at least 60% similarity or at least 60% identity to the amino acid sequence of SEQ ID NO: 65, a homologue of murein DD-endopeptidase having the amino acid sequence of SEQ ID NO: 65, a murein DD-endopeptidase having the amino acid sequence of SEQ ID NO: 66 (MepM), a murein DD-endopeptidase-related protein having at least 60% similarity or at least 60% identity to the amino acid sequence of SEQ ID NO: 66, a homologue of a murein DD-endopeptidase having the amino acid sequence of SEQ ID NO: 66, a murein DD-endopeptidase having the amino acid sequence of SEQ ID NO: 5 (MepS1), a murein DD-endopeptidase-related protein having at least 60% similarity or at least 60% identity to the amino acid sequence of SEQ ID NO: 5, a homologue of murein DD-endopeptidase having the amino acid sequence of SEQ ID NO: 5, a murein DD-endopeptidase having the amino acid sequence of SEQ ID NO: 7 (MepS2), a murein DD-endopeptidase-related protein having at least 60% similarity or at least 60% identity to the amino acid sequence of SEQ ID NO: 7, a homologue of murein DD-endopeptidase having the amino acid sequence of SEQ ID NO: 7, a murein DD-endopeptidase having the amino acid sequence of SEQ ID NO: 72 (*Pseudomonad* MepS), a murein DD-endopeptidase-related protein having at least 60% similarity or at least 60% identity to the amino acid sequence of SEQ ID NO: 72, a homologue of murein DD-endopeptidase having the amino acid sequence of SEQ ID NO: 72, a murein DD-endopeptidase having the amino acid sequence of SEQ ID NO: 73 (*Pseudomonad* MepS), a murein DD-endopeptidase-related protein having at least 60% similarity or at least 60% identity to the amino acid sequence of SEQ ID NO: 73, a homologue of murein DD-endopeptidase having the amino acid sequence of SEQ ID NO: 73, a murein DD-endopeptidase having the amino acid sequence of SEQ ID NO: 32 (*E. coli* MepS), a murein DD-endopeptidase-related protein having at least 60% similarity or at least 60% identity to the amino acid sequence of SEQ ID NO: 32, or a homologue of murein DD-endopeptidase having the amino acid sequence of SEQ ID NO: 32. In these embodiments, the mutation may
be in a gene encoding a murein DD-endopeptidase having an
amino acid sequence that has less than 60% similarity or
identity, less than 50% similarity or identity, less than 40%
similarity or identity, or less than 30% similarity or identity,
to the amino acid sequence of any one of SEQ ID NOS: 1,
63, 65, 66, 5, 7, 72, 73, and 32.

In some embodiments, in any one or more gram-negative
bacterial host cell, e.g., in *E. coli* or a *Pseudomonad*, the
deficiency in an additional protein activity (e.g., protease)
results from a mutation in a gene encoding any one or more
of: a murein DD-endopeptidase having the amino acid
sequence of SEQ ID NO: 5 (MepS1), a murein DD-endo-
peptidase-related protein having at least 60% similarity or at
least 60% identity to the amino acid sequence of SEQ ID
NO: 5, a homologue of murein DD-endopeptidase having
the amino acid sequence of SEQ ID NO: 5, a murein
DD-endopeptidase having the amino acid sequence of SEQ
ID NO: 7 (MepS2), a murein DD-endopeptidase-related
protein having at least 60% similarity or at least 60%
identity to the amino acid sequence of SEQ ID NO: 7, a
homologue of murein DD-endopeptidase having the amino
acid sequence of SEQ ID NO: 7, a murein DD-endopepti-
dase having the amino acid sequence of SEQ ID NO: 72
(*Pseudomonad* MepS), a murein DD-endopeptidase-related
protein having at least 60% similarity or at least 60%
identity to the amino acid sequence of SEQ ID NO: 72, a
homologue of murein DD-endopeptidase having the amino
acid sequence of SEQ ID NO: 72, a murein DD-endopep-
tidase having the amino acid sequence of SEQ ID NO: 73
(*Pseudomonad* MepS), a murein DD-endopeptidase-related
protein having at least 60% similarity or at least 60%
identity to the amino acid sequence of SEQ ID NO: 73, a
homologue of murein DD-endopeptidase having the amino
acid sequence of SEQ ID NO: 73, a murein DD-endopep-
tidase having the amino acid sequence of SEQ ID NO: 32 (*E.
coli* MepS), a murein DD-endopeptidase-related protein
having at least 60% similarity or at least 60% identity to the
amino acid sequence of SEQ ID NO: 32, and a homologue
of murein DD-endopeptidase having the amino acid
sequence of SEQ ID NO: 32. In some embodiments, the
gram-negative bacterial host cell is *E. coli*, and the defi-
ciency in an additional protein activity results from a muta-
tion in a gene encoding a murein DD-endopeptidase having
the amino acid sequence of SEQ ID NO: 32 (MepS), a
murein DD-endopeptidase-related protein having at least
60% similarity or at least 60% identity to the amino acid
sequence of SEQ ID NO: 32, and a homologue of murein
DD-endopeptidase having the amino acid sequence of SEQ
ID NO: 32, wherein the mutation is not at an amino acid that
is or that corresponds to an amino acid selected from: D133,
H145, H157, N31, R62, I70, Q73, C94, S95, V98, Q99,
R100, L108, Y115, V135, L136, G140, R144, and G147. In
related embodiments, the mutation is not a mutation that is
or that corresponds to an mutation resulting in N31Y, R62C,
I70T, Q73R, C94A, S95F, V98E, Q99P, R100G, L108S,
Y115F, D133A, V135D, V135G, L136P, G140C, R144C,
H145A, G147C or H157A.

Overexpressed Proteins

A recombinant gram-negative bacterial host cell of the
invention may overexpress one or more proteins, e.g., an
inactivated protease or a folding modulator, e.g., a chaper-
one. When co-overexpressed with the recombinant protein
of interest in the host cell, the co-overexpressed protein can
improve the quality and/or yield of a recombinant protein of
interest produced. In some embodiments, the co-overex-
pressed protein is expressed from an exogenous expression construct. In some embodiments, the expression construct is
in a plasmid or expression vector. In some embodiments,
when overexpressed in a host cell that also overexpresses the
recombinant protein of interest, the co-overexpressed pro-
tein and the recombinant protein of interest are expressed
from different plasmids. In some embodiments, the co-
overexpressed protein and the recombinant protein of inter-
est are expressed from the same plasmid. In some embodi-
ments, the co-overexpressed protein and the recombinant
protein of interest are expressed by transcription from dif-
ferent promoters on the same plasmid. In some embodi-
ments, the co-overexpressed protein and the recombinant
protein of interest are co-transcribed, that is, they are
expressed by transcription from the same promoter on the
same plasmid. In some embodiments, the co-overexpressed
protein is not expressed from the bacterial chromosome. In
some embodiments, the one or more co-overexpressed pro-
tein is an inactivated protease. In some embodiments, the
one or more co-overexpressed protein is a chaperone or
protein folding modulator. In some embodiments, the
recombinant gram-negative host cell overexpresses 1 co-
overexpressed protein to 20 different co-overexpressed pro-
teins. In some embodiments, the recombinant gram-negative
host cell overexpresses 1 co-overexpressed protein to 2
different co-overexpressed proteins, 1 co-overexpressed
protein to 3 different co-overexpressed proteins, 1 co-over-
expressed protein to 4 different co-overexpressed proteins, 1
co-overexpressed protein to 5 different co-overexpressed
proteins, 1 co-overexpressed protein to 6 different co-over-
expressed proteins, 1 co-overexpressed protein to 7 different
co-overexpressed proteins, 1 co-overexpressed protein to 8
different co-overexpressed proteins, 1 co-overexpressed
protein to 9 different co-overexpressed proteins, 1 co-over-
expressed protein to 10 different co-overexpressed proteins,
1 co-overexpressed protein to 15 different co-overexpressed
proteins, 1 co-overexpressed protein to 20 different co-
overexpressed proteins, 2 different co-overexpressed pro-
teins to 3 different co-overexpressed proteins, 2 different
co-overexpressed proteins to 4 different co-overexpressed
proteins, 2 different co-overexpressed proteins to 5 different
co-overexpressed proteins, 2 different co-overexpressed
proteins to 6 different co-overexpressed proteins, 2 different
co-overexpressed proteins to 7 different co-overexpressed
proteins, 2 different co-overexpressed proteins to 8 different
co-overexpressed proteins, 2 different co-overexpressed
proteins to 9 different co-overexpressed proteins, 2 different
co-overexpressed proteins to 10 different co-overexpressed
proteins, 2 different co-overexpressed proteins to 15 differ-
ent co-overexpressed proteins, 2 different co-overexpressed
proteins to 20 different co-overexpressed proteins, 3 differ-
ent co-overexpressed proteins to 4 different co-overex-
pressed proteins, 3 different co-overexpressed proteins to 5
different co-overexpressed proteins, 3 different co-overex-
pressed proteins to 6 different co-overexpressed proteins, 3
different co-overexpressed proteins to 7 different co-over-
expressed proteins, 3 different co-overexpressed proteins to
8 different co-overexpressed proteins, 3 different co-over-
expressed proteins to 9 different co-overexpressed proteins,
3 different co-overexpressed proteins to 10 different co-
overexpressed proteins, 3 different co-overexpressed pro-
teins to 15 different co-overexpressed proteins, 3 different
co-overexpressed proteins to 20 different co-overexpressed
proteins, 4 different co-overexpressed proteins to 5 different
co-overexpressed proteins, 4 different co-overexpressed
proteins to 6 different co-overexpressed proteins, 4 different
co-overexpressed proteins to 7 different co-overexpressed
proteins, 4 different co-overexpressed proteins to 8 different co-overexpressed proteins, 4 different co-overexpressed proteins to 9 different co-overexpressed proteins, 4 different co-overexpressed proteins to 10 different co-overexpressed proteins, 4 different co-overexpressed proteins to 15 different co-overexpressed proteins, 4 different co-overexpressed proteins to 20 different co-overexpressed proteins, 5 different co-overexpressed proteins to 6 different co-overexpressed proteins, 5 different co-overexpressed proteins to 7 different co-overexpressed proteins, 5 different co-overexpressed proteins to 8 different co-overexpressed proteins, 5 different co-overexpressed proteins to 9 different co-overexpressed proteins, 5 different co-overexpressed proteins to 10 different co-overexpressed proteins, 5 different co-overexpressed proteins to 15 different co-overexpressed proteins, 5 different co-overexpressed proteins to 20 different co-overexpressed proteins, 6 different co-overexpressed proteins to 7 different co-overexpressed proteins, 6 different co-overexpressed proteins to 8 different co-overexpressed proteins, 6 different co-overexpressed proteins to 9 different co-overexpressed proteins, 6 different co-overexpressed proteins to 10 different co-overexpressed proteins, 6 different co-overexpressed proteins to 15 different co-overexpressed proteins, 6 different co-overexpressed proteins to 20 different co-overexpressed proteins, 7 different co-overexpressed proteins to 8 different co-overexpressed proteins, 7 different co-overexpressed proteins to 9 different co-overexpressed proteins, 7 different co-overexpressed proteins to 10 different co-overexpressed proteins, 7 different co-overexpressed proteins to 15 different co-overexpressed proteins, 7 different co-overexpressed proteins to 20 different co-overexpressed proteins, 8 different co-overexpressed proteins to 9 different co-overexpressed proteins, 8 different co-overexpressed proteins to 10 different co-overexpressed proteins, 8 different co-overexpressed proteins to 15 different co-overexpressed proteins, 8 different co-overexpressed proteins to 20 different co-overexpressed proteins, 9 different co-overexpressed proteins to 10 different co-overexpressed proteins, 9 different co-overexpressed proteins to 15 different co-overexpressed proteins, 9 different co-overexpressed proteins to 20 different co-overexpressed proteins, 10 different co-overexpressed proteins to 15 different co-overexpressed proteins, 10 different co-overexpressed proteins to 20 different co-overexpressed proteins, or 15 different co-overexpressed proteins to 20 different co-overexpressed proteins. In some embodiments, the recombinant gram-negative host cell overexpresses 1 co-overexpressed protein, 2 different co-overexpressed proteins, 3 different co-overexpressed proteins, 4 different co-overexpressed proteins, 5 different co-overexpressed proteins, 6 different co-overexpressed proteins, 7 different co-overexpressed proteins, 8 different co-overexpressed proteins, 9 different co-overexpressed proteins, 10 different co-overexpressed proteins, 15 different co-overexpressed proteins, or 20 different co-overexpressed proteins. In some embodiments, the recombinant gram-negative host cell overexpresses at least 1 co-overexpressed protein, 2 different co-overexpressed proteins, 3 different co-overexpressed proteins, 4 different co-overexpressed proteins, 5 different co-overexpressed proteins, 6 different co-overexpressed proteins, 7 different co-overexpressed proteins, 8 different co-overexpressed proteins, 9 different co-overexpressed proteins, 10 different co-overexpressed proteins, or 15 different co-overexpressed proteins. In some embodiments, the recombinant gram-negative host cell overexpresses at most 2 different co-overexpressed proteins, 3 different co-overexpressed proteins, 4 different co-overexpressed proteins, 5 different co-overexpressed proteins, 6 different co-overexpressed proteins, 7 different co-overexpressed proteins, 8 different co-overexpressed proteins, 9 different co-overexpressed proteins, 10 different co-overexpressed proteins, 15 different co-overexpressed proteins, or 20 different co-overexpressed proteins.

Inactivated Proteases

In some embodiments, the one or more co-overexpressed protein is an inactivated protease. An inactivated protease derived from a functional protease present in the host cell can be overexpressed by a host cell to reduce the functional protease activity in a host cell. The inactivated protease mutant can act as dominant negative protease. The overexpressed inactivated protease can be exogenously produced, e.g., from an expression construct on a plasmid. In some embodiments, the recombinant gram-negative host cell overexpresses 1 to 10 different inactivated proteases. In some embodiments, an overexpressed inactivated protease is inactivated by a mutation in a gene encoding the corresponding functional protease.

In some embodiments, an inactivated protease is an inactive form of a gram negative bacterial a serine protease gene from the EC 3.4.21.107 enzyme family. In some embodiments, an inactivated protease is a DegP protease (also known as HtrA). A DegP protease can be, e.g., a DegP2 protease, or a DegP-like protease. DegP proteases are periplasmic serine endoproteases. Their structure is described, e.g., by Pallen, M. J. and Wren, B. W., 1997, "The HtrA family of serine proteases," Molecular Microbiology 26(2): 209-221, both incorporated herein by reference. In some embodiments, the DegP protease is inactivated by mutation in a gene encoding a DegP protease selected from: *P. fluorescens* DegP2 (SEQ ID NO: 31); *P. fluorescens* DegP (SEQ ID NO: 69); *E. coli* DegP/HtrA (SEQ ID NO: 62); or *P. putida* DegP (e.g., UniProtKB—A5W8F5 strain, *P. putida* F1, or B0KV30, strain *P. putida* GB1).

In some embodiments, an overexpressed inactivated protease is inactivated by a mutation in a gene encoding a DegP, a DegP-related protein, or a DegP homologue. In some embodiments, each one or more inactivated protease is independently selected from: *P. fluorescens* DegP2 S219A; an inactivated DegP2 comprising an amino acid substitution or disruption of the amino acid sequence set forth as SEQ ID NO: 31; an inactivated DegP2 comprising an amino acid substitution or disruption of a homologue of the amino acid sequence set forth as SEQ ID NO: 31; an inactivated DegP2-related protein comprising an amino acid substitution or disruption of a DegP2 having at least 60% similarity or at least 35% identity to amino acid sequence set forth as SEQ ID NO: 31; an inactivated DegP comprising an amino acid substitution or disruption of the amino acid sequence set forth as SEQ ID NO: 69; an inactivated DegP comprising an amino acid substitution or disruption of a homologue of the amino acid sequence set forth as SEQ ID NO: 69; an inactivated DegP-related protein comprising an amino acid substitution or disruption of a DegP having at least 60% similarity or at least 35% identity to amino acid sequence set forth as SEQ ID NO: 69; an inactivated DegP/HtrA comprising an amino acid substitution or disruption of the amino acid sequence set forth as SEQ ID NO: 62; an inactivated DegP/HtrA comprising an amino acid substitution or disruption of a homologue of the amino acid sequence set forth as SEQ ID NO: 62; an inactivated DegP/HtrA-related protein comprising an amino acid substitution or disruption of a DegP having at least 60% similarity or at least 35% identity to amino acid sequence set forth as SEQ ID NO: 62; an inactivated DegP, DegP-related protein, or DegP homologue having a substitution or disruption of an amino acid at a position corresponding to any one of positions 131, 134 and 236 of SEQ ID NO: 62 (or when excluding the 26 amino acid leader, positions 105, 108, and 210); an inactivated DegP, DegP-related protein, or DegP homologue having an amino acid substitution corresponding to *E. coli* Htr S210A; an inactivated DegP, DegP-related protein, or DegP homologue having an amino acid substitution corresponding to *E. coli* Htr H105R; an inactivated DegP, DegP-related protein, or DegP homologue having a substitution or disruption of any one or more amino acid at a position corresponding to any one of: 108-122, 146-152, and 217-234 of SEQ ID NO: 31. In some embodiments, the inactivated DegP, DegP-related protein, or DegP homologue has a substitution or disruption of any one or more amino acid at a position corresponding to any one of: 108, 109, 110, 111, 112, 113, 114, 115, 116, 117, 118, 119, 120, 121, 122, 146, 147, 148, 149, 150, 151, 152, 217, 218, 219, 220, 221, 222, 223, 224, 225, 226, 227, 228, 229, 230, 231, 232, 233, and 234 of SEQ ID NO: 31. In some embodiments, the inactivated DegP, DegP-related protein, or DegP homologue has a substitution or disruption of any one or more amino acid at a position corresponding to any one of: 116 (His), 120 (Asp), 122 (Asp) and 219 (Ser).

In some embodiments, an inactivated DegP, DegP-related protein, or DegP homologue comprises an amino acid substitution or disruption in the catalytic site of the corresponding DegP, DegP-related protein, or DegP homologue. Pallen and Wren, 1997, and Skorko-Glonek, J. et al., 1995, "Site-directed mutagenesis of the HtrA(DegP) serine protease, whose proteolytic activity is indispensable for *Escherichia coli* survival at elevated temperatures," Gene 163:47-52, incorporated herein by reference, describe the catalytic site of DegP/HtrA and related proteins. In particular, amino acid residues S210 and H105 are critical for protease activity. The amino acid substitutions S210A and H105R eliminate proteolytic activity. Pallen and Wren describe the catalytic domain, including a "catalytic triad" of the amino acids His, Asp, and Ser. In *E. coli* Htr these critical residues occur at positions 131 (His), 134 (Asp) and 236 (Ser) (SEQ ID NO: 62, referring to numbering including leader sequence 1-26), or at respective positions 105, 108, and 210, when excluding the leader sequence. In *P. fluorescens* DegP2 (SEQ ID NO: 31), the catalytic triad residues occur at positions 116 (His), 120 (Asp) and 219 (Ser), with numbering including leader sequence 1-27; excluding leader sequence, the catalytic triad residues occur at positions 89 (His), 93 (Asp), and 192 (Ser). One of skill in the art may identify the corresponding active site and catalytic triad in any DegP, DegP-related protein, or DegP homologue. In some embodiments, an inactivated DegP, DegP-related protein, or DegP homologue comprises an amino acid substitution or disruption of any one or more catalytic triad amino acid corresponding to any one of positions 116 (His), 120 (Asp) and 219 (Ser) of SEQ ID NO: 31. In some embodiments, an inactivated DegP, DegP-related protein, or DegP homologue comprises an amino acid substitution or disruption of any one or more catalytic triad amino acid corresponding to any one of positions 131 (His), 134 (Asp) and 236 (Ser) (SEQ ID NO: 62, referring to numbering including leader sequence 1-26), or at positions 105, 108, and 210, respectively, when excluding the leader sequence. In some embodiments, an inactivated DegP, DegP-related protein, or DegP homologue comprises an amino acid substitution or disruption of any one or more amino acid corresponding to any one of 108, 109, 110, 111, 112, 113, 114, 115, 116, 117, 118, 119, 120, 121, 122, 146, 147, 148, 149, 150, 151, 152, 217, 218, 219, 220, 221, 222, 223, 224, 225, 226, 227, 228, 229, 230, 231, 232, 233, and 234 of SEQ ID NO: 31.

In some embodiments, the recombinant gram-negative host cell overexpresses 1 inactivated protease to 10 inactivated proteases. In some embodiments, the recombinant gram-negative host cell overexpresses 1 inactivated protease to 2 inactivated proteases, 1 inactivated protease to 3 inactivated proteases, 1 inactivated protease to 4 inactivated proteases, 1 inactivated protease to 5 inactivated proteases, 1 inactivated protease to 6 inactivated proteases, 1 inactivated protease to 7 inactivated proteases, 1 inactivated protease to 8 inactivated proteases, 1 inactivated protease to 9 inactivated proteases, 1 inactivated protease to 10 inactivated proteases, 2 inactivated proteases to 3 inactivated proteases, 2 inactivated proteases to 4 inactivated proteases, 2 inactivated proteases to 5 inactivated proteases, 2 inactivated proteases to 6 inactivated proteases, 2 inactivated proteases to 7 inactivated proteases, 2 inactivated proteases to 8 inactivated proteases, 2 inactivated proteases to 9 inactivated proteases, 2 inactivated proteases to 10 inactivated proteases, 3 inactivated proteases to 4 inactivated proteases, 3 inactivated proteases to 5 inactivated proteases, 3 inactivated proteases to 6 inactivated proteases, 3 inactivated proteases to 7 inactivated proteases, 3 inactivated proteases to 8 inactivated proteases, 3 inactivated proteases to 9 inactivated proteases, 3 inactivated proteases to 10 inactivated proteases, 4 inactivated proteases to 5 inactivated proteases, 4 inactivated proteases to 6 inactivated proteases, 4 inactivated proteases to 7 inactivated proteases, 4 inactivated proteases to 8 inactivated proteases, 4 inactivated proteases to 9 inactivated proteases, 4 inactivated proteases to 10 inactivated proteases, 5 inactivated proteases to 6 inactivated proteases, 5 inactivated proteases to 7 inactivated proteases, 5 inactivated proteases to 8 inactivated proteases, 5 inactivated proteases to 9 inactivated proteases, 5 inactivated proteases to 10 inactivated proteases, 6 inactivated proteases to 7 inactivated proteases, 6 inactivated proteases to 8 inactivated proteases, 6 inactivated proteases to 9 inactivated proteases, 6 inactivated proteases to 10 inactivated proteases, 7 inactivated proteases to 8 inactivated proteases, 7 inactivated proteases to 9 inactivated proteases, 7 inactivated proteases to 10 inactivated proteases, 8 inactivated proteases to 9 inactivated proteases, 8 inactivated proteases to 10 inactivated proteases, or 9 inactivated proteases to 10 inactivated proteases. In some embodiments, the recombinant gram-negative host cell overexpresses 1 inactivated protease, 2 inactivated proteases, 3 inactivated proteases, 4 inactivated proteases, 5 inactivated proteases, 6 inactivated proteases, 7 inactivated proteases, 8 inactivated proteases, 9 inactivated proteases, or 10 inactivated proteases. In some embodiments, the recombinant gram-negative host cell overexpresses at least 1 inactivated protease, 2 inactivated proteases, 3 inactivated proteases, 4 inactivated proteases, 5 inactivated proteases, 6 inactivated proteases, 7 inactivated proteases, 8 inactivated proteases, or 9 inactivated proteases. In some embodiments, the recombinant gram-negative host cell overexpresses at most 2 inactivated proteases, 3 inactivated proteases, 4 inactivated proteases, 5 inactivated proteases, 6 inactivated proteases, 7 inactivated proteases, 8 inactivated proteases, 9 inactivated proteases, or 10 inactivated proteases.

Protein Folding Modulators

In some embodiments, the one or more co-overexpressed protein is a protein folding modulator that improves the quality and/or yield of the recombinant protein of interest. Protein folding modulators, including chaperones, disulfide bond isomerases, and peptidyl-prolyl cis-trans isomerases (PPlases) are a class of proteins present in all cells that aid in the folding, unfolding and degradation of nascent polypeptides. An overexpressed protein folding modulator can be exogenously produced, e.g., from an expression construct on a plasmid. In some embodiments, a recombinant gram-negative host cell of the present invention overexpresses any one or more different protein folding modulator. In some embodiments, a recombinant gram-negative host cell of the present invention overexpresses 1 to 10 different protein folding modulators.

In some embodiments, a protein folding modulator is microbial. In some embodiments, a microbial protein folding modulator is from a bacterium, a mammal, a fungus (e.g., a yeast or a filamentous fungus), an arthropod (e.g., an arachnid or an insect), or a *Plasmodium*. In some embodiments, a bacterial protein folding modulator is from a gram-negative bacteria. In some embodiments, a mammalian protein folding modulator is from a rodent, e.g., a mouse, rat or hamster, e.g., a golden hamster. In some embodiments, a mammalian protein folding modulator is from a pongo, e.g., an orangutan, a human, a horse, a pig, a bird, e.g., a flycatcher. In some embodiments, a gram-negative bacterial protein folding modulator is an *E. coli* or *Pseudomonad* folding modulator protein. In some embodiments, a protein folding modulator or chaperone is a *P. fluorescens* protein folding modulator. An overexpressed protein folding modulator may be any described in, e.g., U.S. Pat. No. 10,118,956, "Fusion Partners for Peptide Production" (e.g., as in Table 1), U.S. Pat. No. 9,580,719 (e.g., providing sequences for each folding modulator by RXF listed in Table 1 of U.S. Pat. No. 10,118,956), and U.S. Pat. No. 8,603,824, (e.g., Tables A to F therein). As used herein, RXF numbers are open reading frame numbers, and PROKKA numbers are designations determined using the Prokka tool as described by, e.g., Seemann, T., 2014, "Prokka: rapid prokaryotic genome annotation," Bioinformatics 30 (14): 2068-2069, incorporated herein by reference.

In some embodiments, a protein folding modulator is any known to those of skill in the art or described in the literature, e.g., in "Guidebook to Molecular Chaperones and Protein-Folding Catalysts," 1997, ed. M. Gething, Melbourne University, Australia, incorporated herein by reference. In some embodiments, each one or more protein folding modulator is independently selected from a GroES/EL, DnaKJ, Clp, Hsp90, SecB, HSP70, HSP110/SSE, HSP40 (DnaJ-related), GRPE-like, HSP90, CPN60, CPN10, cytosolic chaperone, HSP100, small HSP, calnexin, calreticulin, protein disulfide isomerase (PDI), thioredoxin-related protein, disulfide bond isomerase, protein disulfide isomerase, peptidyl-prolyl isomerase, cyclophilin PPlase, FK-506 binding protein, parvulin PPlase, individual chaperone, protein specific chaperone, or an intramolecular chaperone.

In some embodiments, an overexpressed folding modulator protein is a disulfide bond isomerase. In some embodiments, a disulfide bond isomerase is a gram-negative bacterial DsbA, DsbB, DsbC, DsbD, or DsbG. In some embodiments, a disulfide bond isomerase is selected from SEQ ID NOS: 60 (DsbC), 76 (putative cytoplasmic disulfide isomerase DsbA), 77 (DsbA), 78 (DsbB), 80 (DsbD), or 81 (DsbG). In some embodiments, an overexpressed folding modulator protein is a protein disulfide isomerase. In some embodiments, a protein disulfide isomerase is a PDIA6. In some embodiments, a PDIA6 has an amino acid sequence selected from SEQ ID NOS: 27 and 82-98. In some embodi ments, an overexpressed protein folding modulator has an amino acid sequence selected from: SEQ ID NOS: 27, 57, 60, 76-78, and 80-98.

In some embodiments, the recombinant gram-negative host cell overexpresses 1 protein folding modulator to 10 protein folding modulators. In some embodiments, the recombinant gram-negative host cell overexpresses 1 protein folding modulator to 2 protein folding modulators, 1 protein folding modulator to 3 protein folding modulators, 1 protein folding modulator to 4 protein folding modulators, 1 protein folding modulator to 5 protein folding modulators, 1 protein folding modulator to 6 protein folding modulators, 1 protein folding modulator to 7 protein folding modulators, 1 protein folding modulator to 8 protein folding modulators, 1 protein folding modulator to 9 protein folding modulators, 1 protein folding modulator to 10 protein folding modulators, 2 protein folding modulators to 3 protein folding modulators, 2 protein folding modulators to 4 protein folding modulators, 2 protein folding modulators to 5 protein folding modulators, 2 protein folding modulators to 6 protein folding modulators, 2 protein folding modulators to 7 protein folding modulators, 2 protein folding modulators to 8 protein folding modulators, 2 protein folding modulators to 9 protein folding modulators, 2 protein folding modulators to 10 protein folding modulators, 3 protein folding modulators to 4 protein folding modulators, 3 protein folding modulators to 5 protein folding modulators, 3 protein folding modulators to 6 protein folding modulators, 3 protein folding modulators to 7 protein folding modulators, 3 protein folding modulators to 8 protein folding modulators, 3 protein folding modulators to 9 protein folding modulators, 3 protein folding modulators to 10 protein folding modulators, 4 protein folding modulators to 5 protein folding modulators, 4 protein folding modulators to 6 protein folding modulators, 4 protein folding modulators to 7 protein folding modulators, 4 protein folding modulators to 8 protein folding modulators, 4 protein folding modulators to 9 protein folding modulators, 4 protein folding modulators to 10 protein folding modulators, 5 protein folding modulators to 6 protein folding modulators, 5 protein folding modulators to 7 protein folding modulators, 5 protein folding modulators to 8 protein folding modulators, 5 protein folding modulators to 9 protein folding modulators, 5 protein folding modulators to 10 protein folding modulators, 6 protein folding modulators to 7 protein folding modulators, 6 protein folding modulators to 8 protein folding modulators, 6 protein folding modulators to 9 protein folding modulators, 6 protein folding modulators to 10 protein folding modulators, 7 protein folding modulators to 8 protein folding modulators, 7 protein folding modulators to 9 protein folding modulators, 7 protein folding modulators to 10 protein folding modulators, 8 protein folding modulators to 9 protein folding modulators, 8 protein folding modulators to 10 protein folding modulators, or 9 protein folding modulators to 10 protein folding modulators. In some embodiments, the recombinant gram-negative host cell overexpresses 1 protein folding modulator, 2 protein folding modulators, 3 protein folding modulators, 4 protein folding modulators, 5 protein folding modulators, 6 protein folding modulators, 7 protein folding modulators, 8 protein folding modulators, 9 protein folding modulators, or 10 protein folding modulators. In some embodiments, the recombinant gram-negative host cell overexpresses at least 1 protein folding modulator, 2 protein folding modulators, 3 protein folding modulators, 4 protein folding modulators, 5 protein folding modulators, 6 protein folding modulators, 7 protein folding modulators, 8 protein folding modulators, or 9 protein folding modulators. In some embodiments, the recombinant gram-negative host cell overexpresses at most 2 protein folding modulators, 3 protein folding modulators, 4 protein folding modulators, 5 protein folding modulators, 6 protein folding modulators, 7 protein folding modulators, 8 protein folding modulators, 9 protein folding modulators, or 10 protein folding modulators.

Related Proteins

Prior to being modified in accordance with the present invention, e. g., to introduce a mutation in a gene to result in a deficient protein activity, a bacterial host cell may have multiple genes that encode the same protein, or that encode multiple proteins having the same or similar activity, e.g., a protease activity or autolytic factor activity. Under these circumstances, the protein deficiency of the recombinant bacterial host cell may result from mutation of more than one gene.

Two different gram-negative bacterial host cells, e.g., host cells of different genera or species, may have multiple related proteins. These related proteins may have similar sequences, structures, functions, and/or activities. Under these circumstances, a deficient protein activity of the first host cell and a deficient protein activity of the second host cell may result from mutations of genes having a high level of amino acid sequence similarity or identity. Between different host cells (e.g., of different species), and within the same host cell, certain such proteins are described in the literature as homologues based on the knowledge or assumption of an ancestral link.

In the context of the present invention, regardless of an ancestral link, one of skill in the art may identify two proteins as related proteins (within the same host cell, e.g., the same host cell species, or between two different host cells), using methods known in the art and described herein.

In some embodiments, as referred to herein, related proteins, e.g., related proteases or related autolytic factors, have defined amino acid sequence similarity or identity. It is understood that any amino acid sequence similarity or identity range provided elsewhere herein may be replaced with a narrower range falling within that range, and that any minimum amino acid sequence similarity or identity provided herein may be replaced with a higher minimum. In some embodiments, a "related protein" as used herein may have an amino acid sequence similarity or identity, active/catalytic site amino acid sequence similarity or identity, or allosteric region amino acid sequence similarity or identity, of about 30% to about 100%. Sequence similarity or identity of nucleic acid or amino acid sequences as described herein may be determined by methods known to those of skill in the art. In some embodiments, amino acids are similar with regard to polarity, charge, solubility, hydrophobicity, hydrophilicity and/or the amphipathic nature of the residues. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. Thus, a similar amino acid may be an amino acid identified as suitable for a conservative amino acid substitution, e.g., as described in the literature and readily identified by methods known to those of skill in the art, for example, as shown in Table 2, listing conservative amino acid substitutions. In some embodiments, a similar amino acid is an amino acid listed in Table 2, second column (headed "I. Conservative Substitutions") in the row corresponding to the original amino acid.

In some embodiments, a similar amino acid is an amino acid listed in Table 2, third column (headed "II. Alternative Substitutions") in the row corresponding to the original amino acid.

In some embodiments, related proteins have amino acid sequence similarity or identity, active site amino acid sequence similarity or identity, or allosteric region amino acid sequence similarity or identity, of about 30% to about 35%, about 30% to about 40%, about 30% to about 45%, about 30% to about 50%, about 30% to about 55%, about 30% to about 60%, about 30% to about 65%, about 30% to about 70%, about 30% to about 80%, about 30% to about 90%, about 30% to about 100%, about 35% to about 40%, about 35% to about 45%, about 35% to about 50%, about 35% to about 55%, about 35% to about 60%, about 35% to about 65%, about 35% to about 70%, about 35% to about 80%, about 35% to about 90%, about 35% to about 100%, about 40% to about 45%, about 40% to about 50%, about 40% to about 55%, about 40% to about 60%, about 40% to about 65%, about 40% to about 70%, about 40% to about 80%, about 40% to about 90%, about 40% to about 100%, about 45% to about 50%, about 45% to about 55%, about 45% to about 60%, about 45% to about 65%, about 45% to about 70%, about 45% to about 80%, about 45% to about 90%, about 45% to about 100%, about 50% to about 55%, about 50% to about 60%, about 50% to about 65%, about 50% to about 70%, about 50% to about 80%, about 50% to about 90%, about 50% to about 100%, about 55% to about 60%, about 55% to about 65%, about 55% to about 70%, about 55% to about 80%, about 55% to about 90%, about 55% to about 100%, about 60% to about 65%, about 60% to about 70%, about 60% to about 80%, about 60% to about 90%, about 60% to about 100%, about 65% to about 70%, about 65% to about 80%, about 65% to about 90%, about 65% to about 100%, about 70% to about 80%, about 70% to about 90%, about 70% to about 100%, about 80% to about 90%, about 80% to about 100%, or about 90% to about 100%. In some embodiments, related proteins have amino acid sequence similarity or identity, active site amino acid sequence similarity or identity, or allosteric region amino acid sequence similarity or identity, of about 30%, about 35%, about 40%, about 45%, about 50%, about 55%, about 60%, about 65%, about 70%, about 80%, about 90%, or about 100%. In some embodiments, related proteins have amino acid sequence similarity or identity, active site amino acid sequence similarity or identity, or allosteric region amino acid sequence similarity or identity, of at least about 30%, about 35%, about 40%, about 45%, about 50%, about 55%, about 60%, about 65%, about 70%, about 80%, or about 90%. In some embodiments, related proteins have amino acid sequence similarity or identity, active site amino acid sequence similarity or identity, or allosteric region amino acid sequence similarity or identity, of at most about 35%, about 40%, about 45%, about 50%, about 55%, about 60%, about 65%, about 70%, about 80%, about 90%, or about 100%. In some embodiments, related proteins have amino acid sequence similarity or identity, active site amino acid sequence similarity or identity, or allosteric region amino acid sequence similarity or identity, of about 45% to about 50%, about 45% to about 55%, about 45% to about 60%, about 45% to about 65%, about 45% to about 70%, about 45% to about 75%, about 45% to about 80%, about 45% to about 85%, about 45% to about 90%, about 45% to about 95%, about 45% to about 100%, about 50% to about 55%, about 50% to about 60%, about 50% to about 65%, about 50% to about 70%, about 50% to about 75%, about 50% to about 80%, about 50% to about 85%, about 50% to about 90%, about 50% to about 95%, about 50% to about 100%, about 55% to about 60%, about 55% to about 65%, about 55% to about 70%, about 55% to about 75%, about 55% to about 80%, about 55% to about 85%, about 55% to about 90%, about 55% to about 95%, about 55% to about 100%, about 60% to about 65%, about 60% to about 70%, about 60% to about 75%, about 60% to about 80%, about 60% to about 85%, about 60% to about 90%, about 60% to about 95%, about 60% to about 100%, about 65% to about 70%, about 65% to about 75%, about 65% to about 80%, about 65% to about 85%, about 65% to about 90%, about 65% to about 95%, about 65% to about 100%, about 70% to about 75%, about 70% to about 80%, about 70% to about 85%, about 70% to about 90%, about 70% to about 95%, about 70% to about 100%, about 75% to about 80%, about 75% to about 85%, about 75% to about 90%, about 75% to about 95%, about 75% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%. In some embodiments, related proteins have amino acid sequence similarity or identity, active site amino acid sequence similarity or identity, or allosteric region amino acid sequence similarity or identity, of about 45%, about 50%, about 55%, about 60%, about 65%, about 70%, about 75%, about 80%, about 85%, about 90%, about 95%, or about 100%. In some embodiments, related proteins have amino acid sequence similarity or identity, active site amino acid sequence similarity or identity, or allosteric region amino acid sequence similarity or identity, of at least about 45%, about 50%, about 55%, about 60%, about 65%, about 70%, about 75%, about 80%, about 85%, about 90%, or about 95%. In some embodiments, related proteins have amino acid sequence similarity or identity, active site amino acid sequence similarity or identity, or allosteric region amino acid sequence similarity or identity, of at most about 50%, about 55%, about 60%, about 65%, about 70%, about 75%, about 80%, about 85%, about 90%, about 95%, or about 100%.

Related proteins can be homologues, or may not be homologues. In some embodiments, a related protein that is a homologue of a given protein is identified using the protein sequence as a query sequence in a PSI-BLAST (Position-Specific Iterative basic Local Alignment Search Tool) search of all nonredundant (nr) protein sequences from the host cell (e.g., *E. coli*) proteome sequences deposited in the NCBI database, at default settings. PSI-BLAST search methods are known to those of skill in the art and have been described by, e.g., Bhagwat, M., and Aravind, L., 2007, "PSI-BLAST Tutorial," Ch. 10 in Comparative Genomics: Volumes 1 and 2, Bergman N H, ed., Totowa (N.J.): Humana Press, incorporated herein by reference. Approaches to identifying homologues is described in the literature, e.g., by Pearson, W. R., 2014, "BLAST and FASTA similarity searching for multiple sequence alignment," Methods Mol. Biol. 1079: 75-101, incorporated herein by reference in its entirety.

Nucleic acid and amino acid sequence similarity identity may be determined according to any suitable method known in the art, including but not limited to those described herein. For example, alignments and searches for similar sequences can be performed using the U.S. National Center for Biotechnology Information (NCBI, Bethesda, MD) program, MegaBLAST. Use of this program with options for percent identity set at, for example, 70% for amino acid sequences, or set at, for example, 90% for nucleotide sequences, will identify those sequences with 70%, or 90%, or greater sequence identity to the query sequence. Other software known in the art is also available for aligning and/or searching for similar sequences, e.g., sequences at least 70% or 90% identical to an information string containing a secretion signal sequence herein. For example, sequence alignments for comparison to identify sequences at least 70% or 90% identical to a query sequence is often performed by use of, e.g., the GAP, BESTFIT, BLAST, FASTA, and TFASTA programs available in the GCG Sequence Analysis Software Package (available from the Genetics Computer Group, University of Wisconsin Biotechnology Center, 1710 University Avenue, Madison, WI 53705), with the default parameters as specified therein, plus a parameter for the extent of sequence identity set at the desired percentage. Also, for example, the CLUSTAL program (available in the PC/Gene software package from Intelligenetics, Mountain View, CA) may be used.

These and other sequence alignment methods are well known in the art and may be conducted by manual alignment, by visual inspection, or by manual or automatic application of a sequence alignment algorithm, such as any of those embodied by the above-described programs. Various useful algorithms include, e.g.: the similarity search method described in W. R. Pearson & D. J. Lipman, Proc. Natl. Acad. Sci. USA 85:2444-48 (April 1988); the local homology method described in T. F. Smith & M. S. Waterman, in Adv. Appl. Math. 2:482-89 (1981) and in J. Molec. Biol. 147:195-97 (1981); the homology alignment method described in S. B. Needleman & C. D. Wunsch, J. Molec. Biol. 48(3):443-53 (March 1970); and the various methods described, e.g., by W. R. Pearson, in Genomics 11(3):635-50 (November 1991); by W. R. Pearson, in Methods Molec. Biol. 24:307-31 and 25:365-89 (1994); and by D. G. Higgins & P. M. Sharp, in Comp. Appl'ns in Biosci. 5:151-53 (1989) and in Gene 73(1):237-44 (15 Dec. 1988).

GAP Version 10, which uses the algorithm of Needleman and Wunsch (1970) supra, can be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent or similar programs may also be used as will be understood by one of skill in the art. For example, a sequence comparison program can be used that, for any two sequences in question, generates an alignment having identical nucleotide residue matches and an identical percent sequence identity when compared to the corresponding alignment generated by GAP Version 10. In embodiments, the sequence comparison is performed across the entirety of the query or the subject sequence, or both.

Mutations Resulting in a Deficiency of a Recombinant Host Cell Protein or in an Overexpressed Inactivated Protease A recombinant bacterial host cell of the invention having a deficient protein activity can be generated by altering one or more genes encoding a protein having the protein activity, by any known method. A "deficient" protein activity or "deficiency" in a protein activity as used throughout this description, may include a partial deficiency, a substantial deficiency, or a complete deficiency. A "deficient" protein activity or "deficiency" in a protein activity as used throughout this description may include a reduction in, or elimination of, the protein activity. In some embodiments, the recombinant host cell protein activity is accordingly deficient in the host cell as compared with a control cell. In some embodiments, a control cell is a corresponding host cell that has wild-type activity of the protein. In some embodiments, a control cell is a corresponding wild-type cell. In some embodiments, a control cell has wild-type activity of the protein but has other differences relative to a wild-type cell. The recombinant host cell of the invention may be modified by any suitable means, e.g., as described herein, to reduce or eliminate the activity of protein. A recombinant bacterial host cell of the invention may also overexpress an inactivated protease, as described herein. In some embodiments, the overexpressed inactivated protease is partially inactivated, substantially inactivated, or fully inactivated with regard to the protease activity. In some embodiments, the overexpressed inactivated protease is partially inactivated, substantially inactivated, or fully inactivated with regard to the protease activity, and active with respect to another property, e.g., a chaperone activity. In some embodiments, the inactivated protease is inactivated by mutation, e.g., by mutation of a gene encoding the active protease (having protease activity).

In some embodiments, the deficient or reduced protein activity of the recombinant host cell results from a mutation that causes an amino acid change or other disruption, e.g., by amino acid substitution, deletion of one or more amino acid, insertion of one or more amino acid, or protein truncation. In some embodiments, the mutation is an inactivating mutation. In some embodiments, the mutation is a partially-inactivating mutation. In some embodiments, a deficiency in the activity of a protein, e.g., a protease or autolytic factor, results from one or more mutation independently selected from (i) a complete gene deletion (gene knockout), (ii) a partial gene deletion, (iii) a missense mutation, (iv) a nonsense mutation, (v) a frameshift mutation, (vi) an insertion, and (vii) any combination of (ii), (iii), (iv), (v) and (vi). In some embodiments, an overexpressed inactivated protease is inactivated by one or more mutation independently selected from (ii) a partial gene deletion, (iii) a missense mutation, (iv) a nonsense mutation, (v) a frameshift mutation, (vi) an insertion, and (vii) any combination of (ii), (iii), (iv), (v) and (vi). In some embodiments, the mutation resulting in a deficient protein activity or an inactivated protease is in a coding region of a gene encoding the protein or inactivated protease. In some embodiments, the mutation resulting in a deficient protein activity is in a non-coding region of the gene encoding the protein. In some embodiments, the non-coding region of the gene is a regulatory region. In some embodiments, the mutation in the regulatory region of the gene disrupts a regulatory element that is required for production of the protein, for example, an element required for transcription of the corresponding RNA, or translation of the mRNA into protein. For example, a noncoding region regulatory element can be a promoter, enhancer, regulatory protein binding site, ribosome binding site, or any other regulatory element as known to those of skill in the art.

In some embodiments, a mutation disrupts a critical site in a protein to result in a deficient protein in the recombinant host cell, or an inactivated overexpressed protease, e.g., by changing or deleting one or more amino acids at a protease active site. In some embodiments, a mutation disrupts an allosteric region of the protein, e.g., by changing one or more amino acids in an allosteric region. An allosteric region may be a region that interacts with another region to form an active protein conformation. In some embodiments, a mutation results in the substitution of an amino acid with any other amino acid. In some embodiments, the substitution is a non-conservative amino acid substitution. A non-conservative amino acid substitution can be readily selected by one of skill in the art. Table 2 provides examples of conservative amino acid substitutions (column I) and alternative conservative amino acid substitutions (II). In some embodiments, a non-conservative substitution of an original amino acid (e.g., the amino acid in the wild-type protein) is a substitution with any amino acid not listed in (I) for the original amino acid. In some embodiments, a non-conservative substitution of an original amino acid is any amino acid not listed in (II) for the original amino acid. In some embodiments, a non-conservative amino acid substitution is any amino acid not listed in either (I) or (II) for the original amino acid.

TABLE 2

| Amino Acid | I. Conservative Substitutions | II. Alternative Substitutions |
|---|---|---|
| Ala | Gly, Ile, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Arg | His, Lys | any basic amino acid or derivative thereof (Arg, His, Lys) any charged amino acid or derivative thereof (Asp, Arg, Glu, Lys) any basic amino acid with an electrically charged sidechain or derivative thereof (Arg, His, Lys) |
| Asn | Asp, Gln, Glu | any acidic amino acid or derivative thereof, or any amide of any acidic amino acid or derivative thereof (Asn, Asp, Gln, Glu) any polar amino acid or derivative thereof (Asn, Cys, Gln, His, Ser, Thr, Trp, Tyr) |
| Asp | Asn, Gln, Glu | any acidic amino acid or derivative thereof, or any amide of any acidic amino acid or derivative thereof (Asn, Asp, Gln, Glu) any charged amino acid or derivative thereof (Asp, Arg, Glu, Lys) any polar neutral amino acid or derivative thereof (Asp, Cys, Gln, Ser, Thr) any acidic amino acid with an electrically charged sidechain or derivative thereof (Asp, Glu) |
| Cys | Met, Sec, Ser, Thr | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |

TABLE 2-continued

| Amino Acid | I. Conservative Substitutions | II. Alternative Substitutions |
|---|---|---|
| Gln | Asn, Asp, Glu | any acidic amino acid or derivative thereof, or any amide of any acidic amino acid or derivative thereof (Asn, Asp, Gln, Glu) any polar amino acid or derivative thereof (Asn, Cys, Gln, His, Ser, Thr, Trp, Tyr) any polar neutral amino acid or derivative thereof (Asp, Cys, Gln, Ser, Thr) any acidic amino acid with an electrically charged sidechain or derivative thereof (Asp, Glu) |
| Glu | Asn, Asp, Gln | any acidic amino acid or derivative thereof, or any amide of any acidic amino acid or derivative thereof (Asn, Asp, Gln, Glu) any charged amino acid or derivative thereof (Asp, Arg, Glu, Lys) |
| Gly | Ala, Ile, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| His | Arg, Lys | any basic amino acid or derivative thereof (Arg, His, Lys) any polar amino acid or derivative thereof (Asn, Cys, Gln, His, Ser, Thr, Trp, Tyr) any basic amino acid with an electrically charged sidechain or derivative thereof (Arg, His, Lys) |
| Ile | Ala, Gly, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Leu | Ala, Gly, Ile, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Lys | Arg, His | any basic amino acid or derivative thereof (Arg, His, Lys) any charged amino acid or derivative thereof (Asp, Arg, Glu, Lys) any basic amino acid with an electrically charged sidechain or derivative thereof (Arg, His, Lys) |
| Met | Cys, Sec, Ser, Thr | any hydroxyl or sulfur/selenium-containing amino acid or derivative thereof (Cys, Sec, Ser, Met, Thr) any hydrophobic amino acid or derivative thereof (Ala, Gly, Ile, Leu, Met, Phe, Pro, Val) |
| Phe | Trp, Tyr | any aromatic amino acid or derivative thereof (Phe, Trp, Tyr) any hydrophobic amino acid or derivative thereof (Ala, Gly, Ile, Leu, Met, Phe, Pro, Val) |

TABLE 2-continued

| Amino Acid | I. Conservative Substitutions | II. Alternative Substitutions |
|---|---|---|
| Pro | | any cyclic amino acid or derivative thereof (Pro) any hydrophobic amino acid or derivative thereof (Ala, Gly, Ile, Leu, Met, Phe, Pro, Val) |
| Ser | Cys, Met, Sec, Thr | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |
| Thr | Cys, Met, Sec, Ser | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |
| Trp | Phe, Tyr, | any aromatic amino acid or derivative thereof (Phe, Trp, Tyr) any polar amino acid or derivative thereof (Asn, Cys, Gln, His, Ser, Thr, Trp, Tyr) |
| Tyr | Phe, Trp | any aromatic amino acid or derivative thereof (Phe, Trp, Tyr) any polar amino acid or derivative thereof (Asn, Cys, Gln, His, Ser, Thr, Trp, Tyr) |
| Val | Ala, Gly, Ile, Leu | any aliphatic amino acid or derivative thereof (Ala, Gly, Ile, Leu, Val) any hydrophobic amino acid or derivative thereof (Ala, Gly, Ile, Leu, Met, Phe, Pro, Val) |

Recombinant Proteins of Interest

The present invention provides gram-negative bacterial host cells and methods for their use to produce recombinant proteins of interest of high quality and at high yield. In some embodiments, a recombinant protein of interest produced using the described host cells and methods is a protein susceptible to degradation when recombinantly expressed in gram-negative bacterial host cell. In some embodiments the recombinant protein of interest is degraded in a host cell that produces a wild-type, or functional, tail-specific protease, and is observed to be less degraded in a host cell deficient in tail-specific protease activity. As described herein, a recombinant protein of interest may be produced by the recombinant gram-negative bacterial host cell from one or more expression plasmid or vector comprising nucleic acid expression constructs that encode the recombinant protein of interest and from which the recombinant protein can be expressed.

Extensive sequence information required for molecular genetics and genetic engineering techniques is widely publicly available. Access to complete nucleotide sequences of mammalian, as well as human, genes, cDNA sequences, amino acid sequences and genomes are often obtained from GenBank at the website www.ncbi.nlm.nih.gov/Entrez. Additional information may be obtained from GeneCards, an electronic encyclopedia integrating information about genes and their products and biomedical applications, from the Weizmann Institute of Science Genome and Bioinformatics. Nucleotide sequence information may be obtained from the EMBL Nucleotide Sequence Database or the DNA Databank or Japan (DDBJ). Additional sources of information on amino acid sequences include Georgetown's protein information resource website and Swiss-Prot.

In some embodiments, the protein of interest is a mammalian protein or polypeptide or derived from a mammalian protein or polypeptide. The terms "protein" and "polypeptide" are used interchangeably herein, unless the context indicates otherwise. In embodiments, the protein of interest is a human protein or derived from a human protein. In embodiments, the protein of interest is a prokaryotic protein or derived from a prokaryotic protein. In embodiments, the protein of interest is a microbial protein or derived from a microbial protein. In embodiments, the protein of interest is a bacterial protein or derived from a bacterial protein. In some embodiments, the recombinant protein of interest is human, murine, rat, rabbit, guinea pig, camelid, shark, avian, yeast, fungal, gram-negative bacterial, or gram-positive bacterial, or derived therefrom.

In some embodiments, a recombinant protein of interest produced using the compositions and methods of the present invention is selected from: an antibody, antibody fragment, or derivative of an antibody or antibody fragment (antibody, antibody fragment, or derivative thereof); an antibody-based drug, a non-antibody binding protein (e.g., an antibody mimetic, including, but not limited to, an alphabody, an iBody, an affibody, an affilin, an affitin, or an anticalin), a reagent protein; a vaccine antigen; a therapeutic protein or enzyme; non-natural protein; a pathogen protein or derivative thereof; a microbial toxin, a lipoprotein; an extracellular receptor or ligand; a protease; a kinase; a blood protein; a chemokine; a cytokine; a bone morphogenic protein; an anticoagulant; a blood factor; a bone morphogenetic protein; an engineered protein scaffold; an enzyme, e.g., a biocatalytic enzyme; a growth factor; an interferon; an interleukin; a thrombolytic agent; a hormone; and a TGF-beta family member protein.

In some embodiments, a recombinant protein of interest produced using the compositions and methods of the present invention is mammalian, rodent, avian, Chondrichthyes, fungal, or bacterial. In some embodiments, a recombinant protein of interest is human, murine, rat, rabbit, guinea pig, camelid, shark, chicken, yeast, fungal, gram-negative bacterial, or gram-positive bacterial. In some embodiments, the recombinant protein of interest is native to the recombinant gram-negative bacterial host cell. In some embodiments, the recombinant protein of interest is heterologous to the recombinant gram-negative bacterial host cell, that is, the protein of interest is derived from an organism other than the expression host cell. In some embodiments, a recombinant protein of interest produced is a difficult-to-express recombinant protein, e.g., a protein that undergoes rapid proteolytic degradation by intracellular bacterial proteases, including a protein having an N-terminus that is vulnerable to degradation, and a protein that typically is produced in insoluble form in microbial or bacterial expression systems.

In some embodiments, an antibody, antibody fragment, or derivative of an antibody or antibody fragment (antibody, antibody fragment, or derivative thereof is selected from: a monoclonal antibody; a complementarity determining region (CDR) fragment; a CDR-grafted antibody; a single-chain antibody; a single chain antibody fragment; modified antibody, a bispecific antibody, a chimeric antibody; a diabody; a triabody; a tetrabody; a minibody; a linear antibody; a chelating recombinant antibody; a bibody; a tribody; an intrabody; a nanobody; a small modular immunopharmaceutical (SMIP); an antigen-binding-domain immunoglobulin fusion protein; a camelid antibody; a shark single domain antibody, an avian antibody (e.g., a chicken antibody), a VHH-containing antibody; a F(ab); a F(ab)'; F(ab)'$_2$; scFv; an Fc fragment generated from the heavy chain constant region of an antibody; a reduced IgG fragment (e.g., generated by reducing the hinge region disulfide bonds of IgG); an Fc fusion protein (e.g., comprising the Fc domain of IgG fused together with a protein or peptide of interest); a domain antibody; a VL; a VNAR; a VH; a VHH; or any other antibody fragment described in the art, e.g., in U.S. Pat. No. 5,648,237, "Expression of Functional Antibody Fragments," incorporated by reference herein in its entirety. In some embodiments, the VHH-containing antibody is a VHH concatenated antibody. In some embodiments, an antibody or antibody fragment derived from a non-human animal species is humanized.

In some embodiments, an antibody, antibody fragment, or derivative thereof produced using the compositions and methods of the present invention is a therapeutic antibody, antibody fragment, or derivative thereof. In some embodiments, the therapeutic antibody, antibody fragment, or derivative thereof binds to a target selected from: a cytokine; a chemokine; a drug; a cell-surface protein, e.g., a receptor, cell-surface marker, pathogen surface-protein, etc.; a growth factor; a growth factor receptor; immune checkpoint molecule, and a blood factor. In some embodiments, the cytokine is TNF-alpha. In some embodiments, the drug is a platelet-aggregation inhibitor. In some embodiments, the platelet-aggregation inhibitor is ticagrelor.

In some embodiments, the recombinant protein of interest is an antibody fragment selected from a Fab, Fab', or F(ab')$_2$. A Fab comprises one constant region domain and one variable region domain of each of the heavy and the light chain, and lacks the antibody hinge region. In some embodiments, the recombinant protein of interest is a Fab'. A Fab' also comprises one constant region domain and one variable region domain of each of the heavy and the light chain, and also comprises the antibody hinge region of the heavy chain, and thereby has free sulfhydryls. A F(ab')$_2$ comprises two antigen binding regions, each having one constant region domain and one variable region domain of each of the heavy and the light chains, and both heavy chains having the hinge region. This allows disulfide bonding to join the two binding regions.

In some embodiments, the recombinant protein of interest is a Fab' that binds to a target selected from: Carcinoembryonic antigen (CEA); CD22; fibrin II, beta chain; TNF-alpha; and NCA-90 (granulocyte antigen). In some embodiments, the Fab' is selected from: Arcitumomab; Bectumomab; Biciromab; the Fab' moiety of Certolizumab pegol; and Sulesomab. In some embodiments, the recombinant protein of interest is a Fab that binds to a target selected from: EpCAM, Complement factor D (CFD), C242 antigen, 5T4, human scatter factor receptor kinase, VEGF-A, and integrin aIIbβ3. In some embodiments, the Fab is selected from: Abciximab; Abrezekimab; Anatumomab mafenatox; Citatuzumab bogatox; Lampalizumab; Nacolomab tafenatox; Naptumomab estafenatox; Nofetumomab merpentan; Onartuzumab; Ranibizumab; Tadocizumab; and Telimomab aritox. In some embodiments, the recombinant protein of interest is a F(ab')$_2$ that binds to a target selected from: TNF-alpha; VEGFR2; ITGB2 (CD18); and CA-125. In some embodiments, the F(ab')$_2$ is selected from: Afelimomab; Alacizumab pegol; Dorlimomab aritox; Erlizumab; and Igovomab.

In some embodiments, a Fab' that binds to human tumor necrosis factor alpha (human TNF-alpha) is the Fab' moiety of certolizumab. Certolizumab is a recombinant, humanized antibody Fab' fragment, with specificity for human TNF-alpha, conjugated to an approximately 40 kDa polyethylene glycol (PEG2MAL40K). Certolizumab is approved in the United States under the name Cimzia® for treatment of autoimmune conditions including Crohn's disease, rheumatoid arthritis, psoriatic arthritis, ankylosing spondylitis, non-radiographic axial spondyloarthritis, and moderate to severe plaque psoriasis, as described in detail in the Cimzia Prescribing Information (Cimzia Prescribing Information, revised September 2019, incorporated by reference in its entirety). In some embodiments, the recombinant gram-negative bacterial host cell and related methods described herein are used to produce a recombinant Fab' that binds to human TNF-alpha, for use in the treatment of Crohn's disease, rheumatoid arthritis, psoriatic arthritis, ankylo sing spondylitis, non-radiographic axial spondyloarthritis, and moderate to severe plaque psoriasis.

In some embodiments, a recombinant protein of interest is expressed in the recombinant gram-negative bacterial host cell from one or more expression vector, each comprising one or more expression constructs, and each expression construct comprising a nucleic acid sequence for expressing and encoding the recombinant protein of interest. As understood by one of skill in the art, one or more expression construct may be included in a single expression vector, as required to encode each polypeptide chain comprised by the recombinant protein of interest. In some embodiments, a recombinant gram-negative bacterial host cell comprises at least two expression vectors, each comprising one or more expression construct as needed depending upon the recombinant protein of interest. As understood by those of skill in the art, an antibody, antibody fragment, or derivative thereof may be comprised of one or more polypeptides produced from one or more expression constructs. For example, an antibody may be comprised of four polypeptides: two identical heavy chains and two identical light chains, encoded by at least two genes. An antibody may be comprised of two non-identical heavy chains and two non-identical light chains, encoded by at least four different genes. An antibody fragment may be, e.g., comprised of one heavy chain and one light chain (e.g., a Fab or Fab'), two heavy chains and two light chains (e.g., a F(ab')$_2$), one heavy chain (e.g., a VHH, a V$_H$, or a V$_L$), or a single polypeptide comprising both V$_H$ and V$_L$ (scFv). In some embodiments, one or more expression vector in a recombinant host cell may include multiple copies of the same expression construct.

In some embodiments, the at least one expression construct encoding the antibody, antibody fragment, or derivative thereof comprises at least one nucleic acid sequence encoding a heavy chain, at least one nucleic acid sequence encoding a light chain, or both, wherein the heavy chain is full-length or a heavy chain fragment, and the light chain is full-length or a light chain fragment. In some embodiments, the at least one expression construct encoding the antibody, antibody fragment, or derivative thereof comprises at least two nucleic acid sequences, each encoding a heavy chain. In some embodiments, the at least one expression construct encoding the antibody, antibody fragment, or derivative thereof comprises a nucleic acid sequence encoding a heavy chain and a nucleic acid sequence encoding a light chain, wherein the heavy and light chain are expressed from the same mRNA transcript. In some embodiments, the at least one expression construct encoding the antibody, an antibody fragment, or derivative thereof comprises a nucleic acid sequence encoding a heavy chain and a nucleic acid sequence encoding a light chain, wherein the heavy and light chain are expressed from different mRNA transcripts. In some embodiments, each heavy chain-encoding nucleic acid sequence and each light chain-encoding nucleic acid sequence is individually operably linked to an independently selected nucleic acid sequence encoding a periplasmic secretion signal.

Further, as described herein, a recombinant gram-negative host cell of the invention may comprise one or more expression vector that contains one or more expression construct for production of a co-overexpressed protein, e.g., an inactivated protease, folding modulator, chaperone, or any combination thereof. A recombinant protein of interest and a co-overexpressed protein expression may be expressed from the same expression vector. In some embodiments, a recombinant protein of interest and a co-overexpressed protein are co-transcribed, from the same promoter. In some embodiments, a recombinant protein of interest and a co-overexpressed protein are transcribed from different promoters. A recombinant protein of interest and a co-overexpressed protein may be expressed from different expression vectors in the recombinant host cell.

In some embodiments, a recombinant gram-negative bacterial host cell comprises 1 to 5 expression vectors. In some embodiments, each expression vector comprises 1 to 5 expression constructs. In some embodiments, the expression constructs each encode a different protein. In some embodiments, more than one expression construct present in the expression vector(s) encodes the same protein.

Methods for Producing a Recombinant Protein

The present invention includes methods for producing a recombinant protein of interest using the recombinant gram-negative bacterial host cells described herein. The compositions and methods of the invention can be used to produce a recombinant protein of interest of high quality, at high yield, or both. A high quality recombinant protein of interest can be soluble, active, intact, or any combination thereof. In some embodiments, the compositions and methods of the invention are used to produce a recombinant protein that is soluble, active, intact, present at high yield, or any combination thereof.

In some embodiments, a method for producing a recombinant protein of interest comprises: recovering the recombinant protein of interest from a recombinant gram-negative bacterial host cell as set forth herein, wherein the recombinant gram-negative host cell has been cultured under suitable fermentation conditions, wherein the recombinant gram-negative host cell has been transformed with at least one expression vector encoding the recombinant protein of interest. In some embodiments, recovery of the recombinant protein of interest from the recombinant gram-negative bacterial host cell comprises at least one purification step. In some embodiments, the yield and/or quality of the recovered recombinant protein of interest is measured. In some embodiments, the yield and/or quality of the recovered recombinant protein of interest is compared with that recovered from a control cell.

Production and evaluation of a recombinant protein of interest using the inventive gram-negative bacterial host cells as described herein may carried out as set forth herein, in combination with known tools and methods for producing recombinant proteins in bacterial host cells.

Gram-Negative Bacterial Host Cells

Gram-negative bacterial host cells of the present invention include *Pseudomonads* (i.e., host cells in the order Pseudomonadales) and related bacterial organisms known in the art, e.g., *Escherichia, Erwinia, Salmonella, Shigella, Moraxella, Helicobacter, Legionella, Neisseria, Haemophilus, Acinetobacter, Xylella, Bacteroides, Citrobacter, Enterobacter, Klebsiella, Proteus, Serratia, Shigella, Yersinia* and *Vibrio*, and including any species or subspecies, including but not limited to *P. fluorescens, P. aeruginosa, P. putida, E. coli, E. chrysanthemi, S. typhimurium, Helicobacter pylori, L. pneumophila, N. meningitidis, N. gonorrhoeae, Haemophilus influenzae, V. cholerae, X. fastidiosa*, and *A. baylyi*.

In some embodiments, the *Pseudomonad* host cell is *Pseudomonas fluorescens*.

In embodiments, the host cell is of the order Pseudomonadales (referred to herein as a "*Pseudomonad*." Where the host cell is of the order Pseudomonadales, it may be a member of the family Pseudomonadaceae, including the genus *Pseudomonas*.

Gamma Proteobacterial hosts include members of the species *Escherichia coli* and members of the species *Pseudomonas fluorescens*. Other *Pseudomonas* organisms may also be useful. *Pseudomonads* and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA), all are incorporated by reference herein in its entirety. Table 3 presents these families and genera of organisms.

TABLE 3

| Families and Genera ("Gram-Negative Aerobic Rods and Cocci," Bergey's, 1974) | |
| --- | --- |
| Family I. *Pseudomonaceae Gluconobacter* | *Pseudomonas* |
| | *Xanthomonas* |
| | *Zoogloea* |
| Family II. *Azotobacteraceae Azomonas* | *Azotobacter* |
| | *Beijerinckia* |
| | *Derxia* |
| Family III. *Rhizobiaceae Agrobacterium* | *Rhizobium* |
| Family IV. *Methylomonadaceae Methylococcus* | *Methylomonas* |
| Family V. *Halobacteriaceae Halobacterium* | *Halococcus* |
| Other *Genera Acetobacter* | *Alcaligenes* |
| | *Bordetella* |
| | *Brucella* |
| | *Francisella* |
| | *Thermus* |

*Pseudomonas* and closely related bacteria are generally part of the group defined as "Gram(−) Proteobacteria Subgroup 1" or "Gram-Negative Aerobic Rods and Cocci" (Buchanan and Gibbons (eds.) (1974) Bergey's Manual of Determinative Bacteriology, pp. 217-289). *Pseudomonas* host strains are described in the literature, e.g., in U.S. Pat. Nos. 9,458,487 and 9,453,251, both entitled "Expression of mammalian proteins in *Pseudomonas fluorescens*," each incorporated by reference herein.

"Gram-negative Proteobacteria Subgroup 1" also includes Proteobacteria that would be classified in this heading according to the criteria used in the classification. The heading also includes groups that were previously classified in this section but are no longer, such as the genera *Acido-*

*vorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella*, and *Teredinibacter;* 3) Rhizobiaceae family bacteria of the genera *Chelatobacter, Ensifer, Liberibacter* (also called "*Candidatus liberibacter*"), and *Sinorhizobium;* and 4) Methylococcaceae family bacteria of the genera *Methylobacter, Methylocaldum, Methylomicrobium, Methylosarcina*, and *Methylosphaera*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azoto-* formans; Pseudomonas brenneri; Pseudomonas cedrella; Pseudomonas corrugata (ATCC 29736); Pseudomonas extremorientalis; Pseudomonas fluorescens (ATCC 35858); Pseudomonas gessardii; Pseudomonas libanensis; Pseudomonas mandelii (ATCC 700871); Pseudomonas marginalis (ATCC 10844); Pseudomonas migulae; Pseudomonas mucidolens (ATCC 4685); Pseudomonas orientalis; Pseudomonas rhodesiae; Pseudomonas synxantha (ATCC 9890); Pseudomonas tolaasii (ATCC 33618); Pseudomonas veronii (ATCC 700474); Pseudomonas frederiksbergensis; Pseudomonas geniculata (ATCC 19374); Pseudomonas gingeri; Pseudomonas graminis; Pseudomonas grimontii; Pseudomonas halodenitrificans; Pseudomonas halophila; Pseudomonas hibiscicola (ATCC 19867); Pseudomonas huttiensis (ATCC 14670); Pseudomonas hydrogenovora; Pseudomonas jessenii (ATCC 700870); Pseudomonas kilonensis; Pseudomonas lanceolata (ATCC 14669); Pseudomonas lini; Pseudomonas marginate (ATCC 25417); Pseudomonas mephitica (ATCC 33665); Pseudomonas denitrificans (ATCC 19244); Pseudomonas pertucinogena (ATCC 190); Pseudomonas pictorum (ATCC 23328); Pseudomonas psychrophila; Pseudomonas filva (ATCC 31418); Pseudomonas monteilii (ATCC 700476); Pseudomonas mosselii; Pseudomonas oryzihabitans (ATCC 43272); Pseudomonas plecoglossicida (ATCC 700383); Pseudomonas putida (ATCC 12633); Pseudomonas reactans; Pseudomonas spinosa (ATCC 14606); Pseudomonas balearica; Pseudomonas luteola (ATCC 43273); Pseudomonas stutzeri (ATCC 17588); Pseudomonas amygdali (ATCC 33614); Pseudomonas avellanae (ATCC 700331); Pseudomonas caricapapayae (ATCC 33615); Pseudomonas cichorii (ATCC 10857); Pseudomonas ficuserectae (ATCC 35104); Pseudomonas fuscovaginae; Pseudomonas meliae (ATCC 33050); Pseudomonas syringae (ATCC 19310); Pseudomonas viridiflava (ATCC 13223); Pseudomonas thermocarboxydovorans (ATCC 35961); Pseudomonas thermotolerans; Pseudomonas thivervalensis; Pseudomonas vancouverensis (ATCC 700688); Pseudomonas wisconsinensis; and Pseudomonas xiamenensis. In one embodiment, the host cell is Pseudomonas fluorescens.

The host cell can also be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following Pseudomonas species: Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas rnandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii; and Pseudomonas veronii.

Host Strain Backgrounds

Host cells, strains and expression constructs useful in practicing the methods of the invention can be identified or made using reagents and methods known to those of skill in the art and described in the literature. For example, U.S. Pat. No. 8,288,127, "Protein Expression Systems," incorporated herein by reference in its entirety, describes production of a recombinant polypeptide by introduction of a nucleic acid construct into an auxotrophic Pseudomonas fluorescens host cell comprising a chromosomal lacI gene insert (e.g., lsc::lacI$^{Q1}$). The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U.S. Pat. No. 8,288,127, "Protein Expression Systems," and Schneider, et al., 2005, "Auxotrophic markers pyrF and proC can replace antibiotic markers on protein production plasmids in high-cell-density Pseudomonas fluorescens fermentation," Biotechnol. Progress 21(2): 343-8, both incorporated herein by reference in their entirety, describe a production host strain auxotrophic for uracil that was constructed by deleting the pyrF gene in strain MB101. The pyrF gene was cloned from strain MB214 (ATCC deposit PTA-7840) to generate a plasmid that complements the pyrF deletion to restore prototrophy. In particular embodiments, a dual pyrF-proC dual auxotrophic selection marker system in a P. fluorescens host cell is used. Given the published literature, a pyrF deleted production host strain as described can be produced by one of skill in the art using known methods and used as the background for introducing other desired genomic changes, including those described herein as useful in practicing the methods of the invention. It would be understood by one of skill in the art that a production host strain useful in the methods of the present invention can be generated using a publicly available host cell, for example, P. fluorescens MB101, e.g., by inactivating the genes encoding PyrF, Prc1, Prc2, MepM1, and optionally gene encoding an additional protease or autolytic factor, using any of many suitable methods known in the art and described in the literature. It is also understood that a prototrophy restoring plasmid can be transformed into the strain, e.g., a plasmid carrying the pyrF gene from strain MB214, using any suitable method known in the art and described in the literature. Additionally, in such strains inactivated protease and folding modulator overexpression constructs may be introduced, using methods well known in the art.

In embodiments, a P. fluorescens host strain used in the methods of the invention is DC1032 (Δprc1, Δprc2, ΔhslUV, ΔpyrF, lsc:lacI$^{Q1}$), a derivative of deposited strain MB101 in which the genes pyrF is deleted, and the E. coli lacI transcriptional repressor is inserted and fused with the levansucrase gene (lsc). Sequences for these genes and methods for their use are known in the art and described in the literature, e.g., in U.S. Pat. Nos. 8,288,127, 8,017,355, "Mannitol induced promoter systems in bacterial host cells," and 7,794,972, "Benzoate- and anthranilate-inducible promoters," each incorporated by reference herein.

A Pseudomonas host cell equivalent to a host cell as listed in Table 4, e.g., DC1032, DC954, or DC454, or any of the host cells or expression strains described herein can be constructed from MB101 using methods described herein and in the published literature. In embodiments, a host cell equivalent to DC1032 or DC954 is used. Host cell DC454 is described by Schneider, et al., 2005, where it is referred to as DC206, and in U.S. Pat. No. 8,569,015, "rPA Optimization," incorporated herein by reference in its entirety. DC206 is the same strain as DC454; it was renamed DC454 after passage three times in animal-free media. DC454 is parental to DC1032 and DC954.

One of ordinary skill in the art will appreciate that in embodiments, a host cell genomic deletion or mutation (e.g., an inactivating or debilitating mutation) can be made by, e.g., allele exchange, using a deletion plasmid carrying regions that flank the gene to be deleted, which does not replicate in *P. fluorescens*. The deletion plasmid can be constructed by PCR amplifying the gene to be deleted, including the upstream and downstream regions of the gene to be deleted. The deletion can be verified by sequencing a PCR product amplified from genomic DNA using analytical primers, observed after separation by electrophoresis in an agarose slab gel, followed by DNA sequencing of the fragment. In embodiments, a gene is inactivated by complete deletion, partial deletion, or mutation, e.g., frameshift, point, or insertion mutation.

In embodiments, a strain used in the context of the present invention has been transformed with an FMO plasmid according to methods known in the art. The genotypes for certain examples of recombinant protein expression strains and corresponding host cells useful for expressing recombinant proteins according to the methods of the invention are set forth in Table 10. In embodiments, a host cell equivalent to any host cell described in Table 4 is transformed with an expression vector as described herein, to obtain an expression strain equivalent to one described herein for expressing a recombinant protein of interest using the methods of the invention. As described, appropriate expression strains can be similarly derived according to methods set forth herein and in the literature.

Expression Systems

An appropriate bacterial expression system useful for producing the recombinant protein of interest according to the present methods can be identified by one of skill in the art based on the teachings herein. In some embodiments, an expression construct comprising a nucleotide sequence encoding a recombinant protein of interest is provided as part of an inducible expression vector. In embodiments, a host cell that has been transformed with the expression vector is cultured, and expression of the recombinant protein of interest from the expression vector is induced. The expression vector can be, for example, a plasmid. In embodiments, the expression vector is a plasmid encoding a recombinant protein coding sequence further comprising a selection marker, and the host cells are grown under selective conditions that allow maintenance of the plasmid. In embodiments, the expression construct is integrated into the host cell genome. In embodiments, the expression construct encodes a recombinant protein of interest fused to a secretory signal that can direct the recombinant protein of interest to the periplasm.

Methods for expressing heterologous proteins, including useful regulatory sequences (e.g., promoters, secretion signals, and ribosome binding sites), in host cells useful in the methods of the present invention, are described in the literature, e.g., in U.S. Pat. No. 7,618,799, "Bacterial leader sequences for increased expression," in U.S. Pat. No. 7,985, 564, "Expression systems with Sec-system secretion," in U.S. Pat. Nos. 9,394,571 and 9,580,719, 9,458,487 and 9,453,251, 8,603,824, 8,530,171, "High level expression of recombinant toxin proteins," U.S. Pat. Nos. 10,118,956, 5,888,808, Bacterial polypeptide expression employing tryptophan promoter-operator," U.S. Pat. No. 9,534,217, "Method of creating a library of bacterial clones with varying levels of gene expression," and Vellanoweth, R. L., and Rabinowitz, J. C., May 1992, "The influence of ribosome-binding-site elements on translational efficiency in *Bacillus subtilis* and *Escherichia coli* in vivo," Molecular Microbiology 6(9):1105-1114, each incorporated herein by reference in its entirety. In embodiments, a secretion leader used in the context of the present invention is a secretion leader as disclosed in any of U.S. Pat. Nos. 7,618,799, 7,985,564, 9,394,571, 9,580,719, 9,453,251, 8,603,824, 8,530,171, and 10,118,956. These patents also describe bacterial host strains useful in practicing the methods herein, that have been engineered to overexpress folding modulators or wherein protease mutations have been introduced, in order to increase heterologous protein expression.

Promoters used in accordance with the present invention may be constitutive promoters or regulated promoters. Examples of inducible promoters include those of the family derived from the lac promoter (i.e. the lacZ promoter), e.g., the tac and trc promoters described in U.S. Pat. No. 4,551, 433, "Microbial Hybrid Promoters," incorporated herein by reference, as well as Ptac16, Ptac17, PtacII, PlacUV5, and the T7lac promoter. In embodiments, the promoter is not derived from the host cell organism. In embodiments, the promoter is derived from an *E. coli* organism. In embodiments, a lac promoter is used to regulate expression of a recombinant protein of interest from a plasmid. In the case of the lac promoter derivatives or family members, e.g., the tac promoter, an inducer is IPTG (isopropyl-β-D-1-thiogalactopyranoside, "isopropylthiogalactoside"). In embodiments, IPTG is added to the host cell culture to induce expression of the recombinant protein of interest from a lac promoter in a *Pseudomonas* host cell according to methods known in the art and described in the literature, e.g., in U.S. Pat. Nos. 9,458,487 and 9,453,251.

Examples of non-lac promoters useful in expression systems according to the present invention include, $P_R$ (induced by high temperature), $P_L$ (induced by high temperature), $P_m$ (induced by Alkyl- or halo-benzoates), $P_u$ (induced by alkyl- or halo-toluenes), or $P_{sal}$ (induced by salicylates), described in, e.g. J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK). A promoter having the nucleotide sequence of a promoter native to the selected bacterial host cell also may be used to control expression of the expression construct encoding the polypeptide of interest, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, derived from the same or different organisms. In embodiments, the promoter is Pmtl, as described in, e.g., U.S. Pat. Nos. 7,476,532, and 8,017,355, both titled "Mannitol induced promoter systems in bacterial host cells," incorporated by reference herein in their entirety.

Regulated (inducible) promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* Lad proteins; and dual-function regulatory proteins, e.g., *E. coli* NagC protein. Many regulated-promoter/promoter-regulatory-protein pairs are known in the art. In some embodiments, a promoter used to transcribe a gene encoding a recombinant protein of interest produced using the present compositions and methods is selected from: a tac promoter, a mannitol promoter, a Pben, a T7 promoter, a lac promoter, a T5 promoter, a xylose promoter, a Trp promoter, and an arabinose promoter. When more than one expression construct is used to produce the recombinant protein of interest, more than one different promoter may be used.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the recombinant protein of interest.

In embodiments wherein a lac family promoter is utilized, a lacI gene can also be present in the system. The lacI gene, which is normally a constitutively expressed gene, encodes the Lac repressor protein LacI protein, which binds to the lac operator of lac family promoters. Thus, where a lac family promoter is utilized, the lacI gene can also be included and expressed in the expression system.

Expression Vectors

At least one nucleic acid sequence encoding a recombinant protein of interest can be introduced into a suitable expression vector(s) to produce either the recombinant protein of interest, an overexpressed protein, e.g., a chaperone, folding modulator, or inactivated protease as described herein, or both the recombinant protein of interest, and the overexpressed protein may be produced using the same expression vector. The expression vector can be a plasmid. An expression vector may be selected for use in the context of the present invention by one of skill in the art as desired and appropriate, from commercially available expression vectors. In some embodiments, a plasmid encoding a recombinant protein of interest can comprise a selection marker, and host cells maintaining the plasmid can be grown under selective conditions. In some embodiments, the plasmid does not comprise a selection marker. In some embodiments, the expression vector is integrated into the host cell genome. In some embodiments, the expression vector encodes a recombinant protein of interest fused to a secretion signal that can direct the expressed recombinant protein of interest to the periplasm. In some embodiments, the expression vector encodes a recombinant protein of interest fused to a secretion signal that can direct the expressed recombinant protein of interest to the cytoplasm. In some embodiments, an expression vector encodes a Fab', e.g., an anti-TNF-alpha Fab', fused to a periplasmic secretion signal that can direct the expressed Fab' to the periplasm.

Recombinant proteins of interest that can be produced using the present compositions and methods are described herein. Amino acid sequences of recombinant proteins of interest, and potential coding sequences, may readily be obtained by those of skill in the art. The amino acid sequences of the heavy and light chains of an anti-TNF-alpha Fab', and examples of nucleotide sequences encoding the Fab', are provided in Table 14, the Table of Sequences, herein.

Other Regulatory Elements

In some embodiments, other regulatory elements are present in the expression construct encoding the recombinant protein of interest. In embodiments, the soluble recombinant protein of interest is present in either the cytoplasm or periplasm of the cell during production. Secretion leaders useful for targeting a recombinant protein of interest to either compartment are described herein. In embodiments, an expression construct of the present invention encodes a recombinant protein of interest fused to a secretion signal that can transport the recombinant protein of interest to the cytoplasm of a *Pseudomonad* cell. In embodiments, an expression construct encodes a recombinant protein of interest fused to a secretion leader that can transport a recombinant protein of interest to the periplasm of a *Pseudomonad* cell. In embodiments, the secretion leader is cleaved from the recombinant protein of interest.

Other elements include, but are not limited to, transcriptional enhancer sequences, translational enhancer sequences, other promoters, activators, translational start and stop signals, transcription terminators, cistronic regulators, polycistronic regulators, tag sequences, such as nucleotide sequence tags and tag polypeptide coding sequences, which facilitate identification, separation, purification, and/or isolation of an expressed polypeptide, as previously described. In some embodiments, the expression construct includes, in addition to the protein coding sequence, any of the following regulatory elements operably linked thereto: a promoter, a ribosome binding site (RBS), a transcription terminator, and translational start and stop signals. Useful RBSs can be obtained from any of the species useful as host cells in expression systems according to, e.g., U.S. Pat. Nos. 10,118,956 and 9,580,719, previously referenced. Many RBSs are known, e.g., those described in and referenced by D. Frishman et al., Gene 234(2):257-65 (8 Jul. 1999); and B. E. Suzek et al., Bioinformatics 17(12):1123-30 (December 2001), incorporated herein by reference. In addition, either native or synthetic RBSs may be used, e.g., those described in: EP 0207459 (synthetic RBSs); O. Ikehata et al., Eur. J. Biochem. 181(3):563-70 (1989). In some embodiments, a "Hi" ribosome binding site, aggagg, (SEQ ID NO: 59) is used in the construct. Ribosome binding sites, including the optimization of spacing between the RBS and translation initiation codon, are described in the literature, e.g., by Chen, et al., 1994, "Determination of the optimal aligned spacing between the Shine-Dalgarno sequence and the translation initiation codon of *Escherichia coli* mRNAs," Nucleic Acids Research 22(23):4953-4957, and Ma, et al., 2002, "Correlations between Shine-Dalgarno Sequences and Gene Features Such as Predicted Expression Levels and Operon Structures," J. Bact. 184(20): 5733-45, incorporated herein by reference.

Further examples of methods, vectors, and translation and transcription elements, and other elements useful in the present invention are well known in the art and described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox, all incorporated herein by reference, as well as in other publications incorporated herein by reference.

Secretion Leader Sequences

In embodiments, a secretion signal or leader coding sequence is fused to the N-terminus of the sequence encoding the recombinant protein of interest. Use of secretion signal sequences can increase production of recombinant proteins in bacteria. Additionally, many types of proteins require secondary modifications that are inefficiently achieved using known methods. Secretion leader utilization can increase the harvest of properly folded proteins by secreting the protein from the intracellular environment. In gram-negative bacteria, a protein secreted from the cytoplasm can end up in the periplasmic space, attached to the outer membrane, or in the extracellular broth. These methods may avoid formation of inclusion bodies. Secretion of proteins into the periplasmic space also has the effect of facilitating proper disulfide bond formation (Bardwell et al., 1994, Phosphate Microorg, Chapter 45, 270-5, and Manoil, 2000, Methods in Enzymol. 326:35-47). Other benefits of secretion of recombinant protein include more efficient isolation of the protein, proper folding and disulfide bond formation of the protein leading to an increase in yield represented by, e.g., the percentage of the protein in active form, reduced formation of inclusion bodies and reduced toxicity to the host cell, and an increased percentage of the recombinant protein in soluble form. The potential for excretion of the protein of interest into the culture medium can also potentially promote continuous, rather than batch, culture for protein production. Secretion signals are described, e.g., in U.S. Pat. No. 7,618,799," U.S. Pat. No. 7,985,564, and U.S. Pat. App. Pub. No. 2019/0127744, "Bacterial leader sequences for periplasmic protein expression," each incorporated herein by reference in its entirety, as well as by U.S. Pat. No. 10,118,956.

In some embodiments, the recombinant protein of interest is targeted to the periplasm of the host cell or into the extracellular space. In some embodiments, the expression vector further comprises a nucleotide sequence encoding a secretion signal polypeptide operably linked to the nucleotide sequence encoding the recombinant protein of interest.

Codon Optimization

The present invention contemplates the use of any appropriate coding sequence for the recombinant protein of interest, including any sequence that has been optimized for expression in the host cell being used. A nucleic acid sequence encoding the recombinant protein of interest may be codon-optimized to improve expression in the recombinant gram-negative bacterial host cell, as understood by one of skill in the art. For example, optimization of codons for expression in a *Pseudomonas* host strain is described, e.g., in U.S. Pat. App. Pub. No. 2007/0292918, "Codon Optimization Method," incorporated herein by reference in its entirety. Codon optimization for expression in *E. coli* is described, e.g., by Welch, et al., 2009, PLoS One, "Design Parameters to Control Synthetic Gene Expression in *Escherichia coli*, 4(9): e7002, incorporated by reference herein. It is understood that any suitable sequence encoding a recombinant protein of interest can be generated as desired according to methods well known by those of skill in the art.

Expression Constructs

An appropriate expression construct for producing a recombinant protein of interest according to the methods of the invention may be selected by one of skill in the art in view of the present disclosure.

In some embodiments, a recombinant protein of interest produced in a recombinant gram-negative host cell of the present invention is encoded by an expression vector comprising at least one expression construct encoding the recombinant protein of interest, wherein the expression construct comprises at least one nucleic acid sequence encoding the recombinant protein of interest. In some embodiments, at least two nucleic acid sequences encoding the recombinant protein of interest are transcribed from the same promoter (co-transcribed). In some embodiments at least two nucleic acid sequences encoding the recombinant protein of interest are transcribed from different promoters (not co-transcribed). When not co-transcribed, each of the least two nucleic acid sequences encoding the at least two nucleic acid sequences encoding the recombinant protein of interest may be produced from the same expression vector or separate expression vectors. In some embodiments, a nucleic acid sequence encoding a recombinant protein of interest is operably linked to a nucleic acid sequence encoding a secretion signal. In some embodiments, each of at least two nucleic acid sequences encoding a recombinant protein of interest is individually operably linked to a nucleic acid sequence encoding the same or different secretion signal. In some embodiments, each nucleic acid sequence encoding a recombinant protein of interest in a host cell is individually operably linked to a nucleic acid sequence independently selected from the periplasmic secretion signals having the amino acid sequence set forth as: SEQ ID NO: 11, 13, 25, or 26.

In some embodiments, a recombinant gram-negative bacterial host cell of the present invention is transformed with expression vector(s) comprising the at least one expression construct encoding the recombinant protein of interest. In some embodiments, the transformed recombinant gram-negative bacterial host cell is deficient in a tail-specific protease activity, and a Mep1 endopeptidase activity. In some embodiments, the transformed recombinant gram-negative bacterial host cell is further: optionally deficient in at least one additional protease activity, optionally deficient in at least one autolytic factor activity, optionally overexpresses one or more inactivated protease, optionally overexpresses one or more chaperone or folding modulator, optionally has a functional MepS1 protease, and optionally has a functional MepS2 protease, each as described elsewhere herein in detail. In some embodiments, the transformed recombinant gram-negative bacterial host cell is selected from: a *Pseudomonad* host cell; an *E. coli* host cell; an *Erwinia* host cell, a *Salmonella* host cell, a *Shigella* host cell, a *Moraxella* host cell, a *Helicobacter* host cell, a *Legionella* host cell, a *Neisseria* host cell, a *Haemophilus* host cell, a *Acinetobacter* host cell, a *Bacteroides* host cell, a *Xylella* host cell, a *Citrobacter* host cell, an *Enterobacter* host cell, a *Klebsiella* host cell, a *Yersinia* host cell, a *Serratia* host cell, a *Proteus* host cell, and a *Vibrio* host cell. In some embodiments, the *Pseudomonad* host cell is a *Pseudomonas* host cell. In some embodiments, the *Pseudomonas* host cell is *P. fluorescens, P. putida*, or *P. aeruginosa*.

In some embodiments, the recombinant gram-negative bacterial host cell transformed with expression vector(s) comprising the at least one expression construct encoding the recombinant protein of interest is: (i) lsc::lacIQ1; (ii) Prc1 deficient; (ii) Prc2 deficient; (iii) HslU deficient; (iv) HslV deficient; (v) MepM1 deficient; and (vi) PyrF deficient; wherein the host cell is optionally deficient in a serralysin precursor that is: a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9; optionally overexpresses a DsbC; optionally overexpresses an inactivated DegP2; and optionally overexpresses a PDIA6.

In some embodiments, a recombinant protein or polypeptide of interest is produced in a recombinant gram-negative bacterial host cell that is any one of strains STR92557, STR87639, STR92567, STR94974, STR94975, STR94976, and STR94977. In some embodiments, the recombinant protein or polypeptide of interest is produced in a recombinant gram-negative bacterial host cell that has the genotype (genomic modifications) of, and/or has the protease deficiency, inactivated protease, and folding modulator overexpression profile of, any one of strains STR92557, STR87639, STR92567, STR94974, STR94975, STR94976, and STR94977. In some embodiments, the recombinant protein or polypeptide of interest is produced in a recombinant gram-negative bacterial host cell that has the genotype of, and/or has the protease deficiency, inactivated protease, and folding modulator overexpression profile of, STR94975, STR94976, or STR94977.

In some embodiments, an antibody to be produced in a recombinant gram-negative host cell of the present invention is encoded by an expression vector comprising at least one expression construct encoding the antibody, wherein the expression construct comprises at least two nucleic acid sequences encoding a heavy chain and at least two nucleic acid sequences encoding a light chain. In some embodiments two or more of the at least two nucleic acid sequences encoding the heavy chain and the at least two nucleic acid sequence encoding the light chain are transcribed from the same promoter (co-transcribed). In some embodiments the at least two nucleic acid sequences encoding a heavy chain and the at least two nucleic acid sequences encoding the light chain are transcribed from different promoters (not co-transcribed). When not co-transcribed, each of the at least two nucleic acid sequence encoding the antibody heavy chain and the at least two nucleic acid sequences encoding the antibody light chain may be produced from the same expression vector or multiple expression vectors. In some embodiments, each heavy chain encoding nucleic acid sequence and each light chain encoding nucleic acid sequence is individually operably linked to a nucleic acid sequence encoding a periplasmic secretion signal, resulting in a secretion signal-heavy chain fusion and a secretion signal-light chain fusion. In some embodiments, each heavy chain encoding nucleic acid sequence is operably linked to a nucleic acid sequence encoding a periplasmic secretion signal having the amino acid sequence set forth as SEQ ID NO: 11. In some embodiments, each light chain encoding nucleic acid sequence is operably linked to a nucleic acid sequence encoding a periplasmic secretion signal having the amino acid sequence set forth as SEQ ID NO: 13.

In some embodiments, a recombinant gram-negative bacterial host cell of the present invention is transformed with expression vector(s) comprising the at least one expression construct encoding the antibody. In some embodiments, the transformed recombinant gram-negative bacterial host cell is deficient in a tail-specific protease activity, and a Mep1 endopeptidase activity. In some embodiments, the transformed recombinant gram-negative bacterial host cell is further: optionally deficient in at least one additional protease activity, optionally deficient in at least one autolytic factor activity, optionally overexpresses one or more inactivated protease, optionally overexpresses one or more chaperone or folding modulator, optionally has a functional MepS1 protease, and optionally has a functional MepS2 protease, each as described elsewhere herein in detail. In some embodiments, the transformed recombinant gram-negative bacterial host cell is selected from: a *Pseudomonad* host cell; an *E. coli* host cell; an *Erwinia* host cell, a *Salmonella* host cell, a *Shigella* host cell, a *Moraxella* host cell, a *Helicobacter* host cell, a *Legionella* host cell, a *Neisseria* host cell, a *Haemophilus* host cell, a *Acinetobacter* host cell, a *Bacteroides* host cell, a *Xylella* host cell, a *Citrobacter* host cell, an *Enterobacter* host cell, a *Klebsiella* host cell, a *Yersinia* host cell, a *Serratia* host cell, a *Proteus* host cell, and a *Vibrio* host cell. In some embodiments, the *Pseudomonad* host cell is a *Pseudomonas* host cell. In some embodiments, the *Pseudomonas* host cell is *P. fluorescens, P. putida*, or *P. aeruginosa*. In some embodiments, the transformed recombinant gram-negative bacterial host cell is not an *E. coli* host cell.

In some embodiments, the recombinant gram-negative bacterial host cell transformed with expression vector(s) comprising the at least one expression construct encoding the antibody is: (i) lsc::lacIQ1; (ii) Prc1 deficient; (ii) Prc2 deficient; (iii) HslU deficient; (iv) HslV deficient; (v) MepM1 deficient; (vi) PyrF deficient; wherein the host cell is optionally deficient in a serralysin precursor that is: a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9; optionally overexpresses a DsbC; optionally overexpresses an inactivated DegP2; and optionally overexpresses a PDIA6.

In some embodiments, an antibody is produced in a recombinant gram-negative bacterial host cell that is any one of strains STR92557, STR87639, STR92567, STR94974, STR94975, STR94976, and STR94977. In some embodiments, the antibody is produced in a recombinant gram-negative bacterial host cell that has the genotype of, and/or has the protease deficiency, inactivated protease, and folding modulator overexpression profile of, any one of strains STR92557, STR87639, STR92567, STR94974, STR94975, STR94976, and STR94977. In some embodiments, the antibody is produced in a recombinant gram-negative bacterial host cell that has the genotype of, and/or has the protease deficiency, inactivated protease, and folding modulator overexpression profile of, STR94975, STR94976, and STR94977.

In some embodiments, a Fab or Fab', e.g., a human TNF-alpha Fab', to be produced in a recombinant gram-negative host cell of the present invention is encoded by an expression vector comprising at least one expression construct encoding the Fab or Fab', wherein the expression construct comprises at least one nucleic acid sequence encoding a heavy chain and at least one nucleic acid sequence encoding a light chain. In some embodiments, the heavy chain has the amino acid sequence set forth as SEQ ID NO: 21, and the light chain has the amino acid sequence set forth as SEQ ID NO: 23. In some embodiments the at least one nucleic acid sequence encoding a heavy chain and the at least one nucleic acid sequence encoding a light chain are transcribed from the same promoter (co-transcribed). In some embodiments the at least one nucleic acid sequence encoding a heavy chain and the at least one nucleic acid sequence encoding a light chain are transcribed from different promoters (not co-transcribed). When not co-transcribed, the at least one nucleic acid sequence encoding the Fab or Fab' heavy chain and the at least one nucleic acid sequence encoding the Fab or Fab' light chain may be produced from the same expression vector or separate expression vectors. In some embodiments, each heavy chain encoding nucleic acid sequence and each light chain encoding nucleic acid sequence is individually operably linked to a nucleic acid sequence encoding a periplasmic secretion signal, resulting in a secretion signal-heavy chain fusion and a secretion signal-light chain fusion. In some embodiments, each Fab or Fab' heavy chain encoding nucleic acid sequence is operably linked to a nucleic acid sequence encoding a periplasmic secretion signal having the amino acid sequence set forth as SEQ ID NO: 11. In some embodiments, each Fab or Fb' light chain encoding nucleic acid sequence is operably linked to a nucleic acid sequence encoding a periplasmic secretion signal having the amino acid sequence set forth as SEQ ID NO: 13. In some embodiments, a human TNF-alpha Fab' secretion signal-heavy chain fusion has the amino acid sequence set forth as SEQ ID NO: 25, and a human TNF-alpha Fab' secretion signal-light chain fusion has the amino acid sequence set forth as SEQ ID NO: 26.

In some embodiments, the recombinant protein or polypeptide of interest is produced in a recombinant gram-negative bacterial host cell that has the following genotype: Δprc1, Δprc2, ΔhslU, ΔhslV, ΔmepM1, ΔRXF04495.2, ΔpyrF, and lsc::lacI$^{Q1}$ In some embodiments, the recombinant protein or polypeptide of interest is an anti-TNF-alpha Fab', and the host cell further comprises a plasmid comprising expression constructs selected from:

a) a nucleic acid sequence encoding an anti-TNF-alpha Fab' heavy chain (HC) having the amino acid sequence set forth as SEQ ID NO: 21, a nucleic acid sequence encoding an anti-TNF-alpha Fab' light chain (LC) having the amino acid sequence set forth as SEQ ID NO: 23, wherein the anti-TNF-alpha Fab' HC and the anti-TNF-alpha Fab' LC are co-transcribed, and a nucleic acid sequence encoding PyrF;

b) a nucleic acid sequence encoding an anti-TNF-alpha Fab' HC having the amino acid sequence set forth as SEQ ID NO: 21, a nucleic acid sequence encoding an anti-TNF-alpha Fab' LC having the amino acid sequence set forth as SEQ ID NO: 23, wherein the anti-TNF-alpha Fab' HC and the anti-TNF-alpha Fab' LC are co-transcribed, a nucleic acid sequence encoding DegP2 S219A having the amino acid sequence set forth as SEQ ID NO: 29, and a nucleic acid sequence encoding PyrF;

c) a nucleic acid sequence encoding an anti-TNF-alpha Fab' HC having the amino acid sequence set forth as SEQ ID NO: 21, a nucleic acid sequence encoding an anti-TNF-alpha Fab' LC having the amino acid sequence set forth as SEQ ID NO: 23, and a nucleic acid sequence encoding DegP2 S219A having the amino acid sequence set forth as SEQ ID NO: 29, wherein the anti-TNF-alpha Fab' HC, the anti-TNF-alpha Fab' LC, and DegP2 S219A are co-transcribed, and a nucleic acid sequence encoding PyrF; and d) a nucleic acid sequence encoding an anti-TNF-alpha Fab' HC having the amino acid sequence set forth as SEQ ID NO: 21, a nucleic acid sequence encoding an anti-TNF-alpha Fab' LC having the amino acid sequence set forth as SEQ ID NO: 23, and a nucleic acid sequence encoding PDIA6 having the amino acid sequence set forth as SEQ ID NO: 27, wherein the anti-TNF-alpha Fab' HC, the anti-TNF-alpha Fab' LC, and PDIA6 are co-transcribed, and a nucleic acid sequence encoding PyrF.

In some embodiments, the recombinant protein or polypeptide of interest is an anti-TNF-alpha Fab', and the host cell further comprises a plasmid comprising expression constructs selected from:

a) a nucleic acid sequence encoding a secretion leader-anti-TNF-alpha Fab' heavy chain (HC) fusion having the amino acid sequence set forth as SEQ ID NO: 25, a nucleic acid sequence encoding a secretion leader-anti-TNF-alpha Fab' light chain (LC) fusion having the amino acid sequence set forth as SEQ ID NO: 26, wherein the secretion leader-anti-TNF-alpha Fab' HC fusion and the secretion leader-anti-TNF-alpha Fab' LC fusion are co-transcribed, and a nucleic acid sequence encoding PyrF;

b) a nucleic acid sequence encoding a secretion leader-anti-TNF-alpha Fab' HC fusion having the amino acid sequence set forth as SEQ ID NO: 25, a nucleic acid sequence encoding a secretion leader-anti-TNF-alpha Fab' LC fusion having the amino acid sequence set forth as SEQ ID NO: 26, wherein the secretion leader-anti-TNF-alpha Fab' HC fusion and the secretion leader-anti-TNF-alpha Fab' LC fusion are co-transcribed, a nucleic acid sequence encoding DegP2 S219A having the amino acid sequence set forth as SEQ ID NO: 29, and a nucleic acid sequence encoding PyrF;

c) a nucleic acid sequence encoding a secretion leader-anti-TNF-alpha Fab' HC fusion having the amino acid sequence set forth as SEQ ID NO: 25, a nucleic acid sequence encoding a secretion leader-anti-TNF-alpha Fab' LC fusion having the amino acid sequence set forth as SEQ ID NO: 26, and a nucleic acid sequence encoding DegP2 S219A having the amino acid sequence set forth as SEQ ID NO: 29, wherein the secretion leader-anti-TNF-alpha Fab' HC fusion, the secretion leader-anti-TNF-alpha Fab' LC fusion, and DegP2 S219A are co-transcribed, and a nucleic acid sequence encoding PyrF; and d) a nucleic acid sequence encoding a secretion leader-anti-TNF-alpha Fab' HC fusion having the amino acid sequence set forth as SEQ ID NO: 25, a nucleic acid sequence encoding a secretion leader-anti-TNF-alpha Fab' LC fusion having the amino acid sequence set forth as SEQ ID NO: 26, and a nucleic acid sequence encoding PDIA6 having the amino acid sequence set forth as SEQ ID NO: 27, wherein the secretion leader-anti-TNF-alpha Fab' HC fusion, the secretion leader-anti-TNF-alpha Fab' LC fusion, and PDIA6 are co-transcribed, and a nucleic acid sequence encoding PyrF.

In some embodiments, a recombinant gram-negative bacterial host cell of the present invention is transformed with expression vector(s) comprising the at least one expression construct encoding the Fab or Fab'. In some embodiments, the transformed recombinant gram-negative bacterial host cell is deficient in a tail-specific protease activity, and a Mep1 endopeptidase activity. In some embodiments, the transformed recombinant gram-negative bacterial host cell is further: optionally deficient in at least one additional protease activity, optionally deficient in at least one autolytic factor activity, optionally overexpresses one or more inactivated protease, optionally overexpresses one or more chaperone or folding modulator, optionally has a functional MepS1 protease, and optionally has a functional MepS2 protease, each as described elsewhere herein in detail. In some embodiments, the transformed recombinant gram-negative bacterial host cell is selected from: a *Pseudomonad* host cell; an *E. coli* host cell; an *Erwinia* host cell, a *Salmonella* host cell, a *Shigella* host cell, a *Moraxella* host cell, a *Helicobacter* host cell, a *Legionella* host cell, a *Neisseria* host cell, a *Haemophilus* host cell, a *Acinetobacter* host cell, a *Bacteroides* host cell, a *Xylella* host cell, a *Citrobacter* host cell, an *Enterobacter* host cell, a *Klebsiella* host cell, a *Yersinia* host cell, a *Serratia* host cell, a *Proteus* host cell, and a *Vibrio* host cell. In some embodiments, the

*Pseudomonad* host cell is a *Pseudomonas* host cell. In some embodiments, the *Pseudomonas* host cell is *P. fluorescens, P. putida*, or *P. aeruginosa*. In some embodiments, the transformed recombinant gram-negative bacterial host cell is not an *E. coli* host cell.

In some embodiments, the recombinant gram-negative bacterial host cell transformed with expression vector(s) comprising the at least one expression construct encoding the Fab or Fab', e.g., an anti-TNF Fab', is: (i) lsc::lacIQ1; (ii) Prc1 deficient; (ii) Prc2 deficient; (iii) HslU deficient; (iv) HslV deficient; (v) MepM1 deficient; (vi) PyrF deficient; wherein the host cell is optionally deficient in a serralysin precursor that is: a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9; optionally overexpresses a DsbC; optionally overexpresses an inactivated DegP2; and optionally overexpresses a PDIA6.

In some embodiments, the recombinant gram-negative bacterial host cell is any one of strains STR92557, STR87639, STR92567, STR94974, STR94975, STR94976, and STR94977. In some embodiments, the recombinant gram-negative bacterial host cell that the genotype (genomic modifications) of, and/or has the protease deficiency, inactivated protease, and folding modulator overexpression profile of, any one of strains STR92557, STR87639, STR92567, STR94974, STR94975, STR94976, and STR94977. In some embodiments, the recombinant gram-negative bacterial host cell that has the genotype of, and/or has the protease deficiency, inactivated protease, and folding modulator overexpression profile of, STR94975, STR94976, or STR94977.

In some embodiments, the recombinant gram-negative bacterial host cell has a genotype of, has the protease deficiency, inactivated protease, and folding modulator overexpression profile of, and comprises the at least one expression construct encoding an anti-TNF Fab' of expression strain STR92557, STR87639, STR92567, STR94974, STR94975, STR94976, or STR94977. In some embodiments, the recombinant gram-negative bacterial host cell has a genotype of, has the protease deficiency, inactivated protease, and folding modulator overexpression profile of, and comprises the at least one expression construct encoding an anti-TNF Fab' of expression strain STR94975, STR94976, or STR94977.

In some embodiments, a recombinant protein of interest, an antibody, a Fab or Fab', or an anti-TNF Fab' is produced according to the methods described herein, in a recombinant gram-negative bacterial host cell that has a genotype of, and/or has the protease deficiency, inactivated protease, and folding modulator overexpression profile of, expression strain STR92557, STR87639, STR92567, STR94974, STR94975, STR94976, or STR94977. In some embodiments, an anti-TNF Fab' is produced according to methods described herein, in a recombinant gram-negative bacterial host cell that has a genotype of, and has the protease deficiency, inactivated protease, and folding modulator overexpression profile of expression strain STR94975, STR94976, or STR94977, and comprises the at least one expression construct encoding the anti-TNF Fab', e.g., an anti-TNF Fab' having the heavy chain sequence as set forth in SEQ ID NO: 25 and the light chain sequence as set forth in SEQ ID NO: 26. In some embodiments, the Fab' expression construct is that of an expression strain selected from:

STR92557, STR87639, STR92567, STR94974, STR94975, STR94976, and STR94977. In some embodiments, the anti-TNF Fab' produced from a host strain of the present invention is produced in soluble, active, and/or intact form at a titer of about 0.2 to about 5 g/L.

Fermentation Format

A recombinant protein of interest may be produced using the methods as described herein, by culturing the recombinant gram-negative bacterial host cells transformed with a plasmid encoding the recombinant protein of interest (an expression strain) under suitable fermentation conditions. Any fermentation format, e.g., a batch, fed-batch, semi-continuous, or continuous fermentation mode, may be employed.

The fermentation medium may be selected from rich media, minimal media, and mineral salts media. In some embodiments, a minimal medium or a mineral salts medium is selected. In some embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, Davis, B. D., and Mingioli, E. S., 1950, J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels. Suitable media for use in the methods of the present invention can be prepared using methods described in the literature, e.g., in U.S. Pat. Nos. 9,458,487 and 9,453,251. Details of cultivation procedures and mineral salts media useful in the methods of the present invention are described by Riesenberg, D et al., 1991, "High cell density cultivation of *Escherichia coli* at controlled specific growth rate," J. Biotechnol. 20 (1):17-27, incorporated by reference herein.

In embodiments, production can be achieved in bioreactor cultures. Cultures can be grown in, e.g., up to 2 L bioreactors containing a mineral salts medium, and maintained at 32° C. and pH 6.5 through the addition of ammonia. Dissolved oxygen can be maintained in excess through increases in agitation and flow of sparged air and oxygen into the fermentor. Glycerol can be delivered to the culture throughout the fermentation to maintain excess levels. In embodiments, these conditions are maintained until a target culture cell density, e.g., an optical density of 575 nm (A575), for induction is reached and IPTG is added to initiate the target protein production. It is understood that the cell density at induction, the concentration of IPTG, pH, temperature, $CaCl_2$ concentration, dissolved oxygen flow rate, each can be varied to determine optimal conditions for expression. In embodiments, cell density at induction can be varied from A575 of 40 to 200 absorbance units (AU). IPTG concentrations can be varied in the range from 0.02 to 1.0 mM, pH from 5 to 7.5, temperature from 20 to 35° C., $CaCl_2$ concentration from 0 to 0.5 g/L, and the dissolved oxygen flow rate from 1 LPM (liters per minute) to 10 LPM. After 6-96 hours, the culture from each bioreactor can be harvested by centrifugation and the cell pellet frozen at −80° C. Samples can then be analyzed, e.g., by SDS-CGE, for product formation.

Fermentation may be performed at any scale. The expression systems according to the present invention are useful for recombinant protein expression at any scale. Thus, e.g., microliter-scale, milliliter scale, centiliter scale, and deciliter scale fermentation volumes may be used, and 1 Liter scale and larger fermentation volumes can be used.

In embodiments, the fermentation volume is at or above about 1 Liter. In embodiments, the fermentation volume is about 1 Liter to about 100 Liters. In embodiments, the fermentation volume is about 1 Liter, about 2 Liters, about 3 Liters about 4 Liters, about 5 Liters, about 6 Liters, about 7 Liters, about 8 Liters, about 9 Liters, or about 10 Liters. In embodiments, the fermentation volume is about 1 Liter to about 5 Liters, about 1 Liter to about 10 Liters, about 1 Liter to about 25 Liters, about 1 Liter to about 50 Liters, about 1 Liter to about 75 Liters, about 10 Liters to about 25 Liters, about 25 Liters to about 50 Liters, or about 50 Liters to about 100 Liters. In other embodiments, the fermentation volume is at or above 5 Liters, 10 Liters, 15 Liters, 20 Liters, 25 Liters, 50 Liters, 75 Liters, 100 Liters, 200 Liters, 250 Liters, 300 Liters, 500 Liters, 1,000 Liters, 2,000 Liters, 5,000 Liters, 10,000 Liters, or 50,000 Liters.

In general, the amount of a recombinant protein yielded by a larger culture volume, e.g., a 50 mL shake-flask culture, a 1 liter culture, or greater, is increased relative to that observed in a smaller culture volume, e.g, a 0.5 mL high-throughput screening culture. This can be due to not only the increase in culture size but, e.g., the ability to grow cells to a higher density in large-scale fermentation (e.g., as reflected by culture absorbance). For example, the volumetric yield from the same strain can increase up to ten-fold from HTP scale to large-scale fermentation. In embodiments, the volumetric yield observed for the same expression strain is 2-fold to 10-fold greater following large-scale fermentation than HTP scale growth. In embodiments, the yield observed for the same expression strain is 2-fold, 3-fold, 4-fold, 5-fold, 6-fold, 7-fold, 8-fold, 9-fold, 2-fold to 10-fold, 2-fold to 9-fold, 2-fold to 8-fold, 2-fold to 7-fold, 2-fold to 6-fold, 2-fold to 5-fold, 2-fold to 4-fold, 2-fold to 3-fold, 3-fold to 10-fold, 3-fold to 9-fold, 3-fold to 8-fold, 3-fold to 7-fold, 3-fold to 6-fold, 3-fold to 5-fold, 3-fold to 4-fold, 4-fold to 10-fold, 4-fold to 9-fold, 4-fold to 8-fold, 4-fold to 7-fold, 4-fold to 6-fold, 4-fold to 5-fold, 5-fold to 10-fold, 5-fold to 9-fold, 5-fold to 8-fold, 5-fold to 7-fold, 5-fold to 6-fold, 6-fold to 10-fold, 6-fold to 9-fold, 6-fold to 8-fold, 6-fold to 7-fold, 7-fold to 10-fold, 7-fold to 9-fold, 7-fold to 8-fold, 8-fold to 10-fold, 8-fold to 9-fold, 9-fold to 10-fold, greater following large-scale fermentation than following HTP-scale growth. See, e.g., Retallack, et al., 2012, "Reliable protein production in a *Pseudomonas fluorescens* expression system," Prot. Exp. and Purif. 81:157-165, incorporated herein by reference in its entirety.

Bacterial Growth Conditions

Suitable fermentation conditions useful in the methods of the provided invention can comprise growth at a temperature of about 4 deg C. to about 42 deg C. and a pH of about 5.7 to about 8.8. When an expression construct with a lacZ promoter is used, expression can be induced by adding IPTG to a culture at a final concentration of about 0.01 mM to about 1.0 mM. In some embodiments, the fermentation conditions comprise induction of the inducible promoter at:

an OD575 of about 40 to about 200, a culture pH of about 5.5 to about 7.2, and a temperature of about 20 to about 34 deg C., fed batch. In some embodiments, the fermentation conditions comprise induction of the inducible promoter at: an OD575 of about 80 to about 160, a culture pH of about 5.8 to about 7.0, a temperature of about 28 to about 33 deg C., fed batch. In some embodiments, the resulting recombinant protein titer is about 0.2 to about 5 g/L of cell culture.

The pH of the culture can be maintained using pH buffers and methods known to those of skill in the art. Control of pH during culturing also can be achieved using aqueous ammonia. In embodiments, the pH of the culture during growth, induction, and/or production phase is about 5 to about 8.8. In embodiments, the culture pH is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, or any range therein. In embodiments, the culture pH is about 5 to about 8.8. In embodiments, the culture pH is about 5 to about 5.5, about 5 to about 6, about 5 to about 6.5, about 5 to about 7, about 5 to about 7.5, about 5 to about 8, about 5 to about 8.5, about 5 to about 8.8, about 5.5 to about 6, about 5.5 to about 6.5, about 5.5 to about 7, about 5.5 to about 7.5, about 5.5 to about 8, about 5.5 to about 8.5, about 5.5 to about 8.8, about 6 to about 6.5, about 6 to about 7, about 6 to about 7.5, about 6 to about 8, about 6 to about 8.5, about 6 to about 8.8, about 6.5 to about 7, about 6.5 to about 7.5, about 6.5 to about 8, about 6.5 to about 8.5, about 6.5 to about 8.8, about 7 to about 7.5, about 7 to about 8, about 7 to about 8.5, about 7 to about 8.8, about 7.5 to about 8, about 7.5 to about 8.5, about 7.5 to about 8.8, about 8 to about 8.5, about 8 to about 8.8, or about 8.5 to about 8.8. In embodiments, the culture pH is about 5, about 5.5, about 6, about 6.5, about 7, about 7.5, about 8, about 8.5, or about 8.8. In embodiments, the culture pH is at least about 5, about 5.5, about 6, about 6.5, about 7, about 7.5, about 8, or about 8.5. In embodiments, the culture pH is at most about 5.5, about 6, about 6.5, about 7, about 7.5, about 8, about 8.5, or about 8.8. In embodiments, the culture pH is about 5.8 to about 7. In embodiments, the culture pH is about 5.8 to about 5.9, about 5.8 to about 6, about 5.8 to about 6.1, about 5.8 to about 6.2, about 5.8 to about 6.2, about 5.8 to about 6.4, about 5.8 to about 6.5, about 5.8 to about 6.6, about 5.8 to about 6.7, about 5.8 to about 6.8, about 5.8 to about 7, about 5.9 to about 6, about 5.9 to about 6.1, about 5.9 to about 6.2, about 5.9 to about 6.2, about 5.9 to about 6.4, about 5.9 to about 6.5, about 5.9 to about 6.6, about 5.9 to about 6.7, about 5.9 to about 6.8, about 5.9 to about 7, about 6 to about 6.1, about 6 to about 6.2, about 6 to about 6.2, about 6 to about 6.4, about 6 to about 6.5, about 6 to about 6.6, about 6 to about 6.7, about 6 to about 6.8, about 6 to about 7, about 6.1 to about 6.2, about 6.1 to about 6.2, about 6.1 to about 6.4, about 6.1 to about 6.5, about 6.1 to about 6.6, about 6.1 to about 6.7, about 6.1 to about 6.8, about 6.1 to about 7, about 6.2 to about 6.2, about 6.2 to about 6.4, about 6.2 to about 6.5, about 6.2 to about 6.6, about 6.2 to about 6.7, about 6.2 to about 6.8, about 6.2 to about 7, about 6.2 to about 6.4, about 6.2 to about 6.5, about 6.2 to about 6.6, about 6.2 to about 6.7, about 6.2 to about 6.8, about 6.2 to about 7, about 6.4 to about 6.5, about 6.4 to about 6.6, about 6.4 to about 6.7, about 6.4 to about 6.8, about 6.4 to about 7, about 6.5 to about 6.6, about 6.5 to about 6.7, about 6.5 to about 6.8, about 6.5 to about 7, about 6.6 to about 6.7, about 6.6 to about 6.8, about 6.6 to about 7, about 6.7 to about 6.8, about 6.7 to about 7, or about 6.8 to about 7. In embodiments, the culture pH is about 5.8, about 5.9, about 6, about 6.1, about 6.2, about 6.2, about 6.4, about 6.5, about 6.6, about 6.7, about 6.8, or about 7. In embodiments, the culture pH is at least about 5.8, about 5.9, about 6, about 6.1, about 6.2, about 6.2, about 6.4, about 6.5, about 6.6, about 6.7, or about 6.8. In embodiments, the culture pH is at most about 5.9, about 6, about 6.1, about 6.2, about 6.2, about 6.4, about 6.5, about 6.6, about 6.7, about 6.8, or about 7. In some embodiments, the pH is about 6 to about 6.5. In some embodiments, the culture pH is about 6 to about 6.1, about 6 to about 6.2, about 6 to about 6.3, about 6 to about 6.4, about 6 to about 6.5, about 6.1 to about 6.2, about 6.1 to about 6.3, about 6.1 to about 6.4, about 6.1 to about 6.5, about 6.2 to about 6.3, about 6.2 to about 6.4, about 6.2 to about 6.5, about 6.3 to about 6.4, about 6.3 to about 6.5, or about 6.4 to about 6.5. In some embodiments, the culture pH is about 6, about 6.1, about 6.2, about 6.3, about 6.4, or about 6.5. In some embodiments, the culture pH is at least about 6, about 6.1, about 6.2, about 6.3, or about 6.4. In some embodiments, the culture pH is at most about 6.1, about 6.2, about 6.3, about 6.4, or about 6.5.

In embodiments, the growth temperature of the culture during growth, induction, and/or production phase is maintained at about 4° C. to about 42° C. In embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., or any range therein. In embodiments, the growth temperature is about 25° C. to about 35° C. In embodiments, the growth temperature is about 25° C. to about 35° C. In embodiments, the growth temperature is about 25° C. to about 26° C., about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 25° C. to about 34° C., about 25° C. to about 35° C., about 26° C. to about 27° C., about 26° C. to about 28° C., about 26° C. to about 29° C., about 26° C. to about 30° C., about 26° C. to about 31° C., about 26° C. to about 32° C., about 26° C. to about 33° C., about 26° C. to about 34° C., about 26° C. to about 35° C., about 27° C. to about 28° C., about 27° C. to about 29° C., about 27° C. to about 30° C., about 27° C. to about 31° C., about 27° C. to about 32° C., about 27° C. to about 33° C., about 27° C. to about 34° C., about 27° C. to about 35° C., about 28° C. to about 29° C., about 28° C. to about 30° C., about 28° C. to about 31° C., about 28° C. to about 32° C., about 28° C. to about 33° C., about 28° C. to about 34° C., about 28° C. to about 35° C., about 29° C. to about 30° C., about 29° C. to about 31° C., about 29° C. to about 32° C., about 29° C. to about 33° C., about 29° C. to about 34° C., about 29° C. to about 35° C., about 30° C. to about 31° C., about 30° C. to about 32° C., about 30° C. to about 33° C., about 30° C. to about 34° C., about 30° C. to about 35° C., about 31° C. to about 32° C., about 31° C. to about 33° C., about 31° C. to about 34° C., about 31° C. to about 35° C., about 32° C. to about 33° C., about 32° C. to about 34° C., about 32° C. to about 35° C., about 33° C. to about 34° C., about 33° C. to about 35° C., or about 34° C. to about 35° C. In embodiments, the growth temperature is about 25° C., about 26° C., about 27° C., about 28° C., about 29° C., about 30° C., about 31° C., about 32° C., about 33° C., about 34° C., or about 35° C. In embodiments, the growth temperature is at least about 25°

C., about 26° C., about 27° C., about 28° C., about 29° C., about 30° C., about 31° C., about 32° C., about 33° C., or about 34° C. In embodiments, the growth temperature is at most about 26° C., about 27° C., about 28° C., about 29° C., about 30° C., about 31° C., about 32° C., about 33° C., about 34° C., or about 35° C.

In embodiments, the temperature is changed during culturing. In embodiments, the temperature is maintained at about 30° C. to about 32° C. before an agent, e.g., IPTG, is added to the culture to induce expression from the construct, and after adding the induction agent, the temperature is reduced to about 25° C. to about 28° C. In embodiments, the temperature is maintained at about 30° C. before an agent, e.g., IPTG, is added to the culture to induce expression from the construct, and after adding the induction agent, the temperature is reduced to about 25° C.

As described elsewhere herein, inducible promoters can be used in the expression construct to control expression of the recombinant protein of interest, e.g., a lac promoter. In the case of the lac promoter derivatives or family members, e.g., the tac promoter, the effector compound is an inducer, such as a gratuitous inducer like IPTG. In embodiments, a lac promoter derivative is used, and recombinant protein expression is induced by the addition of IPTG to a final concentration of about 0.01 mM to about 1.0 mM, when the cell density has reached a level identified by an $OD_{575}$ of about 80 to about 300. In some embodiments, the OD575 at the time of culture induction for the recombinant protein is about 80 to about 300. In some embodiments, the OD575 at the time of culture induction for the recombinant protein is about 80 to about 100, about 80 to about 120, about 80 to about 140, about 80 to about 160, about 80 to about 180, about 80 to about 200, about 80 to about 220, about 80 to about 240, about 80 to about 260, about 80 to about 280, about 80 to about 300, about 100 to about 120, about 100 to about 140, about 100 to about 160, about 100 to about 180, about 100 to about 200, about 100 to about 220, about 100 to about 240, about 100 to about 260, about 100 to about 280, about 100 to about 300, about 120 to about 140, about 120 to about 160, about 120 to about 180, about 120 to about 200, about 120 to about 220, about 120 to about 240, about 120 to about 260, about 120 to about 280, about 120 to about 300, about 140 to about 160, about 140 to about 180, about 140 to about 200, about 140 to about 220, about 140 to about 240, about 140 to about 260, about 140 to about 280, about 140 to about 300, about 160 to about 180, about 160 to about 200, about 160 to about 220, about 160 to about 240, about 160 to about 260, about 160 to about 280, about 160 to about 300, about 180 to about 200, about 180 to about 220, about 180 to about 240, about 180 to about 260, about 180 to about 280, about 180 to about 300, about 200 to about 220, about 200 to about 240, about 200 to about 260, about 200 to about 280, about 200 to about 300, about 220 to about 240, about 220 to about 260, about 220 to about 280, about 220 to about 300, about 240 to about 260, about 240 to about 280, about 240 to about 300, about 260 to about 280, about 260 to about 300, or about 280 to about 300. In some embodiments, the OD575 at the time of culture induction for the recombinant protein is about 80, about 100, about 120, about 140, about 160, about 180, about 200, about 220, about 240, about 260, about 280, or about 300. In some embodiments, the OD575 at the time of culture induction for the recombinant protein is at least about 80, about 100, about 120, about 140, about 160, about 180, about 200, about 220, about 240, about 260, or about 280. In some embodiments, the OD575 at the time of culture induction for the recombinant protein is at most about 100, about 120, about 140, about 160, about 180, about 200, about 220, about 240, about 260, about 280, or about 300. In some embodiments, the induction $OD_{575}$ is about 80-160. In some embodiments, the OD575 at the time of culture induction for the recombinant protein is about 80 to about 160. In some embodiments, the OD575 at the time of culture induction for the recombinant protein is about 80 to about 90, about 80 to about 100, about 80 to about 110, about 80 to about 120, about 80 to about 130, about 80 to about 140, about 80 to about 150, about 80 to about 160, about 90 to about 100, about 90 to about 110, about 90 to about 120, about 90 to about 130, about 90 to about 140, about 90 to about 150, about 90 to about 160, about 100 to about 110, about 100 to about 120, about 100 to about 130, about 100 to about 140, about 100 to about 150, about 100 to about 160, about 110 to about 120, about 110 to about 130, about 110 to about 140, about 110 to about 150, about 110 to about 160, about 120 to about 130, about 120 to about 140, about 120 to about 150, about 120 to about 160, about 130 to about 140, about 130 to about 150, about 130 to about 160, about 140 to about 150, about 140 to about 160, or about 150 to about 160. In some embodiments, the OD575 at the time of culture induction for the recombinant protein is about 80, about 90, about 100, about 110, about 120, about 130, about 140, about 150, or about 160. In some embodiments, the OD575 at the time of culture induction for the recombinant protein is at least about 80, about 90, about 100, about 110, about 120, about 130, about 140, or about 150. In some embodiments, the OD575 at the time of culture induction for the recombinant protein is at most about 90, about 100, about 110, about 120, about 130, about 140, about 150, or about 160.

The cell density can be measured by other methods and expressed in other units, e.g., in cells per unit volume. For example, an $OD_{575}$ of about 40 to about 160 of a P. fluorescens culture is equivalent to approximately $4\times10^{10}$ to about $1.6\times10^{11}$ colony forming units per mL or 17.5 to 70 g/L dry cell weight. In embodiments, the cell density at the time of culture induction is equivalent to the cell density as specified herein by the absorbance at OD575, regardless of the method used for determining cell density or the units of measurement. One of skill in the art will know how to make the appropriate conversion for any cell culture.

In some embodiments, the final IPTG concentration of the culture is about 0.01 mM to about 1 mM. In some embodiments, the final IPTG concentration of the culture is about 0.01 mM to about 0.02 mM, about 0.01 mM to about 0.03 mM, about 0.01 mM to about 0.05 mM, about 0.01 mM to about 0.06 mM, about 0.01 mM to about 0.07 mM, about 0.01 mM to about 0.08 mM, about 0.01 mM to about 0.09 mM, about 0.01 mM to about 0.1 mM, about 0.01 mM to about 0.2 mM, about 0.01 mM to about 0.5 mM, about 0.01 mM to about 1 mM, about 0.02 mM to about 0.03 mM, about 0.02 mM to about 0.05 mM, about 0.02 mM to about 0.06 mM, about 0.02 mM to about 0.07 mM, about 0.02 mM to about 0.08 mM, about 0.02 mM to about 0.09 mM, about 0.02 mM to about 0.1 mM, about 0.02 mM to about 0.2 mM, about 0.02 mM to about 0.5 mM, about 0.02 mM to about 1 mM, about 0.03 mM to about 0.05 mM, about 0.03 mM to about 0.06 mM, about 0.03 mM to about 0.07 mM, about 0.03 mM to about 0.08 mM, about 0.03 mM to about 0.09 mM, about 0.03 mM to about 0.1 mM, about 0.03 mM to about 0.2 mM, about 0.03 mM to about 0.5 mM, about 0.03 mM to about 1 mM, about 0.05 mM to about 0.06 mM, about 0.05 mM to about 0.07 mM, about 0.05 mM to about 0.08 mM, about 0.05 mM to about 0.09 mM, about 0.05 mM to about 0.1 mM, about 0.05 mM to about 0.2 mM, about 0.05 mM to about 0.5 mM, about 0.05 mM to about 1 mM, about 0.06 mM to about 0.07 mM, about 0.06 mM to about 0.08 mM, about 0.06 mM to about 0.09 mM, about 0.06 mM to about 0.1 mM, about 0.06 mM to about 0.2 mM, about 0.06 mM to about 0.5 mM, about 0.06 mM to about 1 mM, about 0.07 mM to about 0.08 mM, about 0.07 mM to about 0.09 mM, about 0.07 mM to about 0.1 mM, about 0.07 mM to about 0.2 mM, about 0.07 mM to about 0.5 mM, about 0.07 mM to about 1 mM, about 0.08 mM to about 0.09 mM, about 0.08 mM to about 0.1 mM, about 0.08 mM to about 0.2 mM, about 0.08 mM to about 0.5 mM, about 0.08 mM to about 1 mM, about 0.09 mM to about 0.1 mM, about 0.09 mM to about 0.2 mM, about 0.09 mM to about 0.5 mM, about 0.09 mM to about 1 mM, about 0.1 mM to about 0.2 mM, about 0.1 mM to about 0.5 mM, about 0.1 mM to about 1 mM, about 0.2 mM to about 0.5 mM, about 0.2 mM to about 1 mM, or about 0.5 mM to about 1 mM. In some embodiments, the final IPTG concentration of the culture is about 0.01 mM, about 0.02 mM, about 0.03 mM, about 0.05 mM, about 0.06 mM, about 0.07 mM, about 0.08 mM, about 0.09 mM, about 0.1 mM, about 0.2 mM, about 0.5 mM, or about 1 mM. In some embodiments, the final IPTG concentration of the culture is at least about 0.01 mM, about 0.02 mM, about 0.03 mM, about 0.05 mM, about 0.06 mM, about 0.07 mM, about 0.08 mM, about 0.09 mM, about 0.1 mM, about 0.2 mM, or about 0.5 mM. In some embodiments, the final IPTG concentration of the culture is at most about 0.02 mM, about 0.03 mM, about 0.05 mM, about 0.06 mM, about 0.07 mM, about 0.08 mM, about 0.09 mM, about 0.1 mM, about 0.2 mM, about 0.5 mM, or about 1 mM. In some embodiments, the final IPTG concentration of the culture is about 0.08 mM to about 0.3 mM. In some embodiments, the final IPTG concentration of the culture is about 0.08 mM to about 0.09 mM, about 0.08 mM to about 0.1 mM, about 0.08 mM to about 0.125 mM, about 0.08 mM to about 0.15 mM, about 0.08 mM to about 0.175 mM, about 0.08 mM to about 0.2 mM, about 0.08 mM to about 0.225 mM, about 0.08 mM to about 0.25 mM, about 0.08 mM to about 0.275 mM, about 0.08 mM to about 0.3 mM, about 0.09 mM to about 0.1 mM, about 0.09 mM to about 0.125 mM, about 0.09 mM to about 0.15 mM, about 0.09 mM to about 0.175 mM, about 0.09 mM to about 0.2 mM, about 0.09 mM to about 0.225 mM, about 0.09 mM to about 0.25 mM, about 0.09 mM to about 0.275 mM, about 0.09 mM to about 0.3 mM, about 0.1 mM to about 0.125 mM, about 0.1 mM to about 0.15 mM, about 0.1 mM to about 0.175 mM, about 0.1 mM to about 0.2 mM, about 0.1 mM to about 0.225 mM, about 0.1 mM to about 0.25 mM, about 0.1 mM to about 0.275 mM, about 0.1 mM to about 0.3 mM, about 0.125 mM to about 0.15 mM, about 0.125 mM to about 0.175 mM, about 0.125 mM to about 0.2 mM, about 0.125 mM to about 0.225 mM, about 0.125 mM to about 0.25 mM, about 0.125 mM to about 0.275 mM, about 0.125 mM to about 0.3 mM, about 0.15 mM to about 0.175 mM, about 0.15 mM to about 0.2 mM, about 0.15 mM to about 0.225 mM, about 0.15 mM to about 0.25 mM, about 0.15 mM to about 0.275 mM, about 0.15 mM to about 0.3 mM, about 0.175 mM to about 0.2 mM, about 0.175 mM to about 0.225 mM, about 0.175 mM to about 0.25 mM, about 0.175 mM to about 0.275 mM, about 0.175 mM to about 0.3 mM, about 0.2 mM to about 0.225 mM, about 0.2 mM to about 0.25 mM, about 0.2 mM to about 0.275 mM, about 0.2 mM to about 0.3 mM, about 0.225 mM to about 0.25 mM, about 0.225 mM to about 0.275 mM, about 0.225 mM to about 0.3 mM, about 0.25 mM to about 0.275 mM, about 0.25 mM to about 0.3 mM, or about 0.275 mM to about 0.3 mM. In some embodiments, the final IPTG concentration of the culture is about 0.08 mM, about 0.09 mM, about 0.1 mM, about 0.125 mM, about 0.15 mM, about 0.175 mM, about 0.2 mM, about 0.225 mM, about 0.25 mM, about 0.275 mM, or about 0.3 mM. In some embodiments, the final IPTG concentration of the culture is at least about 0.08 mM, about 0.09 mM, about 0.1 mM, about 0.125 mM, about 0.15 mM, about 0.175 mM, about 0.2 mM, about 0.225 mM, about 0.25 mM, or about 0.275 mM. In some embodiments, the final IPTG concentration of the culture is at most about 0.09 mM, about 0.1 mM, about 0.125 mM, about 0.15 mM, about 0.175 mM, about 0.2 mM, about 0.225 mM, about 0.25 mM, about 0.275 mM, or about 0.3 mM.

In embodiments wherein a non-lac type promoter is used, as described herein and in the literature, other inducers or effectors can be used. In one embodiment, the promoter is a constitutive promoter.

After adding and inducing agent, cultures can be grown for a period of time, for example about 24 hours, during which time the recombinant protein is expressed (production phase). After adding an inducing agent, a culture can be grown for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 36 hr, or about 48 hr. After an inducing agent is added to a culture, the culture can be grown for about 1 to 48 hr, about 1 to 24 hr, about 1 to 8 hr, about 10 to 24 hr, about 15 to 24 hr, or about 20 to 24 hr. Cell cultures can be concentrated by centrifugation, and the culture pellet resuspended in a buffer or solution appropriate for the subsequent lysis procedure.

In some embodiments a constant feed is used. In some embodiments, a fed-batch format is used. In some embodiments, the feed is glycerol or glucose. In some embodiments the feed bolus is about 10 g/L to about 50 g/L. In some embodiments the feed bolus is about 10 g/L to about 15 g/L, about 10 g/L to about 20 g/L, about 10 g/L to about 25 g/L, about 10 g/L to about 30 g/L, about 10 g/L to about 35 g/L, about 10 g/L to about 40 g/L, about 10 g/L to about 45 g/L, about 10 g/L to about 50 g/L, about 15 g/L to about 20 g/L, about 15 g/L to about 25 g/L, about 15 g/L to about 30 g/L, about 15 g/L to about 35 g/L, about 15 g/L to about 40 g/L, about 15 g/L to about 45 g/L, about 15 g/L to about 50 g/L, about 20 g/L to about 25 g/L, about 20 g/L to about 30 g/L, about 20 g/L to about 35 g/L, about 20 g/L to about 40 g/L, about 20 g/L to about 45 g/L, about 20 g/L to about 50 g/L, about 25 g/L to about 30 g/L, about 25 g/L to about 35 g/L, about 25 g/L to about 40 g/L, about 25 g/L to about 45 g/L, about 25 g/L to about 50 g/L, about 30 g/L to about 35 g/L, about 30 g/L to about 40 g/L, about 30 g/L to about 45 g/L, about 30 g/L to about 50 g/L, about 35 g/L to about 40 g/L, about 35 g/L to about 45 g/L, about 35 g/L to about 50 g/L, about 40 g/L to about 45 g/L, about 40 g/L to about 50 g/L, or about 45 g/L to about 50 g/L. In some embodiments the feed bolus is about 10 g/L, about 15 g/L, about 20 g/L, about 25 g/L, about 30 g/L, about 35 g/L, about 40 g/L, about 45 g/L, or about 50 g/L. In some embodiments the feed bolus is at least about 10 g/L, about 15 g/L, about 20 g/L, about 25 g/L, about 30 g/L, about 35 g/L, about 40 g/L, or about 45 g/L. In some embodiments the feed bolus is at most about 15 g/L, about 20 g/L, about 25 g/L, about 30 g/L, about 35 g/L, about 40 g/L, about 45 g/L, or about 50 g/L.

In embodiments, cells are disrupted using equipment for high pressure mechanical cell disruption (which are available commercially, e.g., Microfluidics Micro fluidizer, Constant Cell Disruptor, Niro-Soavi homogenizer or APV-Gaulin homogenizer). Cells expressing the recombinant protein can be disrupted, for example, using sonication. Any appropriate method known in the art for lysing cells can be used to release the soluble fraction. For example, in embodiments, chemical and/or enzymatic cell lysis reagents, such as cell-wall lytic enzyme and EDTA, can be used. Use of frozen or previously stored cultures is also contemplated in the methods of the invention. Cultures can be OD-normalized prior to lysis. For example, cells can be normalized to an OD600 of about 10, about 11, about 12, about 13, about 14, about 15, about 16, about 17, about 18, about 19, or about 20.

Centrifugation can be performed using any appropriate equipment and method. Centrifugation of cell culture or lysate for the purposes of separating a soluble fraction from an insoluble fraction is well-known in the art. For example, lysed cells can be centrifuged at 20,800×g for 20 minutes (at 4° C.), and the supernatants removed using manual or automated liquid handling. The cell pellet obtained by centrifugation of cell culture, or the insoluble fraction obtained by centrifugation of cell lysate, can be resuspended in a buffered solution. Resuspension of the cell pellet or insoluble fraction can be carried out using, e.g., equipment such as impellers connected to an overhead mixer, magnetic stir-bars, rocking shakers, etc.

A "soluble fraction," i.e., the soluble supernatant obtained after centrifugation of a lysate, and an "insoluble fraction," i.e., the pellet obtained after centrifugation of a lysate, result from lysing and centrifuging the cultures.

High Throughput Screens

In embodiments, a high throughput screen is conducted to determine optimal conditions for expressing a recombinant protein of interest. Conditions that can be varied in the screen include, for example, the host cell, genetic background of the host cell (e.g., as described in detail herein), type of promoter in an expression construct, type of secretion leader fused to the encoded polypeptide or protein of interest, temperature of growth, OD of induction when an inducible promoter is used, amount of inducer added (e.g. amount of IPTG used for induction when a lacZ promoter or derivative thereof is used), duration of protein induction, temperature of growth following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" may be identified or selected based on the quantity, quality, and/or location of the expressed protein of interest compared to other populations of phenotypically distinct host cells in the array. Thus, an optimal host strain is the strain that produces the recombinant protein of interest according to a desired specification. While the desired specification will vary depending on the polypeptide being produced, the specification includes the quality and/or quantity of protein, whether the protein is sequestered or secreted, protein folding, and the like. For example, the optimal host strain or optimal expression system produces a yield, characterized by the amount of soluble recombinant protein, the amount of recoverable recombinant protein, the amount of properly processed recombinant protein, the amount of properly folded recombinant protein, the amount of active recombinant protein, and/or the total amount of the recombinant protein of interest, of a certain absolute level or a certain level relative to that produced by a control or indicator strain, i.e., a strain used for comparison. Methods of screening microbial hosts to identify strains with improved yield and/or quality in the expression of recombinant proteins are described, for example, in U.S. Pat. Nos. 9,394,571 and 9,580,719.

Protein Analysis

A recombinant protein of interest produced according to the methods of the present invention may be of high quality, e.g., active, soluble, and/or intact; produced at a high yield or titer; or any combination thereof. In some embodiments, a recombinant protein of interest is produced by a recombinant gram-negative bacterial host cell according to the methods of the present invention at higher quality and/or higher yield when compared to those observed with a control host cell. In some embodiments, a recombinant gram-negative bacterial host cell of the present invention grows to a higher cell density than a control host cell.

In embodiments, recombinant proteins of interest produced by the methods provided herein are analyzed with regard to yield, solubility, activity, and degradation (e.g., by measuring intact protein). A recombinant protein of interest can be analyzed by any appropriate method known to those of skill in the art. The "solubility" and "activity" of a protein, though related qualities, are generally determined by different means. Solubility of a protein, particularly a hydrophobic protein, indicates that hydrophobic amino acid residues are properly located on the inside of the folded protein. Protein activity, which is often evaluated using different methods, e.g., as described below, is another indicator of proper protein conformation.

In some embodiments, a recombinant protein of interest is analyzed by biolayer interferometry, SDS-PAGE, Western blot, Far Western blot, ELISA, absorbance, or mass spectrometry (e.g., tandem mass spectrometry). In some embodiments, the concentration and/or amounts of polypeptides or proteins of interest generated are determined, for example, by Bradford assay, absorbance, Coomassie staining, mass spectrometry, etc. Protein yield and fragmentation in the insoluble and soluble fractions can be analyzed by methods known to those of skill in the art, for example, by capillary gel electrophoresis (CGE), SDS-PAGE, and Western blot analysis. Soluble fractions also can be evaluated, for example, using biolayer interferometry. Protein activity may be measured by any known method as appropriate for the recombinant protein of interest. For a recombinant protein of interest that is a binding protein, this may comprise measuring its binding to a target ligand, e.g., TNF-alpha, or any other target, by any known method.

Useful measures of protein yield include, e.g., the amount of recombinant protein per culture volume (e.g., concentration, which may be expressed in grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of active protein (e.g., amount of active protein/amount protein used in the assay), percent or fraction of total cell protein (tcp), amount of protein/cell, and percent dry biomass. A measure as used herein may refer to that determined for a large-scale fermentation culture.

In some embodiments, a recombinant gram-negative bacterial host cell of the invention grows to an increased cell density in culture than a control cell, under substantially the same growth conditions. In some embodiments, the increase in cell density relative to the control cell is about 2-fold to about 15-fold. In some embodiments, the increase in cell density relative to the control cell is about 2 fold to about 3 fold, about 2 fold to about 4 fold, about 2 fold to about 5 fold, about 2 fold to about 6 fold, about 2 fold to about 7 fold, about 2 fold to about 8 fold, about 2 fold to about 9 fold, about 2 fold to about 10 fold, about 2 fold to about 11 fold, about 2 fold to about 12 fold, about 2 fold to about 15 fold, about 3 fold to about 4 fold, about 3 fold to about 5 fold, about 3 fold to about 6 fold, about 3 fold to about 7 fold, about 3 fold to about 8 fold, about 3 fold to about 9 fold, about 3 fold to about 10 fold, about 3 fold to about 11 fold, about 3 fold to about 12 fold, about 3 fold to about 15 fold, about 4 fold to about 5 fold, about 4 fold to about 6 fold, about 4 fold to about 7 fold, about 4 fold to about 8 fold, about 4 fold to about 9 fold, about 4 fold to about 10 fold, about 4 fold to about 11 fold, about 4 fold to about 12 fold, about 4 fold to about 15 fold, about 5 fold to about 6 fold, about 5 fold to about 7 fold, about 5 fold to about 8 fold, about 5 fold to about 9 fold, about 5 fold to about 10 fold, about 5 fold to about 11 fold, about 5 fold to about 12 fold, about 5 fold to about 15 fold, about 6 fold to about 7 fold, about 6 fold to about 8 fold, about 6 fold to about 9 fold, about 6 fold to about 10 fold, about 6 fold to about 11 fold, about 6 fold to about 12 fold, about 6 fold to about 15 fold, about 7 fold to about 8 fold, about 7 fold to about 9 fold, about 7 fold to about 10 fold, about 7 fold to about 11 fold, about 7 fold to about 12 fold, about 7 fold to about 15 fold, about 8 fold to about 9 fold, about 8 fold to about 10 fold, about 8 fold to about 11 fold, about 8 fold to about 12 fold, about 8 fold to about 15 fold, about 9 fold to about 10 fold, about 9 fold to about 11 fold, about 9 fold to about 12 fold, about 9 fold to about 15 fold, about 10 fold to about 11 fold, about 10 fold to about 12 fold, about 10 fold to about 15 fold, about 11 fold to about 12 fold, about 11 fold to about 15 fold, or about 12 fold to about 15 fold. In some embodiments, the increase in cell density relative to the control cell is about 2 fold, about 3 fold, about 4 fold, about 5 fold, about 6 fold, about 7 fold, about 8 fold, about 9 fold, about 10 fold, about 11 fold, about 12 fold, or about 15 fold. In some embodiments, the increase in cell density relative to the control cell is at least about 2 fold, about 3 fold, about 4 fold, about 5 fold, about 6 fold, about 7 fold, about 8 fold, about 9 fold, about 10 fold, about 11 fold, or about 12 fold. In some embodiments, the increase in cell density relative to the control cell is at most about 3 fold, about 4 fold, about 5 fold, about 6 fold, about 7 fold, about 8 fold, about 9 fold, about 10 fold, about 11 fold, about 12 fold, or about 15 fold.

In some embodiments, a recombinant gram-negative bacterial host cell of the invention produces an increased yield of high-quality recombinant protein relative to a control cell. In some embodiments, the increased yield relative to the control cell is about 2-fold to about 100-fold. In some embodiments, the increased yield relative to the control cell is about 2 fold to about 5 fold, about 2 fold to about 10 fold, about 2 fold to about 20 fold, about 2 fold to about 30 fold, about 2 fold to about 40 fold, about 2 fold to about 50 fold, about 2 fold to about 60 fold, about 2 fold to about 70 fold, about 2 fold to about 80 fold, about 2 fold to about 90 fold, about 2 fold to about 100 fold, about 5 fold to about 10 fold, about 5 fold to about 20 fold, about 5 fold to about 30 fold, about 5 fold to about 40 fold, about 5 fold to about 50 fold, about 5 fold to about 60 fold, about 5 fold to about 70 fold, about 5 fold to about 80 fold, about 5 fold to about 90 fold, about 5 fold to about 100 fold, about 10 fold to about 20 fold, about 10 fold to about 30 fold, about 10 fold to about 40 fold, about 10 fold to about 50 fold, about 10 fold to about 60 fold, about 10 fold to about 70 fold, about 10 fold to about 80 fold, about 10 fold to about 90 fold, about 10 fold to about 100 fold, about 20 fold to about 30 fold, about 20 fold to about 40 fold, about 20 fold to about 50 fold, about 20 fold to about 60 fold, about 20 fold to about 70 fold, about 20 fold to about 80 fold, about 20 fold to about 90 fold, about 20 fold to about 100 fold, about 30 fold to about 40 fold, about 30 fold to about 50 fold, about 30 fold to about 60 fold, about 30 fold to about 70 fold, about 30 fold to about 80 fold, about 30 fold to about 90 fold, about 30 fold to about 100 fold, about 40 fold to about 50 fold, about 40 fold to about 60 fold, about 40 fold to about 70 fold, about 40 fold to about 80 fold, about 40 fold to about 90 fold, about 40 fold to about 100 fold, about 50 fold to about 60 fold, about 50 fold to about 70 fold, about 50 fold to about 80 fold, about 50 fold to about 90 fold, about 50 fold to about 100 fold, about 60 fold to about 70 fold, about 60 fold to about 80 fold, about 60 fold to about 90 fold, about 60 fold to about 100 fold, about 70 fold to about 80 fold, about 70 fold to about 90 fold, about 70 fold to about 100 fold, about 80 fold to about 90 fold, about 80 fold to about 100 fold, or about 90 fold to about 100 fold. In some embodiments, the increased yield relative to the control cell is about 2 fold, about 5 fold, about 10 fold, about 20 fold, about 30 fold, about 40 fold, about 50 fold, about 60 fold, about 70 fold, about 80 fold, about 90 fold, or about 100 fold. In some embodiments, the increased yield relative to the control cell is at least about 2 fold, about 5 fold, about 10 fold, about 20 fold, about 30 fold, about 40 fold, about 50 fold, about 60 fold, about 70 fold, about 80 fold, or about 90 fold. In some embodiments, the increased yield relative to the control cell is at most about 5 fold, about 10 fold, about 20 fold, about 30 fold, about 40 fold, about 50 fold, about 60 fold, about 70 fold, about 80 fold, about 90 fold, or about 100 fold.

Any suitable control cell may be selected by one of skill in the art for comparison with the recombinant gram-negative bacterial host cell. In some embodiments, the recombinant gram-negative bacterial host cell and the control cell, respectively, are selected from: (i) a recombinant gram-negative bacterial host cell deficient in a first protease activity and a second protease activity as described herein, and a corresponding gram-negative bacterial host cell deficient in the first protease activity and wherein the second protease is functional; (ii) a recombinant gram-negative bacterial host cell deficient in the first protease activity, the second protease activity, and an additional protease activity as described herein, and a corresponding gram-negative bacterial host cell deficient in the first protease activity and the second protease activity, and wherein the additional protease activity that is deficient in the compared recombinant gram-negative bacterial host cell is functional; and (iii) a recombinant gram-negative bacterial host cell deficient in the first protease activity and the second protease activity, and comprising a functional protease that is: a MepS1 having the amino acid sequence set forth as SEQ ID NO: 5; a homologue of the MepS1 having the amino acid sequence set forth as SEQ ID NO: 5; or a MepS1 related protein having at least 50% sequence similarity to the P. fluorescens MepS1 amino acid sequence set forth as SEQ ID NO: 5, and a corresponding gram-negative bacterial host cell deficient in the activity of the first protease and the second protease, and deficient in the functional protease of the compared recombinant gram-negative bacterial host cell.

In embodiments, the methods herein are used to obtain a yield of active, soluble, and/or intact recombinant protein of interest of about 20% to about 90% total cell protein. In certain embodiments, the yield of active, soluble, and/or intact polypeptide or protein of interest is about 20% total cell protein, about 25% total cell protein, about 30% total cell protein, about 31% total cell protein, about 32% total cell protein, about 33% total cell protein, about 34% total cell protein, about 35% total cell protein, about 36% total cell protein, about 37% total cell protein, about 38% total cell protein, about 39% total cell protein, about 40% total cell protein, about 41% total cell protein, about 42% total cell protein, about 43% total cell protein, about 44% total cell protein, about 45% total cell protein, about 46% total cell protein, about 47% total cell protein, about 48% total cell protein, about 49% total cell protein, about 50% total cell protein, about 51% total cell protein, about 52% total cell protein, about 53% total cell protein, about 54% total cell protein, about 55% total cell protein, about 56% total cell protein, about 57% total cell protein, about 58% total cell protein, about 59% total cell protein, about 60% total cell protein, about 65% total cell protein, about 70% total cell protein, about 75% total cell protein, about 80% total cell protein, about 85% total cell protein, or about 90% total cell protein. In some embodiments, the yield of active, soluble, and/or intact recombinant protein of interest is about 20% to about 25% total cell protein, about 20% to about 30% total cell protein, about 20% to about 35% total cell protein, about 20% to about 40% total cell protein, about 20% to about 45% total cell protein, about 20% to about 50% total cell protein, about 20% to about 55% total cell protein, about 20% to about 60% total cell protein, about 20% to about 65% total cell protein, about 20% to about 70% total cell protein, about 20% to about 75% total cell protein, about 20% to about 80% total cell protein, about 20% to about 85% total cell protein, about 20% to about 90% total cell protein, about 25% to about 90% total cell protein, about 30% to about 90% total cell protein, about 35% to about 90% total cell protein, about 40% to about 90% total cell protein, about 45% to about 90% total cell protein, about 50% to about 90% total cell protein, about 55% to about 90% total cell protein, about 60% to about 90% total cell protein, about 65% to about 90% total cell protein, about 70% to about 90% total cell protein, about 75% to about 90% total cell protein, about 80% to about 90% total cell protein, about 85% to about 90% total cell protein, about 31% to about 60% total cell protein, about 35% to about 60% total cell protein, about 40% to about 60% total cell protein, about 45% to about 60% total cell protein, about 50% to about 60% total cell protein, about 55% to about 60% total cell protein, about 31% to about 55% total cell protein, about 31% to about 50% total cell protein, about 31% to about 45% total cell protein, about 31% to about 40% total cell protein, about 31% to about 35% total cell protein, about 35% to about 55% total cell protein, or about 40% to about 50% total cell protein.

In embodiments, the methods herein are used to obtain a yield (which may be referred to as a titer when expressed as a concentration) of active, soluble, and/or intact recombinant protein of interest of about 1 gram per liter to about 50 grams per liter. In some embodiments, the methods herein are used to obtain a yield of active, soluble, and/or intact recombinant protein of interest of about 0.1 g/L to about 50 g/L. In some embodiments, the methods herein are used to obtain a yield of active, soluble, and/or intact recombinant protein of interest of about 0.1 g/L to about 1 g/L, about 0.1 g/L to about 5 g/L, about 0.1 g/L to about 10 g/L, about 0.1 g/L to about 15 g/L, about 0.1 g/L to about 20 g/L, about 0.1 g/L to about 25 g/L, about 0.1 g/L to about 30 g/L, about 0.1 g/L to about 35 g/L, about 0.1 g/L to about 40 g/L, about 0.1 g/L to about 45 g/L, about 0.1 g/L to about 50 g/L, about 1 g/L to about 5 g/L, about 1 g/L to about 10 g/L, about 1 g/L to about 15 g/L, about 1 g/L to about 20 g/L, about 1 g/L to about 25 g/L, about 1 g/L to about 30 g/L, about 1 g/L to about 35 g/L, about 1 g/L to about 40 g/L, about 1 g/L to about 45 g/L, about 1 g/L to about 50 g/L, about 5 g/L to about 10 g/L, about 5 g/L to about 15 g/L, about 5 g/L to about 20 g/L, about 5 g/L to about 25 g/L, about 5 g/L to about 30 g/L, about 5 g/L to about 35 g/L, about 5 g/L to about 40 g/L, about 5 g/L to about 45 g/L, about 5 g/L to about 50 g/L, about 10 g/L to about 15 g/L, about 10 g/L to about 20 g/L, about 10 g/L to about 25 g/L, about 10 g/L to about 30 g/L, about 10 g/L to about 35 g/L, about 10 g/L to about 40 g/L, about 10 g/L to about 45 g/L, about 10 g/L to about 50 g/L, about 15 g/L to about 20 g/L, about 15 g/L to about 25 g/L, about 15 g/L to about 30 g/L, about 15 g/L to about 35 g/L, about 15 g/L to about 40 g/L, about 15 g/L to about 45 g/L, about 15 g/L to about 50 g/L, about 20 g/L to about 25 g/L, about 20 g/L to about 30 g/L, about 20 g/L to about 35 g/L, about 20 g/L to about 40 g/L, about 20 g/L to about 45 g/L, about 20 g/L to about 50 g/L, about 25 g/L to about 30 g/L, about 25 g/L to about 35 g/L, about 25 g/L to about 40 g/L, about 25 g/L to about 45 g/L, about 25 g/L to about 50 g/L, about 30 g/L to about 35 g/L, about 30 g/L to about 40 g/L, about 30 g/L to about 45 g/L, about 30 g/L to about 50 g/L, about 35 g/L to about 40 g/L, about 35 g/L to about 45 g/L, about 35 g/L to about 50 g/L, about 40 g/L to about 45 g/L, about 40 g/L to about 50 g/L, or about 45 g/L to about 50 g/L. In some embodiments, the methods herein are used to obtain a yield of active, soluble, and/or intact recombinant protein of interest of about 0.1 g/L, about 1 g/L, about 5 g/L, about 10 g/L, about 15 g/L, about 20 g/L, about 25 g/L, about 30 g/L, about 35 g/L, about 40 g/L, about 45 g/L, or about 50 g/L. In some embodiments, the methods herein are used to obtain a yield of active, soluble, and/or intact recombinant protein of interest of at least about 0.1 g/L, about 1 g/L, about 5 g/L, about 10 g/L, about 15 g/L, about 20 g/L, about 25 g/L, about 30 g/L, about 35 g/L, about 40 g/L, or about 45 g/L. In some embodiments, the methods herein are used to obtain a yield of active, soluble, and/or intact recombinant protein of interest of at most about 1 g/L, about 5 g/L, about 10 g/L, about 15 g/L, about 20 g/L, about 25 g/L, about 30 g/L, about 35 g/L, about 40 g/L, about 45 g/L, or about 50 g/L. In some embodiments, the methods herein are used to obtain a yield of active, soluble, and/or intact recombinant protein of interest of about 0.1 g/L to about 10 g/L. In some embodiments, the methods herein are used to obtain a yield of active, soluble, and/or intact recombinant protein of interest of about 0.1 g/L to about 0.5 g/L, about 0.1 g/L to about 1 g/L, about 0.1 g/L to about 2 g/L, about 0.1 g/L to about 3 g/L, about 0.1 g/L to about 4 g/L, about 0.1 g/L to about 5 g/L, about 0.1 g/L to about 6 g/L, about 0.1 g/L to about 7 g/L, about 0.1 g/L to about 8 g/L, about 0.1 g/L to about 9 g/L, about 0.1 g/L to about 10 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 5 g/L to about 6 g/L, about 5 g/L to about 7 g/L, about 5 g/L to about 8 g/L, about 5 g/L to about 9 g/L, about 5 g/L to about 10 g/L, about 6 g/L to about 7 g/L, about 6 g/L to about 8 g/L, about 6 g/L to about 9 g/L, about 6 g/L to about 10 g/L, about 7 g/L to about 8 g/L, about 7 g/L to about 9 g/L, about 7 g/L to about 10 g/L, about 8 g/L to about 9 g/L, about 8 g/L to about 10 g/L, or about 9 g/L to about 10 g/L. In some embodiments, the methods herein are used to obtain a yield of active, soluble, and/or intact recombinant protein of interest of about 0.1 g/L, about 0.5 g/L, about 1 g/L, about 2 g/L, about 3 g/L, about 4 g/L, about 5 g/L, about 6 g/L, about 7 g/L, about 8 g/L, about 9 g/L, or about 10 g/L. In some embodiments, the methods herein are used to obtain a yield of active, soluble, and/or intact recombinant protein of interest of at least about 0.1 g/L, about 0.5 g/L, about 1 g/L, about 2 g/L, about 3 g/L, about 4 g/L, about 5 g/L, about 6 g/L, about 7 g/L, about 8 g/L, or about 9 g/L. In some embodiments, the methods herein are used to obtain a yield of active, soluble, and/or intact recombinant protein of interest of at most about 0.5 g/L, about 1 g/L, about 2 g/L, about 3 g/L, about 4 g/L, about 5 g/L, about 6 g/L, about 7 g/L, about 8 g/L, about 9 g/L, or about 10 g/L. In some embodiments, the methods herein are used to obtain a yield of active, soluble, and/or intact recombinant protein of interest of about 0.2 to about 5 g/L. In some embodiments, the methods herein are used to obtain a yield of active, soluble, and/or intact recombinant protein of interest of about 0.2 g/L to about 5 g/L. In some embodiments, the methods herein are used to obtain a yield of active, soluble, and/or intact recombinant protein of interest of about 0.2 g/L to about 0.3 g/L, about 0.2 g/L to about 0.4 g/L, about 0.2 g/L to about 0.5 g/L, about 0.2 g/L to about 0.75 g/L, about 0.2 g/L to about 1 g/L, about 0.2 g/L to about 1.25 g/L, about 0.2 g/L to about 1.5 g/L, about 0.2 g/L to about 2 g/L, about 0.2 g/L to about 3 g/L, about 0.2 g/L to about 4 g/L, about 0.2 g/L to about 5 g/L, about 0.3 g/L to about 0.4 g/L, about 0.3 g/L to about 0.5 g/L, about 0.3 g/L to about 0.75 g/L, about 0.3 g/L to about 1 g/L, about 0.3 g/L to about 1.25 g/L, about 0.3 g/L to about 1.5 g/L, about 0.3 g/L to about 2 g/L, about 0.3 g/L to about 3 g/L, about 0.3 g/L to about 4 g/L, about 0.3 g/L to about 5 g/L, about 0.4 g/L to about 0.5 g/L, about 0.4 g/L to about 0.75 g/L, about 0.4 g/L to about 1 g/L, about 0.4 g/L to about 1.25 g/L, about 0.4 g/L to about 1.5 g/L, about 0.4 g/L to about 2 g/L, about 0.4 g/L to about 3 g/L, about 0.4 g/L to about 4 g/L, about 0.4 g/L to about 5 g/L, about 0.5 g/L to about 0.75 g/L, about 0.5 g/L to about 1 g/L, about 0.5 g/L to about 1.25 g/L, about 0.5 g/L to about 1.5 g/L, about 0.5 g/L to about 2 g/L, about 0.5 g/L to about 3 g/L, about 0.5 g/L to about 4 g/L, about 0.5 g/L to about 5 g/L, about 0.75 g/L to about 1 g/L, about 0.75 g/L to about 1.25 g/L, about 0.75 g/L to about 1.5 g/L, about 0.75 g/L to about 2 g/L, about 0.75 g/L to about 3 g/L, about 0.75 g/L to about 4 g/L, about 0.75 g/L to about 5 g/L, about 1 g/L to about 1.25 g/L, about 1 g/L to about 1.5 g/L, about 1 g/L to about 2 g/L, about 1 g/L to about 3 g/L, about 1 g/L to about 4 g/L, about 1 g/L to about 5 g/L, about 1.25 g/L to about 1.5 g/L, about 1.25 g/L to about 2 g/L, about 1.25 g/L to about 3 g/L, about 1.25 g/L to about 4 g/L, about 1.25 g/L to about 5 g/L, about 1.5 g/L to about 2 g/L, about 1.5 g/L to about 3 g/L, about 1.5 g/L to about 4 g/L, about 1.5 g/L to about 5 g/L, about 2 g/L to about 3 g/L, about 2 g/L to about 4 g/L, about 2 g/L to about 5 g/L, about 3 g/L to about 4 g/L, about 3 g/L to about 5 g/L, or about 4 g/L to about 5 g/L. In some embodiments, the methods herein are used to obtain a yield of active, soluble, and/or intact recombinant protein of interest of about 0.2 g/L, about 0.3 g/L, about 0.4 g/L, about 0.5 g/L, about 0.75 g/L, about 1 g/L, about 1.25 g/L, about 1.5 g/L, about 2 g/L, about 3 g/L, about 4 g/L, or about 5 g/L. In some embodiments, the methods herein are used to obtain a yield of active, soluble, and/or intact recombinant protein of interest of at least about 0.2 g/L, about 0.3 g/L, about 0.4 g/L, about 0.5 g/L, about 0.75 g/L, about 1 g/L, about 1.25 g/L, about 1.5 g/L, about 2 g/L, about 3 g/L, or about 4 g/L. In some embodiments, the methods herein are used to obtain a yield of active, soluble, and/or intact recombinant protein of interest of at most about 0.3 g/L, about 0.4 g/L, about 0.5 g/L, about 0.75 g/L, about 1 g/L, about 1.25 g/L, about 1.5 g/L, about 2 g/L, about 3 g/L, about 4 g/L, or about 5 g/L.

In embodiments, the amount of active, soluble, and/or intact recombinant protein of interest is about 10% to about 100% of the amount of the total active, soluble, and/or intact recombinant protein of interest produced. In embodiments, this amount is about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%, or about 100% of the amount of the active, soluble, and/or intact recombinant protein of interest produced. In embodiments, this amount is about 10% to about 20%, 20% to about 50%, about 25% to about 50%, 25% to about 50%, about 25% to about 95%, about 30% to about 50%, about 30% to about 40%, about 30% to about 60%, about 30% to about 70%, about 35% to about 50%, about 35% to about 70%, about 35% to about 75%, about 35% to about 95%, about 40% to about 50%, about 40% to about 95%, about 50% to about 75%, about 50% to about 95%, about 70% to about 95%, or about 80 to about 100% of the amount of the active, soluble, and/or intact recombinant protein of interest produced.

In some embodiments, the amount of active, soluble, and/or intact recombinant protein of interest is expressed as a percentage of the total active, soluble, and/or intact protein produced in a culture. Data expressed in terms of active, soluble, and/or intact recombinant protein of interest weight/volume of cell culture at a given cell density can be converted to data expressed as percent recombinant protein of total cell protein. It is within the capabilities of a skilled artisan to convert volumetric protein yield to % total cell protein, for example, knowing the amount of total cell protein per volume of cell culture at the given cell density. This number can be determined if one knows 1) the cell weight/volume of culture at the given cell density, and 2) the percent of cell weight comprised by total protein. For example, at an OD550 of 1.0, the dry cell weight of E. coli is reported to be 0.5 grams/liter ("Production of Heterologous Proteins from Recombinant DNA Escherichia coli in Bench Fermentors," Lin, N. S., and Swartz, J. R., 1992, METHODS: A Companion to Methods in Enzymology 4: 159-168). A bacterial cell is comprised of polysaccharides, lipids, and nucleic acids, as well as proteins. An E. coli cell is reported to be about 52.4 to 55% protein by references including, but not limited to, Da Silva, N. A., et al., 1986, "Theoretical Growth Yield Estimates for Recombinant Cells," Biotechnology and Bioengineering, Vol. XXVIII: 741-746, estimating protein to make up 52.4% by weight of E. coli cells, and "Escherichia coli and Salmonella typhimurium Cellular and Molecular Biology," 1987, Ed. in Chief Frederick C. Neidhardt, Vol. 1, pp. 3-6, reporting protein content in E. coli as 55% dry cell weight. Using the measurements above (i.e., a dry cell weight of 0.5 grams/liter, and protein as 55% cell weight), the amount of total cell protein per volume of cell culture at an A550 of 1.0 for E.

coli is calculated as 275 μg total cell protein/ml/A550. A calculation of total cell protein per volume of cell culture based on wet cell weight can use, e.g., the determination by Glazyrina, et al. (Microbial Cell Factories 2010, 9:42, incorporated herein by reference) that an A600 of 1.0 for E. coli resulted in a wet cell weight of 1.7 grams/liter and a dry cell weight of 0.39 grams/liter. For example, using this wet cell weight to dry cell weight comparison, and protein as 55% dry cell weight as described above, the amount of total cell protein per volume of cell culture at an A600 of 1.0 for E. coli can be calculated as 215 μg total cell protein/ml/A600. For Pseudomonas fluorescens, the amount of total cell protein per volume of cell culture at a given cell density is similar to that found for E. coli. P. fluorescens, like E. coli, is a gram-negative, rod-shaped bacterium. The dry cell weight of P. fluorescens ATCC 11150 as reported by Edwards, et al., 1972, "Continuous Culture of Pseudomonas fluorescens with Sodium Maleate as a Carbon Source," Biotechnology and Bioengineering, Vol. XIV, pages 123-147, is 0.5 grams/liter/A500. This is the same weight reported by Lin, et al., for E. coli at an A550 of 1.0. Light scattering measurements made at 500 nm and at 550 nm are expected to be very similar. The percent of cell weight comprised by total cell protein for P. fluorescens HK44 is described as 55% by, e.g., Yarwood, et al., July 2002, "Noninvasive Quantitative Measurement of Bacterial Growth in Porous Media under Unsaturated-Flow Conditions," Applied and Environmental Microbiology 68(7): 3597-3605. This percentage is similar to or the same as those given for E. coli by the references described above.

In embodiments, the amount of active, soluble, and/or intact recombinant protein of interest produced is about 0.1% to about 95% of the total active, soluble, and/or intact protein produced in a culture. In embodiments, this amount is more than about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total active, soluble, and/or intact protein produced in a culture. In embodiments, this amount is about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total active, soluble, and/or intact protein produced in a culture. In embodiments, this amount is about 5% to about 95%, about 10% to about 85%, about 20% to about 75%, about 30% to about 65%, about 40% to about 55%, about 1% to about 95%, about 5% to about 30%, about 1% to about 10%, about 10% to about 20%, about 20% to about 30%, about 30% to about 40%, about 40% to about 50%, about 50 to about 60%, about 60% to about 70%, or about 80% to about 90% of the total active, soluble, and/or intact protein produced in a culture.

In embodiments, the amount of active, soluble, and/or intact recombinant protein of interest produced is about 0.1% to about 50% of the dry cell weight (DCW). In embodiments, this amount is more than about 0.1%, 0.5%, 1%, 5%, 10%, 15%, 20%, 25%, 30%, 40%, 45%, or 50% of DCW. In embodiments, this amount is about 0.1%, 0.5%, 1%, 5%, 10%, 15%, 20%, 25%, 30%, 40%, 45%, or 50% of DCW. In embodiments, this amount is about 5% to about 50%, about 10% to about 40%, about 20% to about 30%, about 1% to about 20%, about 5% to about 25%, about 1% to about 10%, about 10% to about 20%, about 20% to about 30%, about 30% to about 40%, or about 40% to about 50% of the total active, soluble, and/or intact protein produced in a culture.

In embodiments, the amount of an active, soluble, and/or intact recombinant protein of interest produced using the methods of the invention is greater than the amount of the protein produced by a control host cell under substantially similar conditions, e.g., the same growth conditions. A control host cell may be a host cell that is the same in all respects to the recombinant gram-negative host cell, but that (a) is not deficient in one or more activities deficient in the recombinant gram-negative host cell, (b) does not overexpress one or more chaperones, folding modulators, or inactivated proteases that are overexpressed in the recombinant gram-negative host cell, or (c) any combination of (a) and (b). A control host cell may be a host cell that has the wild-type background of the recombinant gram-negative host cell, but that (a) is not deficient in one or more activities deficient in the recombinant gram-negative host cell, (b) does not overexpress one or more chaperones, folding modulators, or inactivated proteases that are overexpressed in the recombinant gram-negative host cell, or (c) any combination of (a) and (b). In some embodiments, an active, soluble, and/or intact recombinant protein of interest produced according to the present methods using a recombinant gram-negative host cell of the invention, is produced in an amount greater than the amount of the protein produced by a control host cell. In some embodiments, an active, soluble, and/or intact recombinant protein of interest produced by a recombinant gram-negative host cell of the invention is produced at a yield that is about 1.5 fold to about 10 fold. In some embodiments, an active, soluble, and/or intact recombinant protein of interest produced by a recombinant gram-negative host cell of the invention is produced at a yield that is about 1.5 fold to about 2 fold, about 1.5 fold to about 2.5 fold, about 1.5 fold to about 3 fold, about 1.5 fold to about 3.5 fold, about 1.5 fold to about 4 fold, about 1.5 fold to about 5 fold, about 1.5 fold to about 6 fold, about 1.5 fold to about 7 fold, about 1.5 fold to about 8 fold, about 1.5 fold to about 9 fold, about 1.5 fold to about 10 fold, about 2 fold to about 2.5 fold, about 2 fold to about 3 fold, about 2 fold to about 3.5 fold, about 2 fold to about 4 fold, about 2 fold to about 5 fold, about 2 fold to about 6 fold, about 2 fold to about 7 fold, about 2 fold to about 8 fold, about 2 fold to about 9 fold, about 2 fold to about 10 fold, about 2.5 fold to about 3 fold, about 2.5 fold to about 3.5 fold, about 2.5 fold to about 4 fold, about 2.5 fold to about 5 fold, about 2.5 fold to about 6 fold, about 2.5 fold to about 7 fold, about 2.5 fold to about 8 fold, about 2.5 fold to about 9 fold, about 2.5 fold to about 10 fold, about 3 fold to about 3.5 fold, about 3 fold to about 4 fold, about 3 fold to about 5 fold, about 3 fold to about 6 fold, about 3 fold to about 7 fold, about 3 fold to about 8 fold, about 3 fold to about 9 fold, about 3 fold to about 10 fold, about 3.5 fold to about 4 fold, about 3.5 fold to about 5 fold, about 3.5 fold to about 6 fold, about 3.5 fold to about 7 fold, about 3.5 fold to about 8 fold, about 3.5 fold to about 9 fold, about 3.5 fold to about 10 fold, about 4 fold to about 5 fold, about 4 fold to about 6 fold, about 4 fold to about 7 fold, about 4 fold to about 8 fold, about 4 fold to about 9 fold, about 4 fold to about 10 fold, about 5 fold to about 6 fold, about 5 fold to about 7 fold, about 5 fold to about 8 fold, about 5 fold to about 9 fold, about 5 fold to about 10 fold, about 6 fold to about 7 fold, about 6 fold to about 8 fold, about 6 fold to about 9 fold, about 6 fold to about 10 fold, about 7 fold to about 8 fold, about 7 fold to about 9 fold, about 7 fold to about 10 fold, about 8 fold to about 9 fold, about 8 fold to about 10 fold, or about 9 fold to about 10 fold greater than the amount of the protein produced by a control host cell. In some embodiments, an active, soluble, and/or intact recombinant protein of interest produced by a recombinant gram-negative host cell of the invention is produced at a yield that is about 1.5 fold, about 2 fold, about 2.5 fold, about 3 fold, about 3.5 fold, about 4 fold, about 5 fold, about 6 fold, about 7 fold, about 8 fold, about 9 fold, or about 10 fold greater than the amount of the protein produced by a control host cell. In some embodiments, active, soluble, and/or intact recombinant protein of interest produced by a recombinant gram-negative host cell of the invention is produced at a yield that is at least about 1.5 fold, about 2 fold, about 2.5 fold, about 3 fold, about 3.5 fold, about 4 fold, about 5 fold, about 6 fold, about 7 fold, about 8 fold, or about 9 fold greater than the amount of the protein produced by a control host cell. In some embodiments, active, soluble, and/or intact recombinant protein of interest produced by a recombinant gram-negative host cell of the invention is produced at a yield that is at most about 2 fold, about 2.5 fold, about 3 fold, about 3.5 fold, about 4 fold, about 5 fold, about 6 fold, about 7 fold, about 8 fold, about 9 fold, or about 10 fold greater than the amount of the protein produced by a control host cell.

Activity Assays

Assays for evaluating the activity of a recombinant protein of interest are known in the art and include but are not limited to fluorometric, colorometric, chemiluminescent, spectrophotometric, and other enzyme assays available to one of skill in the art. A binding protein such as an antibody, antibody fragment, or derivative thereof may be evaluated by any appropriate target binding assay known in the art. These assays may be used to compare activity of a preparation of a recombinant protein of interest to a commercial or other preparation of the recombinant protein.

In embodiments, activity is represented by the percent active protein in the extract supernatant as compared with the total amount assayed. This is based on the amount of protein determined to be active by the assay relative to the total amount of protein used in assay. In other embodiments, activity is represented by the % activity level of the protein compared to a standard, e.g., native protein. This is based on the amount of active protein in supernatant extract sample relative to the amount of active protein in a standard sample (where the same amount of protein from each sample is used in assay).

In embodiments, about 40% to about 100% of the peptide, polypeptide or protein of interest, is determined to be active. In embodiments, about 40%, about 50%, about 60%, about 70%, about 80%, about 90%, or about 100% of the peptide, polypeptide or protein of interest is determined to be active. In embodiments, about 40% to about 50%, about 50% to about 60%, about 60% to about 70%, about 70% to about 80%, about 80% to about 90%, about 90% to about 100%, about 50% to about 100%, about 60% to about 100%, about 70% to about 100%, about 80% to about 100%, about 40% to about 90%, about 40% to about 95%, about 50% to about 90%, about 50% to about 95%, about 50% to about 100%, about 60% to about 90%, about 60% to about 95%, about 60% to about 100%, about 70% to about 90%, about 70% to about 95%, about 70% to about 100%, or about 70% to about 100% of the peptide, polypeptide or protein of interest is determined to be active.

In other embodiments, about 75% to about 100% of the peptide, polypeptide or protein of interest is determined to be active. In embodiments, about 75% to about 80%, about 75% to about 85%, about 75% to about 90%, about 75% to about 95%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100% of the peptide, polypeptide or protein of interest is determined to be active.

SlmT Secretion Signal Peptide

Compositions and methods for producing high levels of properly processed recombinant proteins or polypeptides in a host cell are provided. In some aspects, a novel secretion signal, Slmt, that promotes the targeting of the recombinant protein or polypeptide of interest to the periplasm of Gram-negative bacteria or into the extracellular environment is provided. The Slmt periplasmic secretion signal peptide disclosed herein enables transport of proteins across the inner membrane to the periplasmic space in Gram negative bacteria. In some aspects, Slmt periplasmic secretion signal peptide provided herein promotes the targeting of the recombinant protein or polypeptide of interest to the extracellular space in Gram-positive bacteria. Periplasmic protein expression allows for proper formation of disulfide bonds in the periplasm and can result in high level recombinant protein expression. Expression to the periplasmic space may enable more efficient recovery/purification of the recombinant protein. For the purposes of the present disclosure, a "secretion signal," "secretion leader," "secretion signal polypeptide," "signal peptide," "leader peptide" or "leader sequence" are intended to refer to a peptide sequence (or the polynucleotide encoding the peptide sequence) that is useful for targeting a protein or polypeptide of interest to a cell compartment, e.g., the periplasm of Gram-negative bacteria or into the extracellular space. The secretion signal sequence includes the Slmt secretion signal (amino acid sequence set forth in SEQ ID NO: 11), and fragments and variants thereof. One example of a nucleotide sequence encoding SEQ ID NO: 11 and useful in the present methods is provided in SEQ ID NO: 12. As known to those of skill in the art, an amino acid sequence can be encoded by different nucleotide sequences due to the redundancy in the genetic code. The compositions and methods of the present invention thus may include the same secretion signal amino acid sequence whilst encoded by different nucleotide sequences. Also provided herein are fragments and variants of the secretion signal peptide sequence that can direct periplasmic expression of an operably linked recombinant protein or polypeptide of interest.

A secretion signal coding sequence that encodes the amino acid sequence as set forth in SEQ ID NO: 11 may be fused to the N-terminus of a sequence encoding a heterologous recombinant protein or polypeptide of interest to be expressed and targeted to the host cell periplasm or into the extracellular space. As used herein with regard to a heterologous secretion signal and protein or polypeptide of interest, a "heterologous" secretion signal peptide is not native to the protein or polypeptide of interest. Conversely, with regard to a secretion signal peptide, a "heterologous" protein or polypeptide of interest is not native to the secretion signal. With regard to SEQ ID NO: 11, a heterologous protein or polypeptide of interest is one that is not *P. fluorescens* Soluble lytic murein transglycosylase (SlmT). With regard to a construct comprising a secretion signal coding sequence that encodes the amino acid sequence as set forth in SEQ ID NO: 11, a sequence encoding a heterologous protein or polypeptide of interest is one that does not encode *P. fluorescens* Soluble lytic murein transglycosylase (SlmT). In the context of the host cell, the term heterologous may refer to a protein or polypeptide of interest that is not native to a particular host cell.

The invention includes a method of producing a protein or polypeptide of interest in a prokaryotic host cell, comprising producing the protein or polypeptide of interest in the periplasm of a prokaryotic host cell cultured in a cell culture growth medium, wherein the prokaryotic host cell comprises an expression construct comprising a nucleic acid encoding a recombinant polypeptide comprising the protein or polypeptide of interest operably linked to a secretion signal peptide that directs expression of the protein or polypeptide of interest to the periplasm of the prokaryotic host cell, wherein the secretion signal peptide comprises the amino acid sequence of SEQ ID NO: 11, and wherein the secretion signal peptide is not native to the protein or polypeptide of interest.

In some embodiments, the protein or polypeptide of interest is expressed in the periplasm properly cleaved from the secretion signal peptide, e.g., SEQ ID NO: 11. In some embodiments, the secretion signal peptide directs expression of the protein or polypeptide of interest to the periplasm or the extracellular space of a prokaryotic host cell in properly cleaved form, soluble form, active form, or any combination thereof. A correctly or properly cleaved or processed protein or polypeptide of interest may have an intact or substantially intact N-terminus. In some embodiments, the properly cleaved protein or polypeptide of interest having an intact or substantially intact N-terminus comprises the N-terminal methionine. In some embodiments, the properly cleaved protein or polypeptide of interest having an intact or substantially intact N-terminus does not comprise the N-terminal methionine. A protein or polypeptide of interest may require a substantially intact N-terminus for activity, solubility, or both. In some embodiments, a protein or polypeptide of interest has about 80-100% activity when compared to a control. In some embodiments, the control is the same protein or polypeptide of interest that comprises an N-terminal methionine. In some embodiments, the control is the same protein or polypeptide of interest that does not comprise an N-terminal methionine. In some embodiments, the control is the same protein or polypeptide of interest that has a substantially intact N-terminus. In some embodiments, the expressed or produced protein or polypeptide of interest has an activity relative to a control of about 80% to about 100%. In some embodiments, a protein or polypeptide of interest having a substantially intact N-terminus has an activity relative to a control of about 80% to about 85%, about 80% to about 90%, about 80% to about 92%, about 80% to about 94%, about 80% to about 95%, about 80% to about 96%, about 80% to about 97%, about 80% to about 98%, about 80% to about 99%, about 80% to about 100%, about 85% to about 90%, about 85% to about 92%, about 85% to about 94%, about 85% to about 95%, about 85% to about 96%, about 85% to about 97%, about 85% to about 98%, about 85% to about 99%, about 85% to about 100%, about 90% to about 92%, about 90% to about 94%, about 90% to about 95%, about 90% to about 96%, about 90% to about 97%, about 90% to about 98%, about 90% to about 99%, about 90% to about 100%, about 92% to about 94%, about 92% to about 95%, about 92% to about 96%, about 92% to about 97%, about 92% to about 98%, about 92% to about 99%, about 92% to about 100%, about 94% to about 95%, about 94% to about 96%, about 94% to about 97%, about 94% to about 98%, about 94% to about 99%, about 94% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100%. In some embodiments, a protein or polypeptide of interest having a substantially intact N-terminus has an activity relative to a control of about 80%, about 85%, about 90%, about 92%, about 94%, about 95%, about 96%, about 97%, about 98%, about 99%, or about 100%. In some embodiments, a protein or polypeptide of interest having a substantially intact N-terminus has an activity relative to a control of at least about 80%, about 85%, about 90%, about 92%, about 94%, about 95%, about 96%, about 97%, about 98%, or about 99%. In some embodiments, a protein or polypeptide of interest having a substantially intact N-terminus has an activity relative to a control of at most about 85%, about 90%, about 92%, about 94%, about 95%, about 96%, about 97%, about 98%, about 99%, or about 100%.

In some embodiments, the process produces correctly processed periplasmic or extracellular protein at about 0.1 g/L to about 50 g/L. In some embodiments, the process produces correctly processed periplasmic or extracellular protein at about 0.1 g/L to about 3 g/L. In some embodiments, the process produces correctly processed periplasmic or extracellular protein at about 0.1 g/L to about 0.2 g/L, about 0.1 g/L to about 0.3 g/L, about 0.1 g/L to about 0.4 g/L, about 0.1 g/L to about 0.5 g/L, about 0.1 g/L to about 0.6 g/L, about 0.1 g/L to about 0.7 g/L, about 0.1 g/L to about 0.8 g/L, about 0.1 g/L to about 0.9 g/L, about 0.1 g/L to about 1 g/L, about 0.1 g/L to about 2 g/L, about 0.1 g/L to about 3 g/L, about 0.2 g/L to about 0.3 g/L, about 0.2 g/L to about 0.4 g/L, about 0.2 g/L to about 0.5 g/L, about 0.2 g/L to about 0.6 g/L, about 0.2 g/L to about 0.7 g/L, about 0.2 g/L to about 0.8 g/L, about 0.2 g/L to about 0.9 g/L, about 0.2 g/L to about 1 g/L, about 0.2 g/L to about 2 g/L, about 0.2 g/L to about 3 g/L, about 0.3 g/L to about 0.4 g/L, about 0.3 g/L to about 0.5 g/L, about 0.3 g/L to about 0.6 g/L, about 0.3 g/L to about 0.7 g/L, about 0.3 g/L to about 0.8 g/L, about 0.3 g/L to about 0.9 g/L, about 0.3 g/L to about 1 g/L, about 0.3 g/L to about 2 g/L, about 0.3 g/L to about 3 g/L, about 0.4 g/L to about 0.5 g/L, about 0.4 g/L to about 0.6 g/L, about 0.4 g/L to about 0.7 g/L, about 0.4 g/L to about 0.8 g/L, about 0.4 g/L to about 0.9 g/L, about 0.4 g/L to about 1 g/L, about 0.4 g/L to about 2 g/L, about 0.4 g/L to about 3 g/L, about 0.5 g/L to about 0.6 g/L, about 0.5 g/L to about 0.7 g/L, about 0.5 g/L to about 0.8 g/L, about 0.5 g/L to about 0.9 g/L, about 0.5 g/L to about 1 g/L, about 0.5 g/L to about 2 g/L, about 0.5 g/L to about 3 g/L, about 0.6 g/L to about 0.7 g/L, about 0.6 g/L to about 0.8 g/L, about 0.6 g/L to about 0.9 g/L, about 0.6 g/L to about 1 g/L, about 0.6 g/L to about 2 g/L, about 0.6 g/L to about 3 g/L, about 0.7 g/L to about 0.8 g/L, about 0.7 g/L to about 0.9 g/L, about 0.7 g/L to about 1 g/L, about 0.7 g/L to about 2 g/L, about 0.7 g/L to about 3 g/L, about 0.8 g/L to about 0.9 g/L, about 0.8 g/L to about 1 g/L, about 0.8 g/L to about 2 g/L, about 0.8 g/L to about 3 g/L, about 0.9 g/L to about 1 g/L, about 0.9 g/L to about 2 g/L, about 0.9 g/L to about 3 g/L, about 1 g/L to about 2 g/L, about 1 g/L to about 3 g/L, or about 2 g/L to about 3 g/L. In some embodiments, the process produces correctly processed periplasmic or extracellular protein at about 0.1 g/L, about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 2 g/L, or about 3 g/L. In some embodiments, the process produces correctly processed periplasmic or extracellular protein at at least about 0.1 g/L, about 0.2 g/L, about 0.3 g/L, about 0.4 g/L, about 0.5 g/L, about 0.6 g/L, about 0.7 g/L, about 0.8 g/L, about 0.9 g/L, about 1 g/L, or about 2 g/L. In some embodiments, the process produces correctly processed periplasmic or extracellular protein at most about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 2 g/L, or about 3 g/L. In some embodiments, the process produces correctly processed periplasmic or extracellular protein at about 0.1 g/L to about 50 g/L. In some embodiments, the process produces correctly processed periplasmic or extracellular protein at about 0.1 g/L to about 0.5 g/L, about 0.1 g/L to about 1 g/L, about 0.1 g/L to about 2 g/L, about 0.1 g/L to about 5 g/L, about 0.1 g/L to about 10 g/L, about 0.1 g/L to about 15 g/L, about 0.1 g/L to about 20 g/L, about 0.1 g/L to about 25 g/L, about 0.1 g/L to about 30 g/L, about 0.1 g/L to about 40 g/L, about 0.1 g/L to about 50 g/L, about 0.5 g/L to about 1 g/L, about 0.5 g/L to about 2 g/L, about 0.5 g/L to about 5 g/L, about 0.5 g/L to about 10 g/L, about 0.5 g/L to about 15 g/L, about 0.5 g/L to about 20 g/L, about 0.5 g/L to about 25 g/L, about 0.5 g/L to about 30 g/L, about 0.5 g/L to about 40 g/L, about 0.5 g/L to about 50 g/L, about 1 g/L to about 2 g/L, about 1 g/L to about 5 g/L, about 1 g/L to about 10 g/L, about 1 g/L to about 15 g/L, about 1 g/L to about 20 g/L, about 1 g/L to about 25 g/L, about 1 g/L to about 30 g/L, about 1 g/L to about 40 g/L, about 1 g/L to about 50 g/L, about 2 g/L to about 5 g/L, about 2 g/L to about 10 g/L, about 2 g/L to about 15 g/L, about 2 g/L to about 20 g/L, about 2 g/L to about 25 g/L, about 2 g/L to about 30 g/L, about 2 g/L to about 40 g/L, about 2 g/L to about 50 g/L, about 5 g/L to about 10 g/L, about 5 g/L to about 15 g/L, about 5 g/L to about 20 g/L, about 5 g/L to about 25 g/L, about 5 g/L to about 30 g/L, about 5 g/L to about 40 g/L, about 5 g/L to about 50 g/L, about 10 g/L to about 15 g/L, about 10 g/L to about 20 g/L, about 10 g/L to about 25 g/L, about 10 g/L to about 30 g/L, about 10 g/L to about 40 g/L, about 10 g/L to about 50 g/L, about 15 g/L to about 20 g/L, about 15 g/L to about 25 g/L, about 15 g/L to about 30 g/L, about 15 g/L to about 40 g/L, about 15 g/L to about 50 g/L, about 20 g/L to about 25 g/L, about 20 g/L to about 30 g/L, about 20 g/L to about 40 g/L, about 20 g/L to about 50 g/L, about 25 g/L to about 30 g/L, about 25 g/L to about 40 g/L, about 25 g/L to about 50 g/L, about 30 g/L to about 40 g/L, about 30 g/L to about 50 g/L, or about 40 g/L to about 50 g/L. In some embodiments, the process produces correctly processed periplasmic or extracellular protein at about 0.1 g/L, about 0.5 g/L, about 1 g/L, about 2 g/L, about 5 g/L, about 10 g/L, about 15 g/L, about 20 g/L, about 25 g/L, about 30 g/L, about 40 g/L, or about 50 g/L. In some embodiments, the process produces correctly processed periplasmic or extracellular protein at at least about 0.1 g/L, about 0.5 g/L, about 1 g/L, about 2 g/L, about 5 g/L, about 10 g/L, about 15 g/L, about 20 g/L, about 25 g/L, about 30 g/L, or about 40 g/L. In some embodiments, the process produces correctly processed periplasmic or extracellular protein at at most about 0.5 g/L, about 1 g/L, about 2 g/L, about 5 g/L, about 10 g/L, about 15 g/L, about 20 g/L, about 25 g/L, about 30 g/L, about 40 g/L, or about 50 g/L.

In some embodiments, the % of total recombinant protein or polypeptide that is produced in correctly processed form is about 5 to about 100. In some embodiments, the % of total recombinant protein or polypeptide that is produced in correctly processed form is about 5 to about 10, about 5 to about 20, about 5 to about 30, about 5 to about 40, about 5 to about 50, about 5 to about 60, about 5 to about 70, about 5 to about 80, about 5 to about 90, about 5 to about 95, about 5 to about 100, about 10 to about 20, about 10 to about 30, about 10 to about 40, about 10 to about 50, about 10 to about 60, about 10 to about 70, about 10 to about 80, about 10 to about 90, about 10 to about 95, about 10 to about 100, about 20 to about 30, about 20 to about 40, about 20 to about 50, about 20 to about 60, about 20 to about 70, about 20 to about 80, about 20 to about 90, about 20 to about 95, about 20 to about 100, about 30 to about 40, about 30 to about 50, about 30 to about 60, about 30 to about 70, about 30 to about 80, about 30 to about 90, about 30 to about 95, about 30 to about 100, about 40 to about 50, about 40 to about 60, about 40 to about 70, about 40 to about 80, about 40 to about 90, about 40 to about 95, about 40 to about 100, about 50 to about 60, about 50 to about 70, about 50 to about 80, about 50 to about 90, about 50 to about 95, about 50 to about 100, about 60 to about 70, about 60 to about 80, about 60 to about 90, about 60 to about 95, about 60 to about 100, about 70 to about 80, about 70 to about 90, about 70 to about 95, about 70 to about 100, about 80 to about 90, about 80 to about 95, about 80 to about 100, about 90 to about 95, about 90 to about 100, or about 95 to about 100. In some embodiments, the % of total recombinant protein or polypeptide that is produced in correctly processed form is about 5, about 10, about 20, about 30, about 40, about 50, about 60, about 70, about 80, about 90, about 95, or about 100. In some embodiments, the % of total recombinant protein or polypeptide that is produced in correctly processed form is at least about 5, about 10, about 20, about 30, about 40, about 50, about 60, about 70, about 80, about 90, or about 95. In some embodiments, the % of total recombinant protein or polypeptide that is produced in correctly processed form is at most about 10, about 20, about 30, about 40, about 50, about 60, about 70, about 80, about 90, about 95, or about 100.

The following patents and patent applications are incorporated herein by reference in their entirety, including as they relate to processing/cleavage and periplasmic expression of recombinant proteins and polypeptides fused to secretion signal peptides: U.S. Pat. No. 7,618,799, "Bacterial leader sequences for increased expression," in U.S. Pat. No. 7,985,564, "Expression systems with Sec-system secretion," in U.S. Pat. Nos. 9,394,571 and 9,580,719, both titled "Method for Rapidly Screening Microbial Hosts to Identify Certain Strains with Improved Yield and/or Quality in the Expression of Heterologous Proteins," U.S. Pat. No. 9,453,251, "Expression of Mammalian Proteins in *Pseudomonas fluorescens*," U.S. Pat. No. 8,603,824, "Process for Improved Protein Expression by Strain Engineering," and U.S. Pat. No. 8,530,171, "High Level Expression of Recombinant Toxin Proteins," and U.S. Pat. Pub. No. 2019/0127744, "Bacterial Leader Sequences for Periplasmic Protein Expression."

In embodiments, the secretion signal sequence is identical to or substantially identical to a secretion signal peptide set forth in SEQ ID NO: 11, and/or is encoded by a polynucleotide sequence set forth in SEQ ID NO: 12. In another embodiment, the secretion signal sequence comprises at least amino acids 2-29 of SEQ ID NO: 11. In yet another embodiment, the secretion signal sequence comprises a fragment of SEQ ID NO: 11, which is truncated by 1, 2, 3, 4, 5, 6, 7, 8, 9, or 10 amino acids from the amino terminus but retains biological activity, i.e., secretion signal activity.

In one embodiment the amino acid sequence of the peptide is a variant of a given original peptide, wherein the sequence of the variant is obtainable by replacing up to or about 30% of the original peptide's amino acid residues with other amino acid residue(s), including up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, provided that the variant retains the desired function of the original peptide. A variant amino acid with substantial homology will be at least about 70%, at least about 75%, at least about 80%, about 85%, about 90%, about 95%, about 96%, about 97%, about 98%, or at least about 99% homologous to the original peptide. A variant amino acid sequence may be obtained in various ways including amino acid substitutions, deletions, truncations, and insertions of one or more amino acids of SEQ ID NO: 11. In some embodiments, a variant amino acid sequence comprises 1-9 amino acid substitutions, deletions, insertions, or any combination thereof. In some embodiments, the number of amino acid substitutions, deletions, insertions, or any combination thereof, in a variant of SEQ ID NO: 11, is 1 to 10. In some embodiments, the number of amino acid substitutions, deletions, insertions, or any combination thereof, in a variant of SEQ ID NO: 11, is 1 to 2, 1 to 3, 1 to 4, 1 to 5, 1 to 6, 1 to 7, 1 to 8, 1 to 9, 1 to 10, 2 to 3, 2 to 4, 2 to 5, 2 to 6, 2 to 7, 2 to 8, 2 to 9, 2 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10. In some embodiments, the number of amino acid substitutions, deletions, insertions, or any combination thereof, in a variant of SEQ ID NO: 11, is 1, 2, 3, 4, 5, 6, 7, 8, 9, or 10. In some embodiments, the number of amino acid substitutions, deletions, insertions, or any combination thereof, in a variant of SEQ ID NO: 11, is at least 1, 2, 3, 4, 5, 6, 7, 8, or 9. In some embodiments, the number of amino acid substitutions, deletions, insertions, or any combination thereof, in a variant of SEQ ID NO: 11, is at most 2, 3, 4, 5, 6, 7, 8, 9, or 10.

By "substantially homologous," "substantially identical," or "substantially similar" is intended an amino acid or nucleotide sequence that has about or at least about 60%, about or at least about 65%, about or at least about 70%, about or at least about 75%, about or at least about 80%, about or at least about 85%, about or at least about 81%, about or at least about 82%, about or at least about 83%, about or at least about 84%, about or at least about 85%, about or at least about 86%, about or at least about 87%, about or at least about 88%, about or at least about 89%, about or at least about 90%, about or at least about 91%, about or at least about 92%, about or at least about 93%, about or at least about 94%, about or at least about 95%, about or at least about 96%, about or at least about 97%, about or at least about 98% or about or at least about 99%, or greater sequence identity as compared to a reference sequence using a suitable alignment program described herein or known in the art using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

In embodiments, a secretion signal peptide used in the present invention may include one or more modifications of a "non-essential" amino acid residue. In this context, a "non-essential" amino acid residue is a residue that can be altered, e.g., deleted, substituted, or derivatized, in the novel amino acid sequence without abolishing or substantially reducing the activity (e.g., the agonist activity) of the original secretion signal peptide (also referred to as the "analog" or "reference" peptide). In some embodiments, a secretion signal peptide may include one or more modifications of an "essential" amino acid residue. In this context, an "essential" amino acid residue is a residue that when altered, e.g., deleted, substituted, or derivatized, in the novel amino acid sequence the activity of the reference peptide is substantially reduced or abolished. In such embodiments where an essential amino acid residue is altered, the modified secretion signal peptide may possess an activity of the original secretion signal. The substitutions, insertions and deletions may be at the N-terminal or C-terminal end, or may be at internal portions of the secretion signal. By way of example, the secretion signal peptide may include 1, 2, 3, 4, 5, 6, 7, 8, 9, 10, or more substitutions, both in a consecutive manner or spaced throughout the secretion signal peptide. Alone or in combination with the substitutions, the secretion signal peptide may include 1, 2, 3, 4, 5, 6, 7, 8, 9, 10, or more insertions, again either in consecutive manner or spaced throughout the secretion signal peptide. The secretion signal peptide, alone or in combination with the substitutions and/or insertions, may also include 1, 2, 3, 4, 5, 6, 7, 8, 9, 10, or more deletions, again either in consecutive manner or spaced throughout the peptide. The secretion signal peptide, alone or in combination with the substitutions, insertions and/or deletions, may also include 1, 2, 3, 4, 5, 6, 7, 8, 9, 10, or more amino acid additions.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or unnatural. Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

Variant proteins or polypeptide of interest encompassed herein are biologically active, that is they continue to possess the desired biological activity of the original protein or polypeptide of interest; for example, a variant secretion leader peptide retains secretion signal activity. By "retains activity" is intended that the variant will have about or at least about 30%, about or at least about 35%, about or at least about 40%, about or at least about 45%, about or at least about 50%, about or at least about 55%, about or at least about 60%, about or at least about 65%, about or at least about 70%, about or at least about 75%, about or at least about 80%, about or at least about 85%, about or at least about 81%, about or at least about 82%, about or at least about 83%, about or at least about 84%, about or at least about 85%, about or at least about 86%, about or at least about 87%, about or at least about 88%, about or at least about 89%, about or at least about 90%, about or at least about 91%, about or at least about 92%, about or at least about 93%, about or at least about 94%, about or at least about 95%, about or at least about 96%, about or at least about 97%, about or at least about 98% or about or at least about 99%, about or at least about 100%, about or at least about 110%, about or at least about 125%, about or at least about 150%, about or at least about 200% or greater activity, e.g., secretion signal activity, of the original peptide, protein, or polypeptide.

Polynucleotides

The disclosure also includes a nucleic acid with a sequence that encodes a novel secretion signal useful for targeting a protein or polypeptide of interest to the periplasm of Gram-negative bacteria or into the extracellular space. In one embodiment, the isolated polynucleotide encodes a peptide sequence substantially homologous to a Slmt secretion signal peptide. In another embodiment, the present disclosure provides a nucleic acid that encodes a peptide sequence having substantial sequence identity to at least amino acids 2-29 of SEQ ID NO: 11, or provides a nucleic acid having substantial sequence identity to a nucleotide sequence set forth as SEQ ID NO: 12, including biologically active variants and fragments thereof. In another embodiment, the nucleic acid sequence has about or at least about 60%, about or at least about 65%, about or at least about 70%, about or at least about 75%, about or at least about 80%, about or at least about 85%, about or at least about 81%, about or at least about 82%, about or at least about 83%, about or at least about 84%, about or at least about 85%, about or at least about 86%, about or at least about 87%, about or at least about 88%, about or at least about 89%, about or at least about 90%, about or at least about 91%, about or at least about 92%, about or at least about 93%, about or at least about 94%, about or at least about 95%, about or at least about 96%, about or at least about 97%, about or at least about 98% or about or at least about 99%, or greater identity to a nucleic acid sequence set forth as SEQ ID NO: 12.

In embodiments, secretion signal peptides herein are encoded by a nucleotide sequence substantially identical to a nucleotide sequence set forth as SEQ ID NO: 12. Corresponding secretion signal peptide sequences having substantial identity to the secretion signal sequences of the present invention can be identified using any appropriate method known in the art, e.g., PCR, hybridization methods, or as described in the literature. See, for example, Sambrook J., and Russell, D. W., 2001, Molecular Cloning: A Laboratory Manual. Cold Spring Harbor Laboratory Press, Cold Spring Harbor, N.Y.; and Innis, et al., 1990, PCR Protocols: A Guide to Methods and Applications; Academic Press, NY. A variant nucleotide sequence can include a synthetically derived nucleotide sequence that has been generated, for example, by using site-directed mutagenesis. In embodiments, a mutagenized sequence still encodes the secretion signal peptides disclosed herein. Variant secretion signal peptides are biologically active, that is, they continue to possess the desired biological activity of the native protein, that is, they retain secretion signaling activity. By "retains activity" is meant that the variant will have about 30%, about or at least about 35%, about or at least about 40%, about or at least about 45%, about or at least about 50%, about or at least about 55%, about or at least about 60%, about or at least about 65%, about or at least about 70%, about or at least about 75%, about or at least about 80%, about or at least about 85%, about or at least about 81%, about or at least about 82%, about or at least about 83%, about or at least about 84%, about or at least about 85%, about or at least about 86%, about or at least about 87%, about or at least about 88%, about or at least about 89%, about or at least about 90%, about or at least about 91%, about or at least about 92%, about or at least about 93%, about or at least about 94%, about or at least about 95%, about or at least about 96%, about or at least about 97%, about or at least about 98% or about or at least about 99%, about or at least about 100%, about or at least about 110%, about or at least about 125%, about or at least about 150%, about or at least about 200% or greater of the activity of the original secretion signal peptide. Any appropriate method may be used for measuring peptide, protein, or polypeptide activity, e.g., secretion signal activity. Such methods are well known in the art, with examples discussed herein.

The skilled artisan will further appreciate that changes, in some cases, are introduced by mutation into the nucleotide sequences provided herein thereby leading to changes in the amino acid sequence of the encoded secretion signal peptides, without altering the biological activity of the secretion signal peptides. Thus, variant isolated nucleic acid molecules are often created by introducing one or more nucleotide substitutions, additions, or deletions into the corresponding nucleotide sequence disclosed herein, such that one or more amino acid substitutions, additions or deletions are introduced into the encoded protein. Mutations can be introduced by any standard technique known to those of skill in the art, e.g., site-directed mutagenesis and PCR-mediated mutagenesis.

Nucleic acid and amino acid sequence identity or homology may be determined according to any suitable method known in the art, including but not limited to those described herein.

Methods herein, in some cases, comprise expressing polypeptides comprising a protein or polypeptide of interest operably linked to a secretion signal peptide selected from the group consisting of an Slmt secretion signal sequence, or a sequence that is substantially homologous or similar to the secretion signal peptide sequence disclosed herein as SEQ ID NO: 11. In embodiments, the secretion signal peptide sequence is encoded by a nucleotide sequence set forth as SEQ ID NO: 12. In some embodiments, an expression construct is in a *Pseudomonad* host cell. The expression construct, in some cases, is a plasmid. In some embodiments, a plasmid encoding the polypeptide or protein of interest sequence comprises a selection marker, and host cells maintaining the plasmid are grown under selective conditions. In some embodiments, the plasmid does not comprise a selection marker. In some embodiments, the expression construct is integrated into the host cell genome.

The invention includes an expression construct for producing a recombinant polypeptide comprising a secretion signal peptide operably linked to a heterologous protein or polypeptide of interest. The expression construct may comprise: a nucleic acid sequence encoding a secretion signal peptide identical or substantially identical to the amino acid sequence set forth in SEQ ID NO: 11, operably linked to a nucleic acid sequence encoding the protein or polypeptide of interest. In some embodiments, the nucleic acid sequence encoding a secretion signal peptide identical or substantially identical to the amino acid sequence set forth in SEQ ID NO: 11 has a sequence that is identical or substantially identical to the nucleic acid sequence set forth as SEQ ID NO: 12. In some embodiments, the nucleic acid sequence has at least 85%, at least 90%, or at least 95% sequence identity to the nucleic acid sequence set forth as SEQ ID NO: 12.

The expression vector may comprise an expression construct comprising a nucleic acid sequence encoding a secretion signal peptide identical or substantially identical to the amino acid sequence set forth in SEQ ID NO: 11, operably linked to a nucleic acid sequence encoding the protein or polypeptide of interest. In some embodiments, the nucleic acid sequence encoding a secretion signal peptide identical or substantially identical to the amino acid sequence set forth in SEQ ID NO: 11 has a sequence that is identical or substantially identical to the nucleic acid sequence set forth as SEQ ID NO: 12. In some embodiments, the nucleic acid sequence has at least 85%, at least 90%, or at least 95% sequence identity to the nucleic acid sequence set forth as SEQ ID NO: 12.

Methods for expressing heterologous proteins, including regulatory sequences (e.g., promoters, secretion leaders, and ribosome binding sites) useful in the methods of the invention in host strains, including *Pseudomonas* host strains, may be used as disclosed herein throughout. Such methods are known in the art and are described, e.g., in U.S. Pat. No. 7,618,799, "Bacterial leader sequences for increased expression," in U.S. Pat. No. 7,985,564, "Expression systems with Sec-system secretion," in U.S. Pat. Nos. 9,394,571 and 9,580,719, both titled "Method for Rapidly Screening Microbial Hosts to Identify Certain Strains with Improved Yield and/or Quality in the Expression of Heterologous Proteins," U.S. Pat. Nos. 9,458,487 and 9,453,251, both entitled "Expression of mammalian proteins in *Pseudomonas fluorescens*," U.S. Pat. No. 8,603,824, "Process for Improved Protein Expression by Strain Engineering," and U.S. Pat. No. 8,530,171, "High Level Expression of Recombinant Toxin Proteins," each incorporated herein by reference in its entirety. In embodiments, a secretion leader used in the context of the present invention is a secretion leader as disclosed in any of U.S. Pat. Nos. 7,618,799, 7,985,564, 9,394,571, 9,580,719, 9,453,251, 8,603,824, and 8,530,171. These patents also describe bacterial host strains useful in practicing the methods herein, that have been engineered to overexpress folding modulators or wherein protease mutations have been introduced, in order to increase heterologous protein expression. In embodiments, an expression host cell used in the methods of the invention is any described herein.

Exemplary Embodiments

1. A recombinant gram-negative bacterial host cell for recombinant protein expression, wherein the host cell is:
   (a) deficient in a first protease activity, wherein the first protease activity is tail-specific protease activity, wherein the deficient first protease activity results from a mutation in at least one gene encoding a tail-specific protease;
   (b) deficient in a second protease activity, wherein the second protease activity is murein DD-endopeptidase activity, wherein the deficient second protease activity results from a mutation in at least one gene encoding a murein DD-endopeptidase.

2. The recombinant gram-negative bacterial host cell of embodiment 1, wherein the host cell further: (c) is deficient in at least one additional protease activity, wherein the deficient additional protease activity results from a mutation in at least one gene encoding an additional protease, wherein the additional protease is different from the proteases of (a) and (b);
   (d) is deficient in one or more autolytic factor activity, wherein the deficient autolytic factor activity results from a mutation in at least one gene encoding an autolytic factor;
   (e) overexpresses one or more inactivated protease;
   (f) overexpresses one or more folding modulator; or
   (g) any combination of (c), (d), (e) and (f).

3. The recombinant gram-negative bacterial host cell of embodiment 1 or 2, wherein the deficient tail-specific protease activity results from a mutation in a gene encoding one or more of: (i) a Prc1 tail-specific protease having the amino acid sequence set forth as SEQ ID NO: 33, a homologue of SEQ ID NO: 33, or a Prc1 tail-specific protease related protein having an amino acid sequence at least 30% similar to SEQ ID NO: 33; (ii) a Prc2 tail-specific protease having the amino acid sequence set forth as SEQ ID NO: 35, a homologue of SEQ ID NO: 35, or a Prc2 tail-specific protease related protein having an amino acid sequence at least 30% similar to SEQ ID NO: 35; or (iii) a Tsp tail-specific protease having the amino acid sequence set forth as SEQ ID NO: 71, a homologue of SEQ ID NO: 71, or an Tsp tail-specific protease related protein having an amino acid sequence at least 30% similar to SEQ ID NO: 71.

4. The recombinant gram-negative bacterial host cell of any one of embodiments 1-3, wherein the deficient murein DD-endopeptidase activity results from a mutation in a gene encoding one or more of:

(i) a MepM1 murein DD-endopeptidase having the amino acid sequence set forth as SEQ ID NO: 1, a homologue of SEQ ID NO: 1, or a murein DD-endopeptidase related protein having an amino acid sequence at least 30% similar to SEQ ID NO: 1;

(ii) a MepM murein DD-endopeptidase having the amino acid sequence set forth as SEQ ID NO: 63, a homologue of SEQ ID NO: 63, or a murein DD-endopeptidase related protein having an amino acid sequence at least 30% similar to SEQ ID NO: 63;

(iii) a MepM1 murein DD-endopeptidase having the amino acid sequence set forth as SEQ ID NO: 65, a homologue of SEQ ID NO: 65, or a murein DD-endopeptidase related protein having an amino acid sequence at least 30% similar to SEQ ID NO: 65; and (iv) a MepM1 murein DD-endopeptidase having the amino acid sequence set forth as SEQ ID NO: 66, a homologue of SEQ ID NO: 66, or a murein DD-endopeptidase related protein having an amino acid sequence at least 30% similar to SEQ ID NO: 66.

5. The recombinant gram-negative bacterial host cell of any one of embodiments 2-4, wherein: the host cell of (c) is deficient in 1 to 10 different additional protease activities; the host cell of (d) is deficient in 1-5 different autolytic factor activities; the host cell of (e) overexpresses 1 to 10 different inactivated proteases, wherein each inactivated protease is different; the host cell of (f) overexpresses 1-10 different folding modulators, or any combination thereof.

6. The recombinant gram-negative bacterial host cell of any one of embodiments 2-5, wherein:

the one or more deficient additional protease activity of (c) results from a mutation of at least one gene encoding an additional protease independently selected from: a serralysin precursor, a membrane-localized protease, a murein L,D transpeptidase, a hemolysin precursor, a D-alanyl-D-alanine carboxypeptidase/endopeptidase AmpH precursor, a periplasmic serine endoprotease, an AAA+ family proteolytic machine, and a murein DD-endopeptidase different from that of (a);

the one or more deficient autolytic factor activity of (d) results from a mutation of at least one gene encoding an autolytic factor independently selected from: an S-type pyocin, a linear gramicidin synthase subunit D, a hemolysin precursor, a leukotoxin, and a porin;

the one or more inactivated protease of (e) is a mutant periplasmic serine endoprotease; and the one or more folding modulator of (f) is a disulfide isomerase.

7. The recombinant gram-negative bacterial host cell of embodiment 6, wherein:

the serralysin precursor is selected from:

a serralysin precursor having the amino acid sequence set forth as SEQ ID NO: 9; a homologue of the serralysin precursor having the amino acid sequence set forth as SEQ ID NO: 9; a serralysin precursor related protein having at least 60% similarity or at least 60% identity to the amino acid sequence set forth as SEQ ID NO: 9;

a serralysin precursor having the amino acid sequence set forth as SEQ ID NO: 47; a homologue of the serralysin precursor having the amino acid sequence set forth as SEQ ID NO: 47; and a serralysin precursor related protein having at least 60% similarity or at least 60% identity to the amino acid sequence set forth as SEQ ID NO: 47;

the membrane-localized protease is an HtpX having the amino acid sequence set forth as SEQ ID NO: 39, a homologue of the HtpX having the amino acid sequence set forth as SEQ ID NO: 39, or an HtpX related protein having at least 60% similarity or at least 60% identity to the amino acid sequence set forth as SEQ ID NO: 39;

the murein L,D transpeptidase is a murein L,D transpeptidase having the amino acid sequence set forth as SEQ ID NO: 41, a homologue of the murein L,D transpeptidase having the amino acid sequence set forth as SEQ ID NO: 41, or a murein L,D transpeptidase related protein having at least 60% similarity or at least 60% identity to the amino acid sequence set forth as SEQ ID NO: 41;

the hemolysin precursor is a hemolysin precursor having the amino acid sequence set forth as SEQ ID NO: 43, a homologue of the hemolysin precursor having the amino acid sequence set forth as SEQ ID NO: 43, or a hemolysin precursor related protein having at least 60% similarity or at least 60% identity to the amino acid sequence set forth as SEQ ID NO: 43;

the D-alanyl-D-alanine carboxypeptidase/endopeptidase AmpH precursor is a D-alanyl-D-alanine carboxypeptidase/endopeptidase AmpH precursor having the amino acid sequence set forth as SEQ ID NO: 45, a homologue of the D-alanyl-D-alanine carboxypeptidase/endopeptidase AmpH precursor having the amino acid sequence set forth as SEQ ID NO: 45, or a D-alanyl-D-alanine carboxypeptidase/endopeptidase AmpH precursor related protein having at least 60% similarity or at least 60% identity to the amino acid sequence set forth as SEQ ID NO: 45;

the periplasmic serine endoprotease is selected from:

a DegP2 having the amino acid sequence set forth as SEQ ID NO: 31; a homologue of the DegP2 having the amino acid sequence set forth as SEQ ID NO: 31; a DegP2 related protein having at least 60% similarity or at least 60% identity to the amino acid sequence set forth as SEQ ID NO: 31;

a DegP having the amino acid sequence set forth as SEQ ID NO: 69; a homologue of the DegP having the amino acid sequence set forth as SEQ ID NO: 69; a DegP related protein having at least 60% similarity or at least 60% identity to the amino acid sequence set forth as SEQ ID NO: 69; a DegP having the amino acid sequence set forth as SEQ ID NO: 62; a homologue of the DegP having the amino acid sequence set forth as SEQ ID NO: 62; and a DegP related protein having at least 60% similarity or at least 60% identity to the amino acid sequence set forth as SEQ ID NO: 62; the AAA+ family proteolytic machine comprises: an HslU protease having the amino acid sequence set forth as SEQ ID NO: 37, a homologue of the HslU protease having the amino acid sequence set forth as SEQ ID NO: 37, or a HslU related protein having at least 60% similarity or at least 60% identity to the amino acid sequence set forth as SEQ ID NO: 37; and an HslV protease having the amino acid sequence set forth as SEQ ID NO: 38, a homologue of the HslV protease having the amino acid sequence set forth as SEQ ID NO: 38, or a HslV related protein having at least 60% similarity or at least 60% identity to the amino acid sequence set forth as SEQ ID NO: 38; the murein DD-endopeptidase is selected from:

a *P. fluorescens* MepM2 protease having the amino acid sequence set forth as SEQ ID NO: 3; a homologue of the MepM2 protease having the amino acid sequence set forth as SEQ ID NO: 3; a MepM2-related protein having at least 60% similarity or at least 60% identity to the amino acid sequence set forth as SEQ ID NO: 3;

a MepM2 protease having the amino acid sequence set forth as SEQ ID NO: 64; a homologue of the MepM2 protease having the amino acid sequence set forth as SEQ ID NO: 64; a MepM2-related protein having at least 60% similarity or at least 60% identity to the amino acid sequence set forth as SEQ ID NO: 64;

a MepM2 protease having the amino acid sequence set forth as SEQ ID NO: 67; a homologue of the MepM2 protease having the amino acid sequence set forth as SEQ ID NO: 67; a MepM2-related protein having at least 60% similarity or at least 60% identity to the amino acid sequence set forth as SEQ ID NO: 67;

a MepM2 protease having the amino acid sequence set forth as SEQ ID NO: 68; a homologue of the MepM2 protease having the amino acid sequence set forth as SEQ ID NO: 68; and a MepM2-related protein having at least 60% similarity or at least 60% identity to the amino acid sequence set forth as SEQ ID NO: 68;

the S-type Pyocin is an S-type Pyocin having the amino acid sequence set forth as SEQ ID NO: 49, a homologue of the S-type Pyocin having the amino acid sequence set forth as SEQ ID NO: 49, or an S-type Pyocin related protein having at least 60% similarity or at least 60% identity to the amino acid sequence set forth as SEQ ID NO: 49;

the linear gramicidin synthase is a linear gramicidin synthase having the amino acid sequence set forth as SEQ ID NO: 51, a homologue of the linear gramicidin synthase having the amino acid sequence set forth as SEQ ID NO: 51, or a linear gramicidin synthase related protein having at least 60% similarity or at least 60% identity to the amino acid sequence set forth as SEQ ID NO: 51; the leukotoxin is a leukotoxin having the amino acid sequence set forth as SEQ ID NO: 53, a homologue of the leukotoxin having the amino acid sequence set forth as SEQ ID NO: 53, or a leukotoxin related protein having at least 60% similarity or at least 60% identity to the amino acid sequence set forth as SEQ ID NO: 53;

the ShlB hemolysin transporter is an ShlB hemolysin transporter having the amino acid sequence set forth as SEQ ID NO: 55, a homologue of the an ShlB hemolysin transporter having the amino acid sequence set forth as SEQ ID NO: 55, or an ShlB hemolysin transporter related protein having at least 60% similarity or at least 60% identity to the amino acid sequence set forth as SEQ ID NO: 55; each of the one or more overexpressed inactivated proteases is independently selected from: *P. fluorescens* DegP2 S219A; an inactivated DegP2 comprising an amino acid substitution or disruption of the amino acid sequence set forth as SEQ ID NO: 31; an inactivated DegP2 comprising an amino acid substitution or disruption of a homologue of the amino acid sequence set forth as SEQ ID NO: 31; an inactivated DegP2-related protein comprising an amino acid substitution or disruption of a DegP2 having at least 60% similarity or at least 35% identity to amino acid sequence set forth as SEQ ID NO: 31; an inactivated DegP comprising an amino acid substitution or disruption of the amino acid sequence set forth as SEQ ID NO: 69; an inactivated DegP comprising an amino acid substitution or disruption of a homologue of the amino acid sequence set forth as SEQ ID NO: 69; an inactivated DegP-related protein comprising an amino acid substitution or disruption of a DegP having at least 60% similarity or at least 35% identity to amino acid sequence set forth as SEQ ID NO: 69; an inactivated DegP/HtrA comprising an amino acid substitution or disruption of the amino acid sequence set forth as SEQ ID NO: 62; an inactivated DegP/HtrA comprising an amino acid substitution or disruption of a homologue of the amino acid sequence set forth as SEQ ID NO: 62; an inactivated DegP/HtrA-related protein comprising an amino acid substitution or disruption of a DegP having at least 60% similarity or at least 35% identity to amino acid sequence set forth as SEQ ID NO: 62; an inactivated DegP, DegP-related protein, or DegP homologue having a substitution or disruption of an amino acid at a position corresponding to any one of 131 (His), 134 (Asp) and 236 (Ser) (SEQ ID NO: 62, numbering including leader sequence 1-26), or respective positions 105, 108, and 210, when excluding the leader sequence; an inactivated DegP, DegP-related protein, or DegP homologue having an amino acid substitution corresponding to *E. coli* Htr S210A; an inactivated DegP, DegP-related protein, or DegP homologue having an amino acid substitution corresponding to *E. coli* Htr H105R; and an inactivated DegP, DegP-related protein, or DegP homologue having a substitution or disruption of any one or more amino acid at a position corresponding to any one of: 108, 109, 110, 111, 112, 113, 114, 115, 116, 117, 118, 119, 120, 121, 122, 146, 147, 148, 149, 150, 151, 152, 217, 218, 219, 220, 221, 222, 223, 224, 225, 226, 227, 228, 229, 230, 231, 232, 233, and 234 of SEQ ID NO: 31; and each of the one or more folding modulators is independently selected from: a disulfide bond isomerase having an amino acid sequence set forth as any one of SEQ ID NOS: 60, 76, 77, 78, 80, and 81; a homologue of a disulfide bond isomerase having an amino acid sequence set forth as any one of SEQ ID NOS: 60, 76, 77, 78, 80, and 81; a disulfide bond isomerase-related protein having at least 60% similarity or at least 60% identity to an amino acid sequence set forth as any one of SEQ ID NOS: 60, 76, 77, 78, 80, and 81; a protein disulfide isomerase having an amino acid sequence set forth as any one of SEQ ID NOS: 27 and 82-98; a homologue of a protein disulfide isomerase having an amino acid sequence set forth as any one of SEQ ID NOS: 27 and 82-98; and a protein disulfide isomerase-related protein having at least 60% similarity or at least 60% identity to an amino acid sequence set forth as SEQ ID NOS: 27 and 82-98.

8. The recombinant gram-negative bacterial host cell of any preceding embodiment, wherein the mutation is in a coding sequence or noncoding sequence of the corresponding gene, and wherein the mutation is independently selected from: (i) a complete gene deletion, (ii) a partial gene deletion, (iii) a missense mutation, (iv) a nonsense mutation, (v) a frameshift mutation, (vi) an insertion, and (vii) any combination of (ii), (iii), (iv), (v) and (vi).

9. The recombinant gram-negative bacterial host cell of embodiment 8, wherein the missense mutation of (iii) results in a conservative or non-conservative amino acid substitution.

10. The recombinant gram-negative bacterial host cell of embodiment 8 or 9, wherein the noncoding sequence is a regulatory sequence.

11. The recombinant gram-negative bacterial host cell of any preceding embodiment, wherein the gram-negative bacterial host cell further comprises a functional protease activity, wherein the functional protease activity is the activity of: a MepS1 having the amino acid sequence set forth as SEQ ID NO: 5; a homologue of the MepS1 having the amino acid sequence set forth as SEQ ID NO: 5; or a MepS1 related protein having at least 50% sequence similarity to the *P. fluorescens* MepS1 protease amino acid sequence set forth as SEQ ID NO: 5.

12. The recombinant gram-negative bacterial host cell of any preceding embodiment, wherein the gram-negative bacterial host cell further comprises a functional protease activity, wherein the functional protease activity is: a MepS2 having the amino acid sequence set forth as SEQ ID NO: 7; a homologue of the MepS2 having the amino acid sequence set forth as SEQ ID NO: 7; or a MepS2 related protein having at least 50% sequence similarity to the *P. fluorescens* MepS2 protease amino acid sequence set forth as SEQ ID NO: 7.

13. The recombinant gram-negative bacterial host cell of embodiment 11 or embodiment 12, wherein the gram-negative bacterial host cell is a *Pseudomonad.*

14. The recombinant gram-negative bacterial host cell of any preceding embodiment, wherein the gram-negative bacterial host cell is a *Pseudomonad*, and the deficient first protease activity results from a mutation of a coding sequence and/or noncoding sequence of a gene encoding *P. fluorescens* Prc1 and/or a mutation of a coding sequence and/or noncoding sequence of a gene encoding *P. fluorescens* Prc2.

15. The recombinant gram-negative bacterial host cell of any preceding embodiment, wherein the second protease activity is deficient due to a mutation that results in a conservative or non-conservative substitution in an active site amino acid or an allosteric site amino acid of a protease having the second protease activity.

16. The recombinant gram-negative bacterial host cell of any preceding embodiment, wherein the deficient second protease activity results from at least one mutation of the second protease gene, wherein the mutation results in a disruption of the amino acid sequence at a position corresponding to: (i) any one or more of residues 134 to 145 of SEQ ID NO: 1; (ii) any one or more of residues 319 to 411 of SEQ ID NO: 1; (iii) one or more of residues any 361 to 378 of SEQ ID NO: 1; (iv) any one or more residue selected from 248, 319, 330, 332, 334, 337, 378, 410, and 411 of SEQ ID NO: 1; or any combination of (i), (ii), (iii), and (iv).

17. The recombinant gram-negative bacterial host cell of any preceding embodiment, wherein the bacterial host cell is *Pseudomonas fluorescens*, wherein the deficient second protease activity results from a gene mutation that results in an amino acid substitution of SEQ ID NO: 1 selected from: Y248stop, G332S, D334N, A337T, H411Y, P410L, and any conservative or non-conservative amino acid substitution of any one of R319, H330, D334, H378, and H411.

18. The recombinant gram-negative bacterial host cell of any preceding embodiment, wherein the host cell is capable of high-density cell growth in culture.

19. The recombinant gram-negative bacterial host cell of embodiment 18, wherein the high-density cell growth in culture comprises growth to OD575 of about 80 to about 300.

20. The recombinant gram-negative bacterial host cell of embodiment 18 or 19, wherein the high-density cell growth in culture is increased in comparison to a control cell by about 2-fold to about 15-fold.

21. The recombinant gram-negative bacterial host cell of embodiment 20, wherein the recombinant gram-negative bacterial host cell and the control cell, respectively, are selected from:
(i) a recombinant gram-negative bacterial host cell deficient in the first protease activity and the second protease activity, and a corresponding gram-negative bacterial host cell deficient in the first protease activity and wherein the second protease is functional;
(ii) a recombinant gram-negative bacterial host cell deficient in the first protease activity, the second protease activity, and an additional protease activity as recited in 2(c), and a corresponding gram-negative bacterial host cell deficient in the first protease activity and the second protease activity, and wherein the additional protease activity of 2(c) that is deficient in the compared recombinant gram-negative bacterial host cell is functional; and
(iii) a recombinant gram-negative bacterial host cell deficient in the first protease activity and the second protease activity, and comprising a functional protease that is: a MepS1 having the amino acid sequence set forth as SEQ ID NO: 5; a homologue of the MepS1 having the amino acid sequence set forth as SEQ ID NO: 5; or a MepS1 related protein having at least 50% sequence similarity to the *P. fluorescens* MepS1 amino acid sequence set forth as SEQ ID NO: 5, and a corresponding gram-negative bacterial host cell deficient in the activity of the first protease and the second protease, and deficient in the functional protease of the compared recombinant gram-negative bacterial host cell.

22. The recombinant gram-negative bacterial host cell of embodiment 21, wherein the additional protease activity of 2(c) is an activity of a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9.

23. The recombinant gram-negative bacterial host cell of any preceding embodiment, further comprising at least one expression construct, each expression construct comprising at least one nucleic acid sequence encoding a recombinant protein of interest.

24. The recombinant gram-negative bacterial host cell of embodiment 23, wherein the recombinant protein of interest is native or heterologous to the recombinant gram-negative bacterial host cell.

25. The recombinant gram-negative bacterial host cell of embodiment 23, wherein the recombinant protein of interest is selected from: an antibody, antibody fragment, or derivative of an antibody or antibody fragment; an antibody-based drug, a non-antibody binding protein (e.g., an antibody mimetic, including, but not limited to, an alphabody, an iBody, an affibody, an affilin, an affitin, or an anticalin), a reagent protein; a vaccine antigen; a therapeutic protein or enzyme; non-natural protein; a pathogen protein or derivative thereof; a microbial toxin, a lipoprotein; an extracellular receptor or ligand; a protease; a kinase; a blood protein; a chemokine; a cytokine; a bone morphogenic protein; an anticoagulant; a blood factor; a bone morphogenetic protein; an engineered protein scaffold; an enzyme, e.g., a biocatalytic enzyme; a growth factor; an interferon; an interleukin; a thrombolytic agent; a hormone; and a TGF-beta family member protein.

26. The recombinant gram-negative bacterial host cell of any one of embodiments 23-25, wherein the recombinant protein of interest is human, murine, rat, rabbit, guinea pig, camelid, shark, avian, yeast, fungal, gram-negative bacterial, or gram-positive bacterial.

27. The recombinant gram-negative bacterial host cell of embodiment 25 or 26, wherein the antibody, antibody fragment, or derivative thereof is selected from: a monoclonal antibody; a complementarity determining region (CDR) fragment; a CDR-grafted antibody; a single-chain antibody; a single chain antibody fragment; modified antibody, a bispecific antibody, a chimeric antibody; a diabody; a triabody; a tetrabody; a minibody; a linear antibody; a chelating recombinant antibody; a bibody; a tribody; an intrabody; a nanobody; a small modular immunopharmaceutical (SMIP); an antigen-binding-domain immunoglobulin fusion protein; a camelid antibody; a shark single domain antibody, an avian antibody (e.g., a chicken antibody), a VHH-containing antibody; a F(ab); a F(ab)'; F(ab)'2; scFv; an Fc fragment generated from the heavy chain constant region of an antibody; a reduced IgG fragment (e.g., generated by reducing the hinge region disulfide bonds of IgG); an Fc fusion protein (e.g., comprising the Fc domain of IgG fused together with a protein or peptide of interest); a domain antibody; a VL; a VNAR; a VH; and a VHH.

28. The recombinant gram-negative bacterial host cell of embodiment 27, wherein the VHH-containing antibody is a VHH concatenated antibody.

29. The recombinant gram-negative bacterial host cell of any one of embodiments 25 to 28, wherein the antibody, antibody fragment, or derivative thereof, binds to a target selected from: a cytokine; a chemokine; a drug; a cell-surface protein, e.g., a receptor, cell-surface marker, pathogen surface-protein, etc.; a growth factor; a growth factor receptor; immune checkpoint molecule, and a blood factor.

30. The recombinant gram-negative bacterial host cell of any one of embodiments 25 to 29, wherein the antibody, antibody fragment, or derivative thereof is a Fab'.

31. The recombinant gram-negative bacterial host cell of embodiment 30, wherein the Fab' binds to a target selected from: Carcinoembryonic antigen (CEA); CD22; fibrin II, beta chain; TNF-alpha; and NCA-90 (granulocyte antigen).

32. The recombinant gram-negative bacterial host cell of any one of embodiments 25 to 31, wherein the at least one expression construct encoding the antibody, antibody fragment, or derivative thereof comprises at least one nucleic acid sequence encoding a heavy chain, at least one nucleic acid sequence encoding a light chain, or both, wherein the heavy chain is full-length or a heavy chain fragment, and the light chain is full-length or a light chain fragment.

33. The recombinant gram-negative bacterial host cell of embodiment 32, wherein the at least one expression construct encoding the antibody, antibody fragment, or derivative thereof comprises at least two nucleic acid sequences, each encoding a heavy chain.

34. The recombinant gram-negative bacterial host cell of embodiment 32 or 33, wherein the at least one expression construct encoding the antibody, antibody fragment, or derivative thereof comprises a nucleic acid sequence encoding a heavy chain and a nucleic acid sequence encoding a light chain, wherein the heavy and light chain are expressed from the same mRNA transcript.

35. The recombinant gram-negative bacterial host cell of embodiment 32 or 33, wherein the at least one expression construct encoding the antibody, an antibody fragment, or derivative thereof comprises a nucleic acid sequence encoding a heavy chain and a nucleic acid sequence encoding a light chain, wherein the heavy and light chain are expressed from different mRNA transcripts.

36. The recombinant gram-negative bacterial host cell of embodiment 34 or 35, wherein each heavy chain-encoding nucleic acid sequence and each light chain-encoding nucleic acid sequence is individually operably linked to an independently selected nucleic acid sequence encoding a periplasmic secretion signal.

37. The recombinant gram-negative bacterial host cell of embodiment 36, wherein the periplasmic secretion signal has the amino acid sequence set forth as SEQ ID NO: 11, 13, 15, or 17.

38. The recombinant gram-negative bacterial host cell of any one of embodiments 34 to 37, wherein the expression construct comprises: a nucleic acid sequence encoding an antibody heavy chain, operably linked to a nucleic acid sequence encoding a periplasmic secretion signal, wherein the periplasmic secretion signal has the amino acid sequence set forth as SEQ ID NOS: 11, 13, 15, or 17; a nucleic acid sequence encoding a light chain, operably linked to a nucleic acid sequence encoding a periplasmic secretion signal, wherein the periplasmic secretion signal has the amino acid sequence set forth as SEQ ID NOS: 11, 13, 15, or 17; or both.

39. The recombinant gram-negative bacterial host cell of any one of embodiments 25 to 38, wherein the antibody, antibody fragment, or derivative thereof is humanized.

40. The recombinant gram-negative bacterial host cell of any one of embodiments 30 to 39, wherein the Fab' is certolizumab.

41. The recombinant gram-negative bacterial host cell of embodiment 40, wherein the Fab' heavy chain has the amino acid sequence set forth as SEQ ID NO: 21, and the Fab' light chain has the amino acid sequence set forth as SEQ ID NO: 23.

42. The recombinant gram-negative bacterial host cell of any one of embodiments 32-41, wherein the nucleic acid sequence encoding the heavy chain is operably linked to a nucleic acid sequence encoding a secretion leader having the amino acid sequence set forth as SEQ ID NO: 11, and the nucleic acid sequence encoding the light chain is operably linked to a nucleic acid sequence encoding a secretion leader having the amino acid sequence set forth as SEQ ID NO: 13.

43. The recombinant gram-negative bacterial host cell of any one of embodiments 1-42, wherein the host cell is deficient in:
(i) the first protease activity;
(ii) the second protease activity;
(iii) the activity of a serralysin precursor having the amino acid sequence set forth as SEQ ID NO: 9, a homologue of the serralysin precursor having the amino acid sequence set forth as SEQ ID NO: 9, or a serralysin precursor related protein having at least 60% similarity or at least 60% identity to the amino acid sequence set forth as SEQ ID NO: 9;
(iv) an HslU protease having the amino acid sequence set forth as SEQ ID NO: 37, a homologue of the HslU protease having the amino acid sequence set forth as SEQ ID NO: 37, or a HslU related protein having at least 60% similarity or at least 60% identity to the amino acid sequence set forth as SEQ ID NO: 37; and (v) an HslV protease having the amino acid sequence set forth as SEQ ID NO: 38, a homologue of the HslV protease having the amino acid sequence set forth as SEQ ID NO: 38, or a HslV related protein having at least 60% similarity or at least 60% identity to the amino acid sequence set forth as SEQ ID NO: 38.

44. The recombinant gram-negative bacterial host cell of embodiment 43, wherein the host cell further overexpresses an exogenous inactivated DegP, wherein the inactivated DegP is selected from: *P. fluorescens* DegP2 S219A; an inactivated DegP2 derived from the amino acid sequence set forth as SEQ ID NO: 31; an inactivated DegP2 derived from the amino acid sequence set forth as SEQ ID NO: 62; an inactivated DegP2 derived from a homologue of the amino acid sequence set forth as SEQ ID NO: 31; an inactivated DegP2 derived from a DegP2 having at least 60% similarity or at least 60% identity to amino acid sequence set forth as SEQ ID NO: 31; an inactivated DegP2 derived from a DegP2 having at least 60% similarity or at least 60% identity to amino acid sequence set forth as SEQ ID NO: 62; and each of the proteases having the amino acid sequence set forth as SEQ ID NO: 31 comprising a conservative or nonconservative amino acid substitution or disruption of any one or more of positions: 108, 109, 110, 111, 112, 113, 114, 115, 116, 117, 118, 119, 120, 121, 122, 146, 147, 148, 149, 150, 151, 152, 217, 218, 219, 220, 221, 222, 223, 224, 225, 226, 227, 228, 229, 230, 231, 232, 233, and 234.

45. The recombinant gram-negative bacterial host cell of embodiment 43 or 44, wherein the host cell overexpresses an exogenous disulfide isomerase selected from any one of: a disulfide isomerase having at least 60% similarity or at least 60% identity to an amino acid sequence set forth as SEQ ID NO: 27, 62, 63, 64, 65, 66, 67, 68, 69, 70, 71, 72, or 73, and a homologue of a disulfide isomerase having the amino acid sequence set forth as SEQ ID NO: 27, 62, 63, 64, 65, 66, 67, 68, 69, 70, 71, 72, and 73.

46. The recombinant gram-negative bacterial host cell of any one of embodiments 1-45, wherein the recombinant gram-negative bacterial host cell is selected from: a *Pseudomonad* host cell; an *E. coli* host cell; and a *Vibrio* host cell.

47. The recombinant gram-negative bacterial host cell of embodiment 46, wherein the *Pseudomonad* host cell is a *Pseudomonas* host cell.

48. The recombinant gram-negative bacterial host cell of embodiment 47, wherein the *Pseudomonas* host cell is *P. fluorescens, P. putida*, or *P. aeruginosa*.

49. The recombinant gram-negative bacterial host cell of embodiment 47 or 48, wherein the cell is:
(i) lsc::lacIQ1;
(ii) Prc1−
(ii) Prc2−
(iii) HslU−
(iv) HslV−
(v) MepM1−
(vi) PyrF−
and (vii) deficient in a serralysin precursor that is: a serralysin precursor having the amino acid sequence set forth as SEQ ID NO: 9; a homologue of the serralysin precursor having the amino acid sequence set forth as SEQ ID NO: 9; or a serralysin precursor related protein having at least 60% similarity or at least 60% identity to the amino acid sequence set forth as SEQ ID NO: 9; wherein the serralysin precursor deficiency results from a mutation in a gene encoding the serralysin precursor.

50. The recombinant gram-negative bacterial host cell of embodiment 49, wherein the cell is *P. fluorescens*, the Prc1 has the amino acid sequence set forth in SEQ ID NO: 33, the Prc2 has the amino acid sequence set forth in (SEQ ID NO: 35), the HslU has the amino acid sequence set forth in (SEQ ID NO: 37), the HslV has the amino acid sequence set forth in (SEQ ID NO: 38), the MepM1 has the amino acid sequence set forth in (SEQ ID NO: 1), and the serralysin precursor has the amino acid sequence set forth as SEQ ID NO: 9.

51. The recombinant gram-negative bacterial host cell of embodiment 50, further comprising an expression vector comprising a nucleic acid sequence encoding DegP2 S219A (SEQ ID NO: 29).

52. The recombinant gram-negative bacterial host cell of embodiment 50 or 51, further comprising an expression vector comprising a nucleic acid sequence encoding disulfide isomerase PDIA6 (SEQ ID NO: 27).

53. The recombinant gram-negative bacterial host cell of any one of embodiments 1-52, further comprising an expression vector encoding a recombinant protein.

54. The recombinant gram-negative bacterial host cell of embodiment 53, wherein the expression vector encodes a Fab'.

55. The recombinant gram-negative bacterial host cell of embodiment 54, wherein the expression vector comprising the nucleic acid sequence encoding DegP2 S219A or disulfide isomerase PDIA6 further comprises a nucleic acid sequence encoding the Fab'.

56. The recombinant gram-negative bacterial host cell of embodiment 54 or 55, wherein the Fab' heavy chain is encoded by SEQ ID NO: 21, and the Fab' light chain is encoded by SEQ ID NO: 23.

57. The recombinant gram-negative bacterial host cell of embodiment 1, wherein the recombinant gram-negative bacterial host cell is a *Pseudomonad* having the genotype of strain STR94975, STR94976, or STR94977.

58. The recombinant gram-negative bacterial host cell of embodiment 57, further comprising the expression construct or constructs of STR94975, STR94976, or STR94977, for use in producing a recombinant anti-TNF-alpha Fab'.

59. A method for producing a recombinant protein of interest comprising: (a) recovering the recombinant protein of interest from a recombinant gram-negative bacterial host cell of any one of embodiments 1-57 cultured under suitable fermentation conditions, wherein the recombinant gram-negative host cell is transformed with a plasmid comprising a nucleic acid encoding the recombinant protein of interest.

60. The method of embodiment 59, wherein transcription of the nucleic acid sequence encoding the recombinant protein of interest is regulated by an inducible promoter.

61. The method of embodiment 60, wherein the inducible promoter is selected from: a tac promoter, a mannitol promoter, a Pben, a T7 promoter, a lac promoter, a T5 promoter, a xylose promoter, and an arabinose promoter.

62. The method of any one of embodiments 59-61, wherein the recombinant gram-negative bacterial host cell can grow to high cell density.

63. The method of embodiment 62, wherein the high cell density comprises an OD575 of about 80 to about 300.

64. The method of any one of embodiments 58-63, wherein the suitable fermentation conditions comprise induction of the inducible promoter at: an OD575 of about 80 to about 160, a culture pH of about 5.8 to about 7.0, a temperature of about 28-33 deg C., fed-batch, and a titer range of about 0.2 to about 5 g/L.

65. The method of embodiment 64, wherein the inducible promoter is induced by IPTG, and wherein the IPTG is added to a final concentration of about 0.08-0.3 mM.

66. The method of embodiment 65, wherein the IPTG is added to a final concentration of about 0.2 mM.

67. The method of any one of embodiments 63-66, wherein induction is carried out at a culture pH of about 6.0 to about 6.5.

68. The method of any one of embodiments 63-67, wherein induction is carried out at a temperature of about 28-33 deg C.

69. The method of embodiment 68, wherein induction is carried out at a temperature of about 32 deg C.

70. The method of any one of embodiments 59-69, wherein the recombinant gram-negative bacterial host cell grows to a cell density that is increased in comparison to a control cell grown under the same fermentation conditions.

71. The method of embodiment 70, wherein the increase in cell density is about 2-fold to about 15-fold.

72. The method of any one of embodiments 59-71, further comprising: (b) measuring the yield of intact, soluble, and/or active, recombinant protein of interest recovered from the recombinant gram-negative bacterial host cell.

73. The method of embodiment 72, wherein the measured yield of intact, soluble, and/or active, recombinant protein is about 0.1 to about 10 g/L.

74. The method of embodiment 72 or 73, further comprising: (c) measuring the yield of recombinant protein of interest recovered from a control cell that is intact, soluble, active, or a combination thereof.

75. The method of embodiment 74, further comprising (d) comparing the yield measured in step (b) to the yield measured in step (c).

76. The method of embodiment 75, wherein the yield measured in step (b) is about 2-fold to about 100-fold higher than that measured in step (c).

77. The method of any one of embodiments 70-76, wherein the recombinant gram-negative bacterial host cell and the control cell, respectively, are selected from:

(i) a recombinant gram-negative bacterial host cell deficient in the first protease activity and the second protease activity, and a corresponding gram-negative bacterial host cell deficient in the first protease activity and wherein the second protease is functional;

(ii) a recombinant gram-negative bacterial host cell deficient in the first protease activity, the second protease activity, and an additional protease activity as recited in 2(a), and a corresponding gram-negative bacterial host cell deficient in the first protease activity and the second protease activity, and wherein the additional protease activity of 2(a) that is deficient in the compared recombinant gram-negative bacterial host cell is functional; and (iii) a recombinant gram-negative bacterial host cell deficient in the first protease activity and the second protease activity, and comprising a functional protease that is: a MepS1 having the amino acid sequence set forth as SEQ ID NO: 5; a homologue of the MepS1 having the amino acid sequence set forth as SEQ ID NO: 5; or a MepS1 related protein having at least 50% sequence similarity to the *P. fluorescens* MepS1 amino acid sequence set forth as SEQ ID NO: 5, and a corresponding gram-negative bacterial host cell deficient in the activity of the first protease and the second protease, and deficient in the functional protease of the compared recombinant gram-negative bacterial host cell.

78. The recombinant gram-negative bacterial host cell of any one of embodiments 1-45, or any one of embodiments 47-77, wherein the gram-negative bacterial host cell is not *E. coli*.

79. recombinant polypeptide comprising: a secretion signal peptide operably linked to a heterologous protein or polypeptide of interest, wherein the secretion signal peptide has the amino acid sequence set forth in SEQ ID NO: 11.

80. The polypeptide of embodiment 79, wherein the protein or polypeptide of interest is selected from: an antibody, antibody fragment, or a derivative of an antibody or an antibody fragment; an enzyme; a cytokine; a chemokine; a growth factor; a fusion protein; and a vaccine antigen.

81. The polypeptide of embodiment 79 or 80, wherein the antibody, antibody fragment, or a derivative of an antibody or antibody fragment is selected from: a monoclonal antibody; a full chain antibody; a complementarity determining region (CDR) fragment; a CDR-grafted antibody; a single-chain antibody; a single chain antibody fragment; a modified antibody; a variable-region only antibody fragment; a bispecific antibody, a chimeric antibody; a triabody; a tetrabody; a minibody; a linear antibody; a chelating recombinant antibody; a bibody; a dibody; an intrabody; a nanobody; a small modular immunopharmaceutical; an antigen-binding-domain immunoglobulin fusion protein; a camelid antibody; a shark single domain antibody (VNAR); an avian antibody; a VHH; a VHH-containing antibody; a VHH concatemer; a F(ab); a F(ab)'; F(ab)'2; an scFv; an Fc fragment generated from the heavy chain constant region of an antibody; a reduced IgG fragment; an Fc fusion protein; a domain antibody; a VL; and a VH.

82. The polypeptide of embodiment 80 or 81, wherein the antibody, antibody fragment, or derivative of the antibody or antibody fragment is humanized.

83. The polypeptide of embodiment 80, wherein the enzyme is a therapeutic enzyme.

84. The polypeptide of embodiment 83, wherein the therapeutic enzyme is selected from: a peptidase; a lactase; an amylase; a PEP; a digestive enzyme; a uricase; a rhodanase; a urokinase; a streptokinase; a staphylokinase; a phenylase; a sacrosidase; a lysozyme; a chitinase; a ribonuclease; a glutaminase; an arginase; a vibrilase; a chondroitinase; a hyaluronidase; a galactosidase; a glucuronidase; a glucocerebrosidase; a thymidine phosphorylase; a carbonic anhydrase; a uricase thiosulfate-cyanide; a sulfurtransferase; a phosphothioesterase; an alcohol oxidase; an alcohol dehydrogenase; an asparaginase; a glutamine synthase; an adenosine deaminase; bovine pegademase; alglucerase; dornase alpha; imiglucerase; sacrosidase; rasburicase; agalsidase beta; and nattokinase.

85. The polypeptide of embodiment 80, wherein the fusion protein is selected from: an enzyme fusion protein; a protein A fusion protein; an albumin fusion protein; a thioredoxin fusion protein; a ubiquitin fusion protein; a streptavidin fusion protein; a maltose binding protein fusion protein; a chitin being protein fusion protein; a SUMO fusion protein; and a glutathione-S-transferase fusion protein.

86. The polypeptide of any one of embodiments 79-85, further comprising a linker.

87. The polypeptide of any one of embodiments 79-86, further comprising a cleavage domain.

88. The polypeptide of any one of embodiments 79-87, wherein the secretion signal peptide directs expression of the protein or polypeptide of interest to the periplasm or the extracellular space of a prokaryotic host cell.

89. The polypeptide of embodiment 88, wherein the prokaryotic host cell is a gram-negative bacterium.

90. The polypeptide of embodiment 88, wherein the prokaryotic host cell is a gram-positive bacterium.

91. The polypeptide of embodiment 89, wherein the gram-negative bacterium is a *Pseudomonad, V. natriegens,* or *E. coli.*

92. The polypeptide of embodiment 90, wherein the gram-positive bacterium is a *Corynebacterium* or a *Bacillus.*

93. A method of producing a protein or polypeptide of interest in a prokaryotic host cell, the method comprising: producing the protein or polypeptide of interest in the periplasm of a prokaryotic host cell cultured in a cell culture growth medium, wherein the prokaryotic host cell comprises an expression construct comprising a nucleic acid encoding a recombinant polypeptide comprising the protein or polypeptide of interest operably linked to a secretion signal peptide that directs expression of the protein or polypeptide of interest to the periplasm of the prokaryotic host cell, wherein the secretion signal peptide comprises the amino acid sequence of SEQ ID NO: 11, and wherein the secretion signal peptide is not native to the protein or polypeptide of interest.

94. The method of embodiment 93, further comprising isolating the produced protein or polypeptide of interest.

95. The method of embodiment 94, wherein the protein or polypeptide of interest is selected from: an antibody, antibody fragment, or a derivative of an antibody or an antibody fragment; an enzyme; a cytokine; a chemokine; a growth factor; a fusion protein; and a vaccine antigen.

96. The method of embodiment 95, wherein the antibody, antibody fragment, or a derivative of an antibody or an antibody fragment is selected from: a monoclonal antibody; a full chain antibody; a complementarity determining region (CDR) fragment; a CDR-grafted antibody; a single-chain antibody; a single chain antibody fragment; a modified antibody; a variable-region only antibody fragment; a bispecific antibody, a chimeric antibody; a triabody; a tetrabody; a minibody; a linear antibody; a chelating recombinant antibody; a bibody; a dibody; an intrabody; a nanobody; a small modular immunopharmaceutical; an antigen-binding-domain immunoglobulin fusion protein; a camelid antibody; a shark single domain antibody (VNAR); an avian antibody; a VHH; a VHH-containing antibody; a VHH concatemer; a F(ab); a F(ab)'; F(ab)'2; an scFv; an Fc fragment generated from the heavy chain constant region of an antibody; a reduced IgG fragment; an Fc fusion protein; a domain antibody; a VL; and a VH.

97. The method of embodiment 95 or 96, wherein the antibody, antibody fragment, or derivative of the antibody or antibody fragment is humanized.

98. The method of embodiment 95, wherein the enzyme is a therapeutic enzyme.

99. The method of embodiment 98, wherein the therapeutic enzyme is selected from: a peptidase; a lactase; an amylase; a PEP; a digestive enzyme; a uricase; a rhodanase; a urokinase; a streptokinase; a staphylokinase; a phenylase; a sacrosidase; a lysozyme; a chitinase; a ribonuclease; a glutaminase; an arginase; a vibrilase; a chondroitinase; a hyaluronidase; a galactosidase; a glucuronidase; a glucocerebrosidase; a thymidine phosphorylase; a carbonic anhydrase; a uricase thiosulfate-cyanide; a sulfurtransferase; a phosphothioesterase; an alcohol oxidase; an alcohol dehydrogenase; an asparaginase; a glutamine synthase; an adenosine deaminase; bovine pegademase; alglucerase; dornase alpha; imiglucerase; sacrosidase; rasburicase; agalsidase beta; and nattokinase.

100. The method of embodiment 95, wherein the fusion protein is selected from: an enzyme fusion protein; a protein A fusion protein; an albumin fusion protein; a thioredoxin fusion protein; a ubiquitin fusion protein; a streptavidin fusion protein; a maltose binding protein fusion protein; a chitin being protein fusion protein; a SUMO fusion protein; and a glutathione-S-transferase fusion protein.

101. The method of any one of embodiments 93-100, wherein the nucleic acid encodes a linker.

102. The method of embodiment 101, wherein the linker comprises a cleavage domain.

103. The method of any one of embodiments 93-102, wherein the prokaryotic host cell is a gram-negative bacterium.

104. The method of any one of embodiments 93-102, wherein the prokaryotic host cell is a gram-positive bacterium.

105. The method of embodiment 93, wherein the gram-negative bacterium is a *Pseudomonad, V. natriegens,* or *E. coli.*

106. The method of embodiment 94, wherein the gram-positive bacterium is a *Corynebacterium* or a *Bacillus.*

107. An expression vector comprising a nucleic acid sequence encoding a recombinant polypeptide of any one of embodiments 79-92.

108. A prokaryotic host cell comprising an expression vector of embodiment 107.

109. The prokaryotic host cell of embodiment 108, wherein the prokaryotic host cell is a gram-negative bacterium.

110. The prokaryotic host cell of embodiment 108, wherein the prokaryotic host cell is a gram-positive bacterium.

111. The prokaryotic host cell of embodiment 109, wherein the gram-negative bacterium is a *Pseudomonad, V. natriegens,* or *E. coli.*

112. The prokaryotic host cell of embodiment 110, wherein the gram-positive bacterium is a *Corynebacterium* or a *Bacillus.*

113. The prokaryotic host cell of any one of embodiments 108-112, wherein the nucleic acid sequence encoding the recombinant polypeptide is optimized for expression in the prokaryotic host cell.

114. Use of a recombinant polypeptide of any one of embodiments 79-92, an expression vector of embodiment 107, or a prokaryotic host cell of any one of embodiments 108-113, for expressing a protein or polypeptide of interest in the periplasm or the extracellular space of a prokaryotic host cell.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following examples are given for the purpose of illustrating various embodiments of the disclosure and are not meant to limit the present disclosure in any fashion. The present examples, along with the methods described herein are presently representative embodiments, are exemplary, and are not intended as limitations on the scope. Changes therein and other uses which are encompassed within the spirit of the disclosure as defined by the scope of the claims will occur to those skilled in the art.

Example 1. Recombinant Protein Expression in Protease-Deficient Bacterial Host Cells Screening of protease-deficient host cell strains for production of intact recombinant protein was carried out at 0.5 mL scale. In each of fifteen different protease-deficient *P. fluorescens* strains, each of ten anti-TNF Fab' (certolizumab) overexpression plasmids were tested. Each of the ten overexpression plasmids (constructs 1-10) contained an expression construct encoding the anti-TNF-alpha Fab' heavy chain (HC, SEQ ID NO: 21, encoded by SEQ ID NO: 22), and the anti-TNF-alpha Fab' light chain (LC, SEQ ID NO: 23, encoded by SEQ ID NO: 24), under control of the same promoter, Ptac. Constructs 1-9 each contained a plasmid comprising an expression construct having sequences encoding, from 5'-3': Leader 1 (L1)—HC (SEQ ID NO: 21, encoded by SEQ ID NO: 22)—Leader 2 (L2)—LC (SEQ ID NO: 23, encoded by SEQ ID NO: 24)—DsbC (SEQ ID NO: 60, encoded by SEQ ID NO: 79) (a co-transcriptional *P. fluorescens* DsbC protein disulfide isomerase). Construct 10 contained p688-005, which did not co-express DsbC. Like constructs 1-9, construct 10 comprised sequences encoding, from 5'-3', Leader 1 (L1)—HC (HC, SEQ ID NO: 21, encoded by SEQ ID NO: 22)—Leader 2 (L2)—LC (SEQ ID NO: 23, encoded by SEQ ID NO: 24). The ten plasmids were the same except for the differences in secretion signal sequences and differences noted for construct 10. In each of constructs 1-9, L1 was a different secretion signal; constructs 3 and 10 had the same secretion signal. In each of constructs 1-10, L2 was the Azu periplasmic secretion signal (SEQ ID NO: 13, encoded by SEQ ID NO: 14). In construct 8, L1 was the Slmt secretion signal (SEQ ID NO: 11, encoded by SEQ ID NO: 12). Each light and heavy chain gene comprised a high translation efficiency ribosome binding sequence (having 100% of the activity of the canonical Shine-Dalgarno sequence, SEQ ID NO: 59) upstream of the start codon.

The expression plasmids were transformed into the *P. fluorescens* host strains in an array format. The transformation reaction was initiated by mixing *P. fluorescens* competent cells and plasmid DNA. A 25 µL aliquot of the mixture was transferred to a 96-multi-well Nucleovette® plate (Lonza). Electroporation was carried out using the Nucleofector™ 96-well Shuttle™ system (Lonza AG), and the electroporated cells were subsequently transferred to a fresh 96-well deep well plate, containing 500 µL M9 salts supplemented with 1% glucose medium, and trace elements. The plates were incubated at 30° C. with shaking for 48 hours, to generate seed cultures.

Ten µL aliquots of the seed cultures were transferred in duplicate into 96-well deep well plates. Each well contained 500 µL of HTP-YE medium (Teknova), supplemented with trace elements and 5% glycerol. The seed cultures, plated in the glycerol supplemented HTP media, were incubated for 24 hours, in a shaker, at 30° C. Isopropyl-β-D-1-thiogalactopyranoside (IPTG) was added to each well at a final concentration of 0.3 mM to induce expression of the Fab'. After 24 hours of induction, cell density was calculated by measuring the optical density at 600 nm ($OD_{600}$). The cells were subsequently harvested, diluted 1:3 with 1× Phosphate Buffered Saline (PBS) to a final volume of 400 µL, and frozen for later processing.

Soluble Lysate Sample Preparation for Analytical Characterization: The harvested cell samples were diluted and lysed by sonication with a Cell Lysis Automated Sonication System (CLASS, Scinomix) using a 24 probe tip horn. The lysates were centrifuged at 5,500×g for 15 minutes at 8° C. The supernatant was collected and labeled as the soluble fraction. The pellets were collected, resuspended in 400 µL of 1×PBS pH 7.4 by another round of sonication, and labeled as the insoluble fraction.

Nonreducing SDS-CGE Analysis: The soluble and insoluble fractions were analyzed by HTP microchip SDS capillary gel electrophoresis using a LabChip GXII instrument (Caliper LifeSciences) with a HT Protein Express v2 chip and corresponding reagents (part numbers 760499 and 760328, respectively, Caliper LifeSciences). Samples were prepared following the manufacturer's protocol (Protein User Guide Document No. 450589, Rev. 3). Briefly, 4 µL aliquots of either the soluble or the insoluble fraction samples was mixed with 14 µL of buffer in 96-well polypropylene conical well PCR plates heated at 95° C. for 5 minutes, and diluted with 70 µL deionized water. Lysates from null host strains, which were not transformed with the Fab' expression plasmid, as well as host strains transformed with construct 10, were run as control in parallel with test samples, and quantified using the system internal standard.

Figure 1:
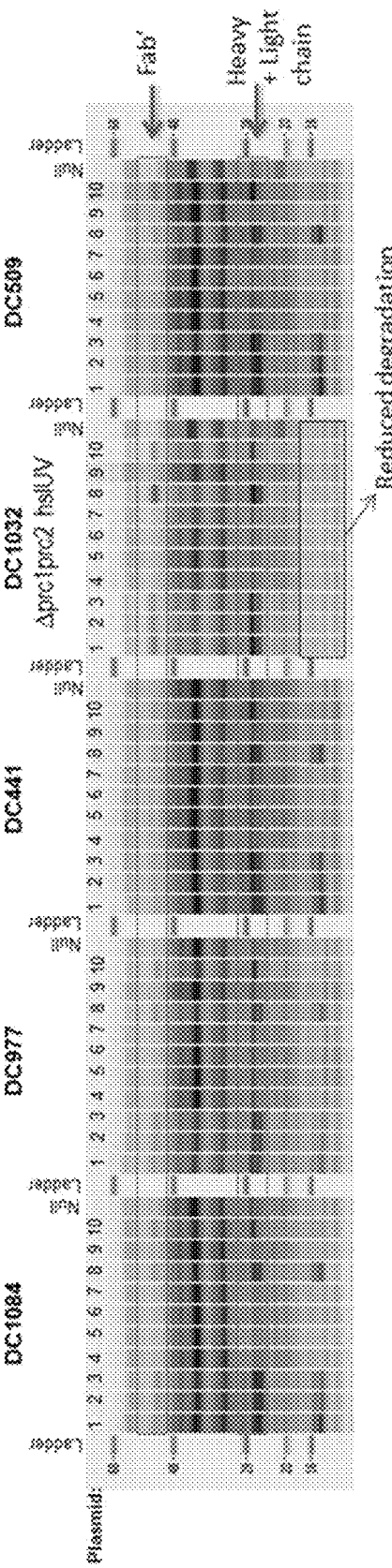
FIG. 1. Recombinant protein production in protease-deficient host cells at 0.5 mL scale. Nonreducing SDS-CGE analysis of Fab' protein produced by DC1032 and four other protease-deficient *P. fluorescens* strains tested is shown. The twelve lanes for each strain show, from left to right: far left lane—MW ladder with MW's 16, 20, 29, 48, and 68 kD; lanes numbered 1-10—protein expressed using constructs 1-10, each encoding the Fab' heavy and light chain. Each of constructs 1-9 had a nucleic acid sequence encoding a different periplasmic secretion signal operably linked to the heavy chain gene and each had a nucleic acid sequence encoding the Azu secretion signal operably linked to the light chain gene. Construct 10 had the same heavy chain secretion signal as construct 3. Constructs 1-9 each co-expressed *P. fluorescens* derived DsbC, while construct 10 did not. Lane 12 (far right lane in each set)—null host strain (with a null expression plasmid). From left to right, the first 12 lanes show Fab' expression in host strain DC1084; the second 12 lanes show Fab' protein expression in DC977; the third 12 lanes show Fab' protein expression in DC441; the fourth 12 lanes show Fab' protein expression in DC1032; and the fifth 12 lanes show Fab' protein expression in DC509. The arrow below the DC1032 lanes indicates the area of migration for the Fab' degradation products.

FIG. 1 shows the nonreducing SDS-CGE analysis of Fab' protein produced by DC1032 and four other protease-deficient *P. fluorescens* strains tested. The twelve lanes for each strain show, from left to right: far left lane—MW ladder with MW's 16, 20, 29, 48, and 68 kD; lanes numbered 1-10—protein expressed using constructs 1-10, each encoding the Fab' heavy and light chain, and each having a nucleic acid sequence encoding a different periplasmic secretion signal operably linked to the heavy chain gene and each having a nucleic acid sequence encoding the Azu secretion signal operably linked to the light chain gene. Constructs 1-9 each co-express *P. fluorescens* derived DsbC while construct 10 does not. Lane 12 (far right lane in each set)—null host strain (with a null expression plasmid). From left to right, the first 12 lanes show Fab' expression in host strain DC1084; the second 12 lanes show Fab' protein expression in DC977; the third 12 lanes show Fab' protein expression in DC441; the fourth 12 lanes show Fab' protein expression in DC1032; and the fifth 12 lanes show Fab' protein expression in DC509. The arrow below the DC1032 lanes indicates the area of migration for the Fab' degradation products. HPLC and LC-MS analyses of Protein L enriched Fab' confirmed that the observed fragments were derived from the Fab'.

Conclusion: In contrast with the other fourteen host strains tested, DC1032, which has Prc1, Prc2 and HslUV protease deficiencies (by gene knockout), produced a high yield of assembled Fab' (up to 130 mg/L), with reduced degradation (see arrow at right indicating Fab'). Construct 8 comprised a nucleic acid sequence encoding secretion signal Slmt (SEQ ID NO: 11) operably linked to the heavy chain gene, and a nucleic acid sequence encoding secretion signal Azu (SEQ ID NO: 13) operably linked to the light chain gene, produced the highest assembled Fab' yields, and reduced degradation.

Example 2. Restoration of Protease-Deficient Bacterial Host Cell Growth

Growth of Identified Host Strains at Large Scale

P. fluorescens host strains identified as described in Example 1 at the 0.5 mL scale were grown at 2-liter (2 L) scale (conventional bioreactor, CBR). Complete inactivation of both tail-specific protein genes (Prc) in P. fluorescens prevented high cell density growth in bioreactors. A similar effect previously was reported regarding E. coli tail-specific protease mutants, e.g., by U.S. Pat. No. 9,493,559, EP1341899 B1, "Bacterial host strains," and Hara, H. et al., 1991, each incorporated herein by reference in its entirety.

Figure 2:
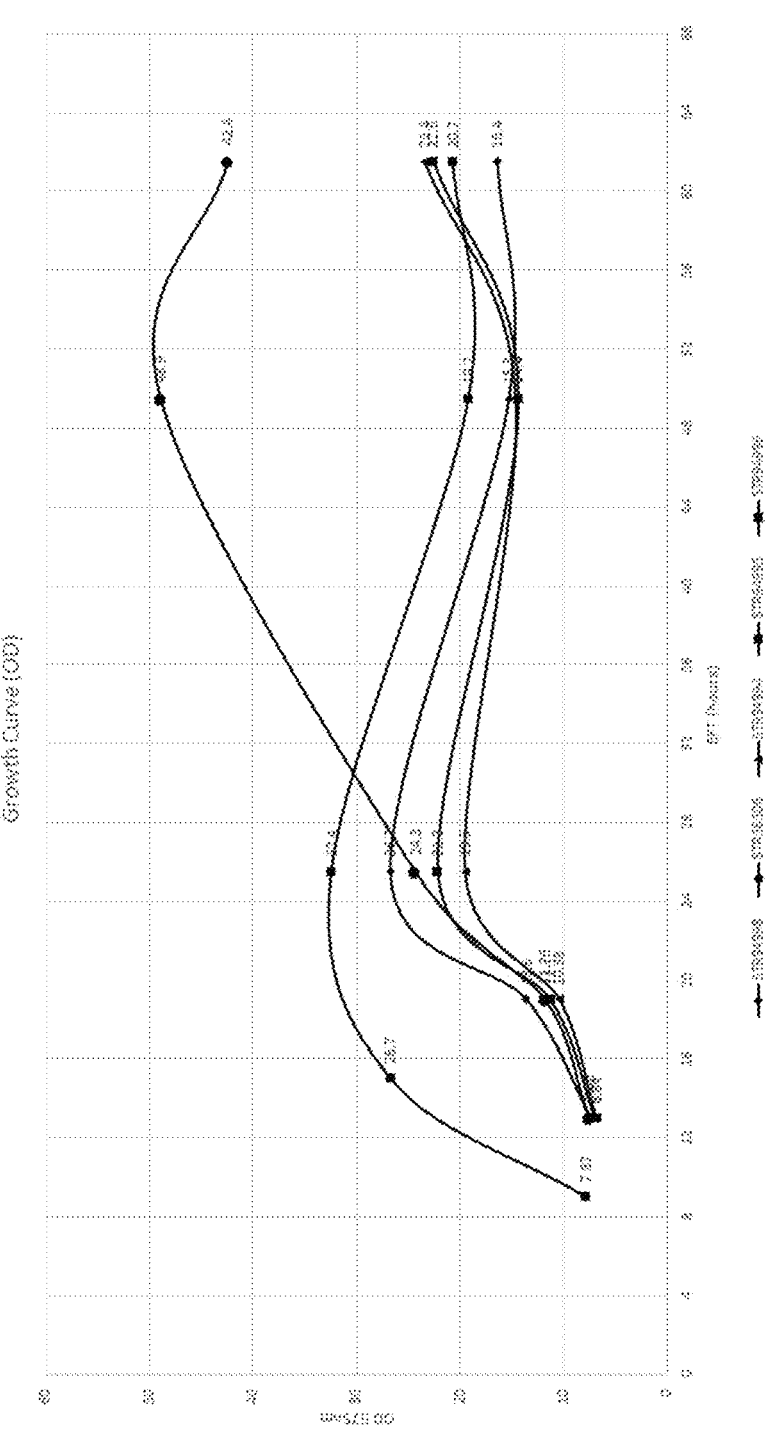
FIG. 2. Growth of Prc null host strains at 2 L scale under sub-optimal conditions. Y-axis: OD575, X-axis: elapsed fermentation time at 36 deg C. in hours. The gridlines mark 4-hour intervals, with the last timepoint taken at 62 hours.

FIG. 2 shows growth curves (OD575 vs fermentation time in hours) for DC1032 host cell strains at 2 L scale. Cells were grown at 32 degrees C., pH 6.5 induced with IPTG at 25.5 hours and the induction phase proceeded for 36 hours. Strain STR36306 (DC1032+p688-048 (Fab' expression plasmid); grew to a maximum OD575 of about 27, and STR94998 (DC1032+null plasmid, grew to a maximum OD575 of about 50). These Prc-deficient strains failed to grow beyond an OD575 of 20-50, and showed evidence of cell lysis. In contrast, strains expressing both functional copies of Prc (Prc1 and Prc2) grew to an OD575 of up to 130 in 2 L bioreactors within 18-26 hours (data not shown).

E. coli Strategy Fails to Restore High-Density Cell Growth to Pseudomonas Host Strains Previous studies showed that in E. coli, deletion of the gene encoding tail-specific protease Tsp/Prc (an orthologue of Pseudomonas Prc) inhibits growth at high density fermentation, and that inactivation of Spr (the E. coli analogue of Pseudomonas MepS1) by amino acid substitution restored E. coli growth to an OD of greater than or equal to 200 at 575 nm (e.g., U.S. Pat. No. 9,493,559, EP1341899 B1, and Hara, H. et al., 1991). This strategy proved unsuccessful in P. fluorescens Prc null strains. As shown in FIG. 2, growth of Prc null strains was not restored by deficiency in MepS1, MepS2, or both. As shown, the strain STR94994, DC1032 additionally having a MepS1 deletion, grew to a maximum OD575 of about 23, the strain STR94995, DC1032 having a MepS2 deletion, grew to a maximum OD575 of about 33, and the strain STR94996, DC1032 having deletions of both MepS1 and MepS2, grew to a maximum OD575 of about 23. (Strains STR94994, STR94995 and STR94996 each contained p688-048).

Adaptive Laboratory Evolution of Prc1- and Prc2-Deficient Host Cells

Prc deficient host strains with restored high-cell density growth were developed.

TABLE 4

| P. fluorescens host strains used in Adaptive Laboratory Evolution Studies | | |
| --- | --- | --- |
| Strain | Gene Deletions | Other |
| DC1032 | prc1, prc2, hslUV, pyrF | lsc::lacIQ1 |
| DC954 | prc1, prc2, pyrF | lsc::lacIQ1 |
| DC454 | pyrF | lsc::lacIQ1 |

DC954 was subjected to adaptive laboratory evolution (ALE) under growth conditions that are lethal to Prc null strains. ALE and similar strategies have been described in the literature, e.g., in E. coli, by Hara, H. et al., 1991. In ALE, bacterial strains with reduced tolerance to stress (including protease-deficient mutants) are subjected to sub-optimal growth conditions—here, low salt and high temperature—that prohibit growth unless further chromosomal mutation arises.

DC954 was grown at high temperature (36 deg C., as opposed to the cells' optimal growth temperature of 30-32 deg C.) on a modified hypotonic Luria-Bertani (LB) medium agar recipe similar to that described by Hara et al., 1991. FIG. 3A shows growth of DC954 colonies, on 1×LB agar medium in the absence of NaCl, and in the presence of uracil added to allow growth given the pyrF deletion, at 36 deg C. As shown, under these conditions DC954 formed colonies with background growth. In FIG. 3B, the left plate shows growth of DC454 (essentially wild-type) on only one-half-X LB agar medium in the absence of NaCl, with uracil, at 36 deg C. Growth was slower than on 1×LB, but these growth conditions were not lethal to DC454. The right plate in FIG. 3B shows growth of DC954 on one-half-X LB agar medium in the absence of NaCl, with uracil, at 36 deg C. Under these growth conditions, background growth was greatly reduced or eliminated, but several robust single colonies survived. The single colonies, as indicated, suggested cells that had adapted (evolved) to the sub-optimal growth conditions by further mutation. These colonies were picked for further characterization.

The chromosomal MepS, MepM and MepH orthologues in the evolved cells were sequenced. MepM1 was found to have acquired mutations consistent with its inactivation. The identified mutations were: Y248stop, D334N, G332S, A337T, H411Y, and P410L. These mutations restored growth at 2 L scale when co-expressed with an empty vector rescuing auxotrophy to uracil. Therefore, inactivation of MepM1 restored high cell density growth to DC954.

TABLE 5

| Growth of Evolved vs Unevolved P. fluorescens host strains (FIG. 4) | | | | | |
| --- | --- | --- | --- | --- | --- |
| Strain # | Evolved | Pre | Host Cell Genotype | Plasmid | Density (OD575) |
| 1 PF1550 | Yes | Null | Evolved from DC954: Δprc1, Δprc2, MepM1(P410L), ΔpyrF, lsc::lacIQ1 | p688-048 (Fab' DsbC) | High (at least 140) |
| 2 STR36306 | No | Null | DC1032: Δprc1, Δprc2, ΔhslUV, ΔpyrF, lsc::lacIQ1 | p688-048 (Fab' DsbC) | Low (less than 50) |
| 3 PF1557 | Yes | Null | Δprc1, Δprc2, MepM1(P410L), ΔpyrF, lsc::lacIQ1 | pDOW1169 (empty expression vector) | High (at least 150) |
| 4 DC432 | No | + | DC454: ΔpyrF | pDOW1169 (empty expression vector) | High (at least 175) |

*Bolding in column 4 indicates mutation acquired by evolution.

FIG. 4 shows that evolved Prc null strain #'s 1 and 3 grew to high cell densities (OD575 of 132-150), as did unevolved Prc+ strain #4. However, unevolved Prc null strain 2 grew to an OD575 of less than 50. (See Table 5.) The Production phase was conducted at 32 deg C., pH 6.5 for a duration of 48 hrs.

Generation of Combinatorial MepS and MepM Deficiencies in a Prc Null Background

A series of MepS and MepM knockout mutants were generated for systematic testing in Prc-deficient *P. fluorescens* (Δprc1Δprc2, ΔpyrF). Homologous regions to MepS1, MepS2, MepM1 and MepM2 were synthesized and subcloned by blunt end restriction digest into a non-*pseudomonas* replicating vector, and selected by rescued prototrophy for uracil.

Transformation was carried out electroporating 1 ug of plasmid DNA into electro competent prc knockout *P. fluorescens* cell lines. Selection for integration was done by plating transformed cells onto M9 minimal media+1 mM MgCl$_2$+1.5% agar and allowed to select for 2-3 days at 30 deg C. A second recombination step was selected for by picking single colonies into LB media+250 ug/ml uracil overnight. The following day several dilutions of the saturated culture was spread onto a 0.5×LB, 500 ug/ml5-FOA+ 250 ug/ml uracil 1.5% agar plate. This second recombination event knocks out out the open reading frame, and a non-replicating plasmid is dropped from cells through 5-FOA counter-selection of the pyrF gene. Single colonies were picked into liquid 0.5×LB, 500 ug/ml5-FOA+250 ug/ml uracil and grown overnight at 30 deg C. For colony PCR, primers were designed outside of the homology arm regions above and knockouts were confirmed by size analysis on an ethidium bromide stained agarose after amplification by PCR.

Screening of Combinatorial Mutants

For growth phenotype analysis, the knockout strains were grown overnight in M9 media+1 mM MgCl$_2$+250 ug/ml uracil (M9/Ura) to allow growth given the pyrF deletion. The following day, saturated liquid cultures were diluted 1:100 in M9/Ura followed by five 10-fold serial dilutions in M9/Ura. The cultures were then incubated under suboptimal conditions by spotting (5 ul) onto a 0.5×LB (no NaCl, 250 ug/ml uracil) 1.5% agar plate and incubating at 36 deg C. for 48 hours.

Table 6 shows the combinatorial Mep deficient mutants screened. Unlike rescue of Tsp mutants by Spr mutation reported in *E. coli*, MepS1 deficiency in *P. fluorescens* unexpectedly did not restore high density growth to the Prc deficient mutant. FIG. 5 shows the screening results. The sequentially lower dilutions were applied from the top to bottom of each row on the plate as oriented in the figure. Column 1 contains Prc-deficient mutant DC1032, which fails to grow under the sub-optimal conditions, and Row 10 shows growth of a Prc+ΔpyrF strain (wild-type control) under the same conditions. As observed in the other rows:

Column 2—the presence of a MepM1 deficiency successfully restores growth to the Prc deficient mutant at all titers.

Column 3—the presence of a MepS1 deficiency eliminates the ability of a MepM1 deficiency to restore growth.

Column 4—the presence of a MepS2 deficiency does not affect the ability of a MepM1 deficiency to restore growth.

Column 5—the presence of MepS1 and MepS2 deficiencies eliminate the ability of a MepM1 deficiency to restore growth.

Column 6—the presence of a MepM2 deficiency fails to restore growth to the Prc deficient mutant.

Column 7—the presence of MepM2 and MepS1 deficiencies do not restore growth to the Prc deficient mutant.

Column 8—the presence of MepM2 and MepS2 deficiencies do not restore growth to the Prc deficient mutant.

Column 9—the presence of MepM2, MepS1, and MepS2 deficiencies do not restore growth to the Prc deficient mutant.

A host cell having all four deficiencies (MepM1, MepM2, MepS1, and MepS2) was not successfully isolated, suggesting lethality in the Prc deficient mutant.

The growth observed in FIG. 5 is noted in the fourth column of Table 6.

TABLE 6

| Combinatorial Mep knockout (KO) mutants screened (all Prc null) | | | |
|---|---|---|---|
| Mep KO | ID | Genotype | FIG. 5 Result |
| MepS1 | PF1561 | Δprc1Δprc2, ΔhslUV, ΔmepS1, ΔpyrF, lsc::lacIQ1 | No growth |
| MepS2 | PF1582 | Δprc1Δprc2, ΔhslUV, ΔmepS2, ΔpyrF, lsc::lacIQ1 | Not tested |
| MepS1/ MepS2 | PF1562 | Δprc1Δprc2, ΔhslUV, ΔmepS1, ΔmepS2, ΔpyrF, lsc::lacIQ1 | Not tested |
| MepM1 | PF1559 | Δprc1Δprc2, ΔhslUV, ΔmepM1, ΔpyrF, lsc::lacIQ1 | Row 2: growth ++ |
| MepM2 | PF1572 | Δprc1Δprc2, ΔhslUV, ΔmepM2, ΔpyrF, lsc::lacIQ1 | Row 6: no growth |
| MepM1/ MepM2 | PF1584 | Δprc1Δprc2, ΔhslUV, ΔmepM1, ΔmepM2, ΔpyrF, lsc::lacIQ | Not tested |
| MepS1/ MepM1 | PF1588 | Δprc1Δprc2, ΔhslUV, ΔmepS1, ΔmepM1, ΔpyrF, lsc::lacIQ | Row 3: no growth |
| MepS1/ MepS2/ MepM1 | PF1590 | Δprc1Δprc2, ΔhslUV, ΔmepS1, ΔmepS2, ΔmepM1, ΔpyrF, lsc::lacIQ1 | Row 5: no growth |
| MepS1/ MepS2/ MepM1/ MepM2 | unable to isolate | Δprc1Δprc2, ΔhslUV, ΔmepS1, ΔmepS2, ΔmepM1, ΔmepM2, ΔpyrF, lsc::lacIQ1 | Not tested |
| MepS1/ MepM2 | PF1577 | Δprc1Δprc2, ΔhslUV, Δ mepS1, Δ mepM2, ΔpyrF, lsc::lacIQ1 | Row 7: no growth |
| MepS2/ MepM1 | PF1560 | Δprc1Δprc2, ΔhslUV, Δ mepS2, Δ mepM1, ΔpyrF, lsc::lacIQ1 | Row 4: growth + |
| MepS2/ MepM2 | PF1573 | Δprc1Δprc2, ΔhslUV, Δ mepS2, Δ mepM2, ΔpyrF, lsc::lacIQ1 | Row 8: no growth |
| MepS1/ MepS2/ MepM2 | PF1575 | Δprc1Δprc2, ΔhslUV, Δ mepS1, Δ mepS2, Δ mepM2, ΔpyrF, lsc::lacIQ1 | Row 9: no growth |

Conclusion: MepM1 deficiency restores growth to Prc-deficient *Pseudomonas* strains. Deficiency in any one or more of MepS1, MepS2, and MepM2 activity fails to restore growth to a *Pseudomonas* Prc-deficient mutant. Unexpectedly, in the presence of a MepS1 deficiency the growth advantage conferred by the MepM1 deficiency is eliminated. To restore high cell density growth to Prc-deficient *P. fluorescens*, it is necessary to inactivate MepM1 while leaving a functional copy of MepS1.

Example 3. Optimal Conditions for Robust Growth and Fab' Production by Recombinant Host Strains Based on the combinatorial knockout data, two host strains having different protease knockouts and containing the anti-TNF-alpha Fab' expression plasmid, p688-48, were generated and tested for growth and recombinant protein production under varying induction conditions including two temperatures (25 deg C. and 32 deg C.), pH (6 and 7.2), and induction OD575 (60 and 120). Table 7 shows pH, temperature, induction OD575, and Fab' titers at 24, 48, 72, and 120 hours post induction for each of the two strains, STR87639 (ΔprcΔ1prc2, ΔhslUV, Δ mepM1, ΔpyrF, lsc::

125 lacIQ1)+p688-048 and STR87640 (Δprc1Δprc2, ΔhslUV, ΔmepM1, ΔmepS2, ΔpyrF, lsc::lacIQ1)+p688-048. Samples analyzed were prepared from soluble fractions of whole fermentation broth harvested at 24, 48 and 72 hours post induction. Soluble fractions were prepared by sonication of diluted whole fermentation, followed by centrifugation to separate soluble and insoluble fractions. At 120 hours post induction, samples analyzed were prepared from cell free culture supernatant (cell free broth) following centrifugation of whole broth to separate the cell pellet and cell free broth. Titer of assembled Fab measured using non-reducing SDS-CGE analysis, using the system internal mass ladder.

TABLE 7

Growth condition study data

| Ferm. Run No. | Strain ID | pH | Temp (C.) | Induction OD575 | Titer at I24 (mg/L) | Titer at I48 (mg/L) | Titer at I72 (mg/L) | Titer at I120 (mg/L) |
|---|---|---|---|---|---|---|---|---|
| 1 | STR87639 | 7.2 | 25 | 60 | 0 | 0 | 0 | 0 |
| 2 | STR87639 | 6 | 25 | 120 | 0 | 0 | 147 | 230 |
| 3 | STR87639 | 6 | 32 | 60 | 0 | 549 | 414 | 272 |
| 4 | STR87639 | 7.2 | 32 | 120 | 0 | 0 | 46 | 12 |
| 5 | STR87640 | 7.2 | 25 | 60 | 0 | 0 | 0 | 55 |
| 6 | STR87640 | 6 | 25 | 120 | 0 | 0 | 0 | 96 |
| 7 | STR87640 | 6 | 32 | 60 | 176 | 237 | 204 | 254 |
| 8 | STR87640 | 7.2 | 32 | 120 | 0 | 0 | 0 | 70 |

I24: 24 hours post induction; I48: 48 hours post induction, I72: 72 hours post induction, I120: 120 hours post induction. Samples analyzed prepared from whole broth at 24, 48 and 72 hours post induction. Samples analyzed prepared from cell free culture supernatant (cell free broth) 120 hours post induction. Titer=assembled Fab measured using non-reducing SDS-CGE analysis.

The STR87639 lysate was analyzed by LC-MS and found to contain several species in the non-reduced intact mass, including HC/LC/LC dimer, and fragments of both HC and LC, and assemblies that include HC and LC fragments. The correct Fab mass (47,761) was observed in low abundance.

Conclusion: Both STR87639 and STR87640 produced the highest Fab' yields at pH 6.0, 32 deg C., and when induced at an OD575 of 60. STR87639 produced the highest yield, but accumulated proteolytic fragments of the Fab' heavy and light chains.

Example 4. Optimization of Host Strains for Recombinant Protein Production I: Identification of Additional Proteases that Influence Recombinant Protein Quality Identification of Proteases To identify other factors that influence proteolysis of the anti-TNF-alpha Fab' fragment, two intermediate strains were created by introducing plasmid p688-048 containing the open reading frame of the anti-TNF-alpha Fab' heavy chain and light chain, and a co-transcriptional P. fluorescens DsbC protein disulfide isomerase on host backgrounds DC1032: Δprc1, Δprc2, ΔhslUV, ΔpyrF, lsc::lacIQ1 (creating STR36036), and DC867: Δprc1Δprc2, MepM1(P410L), ΔpyrF, lsc::lacIQ1 (creating PF1558). Biological replicates were grown in duplicate and sampled along the growth curve representing the initial culture seeded at low cell density, mid log phase growth, time post induction (I) at 12 hr, and 48 hr. The samples were processed for whole transcriptomic RNA sequencing at Genewiz (San Diego, CA). Quality trimmed Fastq files were returned and processed using the open sourced software STAR aligner compiled from source code and run with the following parameters: outSAMtype BAM SortedByCoordinate and quantMode GeneCounts. (See, e.g., Dobin A, Davis C A, Schlesinger F, Drenkow J, Zaleski C, Jha S, Batut P, Chaisson M, Gingeras T R. STAR: ultrafast universal RNA-seq aligner. Bioinformatics. 2013 Jan. 1; 29(1):15-21. doi: 10.1093/bioinformatics/bts635. Epub 2012 Oct. 25. PMID: 23104886; PMCID: PMC3530905, incorporated herein by reference.) Quantified genes were annotated into a data frame using the open sourced featurecounts software compiled from source code (as described by Liao Y, Smyth G K and Shi W. featureCounts: an efficient general-purpose program for assigning sequence reads to genomic features. Bioinformatics, 30(7):923-30, 2014, incorporated herein by reference) and the data was normalized and fitted to a linear regression model with interactions. Statistical significance of gene counts was done by calculating pValues based on the Wald test of the mean normalized gene counts between STR36306 (functional MepM1) and PF1558 (deficient MepM1). Genes impacting upregulation were visualized by volcano plot by plotting statistical significance (pValue) versus log 2fold change of the mean normalized transcript counts cumulatively over time and between seed and I12. Time points used for comparison were taken from samples exhibiting the greatest change via a principal component analysis. The results are shown in Tables 8 and 9.

TABLE 8

RNAseq comparing DC1032 host with MepM1-deficient host

| Gene | GeneID | log2fold change* | SEQ ID NO |
|---|---|---|---|
| PROKKA01104 | Serralysin precursor; extracellular alkaline metalloprotease (RXF04495.2; PROKKA_01104) | 0.61382 | 9 |
| PROKKA01141 | Protease HtpX (RXF05137; PROKKA_01141) amino acid | 1.7 | 39 |
| PROKKA02909 | Protease Murein L,D transpeptidase (RXF01911; PROKKA_02909) amino acid | 1.11 | 41 |
| PROKKA01390 | DegP2 | −0.423888 (p = 0.18) | 31 |

*Cumulative difference across all fermentation time up to I12; p value <0.05.

TABLE 9

Transcription over fermentation time in MepM1-deficient host

| Gene | GeneID | log2fold change* | SEQ ID NO |
|---|---|---|---|
| PROKKA01104 | Serralysin precursor; extracellular alkaline metalloprotease (RXF04495.2; PROKKA_01104) | 3.01 | 9 |
| PROKKA01141 | Protease HtpX (RXF05137; PROKKA_01141) amino acid | 4.96 | 39 |
| PROKKA02909 | Protease Murein L,D transpeptidase (RXF01911; PROKKA_02909) amino acid | 2.0 | 41 |
| PROKKA01390 | DegP2 | -0.783 (p = 0.01) | 31 |

*I12 vs. Seed; p value <0.05.

Conclusion: This comparative analysis showed that extracellular alkaline metalloprotease RXF04495.2 belonging to the matrix metalloprotease class EC 3.4.24.40 (SEQ ID NO: 9) is upregulated both cumulatively and temporally across fermentation time in a Prc-deficient host cell having a MepM1 deficiency when compared with a Prc-deficient MepM1+ host cell.

Example 5. Optimization of Host Strains for Recombinant Protein Production II: Introduction of Additional Protease Mutations and Strain Evaluation Extracellular Alkaline Metalloprotease RXF04495.2 Deficiency Using a *P. fluorescens* host of genotype Δprc1, Δprc2, ΔhslUV, ΔmepM1, an RXF04495.2-deficient host was made by a method similar to that used to generate the combinatorial knockouts of the genes described in Example 2, in this case using a RXF04495.2 homology arm (SEQ ID NO: 61). Colony PCR verified knockouts were used to create the PF1596 host background having the following genotype: Δprc1, Δprc2, ΔhslUV, ΔmepM1, ΔRXF04495.2 metalloprotease, ΔpyrF, lsc::lacIQ1. Resulting host PF1596 was then transformed with plasmid pFNX7800 containing the Fab' only expression cassette encoding the Fab' heavy chain operably linked to the Slmt secretion signal (SEQ ID NO: 25) and the Fab' light chain operably linked to the Azu secretion signal (SEQ ID NO: 26). These heavy and light chains were expressed co-transcriptionally, in a variety of host backgrounds under the control of a tac promoter for IPTG inducible expression.

Further Protease Deficiencies and Overexpressed Proteins

DegP2 was selected as a further protease to inactivate and test in host strains for recombinant protein expression. However, despite screening more than 2000 clones, no DegP2 inactivation was obtained in the candidate protease-deficient host backgrounds. As an alternative approach, a catalytically dead DegP2 protease (DegP2 S219A, SEQ ID NO: 29) that outcompetes the endogenous protease was expressed, either on a separate plasmid under the control of the mannitol promoter (Pmtl), on the same plasmid under control of Pmtl, or co-transcriptionally with the Fab' HC and LC. Folding modulator PDIA6 (SEQ ID NO: 27) was expressed co-transcriptionally.

Evaluation of Protease-Deficient Host Strains

The anti-TNF-alpha Fab' produced by the recombinant host strains described in Table 10 was evaluated for light chain proteolysis and/or heavy chain clipping.

TABLE 10

Recombinant protease-deficient host strains

| | Strain ID | Host ID | Genotype | Plasmid and Encoded Amino Acid Sequences* |
|---|---|---|---|---|
| 1 | STR92557 | PF1559 | Δprc1Δprc2, ΔhslUV, ΔmepM1, ΔpyrF, lsc::lacIQ1 | pFNX7420: Fab' HC (SEQ ID NO: 25), LC (SEQ ID NO: 26) (genes co-transcribed from Ptac), DegP2S219A (SEQ ID NO: 29) (gene transcribed from Pmtl), PyrF |
| 2 | STR87639 | PF1559 | Δprc1Δprc2, ΔhslUV, ΔmepM1, ΔpyrF, lsc::lacIQ1 | P688-048: Fab' HC (SEQ ID NO: 25), LC (SEQ ID NO: 26), DsbC (SEQ ID NO: 60) (genes co-transcribed from Ptac), PyrF |
| 3 | STR92567 | PF1559 | Δprc1Δprc2, ΔhslUV, ΔmepM1, ΔpyrF, lsc::lacIQ1 | pFNX7422: Fab' HC (SEQ ID NO: 25), LC (SEQ ID NO: 26), PDIA6 (SEQ ID NO: 27) (genes all co-transcribed from Ptac), PyrF |
| 4 | STR94974 | PF1596 | Δprc1Δprc2, ΔhslUV, ΔmepM1, ΔRXF04495.2; metalloendopeptidase, ΔpyrF lsc::lacIQ1 | pFNX7800: Fab' HC (SEQ ID NO: 25), LC (SEQ ID NO: 26) (genes co-transcribed from Ptac), PyrF |
| 5 | STR94975 | PF1596 | Δprc1Δprc2, ΔhslUV, ΔmepM1, ΔRXF04495.2; metalloendopeptidase, ΔpyrF, lsc::lacIQ1 | pFNX7420: Fab' HC (SEQ ID NO: 25), LC (SEQ ID NO: 26) (genes co-transcribed from Ptac) DegP2S219A (SEQ ID NO: 29) (transcribed from Pmtl), PyrF |

TABLE 10-continued

Recombinant protease-deficient host strains

| | Strain ID | Host ID | Genotype | Plasmid and Encoded Amino Acid Sequences* |
|---|---|---|---|---|
| 6 | STR94976 | PF1596 | Δprc1Δprc2, ΔhslUV, ΔmepM1, ΔRXF04495.2; metalloendopeptidase, ΔpyrF, lsc::lacI$^{Q1}$ | pFNX7421: Fab' HC (SEQ ID NO: 25), LC (SEQ ID NO: 26), DegP2S219A (SEQ ID NO: 29) (genes co-transcribed from Ptac), PyrF |
| 7 | STR94977 | PF1596 | Δprc1Δprc2, ΔhslUV, ΔmepM1, ΔRXF04495.2; metalloendopeptidase, ΔpyrF, lsc::lacI$^{Q1}$ | pFNX7422: Fab' HC (SEQ ID NO: 25), LC (SEQ ID NO: 26), PDIA6 (SEQ ID NO: 27) (genes co-transcribed from Ptac), PyrF |

*In each plasmid, the HC (heavy chain) and LC (light chain) amino acid sequences include N-terminally fused secretion signals Slmt (SEQ ID NO: 11) and Azu (SEQ ID NO: 13), respectively, as annotated in Table 14 for SEQ ID NOS: 25 and 26. Corresponding nucleic acid sequences used are as shown in Table 14 (SEQ ID NO: 25 is a fusion of SEQ ID NOS: 11 and 21, encoded by SEQ ID NOS: 12 and 22, respectively; SEQ ID NO: 26 is a fusion of SEQ ID NOS: 13 and 23, encoded by SEQ ID NOS: 14 and 24, respectively).

The host strains in Table 10 above were cultured and induced according to the design shown in Table 11 below.

TABLE 11

Induction Design

| Unit | Harvest at | Strain ID | Actual Induction OD |
|---|---|---|---|
| DG3_u1 | I24 | STR92557 | 105 |
| DG3_u2 | I24 | STR92557 mtl promoter | 96.8 |
| DG3_u3 | I36 | STR92557 | 100 |
| DG3_u4 | I48 | STR92557 | 108.6 |
| DG3_u5 | I24 | STR94973 | 97.6 |
| DG3_u6 | I36 | STR94973 | 83 |
| DG3_u7 | I48 | STR94973 | 87.4 |
| DG3_u8 | I24 | STR94974 | 105.8 |
| DG4_u1 | I36 | STR94974 | 87.6 |
| DG4_u2 | I48 | STR94974 | 97.4 |
| DG4_u3 | I24 | STR94975 | 110.4 |
| DG4_u4 | I36 | STR94975 | 106.8 |
| DG4_u5 | I48 | STR94975 | 103 |
| DG4_u6 | I24 | STR94976 | 78.8 |
| DG4_u7 | I36 | STR94976 | 87 |
| DG4_u8 | I48 | STR94976 | 93.8 |

Strains were grown at pH 6.0, 32 deg C., in mineral salts medium with glycerol as a carbon source induced at the OD575 as shown, and harvested at 24, 36, or 48 hours after induction. The harvested cells were suspended to 25% solids in 75 mM phosphate, 100 mM sodium chloride, pH 7. The cell suspension was then lysed/homogenized and centrifuged at 15,000×g for 30 minutes. Clarified lysate was then loaded onto a Protein L resin pre-equilibrated with 75 mM phosphate, 100 mM NaCl, pH 7.4. The affinity captured Fab' was washed with 3 column volumes (CV's) of 50 mM BisTris, 1M NaCl, pH 7.0 followed by 3 CV's of 50 mM Tris, pH 7.2. The Fab' was eluted with 3-10 CV's of elution buffer (75 mM acetate, pH 3.4) and immediately neutralized to pH 7-8 with 2.4 M Tris base. Purity of the Fab' was assessed with reduced and non-reduced SDS-CGE.

Light Chain Proteolysis in Protease-Deficient Host Strains

Proteolysis of the Fab' fragment was quantitated by enriching the Fab' using capto-L affinity chromatography and subsequent imaging and quantification by NR-SDS-CGE. The results are shown in FIG. 6. Strains were grown and harvested at the post-induction times (in hours) as shown on the y-axis, and the recombinant protein was Capto-L enriched and analyzed by NR-SDS-CGE. The x-axis shows the percent of proteolyzed light chain species in each lane. A brief summary of the strains tested is shown in Table 12 below.

TABLE 12

Summary of recombinant protease-deficient host strains

| Strain ID | Host ID | Secretion Signal (HC/LC) | Deficient Protease Activities | Co-overexpressed Folding Modulator |
|---|---|---|---|---|
| STR92557 | PF1559 | Slmt/Azu | Prc1/Prc2/hslUV/ MepM1 | DegP2S219A |
| STR87639 | PF1559 | Slmt/Azu | Prc1/Prc2/hslUV/ MepM1 | DsbC |
| STR92567 | PF1559 | Slmt/Azu | Prc1/Prc2/hslUV/ MepM1 | PDIA6 (co-transcriptional with Fab') |
| STR94974 | PF1596 | Slmt/Azu | Prc1/Prc2/hslUV/ MepM1/ Metalloprotease | — |
| STR94975 | PF1596 | Slmt/Azu | Prc1/Prc2/hslUV/ MepM1/ Metalloprotease | DegP2S219A |
| STR94976 | PF1596 | Slmt/Azu | Prc1/Prc2/hslUV/ MepM1/ Metalloprotease | DegP2S219A (co-transcriptional with Fab') |
| STR94977 | PF1596 | Slmt/Azu | Prc1/Prc2/hslUV/ MepM1/ Metalloprotease | PDIA6 (co-transcriptional with Fab') |

As shown by FIG. 6, the recombinant Fab' light chain produced by STR94974, which is deficient in MepM1 and the RXF04495.2 metalloprotease, was least proteolyzed. Proteolysis was significantly decreased at I24 and I36. At I24 virtually no proteolysis was observed in backgrounds containing deletion of RXF04495.2. The Fab' expression in PF1596 shows a further decrease of proteolysis by half at I36. The RXF04495.2 deficiency dramatically reduced the degradation of the light chain (LC) of the Fab.

Titer of Recombinant Fab' Produced by Protease-Deficient Host Strains

The anti-TNF-alpha Fab' sample titers were obtained via biolayer interferometry using the Octet Red 96 system, measuring TNF-α binding activity. Data were collected in Data Acquisition software version 11.0. All experiments were performed in 1× kinetics buffer (Sartorius, part number 18-1105). High-precision streptavidin biosensors (Sartorius, part number 18-5117) were incubated with 115 nM biotinylated TNF-α (Acro Biosystem, part number TNA-H8211) for 60 seconds followed by incubation in assay buffer for 60 seconds to establish a baseline. The binding of the samples was then measured to detect active Fab'. The results for the expression strains that produced the highest titers of active Fab' are summarized below.

FIG. 7 shows that in host strains STR94974, STR94975, and STR94977, the anti-TNF-alpha Fab' fragment was produced at titers up to 1 g/L at 24 hrs and 4 g/L at 72 hrs, as assessed by NR-SDS-CGE or by biolayer interferometry (BLI) with immobilized TNF-alpha. Host cell line PF1596 can also be transformed with an expression cassette containing a fusion of the DsbA and Azu secretion signals to the heavy and light chain amino acid sequences, respectively, which can result in Fab' titers up to 1 g/L at the 2 L scale in MepM KO prc null lines by NR-CGE analysis (data not shown).

Growth Comparison of Protease-Deficient Host Strains

FIGS. 8A and 8B compare growth of STR87639, which is Prc and MepM1 deficient, with STR92557, STR92567, STR94974, and STR94976 for 24 and 48 hours after induction, respectively. Growth phase was conducted at 32 deg C., pH 6.5, and the induction target was OD575=80. The cells were induced with IPTG and production phase was conducted at 32 deg C., pH 6.5 for either 24 or 48 hours. The overexpression of various folding modulators did not appear to impact growth significantly, nor did stacking of the metalloprotease deletion (STR94974 and STR94976). With the exception of STR87639 all strains continued to increase in cell density for a period of time post induction FIG. 9 compares growth of *P. fluorescens* Prc-deficient Fab' expression strains STR87639, STR92473, STR94994, STR94995, and STR94996, and STR94998 (see Table 13). Growth phase was conducted at 32 deg C., pH 6.5. Induction target OD575 was 100, carried out at 32 deg, pH 6 (STR87639, STR92473), or was 80, carried out at 32 deg, pH 6.5 (others).

Lines, from top to bottom:

Closed circles, solid line: STR87639 (MepM1 deficient)

Triangles, solid line: STR92473 (MepM1 and MepM2 deficient)

Diamonds, solid line: STR94995 (MepS2 deficient)

Circles, dashed line: STR94998 (not MepM or MepS deficient; no expression construct)

Open circles, solid line: STR94996 (MepS1 and MepS2 deficient)

Squares, solid line: STR94994 (MepS1 deficient)

The results showed that deficiency in MepS1, MepS2, or both MepS1 and MepS2, failed to restore growth in Prc-deficient host cells. Deficiency in MepM1 or both MepM1 and MepM2, restored growth in Prc-deficient host cells.

TABLE 13

Recombinant protease-deficient host strains used in FIG. 9 growth comparison

| | Strain ID | Host ID | Genotype | Plasmid and Encoded Amino Acid Sequences* |
|---|---|---|---|---|
| 1 | STR87639 | PF1559 | Δprc1Δprc2, ΔhslUV, ΔmepM1, ΔpyrF, lsc::lacI$^{Q1}$ | P688-048: Fab' HC (SEQ ID NO: 25), LC (SEQ ID NO: 26), DsbC (SEQ ID NO: 60) all co-transcribed from Ptac, PyrF |
| 2 | STR92473 | PF1584 | Δprc1Δprc2, ΔhslUV, ΔmepM1, ΔmepM2, ΔpyrF, lsc::lacI$^{Q1}$ | P688-048: Fab' HC (SEQ ID NO: 25), LC (SEQ ID NO: 26), DsbC (SEQ ID NO: 60) all co-transcribed from Ptac, PyrF |
| 3 | STR94995 | PF1582 | Δprc1, Δprc2, ΔhslUV, ΔmepS2, ΔpyrF, lsc::lacIQ1 | P688-048: Fab' HC (SEQ ID NO: 25), LC (SEQ ID NO: 26), DsbC (SEQ ID NO: 60) all co-transcribed from Ptac, PyrF |
| 4 | STR94998 | DC1032 | Δprc1, Δprc2, ΔhslUV, ΔpyrF, lsc::lacIQ1 | pDOW1169: empty expression vector |
| 5 | STR94996 | PF1562 | Δprc1, Δprc2, ΔhslUV, ΔmepS1, ΔmepS2, ΔpyrF, lsc::lacIQ1 | P688-048: Fab' HC (SEQ ID NO: 25), LC (SEQ ID NO: 26), DsbC (SEQ ID NO: 60) all co-transcribed from Ptac, PyrF |
| 6 | STR94994 | PF1583 | Δprc1, Δprc2, ΔhslUV, ΔmepS1, ΔpyrF, lsc::lacIQ1 | P688-048: Fab' HC (SEQ ID NO: 25), LC (SEQ ID NO: 26), DsbC (SEQ ID NO: 60) all co-transcribed from Ptac, PyrF |

*In each plasmid, the HC (heavy chain) and LC (light chain) amino acid sequences include N-terminally fused secretion signals Slmt (SEQ ID NO: 11) and Azu (SEQ ID NO: 13), respectively, as annotated in Table 14 for SEQ ID NOS: 25 and 26. Corresponding nucleic acid sequences used are as shown in Table 14 (SEQ ID NO: 25 is a fusion of SEQ ID NOS: 11 and 21, encoded by SEQ ID NOS: 12 and 22, respectively; SEQ ID NO: 26 is a fusion of SEQ ID NOS: 13 and 23, encoded by SEQ ID NOS: 14 and 24, respectively).

TABLE 14

Table of Sequences

| SEQ ID NO | Name | Sequence* |
|---|---|---|
| 1 | MepM1 amino acid RXF01291 *P. fluorescens* | MTTEPSKAPPLYPKTHLLAASGIAALLSLALLVFPSSDVEAKRT SLSLDLESPVEQLTQDQDASDAQQATNTATESPFAQIESTPEDT QQAAQEAPAAAKSPQHREVIVGKGDTLSTLFEKVGLPAAAVNDV LASDKQAKQFTQLKRGQKLEFELTPDGQLNNLYTSISDLESISL SKGAKGFAFNRITTKPVMRSAYVHGVINSSLSQSAARAGLSHSM TMDMASVFGYDIDFAQDIRQGDEFDVIYEQKVANGKVVGTGNIL SARFTNRGKTYTAVRYTNKQGNSSYYTADGNSMRKAFIRTPVDF ARISSRFSMGRKHPILNKIRAHKGVDYAAPRGTPIKAAGDGKVL LAGRRGGYGNTVIIQHGNTYRTLYGHMQGFAKGVKTGGNVKQGQ VIGYIGTTGLSTGPHLHYEFQVNGVHVDPLGQKLPMADPIAKAE RARFMQQSQPLMARMDQERSTLLASAKR |

TABLE 14-continued

| Table of Sequences | | |
|---|---|---|

| SEQ ID NO | Name | Sequence* |
|---|---|---|
| 2 | MepM1 example nucleic acid encoding SEQ ID NO: 1 | ATGACCACTGAACCGTCTAAAGCGCCGCCGCTTTACCCGAAGAC CCACCTGCTCGCCGCAAGTGGTATCGCCGCCCTTCTCAGCCTGG CACTGCTGGTATTCCCTTCCAGTGACGTTGAAGCCAAACGAACA TCCCTGAGCCTTGATCTGGAAAGCCCAGTTGAACAACTGACACA AGATCAAGACGCTTCCGACGCTCAACAAGCCACAAACACTGCAA CTGAATCACCTTTCGCCCAGATCGAAAGCACACCCGAAGACACC CAGCAAGCCGCCCAGGAAGCACCTGCAGCAGCCAAGAGTCCCCA GCATCGCGAAGTCATCGTGGGCAAAGGCGACACACTCTCGACCC TGTTCGAAAAAGTTGGGTTGCCTGCCGCCGCTGTAAATGACGTG CTCGCCAGCGATAAGCAAGCCAAGCAATTCACTCAGCTCAAACG TGGTCAAAAGCTTGAATTTGAGCTGACGCCAGACGGCCAGTTGA ACAACCTGTACACCAGCATCAGTGACTTGGAAAGCATCAGCCTG AGCAAAGGCGCCAAAGGCTTCGCATTCAACAGAATCACCACCAA ACCCGTCATGCGTTCCGCCTACGTACATGGCGTGATCAACAGCT CCCTGTCGCAGTCGGCCGCGCGTGCGGGCCTGTCGCATAGCATG ACCATGGACATGGCCAGCGTATTTGGCTACGACATCGACTTCGC CCAGGACATCCGTCAAGGCGACGAATTCGACGTGATCTACGAAC AGAAAGTAGCCAACGGAAAAGTGGTCGGCACTGGCAACATTCTT TCTGCACGCTTCACAAACCGTGGCAAAACCTACACCGCCGTGCG CTACACCAACAAACAAGGCAACAGCAGCTACTACACGGCTGATG GCAACAGCATGCGTAAGGCCTTCATCCGTACACCCGTTGACTTT GCCCGTATTAGCTCGCGTTTCTCCATGGGCCGCAAGCATCCAAT TCTGAACAAAATTCGCGCACACAAGGGCGTCGACTATGCCGCGC CGCGTGGCACGCCAATCAAAGCAGCGGGCGACGGCAAGGTCTTG TTGGCGGGGCGCCGTGGTGGTTACGGCAATACGGTGATCATCCA GCACGGCAACACTTACCGCACGCTGTACGGCCACATGCAAGGGT TCGCCAAGGGCGTCAAGACAGGCGGCAACGTGAAACAGGGCCAA GTGATCGGCTACATCGGTACCACCGGCCTCTCCACCGGCCCGCA CTTGCACTACGAGTTCCAGGTCAACGGCGTACACGTCGACCCAT TGGGCCAGAAGCTGCCGATGGCCGACCCGATTGCCAAGGCCGAA CGCGCGCGCTTCATGCAACAGAGCCAGCCGCTGATGGCACGGAT GGATCAAGAGCGCTCCACCTTGCTGGCTTCGGCGAAGCGTTAA |
| 3 | MepM2 amino acid RXF03916 *P. fluorescens* | MPRLLSLLMLLCLTFNAHADSYITRTLNKPVPGGVAVVELGPSA TAPKATYQGKPVLVVKEQDNWLAIVGIPLTVKPGNERISSGGRN LPFIVGYKKYPEQRITLKNKSQVNPDPAQLKRIEGELAVQLKAY RSFSPNLPSNLVLDKPVNGPLSSKFGVRRFFNGEERNPHSGLDF AVPAGTPIKTPANGKVILVGNYFFNGNTVFVDHGQGFISMFCHM SKIDVRVGQQLVRGAVVGKVGSTGRATGPHMHWNVSLNDARVDP AIFIGAFQP |
| 4 | MepM2 example nucleic acid encoding SEQ ID NO: 3 | ATGCCACGCCTACTGAGCCTGTTGATGCTGTTGTGCCTCACGTT TAACGCCCACGCCGACAGCTACATCACGCGAACCCTGAACAAAC CCGTGCCTGGCGGCGTGGCCGTCGTCGAACTAGGCCCTTCGGCC ACAGCGCCGAAAGCCACCTACCAGGGCAAGCCGGTGCTGGTGGT CAAGGAGCAGGACAACTGGCTGGCGATTGTCGGCATCCCGTTGA CGGTCAAGCCTGGCAACGAGCGCATCAGCAGCGGGGGGCGCAAC CTGCCGTTTATCGTCGGCTACAAGAAGTATCCGGAACAACGCAT CACCTTGAAGAACAAAAGCCAGGTCAACCCCGACCCGGCCCAGC TCAAGCGCATCGAAGGCGAATTGGCAGTGCAGCTCAAGGCTTAC CGCAGCTTCAGCCCGAATTTGCCGAGCAATCTGGTGCTGGATAA ACCGGTGAACGGGCCGCTGTCGAGCAAGTTCGGGGGTGCGACGCT TCTTCAACGGCGAAGAGCGCAACCCGCACTCGGGCCTGGACTTC GCCGTACCGGCCGGCACACCGATCAAGACACCCGCCAATGGCAA GGTGATTCTGGTCGGCAATTACTTCTTCAACGGCAATACCGTGT TTGTCGACCATGGCCAGGGGTTTATCAGCATGTTCTGCCATATG TCGAAGATCGATGTGAGGGTGGGTCAGCAACTGGTGCGCGGTGC GGTAGTCGGCAAAGTAGGCTCGACAGGCCGGGCCACTGGGCCGC ATATGCACTGGAACGTCAGCCTGAACGATGCACGGGTAGATCCG GCGATTTTTATCGGCGCGTTTCAACCCTGA |
| 5 | MepS1 amino acid RXF04923 *P. fluorescens* | MLNRFAPLVPLALVTLLFGCASHPQQVAEQQKPQVQNQAKFVAA QSASVYEEEVATEKELAEFSDSKPYQLPLLADSILERGMSLIGT RYRFGGTSEAGFDCSGFIGYLFREEAGMNLPRSTREMINVNAPL VARNNLKPGDLLFFSTSGRGRVSHAGIYLGDNQFIHSSSRRSGG VRVDNLGDSYWSKTFIEAKRALAMAPTTVTASK |
| 6 | MepS1 example nucleic acid encoding SEQ ID NO: 5 | ATGCTAAATCGCTTCGCACCCCTCGTGCCTCTCGCACTCGTTAC CCTGTTGTTTGGTTGCGCCTCCCACCCTCAGCAGGTGGCAGAAC AGCAAAAACCACAGGTTCAAAATCAGGCAAAGTTCGTTGCTGCA CAGTCTGCTTCTGTTTATGAAGAAGAGGTGGCAACCGAAAAGA ACTCGCCGAGTTCTCCGACAGCAAGCCTTACCAGCTGCCACTTC TGGCCGACAGCATCCTTGAGCGCGGCATGTCCTTGATCGGTACC CGTTACCGTTTCGGCGGCACCTCGGAAGCCGGTTTTGATTGCAG |

TABLE 14-continued

Table of Sequences

| SEQ ID NO | Name | Sequence* |
|---|---|---|
| | | CGGTTTCATTGGCTACCTGTTTCGTGAAGAAGCCGGTATGAACC TGCCGCGCTCCACGCGCGAGATGATCAACGTGAATGCACCGTTG GTCGCACGAAACAACCTCAAGCCCGGTGATCTGCTTTTCTTTAG TACCAGTGGCCGCGGTCGTGTCAGCCACGCCGGTATCTACCTGG GCGATAACCAGTTTATTCATTCCAGCAGCCGCCGCAGTGGTGGT GTTCGGGTCGATAACCTCGGTGACAGCTACTGGAGCAAAACCTT CATCGAAGCCAAGCGCGCACTCGCCATGGCCCCGACGACGGTTA CCGCTAGTAAGTAA |
| 7 | MepS2 amino acid *P. fluorescens* | MSTSARLMLIVCAALLSACASRTPPPAPVAVKPKPVFNYATQNF SPAAEDVLFRALGLVGTPYRWGGNTPDSGFDCSGLIGFVFRDAA GISLPRTTRELIVMRAQDVSEQNLQTGDLLFFATGGGSRVSHAG IYVGEGRFVHAPQTGGTVKLDTLSKAYWQNAYLSAKRVLPGNLA RNP |
| 8 | MepS2 example nucleic acid encoding SEQ ID NO: 7 | ATGTCGACCTCGGCCCGCCTGATGCTTATTGTTTGCGCCGCGCT GCTCAGCGCCTGCGCCAGTCGCACACCGCCGCCCGCGCCCGTCG CGGTCAAGCCTAAGCCGGTGTTCAACTATGCCACCCAGAATTTC TCGCCAGCTGCCGAAGACGTGCTCTTTCGTGCGCTGGGCCTGGT CGGCACGCCTTATCGCTGGGGCGGCAACACACCGGACTCGGGTT TTGATTGCAGCGGCCTGATCGGCTTTGTATTCCGCGACGCTGCT GGCATCTCATTGCCGCGCACCACCCGTGAACTGATCGTGATGCG TGCCCAGGACGTCAGCGAACAAAACCTGCAGACCGGCGACCTGC TGTTCTTCGCCACCGGTGGTGGTTCGCGGGTCAGCCATGCGGGT ATTTATGTGGGGGAGGGGCGCTTCGTACACGCGCCGCAAACCGG CGGTACGGTGAAGCTGGATACGCTATCCAAAGCGTATTGGCAGA ATGCCTACCTGAGTGCCAAACGCGTGTTGCCAGGGAATCTGGCG CGTAACCCCTGA |
| 9 | Serralysin precursor; extracellular alkaline metalloprotease amino acid (RXF04495.2; PROKKA_01104) *P. fluorescens* | MHIPVRQSSYSRPSDKLQPDLSPDEHQVVLWANNKKSFTTDQAA KHITRGGFKPHDRNNDGKIVVGYNFAGGFNAAQKERARQALQYW ADVANIEFVENGPNTDGTISIKGVPGSAGVAGLPNKYNSNVQAN IGTQGGQNPAMGSHFLGLLIHELGHTLGLSHPGKYDGQGFNYDR AAEYAQDTKARSVMSYWTETHQPGHNFAGRSPGAPMMDDIAAAQ RLYGANTKTRNTDTTYGFNSNSGREAYSLKQGSDKPIFTVWDGG GNDTLDFSGFTQNQTINLKAESFSDVGGLRGNVSIAKGVSVENA IGGTGNDTLTGNEGNNRLTGGKGADKLHGGAGADTFVYRRASDS TPQAPDIIQDFQSGSDKIDLTGVVQEAGLKSLSFVEKFSGKAGE AVLGQDAKTGRFTLAVDTTGNGTADLLVASQSQIKQADVIWNGQ APTVTPTPEPTVVPVSDPVPTPTSEPTEPEPTPEPAPLPVPTPR PGGGFIGKIFSSFKGFIKKVWSIFR |
| 10 | RXF04495.2 example nucleic acid encoding sequence SEQ ID NO: 9 | ATGCATATCCCTGTTAGGCAGTCTTCTTACTCGCGTCCTTCAGA TAAGTTACAGCCCGATCTTTCACCCGATGAACACCAAGTTGTTC TCTGGGCCAACAATAAAAAATCTTTCACCCACGGATCAGGCCGCG AAACACATCACCCGCGGTGGCTTCAAGTTTCATGATCGCAACAA TGATGGAAAAATCGTCGTGGGTTATAACTTTGCGGGCGGCTTCA ATGCGGCTCAGAAAGAACGGGCCAGGCAAGCCCTTCAGTACTGG GCGGATGTTGCTAATATCGAATTTGTTGAAAATGGCCCGAACAC GGATGGCACAATAAGCATCAAGGGTGTTCCGGGTTCGGCAGGCG TCGCGGGGGTTGCCCAACAAATATAATTCGAACGTCCAGGCCAAT ATAGGCACCCAGGGTGGGCAAAACCCGGCGATGGGCAGTCACTT CCTGGGCTTATTGATCCATGAACTGGGGCATACCCTGGGGCTGA GTCATCCAGGTAAATACGACGGCCAGGGTTTCAATTACGATCGG GCTGCCGAATATGCCCAGGACACCAAGGCTCGCAGTGTCATGAG CTATTGGACGGAGACTCATCAGCCGGGGCACAATTTTGCCGGGC GCAGCCCGGGTGCCCCGATGATGGACGATATCGCCGCCGCCCAG CGGCTCTACGGCGCCAACACCAAAACCCGGAATACCGACACCAC CTACGGCTTCAATTCCAATTCAGGCCGGGAGGCTTATAGCCTCA AGCAGGGGAGCGACAAGCCGATCTTCACCGTCTGGGACGGTGGA GGTAATGACACGCTCGACTTCTCCGGGTTCACCCAGAACCAAAC CATCAACCTCAAGGCTGAGTCATTCTCGGACGTGGGGGGCTTGC GAGGAAATGTGTCGATTGCCAAGGGTGTGAGTGTGGAAAACGCC ATTGGCGGTACAGGCAACGATACCTTGACGGGGAACGAGGGCAA CAATCGGCTCACGGGCGGCAAGGGGGCCGATAAGCTGCACGGCG GAGCTGGAGCAGACACGTTTGTTTACCGCCGCGCCAGCGATTCA ACGCCGCAGGCACCGGACATCATCCAGGACTTCCAGAGCGGGAG CGACAAGATCGACCTGACCGGTGTTGTTCAGGAGGCGGGGCTCA AGTCGCTGAGCTTCGTCGAGAAATTCAGCGGCAAGGCGGGCGAG GCCGTGCTCGGCCAAGACGCGAAAACCGGCCGTTTCACGTTGGC GGTGGACACAACGGGGAAATGGTACGGCGGATCTACTGGTTGCCA GCCAAAGCCAGATCAAACAGGCGGATGTGATCTGGAACGGTCAG GCGCCGACAGTGACGCCAACGCCTGAACCCACTGTGGTGCCTGT GTCAGATCCCGTGCCGACCCCTACTTCAGAGCCGACTGAACCTG |

TABLE 14-continued

Table of Sequences

| SEQ ID NO | Name | Sequence* |
|---|---|---|
| | | AACCCACGCCTGAGCCCGCCCCTTTGCCCGTCCCGACTCCACGG CCTGGAGGAGGGTTTATCGGGAAAATTTTTTCATCATTCAAGGG GTTCATAAAAAAAGTGTGGTCGATATTCAGGTGA |
| 11 | Slmt secretion signal amino acid *P. fluorescens* | MRSRLFNFLSCLLLSATAVQSAQA |
| 12 | Slmt example nucleic acid encoding SEQ ID NO: 11 | ATGCGCAGTCGCCTTTTCAACTTTTTATCTTGTCTGCTTCTTTC CGCCACTGCCGTTCAATCCGCCCAG |
| 13 | Azu secretion signal amino acid *P. fluorescens* | MFAKLVAVSLLTLASGQLLA |
| 14 | Azu example nucleic acid encoding SEQ ID NO: 13 | ATGTTTGCCAAACTCGTTGCTGTTTCCCTGCTGACTCTGGCGAG CGGCCAGTTGCTT |
| 15 | DsbA secretion signal amino acid *P. fluorescens* | MRNLILSAALVTASLFGMTAQA |
| 16 | DsbA example nucleic acid encoding SEQ ID NO: 15 | ATGCGTAATCTGATCCTCAGCGCCGCTCTCGTCACTGCCAGCCT CTTCGGCATGACCGCACAA |
| 17 | AnsB secretion signal amino acid *P. fluorescens* | MKSALKNVIPGALALLLLFPVAAQA |
| 18 | AnsB example nucleic acid encoding SEQ ID NO: 17 | ATGAAATCTGCATTGAAGAACGTTATTCCGGGCGCCCTGGCCCT TCTGCTGCTATTCCCCGTCGCCGCCCAGGCC |
| 19 | PorE secretion signal amino acid *P. fluorescens* | MKKSTLAVAVTLGAIAQQAGA |
| 20 | PorE example nucleic acid encoding SEQ ID NO: 19 | ATGAAGAAGTCCACCTTGGCTGTGGCTGTAACGTTGGGCGCAAT CGCCCAGCAAGCAGGCGCC |
| 21 | Anti-TNF-alpha Fab' heavy chain amino acid (certolizumab) | EVQLVESGGGLVQPGGSLRLSCAASGYVFTDYGMNWVRQAPGKG LEWMGWINTYIGEPIYADSVKGRFTFSLDTSKSTAYLQMNSLRA EDTAVYYCARGYRSYAMDYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKKVEPKS CDKTHTCAA |
| 22 | Anti-TNF-alpha Fab' heavy chain example nucleic acid encoding SEQ ID NO: 21 | GAAGTGCAACTGGTGGAGAGCGGCGGTGGCTTGGTTCAGCCGGG TGGCTCCCTGCGTCTGTCGTGTGCGGCCTCCGGGTACGTGTTCA CCGACTACGGCATGAACTGGGTCCGCCAGGCCCCAGGGAAGGGT CTGGAATGGATGGGCTGGATCAACACGTATATCGGCGAACCGAT TTATGCGGACAGCGTAAAAGGGCGCTTCACCTTTAGCTTGGATA CCTCCAAAAGTACGGCCTACCTGCAGATGAATTCCCTGCGGGCA GAGGATACCGCGGTGTATTACTGCGCTCGCGGCTACCGCAGCTA CGCGATGGACTACTGGGGCCAAGGCACCCTGGTGACGGTGAGTT CGGCCAGCACCAAGGGCCCTAGCGTGTTCCCACTCGCCCCCAGC AGCAAATCGACCTCGGGCGGTACGGCCGCACTCGGCTGCCTGGT GAAGGACTATTTCCCGGAGCCGGTGACCGTCAGTTGGAACAGTG GTGCCCTGACTAGCGGCGTGCACACCTTTCCCGCCGTTCTGCAG AGCTCGGGCTTGTACTCCTTGTCGTCCGTCGTAACTGTGCCCAG CAGCTCGCTCGGCACCCAGACCTACATCTGCAATGTCAACCACA AGCCGAGCAACACCAAAGTGGATAAGAAGGTCGAACCGAAGTCC TGCGACAAGACCCATACCTGTGCGGCC |

TABLE 14-continued

Table of Sequences

| SEQ ID NO | Name | Sequence* |
|---|---|---|
| 23 | Anti-TNF-alpha Fab' light chain amino acid (certolizumab) | DIQMTQSPSSLSASVGDRVTITCKASQNVGTNVAWYQQKPGKAP KALIYSASFLYSGVPYRFSGSGSGTDFTLTISSLQPEDFATYYC QQYNIYPLTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 24 | Anti-TNF-alpha Fab' light chain example nucleic acid encoding SEQ ID NO: 23 | GACATTCAGATGACCCAGAGCCCCAGCAGCCTGAGCGCCAGCGT AGGGGACCGCGTGACCATCACCTGTAAAGCCAGTCAAAACGTCG GTACCAACGTGGCATGGTATCAACAAAAACCGGGTAAAGCCCCC AAAGCGTTGATCTACTCCGCCAGTTTCCTGTATAGCGGCGTGCC GTACCGCTTCAGCGGCTCCGGCAGCGGTACCGACTTTACCCTGA CCATTTCCTCGCTGCAACCCGAGGACTTTGCGACCTACTATTGC CAGCAGTATAACATCTACCCGCTGACGTTCGGGCAGGGCACGAA GGTCGAAATCAAACGGACCGTAGCGGCACCGAGTGTGTTCATCT TCCCTCCGAGCGACGAACAGTTGAAGTCCGGCACCGCCTCGGTC GTGTGCCTGCTCAATAACTTCTACCCACGCGAGGCTAAGGTGCA ATGGAAGGTGGACAACGCCCTGCAGTCGGGCAATAGTCAGGAAT CGGTGACTGAACAGGATTCCAAGGATAGCACCTACTCGCTCAGC AGCACGCTGACCTTGTCGAAGGCCGATTACGAGAAGCATAAGGT CTACGCGTGCGAAGTGACGCACCAGGGCCTGTCCTCGCCGGTTA CTAAGAGCTTTAACCGTGGCGAGTGC |
| 25 | Slmt leader (underlined text) fused to anti-TNF-alpha Fab' heavy chain amino acid | <u>MRSRLFNFLSCLLLSATAVQSAQA</u>EVQLVESGGGLVQPGGSLRL SCAASGYVFTDYGMNWVRQAPGKGLEWMGWINTYIGEPIYADSV KGRFTFSLDTSKSTAYLQMNSLRAEDTAVYYCARGYRSYAMDYW GQGTLVTVSSASTKGPSVFPLAPSSKSTSGGTAALGCLVKDYFP EPVTVSWNSGALTSGVHTFPAVLQSSGLYSLSSVVTVPSSSLGT QTYICNVNHKPSNTKVDKKVEPKSCDKTHTCAA |
| 26 | Azu leader (underlined text) fused to anti-TNF-alpha Fab' light chain amino acid | <u>MFAKLVAVSLLTLASGQLLA</u>DIQMTQSPSSLSASVGDRVTITCK ASQNVGTNVAWYQQKPGKAPKALIYSASFLYSGVPYRFSGSGSG TDFTLTISSLQPEDFATYYCQQYNIYPLTFGQGTKVEIKRTVAA PSVFIFPPSDEQLKSGTASVVCLLNNFYPREAKVQWKVDNALQS GNSQESVTEQDSKDSTYSLSSTLTLSKADYEKHKVYACEVTHQG LSSPVTKSFNRGEC |
| 27 | PDIA6 folding modulator amino acid (Q15084) human PDI isoform 6 | LYSSSDDVIELTPSNFNREVIQSDSLWLVEFYAPWCGHCQRLTP EWKKAATALKDVVKVGAVDADKHHSLGGQYGVQGFPTIKIFGSN KNRPEDYQGGRTGEAIVDAALSALRQLVKDRLGGRSGGYSSGKQ GRSDSSSKKDVIELTDDSFDKNVLDSEDVWMVEFYAPWCGHCKN LEPEWAAAASEVKEQTKGKVKLAAVDATVNQVLASRYGIRGFPT IKIFQKGESPVDYDGGRTRSDIVSRALDLFSDNAPPPELLEIIN EDIAKRTCEEHQLCVVAVLPHILDTGAAGRNSYLEVLLKLADKY KKKMWGWLWTEAGAQSELETALGIGGFGYPAMAAINARKMKFAL LKGSFSEQGINEFLRELSFGRGSTAPVGGGAFPTIVEREPWDGR DGELPVEDDIDLSDVELDDLGKDEL |
| 28 | PorE leader (underlined text) fused to PDIA6 folding modulator amino acid | <u>MKKSTLAVAVTLGAIAQQAGA</u>LYSSSDDVIELTPSNFNREVIQS DSLWLVEFYAPWCGHCQRLTPEWKKAATALKDVVKVGAVDADKH HSLGGQYGVQGFPTIKIFGSNKNRPEDYQGGRTGEAIVDAALSA LRQLVKDRLGGRSGGYSSGKQGRSDSSSKKDVIELTDDSFDKNV LDSEDVWMVEFYAPWCGHCKNLEPEWAAAASEVKEQTKGKVKLA AVDATVNQVLASRYGIRGFPTIKIFQKGESPVDYDGGRTRSDIV SRALDLFSDNAPPPELLEIINEDIAKRTCEEHQLCVVAVLPHIL DTGAAGRNSYLEVLLKLADKYKKKMWGWLWTEAGAQSELETALG IGGFGYPAMAAINARKMKFALLKGSFSEQGINEFLRELSFGRGS TAPVGGGAFPTIVEREPWDGRDGELPVEDDIDLSDVELDDLGKD EL |
| 29 | DegP2 (S219A) amino acid *P. fluorescens* (Do family serine endopeptidase; NCBI Reference Sequence WP_198833397.1 with S219A included as indicated by bold text) | MSIPRLKSYLSIVATVLVLGQALPAQAVELPDFTQLVEQASPAV VNISTTQKLPDRKVSNQQMPDLEGLPPMLREFFERGMPQPRSPR GGGGQREAQSLGSGFIISPDGYILTNNHVIADADEILVRLADRS ELKAKLIGTDPRSDVALLKIEGKDLPVLKLGKSQDLKAGQWVVA IGSPFGFDHTVTQGIVSAIGRSLPNENYVPFIQTDVPINPGNAG GPLFNLAGEVVGINSQIYTRSGGFMGVSFAIPIDVAMDVSNQLK SGGKVSRGWLGVVIQEVNKDLAESFGLDKPAGALVAQIQDNGPA AKGGLKVGDVILSMNGQPIIMSADLPHLVGALKAGGKAKLEVIR DGKRQNVELTVGAIPEEGATLDALGNAKPGAERSSNRLGIAVVE LTAEQKKTFDLQSGVVIKEVQDGPAALIGLQPGDVITHLNNQAI DTTKEFADIAKALPKNRSVSMRVLRQGRASFITFKLAE |

TABLE 14-continued

Table of Sequences

| SEQ ID NO | Name | Sequence* |
|---|---|---|
| 30 | DegP2 (S219A) example nucleic acid encoding SEQ ID NO: 29 | ATGTCGATACCACGTTTGAAGTCTTACTTATCCATAGTCGCCAC AGTGCTGGTGCTGGGTCAGGCCTTACCTGCGCAAGCGGTCGAGT TGCCTGACTTCACCCAACTGGTGGAGCAGGCCTCGCCTGCCGTG GTGAACATCAGTACCACGCAGAAGCTGCCGGATCGCAAAGTCTC GAACCAGCAGATGCCCGACCTGGAAGGCTTGCCGCCCATGCTGC GCGAGTTCTTCGAACGAGGGATGCCGCAACCACGCTCCCCCCGT GGCGGCGGTGGCCAGCGCGAAGCCCAATCCCTGGGCTCCGGCTT CATCATTTCGCCTGACGGCTATATCCTCACCAACAACCACGTGA TTGCCGATGCCGACGAGATTCTCGTGCGCCTGGCCGACCGCAGT GAACTCAAGGCCAAGCTGATTGGCACCGATCCACGTTCCGACGT GGCCTTGCTTAAAATCGAGGGCAAGGACTTGCCGGTGCTTAAGC TGGGCAAGTCCCAGGACCTGAAGGCCGGTCAGTGGGTGGTCGCG ATCGGTTCGCCGTTCGGCTTTGACCACACCGTTACCCAAGGCAT CGTCAGCGCCATCGGTCGCAGCCTGCCGAACGAAAACTACGTAC CGTTCATCCAGACCGACGTGCCGATCAACCCGGGTAACGCCGGT GGCCCGCTGTTCAACCTGGCCGGCGAAGTGGTGGGGATCAACTC GCAGATCTACACCCGCTCCGGCGGCTTCATGGGCGTGTCTTTCG CGATCCCAATCGATGTGGCCATGGACGTCTCCAATCAGCTCAAA AGCGGCCGGCAAGGTCAGCCGCGGCTGGTTGGGCGTGGTAATCCA GGAAGTGAACAAGGACCTGGCTGAGTCCTTCGGTCTCGACAAGC CGGCCGGTGCCCTGGTTGCGCAGATTCAGGACAATGGCCCTGCG GCCAAAGGCGGCCTGAAAGTCGGTGACGTCATCCTGAGCATGAA CGGCCAGCCGATCATCATGTCGGCAGACTTGCCTCATTTGGTCG GCGCGCTCAAGGCCGGCGGCAAAGCCAAGCTGGAAGTGATTCGT GATGGCAAGCGCCAGAACGTCGAACTGACCGTAGGTGCCATCCC GGAAGAAGGCGCGACCCTGGATGCCCTGGGCAACGCCAAGCCCG GTGCCGAGCGCAGCAGTAACCGCCTGGGTATCGCCGTGGTTGAA CTGACCGCCGAGCAGAAGAAAACCTTCGACCTGCAAAGCGGTGT GGTGATCAAGGAAGTTCAGGACGGCCCAGCCGCCTTGATCGGCC TGCAACCGGGTGACGTGATCACTCACTTGAACAACCAGGCAATC GATACCACCAAGGAATTCGCCGACATCGCCAAGGCGTTGCCGAA GAATCGCTCGGTGTCGATGCGCGTCCTGCGTCAAGGCCGTGCCA GCTTCATTACCTTCAAGCTGGCTGAG |
| 31 | DegP2 amino acid (Protease RXF07210; PROKKA_01390) *P. fluorescens* (Do family serine endopeptidase; NCBI Reference Sequence WP_198833397.1) (leader underlined at 1-27; DegP2 protein 28-478; catalytic triad amino acids with/without leader at H116/89, D120/93, S219/192, in bold) | <u>MSIPRLKSYLSIVATVLVLGQALPAQA</u>VELPDFTQLVEQASPAV VNISTTQKLPDRKVSNQQMPDLEGLPPMLREFFERGMPQPRSPR GGGGQREAQSLGSGFIISPDGYILTNNHVIADADEILVRLADRS ELKAKLIGTDPRSDVALLKIEGKDLPVLKLGKSQDLKAGQWVVA IGSPFGFDHTVTQGIVSAIGRSLPNENYVPFIQTDVPINPGNSG GPLFNLAGEVVGINSQIYTRSGGFMGVSFAIPIDVAMDVSNQLK SGGKVSRGWLGVVIQEVNKDLAESFGLDKPAGALVAQIQDNGPA AKGGLKVGDVILSMNGQPIIMSADLPHLVGALKAGGKAKLEVIR DGKRQNVELTVGAIPEEGATLDALGNAKPGAERSSNRLGIAVVE LTAEQKKTFDLQSGVVIKEVQDGPAALIGLQPGDVITHLNNQAI DTTKEFADIAKALPKNRSVSMRVLRQGRASFITFKLAE |
| 32 | MepS (Spr) amino acid *E. coli* (UniProtKB - P0AFV4; EC 3.4.17.13; U.S. Pat. No. 9,493,559, incorporated herein by reference) | MVKSQPILRYILRGIPAIAVAVLLSACSANNTAKNMHPETRAVG SETSSLQASQDEFENLVRNVDVKSRIMDQYADWKGVRYRLGGST KKGIDCSGFVQRTFREQFGLELPRSTYEQQEMGKSVSRSNLRTG DLVLFRAGSTGRHVGIYIGNNQFVHASTSSGVIISSMNEPYWKK RYNEARRVLSRS |
| 33 | Prc1 amino acid *P. fluorescens* | MKHLFPSTALAFFIGLGFASMSTNTFAANSWDNLQPDRDEVIAS LNVVELLKRHHYSKPPLDDARSVIIYDSYLKLLDPSRSYFLASD IAEFDKWKTQFDDFLKSGDLQPGFTIYKRYLDRVKARLDFALGE LNKGVDKLDFTQKETLLVDRKDAPWLTSTAALDDLWRKRVKDEV LRLKIAGKEPKAIQELLTKRYKNQLARLDQTRAEDIFQAYINTF AMSYDPHTNYLSPDNAENFDINMSLSLEGIGAVLQSDNDQVKIV RLVPAGPADKTKQVAPADKIIGVAQADKEMVDVVGWRLDEVVKL IRGPKGSVVRLEVIPHTNAPNDQTSKIVSITREAVKLEDQAVQK KVLNLKQDGKDYKLGVIEIPAFYLDFKAFRAGDPDYKSTTRDVK KILTELQKEKVDGVVIDLRNNGGGSLQEATELTSLFIDKGPTVL VRNADGRVDVLEDENPGAFYKGPMALLVNRLSASASEIFAGAMQ |

TABLE 14-continued

Table of Sequences

| SEQ ID NO | Name | Sequence* |
|---|---|---|
| | | DYHRALIIGGQTFGKGTVQTIQPLNHGELKLTLAKFYRVSGQST QHQGVLPDIDFPSIIDTKEIGESALPEAMPWDTIRPAIKPASDP FKPFLAQLKADHDTRSAKDAEFVFIRDKLALAKKLMEEKTVSLN EADRRAQHSSIENQQLVLENTRRKAKGEDPLKELKKEDEDALPT EADKTKPEDDAYLAETGRILLDYLKITKQVAKQ |
| 34 | Prc1 example nucleic acid encoding SEQ ID NO: 33 | ATGAAGCATCTGTTCCCCAGCACCGCCCTCGCTTTTTTCATTGG TCTCGGCTTCGCGTCGATGTCGACCAATACGTTCGCAGCCAATA GCTGGGACAACCTTCAGCCTGATCGCGATGAGGTGATTGCCAGC CTTAACGTCGTCGAGTTGCTTAAGCGCCATCACTACAGCAAGCC GCCGCTGGACGACGCTCGCTCAGTGATCATCTACGACAGCTACC TCAAGCTGCTGGACCCGTCGCGCAGCTACTTCCTGGCCAGCGAT ATCGCTGAGTTCGACAAGTGGAAGACGCAATTCGACGACTTCCT CAAGAGCGGCGACCTGCAGCCTGGCTTCACCATCTACAAGCGCT ACCTAGACCGCGTCAAAGCGCGTCTGGACTTCGCCCTGGGTGAG CTGAACAAAGGCGTCGACAAGCTCGATTTCACCCAGAAAGAAAC CCTTCTGGTGGACCGCAAGGACGCCCCTTGGCTGACCAGCACCG CAGCCCTAGACGACCTGTGGCGCAAACGCGTCAAGGACGAAGTG CTGCGCTTGAAGATCGCCGGCAAAGAGCCCAAGGCCATTCAAGA GCTGTTGACCAAGCGCTACAAAAACCAGCTGGCGCGCCTGGACC AGACCCGTGCCGAGGATATCTTCCAGGCCTACATCAACACCTTT GCGATGTCCTACGACCCGCACACCAATTATCTGTCGCCAGATAA CGCGGAAAATTTCGATATCAATATGAGTCTGTCCCTGGAAGGCA TCGGTGCCGTCCTGCAAAGCGACAATGACCAGGTGAAGATTGTA CGTCTGGTGCCGGCAGGCCCGGCTGACAAAACCAAGCAAGTGGC ACCGGCCGACAAGATCATCGGCGTGGCCCAGGCCGACAAAGAGA TGGTCGATGTGGTCGGCTGGCGCCTGGACGAAGTGGTCAAGCTG ATCCGTGGGCCTAAAGGCAGCGTGGTGCGCCTGGAAGTGATTCC GCACACCAATGCACCGAACGACCAGACCAGCAAGATCGTGTCCA TCACCCGTGAAGCGGTGAAGCTCGAAGACCAGGCCGTGCAGAAG AAAGTCCTCAACCTCAAGCAGGATGGCAAGGACTACAAGCTGGG GGTGATTGAAATCCCGGCCTTCTACCTGGACTTCAAGGCGTTCC GTGCCGGTGATCCGGACTACAAGTCCACCACCCGCGACGTGAAG AAAATCCTCACAGAACTGCAGAAAGAGAAAGTCGACGGCGTGGT CATCGACCTGCGCAACAACGGCGGCGGCTCCCTGCAGGAAGCCA CCGAGCTGACCAGCCTGTTTATCGACAAGGGCCCGACCGTGTTG GTACGCAACGCTGACGGCCGTGTCGACGTGCTCGAAGACGAGAA CCCGGGGGGCCTTCTACAAAGGGCCGATGGCGCTGCTGGTCAACC GCCTCTCGGCCTCGGCCTCGGAGATTTTCGCCGGTGCCATGCAG GACTACCACCGTGCACTGATCATCGGCGGCCAGACCTTCGGCAA AGGCACCGTGCAGACCATCCAGCCGCTGAACCATGGCGAGCTTA AGCTGACACTGGCCAAGTTCTACCGGGTCTCCGGGCAGAGCACC CAGCATCAGGGCGTACTGCCGGATATCGATTTCCCGTCGATCAT CGACACCAAGGAAATTGGCGAAAGCGCCCTGCCTGAAGCCATGC CGTGGGACACCATCCGCCCTGCGATCAAGCCGGCGTCGGATCCG TTCAAGCCGTTCCTGGCACAGCTGAAGGCTGACCACGACACCCG CTCTGCCAAGGATGCCGAGTTCGTGTTTATCCGCGACAAGCTGG CCCTGGCCAAGAAGCTGATGGAAGAGAAGACCGTCAGCCTCAAC GAAGCGGATCGCCGTGCACAGCACTCCAGCATCGAGAATCAGCA ACTGGTGCTGGAAAACACCCGCCGCAAGGCCAAAGGTGAAGACC CGCTCAAAGAGCTGAAGAAGAAGATGAAGACGCGCTGCCGACC GAGGCGGATAAAACCAAGCCGGAAGACGACGCCTACTTGGCCGA GACTGGCCGGATCCTGCTGGATTACCTGAAGATCACCAAGCAGG TGGCCAAGCAGTAA |
| 35 | Prc2 amino acid *P. fluorescens* | MLHLSRLTSLALTIALVIGAPLAFADQAAPAAPATAATTKAPLP LDELRTFAEVMDRIKAAYVEPVDDKALLENAIKGMLSNLDPHSA YLGPEDFAELQESTSGEFGGLGIEVGSEDGQIKVVSPIDDTPAS KAGIQAGDLIVKINGQPTRGQTMTEAVDKMRGKLGQKITLTLVR DGGNPFDVTLARATITVKSVKSQLLESGYGYIRITQFQVKTGDE VAKALAKLRKDNGKKLNGIVLDLRNNPGGVLQSAVEVVDHFVTK GLIVYTKGRIANSELRFSATGNDLSENVPLAVLINGGSASASEI VAGALQDLKRGVLMGTTSFGKGSVQTVLPLNNERALKITTALYY TPNGRSIQAQGIVPDIEVRRAKITNEIDGEYYKEADLQGHLGNG NGGADQPTGSRAKAKPMPQDDDYQLAQALSLLKGLSITRSR |
| 36 | Prc2 example nucleic acid encoding SEQ ID NO: 35 | ATGCTGCATTTGTCCCGCCTCACTTCGCTGGCCCTGACGATCGC CCTGGTGATCGGCGCGCCTCTGGCTTTTGCCGACCAGGCCGCAC CGGCTGCACCCGCCACGGCTGCGACGACCAAGGCGCCATTGCCG CTGGACGAGCTGCGTACCTTTGCCGAGGTCATGGACCGGATCAA GGCAGCGTATGTCGAACCCGTAGACGACAAGGCCCTGCTGGAAA ATGCCATCAAGGGCATGCTCAGCAACCTCGACCCGCACTCCGCC TACCTGGGCCCGGAAGATTTCGCCGAGCTGCAGGAAAGCACCAG CGGTGAGTTCGGCGGCCTGGGCATCGAAGTGGGCTCCGAAGACG |

TABLE 14-continued

Table of Sequences

| SEQ ID NO | Name | Sequence* |
|---|---|---|
| | | GCCAGATCAAAGTGGTCTCGCCTATCGACGACACCCCGGCGTCC AAGGCCGGTATCCAGGCCGGCGACCTGATCGTGAAGATCAACGG CCAGCCAACCCGCGGCCAGACCATGACCGAAGCCGTCGACAAGA TGCGCGGCAAGCTCGGCCAGAAGATCACCCTGACCCTGGTACGC GACGGCGGCAACCCGTTTGACGTGACCCTGGCCCGCGCGACCAT CACGGTCAAGAGCGTGAAAAGCCAGCTGCTGGAGTCGGGCTACG GTTATATCCGTATCACCCAGTTCCAGGTCAAGACCGGCGACGAA GTGGCCAAGGCCCTGGCCAAGCTGCGCAAAGACAACGGCAAGAA GCTCAACGGCATCGTGCTTGACCTGCGCAACAACCCAGGCGGCG TGTTGCAGTCGGCGGTCGAGGTGGTCGACCACTTCGTCACCAAG GGCCTGATCGTCTACACCAAGGGCCGTATCGCCAACTCAGAGTT GCGCTTCTCGGCCACCGGCAACGACCTCAGCGAGAACGTGCCAC TGGCGGTATTGATCAACGGTGGCAGCGCCTCGGCTTCGGAAATC GTCGCCGGTGCCCTGCAAGACCTCAAGCGCGGCGTGCTGATGGG CACCACCAGCTTCGGCAAAGGCTCGGTGCAGACCGTATTGCCGC TGAACAACGAGCGTGCGCTGAAGATCACCACGGCGCTGTACTAC ACGCCCAACGGCCGCTCGATCCAGGCCCAGGGCATCGTGCCGGA CATCGAAGTACGCCGCGCCAAGATCACCAACGAGATCGACGGCG AATACTACAAAGAGGCCGACCTGCAAGGTCACCTGGGCAATGGC AACGGCGGTGCCGACCAGCCAACCGGCAGCCGCGCCAAGGCCAA GCCGATGCCGCAGGACGATGACTACCAACTGGCCCAGGCACTCA GCCTGCTCAAGGGCTTGAGCATCACCCGCAGCCGTTGA |
| 37 | HslU amino acid (RXF01957; PROKKA_01919) *P. fluorescens* | MSMTPREIVHELNRHIIGQDDAKRAVAIALRNRWRRMQLPEELR VEVTPKNILMIGPTGVGKTEIARRLAKLANAPFIKVEATKFTEV GYVGRDVESIIRDLADAALKMLREQEVTKVSHRAEDAAEERILD ALLPPARMGFNEDAAPATDSNTRQLFRKRLREGQLDDKEIEIEV AEVSGVDISAPPGMEEMTSQLQNLFANMGKGKKKSRKLKVKEAL KLVRDEEAGRLVNEEELKAKALEAVEQHGIVFIDEIDKVAKRGN SGGVDVSREGVQRDLLPLIEGCTVNTKLGMVKTDHILFIASGAF HLSKPSDLVPELQGRLPIRVELKALTPGDFERILSEPHASLTEQ YRELLKTEGLGIEFQADGIKRLAEIAWQVNEKTENIGARRLHTL LERLLEEVSFSAGDMAGAQNGEAIKIDADYVNSHLGELAQNEDL SRYIL |
| 38 | HslV amino acid (RXF01961; PROKKA_01920) *P. fluorescens* | MTTIVSVRRHGKVVMGGDGQVSLGNTVMKGNAKKVRRLYHGQVL AGFAGATADAFTLFERFEGQLEKHQGHLVRAAVELAKEWRTDRS LSRLEAMLAVANKDASLIITGNGDVVEPEHGLIAMGSGGGYAQA AASALLKKTDLSAREIVETALGIAGDICVFTNHNQTIEEQDLAE |
| 39 | Protease HtpX amino acid (RXF05137; PROKKA_01141) *P. fluorescens* | MMRILLFLATNLAVVLIASVTLSLFGFNGFMAANGVDLNLNQLL IFCAVFGFAGSLFSLFISKWMAKMSTSTQIITQPRTRHEQWLMQ TVEQLSQEAGIKMPEVGIFPAYEANAFATGWNKNDALVAVSQGL LERFSPDEVKAVLAHEIGHVANGDMVTLALVQGVVNTFVMFFAR IIGNFVDKVIFKNEEGRGIAYFVATIFAELVLGFLASAIVMWFS RKREFRADEAGARLAGTSAMIGALQRLRSEQGLPVHMPDSLTAF GINGGIKQGLARLFMSHPPLEERIDALRRRG |
| 40 | Protease HtpX example nucleic acid encoding SEQ ID NO: 39 | ATGATGCGCATCCTGCTGTTCTTGGCCACTAACCTGGCGGTCGT ACTGATTGCCAGCGTCACCCTGAGCCTTTTTGGCTTCAACGGGT TCATGGCGGCCAATGGGGTTGATCTGAACCTCAATCAGCTGCTG ATTTTCTGTGCGGTCTTTGGTTTTGCCGGCTCGCTGTTCTCGCT GTTCATCTCCAAGTGGATGGCGAAGATGAGCACCAGCACCCAGA TCATCACTCAACCCCGCACTCGCCATGAACAATGGCTGATGCAA ACCGTGGAGCAGTTGTCTCAAGAAGCAGGCATCAAAATGCCCGA AGTGGGGATTTTTCCTGCTTATGAGGCCAACGCCTTTGCCACCG GCTGGAACAAGAACGACGCACTGGTGGCTGTGAGCCAGGGCCTG CTGGAGCGGTTTTCGCCCGATGAAGTCAAGGCGGTGCTGGCCCA CGAGATCGGCCACGTAGCCAACGGCGACATGGTCACCCTGGCAC TGGTACAGGGCGTGGTGAACACCTTCGTGATGTTCTTTGCGCGG ATCATCGGCAACTTTGTCGACAAGGTCATCTTCAAGAACGAAGA AGGCCGTGGCATTGCCTACTTCGTGGCGACCATTTTCGCCGAGT TGGTCCTGGGCTTCCTGGCCAGCGCCATCGTGATGTGGTTCTCG CGCAAACGCGAGTTCCGCGCAGATGAAGCCGGCGCACGCCTGGC GGGCACCAGCGCAATGATCGGCGCGCTGCAACGCCTGCGCTCCG AACAGGGCCTGCCGGTGCATATGCCGGACAGCCTGACCGCCTTC GGCATCAACGGCGGCATCAAGCAGGGCCTGGCTCGCTTGTTCAT GAGCCACCCGCCGCTGGAAGAGCGGATTGACGCACTGCGTCGCC GGGGCTGA |

TABLE 14-continued

Table of Sequences

| SEQ ID NO | Name | Sequence* |
|---|---|---|
| 41 | Protease Murein L, D transpeptidase amino acid (RXF01911; PROKKA_02909) *P. fluorescens* | MFKKHACYLSICLLVAPLVATAETLPLEPLPVTTPAPVALAPLQ QALAQLTSVCPHLAPRIDAAALARLQTFYQQQGDAPLWAADERR QALHAQLLMLADDGLDPTHYSLPAVDATANVLCSDIANSQQYLQ ALQDLHYGRLQQSRFEPLWHSQPPSGDPNTEVLAFAATGLHDMA QAFDQARPSADLYRSLRNAYAGVRQQPLPHWDPVAEGTLLRPGM NDPRVPELARRLHSGGYLAQLPSGNGKQYQGELVKAVKAFQLSH SLQADGVIGAGTVAELNISPAMRREQLRINLERFRWLAQDLEPE GVVVNVAAAQLSVYQSGIPVWQTRLQVGRAERQTPLLKSRITRL TLNPTWTIPPTIMREDKLPAIRLNPEYLRQQNLQVLDAEGHPLT PDQVDWARPGNILLRQQAGPRNPLGKIVMRFPNPYSVYLHDTPS QPLFTKGPRAFSSGCVRVEQPLLLRDLLVTPAERTRTDELLATG ETHEFRLATPVPVLLGYWTVEVDRQGELVYAPDIYARDPALIKA MGSVL |
| 42 | Protease Murein L, D transpeptidase example nucleic acid encoding SEQ ID NO: 41 | ATGTTCAAAAAACACGCATGTTACTTGAGCATTTGCCTGCTCGT TGCACCATTGGTCGCTACAGCCGAAACGCTGCCGTTAGAACCAC TGCCCGTCACCACCCCTGCACCGGTCGCGCTCGCGCCGCTGCAA CAGGCCTTGGCGCAGTTGACCAGTGTCTGCCCGCACCTTGCGCC GCGTATCGATGCCGCCGCGTTGGCGCGCCTGCAAACCTTTTACC AGCAGCAGGGCGATGCCCCGCTATGGGCGGCTGACGAACGCCGG CAAGCCTTGCATGCCCAGTTGCTGATGCTTGCCGACGATGGCCT GGACCCCACCCACTATAGCTTGCCTGCGGTGGATGCCACGGCCA ACGTGCTGTGCAGCGATATCGCCAACAGCCAGCAGTACCTGCAA GCTCTGCAGGATTTGCACTACGGGCGCCTGCAGCAATCGCGCTT TGAGCCCCTCTGGCATTCCCAGCCACCCAGTGGCGATCCGAATA CCGAGGTGCTGGCGTTCGCCGCCACCGGCCTGCACGACATGGCC CAAGCCTTCGATCAGGCCCGGCCCAGCGCCGATTTGTACCGCAG CCTGCGCAATGCCTATGCCGGCGTGCGCCAGCAACCGCTGCCCC ATTGGGACCCGGTCGCCGAGGGCACGTTGTTGCGTCCTGGGATG AATGACCCTCGCGTGCCGGAACTGGCGCGGCGCCTGCACAGCGG CGGCTACCTGGCCCAGTTACCCAGCGGCAACGGCAAGCAGTACC AGGGCGAACTGGTCAAGGCGGTGAAAGCCTTCCAGCTCAGCCAC TCGTTGCAGGCCGACGGCGTGATCGGCGCCGGCACCGTGGCCGA ACTCAATATCAGCCCGGCGATGCGTCGTGAACAACTGCGCATCA ACCTCGAGCGTTTCCGCTGGCTGGCCCAGGACCTGGAGCCTGAA GGCGTCGTGGTCAATGTGGCCGCCGCGCAACTGAGCGTGTACCA GAGCGGCATCCCAGTGTGGCAAACCCGCCTGCAAGTGGGCCGGG CCGAACGCCAGACGCCGTTGCTCAAGTCGCGCATCACCCGGCTG ACCCTCAACCCCACCTGGACCATCCCGCCGACCATCATGCGCGA GGACAAACTGCCGGCCATCCGCCTCAACCCTGAATACCTGCGCC AGCAAAACCTGCAAGTGCTCGACGCCGAAGGTCACCCGTTGACC CCCGACCAGGTCGACTGGGCGCGCGCCCCGGCAATATCCTGCTGCG CCAGCAGGCCGGCCCGCGTAACCCGCTGGGCAAGATTGTGATGC GTTTCCCCAATCCGTATTCCGTATATCTGCACGACACCCCCAGC CAACCCTTGTTCACCAAGGGGCCGCGGGCGTTCAGTTCGGGATG CGTGCGGGTCGAGCAACCGTTGTTATTGCGCGACCTGCTGGTAA CGCCGGCCGAACGCACTCGCACCGATGAGCTGCTGGCGACCGGC GAAACCCATGAATTCAGGTTGGCCACGCCCGGTACCGGTGCTGTT GGGGTATTGGACCGTGGAAGTGGATCGCCAGGGCGAGCTGGTGT ACGCGCCGGATATTTATGCGCGTGACCCGGCGTTGATCAAGGCC ATGGGTAGCGTGTTATAG |
| 43 | Protease/Autolytic Factor Hemolysin precursor amino acid (RXF09262; PROKKA_04435) *P. fluorescens* | MDVRQFAFLARQPSAALKRRDAFFGLPKRGLALILANALFWQPL LAQAEGIVVSAPGTTVGAAGNGVPVVNIATPNGAGLSHNQFKDY NVGPNGVILNNGNGAMVNTQLGGIIVGNPNLKGGAANVILNEVN GGSPSQLRGYTEVAGQSAKVIVANPYGVTCSGCGFINTPNVTLT TGKPVLDASGQLQRYEVDGGAVTIDGQGLNASNVERFDIITRSA KINAQINARELNVIAGRNDVDAQSLKTTARADDGSAKPELAIDS SALGGMYAGAIKLVGTEAGVGVKLDGTLAASGGDIQLDANGRLS MAQAAATGNVKVTAQNVDLTDKVYANGNVQVTSAQALVNRKSIA AGQRIEINAASVNNPGIIEAGVAADNSRNTTGDLVVNAQTVTTS GNLLASRALAITAAQALTNQGAIIQAKTVEVSSAKLTNQGASAR LFGEQSLAINSPAIVNLGGLIRFGEGQAATLNSASLDNRQGRIE MAGGSLVLTSADLNNSGGQVIANDLTVNAGNLNNQNGVLVAKTA TVTASNLDNSLKGLIQADGGALNLAVSNTFNNNQGFAQASTDLN VTAGTLSSNAGGVLSADTGKLTLTAAQQLNNAQGRLQAGQGDIE LHAANLDNQSGTIVGKQLLLDVAGGDIDNRAGRVLGDHLDVRAS GLDNRNAGLLAGGAQGVSLLLKGPGQLLNAQGRIQSEGLLQLQG ERFDNSAGILLGQTVDVTAQTFNNSNKGALVSDGGDVVFKVSDL LTNVGGQIDAGERSVLVKQLTTLNNDGGTLRGKRLDIAAQHLNN DNGQLLAGAEGLSYSGQDVSNRKGLILSGGALTELNTTRLDNQG GTVQGDSLTVTANNVDNGSGGLMASLVGNLQLTVEALANRGGKL FGKEQVTVSGASLDNSAGQISGNQINLTSRDTLTNQGGLVEANQ GLTLTGGNLDNSANGQLRALGGASSRVNLSGALNNQNGTLEFGS |

TABLE 14-continued

| Table of Sequences | |
|---|---|

| SEQ ID NO | Name | Sequence* |
|---|---|---|
| | | QAFSLDAASLNNQNGMLQHAGTGLFHLNIASLEGSQGNIQGMGS |
| | | ADWAFGKVDGLGRVQLNDVLTYKSDQGLALQAGDRMASAKGLIL |
| | | NVASLDNGGELLSDGDISITTGDITNSGRVSALQTLTVAANNLS |
| | | QNGGRLAATNARLTLGGTLDNLGFLTARQQLDIAAAQINNRGTL |
| | | GAQGAVNLTAVNGITNAADTLLFSGGDMTLRSNGFSNSYGDVYS |
| | | KGNLSFAARDGGRAVLFSNRSGTVESEGSIGINAGFIENAKDEF |
| | | ELGQTLTTGSLSWICGQHCGESDNWERGEITIYETYLEAATKDS |
| | | VAARLVAGKNMLLQGDTVQNRYSLMAANGDLSITAGDLLNQGAA |
| | | TRTGQRKLVIGTPGHVSDDLFERMQYVDVPAFNAATAAGNFDKA |
| | | RFEELKSRSPNSLPFAYASDVTTWTNNSGPGYDATLQAGGTVNL |
| | | NVARTLQNGTLHNNTLAQLTGTLGDDQTGIPVGGININLSKHAN |
| | | DPSAQAPGSVLPVVGVAPGGGFVPVDYTGTAFAPVDPTTSPTFQ |
| | | LPKGEYGLFVKNADPTSHYLIETNPEFTSVSGFFSSDYMLGKLG |
| | | FTADNAWRRLGDGQYETRLIRDAVLAQTGQRFLAGGLYSDADQF |
| | | RYLMDNGLASKDALRLSLGVALTDQQVGALTHDIVWMENRVIEG |
| | | QTVLVPVLYLAQADSRNVRGNSLIQGRDLNLVTGGDLINVGTLR |
| | | ASNNLSAISSGSIYTGGLVEAGNNLSLLAQDSIRNAMAGEIRGK |
| | | QVSLTALKGDITNETTAIQVRDGAGMRTLTDTSAGTIVARENLA |
| | | IDAGRDLTNRGALVAGNDANLTAGRDLNLIAASDTRVKHETRDG |
| | | GEKSSITTDVKNLAASVTAGGNLNMQAGQDVNIIGSNATAGKDL |
| | | NIAAGRDLNVASVSDMHNVEGKEKDGKKRIRTSDDQTTQVASVL |
| | | TAGGDFVSQAGRDTTIVASMISAGNEAYLYSGDKLSLLAAENST |
| | | HTLYDMKEKGSWGAKKAQMDEVTRTTQVGTEIKTGGNLVLKSDG |
| | | DQLYQVAKLNSGKDIILDSGGAIVFEGVKDLHDESHTKSKSDLS |
| | | WFSAKGKGNTDETLRQSELVAQGQLVIKAAEGIRIDVKQVDQQT |
| | | VSQTVDAMVKADPNLAWLKQAEARGDIDWRQVKEIHESFKYDNS |
| | | GLGAGAKIAIAIMMAAIMGPVGFGLQGATLAVSTSLSTTAVTST |
| | | INNKGNLGAALKETVSANSLKSAAVAGFTAGALEYADTNWFAGA |
| | | DGAGAGAGTSTSTVQGVTPSTGSTLAVTNSSKDIFTWTSAGDIA |
| | | LRTGGRAVISSGISTAIQGGSFGDNFNAALLGEAGNVAMATGFN |
| | | WVGDYVTFPNGSPQKI1AHALMGGLLAEATGSDFKTGAAAAGLN |
| | | EALINQLVWAAQGNDDITLMLSQLTGLLAAAAVDGDLEKGSQIA |
| | | QKATTFNYLYHEEVEEMLREVDSKTTEQEKREVRQRYAELDQQR |
| | | NDELDALCARDPQRCRGIATSLANDDQKLVDLVGRLRSQGQGGA |
| | | ASAVGFVIGNNLDASSQIAADISSAGGGPLVKLGAEAIKAGVGI |
| | | TLPSRSSSGKGKGSQVGAGSLEEAAGPKATGEVVPPAPIVTSGA |
| | | TRTGVVRTNAADWRALRNNWDDLGYGQILSTENRAAIAKGRTPK |
| | | VDDAWVKVFPEDAGLKGERIPMHHVQGSPLTVPLPDTRHLDAHM |
| | | PGGFRYNPGGPGSALPAYPPKKGAE |
| 44 | Protease/Autolytic Factor Hemolysin precursor example nucleic acid encoding SEQ ID NO: 43 | ATGGATGTTCGCCAATTCGCCTTCCTGGCCCGCCAACCTTCTGC |
| | | CGCCCTGAAGCGCCGGGACGCGTTCTTCGGCCTGCCCAAGCGCG |
| | | GGCTGGCCTTGATCCTTGCCAACGCACTGTTCTGGCAGCCGCTG |
| | | CTGGCCCAGGCCGAGGGCATTGTGGTCAGTGCGCCGGGCACCAC |
| | | CGTGGGCGCGGCAGGCAATGGCGTGCCGGTGGTAAACATTGCCA |
| | | CCCCCAATGGCGCGGGCTTGTCCCATAACCAGTTCAAGGACTAC |
| | | AACGTCGGCCCCAACGGCGTGATTCTCAACAATGGCAACGGCGC |
| | | CATGGTCAACACCCAGCTGGGCGGGATCATCGTCGGCAACCCCA |
| | | ACCTCAAGGGCGGCGCGGCGAACGTCATCCTCAACGAAGTCAAC |
| | | GGCGGCAGCCCCAGCCAGTTGCGCGGCTATACCGAAGTGGCGGG |
| | | GCAGTCGGCCAAGGTCATCGTGGCCAACCCGTACGGCGTGACGT |
| | | GCAGCGGTTGCGGCTTTATCAACACCCCCAACGTCACCCTCACC |
| | | ACCGGCAAACCGGTGCTCGACGCCAGCGGTCAATTGCAGCGCTA |
| | | TGAAGTGGATGGCGGCGCGGTGACCATCGACGGCCAAGGCTTGA |
| | | ACGCCAGCAACGTCGAACGCTTCGACATCATCACCCGCTCGGCC |
| | | AAGATCAACGCACAAATCAACGCCCGCGAACTCAACGTGATCGC |
| | | CGGGCGCAACGACGTCGATGCGCAAAGCCTGAAAACCACCGCCC |
| | | GCGCCGATGACGGCAGCGCCAAGCCCGAGCTGGCGATCGACTCG |
| | | TCGGCCCTGGGCGGCATGTATGCCGGCGCGATCAAACTGGTGGG |
| | | CACCGAGGCCGGTGTGGGCGTGAAGCTCGACGGCACCCTGGCCG |
| | | CCAGTGGCGGCGATATTCAGCTCGACGCCAACGGGCGCCTGAGC |
| | | ATGGCGCAGGCGGCGGCCACCGGTAACGTCAAGGTCACCGCGCA |
| | | AAACGTCGACCTCACCGACAAGGTCTACGCCAACGGCAACGTGC |
| | | AGGTCACCAGCGCCCAGGCTTTGGTCAACCGCAAGAGCATCGCC |
| | | GCCGGCCAGCGCATCGAGATCAACGCGGCCAGCGTGAACAACCC |
| | | CGGCATCATCGAAGCCGGCGTCGCCGCCGATAACAGCCGCAACA |
| | | CCACGGGCGACCTGGTGGTGAACGCGCAAACCGTCACCACCAGC |
| | | GGCAACCTGTTGGCCAGCCGCGCCCTGGCGATCACTGCCGCGCA |
| | | AGCGCTGACCAACCAGGGCGCGATCATCCAGGCCAAGACCGTCG |
| | | AGGTCAGCAGCGCCAAACTCACCAACCAGGGCGCCAGCGCTCGC |
| | | CTGTTTGGCGAGCAGAGCCTGGCGATCAACTCGCCGGCCATCGT |
| | | CAACCTCGGCGGCTTGATCCGCTTCGGCGAAGGCCAGGCCGCCA |
| | | CGCTCAACAGCGCCTCCCTGGACAACCGCCAAGGCCGTATCGAA |
| | | ATGGCCGGTGGCAGCCTGGTGCTCACCAGTGCCGACCTGAACAA |

TABLE 14-continued

Table of Sequences

SEQ
ID
NO   Name          Sequence*

CAGCGGCGGGCAAGTCATCGCCAACGACCTGACCGTCAACGCCG
GCAACCTGAACAACCAGAACGGCGTGCTGGTGGCCAAGACCGCG
ACCGTCACTGCCAGCAACCTTGACAACAGCCTCAAGGGTTTGAT
CCAGGCTGACGGTGGCGCGCTCAACCTCGCCGTTTCCAACACCT
TCAACAACAACCAGGGTTTCGCCCAGGCCAGCACCGATCTGAAC
GTTACGGCCGGCACCCTCAGCAGCAACGCAGGCGGCGTACTGAG
CGCCGACACCGGCAAGCTCACCCTCACCGCCGCACAACAACTCA
ACAACGCCCAGGGCCGCTTGCAGGCCGGGCAGGGCGATATCGAA
CTGCACGCCGCGAACCTGGATAACCAGAGCGGCACGATCGTCGG
CAAGCAACTGCTGCTCGACGTGGCCGGCGGCGACATCGACAACC
GTGCCGGGCGCGTGTTGGGTGACCACCTCGACGTGCGCGCCTCG
GGCCTGGACAACCGCAACGCCGGCCTGCTGGCCGGTGGTGCCCA
GGGCGTAAGCCTGCTGCTCAAAGGCCCGGGCCAGTTGCTCAACG
CCCAGGGCCGCATCCAGAGCGAGGGCCTGCTGCAACTGCAAGGC
GAGCGCTTCGACAACAGCGCCGGCATCCTGCTGGGGCCAGACCGT
CGACGTGACCGCGCAGACCTTCAACAACAGCAACAAAGGCGCGC
TGGTCAGCGATGGCGGTGATGTGGTGTTCAAGGTCAGCGACCTG
CTCACCAACGTCGGTGGCCAGATCGACGCGGGCGAACGCAGCGT
GTTGGTCAAGCAGCTCACCACCCTCAACAACGACGGCGGCACCC
TGCGCGGCAAGCGCCTGGACATCGCCGCCCAGCACCTGAACAAC
GACAACGGCCAACTGCTGGCCGGCGCCGAAGGCCTGAGCTACAG
CGGCCAGGATGTGAGCAACCGCAAGGGCCTGATCCTCAGCGGCG
GCGCCCTCACCGAACTGAACACCACCCGCCTGGATAATCAGGGC
GGCACTGTGCAGGGCGACAGCCTGACCGTCACCGCCAACAACGT
CGACAACGGCAGCGGCGGCCTGATGGCAAGCCTGGTCGGCAACC
TGCAGCTCACTGTCGAAGCCCTGGCCAACCGTGGCGGCAAGCTG
TTCGGCAAAGAACAAGTGACCGTCAGCGGCGCCAGCCTCGACAA
CAGCGCGGGCCAGATCAGCGGCAATCAGATCAACCTGACCTCAC
GCGACACGCTCACCAACCAGGGCGGTTTGGTTGAAGCCAACCAG
GGCCTGACCCTCACTGGTGGCAACCTCGATAACAGCGCCAACGG
CCAACTGCGTGCCCTGGGCGGCGCCAGCAGCCGCGTCAACCTCA
GCGGTGCGTTGAACAACCAGAACGGCACCCTCGAATTCGGTAGC
CAGGCCTTCAGCCTTGACGCGGCCAGCCTCAACAACCAGAACGG
GATGCTGCAACACGCCGGCACCGGCCTGTTCCACCTCAACATCG
CCAGCCTCGAAGGCAGCCAGGGCAATATCCAGGGCATGGGCAGC
GCCGACTGGGCATTCGGCAAGGTCGACGGCCTGGGCCCGCGTGCA
ACTCAACGATGTGCTCACCTACAAGAGCGACCAAGGGCTGGCCC
TCCAGGCCGGCGACCGCATGGCCAGCGCCAAGGGCTTGATCCTC
AACGTGGCCAGCCTGGACAACGGCGGCGAACTGCTCAGCGACGG
TGACATCAGCATCACCACCGGCGATATCACCAACAGCGGCCGCG
TCTCGGCCCTGCAAACACTCACCGTCGCCGCCAACAACCTCAGC
CAGAACGGCGGCCGCCTGGCCGCAACCAATGCCCGCCTGACCCT
GGGCGGCACCCTGGACAACCTCGGTTTCCTCACCGCCCGCCAGC
AACTGGACATCGCCGCCGCGCAAATCAACAACCGTGGCACCCTC
GGTGCCCAGGGCGCAGTGAACCTCACGGCGGTCAACGGCATCAC
CAACGCCGCCGACACGCTGCTGTTCAGCGGCGGCGACATGACCC
TGCGCAGCAATGGCTTCAGCAACAGCTATGGCGATGTCTACAGC
AAAGGCAACCTGAGTTTCGCCGCCCGCGATGGCGGACGTGCCGT
GCTGTTCAGCAACCGCTCCGGCACCGTGGAAAGCGAAGGCTCAA
TTGGCATCAATGCAGGCTTTATCGAAAACGCCAAAGACGAATTC
GAACTCGGGCAGACACTGACCACCGGTAGCTTGAGCTGGATCTG
TGGCCAGCACTGCGGCGAGAGCGACAACTGGGAACGTGGCGAGA
TCACCATCTACGAAACGTACCTCGAGGCGGCGACCAAGGACTCG
GTAGCGGCGCGCCTGGTGGCGGGCAAAAACATGCTGCTGCAAGG
CGACACGGTGCAGAACCGCTACAGCCTGATGGCCGCCAATGGCG
ACCTGAGCATCACTGCCGGGAGACCTGCTCAACCAGGGCGCCGCC
ACGCGCACGGGCCAGCGCGCAAGCTTGTCATCGGCACGCCAGGTCA
CGTCTCCGACGATTTGTTTGAACGCATGCAATATGTTGATGTGC
CCGCGTTCAATGCGGCCACGGCGGCTGGGAATTTCGACAAGGCG
CGCTTCGAAGAACTCAAAAGCCGCTCACCCAATAGCCTGCCGTT
CGCCTACGCCAGTGACGTCACCACCTGGACCAACAACAGCGGCC
CCGGCTACGACGCCACCCTGCAAGCGGGCGGCACGGTCAACCTC
AACGTCGCCCGCACCCTGCAAAACGGCACGCTGCACAACAACAC
CCTGGCCCAGTTGACCGGCACCCTCGGCGACGACCAGACCGGCA
TCCCCGTCGGCGGCATCAACATCAACCTGAGCAAACACGCCAAC
GACCCGAGCGCCCAGGCGCCCGGCAGTGTCTTGCCCGTCGTGGG
CGTGGCCCCTGGTGGCGGCTTCGTGCCCGTGGATTACACCGGCA
CCGCGTTTGCCCCGGTCGACCCCACCACCTCGCCCACCTTCCAA
CTGCCCAAGGGCGAATACGGCCTGTTCGTCAAAAACGCCGACCC
CACCAGCCACTACCTGATCGAGACCAACCCCGAGTTCACCTCGG
TGTCGGGCTTCTTCAGCTCCGACTACATGCTCGGCAAACTCGGT
TTCACCGCCGACAACGCCTGGCGCCGCCTCGGTGACGGCCAGTA
CGAAACCCGCCTGATCCGCGACGCCGTCCTCGCGCAAACCGGCC
AGCGCTTCCTCGCCGGCGGCGCCTGTACAGCGACGCCGACCAGTTC

TABLE 14-continued

Table of Sequences

SEQ
ID
NO  Name                Sequence*

```
CGCTACCTGATGGACAACGGCCTCGCCAGCAAAGACGCCCTGCG
CCTGAGCCTGGGCGTGGCCCTCACCGACCAGCAAGTCGGCGCCC
TGACCCACGACATCGTGTGGATGGAAAACCGCGTCATCGAAGGC
CAGACCGTGCTCGTGCCGGTGCTGTACCTGGCCCAGGCCGACTC
GCGCAACGTGCGCGGCAACAGCCTCATCCAGGGCCGCGACCTCA
ACCTGGTCACCGGCGGCGACCTGATCAACGTCGGCACCCTGCGC
GCCAGCAACAACCTCTCCGCCATCAGTAGCGGCAGCATTTATAC
CGGCGGCCTGGTCGAAGCCGGCAACAATCTCAGCCTGCTGGCCC
AGGACAGCATCCGCAACGCCATGGCCGGCGAAATCCGCGGCAAG
CAAGTCAGCCTCACGGCGCTCAAAGGCGATATCACCAACGAAAC
CACCGCCATCCAGGTGCGTGACGGCGCCGGTATGCGCACCCTCA
CCGACACCAGCGCCGGCACCATCGTCGCCCGCGAAAACCTCGCC
ATCGACGCTGGCCGCGACCTCACCAACCGAGGCGCGCTGGTAGC
GGGCAACGACGCCAACCTCACCGCCGGCCGCGACCTCAACCTCA
TCGCCGCCAGCGACACCCGCGTCAAACACGAGACCCGCGACGGC
GGCGAGAAATCCAGCATCACCACCGACGTCAAAAACCTCGCCGC
CAGCGTCACGGCGGGCGGCAACCTCAACATGCAGGCCGGGCAAG
ACGTCAACATCATCGGCAGCAATGCCACGGCCGGCAAAGACCTC
AACATCGCCGCCGGCCGCGACCTCAACGTCGCCTCGGTCAGCGA
CATGCACAACGTCGAGGGCAAGGAAAAGGACGGCAAAAAACGCA
TCAGGACCTCGGACGACCAGACCACTCAAGTGGCAAGCGTGCTG
ACGGCGGGTGGGGATTTTGTCAGCCAGGCGGGGCGTGATACCAC
GATTGTGGCGAGCATGATCAGTGCGGGGAATGAGGCTTATCTGT
ATAGCGGGGATAAGTTGAGTTTGTTGGCGGCTGAGAACAGTACG
CATACGTTGTATGACATGAAGGAGAAGGGAAGCTGGGGCGCTAA
AAAGGCGCAGATGGATGAAGTGACCCGCACCACCCAGGTAGGGA
CCGAGATCAAGACAGGTGGCAACCTAGTCCTTAAAAGCGACGGC
GACCAGCTGTATCAAGTTGCGAAGCTTAATAGCGGCAAGGACAT
CATCCTTGATAGCGGTGGTGCAATTGTCTTTGAAGGCGTCAAGG
ACCTGCACGATGAGAGCCACACTAAGAGCAAAAGCGACCTCTCG
TGGTTCAGCGCTAAGGGCAAAGGTAATACAGACGAAACCTTGCG
TCAGAGCGAGTTGGTTGCCCAAGGACAGCTTGTCATCAAGGCCG
CCGAAGGCATTCGTATCGACGTCAAACAGGTCGATCAGCAGACT
GTAAGCCAGACCGTTGATGCGATGGTCAAGGCTGATCCTAATTT
GGCCTGGCTCAAGCAAGCTGAGGCACGTGGCGACATTGATTGGC
GCCAGGTAAAGGAGATTCACGAGAGCTTCAAGTACGACAACTCA
GGGTTGGGCGCCGGTGCCAAGATTGCGATTGCGATCATGATGGC
GGCGATCATGGGGCCGGTAGGATTCGGGTTGCAGGGAGCCACCC
TTGCGGTGAGCACCAGCCTGAGTACGACGGCAGTCACTAGCACC
ATCAACAACAAAGGCAATTTGGGTGCAGCGCTTAAGGAAACGGT
CAGCGCCAATAGCCTGAAAAGCGCAGCAGTCGCCGGGTTCACGG
CGGGGGCTCTTGAGTATGCCGACACCAATTGGTTCGCTGGTGCT
GACGGTGCAGGTGCAGGTGCAGGCACAAGTACAAGCACAGTCCA
AGGTGTTACCCCGAGTACGGGTTCAACCTTGGCGGTTACGAACT
CCTCCAAAGATATTTTCACCTGGACGTCAGCAGGCGATATCGCG
CTGCGTACCGGTGGCCGGGCGGTAATCTCTAGCGGAATATCGAC
GGCCATTCAAGGGGGAAGCTTCGGCGACAACTTCAATGCGGCCC
TGTTGGGAGAGGCTGGCAACGTTGCAATGGCTACCGGTTTTAAT
TGGGTGGGTGACTACGTCACGTTCCCCAATGGCAGCCCTCAAAA
GATTATTGCGCACGCTTTGATGGGGGGGATTGCTGGCTGAAGCCA
CAGGTAGCGATTTCAAAACCGGGGCTGCCGCTGCCGGGCTGAAT
GAGGCACTCATCAATCAGTTGGTGTGGGCTGCTCAAGGCAATGA
CGACATCACGCTGATGCTTTCACAGCTGACAGGCTTGTTAGCAG
CTGCGGCGGTCGATGGAGATTTGGAAAAAGGCTCTCAGATTGCT
CAGAAGGCGACGACGTTCAACTATCTTTACCACGAAGAAGTCGA
GGAAATGCTTCGGGAGGTAGATAGCAAGACTACGGAGCAAGAGA
AGCGTGAGGTCAGGCAGCGCTATGCGGAACTTGATCAGCAGAGA
AATGACGAGTTGGATGCGCTTTGCGCACGCGATCCGCAACGCTG
CCGAGGTATTGCCACTTCCTTGGCGAACGATGATCAGAAACTCG
TTGATCTGGTAGGTAGGTTGAGATCCCAAGGGCAGGGCGGTGCT
GCTTCTGCGGTTGGTTTTGTGATAGGGAACAACCTAGACGCGTC
CAGCCAAATTGCAGCAGATATCAGCTCTGCGGGCGGTGGGCCAT
TAGTTAAGCTCGGTGCGGAGGCAATTAAGGCCGGAGTTGGGATC
ACACTGCCTTCACGTTCAAGCTCTGGTAAGGGGAAAGGAAGCCA
AGTCGGCGCGGGTTCCCTTGAAGAGGCGGCGGGTCCAAAGGCGA
CAGGCGAAGTAGTGCCTCCCGCGCCTATTGTGACTTCTGGTGCG
ACTAGGACAGGTGTTGTTCGTACAAATGCCGCAGATTGGAGAGC
ACTGCGTAATAATTGGGATGACCTTGGGTATGGTCAAATCTTAA
GTACTGAAAATCGGGCCGCGATTGCTAAAGGACGGACTCCAAAA
GTCGACGATGCATGGGTTAAGGTTTTTCCTGAAGATGCAGGGCT
AAAGGGCGAGAGAATTCCTATGCACCATGTTCAGGGTTCGCCAC
TTACTGTGCCACTGCCTGATACACGGCATTTGGATGCGCATATG
CCAGGAGGGTTTAGATATAATCCAGGCGGTCCAGGGTCGGCTCT
CCCGGCATACCCTCCAAAAAAAGGAGCTGAATAA
```

TABLE 14-continued

Table of Sequences

| SEQ ID NO | Name | Sequence* |
|---|---|---|
| 45 | Protease D-alanyl-D-alanine carboxypeptidase/ endopeptidase AmpH precursor amino acid (RXF01040; PROKKA_04307) *P. fluorescens* | MFRRLRGIPLLGCLMGSIGCHSQPPAPPPIQKGDYGAIIRYLQT RIPREMARDNVAGLSIALVNGQELIWARGFGLADKDQGVPVTPN TAFRAGGISKLLSATAALQLVEQHHLALDAPIQQTLREFYVRSR FHSDQAEADRAITLRRLLSHQSGLPSEHLRDLRSTYAMGQMPMR VSGVWLSSLPGSQVAYSNLGYSLVGAAIERSSGKSFEAQLQSSL LTPLRMNQSSFVGTGAQMGFRAHGYEDGKASTDAQVRDLAAGGL WTSPKDLSRYVRMLFANGTYKGSQILGSASIDAMFTQQNTGNAL DFDCQIGLGWFLAPCGDEPIGPGVRTYQHSGGGDDFVAQLTLLP DQQLAVIIMANDSNAEDMVVSLTTDSLRLMLQAQTGQPVCADDC QAPSHGLKLRHVPAAVDRKRLAGFYATAWGVFRIRDYHARLTGE LAGYDFELLRDEQGWLRAQKKILGFWRKDLGELGRVQLDVIQVQ GRQMLTARSHGQRIAIGERIEPPPLPAAWANTVGTYQVLSSHEP DAPLSGISVRQEDGFLVIRGQLHGEPLTDYILLPIDNAHAVLAG NGYGLGDTVSRQVNGLSASGYSFKRTQSPHIPSNF |
| 46 | Protease D-alanyl-D-alanine carboxypeptidase/ endopeptidase AmpH precursor example nucleic acid encoding SEQ ID NO: 45 | ATGTTTCGCAGGTTGCGCGGTATTCCGCTCTTGGGTTGCCTGAT GGGCAGTATCGGTTGCCACTCGCAACCGCCTGCCCCGCCGCCGA TTCAAAAAGGCGATTACGGCGCAATCATCCGCTACTTGCAAACC CGCATTCCCCGGGAGATGGCTCGGGACAATGTGGCAGGTTTGTC GATTGCGCTGGTCAATGGCCAGGAGCTGATCTGGGCTCGTGGCT TTGGCCTGGCTGACAAAGACCAGGGGGTGCCGGTCACGCCCAAT ACCGCGTTTCGCGCCGGTGGCATTTCCAAACTGCTGAGCGCCAC GGCGGCGCTGCAGCTGGTGGAGCAGCACCACCTGGCGCTGGATG CACCGATCCAGCAGACCCTGCGTGAGTTCTACGTACGTTCACGC TTTCACAGCGACCAGGCCGAGGCGGATCGAGCGATCACTTTGCG GCGCTTGCTCAGCCATCAATCCGGCTTGCCCAGCGAGCACCTGC GCGACCTGCGCAGCACCTACGCCATGGGGCAAATGCCAATGCGC GTGTCGGGTGTGTGGCTGAGCAGCCTGCCGGGGTCCCAGGTGGC GTACTCCAACCTTGGTTATTCACTGGTGGGCGCGGCCATCGAGC GCAGCAGCGGTAAAAGCTTTGAAGCCCAGTTGCAAAGCAGCCTG CTCACGCCCCTGCGAATGAACCAGTCCAGCTTCGTAGGCACCGG TGCACAAATGGGCTTTCGCGCCCATGGTTACGAGGACGGCAAGG CCAGCACCGACGCCCAAGTGCGTGACCTCGCCGCCGGTGGCCTG TGGACCAGCCCCAAAGACCTCAGCCGCTACGTACGCATGCTGTT TGCCAACGGCACCTACAAGGGCAGCCAGATCCTCGGCAGCGCTT CTATCGACGCCATGTTTACCCAGCAAAACACCGGCAACGCCCTG GATTTCGACTGCCAGATCGGCCTGGGCTGGTTTCTGGCGCCCTG CGGTGACGAGCCCATCGGCCCCGGTGTGCGCACCTACCAGCACA GCGGTGGCGGCGATGACTTCGTCGCCCAATTGACCCTGCTACCG GATCAGCAGCTGGCGGTGATCATCATGGCCAACGACAGCAACGC CGAAGACATGGTGGTGTCACTGACCACCGACAGCCTGCGCCTGA TGCTCCAGGCACAGACTGGCCAGCCCGTGTGCGCCGATGACTGC CAGGCGCCGAGCCACGGCCTCAAGCTGCGCCATGTGCCGGCCGC GGTGGATCGCAAGCGCCTGGCTGGTTTCTATGCGACCGCCTGGG GCGTGTTCCGCATCAGGGATTACCATGCACGCTTGACCGGCGAA CTGGCCGGCTACGATTTCGAGCTGTTACGTGATGAACAAGGCTG GCTGCGCGCGCAGAAAAAGATCCTCGGCTTCTGGCGCAAGGACC TGGGCGAGTTGGGCCGCGTGCAGTTGGATGTAATCCAGGTACAA GGCCGCCAAATGCTCACCGCGCGCAGCCACGGCCAACGCATTGC CATCGGTGAACGCATCGAGCCACCGCCCTTGCCTGCCGCCTGGG CCAACACGGTCGGCACCTATCAGGTGCTCAGCAGCCATGAACCC GACGCGCCATTGAGTGGCATCAGCGTGCGTCAGGAGGACGGCTT TCTGGTGATTCGTGGCCAATTGCACGGCGAGCCGCTGACCGACT ACATCCTGCTACCCATCGACAACGCCCATGCGGTACTGGCCGGC AACGGTTACGGCTTGGGCGATACCGTCAGCCGCCAGGTCAACGG GCTGAGCGCTTCGGGTTATTCCTTCAAACGTACCCAATCACCCC ACATACCCTCGAATTTCTAA |
| 47 | Autolytic factor Serralysin precursor amino acid (PROKKA_01103; RXF04500) *P. fluorescens* | MRVPGPTATNSNAGQVPDPRSGISPEGPTQVYTLNSKKTVFTTE QAGKHITRSGFKFHDSNGDGKTTLSYRVSKGFTPQQADQARQAL QSWQDVANVTFTEKRQGADGHIDINEMHGTSGGMASLPNRYMSQ TFANVGTANAGANPPRGHYFREVLVHEIGHTIGLEHPGDYDGSG NYGRDAAYAGDTRARSVMSYYSEKNQPGHDFKSLNPSAPMMDDI SAVQKLYGANTKTRNTDTTYGFNSNTNREAYSLKSANDTPIFCV WDGGGNDTLDFSGYSHHQKINLNAESFSDVGALKGNVSVAKGVT LENAVGGKGDDTLIGNHVANRLKGGAGADRLSGGGGADTFVYDH ASDSTPDNPDVILDFASGADKIDVSAVLKRANVSALKFVDRLTG QPGQAVMSYDEGRNEGGLALDLTGNGKADLLIKSIGQIKAADIL AHGDTTAPNPEPKDPKPQPRPQPEEPKPKPESKPKEPKPEEPKP RPDSCEPKPRPDPCEPKPRPDPCEPKPRPDSCEPKPRPDPCEPK PRPDPREPQPRPDPREPQPRPDPREPQPRPDPREPQPCPDPREP QPRPDPCEPQPRPDPCEPQPRPDPREPRPNPREPQPRPDPRE PQPQPRPDPREPYPRPDPREPRPNPREPRPRPNPREPQPRPD |

TABLE 14-continued

Table of Sequences

| SEQ ID NO | Name | Sequence* |
|---|---|---|
|  |  | PREPRPRPDPCEPQPRPDPREPRPRPNPREPQPRPDPREPQPRP DPREPRPRPDPREPQPRPDPCEPQPRPEPCEPRPRPNPREPQPR PDPCEPKPTPRTDPCEPKAVTRNVRPAYGLSAHSGEYRAMQAPA FDSRHFQGGLAGEFIRRQKRAE |
| 48 | Autolytic factor Serralysin precursor example nucleic acid encoding SEQ ID NO: 47 | ATGAGAGTGCCAGGACCAACCGCAACGAATTCTAATGCAGGGCA GGTGCCAGATCCGAGGAGTGGCATCAGCCCGGAGGGCCCTACGC AGGTATATACACTAAACAGCAAAAAAACCGTCTTCACTACGGAA CAGGCCGGGAAACATATCACCCGCAGCGGTTTCAAGTTTCATGA CAGTAACGGTGATGGCAAAACCACGTTGTCCTATCGTGTTTCCA AGGGCTTTACCCCACAGCAGGCAGATCAAGCCAGGCAGCACTG CAATCCTGGCAGGATGTCGCTAACGTCACATTCACTGAAAAAAG GCAGGGGGCTGACGGCCATATAGATATCAATGAGATGCACGGAA CCTCTGGGGGTATGGCCTCACTCCCCAACCGCTATATGAGTCAA ACTTTCGCAAATGTCGGAACAGCGAATGCAGGTGCAAACCCTCC ACGGGGTCATTATTTTCGCGAAGTTCTAGTTCACGAAATAGGCC ACACCATTGGGCTGGAACACCCGGGGGACTATGATGGCTCTGGT AACTATGGACGGGACGCAGCGTATGCCGGGGATACTCGAGCGCG TTCTGTGATGAGTTACTATTCGGAAAAAAACCAGCCGGGACATG ATTTCAAATCATTGAACCCCTCTGCGCCGATGATGGATGATATA TCGGCCGTTCAGAAACTCTATGGGGCGAATACTAAAACGCGTAA TACCGATACGACGTATGGATTTAATTCCAATACAAACCGTGAAG CCTATAGTTTGAAGTCGGCTAACGACACACCCATTTTCTGTGTG TGGGATGGTGGTGGTAATGACACATTGGATTTCTCTGGGTATTC ACACCATCAGAAAATCAACCTCAATGCCGAGTCCTTTTCGGATG TAGGGGCGTTGAAAGGTAACGTTTCCGTTGCCAAGGGCGTCACG CTGGAAAATGCAGTGGGCGGTAAGGGCGACGACACACTTATCGG TAATCATGTTGCCAATCGCCTCAAAGGGGGGGCGGGAGCCGACA GACTGTCTGGGGGGGGCGGCGCAGATACCTTTGTTTACGACCAT GCCAGTGATTCCACCCCGGATAACCCTGATGTCATCCTGGATTT TGCGAGTGGCGCAGATAAGATTGATGTATCCGCAGTCCTTAAAA GAGCGAATGTCAGTGCTCTCAAGTTCGTCGATCGCTTAACTGGC CAACCCGGCCAGGCTGTGATGAGTTATGACGAGGGCCGCAACGA GGGGGGGCTGGCCCTGGATCTGACAGGCAACGGCAAGGCTGATC TATTAATAAAAAGCATTGGCCAGATAAAAGCTGCTGATATCTTG GCGCACGGCGATACAACCGCGCCAAACCCTGAACCCAAAGATCC CAAGCCGCAGCCGCGTCCTCAACCCGAGGAGCCCAAACCCAAGC CTGAATCCAAACCGAAGGAGCCAAAACCGGAGGAACCAAAACCG CGTCCGGACTCGTGTGAACCAAAGCCGCGTCCGGATCCGTGTGA GCCGAAGCCGCGTCCGGATCCGTGCGAGCCGAAGCCGCGTCCGG ATTCGTGTGAGCCAAAGCCGCGTCCGGATCCGTGCGAGCCGAAG CCGCGTCCAGATCCACGCGAACCGCAGCCACGTCCGGACCCGCG CGAGCCGCAGCCGCGTCCAGATCCACGCGAACCGCAGCCACGTC CAGACCCACGTGAACCGCAGCCATGTCCGGATCCACGCGAACCG CAGCCGCGTCCGGACCCGTGTGAGCCGCAGCCGCGTCCGGACCC GTGTGAGCCACAGCCGCGTCCAGACCCACGTGAACCGAGGCCGC GTCCGAACCCACGTGAACCGCAGCCACGTCCGGACCCACGCGAG CCGCAGCCGCAGCCGCGTCCGGACCCACGTGAACCGTACCCACG TCCAGACCCACGTGAACCGAGGCCGCGCCCGAACCCACGTGAGC CGAGGCCGCGTCCGAACCCACGTGAACCACAGCCGCGTCCAGAC CCACGTGAGCCGAGGCCGCGTCCGGACCCGTGTGAGCCACAGCC GCGTCCAGACCCACGTGAGCCGAGGCCGCGTCCGGAACCCACGTG AACCACAGCCGCGTCCAGACCCACGTGAACCGCAGCCACGCCCG GACCCGCGTGAGCCGAGGCCGCGTCCGGACCCACGTGAACCGCA GCCACGCCCGGACCCGTGTGAGCCACAGCCGCGTCCGGAACCAT GTGAGCCGAGACCGCGTCCGAACCCACGTGAACCGCAACCACGT CCGGACCCGTGCGAGCCTAAACCAACCCCTCGCACAGATCCTTG CGAGCCGAAAGCTGTCACTCGAAACGTAAGGCCAGCCTATGGCT TGAGTGCCCATTCAGGCGAGTACCGGGCGATGCAGGCGCCAGCC TTTGATAGTCGTCATTTCCAGGGCGGGCTTGCAGGGGAATTCAT TCGACGTCAGAAGCGCGCTGAATAG |
| 49 | Autolytic factor S-type Pyocin amino acid (PROKKA_02110) *P. fluorescens* | MASTRVRFQFRQDESGELRVYGLHTQPGSGADRVPVAQARWNVD KSAMVAVLDGISITWTPNLGPVVSVPSPYPGTPERLDNMFVHPI AVGQDSAISHYPGRDAENITWQDTIISFPADSGVPPLYLVFAKP AVRPLEVDIYGAFSGRLRNGLHVDHIPSQAAIRRHLERYAISFT EKQLKEALNNAASIAIPSYIHQKFSETYGWRNTEKKQTLDADDL RQAADNNFDAIKPYLLDHGFAETDLEMARTRMHKVNENQGWY |
| 50 | Autolytic factor S-type Pyocin example nucleic acid encoding SEQ ID NO: 49 | ATGGCCAGCACGCGAGTGCGTTTCCAGTTTCGCCAGGATGAGTC CGGTGAACTGCGTGTTTACGGCCTACATACCCAACCTGGCAGTG GCGCCGACCGTGTGCCGGTTGCACAAGCCCGGTGGAATGTGGAC AAAAGCGCGATGGTCGCGGTGCTGGATGGCATCAGCATCACATG GACGCCGAACCTCGGCCCGGTTGTCAGCGTGCCGAGCCCGTATC |

TABLE 14-continued

Table of Sequences

| SEQ ID NO | Name | Sequence* |
|---|---|---|

CCGGAACACCGGAACGCTTGGATAACATGTTTGTTCATCCGATT
GCGGTGGGGCAAGATTCGGCGATCAGTCACTATCCAGGGCGGGA
TGCAGAAAACATCACCTGGCAGGATACGATCATTTCGTTTCCGG
CTGATTCGGGTGTGCCGCCGTTGTATTTGGTGTTTGCCAAGCCG
GCGGTCAGGCCGTTGGAAGTTGATATTTACGGTGCGTTCAGTGG
ACGACTGCGCAACGGGTTGCACGTGGATCACATACCCTCGCAGG
CAGCGATAAGACGTCATCTCGAACGCTATGCAATAAGCTTTACA
GAGAAGCAGCTCAAGGAAGCGTTAAATAATGCTGCGAGCATTGC
TATTCCGTCTTACATCCATCAAAAGTTTAGTGAGACTTACGGTT
GGCGAAACACGGAGAAAAAGCAGACGTTAGATGCCGACGATCTT
CGTCAGGCGGCAGACAACAATTTTGATGCTATCAAGCCATACCT
CCTGGATCACGGCTTCGCTGAGACTGATCTCGAGATGGCACGCA
CCCGAATGCATAAGGTCAACGAAAACCAGGGGTGGTACTAG

| 51 | Autolytic factor Linear gramicidin synthase subunit D amino acid (PROKKA_02750; RXF07469) *P. fluorescens* | MNAEDSLKLARRFIGLPLEKRQLFLQALQKEGVDFSRFPIPAGV... |

MNAEDSLKLARRFIGLPLEKRQLFLQALQKEGVDFSRFPIPAGV
EVEDRQALSYAQQRMWFLWQLDPASGAYNLPGAVRLSGVLSLPA
LEQAFASLVARHETLRTVFQRQADERLAQVAVEPSVAVEHLDFT
ALAFDAREQAVNAAATRQSLLPFDLEHGPLLRVQLLKLAEQEHV
LLLTLHHIVSDGWSMNVLIDEFIRCYDAHERDEAPQLPALPIQY
SDYALWQRRWLEAGEQARQLEYWQARLGDEHPVLELPTDHPRPA
MPSYQGTRHNFAIEPALAAQLRSCAQKHNVTLFMLLLGAFNVLL
HRYTGQGDIRVGVPIANRNRTEVEGLIGFFVNTQVLRTELSGQT
RVAELLQGIKEHALGAQAHQELPFERLVEALKIERSLSHTPLFQ
VMYNHQPVVADIASVSTASGLELALVEWQGRTTQFDLTLDTYEK
SGTLHAALTYANDLFDTPTIERMARHWTRLLQAMVLDGEQRIGE
LPMLDAAEQQRLLHTWNHTAEAYPTERGIHHLIEDQARRSPDAP
ALVFGTTTLTYAQLDARANQLAHALGEQGVGPDVLVGICIERSI
EMVVGLLAILKAGGAYVPLDPEYPQERLAYMIEDSGIQLLLSQQ
SLLASLPVAGIQVIALDQPALWLDGYSSESPNVALHALNLAYVI
YTSGSTGKPKGAGNSHRALVNRLSWMQQAYGLGANDAVLQKTPF
SFDVSVWEFFWPLMSGARLVVAAPGEHREPARLIDTIGRHAITT
LHFVPSMLQAFIHEPGVQACASLTRIVCSGEALPLDAQQQVFAK
LPAAALYNLYGPTEAAIDVTHWTCIDEGVDSVPIGRPIANLGTY
VLDAQLNPVPAGVSGELYLGGVGLARSYHRRPALTAERFVPSPF
VTGERLYRTGDRVRQRADGVIEYLGRLDHQVKLRGLRIELGEIE
ARLMQHPHVREAVVLVHGGKQLVAYLVHPGEAPTDLKAWLLSSL
PEYMVPTHFIALPKLPVTANGKLDRKALPVPDAALQQAFVAPQG
DLQTALAAIWSDVLGVEEVGQDDNFFELGGDSIISIQVVSRARQ
AGIRLSPRDLFQYQSIRSLALVARFEQVSLIDQGPVSGEVMLTP
VQHSFFDQPIPARHHWNQSLLLVPGEVLEPARLEATLARLIEHH
DALRLRFVQQADGWQQSHAAYVSEPLLWQCQASTDAELAALCDE
AQRSLDLAQGPLLRAALVNLADGSQRVLLVIHHLVVDGVSWRIL
LEDLQQAYRDQALPAKTSAYQRWAQQLHRHAQSLDQQLPYWQAQ
SIDAELPCDHPEGGLQNRLGAKLETRLDVEHTRRLLQDAPAAYR
TQVNDLLLTALARVISRWSEQPAALIQLEGHGREDLFDDIDLSR
TVGWFTSLYPVRLHAEGELSAAIKSVKEQLRAVPNKGIGYGLLR
YLGTPDTREALSTLAAPRITFNYLGQFDRQFNDSALFVPARQGS
GQAQDAEAPLANWLTVEGQVYGGELSLQWGFSREMFEAATVQRL
ADEYAAELNALIEHCCATPAGQVSPSDFPLARLTQQQLDALPVA
GPAIADLYPLSPMQQGMLFHTLLEPEAQAYINQLRLDIEGLDVL
AFGRAWQAALDRHDILRSSFHWLGLDSAHQLIQRQVDLQLQVIE
DPNADFDTLAHAERERGFALNAAPLFRLTLVRGAGAAWHFIFTS
HHILMDGWSNAQLLAEVIAHYAGQAVPAPLGQFRDYLAWLQQQS
SGEAFWKTALAALPAPTLLAQALRTPVDGVGMADHHVALESNFT
RRLGEFARQHKVTLNTLLQGAWSLLLQRYTGQDCVAFGATVAGR
SAPLPGIEQQLGLFINTLPIISAASPAQSAATWLSELQVLNLSL
RDHEHVPLYDIQGWAGQQGALFDTLLVFENFPVAEALKQGAPAG
LTFGRLHNHERTHYPLTLGIELGASLRLEFSYDRAQFSEAQVAQ
LSANLQHLLAQLLADAHMPLGNLRLLDAPAQQQMLALSRSAAAP
QANERVHQRIAAQAEATPDALAVQAGDASVSYAQLNQRANRLAH
RLLALGVGPGQRVGLASRRGPQLIVSLLAVLKSGAAYVPLDPEY
PAERLAYMLADSRLDLLLSETGLLADLPLPRGLTRVDFSACGEE
LTGYPTTNPPNHAAAADLAYVIYTSGSTGQPKGVAIDHAALGQF
CDSATLYSRLSAEDRVLQFATFSFDGFVEQCFPPLCAGAALIMR
GDELWDAGQLAREIVEQGVTLADLPAAYWYLLAQECAEHRRSLG
KLRQVHVGGEAMSVEGVRAWYAAGLGNVRLVNTYGPTEATVVSS
VHECQLADANDAYGVPIGQAIAGRALYVLDNGFELLATDGVGEL
CIGAEVGLAQRYFDRPALTAERFLPDPISATPGARLYRSGDLAR
YNPAGALEYVGRIDHQVKIRGLRIEMGEIEASLQALSNVREAAV
LAQPSATGVQLVAYNNPAEGQALATQALAARLRQTLPDYMVPGH
WVALDALPLNHNGKLDRRALPTPDLNQASTTYVAPQSPLQIQLA
AIWQAVLQVEQVGLEDHFFERGGHSLLATQVISRVRHDLKLEVP
LRALFEQPTLAAFAAACAGVQVDTAPVIQAVGRDQPLALSFAQE
RQWFLWQLDPTSAAYHVPTALHLRGELDIAALERAVEALVQRHE

TABLE 14-continued

Table of Sequences

| SEQ ID NO | Name | Sequence* |
|---|---|---|
| | | PLRTTFVESGEHTVQVIHPSLAVPVEQQKVDAGTIEQAVIEEIQ<br>RPFDLRNGPLMRVKLLIVAPDHHVLVITQHHIISDGWSMQVMID<br>EWVALYQGDVGLPALPIQYADYAQWQRDWMAAGEQQRQLDYWCA<br>RLGHEHSLLDLPLDHPRPAVQSHRGARRQIHLERVLLTELKALA<br>QRQDVTLFMLLLASFQTLLHRYSGQAQVRVGVPVANRNRFETER<br>LLGFFVNTQVLQADVHGQMPFDQLLAQVKLRALEAQAHQDLPFE<br>QLVQVLQPERSLSHNPLFQVMFNHQDSLRSAPVQLPGLALQPVD<br>WAGHSTQFDLNLETEESVDGLWASLTYATDLFDAATAERLAEHW<br>QNLLRAVLQDASVALDDLAMLSPSQSQQMVHDWNRSDTDYPRER<br>CVHQLFEAQAAAQPDAIALHFNDERLSYGELNRRANRLAHRLID<br>MGVGPDVLVAVHVERSLDMVVGLLATLKAGGAYVPLDPQFPAER<br>LAYMLEDSRARVLLTQPHLLGHLAQPHGVQVLMVEEAGTAQHNP<br>QVAVTPEHLAYVIYTSGSTGKPKGVMVRHKALCSFTSAMAGTLS<br>IGQDARLLSLTTFSFDIFALELYVPLSVGGTVLLSAQAMALDPE<br>AILDLAQRQAANVLQATPSTWRMLLDSPRAHALRGIACLCGGEA<br>LPVDLAQRMLDLQGPLWNLYGPTETTIWSAAHRLHQALPFVGRP<br>IANTRLFILNAGLTPCPQGVSGELLIGGVGLARGYHGQPALTAE<br>RFVPNPFGASGERLYRTGDLARYQADGVVEYIGRVDHQVKVRGF<br>RIELGEIEACLREFDGVREAVVLADNDRLIAYLVSTAPQAPQVY<br>KAALRERLPDYMVPAQWLFLDSLPLTPNGKLDRKALPKPDASLS<br>LKGHVAPVTPREQQVAAIWAEVLELPRVGLDDHFFELGGHSLLA<br>TRVVSRVRQALALEVPLKALFEQPLLGDFVRALGEEGVTAPALI<br>KADRTQPLPLSYAQERQWFLWQLDPAGAAYHIPSALRLQGPLDL<br>TALQESFDSLLARHESLRTYFRQDATGAVQVIDAQSRVDIEQVD<br>SDYAGLKARVAQVVAQPFDLLRGPLLRVTLLRLAEDDHVLVLVQ<br>HHIVSDGWSMQLMVEELVQAYAANSQGQDVQLPTLPIQYADYAV<br>WQRDWMEAGEQARQLAYWREQLSGEQPVLELPFDHPRPAQPSHR<br>GARLGIELHPELLGSLRALAQHAGVTLPMLLLASYQALLHRYSG<br>QEDVRVGVPIANRNRLETEGLIGFFVNTQVLKADIHGQMSTEQL<br>LHQVRQRSLEAQAHQDLPFEQLVQALQPERSLSLSPLFQVLFNH<br>RVSAADSHLHRLADLHVEVLDLDEGVAQFDLALDVEESPTALRA<br>SLSYATDLFAVATIERMAGHWQNLLRAMVVDPQQPISQLSLLGE<br>DEQQQILELWNQTDAGFSAERLVHELVGDRARETPDAVAVKFDA<br>QTLSYGELDRQANRLAHALIARGVGREVRVAIAMPRSAESMVAF<br>LAVMKAGGVYVPLDIEYPRDRLLYMMQDSRAQLLLTHSRALQQL<br>PVPEGLETLAIDRTEEWAGYSDTAPDVALDGDNLAYVIYTSGST<br>GLPKGVAVSHGPLVAHIIATGERYETSPADCELHFMSFAFDGSH<br>EGWMHPLINGASVLIRDDSLWLPEYTYEQMRHNVTMAVFPPVY<br>LQQLAEHAERDGNPPAVRVYCFGGDAVAQASYDLAWRALKPKYL<br>FNGYGPTETVVTPLLWKARKGDPCGAVYAPIGTLLGNRSGYVLD<br>AQLNLQPIGVAGELYLGGEGVARGYLERPALTAERFVPDPFGKP<br>GSRVYRSGDLTRGRPDGVVDYLGRVDHQVKIRGFRIELGEIEAR<br>LREQASVGETVVVAQEGPTGKQLVAYVVPADASLADPVEFRDAL<br>RRALKADLPDYMVPSHFVFLAQMPLTPNGKLDRKGLPLPDASQM<br>QQQYLAPQTELEQQIATIWADILHLPQVGLNDNFFDVGGHSLLA<br>IQITSRVQAELGLDVPLMELFQTESLRAYVQAAATFRAGSVEDF<br>DDLRDFLSELEAI |
| 52 | Autolytic factor<br>Linear gramicidin<br>synthase subunit D<br>example nucleic acid<br>encoding SEQ ID<br>NO: 51 | ATGAATGCTGAAGACTCCTTGAAACTTGCTCGCCGGTTTATCGG<br>GCTGCCCCTGGAAAAACGCCAATTGTTCCTGCAAGCCTTGCAGA<br>AAGAAGGCGTGGATTTTTCAAGGTTTCCGATTCCGGCAGGGGTG<br>GAGGTGGAGGACCGCCAGGCGCTGTCCTACGCACAGCAGCGCAT<br>GTGGTTTCTATGGCAGTTGGACCCGGCCAGTGGCGCCTACAATT<br>TGCCCGGCGCGGTGCGTTTAAGTGGCGTGTTGAGCCTGCCAGCG<br>CTGGAGCAAGCGTTCGCCAGCCTGGTGGCGCGTCACGAAACCCT<br>GCGCACAGTGTTCCAGCGTCAGGCCGATGAGCGGCTGGCGCAGG<br>TGGCGGTGGAGCCGTCGGTGGCCGTCGAGCACCTGGACTTCACC<br>GCCTTGGCCTTTGATGCGCGGGAGCAGGCCGTCAACGCCGCCGC<br>CACCCGTCAATCGCTGTTGCCGTTCGACCTGGAACATGGGCCAC<br>TGCTGCGCGTGCAACTGCTCAAGCTTGCCGAGCAGGAACACGTG<br>CTGCTGCTGACCCTGCACCACATCGTCTCCGACGGTTGGTCGAT<br>GAATGCTGATCGACGAATTCATCCGTTGCTATGACGCCCACG<br>AGCGCGACGAAGCGCCCCAACTGCCGGCGCTGCCCATCCAATAC<br>AGCGACTACGCCCTGTGGCAGCGCCGCTGGCTGGAAGCGGGCGA<br>GCAGGCGCGCCAATTGGAATATTGGCAGGCCCGCCTGGGTGATG<br>AGCATCCGGTGCTGGAACTGCCCACTGATCACCCACGCCCCGCG<br>ATGCCCAGCTACCAGGGCACACGGCATAACTTCGCGATTGAGCC<br>GGCACTGGCCGCGCAACTGCGCAGTTGCGCGCAAAAACACAACG<br>TTACCCTGTTCATGCTGCTGCTCGGTGCCTTCAATGTGCTGTTG<br>CACCGCTATACCGGCCAGGGCGACATTCGCGTCGGTGTGCCGAT<br>TGCCAATCGCAATCGCACCGAAGTCGAGGGCCTGATCGGTTTCT<br>TCGTCAACACCCAGGTGTTGCGCACCGAACTGAGCGGGCAAACC<br>CGGGTTGCCGAGTTGCTGCAAGGTATCAAGGAGCATGCCCTGGG<br>CGCCCAGGCTCATCAGGAATTGCCCTTTGAACGTCTGGTGGAAG |

TABLE 14-continued

Table of Sequences

| SEQ ID NO | Name | Sequence* |
|-----------|------|-----------|
| | | CGCTGAAAATCGAGCGCAGCCTGAGCCACACGCCGCTGTTTCAG |
| | | GTGATGTATAACCATCAGCCGGTAGTCGCCGACATCGCCTCGGT |
| | | CAGTACCGCATCGGGTCTGGAATTGGCCCTGGTGGAATGGCAAG |
| | | GCCGTACCACCCAGTTCGACCTGACCCTGGACACCTATGAAAAG |
| | | TCCGGCACCCTGCATGCCGCGCTGACCTACGCCAATGACTTGTT |
| | | CGATACGCCCACCATCGAGCGCATGGCCCGGCACTGGACCCGCC |
| | | TGCTGCAAGCTATGGTGCTCGATGGCGAACAGCGCATTGGCGAA |
| | | TTGCCCATGCTTGACGCGGCTGAACAGCAACGGTTGCTCCACAC |
| | | CTGGAACCACACCGCCGAGGCGTACCCGACCGAGCGCGGCATTC |
| | | ATCACCTGATCGAAGACCAGGCACGGCGCAGCCCCGATGCTCCG |
| | | GCACTGGTGTTCGGTACCACCACCTTGACCTACGCCCAACTGGA |
| | | TGCGCGCGCCAACCAATTGGCCCATGCCCTGGGCGAGCAGGGCG |
| | | TAGGGCCCGACGTATTGGTGGGTATCTGCATCGAGCGCTCCATC |
| | | GAAATGGTGGTTGGCCTGCTGGCGATTCTCAAGGCCGGTGGCGC |
| | | CTACGTGCCCCTCGACCCTGAGTACCCCCAGGAACGCCTGGCCT |
| | | ACATGATCGAAGACAGTGGCATTCAGTTGTTACTCAGCCAGCAG |
| | | AGCCTGCTGGCGTCGCTGCCCGTCGCCGGTATCCAGGTGATTGC |
| | | CCTGGACCAGCCGGCGCTATGGCTCGACGGATACAGCAGCGAAT |
| | | CGCCGAACGTGGCCCTGCATGCCCTGAACCTGGCCTATGTGATC |
| | | TACACCTCGGGCTCCACCGGCAAGCCCAAAGGCGCTGGCAACAG |
| | | CCATCGCGCGTTGGTCAACCGCTTGAGCTGGATGCAACAGGCGT |
| | | ATGGCCTGGGTGCCAATGACGCGGTCTTGCAGAAAACCCCATTC |
| | | AGCTTTGATGTGTCGGTGTGGGAGTTCTTCTGGCCGCTGATGAG |
| | | CGGCGCACGCCTGGTGGTCGCGGCGCCTGGCGAGCACCGTGAAC |
| | | CGGCGCGCCTGATTGACACCATTGGCCGGCACGCCATCACCACC |
| | | TTGCACTTCGTGCCGTCGATGTTGCAGGCGTTTATCCATGAGCC |
| | | GGGCGTACAGGCGTGCGCGAGCCTCACGCGTATCGTCTGCAGCG |
| | | GCGAAGCCTTGCCCCTGGATGCGCAACAGCAAGTGTTCGCCAAG |
| | | TTGCCCGCTGCGGCGCTGTACAACCTCTATGGCCCGACCGAGGC |
| | | GGCCATCGACGTCACGCACTGGACCTGCATTGACGAAGGCGTCG |
| | | ACAGCGTGCCCATCGGCCGCCCCATCGCCAACCTCGGCACCTAC |
| | | GTGCTGGACGCACAACTCAACCCGGTGCCGGCTGGCGTCAGCGG |
| | | CGAACTCTATCTCGGCGGCGTTGGCCTGGCGCGCAGTTACCACC |
| | | GACGCCCGGCGCTGACCGCCGAACGTTTTGTGCCCAGCCCGTTC |
| | | GTGACGGGCGAGCGCCTGTATCGCACCGGTGACCGCGTGCGCCA |
| | | ACGTGCCGATGGGGTGATCGAATACCTCGGCCGTCTCGATCATC |
| | | AGGTCAAGTTGCGCGGCTTGCGTATCGAGCTGGGCGAAATCGAA |
| | | GCACGCCTGATGCAGCATCCACACGTGCGCGAAGCCGTGGTACT |
| | | GGTACATGGCGGCAAGCAGTTGGTCGCCTATCTGGTGCACCCAG |
| | | GCGAGGCGCCAACGGACCTCAAGGCCTGGTTGCTCAGCAGCTTG |
| | | CCGGAATACATGGTGCCGACGCATTTCATCGCGCTGCCCAAGCT |
| | | GCCGGTGACCGCCAATGGCAAGCTCGATCGCAAGGCGTTGCCAG |
| | | TGCCAGACGCGGCACTGCAACAGGCGTTTGTCGCCCCCCAAGGC |
| | | GACCTGCAAACAGCCCTGGCTGCCATCTGGAGCGACGTACTGGG |
| | | CGTTGAGGAGGTCGGCCAGGACGATAACTTCTTCGAGCTGGGCG |
| | | GCGATTCGATCATCTCCATCCAAGTAGTCAGCCGCGCGCCCGTCAG |
| | | GCCGGCATTCGCCTGAGCCCGCGTGACCTGTTCCAGTACCAGAG |
| | | CATCCGCAGCCTGGCCCTGGTGGCGCGCTTTGAGCAGGTCAGCC |
| | | TGATCGACCAGGGCCCGGTCAGCGGCGAGGTCATGCTGACGCCC |
| | | GTGCAACACAGCTTTTTCGACCAGCCGATCCCGGCGCGGCATCA |
| | | CTGGAATCAATCCTTGTTGCTGGTGCCCGGCGAGGTGCTTGAGC |
| | | CTGCACGGTTGGAGGCAACGCTGGCGCGGTTGATCGAGCATCAC |
| | | GACGCCTTGCGCCTGCGTTTTGTGCAGCAGGCTGACGGCTGGCA |
| | | GCAGAGCCATGCCGCCTACGTCAGCGAACCGCTGTTGTGGCAAT |
| | | GCCAGGCCAGCACCGACGCCGAACTGGCGGCGCTGTGTGATGAA |
| | | GCCCAGCGCAGCCTTGACCTTGCCCAAGGCCCGCTGCTGCGCGC |
| | | CGCGTTGGTGAATTTGGCCGATGGCAGCCAACGTGTGCTGCTGG |
| | | TGATCCACCACCTGGTGGTGGATGGCGTGTCCTGGCGCATCCTG |
| | | CTTGAAGACCTGCAACAGGCCTACCGCGACCAGGCGCTGCCGGC |
| | | GAAAACCAGTGCCTACCAGCGCTGGGCGCAACAGTTGCACCGCC |
| | | ACGCGCAGTCCCTCGACCAGCAACTGCCGTACTGGCAAGCCCAA |
| | | TCCATCGACGCCGAGCTGCCGTGTGATCACCCCGAAGGCGGCCT |
| | | GCAAAACCGCCTGGGTGCCAAGCTGGAAACACGCCTCGACGTCG |
| | | AGCACACCCGCCGACTGCTGCAAGACGCGCCAGCGGCCTATCGC |
| | | ACCCAGGTCAACGACCTGCTGTTGACCGCCCTGGCGCGGGTGAT |
| | | CAGCCGTTGGAGCGAGCAACCTGCTGCGCTCATTCAATTGGAAG |
| | | GTCATGGTCGGGAAGACCTGTTTGACGACATCGACCTGAGCCGC |
| | | ACCGTCGGCTGGTTCACCAGCCTGTACCCGGTGCGCCTGCACGC |
| | | CGAAGGGGAACTGTCGGCGGCGATCAAGTCGGTGAAGGAGCAAC |
| | | TGCGCGCCGTGCCGAACAAAGGCATTGGCTACGGCCTGTTGCGT |
| | | TACCTCGGCACGCCTGACACCCGCGAAGCGTTGTCGACCCTGGC |
| | | CGCGCCGCGCATCACGTTCAACTACCTGGGCCAGTTCGACCGCC |
| | | AGTTCAATGACTCGGCACTGTTCGTGCCGGCCCGCCAGGGCAGT |
| | | GGGCAGGCTCAGGATGCAGAGGCACCGCTGGCCAACTGGTTGAC |

TABLE 14-continued

Table of Sequences

| SEQ ID NO | Name | Sequence* |
|---|---|---|

```
GGTGGAAGGGCAGGTGTATGGCGGTGAGCTGTCGCTTCAATGGG
GCTTCAGTCGAGAGATGTTCGAGGCGGCAACTGTGCAGCGTCTG
GCGGATGAGTACGCAGCCGAACTCAATGCGCTGATCGAGCATTG
CTGTGCCACGCCGGCAGGCCAGGTGAGCCCGTCGGATTTCCCGC
TGGCACGCCTCACCCAGCAGCAACTGGATGCGTTGCCCGTGGCC
GGGCCGGCGATTGCCGACCTTTATCCGCTGTCGCCGATGCAGCA
AGGCATGCTGTTCCACACCCTGTTGGAACCCGAGGCCCAGGCCT
ACATCAACCAGTTGCGCCTCGACATCGAGGGCCTCGATGTGCTC
GCTTTCGGGCGTGCCTGGCAGGCTGCACTGGATCGTCATGACAT
CCTGCGCAGCAGCTTCCATTGGCTGGGCCTGGACAGTGCTCATC
AGCTGATCCAGCGCCAGGTCGACCTGCAACTGCAAGTGATCGAA
GACCCAAACGCCGACTTCGACACCCTGGCCCACGCCGAACGCGA
ACGTGGTTTTGCCCTGAATGCCGCGCCGCTGTTTCGCCTGACGC
TGGTGCGTGGTGCCGGTGCGGCCTGGCACTTTATCTTTACCAGC
CACCACATCCTCATGGACGGCTGGAGTAACGCGCAGTTGCTCGC
CGAGGTCATCGCGCATTATGCGGGGCAGGCAGTACCGGCGCCGC
TCGGGCAGTTCCGCGATTACCTCGCCTGGCTGCAACAACAGTCC
TCGGGCGAGGCGTTCTGGAAAACCGCCCTGGCGGCATTGCCGGC
GCCGACTCTGCTGGCGCAAGCGCTGCGCACGCCGGTCGACGGGG
TGGGCATGGCTGACCATCACGTGGCACTGGAGAGCAACTTTACC
CGCCGCCTCGGCGAGTTCGCACGCCAGCACAAAGTCACCCTCAA
TACCCTGTTGCAAGGGGCTTGGAGCCTGTTGCTGCAACGCTACA
CCGGCCAGGACTGCGTCGCCTTCGGTGCCACGGTGGCCGGGCGT
TCCGCGCCGCTGCCGGGGATCGAGCAGCAACTGGGCCTGTTCAT
CAACACCTTGCCGATCATCAGCGCAGCCTCGCCAGCCCAGTCGG
CTGCGACTTGGCTCAGCGAACTGCAAGTGCTCAACCTCAGCCTG
CGCGACCATGAACATGTGCCGCTCTACGACATCCAGGGCTGGGC
CGGCCAGCAAGGCGCGCTGTTCGACACCTTGCTGGTGTTCGAGA
ACTTCCCGGTCGCCGAGGCGCTCAAGCAAGGCGCGCCGGCCGGC
CTGACCTTCGGTCGCCTGCACAACCATGAGCGCACGCACTATCC
ATTAACCCTGGGCATCGAACTGGGCGCCAGCCTGCGCCTGGAGT
TCAGCTATGACCGTGCCCAGTTCAGCGAGGCGCAAGTGGCGCAG
TTGAGCGCCAACCTGCAACACCTGCTGGCGCAATTGCTCGCAGA
CGCTCACATGCCGCTGGGCAACCTGCGCCTTCTCGACGCCCCTG
CGCAACAGCAGATGCTCGCGCTGAGCCGCTCAGCCGCAGCGCCA
CAGGCCAACGAGCGCGTGCATCAGCGTATAGCCGCCCAGGCCGA
GGCGACGCCGGACGCCCTGGCTGTGCAGGCCGGTGACGCCAGCG
TGAGCTACGCCCAGTTGAACCAGCGCGCCAACCGCCTGGCCCAT
CGCCTGTTGGCGCTGGGTGTCGGCCCCGGCCAACGGGTGGGCCT
GGCTTCGCGGCGTGGCCCGCAGTTGATCGTCAGCCTGCTGGCAG
TGCTCAAAAGCGGGGCGGCCTACGTACCGCTGGACCCTGAATAC
CCGGCGGAGCGTTTGGCCTACATGCTCGCCGACAGCCGCCTGGA
CCTGCTGCTCAGCGAAACCGGCTTGCTCGCCGACTTGCCTTTGC
CCCGCGGCCTGACCCGCGTGGATTTCAGCGCCTGTGGCGAGGAG
CTCACCGGCTACCCGACGACCAATCCGCCTAATCACGCAGCGGC
GGCTGACCTGGCCTACGTGATCTACACCTCTGGCTCCACCGGCC
AGCCCAAGGGTGTGGCCATCGACCATGCCGCCCTCGGCCAGTTC
TGCGACAGCGCCACGCTGTACAGCCGACTGAGCGCCGAGGACCG
CGTGTTGCAGTTTGCGACCTTCAGTTTCGATGGTTTTGTCGAAC
AGTGCTTCCCGCCCCTGTGTGCGGGTGCGGCGTTGATCATGCGT
GGCGATGAACTCTGGGACGCCGGGCAACTGGCGCGAGAAATCGT
TGAGCAGGGCGTGACTCTGGCCGATTTGCCCGCCGCCTACTGGT
ACCTGTTGGCGCAGGAATGCGCCGAGCACCGTCGCTCCCTGGGC
AAGCTGCGCCAGGTGCATGTGGGTGGTGAAGCCATGTCAGTGGA
AGGCGTGCGTGCGTGGTACGCCGCGGGCTTGGGCAATGTGCGCC
TGGTCAACACCTACGGGCCCACCGAAGCCACGGTTGTGTCCAGT
GTGCATGAGTGCCAATTGGCCGATGCCAACGACGCCTACGGCGT
GCCAATCGGGCAGGCGATTGCCGGGCGCGCGCTGTATGTACTCG
ACAACGGTTTCGAACTGTTGGCCACCGATGGCGTGGGCGAGCTG
TGCATTGGCGCCGAGGTTGGCTTGGCGCAACGCTACTTCGACCG
CCCGGCGCTGACCGCCGAGCGCTTCTTGCCGGACCCGATTTCCG
CCACGCCCGGTGCGCGGCTTTATCGCAGTGGCGACCTGGCCCGG
TACAACCCCGGCGGGTGCGCTGGAGTACGTCGGGCGTATCGACCA
TCAAGTGAAGATTCGTGGCCTGCGTATCGAAATGGGCGAAATCG
AAGCCAGCCTGCAAGCCTTGTCCAATGTGCGCGAAGCCGCCGTG
CTTGCGCAGCCGAGCGCGACCGGCGTGCAGTTGGTGGCGTACGT
GGTGCCAGCCGAAGGCCAAGCGCTGGCGACCCAGGCACTGGCAG
CGCGCTTGCGCCAGACATTGCCGGACTACATGGTGCCGGGCCAT
TGGGTGGCCCTTGATGCCTTGCCGTTGAACCACAACGGCAAGCT
CGACCGCCGTGCACTGCCCACACCCGACCTGAACCAAGCCAGCA
CCACCTACGTGGCGCCGCAGAGTCCATTGCAAATCCAGTTGGCG
GCGATCTGGCAAGCAGTGTTGCAGGTCGAGCAGGTTGGCCTGGA
AGATCACTTCTTCGAACGCGGCGGCCACTCTTTGTTGGCTACCC
AAGTGATCTCCCGGGGTGCGCCACGACCTCAAGCTGGAAGTGCCG
```

TABLE 14-continued

Table of Sequences

| SEQ ID NO | Name | Sequence* |
|---|---|---|
| | | TTGCGGGCGCTGTTCGAACAGCCGACGCTGGCAGCCTTTGCTGC |
| | | GGCGTGCGCAGGCGTGCAGGTCGATACGGCGCCCGTGATCCAGG |
| | | CAGTTGGCCGTGACCAGCCACTGGCGTTGTCATTTGCTCAGGAA |
| | | CGGCAGTGGTTTCTCTGGCAATTGGATCCCACCAGCGCGGCCTA |
| | | TCATGTGCCCACCGCTTTGCACCTGCGCGGTGAACTCGACATCG |
| | | CGGCGCTGGAGCGCGCCGTCGAGGCCCTGGTGCAGCGCCATGAA |
| | | CCGCTGCGCACCACCTTTGTGGAGTCGGGCGAGCACACTGTGCA |
| | | AGTCATCCACCCAAGCCTGGCAGTGCCGGTTGAGCAACAAAAGG |
| | | TCGACGCCGGCACTATCGAGCAGGCTGTCATCGAAGAGATCCAG |
| | | CGCCCGTTCGACCTGCGCAACGGCCCGCTGATGCGCGTCAAGTT |
| | | GCTGATCGTCGCGCCTGATCACCATGTGCTGGTTATCACCCAGC |
| | | ACCACATCATCTCTGACGGCTGGTCGATGCAAGTGATGATCGAC |
| | | GAGTGGGTGGCGCTGTACCAAGGCGACGTTGGCTTGCCGGCCTT |
| | | GCCGATCCAGTACGCCGACTACGCCCAGTGGCAGCGCGACTGGA |
| | | TGGCGGCTGGGGAACAACAACGCCAGCTCGATTACTGGTGCGCT |
| | | CGTCTGGGTCACGAACATTCGCTGCTGGACCTGCCCCTCGACCA |
| | | TCCGCGCCCCGCAGTGCAGAGCCATCGTGGCGCGCGCCGCCAGA |
| | | TTCATCTGGAACGTGTGCTGTTGACTGAACTCAAGGCCCTGGCC |
| | | CAGCGTCAGGACGTGACGCTGTTCATGCTGTTGCTGGCCTCGTT |
| | | CCAGACCTTGCTGCACCGCTACAGCGGCCAGGCGCAGGTGCGTG |
| | | TCGGCGTGCCGGTCGCCAACCGTAATCGCTTCGAAACCGAACGA |
| | | CTGCTGGGCTTTTTCGTCAACACCCAGGTGCTGCAAGCTGACGT |
| | | GCACGGACAGATGCCGTTCGACCAGTTGCTGGCCCAGGTCAAGC |
| | | TGCGTGCCCTGGAGGCGCAGGCCCATCAGGACCTGCCGTTCGAG |
| | | CAGCTCGTGCAAGTGTTGCAGCCCGAGCGCAGCCTGAGCCATAA |
| | | CCCGCTGTTCCAGGTGATGTTCAACCATCAGGACAGCCTGCGTT |
| | | CAGCGCCGGTGCAATTGCCCGGCCTGGCTTTGCAGCCCGTGGAT |
| | | TGGGCCGGTCACAGCACGCAGTTCGACCTGAACCTGGAAACCGA |
| | | GGAATCGGTGGACGGTCTCTGGGCCTCGCTGACTTACGCCACGG |
| | | ATCTGTTTGACGCGGCGACCGCGGAACGCCTGGCCGAGCATTGG |
| | | CAAAACCTGCTGCGCGCGGTCCTGCAGGATGCCTCGGTGGCCTT |
| | | GGACGACCTGGCGATGCTCAGCCCGTCGCAATCGCAGCAAATGG |
| | | TGCACGACTGGAACCGCAGCGACACTGACTACCCGCGCGAACGC |
| | | TGCGTACACCAGTTGTTTGAGGCCCAGGCCGCGGCGCAACCCGA |
| | | CGCCATTGCGCTGCACTTCAATGACGAGCGCCTGAGCTACGGCG |
| | | AACTCAACCGCCGCGCCAATCGGCTGGCCCATCGTCTGATCGAC |
| | | ATGGGCGTCGGCCCGGACGTGCTGGTGGCGGTGCACGTGGAGCG |
| | | TTCCCTGGACATGGTGGTTGGCTTGCTCGCGACCCTCAAGGCCG |
| | | GTGGCGCCTATGTGCCGCTCGACCCACAATTCCCGGCAGAGCGC |
| | | CTGGCCTACATGCTTGAAGACAGCCGCGCCCGGGTATTGCTGAC |
| | | GCAACCGCACCTGCTGGGGCACCTGGCGCAGCCGCACGGCGTGC |
| | | AGGTGCTGATGGTGGAGGAGGCCGGCACAGCGCAGCACAATCCC |
| | | CAGGTTGCCGTGACACCGGAGCATCTGGCCTACGTGATCTACAC |
| | | CTCTGGCTCCACTGGCAAGCCCAAAGGGGTGATGGTTCGTCACA |
| | | AGGCGCTGTGCAGCTTCACCAGCGCCATGGCCGGCACGTTGAGT |
| | | ATCGGCCAGGATGCGCGGCTGTTGTCGCTGACCACCTTCTCGTT |
| | | CGACATTTTCGCCCTGGAGCTGTATGTGCCGCTGAGTGTCGGCG |
| | | GTACCGTGTTGCTGAGCGCCCAGGCAATGGCCCTCGACCCGGAG |
| | | GCGATCCTCGATCTGGCCCAGCGCCAGGCGGCGAATGTGCTGCA |
| | | AGCCACGCCCTCGACCTGGCGCATGTTGCTCGACAGCCCACGGG |
| | | CTCATGCACTGCGTGGCATCGCCTGCCTCTGCGGTGGCGAAGCG |
| | | CTGCCCGTCGATTTGGCCCAGCGCATGCTCGATCTGCAAGGCCC |
| | | GTTGTGGAACCTCTATGGTCCGACGGAAACCACCATCTGGTCGG |
| | | CGGCTCATCGTTTGCACCAGGCATTGCCGTTCGTGGGGCGGCCC |
| | | ATCGCCAATACCCGCTTGTTCATTCTCAATGCCGGTCTCACGCC |
| | | ATGCCCCCAAGGTGTGTCCGGTGAGCTGCTGATCGGCGGTGTCG |
| | | GCCTGGCGCGCGGTTACCACGGGCAGCCGGCGCTGACCGCCGAA |
| | | CGCTTCGTGCCTAACCCGTTTGGGGCATCGGGCGAACGCCTGTA |
| | | CCGTACCGGCGACCTGGCACGCTATCAGGCGGACGGCGTGGTGG |
| | | AATACATCGGCCGTGTCGACCATCAGGTCAAGGTCCGGGGTTTC |
| | | CGTATCGAGCTGGGTGAAATCGAAGCCTGCCTGCGTGAGTTCGA |
| | | CGGCGTACGTGAAGCCGTGGTGCTGGCCGATAACGACCGGCTGA |
| | | TCGCTTACCTGGTCAGCACCGCGCCGCAGGCACCGCAGGTGTAT |
| | | AAAGCCGCGCTGCGCGAGCGTCTGCCGGACTACATGGTGCCAGC |
| | | GCAGTGGCTGTTCCTCGACAGCCTGCCGCTGACCCCCAACGGTA |
| | | AGCTCGACCGCAAGGCACTGCCCAAACCGGATGCCAGCCTGTCG |
| | | CTCAAAGGCCATGTAGCGCCCGTCACCCGCGCGAGCAGCAGGT |
| | | GGCGGCGATCTGGGCCGAGGTACTGGAATTGCCCCGTGTGGGCC |
| | | TCGACGATCATTTCTTCGAGTTGGGCGGGCATTCATTGCTGGCC |
| | | ACGCGGGTGGTGTCACGGGTGCGTCAGGCCCTGGCGCTGGAGGT |
| | | CCCACTCAAAGCCTTGTTCGAACAGCCGCTACTGGGTGATTTCG |
| | | TGCGGGCCTTGGGCGAGGAGGGCGTCACCGCGCCTGCGCTGATC |
| | | AAGGCCGACCGCACGCAACCTCTACCGCTGTCTTATGCCCAGGA |
| | | GCGCCAATGGTTCCTTTGGCAACTGGACCCGGCCGGCGCCGCGT |

TABLE 14-continued

Table of Sequences

| SEQ ID NO | Name | Sequence* |
|---|---|---|

```
ATCACATCCCCAGCGCCTTGCGTTTGCAGGGGCCGTTGGACCTG
ACCGCGCTGCAAGAGAGCTTCGATAGCTTGCTGGCTCGCCATGA
AAGCCTGCGCACGTATTTCCGTCAGGACGCCACCGGCGCGGTTC
AAGTCATTGACGCGCAGAGCCGGGTCGATATCGAGCAGGTCGAC
AGCGACTATGCCGGCCTCAAGGCGCGGGTCGCGCAGGTGGTCGC
CCAGCCTTTCGACCTGCTGCGTGGGCCGCTGCTGCGGGTTACCT
TGCTGCGCCTGGCCGAGGACGACCATGTGCTGGTGCTGGTGCAG
CATCACATCGTCTCTGACGGCTGGTCGATGCAGTTGATGGTCGA
GGAACTGGTGCAGGCGTATGCCGCTAACAGCCAAGGCCAGGACG
TGCAATTGCCGACGCTGCCGATCCAGTACGCCGATTATGCCGTG
TGGCAGCGCGATTGGATGGAGGCGGGTGAGCAGGCGCGTCAATT
GGCCTACTGGCGTGAGCAATTGAGCGGCGAGCAACCGGTGCTGG
AGTTGCCGTTCGACCACCCGCGCCCGGCACAGCCAAGCCATCGC
GGCGCACGCTTGGGTATCGAGTTGCATCCGGAGTTGTTGGGCAG
TTTGCGCGCGCTGGCGCAGCACGCTGGCGTCACGCTGCCGATGC
TGCTGCTGGCGTCTTACCAGGCATTGCTGCATCGCTACAGCGGC
CAGGAAGATGTGCGCGTGGGCGTGCCGATTGCCAACCGTAATCG
CCTGGAAACCGAGGGGTTGATCGGCTTCTTCGTCAACACCCAAG
TGCTCAAGGCCGATATCCACGGGCAAATGAGCACCGAGCAATTG
CTGCACCAGGTGCGTCAGCGTTCCCTCGAGGCCCAGGCTCACCA
GGACCTGCCGTTCGAACAGCTTGTGCAGGCATTGCAACCGGAGC
GCAGCCTGAGCCTGAGCCCGTTGTTCCAAGTGTTGTTCAACCAC
CGTGTGAGCGCTGCCGACAGCCACCTGCATCGCCTGGCCGACCT
GCACGTCGAAGTCCTGGATTTGGACGAGGGCGTGGCCCAGTTCG
ACCTGGCGCTGGATGTGGAAGAAAGCCCGACGGCCCTGCGTGCC
TCCCTGAGTTATGCCACCGACCTGTTCGCCGTGGCGACCATCGA
GCGCATGGCCGGGCATTGGCAGAACCTGTTGCGGGCAATGGTGG
TCGACCCACAGCAGCCCATTAGCCAATTGAGCCTGCTGGGCGAG
GATGAGCAACAGCAGATTCTTGAATTGTGGAACCAGACCGACGC
CGGTTTTTCAGCCGAGCGCCTGGTGCACGAATTGGTCGGTGATC
GCGCCCGGGAAACCCCGGACGCGGTGGCGGTGAAATTCGATGCT
CAAACCCTGAGTTACGGCGAGCTGGATCGTCAGGCCAACCGCCT
GGCCCATGCCTTGATCGCCCGTGGCGTCGGCAGGGAAGTGCGGG
TGGCCATCGCCATGCCGCGCAGTGCCGAGAGCATGGTGGCCGTTC
CTGGCGGTGATGAAAGCCGGCGGTGTGTATGTGCCGCTGGATAT
CGAATACCCACGTGATCGCCTGCTGTACATGATGCAAGACAGCC
GTGCGCAACTGCTGCTGACTCACAGCCGGGCGCTGCAGCAACTG
CCAGTCCCCGAGGGCCTGGAGACCCTGGCGATTGATCGCACCGA
AGAGTGGGCCGGTTACAGCGATACGGCACCGGATGTGGCGCTGG
ACGGCGACAACCTTGCCTACGTGATCTATACCTCCGGCTCCACC
GGTTTGCCCAAGGGCGTGGCGGTGTCACACGGGCCGCTGGTGGC
GCATATCATCGCTACCGGCGAGCGCTATGAAACCTCACCGGCCG
ATTGCGAACTGCACTTCATGTCCTTCGCCTTCGACGGTTCCCAC
GAAGGCTGGATGCACCCGCTGATCAACGGCGCCAGCGTGTTGAT
CCGTGACGACAGCCTGTGGCTGCCGGAATACACCTACGAGCAGA
TGCACCGCCACAACGTGACCATGGCGGTGTTCCCCACCGGTGTAC
TTGCAACAGTTGGCCGAACATGCCGAGCGCGACGGCAACCCGCC
GGCGGTGCGGGTGTATTGCTTCGGCGGTGATGCCGTTGCTCAAG
CCAGCTATGACCTGGCCTGGCGCGCGCTGAAACCCAAGTACCTG
TTCAACGGCTATGGCCCGACGGAAACCGTGGTTACACCGTTGTT
GTGGAAGGCCCGCAAAGGCGATCCCTGCGGCGCTGTCTATGCGC
CCATCGGCACCTTGCTGGGCAACCGCAGTGGCTACGTGCTGGAT
GCGCAACTGAATCTGCAACCCATCGGCGTGGCCGGCGAGTTGTA
CCTGGGCGGCGAGGGCGTGGCCCGGGGTTACCTGGAGCGTCCGG
CACTGACTGCCGAGCGTTTCGTACCGGACCCGTTCGGCAAACCG
GGCAGCCGCGTGTATCGCAGCGGCGACCTGACCCGTGGGCGTCC
GGATGGCGTGGTGGATTACCTGGGGCGTGTGGACCATCAAGTGA
AGATCCGCGGTTTTCGTATCGAACTGGGGGAAATCGAAGCGCGT
CTGCGTGAGCAAGCCAGTGTCGGTGAAACCGTGGTGGTGGCCCA
GGAGGGGCCGACCGGTAAGCAACTGGTGGCCTATGTGGTACCGG
CCGACGCCAGCCTGGCCGACCCGGTTGAGTTCCGTGACGCCCTG
CGTCGTGCCCTGAAAGCCGACCTGCCGGACTACATGGTGCCCAG
CCACTTCGTATTCCTGGCGCAGATGCCGCTGACCCCCAACGGCA
AGCTCGACCGCAAGGGCCTGCCGCTGCCGGATGCGAGCCAGATG
CAGCAGCAGTACCTGGCTCCGCAAACCGAGCTTGAGCAGCAGAT
CGCCACGATCTGGGCCGACATCCTGCACCTGCCGCAAGTGGGCC
TGAACGACAACTTCTTTGACGTCGGTGGCCACTCCTTGCTGGCG
ATCCAGATTACCTCGCGGGTGCAGGCCGAGCTCGGCCTGGACGT
ACCGTTGATGGAACTGTTCCAGACCGAATCGCTGCGCGCCTACG
TGCAGGCCGCAGCCACTTTCCGCGCCGGCAGCGTGGAAGATTTT
GATGACCTTCGTGACTTTTTGAGCGAACTAGAGGCGATTTGA
```

TABLE 14-continued

Table of Sequences

| SEQ ID NO | Name | Sequence* |
|---|---|---|
| 53 | Autolytic factor Leukotoxin amino acid (PROKKA_04470) *P. fluorescens* | MTGGEHFENLVPGTTPVNTTVTDTPGTDNTTTVTLTAPSAVNEG GQITYTATLSNKAGTDVTLKLDNGSSITIKAGETVGTVTVPAPT DDVFIDKSTQTVKITETTGGNFEKLEVAGNGATTTINDTIDKVD VVLTATTTVGEGGNIVYTASLVDKNGAPVTNITNPLTVTLDNGQ TITIGVNQSSGSITTIAPDDVYKGDQTVTTAIKGVTGGEHFENL VPGTTPVNTTVTDTPGTDNTTTVTLTAPAEANEGGQITYTATLS NKAGTDVTLKLDNGSSITIKAGDTVGTVTVPAPSDDVFIDKSTQ TVKITDASGGNFEKLEVAGNGATTTINDTIDKVDVVLTATTTVG EGGNIVYTASLVDKNGAPVTNITNPLTVTLDNGKTITIGVNQSS GSVSVLAPDDVYKGDQTVTTAIKGVTGGEHFENLVPGTTAVNTT VTDTPGTDNTTTVTLTAPSAVNEGGQITYTATLSNKAGTDVTLK LDNGSSITIKAGETVGTVTVPAPTDDVFIDKSTQTVKITDASGG NFEKLEVAGSGATTTINDTIDKVDVVLTATTTVGEGGNIVYTAS LVDKNGAPVTNITNPLTVTLDNGKTITIGVNQSSGSVSVLAPDD VYKGDQTVTTAIKGVTGGEHFENLVPGTTPVNTTVTDTPGTDNT TTVTLTAPSAVNEGGQITYTATLSNKAGTDVTLKLDNGSSITIK AGETVGTVTVPAPTDDVFIDKSTQTVKITETTGGNFEKLEVAGN GATTTINDTIDKVDVVLTATTTVGEGGNIVYTASLVDKNGAPVT NITNPLTVTLDNGKTITIGVNQSSGSITTVAPNDVYKGDQTVTT AIKGVTGGEHFENLVPGTTAVNTTVTDTPGSTDLTTVTLTAPTA VNEGGQITYTATLSNKAGSDMLVQLDNGSSITIKQGETVGTVTV PAPTDDVFIDKSTQTVKITGTTGGNFEGVTITPAGATTTINDTI DDVTVVLKATGSVSEGGQIVYTASLVDKNGVAVNNVGSDLVVKL DNGSTITIGNGKSTSFTTATAPNDAYVGANDVTTKITGVVSGGD KYEHLIVDGSTVVTKVTDVVSNTTISITGDASVTEGGTAHYTLT LSNPPQTDVTVTLKYSGTATDGSDFNGVYTVKIPAGSSSVPFDI RTLDDKITEPTENIVITIDKTTGGNFENLVVGNGSVTTNIIDND APPVIDLDANNSSGASGADFKTTFTEGGTGVSIADTDIKITDPD STQLTGATVVLTNSQPGDSLNFSGVSGITVTPTTDPVTGKITLT LTGTASLADYMQQIKNITFTNNSHDPSTTPRTITVTVTDGGNYS NVATTTVNVVAVNDAPVATGGAVTGTEDTALALTWANFGVSDVD SPQASLGVKITELPVAGKLQYLAADGSTWTNVTSGQTFTKAQID GGQLRFTPNANESGADGYGGTGVGNKQADYAQFKFQPTDGKDLG TSATVKVDITPVADAPTLSVADNNVASTGLVKQGWNSIAGLGNN GNGAAPDVLKKAIDNAGTPNNTSVVTNVESVDNVAAGSGSKISG LIYMEAGKSYTFSGIADDSVVVNVGGKDVASGLWGTNSGKFSGS FTPTTTGYYSLEIYQANQAGPGSFDVNLSINGGAVQNLSTSTVP LYTGLTDLTNAGVTVSDLHGSNGDGYYVGYKLNEGQENGTVKLS KVTTALTDTDGSETLSVKISGIPAGSVLTDASGHTFTAGKTVGE VNVTGWDLNTLTIKPPTYYSGQFNLTVTSTSTESIGGSATTTAQ LPVTVHPATYNSVTGTSGSDTINGSDGNDIVVADIAGLNVVQGK NYNIAFMVDSSGSMSVASLDAAKASLTSVFNSLKDSLGANTSGT VNIFLADFDSQVKKSVAINLNDPNALTQLKAVLDSMASGGGTNY EDVFKATANFFQSDLATKNTGATNLTYFITDGKPTYHQSGEQIN PVVTDFYDFRTTDGRLDDYISANNYVLGNTFSINVNGANLQLID SQGQLHQWKQTFLGGWYDNGVIGTVHAQGDGTFEVSYLDGSGSS TTTATINNANSGFALLKGLSAVEAIGINGDISLDDLKPYDTDGK PQTNIDPKDLANAILGHTEATLPGADTVSGGDGNDILFGDLVSF SGINGEGYNALQAFVAQKTGVAVSAVTASNVHQYVTEHYVDFDV SGAKDAGDTLLGGAGDDILFGQGGNDTLDGGKGNDILLGGTGND TLIGGQGNDILIGGSGADTFVWKSGDIGNDVIKDFKASEGDRID LRDLLKGETDSTIDNYLKITTVDGVSTLQVSSEGKLNAAGGLAN ADVTIKLEGNDWSHTSINSLISGADPTIKIDHT |
| 54 | Autolytic factor Leukotoxin example nucleic acid encoding SEQ ID NO: 53 | ATGACCGGCGGCGAGCACTTTGAAAATCTGGTTCCAGGTACTAC CCCGGTTAACACCACCGTTACGGACACACCGGGTACCGATAACA CCACCACCGTTACGCTGACAGCGCCAAGTGCCGTTAACGAAGGT GGGCAGATTACGTACACCGCAACGCTTTCCAATAAAGCGGGCAC TGATGTCACGCTGAAGTTAGATAACGGTTCGTCGATCACCATCA AGGCCGGCGAAACCGTCGGCACCGTGACTGTCCCTGCGCCTACC GATGACGTGTTTATCGATAAGAGCACCCAGACCGTCAAGATCAC CGAAACCACTGGCGGCAACTTCGAAAAACTCGAAGTGGCAGGAA ACGGCGCAACCACCACGATCAACGACACCATCGACAAAGTCGAT GTGGTCCTGACCGCCACTACCACCGTCGGCGAAGGCGGCAATAT CGTCTACACCGCCAGCCTTGTGGATAAGAACGGCGCACCGGTGA CCAACATCACCAATCCGCTGACCGTGACATTGGATAACGGCCAG ACCATCACTATTGGCGTAAACCAGTCGAGCGGTTCTATCACCAC CATCGCGCCAGACGATGTCTACAAAGGCGACCAGACCGTCACTA CCGCCATCAAAGGCGTGACCGGCGGCGAGCACTTTGAAAATCTG GTTCCAGGTACTACCCCGGTTAATACCACCGTTACGGATACACC AGGCACTGACAACACCACTACGGTGACGCTGACCGCTCCGGCCG AGGCAAACGAAGGTGGGCAGATCACGTACACCGCCACGCTTTCC AACAAAGCGGGCACTGACGTAACGCTGAAACTCGACAACGGTTC TTCGATCACCATCAAGGCTGGCGCACTGTTGGCACTGTGACTG |

TABLE 14-continued

Table of Sequences

| SEQ ID NO | Name | Sequence* |
|---|---|---|
| | | TGCCCGCTCCAAGCGATGACGTGTTCATCGATAAAAGTACCCAG |
| | | ACCGTCAAGATTACTGACGCTTCCGGCGGCAACTTCGAAAAACT |
| | | CGAAGTCGCAGGTAACGGCGCAACGACCACGATCAACGACACCA |
| | | TCGACAAGGTGGATGTAGTTCTAACTGCTACCACTACCGTCGGC |
| | | GAAGGCGGCAACATCGTCTACACCGCCAGCCTTGTGGATAAGAA |
| | | CGGCGCGCCGGTGACCAACATCACCAACCCGCTGACCGTGACAT |
| | | TGGATAACGGTAAAACCATCACCATCGGCGTAAACCAATCGAGC |
| | | GGTAGCGTTTCGGTTCTTGCTCCTGATGATGTGTACAAGGGCGA |
| | | CCAAACTGTCACCACCGCTATAAAGGGTGTGACCGGCGGCGAGC |
| | | ATTTCGAGAACCTGGTGCCTGGCACTACGGCAGTGAACACCACT |
| | | GTCACCGATACCCCCGGTACCGACAACACCACCACTGTGACGCT |
| | | GACAGCGCCAAGTGCCGTTAACGAAGGTGGTCAGATCACTTACA |
| | | CCGCGACCTTGAGCAACAAGGCCGGTACTGACGTCACCTTGAAG |
| | | CTGGATAACGGCTCTTCGATCACCATCAAAGCTGGCGAGACCGT |
| | | CGGTACTGTGACCGTGCCTGCGCCTACCGATGACGTGTTCATCG |
| | | ATAAGAGCACTCAGACCGTCAAGATCACCGACGCTTCGGGCGGT |
| | | AACTTCGAAAAACTGGAAGTTGCAGGCAGCGGCGCGACCACTAC |
| | | GATCAACGACACTATCGACAAGGTCGATGTGGTCCTGACCGCCA |
| | | CCACCACCGTCGGCGAAGGCGGCAACATCGTTTACACCGCCAGC |
| | | CTCGTGGATAAAAACGGCGCACCGGTGACCAACATCACCAATCC |
| | | GCTGACCGTGACCCTGGATAACGGCAAGACCATCACCATCGGCG |
| | | TAAACCAATCGAGCGGTAGCGTTTCGGTTCTTGCTCCGGATGAT |
| | | GTGTACAAGGGCGACCAAACTGTCACCACCGCTATCAAGGGTGT |
| | | GACCGGCGGCGAGCACTTTGAAAATCTGGTTCCAGGTACTACCC |
| | | CGGTTAACACCACCGTTACGGACACACCGGGTACCGATAACACC |
| | | ACCACCGTTACGCTGACAGCGCCAAGTGCCGTTAACGAAGGTGG |
| | | GCAGATTACGTACACCGCAACGCTTTCCAATAAAGCGGGCACTG |
| | | ATGTCACGCTGAAGTTAGATAACGGTTCGTCGATCACCATCAAG |
| | | GCCGGCGAAACCGTCGGCACCGTGACTGTCCCTGCGCCTACCGA |
| | | TGACGTGTTTATCGATAAGAGCACCCAGACCGTCAAGATCACCG |
| | | AAACCACTGGCGGCAACTTCGAAAAACTCGAAGTGGCAGGGAAAC |
| | | GGCGCAACCACCACGATCAACGACACCATCGACAAAGTCGATGT |
| | | GGTCCTGACCGCCACTACCACCGTCGGCGAAGGCGGCAACATCG |
| | | TCTACACCGCCAGCCTTGTGGATAAGAACGGCGCACCGGTGACC |
| | | AACATCACCAATCCGCTGACCGTGACCCTGGATAACGGCAAGAC |
| | | CATCACCATCGGTGTGAATCAGTCGAGCGGTTCCATCACCACCG |
| | | TAGCGCCAAACGACGTCTACAAAGGCGACCAAACCGTCACCACC |
| | | GCCATCAAAGGCGTGACCGGCGGCGAGCACTTCGAGAACCTGGT |
| | | GCCGGGCACGACGGCGGTGAACACCACCGTCACCGACACACCAG |
| | | GCTCCACCGACCTGACCACCGTTACCCTGACTGCCCCGACCGCG |
| | | GTCAACGAAGGCGGCCAGATCACCTACACCGCCACCTTGAGCAA |
| | | CAAGGCCGGTAGCGACATGCTGGTCCAGCTCGACAACGGTTCGA |
| | | GCATCACTATCAAGCAAGGTGAGACCGTGGGCACGGTGACCGTC |
| | | CCGGCGCCTACCGATGACGTGTTCATCGACAAGAGCACCCAGAC |
| | | CGTCAAGATCACCGGCACCACCGGCGGCAATTTCGAGGGCGTGA |
| | | CCATCACACCTGCGGGCGCCACGACCACCATCAACGACACCATC |
| | | GATGACGTGACCGTGGTACTCAAGGCCACTGGCTCGGTCAGCGA |
| | | AGGCGGGCAGATCGTGTACACCGCGTCCCTGGTCGACAAGAACG |
| | | GTGTGGCGGTGAACAACGTTGGCTCAGACCTGGTCGTCAAGCTG |
| | | GATAACGGCTCGACCATTACCATCGGCAATGGCAAGTCCACCAG |
| | | CTTCACCACCGCCACCGCACCTAACGATGCGTATGTCGGCGCCA |
| | | ATGACGTCACCACTAAAATCACGGGTGTGGTCAGCGGTGGCGAC |
| | | AAGTACGAACACTTGATCGTCGACGGCAGCACCGTGGTTACCAA |
| | | AGTGACCGATGTGGTCAGCAACACCACCATCAGCATTACCGGCG |
| | | ATGCGTCGGTGACTGAAGGCGGTACGGCGCACTACACGCTGACC |
| | | CTGAGCAACCCGCCGCAAACCGACGTGACCGTGACGCTCAAGTA |
| | | CAGCGGCACCGCTACCGACGGTTCAGACTTCAATGGCGTGTACA |
| | | CCGTGAAGATTCCGGCAGGCTCCAGCAGCGTACCGTTTGATATC |
| | | CGCACGCTCGACGACAAGATCACCGAGCCGACGGAAAATATCGT |
| | | CATCACCATCGACAAGACCACTGGCGGCAACTTCGAAAACCTGG |
| | | TGGTCGGCAATGGCAGTGTTACCACCAACATCATCGACAATGAT |
| | | GCGCCGCCGGTCATCGATCTGGATGCCAACAACTCCAGCGGCGC |
| | | CAGCGGTGCGGACTTCAAGACCACCTTCACCGAAGGCGGCACCG |
| | | GTGTGTCAATTGCTGACACTGACATTAAGATCACCGACCCGGAC |
| | | AGCACCCAACTGACCGGCGCGCCACCGTGGTATTGACCAACAGCCA |
| | | GCCAGGCGACTCGCTGAACTTCAGCGGCGTGAGCGGCATCACCG |
| | | TGACCCCGACTACCGACCCTGTGACCGGTAAAATCACCTTGACC |
| | | CTGACCGGGACGGCGTCGCTGGCCGACTACATGCAGCAGATCAA |
| | | GAACATCACGTTCACCAACAACAGCCACGACCCGAGCACCACGC |
| | | CGCGCACCATCACCGTGACGGTGACCGATGGCGGCAACTACTCC |
| | | AACGTGGCTACCACCACCGTCAACGTGGTAGCAGTCAACGATGC |
| | | ACCAGTGGCCACTGGCGGTGCCGTGACCGGTACGGAAGACACCG |
| | | CGCTGGCCCTGACCTGGGCCAACTTCGGCGTGAGCGATGTGGAC |
| | | TCGCCCACAAGCCAGCCTCGGGGTGAAAATCACCGAGCTGCCGGT |

TABLE 14-continued

Table of Sequences

| SEQ ID NO | Name | Sequence* |
|---|---|---|
| | | AGCCGGCAAGCTGCAATACCTGGCGGCGGACGGCAGCACCTGGA |
| | | CCAACGTGACCAGCGGCCAGACCTTTACCAAGGCTCAGATCGAT |
| | | GGCGGCCAACTGCGCTTTACGCCGAACGCCAACGAGTCCGGCGC |
| | | CGACGGTTATGGCGGCACTGGCGTGGGTAACAAGCAGGCGGATT |
| | | ACGCGCAGTTCAAGTTCCAACCAACCGATGGCAAGGACCTGGGT |
| | | ACCAGCGCCAGGTGAAAGTCGATATCACGCCGGTAGCCGACGC |
| | | GCCGACCCTGAGCGTGGCAGACAACAACGTTGCCTCCACCGGCC |
| | | TGGTCAAACAGGGCTGGAACAGCATTGCCGGCCTCGGCAACAAC |
| | | GGCAACGGCGCTGCACCGGACGTGCTGAAAAAAGCCATCGATAA |
| | | CGCGGGCACGCCGAACAACACCTCGGTGGTGACCAACGTCGAGT |
| | | CTGTCGACAATGTCGCCGCCGGCTCTGGCTCAAAAATCTCCGGC |
| | | CTGATCTACATGGAAGCCGGCAAGAGCTACACCTTCAGCGGCAT |
| | | CGCCGATGACAGCGTGGTGGTCAACGTTGGCGGTAAAGATGTTG |
| | | CCAGCGGTTTGTGGGGCACCAACAGCGGCAAGTTCAGCGGCTCG |
| | | TTCACGCCAACGACCACCGGTTACTACAGCCTTGAGATCTACCA |
| | | GGCCAACCAGGCGGGCCCAGGCAGCTTCGACGTTAACCTGTCGA |
| | | TCAACGGCGGGGCGGTGCAGAACCTGAGCACCAGCACCGTGCCG |
| | | TTGTACACCGGCCTTACCGACCTGACCAACGCCGGCGTCACCGT |
| | | ATCCGACCTGCATGGCAGCAACGGTGACGGCTACTACGTGGGCT |
| | | ACAAGCTCAACGAAGGCCAGGAAAACGGCACGGTCAAACTGTCC |
| | | AAGGTCACCACCGCGCTGACCGATACCGACGGCTCCGAAACCCT |
| | | GAGCGTAAAGATCAGCGGCATTCCGGCAGGCTCGGTGCTTACCG |
| | | ACGCGTCGGGGCACACCTTTACTGCGGGTAAAACCGTGGGCGAA |
| | | GTGAATGTCACCGGCTGGGACCTGAACACCCTGACCATCAAGCC |
| | | GCCGACCTACTACAGCGGCCAGTTCAACCTGACGGTCACCTCGA |
| | | CTTCCACCGAGAGCATCGGCGGTTCAGCGACCACCACCGCGCAA |
| | | TTGCCAGTCACGGTGCATCCGGCGACCTACAATTCGGTCACCGG |
| | | CACCTCGGGCAGCGACACCATCAATGGCAGCGATGGCAACGACA |
| | | TCGTCGTGGCCGACATCGCCGGCCTGAACGTGGTGCAGGGTAAG |
| | | AACTACAACATCGCGTTCATGGTGGACAGCTCCGGCAGTATGAG |
| | | CGTCGCCTCGCTCGACGCGGCGAAGGCCTCGTTGACTTCGGTGT |
| | | TCAACTCGCTCAAGGACAGCCTGGGCGCCAACACATCGGGGACC |
| | | GTGAATATCTTCCTGGCGGACTTTGATAGCCAAGTGAAAAAGTC |
| | | GGTGGCTATCAACCTCAACGATCCTAATGCATTGACTCAGCTGA |
| | | AAGCGGTGCTGGACTCGATGGCATCGGGGAGGAGGTACTAACTAC |
| | | GAAGACGTGTTCAAGGCCACTGCCAACTTCTTCCAGAGCGACCT |
| | | GGCGACCAAAAACACCGGTGCAACCAACTTGACGTACTTCATCA |
| | | CCGACGGCAAGCCGACCTACCACCAGAGCGGCGAGCAGATCAAC |
| | | CCGGTAGTGACTGACTTCTACGACTTCCGCACCACCGATGGGCG |
| | | CTTGGACGACTACATCAGTGCGAACAACTATGTGCTGGGTAACA |
| | | CGTTCAGCATCAACGTCAATGGCGCTAACCTGCAGTTGATCGAC |
| | | AGCCAGGGCCAACTGCACCAATGGAAGCAGACGTTCCTGGGTGG |
| | | CTGGTACGACAACGGCGTCATAGGTACCGTGCACGCCCAGGGTG |
| | | ACGGGACTTTTGAAGTCTCCTACCTCGACGGCTCCGGTAGTAGC |
| | | ACCACCACCGCGACCATTAACAACGCCAACAGCGGTTTTGCACT |
| | | GCTCAAAGGTTTGTCGGCGGTGGAAGCAATCGGCATCAACGGCG |
| | | ACATCAGTCTCGACGATCTCAAGCCGTACGATACCGATGGCAAG |
| | | CCGCAAACCAACATCGATCCGAAGGACCTGGCCAACGCTATCCT |
| | | CGGCCACACCGAGGCGACGTTGCCGGGCGCGGACACCGTCAGCG |
| | | GTGGCGACGGCAACGACATCCTGTTCGGCGACCTGGTGAGTTTC |
| | | AGCGGGATCAATGGCGAGGGTTACAACGCACTGCAGGCCTTTGT |
| | | CGCACAGAAGACCGGCGTGGCTGTCTCGGCAGTGACTGCCTCTA |
| | | ACGTTCACCAGTACGTCACCGAGCACTATGTGGACTTCGACGTC |
| | | TCCGGCGCCAAAGATGCCGGCGACACACTGTTGGGCGGCGCTGG |
| | | CGATGACATCTTGTTCGGCCAAGGCGGCAACGACACGCTCGATG |
| | | GCGGCAAAGGCAATGACATCCTGCTGGGTGGCACGGGTAACGAC |
| | | ACGTTGATTGGCGGCCAGGGCAACGACATCCTGATCGGTGGCTC |
| | | GGGTGCCGACACCTTTGTGTGGAAGTCTGGCGACATCGGCAACG |
| | | ATGTGATCAAGGACTTCAAGGCGTCCGAAGGCGACCGCATTGAC |
| | | CTGCGTGATTTGTTGAAAGGTGAAACCGACAGCACCATCGACAA |
| | | CTACCTCAAGATCACCACGGTAGACGGCGTGTCGACCCTGCAAG |
| | | TGAGCAGTGAAGGCAAGCTCAACGCCGCCGGTGGCTTGGCCAAT |
| | | GCCGATGTGACGATCAAGCTGGAAGGCAACGACTGGTCCCACAC |
| | | CAGCATCAACTCGCTGATCAGTGGTGCCGACCCGACCATCAAGA |
| | | TCGACCACACTTAA |
| 55 | Autolytic factor Hemolysin transporter protein ShlB precursor amino acid (PROKKA_00510; RXF07570) *P. fluorescens* | MSLFLPRTWLLLGVCLLTGFALNSASAAPTPGDQDLIRDRQNRL LEEQQRRLEELKDLPGNEAKPVAPAAPVNTRCFPIKDIELKGAD SLPAADRERLLKPYIGQCLGVSQLNELLKAITDYYIDKGLVTSR AYLPQQDLSKGHLQVLVVEGKLEGLKGADNSKLSDRELAMAFPG KNGDLLNLREIEQAIDQLNRLPSNQAQMELTPGDAVGGSSVLVK NNPQKPWRASLSRNNDGQKSTGEQQWGTGFEWDSPLGLADQLIL RGGHDAISDHQKTSKNVLLYYNVPWGWWNFSYSYNQSDYRSVAQ ADTYNFKQSGDSQNHQLRAERVIHRDAVSKTSVNVGLSHLRTNN |

TABLE 14-continued

Table of Sequences

| SEQ ID NO | Name | Sequence* |
|---|---|---|
| | | YIEDSRLDVSSNRLSELQLGINHGRRIGSAFVNIDLGVQNGIGA<br>FDAQRNDQQRDQRGNLTPTPDYRKYTATVSYLQPFTLWGESFSF<br>TSLATGQRSEDVLFSPQRMSLGGSSSIRGFKDQQLTGDSGGYWR<br>NDLRWARPVTWDWMRPVFAEYGASVGYDQGVIRNDRYNGEVHGR<br>VSSNSLELFARGKYVSTSVTFAHSLERPAVLTEREAPIYFRMGF<br>FL |
| 56 | Autolytic factor<br>Hemolysin<br>transporter protein<br>ShlB precursor<br>example nucleic acid<br>encoding SEQ ID<br>NO: 55 | ATGTCTTTATTCCTGCCACGGACTTGGCTGCTACTTGGCGTCTG<br>CCTGCTGACTGGCTTCGCGCTGAACAGCGCGTCGGCTGCACCTA<br>CGCCCGGCGATCAGGACTTGATCCGCGACCGGCAAAATCGCCTG<br>CTGGAAGAACAACAGCGGCGTCTTGAAGAGCTCAAGGATTTGCC<br>CGGCAACGAGGCCAAGCCCGTCGCTCCCGCCGCTCCAGTGAACA<br>CCCGTTGCTTCCCCATCAAAGACATCGAGCTCAAAGGCGCCGAC<br>AGCCTGCCTGCCGCTGACCGCGAGCGCTTGCTCAAGCCCTATAT<br>CGGCCAGTGCCTGGGTGTGTCCCAGCTCAATGAACTGCTCAAGG<br>CCATCACCGATTACTACATCGACAAAGGCCTGGTCACCAGCCGA<br>GCTTACTTGCCGCAACAGGACCTGTCCAAGGGGCACCTGCAAGT<br>GTTGGTGGTGGAAGGCAAACTCGAAGGTTTGAAAGGCGCCGACA<br>ACAGCAAGCTCTCGGACCGCGAATTGGCCATGGCCTTTCCCGGG<br>AAAAACGGCGACTTGCTGAACCTGCGAGAAATCGAGCAAGCCAT<br>CGACCAACTCAACCGCTTGCCATCCAACCAGGCGCAAATGGAGC<br>TGACGCCAGGTGATGCCGTTGGCGGCAGTTCGGTGCTGGTGAAA<br>AACAACCCACAGAAGCCTTGGCGCGCCAGCTTGTCGCGCAATAA<br>CGACGGCCAGAAAAGCACCGGCGAACAGCAATGGGGTACCGGGT<br>TTGAATGGGACAGCCCATTGGGCCTGGCCGATCAACTGATTCTG<br>CGCGGCGGCCACGACGCCATCAGTGACCACCAGAAAACCTCGAA<br>AAACGTGTTGCTTTACTACAACGTGCCCTGGGGCTGGTGGAACT<br>TCAGCTACAGCTACAACCAGAGCGATTACCGCTCGGTTGCTCAG<br>GCCGACACCTACAACTTCAAGCAAAGCGGCGACAGCCAGAACCA<br>CCAACTGCGCGCCGAACGTGTGATCCACCGCGACGCTGTAAGTA<br>AGACCTCGGTTAACGTCGGCCTATCCCACCTGCGCACCAACAAC<br>TACATCGAAGACAGCCGTCTGGACGTCAGCAGCAATCGCTTGAG<br>CGAACTGCAACTGGGCATCAACCACGGGCGACGGATCGGCAGTG<br>CCTTCGTCAACATCGACCTCGGTGTGCAGAACGGCATAGGTGCC<br>TTCGATGCCCAGCGCAACGATCAGCAGCGCGACCAGCGTGGCAA<br>CCTCACCCCCCACCCCGGACTACCGCAAATACACCGCGACCGTCA<br>GCTATTTGCAGCCGTTCACGTTGTGGGGCGAGTCCTTCAGCTTT<br>ACCAGCCTGGCCACCGGGCAGCGCAGTGAAGACGTGCTGTTCAG<br>CCCTCAGCGCATGAGCCTGGGTGGTTCGTCGTCGATACGCGGTT<br>TCAAGGACCAGCAACTGACCGGCGACAGCGGCGGCTACTGGCGC<br>AACGACCTGCGCTGGGCGCGCCCGGTGACCTGGGATTGGATGCG<br>TCCGGTTTTTGCCGAATACGGTGCCAGTGTCGGTTACGACCAGG<br>GTGTGATTCGCAATGACCGCTACAACGGGGAAGTGCACGGTCGG<br>GTGTCGAGCAACTCGCTGGAGCTATTTGCCCGCGGCAAATACGT<br>CAGCACCAGCGTGACCTTTGCCCATTCCCTGGAACGACCGGCAG<br>TGCTGACCGAGCGCGAAGCGCCGATCTACTTCCGCATGGGTTTC<br>TTCCTGTAA |
| 57 | DegP2 example<br>nucleic acid<br>encoding SEQ ID<br>NO: 31 | ATGTCGATACCACGTTTGAAGTCTTACTTATCCATAGTCGCCAC<br>AGTGCTGGTGCTGGGTCAGGCCTTACCTGCGCAAGCGGTCGAGT<br>TGCCTGACTTCACCCAACTGGTGGAGCAGGCCTCGCCTGCCGTG<br>GTGAACATCAGTACCACGCAGAAGCTGCCGGATCGCAAAGTCTC<br>GAACCAGCAGATGCCCGACCTGGAAGGCTTGCCGCCCATGCTGC<br>GCGAGTTCTTCGAACGAGGGATGCCGCAACCACGCTCCCCCCGT<br>GGCGGCGGTGGCCAGCGCGAAGCCCAATCCCTGGGCTCCGGCTT<br>CATCATTTCGCCTGACGGCTATATCCTCACCAACAACCACGTGA<br>TTGCCGATGCCGACGAGATTCTCGTGCGCCTGGCCGACCGCAGT<br>GAACTCAAGGCCAAGCTGATTGGCACCGATCCACGTTCCGACGT<br>GGCCTTGCTTAAAATCGAGGGCAAGGACTTGCCGGTGCTTAAGC<br>TGGGCAAGTCCCAGGACCTGAAGGCCGGTCAGTGGGTGGTCGCG<br>ATCGGTTCGCCGTTCGGCTTTGACCACACCGTTACCCAAGGCAT<br>CGTCAGCGCCATCGGTCGCAGCCTGCCGAACGAAAACTACGTAC<br>CGTTCATCCAGACCGACGTGCCGATCAACCCGGGTAACTCCGGT<br>GGCCCGCTGTTCAACCTGGCCGGCGAAGTGGTGGGGATCAACTC<br>GCAGATCTACACCCGCTCCGGCGGCTTCATGGGCGTGTCTTTCG<br>CGATCCCAATCGATGTGGCCATGGACGTCTCCAATCAGCTCAAA<br>AGCGGCGGCAAGGTCAGCCGCGGCTGGTTGGGCGTGGTAATCCA<br>GGAAGTGAACAAGGACCTGGCTGAGTCCTTCGGTCTCGACAAGC<br>CGGCCGGTGCCCTGGTTGCGCAGATTCAGGACAATGGCCCTGCG<br>GCCAAAGGCGGCCTGAAAGTCGGTGACGTCATCCTGAGCATGAA<br>CGGCCAGCCGATCATCATGTCGGCAGACTTGCCTCATTTGGTCG<br>GCGCGCTCAAGGCCGGCGGCAAAGCCAAGCTGGAAGTGATTCGT<br>GATGGCAAGCGCCAGAACGTCGAACTGACCGTAGGTGCCATCCC<br>GGAAGAAGGCGCGACCCTGGATGCCCTGGGCAACGCCAAGCCCG |

TABLE 14-continued

Table of Sequences

| SEQ ID NO | Name | Sequence* |
|---|---|---|
| | | GTGCCGAGCGCAGCAGTAACCGCCTGGGTATCGCCGTGGTTGAA CTGACCGCCGAGCAGAAGAAAACCTTCGACCTGCAAAGCGGTGT GGTGATCAAGGAAGTTCAGGACGGCCCAGCCGCCTTGATCGGCC TGCAACCGGGTGACGTGATCACTCACTTGAACAACCAGGCAATC GATACCACCAAGGAATTCGCCGACATCGCCAAGGCGTTGCCGAA GAATCGCTCGGTGTCGATGCGCGTCCTGCGTCAAGGCCGTGCCA GCTTCATTACCTTCAAGCTGGCTGAGTAA |
| 58 | ShyA<br>*Vibrio cholera* | MISKSIILRFSELSMRKKVTLVGLPLLAVAAISSSLNSPTRQQR IELSLPESPLVQFSSAEHTVEVVKVGHPDYEYEIKPGDNLSTIF NQLGFAYTELMKVMETDLNYLALDTLRPGNVLRFWKGSDNTLAK MELEFSLVDRAVYTRLNDGSYEFEERKIPGTWKVEPLIGEVDGS FSLSANRAGLGAADVDQIVTLLKDKINFGRDLRRGDRFEVVLSR QLVGEKLTGNSEIQAIKIFN RGKEITAYLHQDGQYYDKNGDSLQRAFQRYPVDSKWRISSNFDP RRLHPVTKRVAPHNGTDFAMPIGTPVYTSGDGVVVMTRNHPYAG NYVVIQHGNTYMTRYLHLSKILVKKGQKVSRGQRIGLSGNTGRV TGPHLHYELIVRGRPVNAMKANIPMASSVPKKEMAQFIAKRKEL DQMLARQESMLAAQ |
| 59 | Shine Dalgarno ribosome binding sequence | AGGAGG |
| 60 | DsbC amino acid (RXF03307; PROKKA_03627)<br>*P. fluorescens* | MRLTQIIAAAAIALVSTFALADDAAEQTIRKSLANLALDTPIES ISASPMAGLYEVKLKGSRVLYASADGQYIVQGYLFQLKDGKPVN LTEKAERLGVSKLINGIPVAETVVYPAIGETKTHITVFTDTTCP YCHKLHAEIPALNKLGVEVRYVAFPRQGLGSPGDEQLQAVWCSA DKKAAMDKMVDGKEIKSAKCANPVSKQFALGQSIGVNGTPAIVL ADGQVIPGYQPAPQVAKLALGAK |
| 61 | RXF04495.2 KO homology arm | GCTTGACGCTGCTGGGCACCGGTGATGCGCGGCAGGTTCCGGTG CATGGCTGCGAGTGTGCTGCGTGCGGGTTGGCGCGCAGTGATCA AAGCCGCCCCAGCCGCAGGTGCCGCGTAATCACAATGACCTGAC GCTGGCGCTGCAGAGCATCGAAGACACCGGGGCGCAGTTGGGGG GGGCTGACCCATGTGGGGCATACGTTGGATACGTGGTTGCTGGC GCATCGTCATGAGTTGCCCCGACATGTCTCGGTAGGTTGGGACA ATCGAGTCGTGTAAGGCGTGGCCTTGTTAGCAATCAGACAAGAA GCTTGATGTTCAGTTTGTTTTTTCCAGTGTGTTTGATTGTTTTT CTGGATGTTTGAAGCGTGTCGCTTGATTGAGTCAAGTTTGTTGT TTGCACTTTTTTTTCTTCGGTGGCATCAAGGTTTGAGAGTGCTT GGGGGATGCGAGTATTCCACCTCGAATAAAACATGTGTGGTTTT ATTACTGCCATGTTTAATGGTGGGTTGTTGAAATGAAATGTGAG CCCAGTCACTATTCGCTAACCCCCCCCGACAAGCCTGCCCAGGC AGGCGTCTGTGTGCCAGGCAACGACCTCCCGTGGGGTTCTCAGT CCAGGGAACCCCACGATTGCACTAGAACCTTTCTCTTACTTCTG ACCGTATACGCGTGCGGCGCTGCGTGCCTGCTTATCAAGTGAGC ATGGCTACTTTCAAGCCACGTTCATGTCGTGTTTTTTTCACCAA ACTATCAGGGGTTGGTGATGCCTTCCGGTTTTTTCAGTTATTCA AAACTCCCGTTGACTCACTCACTGGGTTTATTGCCTGTGCGTTA TTCATGTTCCCGTTTCAGAGGTGTCGGACTGATCGCCTGTTGCA GTGCATTGAATGACTCATGTGCGGCAGACGGAAGTCGCTGTATG TGGAATGCTGATTTTTTCCTTCATGTTCTATTCTATTGTTCGCC ATTCAAGTTGGTAGTCGCCTGGGGGACGTGAAAAATATGAGGGT GGATGCATATTCAATTGCGTCTCAGG |
| 62 | DegP (HtrA) amino acid (UniProtKB - P0C0V0)<br>*E. coli* K12<br>(leader underlined at 1-26; DegP protein is 27-474; catalytic triad amino acids with/without leader at H131/105, D134/108, S236/210, in bold) | MKKTTLALSALALSLGLALSPLSATAAETSSATTAQQMPSLAPM LEKVMPSVVSINVEGSTTVNTPRMPRNFQQFFGDDSPFCQEGSP FQSSPFCQGGQGGNGGGQQQKFMALGSGVIIDADKGYVVTNNHV VDNATVIKVQLSDGRKFDAKMVGKDPRSDIALIQIQNPKNLTAI KMADSDALRVGDYTVAIGNPFGLGETVTSGIVSALGRSGLNAEN YENFIQTDAAINRGNSGGALVNLNGELIGINTAILAPDGGNIGI GFAIPSNMVKNLTSQMVEYGQVKRGELGIMGTELNSELAKAMKV DAQRGAFVSQVLPNSSAAKAGIKAGDVITSLNGKPISSFAALRA QVGTMPVGSKLTLGLLRDGKQVNVNLELQQSSQNQVDSSSIFNG IEGAEMSNKGKDQGVVVNNVKTGTPAAQIGLKKGDVIIGANQQA VKNIAELRKVLDSKPSVLALNIQRGDSTIYLLMQ |

TABLE 14-continued

Table of Sequences

| SEQ ID NO | Name | Sequence* |
|---|---|---|
| 63 | MepM amino acid (alternative name YebA) P0AFS9 *E. coli* | MQQIARSVALAFNNLPRPHRVMLGSLTVLTLAVAVWRPYVYHRD ATPIVKTIELEQNEIRSLLPEASEPIDQAAQEDEAIPQDELDDK IAGEAGVHEYVVSTGDTLSSILNQYGIDMGDITQLAAADKELRN LKIGQQLSWTLTADGELQRLTWEVSRRETRTYDRTAANGFKMTS EMQQGEWVNNLLKGTVGGSFVASARNAGLTSAEVSAVIKAMQWQ MDFRKLKKGDEFAVLMSREMLDGKREQSQLLGVRLRSEGKDYYA IRAEDGKFYDRNGTGLAKGFLRFPTAKQFRISSNFNPRRTNPVT GRVAPHRGVDFAMPQGTPVLSVGDGEVVAKRSGAAGYYVAIRH GRSYTTRYMHLRKILVKPGQKVKRGDRIALSGNTGRSTGPHLHY EVWINQQAVNPLTAKLPRTEGLTGSDRREFLAQAKEIVPQLRFD |
| 64 | MepM2 WP_153670715.1 *E. coli* | MPRLLAPLLALSLLLAGGAQASYITRTLNKPVPGGVAVVDLGP AASAPSARFDGKPVLVVKEQDNWLAIVGIPLTQKPGTAVLSQGG RTLPFTVGSKKYPEQRITLKNTRQVNPNPADLKRIDRELAEQIK AYRSFSPTLPSNLILDKPVSGPLSSKFGVRRFFNGEERNPHAGL DFAVPAGTPIKTPANGKVILVGDYFFNGRTVFVDHGQGFISMFC HMSKIDVQVGQQLRRGEVVGRVGSTGRATGPHMHWNVSLNDARV DPA |
| 65 | MepM1 A0A0D1M539 *Pseudomonas Putida* | MTNEPTKAPPLYPKSHLLAASGIAALLSLALLVFPSSEVEAKKT TLNLELESPAEQLKQQETTQADVREETTASPFAQIDTAPAPTEE TAKTEPTPTAEPAKDPSHREVTVARGDTLSTLFAKVGLPANVVH EVLASNKQAKQFSQLKHGQVLEIELDKDGQLASLHSKVSDLETI RLTKGDKGYAFNREITKPVVRSAYVHGVIKSSLSASAQRAGLNH SLTMDMARIFGYDIDFAQDIRQGDEFDVIYEQKVVNGKVVGNGN ILSARFTNRGKSFTAVRYTNKQGNTSYYTADGNSMRKAFIRTPV DFARISSRFSAGRKHPILNKIRAHKGVDYAAPRGTPIKAAGDGK VLLAGRRGGYGNTVIIKHGNTYQTLYGHMQGFAKGIKTGGTVKQ GQVIGYIGTTGLSTGPHLHYEFQVNGVHVDPLGQKLPMADPIAK AERQRFLQQSQPLMARMEQEKATMLASAKR |
| 66 | MepM1 PA0667 *Pseudomonas aeruginosa* | MFPSSEVEAKRTTLNLELESNTDRLLQEKDDLLPQSVTNSSDEG TPFAQVEGASDDNTAEQDSDKPGASVADADTKPVDPEWKTITVA SGDTLSTVFTKAGLSTSAMHDMLTSSKDAKRFTHLKVGQEVKLK LDPKGELQALRVKQSELETIGLDKTDKGYSFKREKAQIDLHTAY AHGRITSSLFVAGRNAGLPYNLVTSLSNIFGYDIDFALDLREGD EFDVIYEQHKVNGKQVATGNILAARFVNRGKTYTAVRYTNKQGN TSYYRADGSSMRKAFIRTPVDFARISSRFSLGRRHPILNKIRAH KGVDYAAPIGTPIKATGDGKILEAGRKGGYGNAVVIQHGQRYRT IYGHMSRFAKGIRAGTSVKQGQIIGYVGMTGLATGPHLHYEFQI NGRHVDPLSAKLPMADPLGGADRKRFMAQTQPMIARMDQEKKTL LALNKQR |
| 67 | MepM2 WP_098965471.1 *P. putida* | MPRFFAPLLLLCLTSFNAHADSYITRLLNKPVPGGVAVVDLGSA TQASKATYQGKPVLVVKEQNNWLAIVGVPLTVKPGSQQISSGGR NLPFTVGNKKYPEQHITLKNTQQVNPNPANLKRIEGELAEQIKA YRSFSPNTPSNLLLDKPVNGPLSSKFGVRRFFNGEERNPHAGLD FAVPAGTPIKTPAAGKVILTGNYFFNGNTVFVDHGQGFISMFCH MSKIDVKVGDQLARGAVVGKVGSTGRATGPHMHWNISLNDARVD PAIFIGAFQP |
| 68 | MepM2 TUEID40_04881 *P. aeruginosa* | MPRTLAFVSTLLLAAFCALPTQADSFIMRLLNKPVPGGVAVVDL GEEGPPPRAFYQGKPVLVVREEGRRW IAVVGIPLSTKPGPQKLEVRAATGNHEERFSVGSKHYREQRITL KNKRQVNPLPEDLKRIERELAEQTAA YRRFSPGLPSNLMLDKPVDGPLSSPFGLRRFFNGEERNPHSGLD FAVPAGTPIKAPAAGKVILIGDYFFN GKTVFVDHGQGFISMFCHLSKIDVKLGQQVPRGGVLGKVGATGR ATGPHMHWNVSLNDARVDPAIFIGAF QP |
| 69 | DegP amino acid RXF01250 *P. fluorescens* | MLKALRFFGWPLLAGVLIAMLIIQRYPQWVGLPTLDVNLQQAPQ TNTVVQGPVTYADAVVIAAPAVVNLYTTKVINKPAHPLFEDPQF RRYFGDNGPKQRRMESSLGSGVIMSPEGYILTNNHVTTGADQIV VALRDGRETLARVVGSDPETDLAVLKIDLKNLPAITLGRSDGLR VGDVALAIGNPFGVGQTVTMGIISATGRNQLGLNSYEDFIQTDA AINPGNSGGALVDANGNLTGINTAIFSKSGGSQGIGFAIPVKLA MEVMKSIIEHGQVIRGWLGIEVQPLTKELAESFGLTGRPGIVVA GIFRDGPAQKAGLQLGDVILSIDGAPAGDGRKSMNQVARIKPTD KVAILVMRNGKEIKLSAEIGLRPPPATAPVKEEQ |
| 70 | HtpX *E. coli* | MMRIALFLLTNLAVMVVFGLVLSLTGIQSSSVQGLMIMALLFGF GGSFVSLLMSKWMALRSVGGEVIEQPRNERERWLVNTVATQARQ AGIAMPQVAIYHAPDINAFATGARRDASLVAVSTGLLQNMSPDE |

*

TABLE 14-continued

Table of Sequences

| SEQ ID NO | Name | Sequence* |
|---|---|---|
| | | AEAVIAHEISHIANGDMVTMTLIQGVVNTFVIFISRILAQLAAG FMGGNRDEGEESNGNPLIYFAVATVLELVFGILASIITMWFSRH REFHADAGSAKLVGREKMIA ALQRLKTSYEPQEATSMMALCINGKSKSLSELFMTHPPLDKRIE ALRTGEYLK |
| 71 | Tsp (Pre) E. coli GenBank M75634.1 | MNMFFRLTALAGLLAIAGQTFAVEDITRADQIPVLKEETQHATV SERVTSRFTRSHYRQFDLDQAFSAKIFDRYLNLLDYSHNVLLAS DVEQFAKKKTELGDELRSGKLDVFYDLYNLAQKRRFERYQYALS VLEKPMDFTGNDTYNLDRSKAPWPKNEAELNALWDSKVKFDELS LKLTGKTDKEIRETLTRRYKFAIRRLAQTNSEDVFSLAMTAFAR EIDPHTNYLSPRNTEQFNTEMSLSLEGIGAVLQMDDDYTVINSM VAGGPAAKSKAISVGDKIVGVGQTGKPMVDVIGWRLDDVVALIK GPKGSKVRLEILPAGKGTKTRTVTLTRERIRLEDRAVKMSVKTV GKEKVGVLDIPGFYVGLTDDVKVQLQKLEKQNVSSVIIDLRSNG GGALTEAVSLSGLFIPAGPIVQVRDNNGKVREDSDTDGQVFYKG PLVVLVDRFSASASEIFAAAMQDYGRALVVGEPTFGKGTVQQYR SLNRIYDQMLRPEWPALGSVQYTIQKFYRVNGGSTQRKGVTPDI IMPTGNEETETGEKFEDNALPWDSIDAATYVKSGDLTAFEPELL KEHNARIAKDPEFQNIMKDIARFNAMKDKRN1VSLNYAVREKEN NEDDATRLARLNERFKREGKPELKKLDDLPKDYQEPDPYLDETV NIALDLAKLEKARPAEQPAPVK |
| 72 | MepS Q88MA5 P. putida | MPMLKRFAPLVPLALVTLLFGCAAQGPVSQPQDHTPITAQSAIN AKASSSSVFGEPEELATEDDLASFSGGKPYQLPVLADSILERGM SLIGTRYRFGGTSEKSGFDCSGFIGYLFREEAGMTLPRSTREMI NVDAPKVARNKLKPGDLLFFSTNGRGRVSHAGIYLGDNQFIHSS SRRSGGVRIDSLGDRYWSKTFIEAKRALAMAPTNIARN |
| 73 | MepS MXH34301.1 P. aeruginosa | MVKSQPILRYILRVAPAIAVAVLLSACSSTSTARNMHSETHAVG SGDLSSLQASQDEFETMVRNLDVKSRLMDQYASWKGVRYRLGGS TRKGIDCSAFVQRTFREQFGLELPRSTSEQQETGKSISRTQLRT GDLVLFRAGSTGRHVGIYLGNNQFVHASTSSGVTISSMDEPYWK KRYNEARRVLSRS |
| 74 | HslU example nucleic acid encoding SEQ ID NO: 37 | ATGTCCATGACTCCCCGCGAAATCGTCCATGAACTCAATCGCCA TATCATCGGCCAGGACGATGCCAAGCGCGCCGTTGCCATTGCGC TGCGTAACCGCTGGCGCCGGATGCAACTGCCGGAAGAACTGCGC GTTGAAGTAACGCCCAAGAACATCCTGATGATCGGCCCCACCGG CGTGGGTAAAACCGAGATCGCCCGGCGCCTGGCCAAACTGGCCA ATGCACCGTTCATCAAGGTCGAAGCGACCAAGTTCACCGAAGTC GGCTATGTGGGCCGCGATGTCGAGTCGATCATTCGTGACCTGGC TGACGCCGCCCTGAAGATGCTGCGCGAACAGGAAGTAACCAAGG TCAGCCACCGCGCCGAAGACGCCGCTGAAGAGCGCATCCTCGAC GCCCTGTTGCCACCGGCACGCATGGGTTTCAACGAAGACGCCGC ACCGGCTACCGATTCCAACACTCGCCAGCTGTTCCGCAAGCGCC TGCGTGAAGGCCAGCTGGATGACAAGGAAATCGAGATCGAAGTG GCTGAAGTGTCCGGCGTGGATATTTCTGCCCCGCCTGGCATGGA AGAAATGACCAGCCAGCTGCAGAACCTGTTCGCCAACATGGGCA AGGGCAAGAAGAAAAGCCGCAAGCTCAAGGTGAAAGAGGCGCTC AAGCTCGTGCGCGACGAAGAAGCCGGGCGCCTGGTCAATGAGGA AGAACTCAAGGCCAAGGCCCTGGAAGCGGTGAGCGAACATGGCA TCGTGTTTATCGACGAGATCGACAAAGTGGCCAAGCGAGGCAAC TCAGGCGGCGTGGATGTGTCCCGCGAAGGCGTGCAGCGCGATTT GCTGCCGCTGATCGAGGGCTGACGGTCAACACCAAGCTGGGCA TGGTCAAGACTGACCACATCCTGTTTATCGCTTCCGGTGCTTTC CACCTGAGCAAGCCCAGCGACCTGGTGCCCGAGCTGCAAGGCCG CTTGCCGATTCGGGTGGAGCTCAAGGCGCTGACGCCGGGCGACT TCGAGCGCATCCTCAGCGAGCCGCATGCCTCGCTCACCGAGCAG TACCGCGAGTTGCTGAAAACCGAAGGGCTGGGTATCGAATTCCA GGCAGACGGGATCAAGCGCCTGGCGGAGATCGCCTGGCAGGTCA ACGAGAAGACCGAGAACATCGGTGCCCGTCGCCTGCATACCTTG CTTGAGCGCCTGCTGGAGGAAGTGTCCTTCAGTGCCGGCGACAT GGCCGGTGCGCAGAATGGCGAAGCGATCAAGATCGATGCTGATT ACGTCAACAGCCACTTGGGCGAATTGGCGCAGAACGAAGATCTG TCTCGTTATATCCTGTAA |
| 75 | HslV example nucleic acid encoding SEQ ID NO: 38 | ATGACCACCATCGTTTCAGTACGTCGCCACGGCAAAGTTGTCAT GGGCGGCGACGGCCAGGTTTCCCTGGGCAACACCGTGATGAAAG GCAACGCCAAGAAAGTGCGCCGCCTGTACCACGGCCAGGTGCTT GCCGGCTTCGCAGGCGCAACCGCCGACGCCTTTACCCTGTTCGA GCGTTTCGAAGGCCAGCTTGAGAAACACCAGGGCCACCTGGTGC GCGCCGCTGTGGAACTAGCCAAAGAATGGCGCACCGACCGCTCC CTCAGCCGCCTGGAGGCCATGCTCGCCGGTTGCGAACAAAGACGC |

TABLE 14-continued

Table of Sequences

| SEQ ID NO | Name | Sequence* |
|---|---|---|
| | | TTCCCTGATCATCACTGGCAACGGCGACGTGGTTGAACCCGAGC ATGGCCTGATCGCCATGGGTTCCGGCGGCGGCTACGCCCAGGCT GCGGCCAGCGCGCTGTTGAAGAAAACCGACCTGTCGGCCCGTGA AATCGTCGAGACCGCCCTGGGTATCGCTGGCGATATCTGCGTGT TCACCAACCACAACCAGACCATTGAGGAGCAGGACCTCGCCGAG TAA |
| 76 | Putative cytoplasmic disulfide isomerase DsbA amino acid (RXF07017.2) *P. fluorescens* | MSKTLEFFFDLGSPATYLAYTRLPALCAETGAQVVYQPMLLGGV FKATGNASPITVPAKGRYMLDDLARYAKRYNVPLRFNPHFPINT LLLMRAVTGIQIHQPERFLDPIGCLFRALWVEGRHLGDPEVVAN VLTEQGFDPEQVLALSNDAAVKDALKDKTEQAIKRGVFGAPSFF VGNQLFFGQDRLDFVREALS |
| 77 | Disulfide-bond isomerase DsbA homolog amino acid (RXF01002.1) | MRNLILSAALVTASLFGMTAQAADVPLEAGKTYVELANPVPVAV PGKIEVVELFWYGCPHCYAFEPTINPWAEKLPKDVNFRRIPAMF GGPWDAHGQLFLTLEAMGVEHKVHNAVFEAIQKQGKRLTKPDEM ADFVATQGVDKDKFLATFNSFAIQGQIKQAKELAQKYGVQGVPT LIVNGKYRFDLGSTGGPEATLNVADQLIAKERAAK |
| 78 | Disulfide-bond isomerase DsbB amino acid (RXF03204.1) | MIDDMRLGRERRFLVLLGIICLALIGGALYMQVVLGEAPCPLCI LQRYALLLIALFAFIGAAMRTKGALTFFEGLVVLSALGGVAAAG HHVYTQFFPQVSCGIDVLQPIVDDLPLAKVFPLGFQVDGFCSTP YPPILGLSLAQWALVAFVLTAILVPLCIYRNRHPKA |
| 79 | Disulfide-bond isomerase DsbC example nucleic acid (RXF03307; PROKKA_03627) encoding SEQ ID NO: 60 | ATGCGCTTGACCCAGATTATTGCCGCCGCAGCCATTGCGTTGGT TTCCACCTTTGCGCTCGCCGATGATGCGGCCGAGCAGACCATCC GCAAGAGCCTGGCCAACCTGGCGCTCGACACGCCTATCGAAAGC ATTAGCGCCAGCCCCATGGCCGGCCTGTACGAAGTCAAGCTCAA GGGCAGCCGCGTGCTGTACGCCAGTGCCGATGGCCAGTACATCG TCCAGGGCTACCTGTTCCAGCTCAAGGACGGCAAGCCGGTCAAC CTGACCGAGAAGGCCGAGCGCCTGGGCGTGTCCAAGCTGATCAA CGGCATCCCGGTGGCTGAAACCGTGGTTTACCCGGCCATTGGCG AAACCAAGACCCACATCACCGTGTTCACCGACACCACCTGCCCG TACTGCCACAAGCTGCACGCTGAAATCCCGGCACTGAACAAGCT GGGCGTGGAAGTGCGCTACGTCGCGTTCCCGCGCCAGGGCCTGG GTTCGCCGGGTGACGAGCAGTTGCAAGCCGTATGGTGTTCGGCC GACAAAAAGGCGGCCATGGACAAGATGGTCGACGGCAAGGAAAT CAAATCGGCCAAATGCGCCAACCCGGTTTCCAAGCAGTTCGCCC TGGGCCAGTCCATTGGTGTGAACGGTACACCGGCCATCGTTTTG GCCGACGGCCAGGTGATTCCGGGCTACCAGCCGGCGCCGCAAGT TGCCAAACTGGCACTGGGTGCCAAG |
| 80 | Disulfide-bond isomerase DsbD amino acid (RXF04886.2) | MRHLFTFLLVLFAGFAQAAPGSPFETKPDFLPVGKAFAFTSERL ESGETQLFWQIADGYYLYQQRMKFDGLAEKPVLPEGEAHSDEFF GEQQVYRQGLEVKIPAGTTGQVKLGWQGCADAGLCYPPQSITVD LGGNPAVAATAQAQDQSLASGLQQRSLGWSLLVFFGLGLLLAFA PCSLPMLPILAGLVVGSGASPRRGFALAGSYVVCMALVYAALGV MAALLGANLAALLQTPWILGSFAALFVLLALPMFGFFELQLPAF LRDRLDNVSRQQSGGSLVGAGVLGALSGLLVGPCMTAPLAGALL YIAQSGNALHGGLILFAMGIGIGIPLLLLVTVGNRFLPKPGTWM NVLKGIFGFLFLGTAVLMIRPVVGDSLWIGLWGALALVMAYCGW ALARESGLAAKVFGAGSLVLGLWGAVLVVGAAGGSDELWQPLKV YSGSRVADAPSAHDAFTTVSDPAVLQSQLDSAKAQGQWVLLDYY ADWCVSCKIMEKQVFGKPEVMDALKDVRLLRLDVTADNAASREL LGRYKVPGPPSFVWIGPDGEERRAQRITGEVDAAAFLQRWTQTR DAR |
| 81 | Disulfide-bond isomerase DsbG amino acid (RXF04890.2) | MPRLRHLLTLLPLTLAAALAQAEDLPAPIKQIEAKGAKIIGKFD APSGLTGYAAQYQNRGMALYLTADGKNVIAGNLYDAQGNDLSTA PLEKLVYAPMAKEVWAKMENSSWIQDGDKNAPRTIYLFSDPNCP YCNMFWEQARPWVKAGKVQLRHIMVGIIREDSPGKSAALLAAKD PQKALQDHEAAGKGSKLKALEKIPAEVEAKLDANMKLMDELELS ATPAIFYLDDKGGLQQQQGAPSPDKLVKILGPK |
| 82 | PDIA6 amino acid UniProt Q922R8 mouse | MARLVLGLVSCTFFLAVSGLYSSSDDVIELTPSNFNREVIQSDG LWLVEFYAPWCGHCQRLTPEWKKAATALKDVVKVGAVNADKHQS LGGQYGVQGFPTIKIFGANKNKPEDYQGGRTGEAIVDAALSALR QLVKDRLGGRSGGYSSGKQGRGDSSSKKDVVELTDDTFDKNVLD SEDVWMVEFYAPWCGHCKNLEPEWAAAATEVKEQTKGKVKLAAV DATVNQVLASRYGIKGFPTI KIFQKGESPVDYDGGRTRSDIVSRALDLFSDNAPPPELLEIINE DIAKKTCEEHQLCVVAVLPHILDTGAAGRNSYLEVLLKLADKYK KKMWGWLWTEAGAQYELENALGIGGFGYPAMAAINARKMKFALL |

TABLE 14-continued

Table of Sequences

| SEQ ID NO | Name | Sequence* |
|---|---|---|
| | | KGSFSEQGINEFLRELSFGRGSTAPVGGGSFPTITPREPWDGKD GELPVEDDIDLSDVELDDLEKDEL |
| 83 | PDIA6 amino acid Q3TML0 mouse | MRVIGMARLVLGLVSCTFFLAVSGLYSSSDDVIELTPSNFNREV IQSDGLWLVEFYAPWCGHCQRLTPEWKKAATALKDVVKVGAVNA DKHQSLGGQYGVQGFPTIKIFGANKNKPEDYQGGRTGEAIVDAA LSALRQLVKDRLGGRSGGYSSGKQGRGDSSSKKDVVELTDDTFD KNVLDSEDVWMVEFYAPWCGHCKNLEPEWAAAATEVKEQTKGKV KLAAVDATMNQVLASRYGIK GFPTIKIFQKGESPVDYDGGRTRSDIVSRALDLFSDNAPPPELL EIINEDIAKKTCEEHQLCVVAVLPHILDTGAAGRNSYLEVLLKL ADKYKKKMWGWLWTEAGAQYELENALGIGGFGYPAMAAINARKM KFALLKGSFSEQGINEFLRELSFGRGSTAPVGGGSFPTITPREP WDGKDGELPVEDDIDLSDVELDDLEKDEL |
| 84 | PDIA6 amino acid Q63081 rat | MARLVLGLVSCTFFLAVSALYSSSDDVIELTPSNFNREVIQSDS LWLVEFYAPWCGHCQRLTPEWKKAASALKDVVKVGAVNADKHQS LGGQYGVQGFPTIKIFGANKNKPEDYQGGRTGEAIVDAALSALR QLVKDRLGGRSGGYSSGKQGRGDSSSKKDVVELTDDTFDKNVLD SEDVWMVEFYAPWCGHCKNLEPEWAAAATEVKEQTKGKVKLAAV DATVNQVLASRYGIKGFPTI KIFQKGESPVDYDGGRTRSDIVSRALDLFSDNAPPPELLEIINE DIAKKTCEEHQLCVVAVLPHILDTGATGRNSYLEVLLKLADKYK KKMWGWLWTEAGAQYELENALGIGGFGYPAMAAINARKMKFALL KGSFSEQGINEFLRELSFGRGSTAPVGGGSFPNITPREPWDGKD GELPVEDDIDLSDVELDDLEKDEL |
| 85 | PDIA6 amino acid A0A5F5PFG7 horse | MKPAINGVLFVVSPGLMSCTLFLAVNGLYSSSDDVIELTPSNFN REVIQSDSLWLVEFYAPWCGHCQRLTPEWKKVATALKDVVKVGA VDADKHQSLGGQYGVQGFPTIKIFGANKNRPEDYQGGRSGEAIV DAALSALRQLVKDRLGGRSGGYSSGKQGRSESSSKKDVIELTDD SFDKNVLDSEDVWMVEFYAPWCGHCKNLEPEWAAAATEVKEQTK GKVKLAAVDATVNQVLASRY GIRGFPTIKIFQKGESPVDYDGGRTRSDIISRALDLFSDNAPPP ELLEIINEDIAKKTCEEHQLCVVAVLPHILDTGAAGRNSYLEVL LKLADKYKKKMWGWLWTEAGAQSELETALGIGGFGYPAMAAINA RKMKFALLKGSFSEQGINEFLRELSFGRGSTAPVGGGAFPAIST REPWDGKDGELPVEDDIDLSDVELDDLEKDEL |
| 86 | PDIA6 amino acid A0A5K1UH01 Pig | MARLVLGLMSCTLFVAVNGLYSSSDDVIELTPSNFNREVIQSDS LWLVEFYAPWCGHCQRLTPEWKKVATALKDVVKVGAVDADKHQS LGGQYGVQGFPTIKIFGSNKNRPEDYQGGRTGEAIVDAALSALR QLVKDRLGGRGGGYSSGKQGRSEGSGKKDVIELTDDTFDKNVLD SEDVWMVEFYAPWCGHCKNLEPEWAAAATEVKEQTKGKVKLAAV DATVNQVLASRYGIRGFPTI KIFQKGESPVDYDGGRTRSDIVTRALDLFSDNAPPPELLEIISE DVAKKSCEEHQLCVVAVLPHILDTGAAGRNSYLEVLLKLADKYK KKMWGWLWTEAGAQTELEHALGIGGFGYPAMAAINARKMKFALL KGSFSEQGINEFLRELSFGRGSTAPVGGGAFPAISTREPWDGKD GEVSPATREPGDGKDGQASPATREPWDGKDGQASPATREPGDGK DGEASPAEPRGQDASRLWLSFLASLGPEAGCEPGLCIRAAPRAG PAVAPPGPRGLLLSSSSAPLPPATPQAKAPGSCSPGHSPQAERF STWREAQRGHFEVSLDSRTLPSGLERPTSVAPGVCPRDDGRS |
| 87 | PDIA6 amino acid P38660 Golden hamster | MARLGFGLVSCTFFLAASGLYSSSDDVIELTPSNFNREVIQSNS LWLVEFYAPWCGHCQRLTPEWKKAATALKDVVKVGAVDADKHQS LGGQYGVQGFPTIKIFGANKNKPEDYQGGRTGEAIVDAALSALR QLVKDRLSGRSGGYSSGKQGRGDSSSKKDVIELTDDTFDKNVLD SDDVWMVEFYAPWCGHCKNLEPEWATAATEVKEQTKGKVKLAAV DATVNQVLANRYGIRGFPTI KIFQKGEAPVDYDGGRTRSDIVSRALDLFSDNAPPPELLEIINE DVAKKMCEEHQLCVVAVLPHILDTGAARNSYLEILLKLADKYKK KMWGWLWTEAGAQSELENALGIGGFGYPAMARINARKMKFALLK GSFSEQGINEFLRELSFGRASTAPVGGGSFPAITAREPWDGRDG ELPVEDDIDLSDVELDDLEKDEL |
| 88 | PDIA6 amino acid Q5R6T1 *Pongo abelii* (orangutan) | MALLVLGLVSCAFFLEVNGLYSSSDDVIELTPSNFNREVIQSDS LWLVEFYAPWCGHCQRLTPEWKKAATALKDVVKVGAVDADKHHS LGGQYGVQGFPTIKIFGSNKNRPEDYQGGRTGEAIVDAALSALR QLVKDRLGGQSGGYSSGKQGRSDSSSKKDVIELTDDSFDKNVLD SEDVWMVEFYAPWCGHCKNLEPEWAAAASEVKEQTKGKVKLAAV DATVNQVLASRYGIRGFPTI KIFQKGESPVDYDGGRTRSDIVSRALDLFSDNAPPPELLEIISE DIAKRTCEEHQLCVVSVLPHILDTGAAGRNSYLEVLLKLADKYK |

TABLE 14-continued

Table of Sequences

| SEQ ID NO | Name | Sequence* |
|---|---|---|
| | | KKMWGWLWTEAGAQSELETALG1GGFGYPAMAAINARKMKFALL KGSFSEQGINEFLRELSFGRGSTAPVGGGAFPTIVEREPWDGRD GELPVEDDIDLSDVELDDLGKDEL |
| 89 | PDIA6 amino acid U3JW38 Collared flycatcher | MRESHKCSTGQLMSLLFLVGTVSCTLFLAVNGLYSASDDVIELT PTNFNKEVIQSESLWLVEFYAPWCGHCQRLTPEWKKAATALKGV VKVGAVDADKHQSLGGQYGVRGFPTIKIFGANKNKAEDYQGGRT SDAIVDAALSALRSLVKERLSGRSGGYSSGKQSRGSGGGDKKDV IELTDDSFDKNVINSDDVWMVEFYAPWCGHCKNLEPEWAAAATE VKEQTKGKVKLAAVDATVNQVLASRYGIRGFPTIKIFQKGEDPV DYDGGRTRSDIVSRALDLFSDNAPPPELLEIISEDVLKSTCDAH QLCIISVLPHILDTGASGRNSYLDVMLKMAEKYKKKMWGWLWTE AGAQPDLESSLGIGGFGYPAMAAVNARKMKFALLKGSFSEQGIN EFLRELSVGRGSTAPVGGGAFPKIHSVEPWDGKDGELPVEDDID LSDVDLDDFGKDEL |
| 90 | Protein disulfide-isomerase amino acid P55059.1 Human | MHKAQKFALGLLAAAAVATASDVVQLKKDTFDDFIKTNDLVLAE FFAPWCGHCKALAPEYEEAATTLKEKNIKLAKVDCTEETDLCQQ HGVEGYPTLKVFRGLDNVSPYKGQRKAAAITSYMIKQSLPAVSE VTKDNLEEFKKADKAVLVAYVDASDKASSEVFTQVAEKLRDNYP FGSSSDAALAEAEGVKAPAIVLYKDFDEGKAVFSEKFEVEAIEK FAKTGATPLIGEIGPETYSDYMSAGIPLAYIFAETAEERKELSD KLKPIAEAQRGVINFGTIDAKAFGAHAGNLNLKTDKFPAFAIQE VAKNQKFPFDQEKEITFEAIKAFVDDFVAGKIEPSIKSEPIPEK QEGPVTVVVAKNYNEIVLDDTKDVLIEFYAPWCGHCKALAPKYE ELGALYAKSEFKDRVVIAKVDATANDVPDEIQGFPTIKLYPAGA KGQPVTYSGSRTVEDLIKFIAENGKYKAAISEDAEETSSATETT TETATKSEEAAKETATEHDEL |
| 91 | Protein disulfide-isomerase amino acid O13811 *Schizosaccharomyces pombe* (strain 972/ ATCC24843) | MRLPLLSFVIFALFALVFASGVVELQSLNELENTIRASKKGALI EFYATWCGHCKSLAPVYEELGALFEDHNDVLIGKIDADTHSDVA DKYHITGFPTLIWFPPDGSEPVQYSNARDVDSLTQFVSEKTGIK KRKIVLPSNVVELDSLNFDKVVMDDKKDVLVEFYADWCGYCKRL APTYETLGKVFKNEPNVEIVKINADVFADIGRLHEVASPPTIKF FPKDDKDKPELYEGDRSLESLIEYINKKSGTQRSPDGTLLSTAG RIPTFDEFAAEFLDMSNAAKEVVLEKVKQLALEDSSRWTKYYKK VFEKILNDENWVHKEAKRLSKLLRQKSIALASADDFKTRLNILN SFLPGNH |
| 92 | Protein disulfide-isomerase amino acid A5LHW0 *Haemaphysalis longi cornis* | MATALLAVLAALSPMALAMYGPHTEVVDLSPANFKNRVVDSDEV WIVEFYAPWCGHCQSFAPEYTKAAAALKGIVKVGAVDADKDKSL GGQYGVRGFPTVKIFGANKHNPTDYSGPRTADGVASAALQEARK VVDQRLGRKTSGGSSGGKSDVVELDESNFEELVLKSDDLWLVEF FAPWCGHCKNLAPHWAKAATELKGKVKLGAVDATVHQGLASQFD VKGYPTIKFFPGGKKDRHSAXEYNGGRTADDIVQWGLDKAAESA PAPELHQVTSPSVLKDACEESQLCVVSVLPHIYDCQSECRQGYL DVLKRLGEKYKRNRWGWLWSEALAQPKLEEALEIGGFGYPALAV LNSRKMKYSLLRGSFSYDGINEFLRELAVGRGSSVPVKGAKLPE VQTVEPWDGKDAKLEEPEDIDLSDVELEPEEPGKKHVEL |
| 93 | Protein disulfide-isomerase amino acid Q5UAH0 *Plasmodium chabaudi chabaudi* | MNSKYFSFLLFLIPFLFQNCVRSHEDLFNEHVTSIHDGELTNFI TKNDIVLVMFYAPWCGHCKRLIPEYNDAAIMLAEKKSEIKLASV DATIERGLSQEYGITGYPTMILFNKKNRINYGGGRTAQTIVDWI LQMTGPVSTEITGNIEDVLKEKNINVAFYIEYTSEDHELFKKFN EVGDKNREIAKYFMKKNDKHNKIYCYRKDEKTVEYDEKTPLSDF ITIESFPLFGEINTENYRFY AESPKELVWVCATIEQYNEIKEEVRLAAAELRNKTHFVLLNIPE YADHAKASLGINEFPGLAYQSSEGRYVLTNPKQSLKNHKDIITF FKDVEAGKIEKSLKSEPIPEEDKDAPVKVVVGNSFIDVVLKSGK DVLIEIYAPWCGHCKKLEPVYEELGRKLKKYDHIIVAKMDGTLN ETALKEFEWSGFPTIFFVKAGSKIPLPYEGERSLKGFVDFLNKH STKTPITIDGVSQSDDGASE EL |
| 94 | Protein disulfide-isomerase amino acid XP_024705795.1 *Aspergillus steynii* IBT 23096 | MRSFTPWVLGLLGASAVVSAGDAQADVPSDVKSLTQDTFNDFIK EHDLVLAEFFAPWCGHCKALAPKYEEAASQLKDKNIPLVKIDCT EEEELCRDQGVEGYPTLKIFRGVDSSKPYQGARQTESLVSYMIK QSLPAVSSVNEENLEDTKTMDKIVVIGYFSSDDQAANDAFNALA EAQRDNYLFAATDDAAIAKAEGVEQPSLVLYKDFDEKKAIYTGE IEQDAVLTWVKTASTPLVGEIGPETYSSYITAGIPLAYIFAETS EEREKFTEDFKPIAEKHKGLINIATIDAKMFGAHAGNLNLDPQT FPAFAIQDPEKKAKYPYDQSKEITAKDVGKFIQDVLGGKVEPSI KSEPIPESQEGPVTVVVAHSYKELVVDNEKDVLLEFYAPWCGHC KALAPKYEELASLYADVPDLASKVTIAKIDATANDVPDSITGFP |

TABLE 14-continued

Table of Sequences

| SEQ ID NO | Name | Sequence* |
|---|---|---|
| | | TIKLYPAGGKDAPVEYAGSRTVEDLVNFVKENGQHKVDALANTQ EGGDATESPSASSETEAPAATDDKADHDEL |
| 95 | Protein disulfide-isomerase amino acid PGH31646.1 *Emmonsia crescens* | MRQFRDFAFGLAALGLTALASATEAEAESDVHVLKKDTFNDFMN SHDLVLAEFYAPWCGHCKALAPEYEVAATELKEKNIHLAKIDCT EEADLCQEHGVEGYPTLKIFRGLENVKPYTGPRKSGPIASFMVK QSLPPVTTVTADNIEDVKTLDKIVVIGYFAEDDKASNETFTAVA EALRDDYLFAGTNDAKLAAAEDVKQPAIVLYKEFDERKAVFKNK FVQDDISKFVKTASIPLVGEVGPDTYAGYMASGLPLAYVFAETP EEREEFAAMLKPIAQKQKGSINIATIDAKAFGAHAGNLNLDPEK FPAFAIQDTTNNKKYPFDQTKKITHDDIAKFVQDVLDGKVEPSI KSEPIPESQDAAVTVVVAHSFQEIVIDNDKDVLVEYYAPWCGHC KALAPKYEQLGQLYADVPEFASKVTIAKIDATANDVPEDIQGFP TIKLYAAGSKGSPVDYDGSRTIEDLAKFVRDNGKHGVDAYVAEK VVEDGGDVTNSPAAASPSSTAADKESETSSSDDAEETAEAPRHE EL |
| 97 | Protein disulfide-isomerase Pdi1 amino acid KEY81650.1 *Aspergillus fumigatus* var. RP-2014 | MRSFAPLVLSLLGASAVASADATADTTSDVVSLTKDSFKDFMKE HDLVLAEFYAPWCGHCKALAPKYEEAATELKGKNIPLVKVDCTE EEDLCKENGVEGYPTLKIFRGPDSSKPYQGARQADSIVSYMIKQ SLPAVSAVTEENLEEIKTMDKIVVIGYFASDDKAANDVFTSFAE SQRDNYLFAATSDSAIAKAEGVKQPSIVLYKDFDEKKAVYDGAI EQEAILSWVKTASTPLVGEIGPETYSSYITAGIPLAYIFAETKE ERDQYAEDFKPVAEKHKGAINIATIDAKMFGAHAGNLNLDPQTF PAFAIQDPEKNAKYPYDQSREFNAKEIGKFIQDVLDGKVEPSIK SEPIPETQEGPVTVVVAHSYQDIVINNDKDVLLEFYAPWCGHCK ALAPKYEELAALYAGDFKDKVTIAKIDATANDVPDSITGFPTIK LYPAGAKDSPVEYSGSRTVEDLANFIKENGKYKVDALVAASEKV EEGPDVTASPSATSTEAEAPAATGDEKGDHDEL |
| 98 | Protein disulfide-isomerase FrnE amino acid (RXF08657.2) *P. fluorescens* | MSTPLKIDFVSDVSCPWCIIGLRGLTEALDQLGSEVQAEIHFQP FELNPNMPAEGQNIVEHITEKYGSTAEESQANRARIRDMGAALG FAFRTDGQSRIYNTFDAHRLLHWAGLEGLQYNLKEALFKAYFSD GQDPSDHATLAIIAESVGLDLARAAEILASDEYAAEVREQEQLW VSRGVSSVPTIVFNDQYAVSGGQPAEAFVGAIRQIINESKS |

*Public database numbers identify sequence information that is incorporated by reference herein.

What is claimed is:

1. A recombinant gram-negative *Pseudomonas fluorescens* host cell for recombinant protein expression, wherein the host cell is:

(a) deficient in a first protease activity, wherein the first protease activity is tail-specific protease activity, wherein the deficient first protease activity results from a mutation in a gene encoding a Prc1 tail-specific protease having the amino acid sequence set forth as SEQ ID NO: 33, a Prc1 tail-specific protease related protein having an amino acid sequence at least 90% similar to SEQ ID NO: 33, a Prc2 tail-specific protease having the amino acid sequence set forth as SEQ ID NO: 35, or a Prc2 tail-specific protease related protein having an amino acid sequence at least 90% similar to SEQ ID NO: 35; and, (b) deficient in a second protease activity, wherein the second protease activity is murein DD-endopeptidase activity, wherein the deficient second protease activity results from a mutation in at least one gene encoding a murein DD-endopeptidase; and wherein the host cell further:

(c) is deficient in at least one additional protease activity, wherein the deficient additional protease activity results from a mutation in at least one gene encoding an additional protease, wherein the additional protease is different from the proteases of (a) and (b);

(d) is deficient in one or more autolytic factor activity, wherein the deficient autolytic factor activity results from a mutation in at least one gene encoding an autolytic factor;

(e) overexpresses one or more inactivated protease;

(f) overexpresses one or more folding modulator; or (g) any combination of (c), (d), (e) and (f).

2. The recombinant gram-negative *Pseudomonas fluorescens* host cell of claim 1, wherein the deficient murein DD-endopeptidase activity results from a mutation in a gene encoding a MepM1 murein DD-endopeptidase having the amino acid sequence set forth as SEQ ID NO: 1, or a murein DD-endopeptidase related protein having an amino acid sequence at least 30% similar to SEQ ID NO: 1.

3. The recombinant gram-negative *Pseudomonas fluorescens* host cell of claim 1, wherein: the host cell of (c) is deficient in 1 to 10 different additional protease activities; the host cell of (d) is deficient in 1-5 different autolytic factor activities; the host cell of (e) overexpresses 1 to 10 different inactivated proteases, wherein each inactivated protease is different; the host cell of (f) overexpresses 1-10 different folding modulators; or any combination thereof.

4. The recombinant gram-negative *Pseudomonas fluorescens* host cell of claim 1, wherein:

the one or more deficient additional protease activity of (c) results from a mutation of a gene encoding a serralysin precursor having the amino acid sequence set forth as SEQ ID NO: 9, a serralysin precursor related protein having at least 60% similarity or at least 60% identity to the amino acid sequence set forth as SEQ ID NO: 9, a serralysin precursor having the amino acid sequence set forth as SEQ ID NO: 47, or a serralysin precursor related protein having at least 60% similarity or at least 60% identity to the amino acid sequence set forth as SEQ ID NO: 47, the one or more deficient autolytic factor activity of (d) results from a mutation of a gene encoding an autolytic factor independently selected from: a linear gramicidin synthase subunit D, and a hemolysin precursor; the one or more inactivated protease of (e) is a mutant periplasmic serine endoprotease; and the one or more folding modulator of (f) is a disulfide isomerase.

5. The recombinant gram-negative *Pseudomonas fluorescens* host cell of claim 1, wherein the mutation in (a) or (b) is in a coding sequence or noncoding sequence of the corresponding gene, and wherein the mutation is independently selected from: (i) a complete gene deletion, (ii) a partial gene deletion, (iii) a missense mutation, (iv) a nonsense mutation, (v) a frameshift mutation, (vi) an insertion, and (vii) any combination of (ii), (iii), (iv), (v) and (vi).

6. The recombinant gram-negative *Pseudomonas fluorescens* host cell of claim 5, wherein the missense mutation of (iii) results in a conservative or non-conservative amino acid substitution.

7. The recombinant gram-negative *Pseudomonas fluorescens* host cell of claim 5, wherein the noncoding sequence is a regulatory sequence.

8. The recombinant gram-negative *Pseudomonas fluorescens* host cell of claim 1, wherein the gram-negative bacterial host cell further comprises a functional protease activity, wherein the functional protease activity is the activity of: a MepS1 having the amino acid sequence set forth as SEQ ID NO: 5; or a MepS1 related protein having at least 50% sequence similarity to the *P. fluorescens* MepS1 protease amino acid sequence set forth as SEQ ID NO: 5.

9. The recombinant gram-negative *Pseudomonas fluorescens* host cell of claim 1, wherein the gram-negative bacterial host cell further comprises a functional protease activity, wherein the functional protease activity is: a MepS2 having the amino acid sequence set forth as SEQ ID NO: 7; or a MepS2 related protein having at least 50% sequence similarity to the *P. fluorescens* MepS2 protease amino acid sequence set forth as SEQ ID NO: 7.

10. The recombinant gram-negative *Pseudomonas fluorescens* host cell of claim 1, wherein the deficient first protease activity results from a mutation of a coding sequence and/or noncoding sequence.

11. The recombinant gram-negative *Pseudomonas fluorescens* host cell of claim 1, wherein the second protease activity is deficient due to a mutation that results in a conservative or non-conservative substitution in an active site amino acid or an allosteric site amino acid of a protease having the second protease activity.

12. The recombinant gram-negative *Pseudomonas fluorescens* host cell of claim 1, wherein the deficient second protease activity results from at least one mutation of the second protease gene, wherein the mutation results in a disruption of the amino acid sequence at a position corresponding to: (i) any one or more of residues 134 to 145 of SEQ ID NO: 1; (ii) any one or more of residues 319 to 411 of SEQ ID NO: 1; (iii) any or more of residues 361 to 378 of SEQ ID NO: 1; (iv) any one or more residue selected from 248, 319, 330, 332, 334, 337, 378, 410, and 411 of SEQ ID NO: 1; or any combination of (i), (ii), (iii), and (iv).

13. The recombinant gram-negative *Pseudomonas fluorescens* host cell of claim 1, wherein the deficient second protease activity results from a gene mutation that results in an amino acid substitution of SEQ ID NO: 1 selected from: Y248stop, G332S, D334N, A337T, H411Y, P410L, and any conservative or non-conservative amino acid substitution of any one of R319, H330, D334, H378, and H411.

14. The recombinant gram-negative *Pseudomonas fluorescens* host cell of claim 1, wherein the host cell is capable of high-density cell growth in culture.

15. The recombinant gram-negative *Pseudomonas fluorescens* host cell of claim 1, further comprising at least one expression construct, each expression construct comprising at least one nucleic acid sequence encoding a recombinant protein of interest.

16. The recombinant gram-negative *Pseudomonas fluorescens* host cell of claim 15, wherein the recombinant protein of interest is selected from: an antibody, antibody fragment, or derivative of an antibody or antibody fragment.

17. The recombinant gram-negative *Pseudomonas fluorescens* host cell of claim 16, wherein the antibody, antibody fragment, or derivative thereof is selected from: a monoclonal antibody; a complementarity determining region (CDR) fragment; a CDR-grafted antibody; a single-chain antibody; a single chain antibody fragment; modified antibody, a bispecific antibody, a chimeric antibody; a diabody; a triabody; a tetrabody; a minibody; a linear antibody; a chelating recombinant antibody; a bibody; a tribody; an intrabody; a nanobody; a small modular immunopharmaceutical (SMIP); an antigen-binding-domain immunoglobulin fusion protein; a camelid antibody; a shark single domain antibody, an avian antibody, a VHH-containing antibody; a F(ab); a F(ab)'; F(ab)'₂; scFv; an Fc fragment generated from the heavy chain constant region of an antibody; a reduced IgG fragment; an Fc fusion protein; a domain antibody; a VL; a VNAR; a VH; and a VHH.

18. The recombinant gram-negative *Pseudomonas fluorescens* host cell of claim 16, wherein the antibody, antibody fragment, or derivative thereof, binds to a target selected from: a cytokine; a chemokine; a drug; a cell-surface protein; a growth factor; a growth factor receptor; immune checkpoint molecule, and a blood factor.

19. The recombinant gram-negative *Pseudomonas fluorescens* host cell of claim 16, wherein the antibody, antibody fragment, or derivative thereof is a Fab'.

20. The recombinant gram-negative *Pseudomonas fluorescens* host cell of claim 19, wherein the Fab' binds to a target selected from: Carcinoembryonic antigen (CEA); CD22; fibrin II, beta chain; TNF-alpha; and NCA-90 (granulocyte antigen).

21. The recombinant gram-negative *Pseudomonas fluorescens* host cell of claim 16, wherein the at least one expression construct encoding the antibody, antibody fragment, or derivative thereof comprises at least one nucleic acid sequence encoding a heavy chain, at least one nucleic acid sequence encoding a light chain, or both, wherein the heavy chain is full-length or a heavy chain fragment, and the light chain is full-length or a light chain fragment.

22. The recombinant gram-negative *Pseudomonas fluorescens* host cell of claim 21, wherein each heavy chain-encoding nucleic acid sequence and each light chain-encoding nucleic acid sequence is individually operably linked to an independently selected nucleic acid sequence encoding a periplasmic secretion signal.

23. The recombinant gram-negative *Pseudomonas fluorescens* host cell of claim 20, wherein the Fab' is certolizumab.

24. The recombinant gram-negative *Pseudomonas fluorescens* host cell of claim 1, wherein the host cell is deficient in:

(i) the first protease activity;

(ii) the second protease activity;

(iii) the activity of a serralysin precursor having the amino acid sequence set forth as SEQ ID NO: 9, or a serralysin precursor related protein having at least 60% similarity or at least 60% identity to the amino acid sequence set forth as SEQ ID NO: 9;

(iv) an Hs1U protease having the amino acid sequence set forth as SEQ ID NO: 37, or an Hs1U related protein having at least 60% similarity or at least 60% identity to the amino acid sequence set forth as SEQ ID NO: 37; and (v) an Hs1V protease having the amino acid sequence set forth as SEQ ID NO: 38, or an Hs1V related protein having at least 60% similarity or at least 60% identity to the amino acid sequence set forth as SEQ ID NO: 38.

25. The recombinant gram-negative *Pseudomonas fluorescens* host cell of claim 24, wherein the host cell overexpresses an exogenous disulfide isomerase having at least 60% similarity or at least 60% identity to an amino acid sequence set forth as SEQ ID NO: 27.

26. The recombinant gram-negative *Pseudomonas fluorescens* host cell of claim 1, wherein the cell is:

(i) lsc::lacIQ1;

(ii) Prc1-

(iii) Prc2-

(iii) Hs1U-

(iv) Hs1V-

(v) MepM1-

(vi) PyrFand (vii) deficient in a serralysin precursor that is: a serralysin precursor having the amino acid sequence set forth as SEQ ID NO: 9; or a serralysin precursor related protein having at least 60% similarity or at least 60% identity to the amino acid sequence set forth as SEQ ID NO: 9; wherein the serralysin precursor deficiency results from a mutation in a gene encoding the serralysin precursor.

27. The recombinant gram-negative *Pseudomonas fluorescens* host cell of claim 26, further comprising an expression vector comprising a nucleic acid sequence encoding DegP2 S219A as set forth in SEQ ID NO: 29 or disulfide isomerase PDIA6 as set forth in SEQ ID NO: 27.

28. The recombinant gram-negative *Pseudomonas fluorescens* host cell of claim 1, further comprising an expression vector encoding a recombinant protein.

29. The recombinant gram-negative *Pseudomonas fluorescens* host cell of claim 27, wherein the expression vector encodes a Fab'.

30. The recombinant gram-negative *Pseudomonas fluorescens* host cell of claim 1, wherein the recombinant gram-negative *Pseudomonas fluorescens* host cell has the genotype of strain; STR94976.

31. The recombinant gram-negative *Pseudomonas fluorescens* bacterial host cell of claim 30, further comprising an expression construct-STR94976, for use in producing a recombinant anti-TNF-alpha Fab'.

32. A method for producing a recombinant protein of interest comprising: (a) recovering the recombinant protein of interest from the recombinant gram-negative *Pseudomonas fluorescens* host cell of claim 1, wherein the recombinant gram-negative *Pseudomonas fluorescens* host cell is transformed with a plasmid comprising a nucleic acid encoding the recombinant protein of interest.

33. The method of claim 32, wherein transcription of the nucleic acid sequence encoding the recombinant protein of interest is regulated by an inducible promoter.

34. The method of claim 32, wherein the recombinant gram-negative *Pseudomonas fluorescens* host cell can grow to high cell density.

35. The method of claim 32, wherein the fermentation conditions comprise induction of the inducible promoter at: an OD575 of about 80 to about 160, a culture pH of about 5.8 to about 7.0, a temperature of about 28-33 deg C., fed-batch, and a titer range of about 0.2 to about 5 g/L.

36. The method of claim 32, wherein the recombinant gram-negative *Pseudomonas fluorescens* host cell grows to a cell density that is increased in comparison to a control cell grown under the same fermentation conditions.

37. The method of claim 36, wherein the increase in cell density is about 2-fold to about 15-fold.

38. The method of claim 32, further comprising: (b) measuring the yield of intact, soluble, and/or active, recombinant protein of interest recovered from the recombinant gram-negative bacterial host cell, wherein the measured yield of intact, soluble, and/or active, recombinant protein is about 0.1 to about 10 g/L.

39. The method of claim 38, further comprising: (c) measuring the yield of recombinant protein of interest recovered from a control cell that is intact, soluble, active, or a combination thereof.

40. The method of claim 39, further comprising (d) comparing the yield measured in step (b) to the yield measured in step (c), wherein the yield measured in step (b) is about 2-fold to about 100-fold higher than that measured in step (c).

41. A recombinant gram-negative *Pseudomonas fluorescens* host cell, wherein the host cell is:

(a) deficient in a first protease activity, wherein the deficient first protease activity results from mutations in i. a gene encoding a Prc1 tail-specific protease having the amino acid sequence set forth as SEQ ID NO: 33; and, ii. a gene encoding a Prc2 tail-specific protease having the amino acid sequence set forth as SEQ ID NO: 35; and (b) deficient in a second protease activity, wherein the deficient second protease activity results from a mutation in a gene encoding a MepM1 murein DD-endopeptidase having the amino acid sequence set forth as SEQ ID NO: 1; and additionally wherein the host cell is further:

(c) deficient in one additional protease activity, wherein the deficient additional protease activity results from a mutation of a gene encoding a serralysin precursor having the amino acid sequence set forth as SEQ ID NO: 9;

(d) deficient in one or more autolytic factor activity, wherein the deficient autolytic factor activity results from a mutation in at least one gene encoding an autolytic factor independently selected from: a linear gramicidin synthase subunit D, or a hemolysin precursor;

(e) overexpresses a mutant periplasmic serine endoprotease;

(f) overexpresses a disulfide isomerase folding modulator-having at least 60% similarity or at least 60% identity to an amino acid sequence set forth as SEQ ID NO: 27; or (g) any combination of (c), (d), (e) and (f).

42. The recombinant gram-negative *Pseudomonas fluorescens* host cell of claim 41, wherein the host is (a) and (b).

43. The recombinant gram-negative *Pseudomonas fluorescens* host cell of claim 41, wherein the host cell is (a), (b), and (e), wherein the mutant serine peptidase of (e) is as set forth in SEQ ID NO: 29.

44. The recombinant gram-negative *Pseudomonas fluorescens* host cell of claim 41, wherein the host cell is (a), (b), (e), and (f), wherein the mutant serine peptidase of (e) is as set forth in SEQ ID NO: 29.

* * * * *